(12) United States Patent
Zhang et al.

(10) Patent No.: US 11,390,887 B2
(45) Date of Patent: Jul. 19, 2022

(54) CRISPR-RELATED METHODS AND COMPOSITIONS WITH GOVERNING GRNAS

(71) Applicants: EDITAS MEDICINE, INC., Cambridge, MA (US); THE BROAD INSTITUTE, INC., Cambridge, MA (US); THE UNIVERSITY OF IOWA RESEARCH FOUNDATION, Iowa City, IA (US); MASSACHUSETTS INSTITUTE OF TECHNOLOGY, Cambridge, MA (US)

(72) Inventors: Feng Zhang, Cambridge, MA (US); Deborah Palestrant, Newton, MA (US); Beverly Davidson, Iowa City, IA (US); Jordi Mata-Fink, Somerville, MA (US); Edgardo Rodriguez, Gainesville, FL (US); Alexis Borisy, Boston, MA (US)

(73) Assignees: Editas Medicine, Inc., Cambridge, MA (US); The Broad Institute Inc., Cambridge, MA (US); Massachusetts Institute of Technology, Cambridge, MA (US); University of Iowa Research Foundation, Iowa City, IA (US)

( * ) Notice: Subject to any disclaimer, the term of this patent is extended or adjusted under 35 U.S.C. 154(b) by 0 days.

(21) Appl. No.: 16/835,386

(22) Filed: Mar. 31, 2020

(65) Prior Publication Data

US 2020/0308604 A1    Oct. 1, 2020

Related U.S. Application Data

(60) Continuation of application No. 16/256,615, filed on Jan. 24, 2019, now Pat. No. 10,640,788, which is a continuation of application No. 15/825,616, filed on Nov. 29, 2017, now Pat. No. 10,190,137, which is a division of application No. 14/536,319, filed on Nov. 7, 2014, now Pat. No. 9,834,791.

(60) Provisional application No. 61/901,215, filed on Nov. 7, 2013.

(51) Int. Cl.
| | |
|---|---|
| C07H 21/04 | (2006.01) |
| C12N 15/90 | (2006.01) |
| C12N 15/63 | (2006.01) |
| C12N 15/11 | (2006.01) |
| C12N 15/113 | (2010.01) |
| C12N 9/22 | (2006.01) |

(52) U.S. Cl.
CPC ........... *C12N 15/902* (2013.01); *C12N 9/22* (2013.01); *C12N 15/11* (2013.01); *C12N 15/111* (2013.01); *C12N 15/1137* (2013.01); *C12N 15/63* (2013.01); *C12N 2310/10* (2013.01); *C12N 2310/20* (2017.05); *C12N 2800/80* (2013.01)

(58) Field of Classification Search
None
See application file for complete search history.

(56) References Cited

U.S. PATENT DOCUMENTS

| | | | |
|---|---|---|---|
| 4,235,871 | A | 11/1980 | Papahadjopoulos et al. |
| 4,501,728 | A | 2/1985 | Geho et al. |
| 4,737,323 | A | 4/1988 | Martin et al. |
| 4,837,028 | A | 6/1989 | Allen |
| 5,443,505 | A | 8/1995 | Wong et al. |
| 5,580,737 | A | 12/1996 | Polisky et al. |
| 5,766,242 | A | 6/1998 | Wong et al. |
| 5,767,099 | A | 6/1998 | Harris et al. |
| 5,780,053 | A | 7/1998 | Ashley et al. |
| 5,830,430 | A | 11/1998 | Unger et al. |
| 5,851,548 | A | 12/1998 | Dattagupta et al. |
| 5,855,910 | A | 1/1999 | Ashley et al. |
| 6,007,988 | A | 12/1999 | Chao et al. |
| 6,013,453 | A | 1/2000 | Chao et al. |
| 6,057,153 | A | 5/2000 | George et al. |
| 6,251,090 | B1 | 6/2001 | Avery et al. |
| 6,299,895 | B1 | 10/2001 | Hammang et al. |
| 6,413,540 | B1 | 7/2002 | Yaacobi |
| 6,416,777 | B1 | 7/2002 | Yaacobi |
| 6,453,242 | B1 | 9/2002 | Eisenberg et al. |
| 6,503,717 | B2 | 1/2003 | Case et al. |
| 6,511,808 | B2 | 1/2003 | Wolffe et al. |
| 6,534,261 | B1 | 3/2003 | Cox, III et al. |
| 6,586,240 | B1 | 7/2003 | Singer et al. |
| 6,599,692 | B1 | 7/2003 | Case et al. |
| 6,607,882 | B1 | 8/2003 | Cox, III et al. |
| 6,824,978 | B1 | 11/2004 | Cox, III et al. |
| 6,852,530 | B2 | 2/2005 | Silver et al. |

(Continued)

FOREIGN PATENT DOCUMENTS

| | | | |
|---|---|---|---|
| AU | 2012244264 A1 | 10/2015 | |
| CA | 2632216 A1 | 1/2006 | |

(Continued)

OTHER PUBLICATIONS

Sevilimedu et al., TFIIB aptamers inhibit transcription by perturbing PIC formation at distinct stages, Nucleic Acids Res. 36(9):3118-3127, (2008).

Salamanca et al., An RNA aptamer perturbs heat shock transcription factor activity in *Drosophila melanogaster*, Nucleic Acids Res. 39(15):6729-6740, (2011).

(Continued)

*Primary Examiner* — Kimberly Chong
(74) *Attorney, Agent, or Firm* — Rothwell, Figg, Ernst & Manbeck, P.C.

(57) ABSTRACT

Disclosed herein are methods and compositions useful in targeting a payload to, or editing a target nucleic acid, where a governing gRNA molecule is used to target, optionally inactivate, a Cas9 molecule or a Cas9 molecule/gRNA complex.

8 Claims, 26 Drawing Sheets

Specification includes a Sequence Listing.

(56) References Cited

U.S. PATENT DOCUMENTS

| | | |
|---|---|---|
| 6,933,113 B2 | 8/2005 | Case et al. |
| 6,979,539 B2 | 12/2005 | Cox, III et al. |
| 7,013,219 B2 | 3/2006 | Case et al. |
| 7,021,555 B2 | 4/2006 | Bagnall |
| 7,163,824 B2 | 1/2007 | Cox, III et al. |
| 7,479,573 B2 | 1/2009 | Chu et al. |
| 7,794,931 B2 | 9/2010 | Breaker et al. |
| 7,914,796 B2 | 3/2011 | Miller et al. |
| 7,919,277 B2 | 4/2011 | Russell et al. |
| 8,034,598 B2 | 10/2011 | Miller et al. |
| 8,071,370 B2 | 12/2011 | Wolffe |
| 8,252,535 B2 | 8/2012 | Biekle et al. |
| 8,282,920 B2 | 10/2012 | Heo et al. |
| 8,361,725 B2 | 1/2013 | Russell et al. |
| 8,492,082 B2 | 7/2013 | De Franciscis et al. |
| 8,546,553 B2 | 10/2013 | Terns et al. |
| 8,569,256 B2 | 10/2013 | Heyes et al. |
| 8,680,069 B2 | 3/2014 | de Fougerolles et al. |
| 8,691,750 B2 | 4/2014 | Constien et al. |
| 8,697,359 B1 | 4/2014 | Zhang |
| 8,709,466 B2 | 4/2014 | Coady et al. |
| 8,728,526 B2 | 5/2014 | Heller |
| 8,748,667 B2 | 6/2014 | Budzik et al. |
| 8,758,810 B2 | 6/2014 | Okada et al. |
| 8,759,103 B2 | 6/2014 | Kim et al. |
| 8,759,104 B2 | 6/2014 | Unciti-Broceta et al. |
| 8,771,728 B2 | 7/2014 | Huang et al. |
| 8,771,945 B1 | 7/2014 | Zhang |
| 8,771,986 B2 | 7/2014 | Miller et al. |
| 8,790,664 B2 | 7/2014 | Pitard et al. |
| 8,795,965 B2 | 8/2014 | Zhang |
| 8,846,578 B2 | 9/2014 | McCray et al. |
| 8,865,406 B2 | 10/2014 | Zhang et al. |
| 8,871,445 B2 | 10/2014 | Cong et al. |
| 8,889,356 B2 | 11/2014 | Zhang |
| 8,889,394 B2 | 11/2014 | Chalasani |
| 8,889,418 B2 | 11/2014 | Zhang et al. |
| 8,895,308 B1 | 11/2014 | Zhang et al. |
| 8,906,616 B2 | 12/2014 | Zhang et al. |
| 8,932,814 B2 | 1/2015 | Cong et al. |
| 8,945,839 B2 | 2/2015 | Zhang |
| 8,962,281 B2 | 2/2015 | Doyon |
| 8,993,233 B2 | 3/2015 | Zhang et al. |
| 8,999,641 B2 | 4/2015 | Zhang et al. |
| 9,023,649 B2 | 5/2015 | Mali et al. |
| 9,068,179 B1 | 6/2015 | Liu et al. |
| 9,163,284 B2 | 10/2015 | Liu et al. |
| 9,234,213 B2 | 1/2016 | Wu |
| 9,260,723 B2 | 2/2016 | Mali et al. |
| 9,260,752 B1 | 2/2016 | May et al. |
| 9,267,135 B2 | 2/2016 | Church et al. |
| 9,322,037 B2 | 4/2016 | Liu et al. |
| 9,388,430 B2 | 7/2016 | Liu et al. |
| 9,404,098 B2 | 8/2016 | Terns et al. |
| 9,410,198 B2 | 8/2016 | May et al. |
| 9,422,553 B2 | 8/2016 | Terns et al. |
| 9,567,603 B2 | 2/2017 | Joung et al. |
| 9,567,604 B2 | 2/2017 | Joung et al. |
| 9,587,252 B2 | 3/2017 | Church et al. |
| 9,637,739 B2 | 5/2017 | Siksnys et al. |
| 9,663,782 B2 | 5/2017 | Yu et al. |
| 9,688,971 B2 | 6/2017 | Doudna et al. |
| 9,725,714 B2 | 8/2017 | May et al. |
| 9,738,908 B2 | 8/2017 | Wu |
| 9,790,490 B2 | 10/2017 | Zhang et al. |
| 9,803,194 B2 | 10/2017 | May et al. |
| 9,809,814 B1 | 11/2017 | May et al. |
| 9,840,713 B2 | 12/2017 | Zhang |
| 9,873,894 B2 | 1/2018 | Conway et al. |
| 9,879,269 B2 | 1/2018 | Barrangou et al. |
| 9,885,026 B2 | 2/2018 | Brouns et al. |
| 9,902,974 B2 | 2/2018 | Conway et al. |
| 9,909,122 B2 | 3/2018 | May et al. |
| 9,963,719 B1 | 5/2018 | Friedland et al. |
| 9,970,024 B2 | 5/2018 | Church et al. |
| 10,006,054 B1 | 6/2018 | Friedland et al. |
| 2002/0160940 A1 | 10/2002 | Case et al. |
| 2002/0164575 A1 | 11/2002 | Case et al. |
| 2003/0186238 A1 | 10/2003 | Allawi et al. |
| 2006/0088864 A1 | 4/2006 | Smolke et al. |
| 2006/0199190 A1 | 9/2006 | Russell et al. |
| 2006/0234247 A1 | 10/2006 | Pattaraju |
| 2007/0020627 A1 | 1/2007 | Barbas, III |
| 2008/0124725 A1 | 5/2008 | Barrangou et al. |
| 2008/0182254 A1 | 7/2008 | Hall et al. |
| 2008/0193470 A1 | 8/2008 | Masignani et al. |
| 2009/0130718 A1 | 5/2009 | Short |
| 2009/0234109 A1 | 9/2009 | Han et al. |
| 2010/0034924 A1 | 2/2010 | Fremaux et al. |
| 2010/0055793 A1 | 3/2010 | Chandrasegaran |
| 2010/0055798 A1 | 3/2010 | Battersby et al. |
| 2010/0076057 A1 | 3/2010 | Sontheimer et al. |
| 2010/0093617 A1 | 4/2010 | Barrangou et al. |
| 2010/0104690 A1 | 4/2010 | Barrangou et al. |
| 2010/0120043 A1 | 5/2010 | Sood et al. |
| 2010/0132069 A1 | 5/2010 | Lahaye et al. |
| 2010/0183559 A1 | 7/2010 | Van Sinderen et al. |
| 2010/0184624 A1 | 7/2010 | Samuel et al. |
| 2010/0209998 A1 | 8/2010 | Attwood et al. |
| 2010/0209999 A1 | 8/2010 | Altermann et al. |
| 2010/0221185 A1 | 9/2010 | Altermann et al. |
| 2010/0311061 A1 | 12/2010 | Korlach et al. |
| 2010/0316643 A1 | 12/2010 | Eckert et al. |
| 2011/0002889 A1 | 1/2011 | Barrangou et al. |
| 2011/0016540 A1 | 1/2011 | Weinstein |
| 2011/0059160 A1 | 3/2011 | Essner et al. |
| 2011/0059502 A1 | 3/2011 | Chalasani |
| 2011/0092381 A1 | 4/2011 | Sood et al. |
| 2011/0104787 A1 | 5/2011 | Church et al. |
| 2011/0143348 A1 | 6/2011 | Tomigahara et al. |
| 2011/0171647 A1 | 7/2011 | Tomigahara et al. |
| 2011/0189674 A1 | 8/2011 | Tomigahara et al. |
| 2011/0189776 A1 | 8/2011 | Terns et al. |
| 2011/0201007 A1 | 8/2011 | Waller et al. |
| 2011/0201118 A1 | 8/2011 | Yang et al. |
| 2011/0217739 A1 | 9/2011 | Terns et al. |
| 2011/0217791 A1 | 9/2011 | Tomigahara et al. |
| 2011/0223638 A1 | 9/2011 | Wiedenheft et al. |
| 2011/0236530 A1 | 9/2011 | Manoury et al. |
| 2011/0236894 A1 | 9/2011 | Rao et al. |
| 2011/0269119 A1 | 11/2011 | Hutchison et al. |
| 2011/0286980 A1 | 11/2011 | Brenner |
| 2011/0300528 A1 | 12/2011 | Jassim et al. |
| 2011/0301073 A1 | 12/2011 | Gregory et al. |
| 2012/0027786 A1 | 2/2012 | Gupta et al. |
| 2012/0035065 A1 | 2/2012 | Smolke et al. |
| 2012/0088676 A1 | 4/2012 | Weill et al. |
| 2012/0100569 A1 | 4/2012 | Liu et al. |
| 2012/0141523 A1 | 6/2012 | Castado et al. |
| 2012/0151635 A1 | 6/2012 | Coruzzi et al. |
| 2012/0214160 A1 | 8/2012 | Deng et al. |
| 2012/0270273 A1 | 10/2012 | Zhang et al. |
| 2012/0315670 A1 | 12/2012 | Jacobson et al. |
| 2013/0011516 A1 | 1/2013 | Griffin et al. |
| 2013/0011828 A1 | 1/2013 | Barrangou et al. |
| 2013/0117869 A1 | 5/2013 | Duchateau |
| 2013/0130248 A1 | 5/2013 | Haurwitz et al. |
| 2013/0137160 A1 | 5/2013 | Zhang et al. |
| 2013/0145497 A1 | 6/2013 | Choi et al. |
| 2013/0150240 A1 | 6/2013 | Newman et al. |
| 2013/0158245 A1 | 6/2013 | Russell et al. |
| 2013/0165389 A1 | 6/2013 | Schellenberger et al. |
| 2013/0253040 A1 | 9/2013 | Miller et al. |
| 2013/0288251 A1 | 10/2013 | Horvath et al. |
| 2013/0326645 A1 | 12/2013 | Cost et al. |
| 2013/0326725 A1 | 12/2013 | Shukla et al. |
| 2013/0344117 A1 | 12/2013 | Mirosevich et al. |
| 2014/0005269 A1 | 1/2014 | Ngwuluka et al. |
| 2014/0017214 A1 | 1/2014 | Cost |
| 2014/0018404 A1 | 1/2014 | Chen et al. |
| 2014/0044793 A1 | 2/2014 | Goll et al. |
| 2014/0065711 A1 | 3/2014 | Liu et al. |
| 2014/0068797 A1 | 3/2014 | Doudna et al. |
| 2014/0093941 A1 | 4/2014 | Terns et al. |

(56) References Cited

U.S. PATENT DOCUMENTS

| | | |
|---|---|---|
| 2014/0115726 A1 | 4/2014 | Duchateau et al. |
| 2014/0127752 A1 | 5/2014 | Zhou et al. |
| 2014/0141094 A1 | 5/2014 | Smyth et al. |
| 2014/0141487 A1 | 5/2014 | Feldman et al. |
| 2014/0179770 A1 | 6/2014 | Zhang et al. |
| 2014/0186843 A1 | 7/2014 | Zhang et al. |
| 2014/0186919 A1 | 7/2014 | Zhang et al. |
| 2014/0186958 A1 | 7/2014 | Zhang et al. |
| 2014/0189896 A1 | 7/2014 | Zhang et al. |
| 2014/0199767 A1 | 7/2014 | Barrangou et al. |
| 2014/0234289 A1 | 8/2014 | Liu et al. |
| 2014/0242664 A1 | 8/2014 | Zhang et al. |
| 2014/0242699 A1 | 8/2014 | Zhang |
| 2014/0248702 A1 | 9/2014 | Cong et al. |
| 2014/0256046 A1 | 9/2014 | Zhang et al. |
| 2014/0273037 A1 | 9/2014 | Wu |
| 2014/0273226 A1 | 9/2014 | Wu |
| 2014/0273230 A1 | 9/2014 | Chen et al. |
| 2014/0273233 A1 | 9/2014 | Chen et al. |
| 2014/0287938 A1 | 9/2014 | Zhang et al. |
| 2014/0289882 A1 | 9/2014 | Zhu et al. |
| 2014/0294773 A1 | 10/2014 | Brouns et al. |
| 2014/0295556 A1 | 10/2014 | Joung et al. |
| 2014/0295557 A1 | 10/2014 | Joung et al. |
| 2014/0302563 A1 | 10/2014 | Doudna et al. |
| 2014/0310830 A1 | 10/2014 | Zhang et al. |
| 2014/0315985 A1 | 10/2014 | May et al. |
| 2014/0335620 A1 | 11/2014 | Ran et al. |
| 2014/0342456 A1 | 11/2014 | Mali et al. |
| 2014/0342457 A1 | 11/2014 | Mali et al. |
| 2014/0342458 A1 | 11/2014 | Mali et al. |
| 2014/0349400 A1 | 11/2014 | Jakimo et al. |
| 2014/0356867 A1 | 12/2014 | Peter et al. |
| 2014/0356956 A1 | 12/2014 | Church et al. |
| 2014/0356958 A1 | 12/2014 | Mali et al. |
| 2014/0356959 A1 | 12/2014 | Church et al. |
| 2014/0357523 A1 | 12/2014 | Zeiner et al. |
| 2014/0357530 A1 | 12/2014 | Zhang et al. |
| 2014/0359795 A1 | 12/2014 | Fahrenkrug et al. |
| 2014/0377868 A1 | 12/2014 | Joung et al. |
| 2015/0010526 A1 | 1/2015 | Liu et al. |
| 2015/0020223 A1 | 1/2015 | Zhang et al. |
| 2015/0024499 A1 | 1/2015 | Brouns et al. |
| 2015/0024500 A1 | 1/2015 | Yu et al. |
| 2015/0024954 A1 | 1/2015 | Smolke et al. |
| 2015/0031089 A1 | 1/2015 | Lindstrom |
| 2015/0031132 A1 | 1/2015 | Church et al. |
| 2015/0031133 A1 | 1/2015 | Church et al. |
| 2015/0031134 A1 | 1/2015 | Zhang et al. |
| 2015/0044191 A1 | 2/2015 | Liu et al. |
| 2015/0044192 A1 | 2/2015 | Liu et al. |
| 2015/0044772 A1 | 2/2015 | Zhao |
| 2015/0045546 A1 | 2/2015 | Siksnys et al. |
| 2015/0050699 A1 | 2/2015 | Siksnys et al. |
| 2015/0056177 A1 | 2/2015 | Liu et al. |
| 2015/0056629 A1 | 2/2015 | Guthrie-Honea |
| 2015/0056705 A1 | 2/2015 | Conway et al. |
| 2015/0064138 A1 | 3/2015 | Lu et al. |
| 2015/0064789 A1 | 3/2015 | Paschon et al. |
| 2015/0067922 A1 | 3/2015 | Yang et al. |
| 2015/0071889 A1 | 3/2015 | Musunuru et al. |
| 2015/0071898 A1 | 3/2015 | Liu et al. |
| 2015/0071899 A1 | 3/2015 | Liu et al. |
| 2015/0071900 A1 | 3/2015 | Liu et al. |
| 2015/0071901 A1 | 3/2015 | Liu et al. |
| 2015/0071902 A1 | 3/2015 | Liu et al. |
| 2015/0071903 A1 | 3/2015 | Liu et al. |
| 2015/0071906 A1 | 3/2015 | Liu et al. |
| 2015/0079680 A1 | 3/2015 | Bradley et al. |
| 2015/0079681 A1 | 3/2015 | Zhang |
| 2015/0098954 A1 | 4/2015 | Hyde et al. |
| 2015/0132269 A1 | 5/2015 | Orkin et al. |
| 2015/0140664 A1 | 5/2015 | Byrne et al. |
| 2015/0159172 A1 | 6/2015 | Miller et al. |
| 2015/0165054 A1 | 6/2015 | Liu et al. |
| 2015/0166980 A1 | 6/2015 | Liu et al. |
| 2015/0166981 A1 | 6/2015 | Liu |
| 2015/0166982 A1 | 6/2015 | Liu et al. |
| 2015/0166983 A1 | 6/2015 | Liu et al. |
| 2015/0166984 A1 | 6/2015 | Liu et al. |
| 2015/0166985 A1 | 6/2015 | Liu et al. |
| 2015/0176013 A1 | 6/2015 | Musunuru et al. |
| 2015/0184139 A1 | 7/2015 | Zhang et al. |
| 2015/0191744 A1 | 7/2015 | Wolfe et al. |
| 2015/0197759 A1 | 7/2015 | Xu et al. |
| 2015/0203872 A1 | 7/2015 | Zhang |
| 2015/0211058 A1 | 7/2015 | Carstens et al. |
| 2015/0218573 A1 | 8/2015 | Loque et al. |
| 2015/0225773 A1 | 8/2015 | Farmer et al. |
| 2015/0232833 A1 | 8/2015 | Mali et al. |
| 2015/0232881 A1 | 8/2015 | Glucksmann et al. |
| 2015/0232882 A1 | 8/2015 | Zhang et al. |
| 2015/0240261 A1 | 8/2015 | Siksnys et al. |
| 2015/0247150 A1 | 9/2015 | Zhang et al. |
| 2015/0252358 A1 | 9/2015 | Maeder et al. |
| 2015/0259684 A1 | 9/2015 | Church et al. |
| 2015/0259704 A1 | 9/2015 | Church et al. |
| 2015/0284727 A1 | 10/2015 | Kim et al. |
| 2015/0291961 A1 | 10/2015 | Siksnys et al. |
| 2015/0291965 A1 | 10/2015 | Zhang et al. |
| 2015/0291966 A1 | 10/2015 | Zhang et al. |
| 2015/0322457 A1 | 11/2015 | Kim et al. |
| 2015/0344912 A1 | 12/2015 | Kim et al. |
| 2015/0353905 A1 | 12/2015 | Weiss et al. |
| 2015/0356239 A1 | 12/2015 | Zhang et al. |
| 2016/0002670 A1 | 1/2016 | Church et al. |
| 2016/0010076 A1 | 1/2016 | Joung et al. |
| 2016/0010154 A1 | 1/2016 | Laganiere et al. |
| 2016/0017366 A1 | 1/2016 | Chen et al. |
| 2016/0024523 A1 | 1/2016 | Joung et al. |
| 2016/0024524 A1 | 1/2016 | Joung et al. |
| 2016/0032274 A1 | 2/2016 | Church et al. |
| 2016/0046949 A1 | 2/2016 | May et al. |
| 2016/0046961 A1 | 2/2016 | Jinek et al. |
| 2016/0046962 A1 | 2/2016 | May et al. |
| 2016/0046963 A1 | 2/2016 | May et al. |
| 2016/0046978 A1 | 2/2016 | May et al. |
| 2016/0060653 A1 | 3/2016 | Doudna et al. |
| 2016/0060654 A1 | 3/2016 | Doudna et al. |
| 2016/0068864 A1 | 3/2016 | Doudna et al. |
| 2016/0068887 A1 | 3/2016 | May et al. |
| 2016/0076020 A1 | 3/2016 | May et al. |
| 2016/0090607 A1 | 3/2016 | Conway et al. |
| 2016/0108470 A1 | 4/2016 | May et al. |
| 2016/0115488 A1 | 4/2016 | Zhang et al. |
| 2016/0115489 A1 | 4/2016 | Zhang et al. |
| 2016/0122774 A1 | 5/2016 | Duchateau et al. |
| 2016/0130608 A1 | 5/2016 | Doudna et al. |
| 2016/0130609 A1 | 5/2016 | Doudna et al. |
| 2016/0138008 A1 | 5/2016 | Doudna et al. |
| 2016/0138046 A1 | 5/2016 | Wu |
| 2016/0145646 A1 | 5/2016 | Frendewey et al. |
| 2016/0153003 A1 | 6/2016 | Joung et al. |
| 2016/0153004 A1 | 6/2016 | Zhang et al. |
| 2016/0153006 A1 | 6/2016 | Zhang et al. |
| 2016/0160210 A1 | 6/2016 | Mali et al. |
| 2016/0168592 A1 | 6/2016 | Church et al. |
| 2016/0175462 A1 | 6/2016 | Zhang et al. |
| 2016/0184362 A1 | 6/2016 | Duchateau et al. |
| 2016/0186152 A1 | 6/2016 | Brouns et al. |
| 2016/0186213 A1 | 6/2016 | Zhang et al. |
| 2016/0186214 A1 | 6/2016 | Brouns et al. |
| 2016/0201089 A1 | 7/2016 | Gersbach et al. |
| 2016/0208243 A1 | 7/2016 | Zhang et al. |
| 2016/0215276 A1 | 7/2016 | Liu et al. |
| 2016/0222416 A1 | 8/2016 | Church et al. |
| 2016/0237455 A1 | 8/2016 | Glucksmann et al. |
| 2016/0237456 A1 | 8/2016 | Church et al. |
| 2016/0251640 A1 | 9/2016 | May et al. |
| 2016/0272965 A1 | 9/2016 | Zhang et al. |
| 2016/0281072 A1 | 9/2016 | Zhang |
| 2016/0298125 A1 | 10/2016 | Chen et al. |
| 2016/0298132 A1 | 10/2016 | Chen et al. |
| 2016/0298133 A1 | 10/2016 | Chen et al. |

(56) References Cited

U.S. PATENT DOCUMENTS

| | | | |
|---|---|---|---|
| 2016/0298134 A1 | 10/2016 | Chen et al. |
| 2016/0298135 A1 | 10/2016 | Chen et al. |
| 2016/0298136 A1 | 10/2016 | Chen et al. |
| 2016/0298137 A1 | 10/2016 | Chen et al. |
| 2016/0298138 A1 | 10/2016 | Chen et al. |
| 2016/0304907 A1 | 10/2016 | Mali et al. |
| 2016/0312280 A1 | 10/2016 | May et al. |
| 2016/0319281 A1 | 11/2016 | Tsai et al. |
| 2016/0319349 A1 | 11/2016 | May et al. |
| 2016/0340662 A1 | 11/2016 | Zhang et al. |
| 2016/0355796 A1 | 12/2016 | Davidson et al. |
| 2016/0355797 A1 | 12/2016 | Konermann et al. |
| 2016/0355816 A1 | 12/2016 | Terns et al. |
| 2017/0037416 A1 | 2/2017 | Barrangou et al. |
| 2017/0044569 A9 | 2/2017 | Church et al. |
| 2017/0051276 A1 | 2/2017 | May et al. |
| 2017/0051310 A1 | 2/2017 | Doudna et al. |
| 2017/0051312 A1 | 2/2017 | Jinek et al. |
| 2017/0073705 A1 | 3/2017 | Chen et al. |
| 2017/0107536 A1 | 4/2017 | Zhang et al. |
| 2017/0152508 A1 | 6/2017 | Joung et al. |
| 2017/0152528 A1 | 6/2017 | Zhang |
| 2017/0166893 A1 | 6/2017 | Doudna et al. |
| 2017/0166903 A1 | 6/2017 | Zhang et al. |
| 2017/0175142 A1 | 6/2017 | Zhang et al. |
| 2017/0175144 A1 | 6/2017 | Zhang et al. |
| 2017/0191078 A1 | 7/2017 | Zhang et al. |
| 2017/0191082 A1 | 7/2017 | Chen et al. |
| 2017/0198269 A1 | 7/2017 | Zhang et al. |
| 2017/0211142 A1 | 7/2017 | Smargon et al. |
| 2017/0306335 A1 | 10/2017 | Zhang et al. |
| 2017/0327805 A1 | 11/2017 | Joung et al. |
| 2017/0327820 A1 | 11/2017 | May et al. |
| 2018/0119121 A1 | 5/2018 | Brouns et al. |
| 2018/0119175 A1 | 5/2018 | Conway et al. |
| 2018/0135073 A1 | 5/2018 | Chen et al. |
| 2018/0155716 A1 | 6/2018 | Zhang et al. |

FOREIGN PATENT DOCUMENTS

| | | |
|---|---|---|
| CA | 2832534 A1 | 10/2012 |
| CA | 2853829 A1 | 5/2013 |
| CA | 2872241 A1 | 11/2013 |
| CN | 104342457 A | 2/2013 |
| CN | 103224947 A | 7/2013 |
| CN | 103233028 A | 8/2013 |
| CN | 103343120 A | 10/2013 |
| CN | 103388006 A | 11/2013 |
| CN | 103608027 A | 2/2014 |
| CN | 103614415 A | 3/2014 |
| CN | 103642836 A | 3/2014 |
| CN | 103668472 A | 3/2014 |
| CN | 103820441 A | 5/2014 |
| CN | 103820454 A | 5/2014 |
| CN | 103857797 A | 6/2014 |
| CN | 103911376 A | 7/2014 |
| CN | 103923911 A | 7/2014 |
| CN | 104004778 A | 8/2014 |
| CN | 104109687 A | 10/2014 |
| CN | 104178461 A | 12/2014 |
| CN | 104404036 A | 3/2015 |
| CN | 104450774 A | 3/2015 |
| CN | 104480144 A1 | 4/2015 |
| CN | 104498493 A | 4/2015 |
| CN | 104504304 A | 4/2015 |
| CN | 104531704 A | 4/2015 |
| CN | 104531705 A | 4/2015 |
| CN | 104560864 A | 4/2015 |
| CN | 104593418 A | 5/2015 |
| CN | 104593422 A | 5/2015 |
| CN | 104611370 A | 5/2015 |
| CN | 104651392 A | 5/2015 |
| CN | 104651398 A | 5/2015 |
| CN | 104651399 A | 5/2015 |
| CN | 104651401 A | 5/2015 |
| CN | 104673816 A | 6/2015 |
| CN | 104725626 A | 6/2015 |
| CN | 104726449 A | 6/2015 |
| CN | 104726494 A | 6/2015 |
| CN | 104745626 A | 7/2015 |
| CN | 104762321 A | 7/2015 |
| CN | 104805078 A | 7/2015 |
| CN | 104805099 A | 7/2015 |
| CN | 104805118 A | 7/2015 |
| CN | 104846010 A | 8/2015 |
| CN | 104894068 A | 9/2015 |
| CN | 104894075 A | 9/2015 |
| CN | 104928321 A | 9/2015 |
| EP | 2591770 A3 | 11/2013 |
| EP | 25931891 A1 | 6/2014 |
| JP | 2008515405 A | 5/2008 |
| JP | 2012525146 A | 10/2012 |
| JP | 2012223201 A | 11/2012 |
| WO | WO 2000040089 A1 | 7/2000 |
| WO | WO 2001028474 A1 | 4/2001 |
| WO | WO 2002089767 A1 | 11/2002 |
| WO | WO 2003072788 A1 | 9/2003 |
| WO | WO 2004099366 A2 | 11/2004 |
| WO | WO 2006002547 A1 | 1/2006 |
| WO | WO 2006042112 A3 | 12/2006 |
| WO | WO 2007014275 A2 | 2/2007 |
| WO | WO-2007/025097 A2 | 3/2007 |
| WO | WO 2007025097 A2 | 3/2007 |
| WO | WO 2007136815 A2 | 11/2007 |
| WO | WO 2007143574 A1 | 12/2007 |
| WO | WO 2008108989 A2 | 9/2008 |
| WO | WO 2009134808 A2 | 11/2009 |
| WO | WO-2010/011961 A2 | 1/2010 |
| WO | WO 2010054108 A2 | 5/2010 |
| WO | WO 2010054108 A9 | 5/2010 |
| WO | WO 2010054154 A2 | 5/2010 |
| WO | WO 2010068289 A2 | 6/2010 |
| WO | WO 2010075424 A2 | 7/2010 |
| WO | WO 2010102257 A2 | 9/2010 |
| WO | WO 2010129019 A2 | 11/2010 |
| WO | WO 2010129023 A2 | 11/2010 |
| WO | WO 2010132092 A2 | 11/2010 |
| WO | WO 2010144150 A2 | 12/2010 |
| WO | WO 2011012724 A1 | 2/2011 |
| WO | WO 2011017293 A2 | 2/2011 |
| WO | WO 2011053868 A1 | 5/2011 |
| WO | WO 2011053982 A2 | 5/2011 |
| WO | WO 2011109031 A1 | 9/2011 |
| WO | WO 2011143124 A2 | 11/2011 |
| WO | WO 2011146121 A1 | 11/2011 |
| WO | WO 2012031205 A2 | 3/2012 |
| WO | WO 2012054726 A1 | 4/2012 |
| WO | WO 2012065043 A2 | 5/2012 |
| WO | WO 2012138927 A2 | 10/2012 |
| WO | WO 2012138939 A1 | 10/2012 |
| WO | WO 2012158985 A2 | 11/2012 |
| WO | WO 2012158986 A2 | 11/2012 |
| WO | WO 2012164565 A1 | 12/2012 |
| WO | WO 2012164565 A8 | 12/2012 |
| WO | WO 2012164656 A1 | 12/2012 |
| WO | WO 2012168435 A1 | 12/2012 |
| WO | WO 2013012674 A1 | 1/2013 |
| WO | WO 2013013105 A2 | 1/2013 |
| WO | WO 2013066438 A2 | 5/2013 |
| WO | WO 2013082519 A2 | 6/2013 |
| WO | WO-2013/098244 A1 | 7/2013 |
| WO | WO 2013098244 A1 | 7/2013 |
| WO | WO 2013126794 A1 | 8/2013 |
| WO | WO-2013/141680 A1 | 9/2013 |
| WO | WO-2013/142578 A1 | 9/2013 |
| WO | WO 2013130824 A1 | 9/2013 |
| WO | WO 2013141680 A1 | 9/2013 |
| WO | WO 2013142378 A9 | 9/2013 |
| WO | WO 2013142578 A1 | 9/2013 |
| WO | WO 2013160230 A1 | 10/2013 |
| WO | WO-2013/176772 A1 | 11/2013 |
| WO | WO 2013166315 A1 | 11/2013 |
| WO | WO 2013169398 A2 | 11/2013 |
| WO | WO 2013169802 A1 | 11/2013 |

(56) References Cited

FOREIGN PATENT DOCUMENTS

| | | |
|---|---|---|
| WO | WO 2013176772 A1 | 11/2013 |
| WO | WO 2013176915 A1 | 11/2013 |
| WO | WO 2013176916 A1 | 11/2013 |
| WO | WO 2013181440 A1 | 12/2013 |
| WO | WO 2013186754 A2 | 12/2013 |
| WO | WO 2013188037 A2 | 12/2013 |
| WO | WO 2013188522 A2 | 12/2013 |
| WO | WO 2013188638 A2 | 12/2013 |
| WO | WO 2013192278 A1 | 12/2013 |
| WO | WO-2014/018423 A2 | 1/2014 |
| WO | WO 2014005042 A2 | 1/2014 |
| WO | WO 2014011237 A1 | 1/2014 |
| WO | WO 2014011901 A2 | 1/2014 |
| WO | WO 2014018423 A2 | 1/2014 |
| WO | WO 2014020608 A1 | 2/2014 |
| WO | WO 2014022120 A1 | 2/2014 |
| WO | WO 2014022702 A2 | 2/2014 |
| WO | WO 2014036219 A2 | 3/2014 |
| WO | WO 2014039513 A2 | 3/2014 |
| WO | WO 2014039523 A1 | 3/2014 |
| WO | WO 2014039684 A1 | 3/2014 |
| WO | WO 2014039692 A2 | 3/2014 |
| WO | WO 2014039702 A2 | 3/2014 |
| WO | WO 2014039872 A1 | 3/2014 |
| WO | WO 2014039970 A1 | 3/2014 |
| WO | WO 2014041327 A1 | 3/2014 |
| WO | WO 2014043143 A1 | 3/2014 |
| WO | WO 2014047103 A2 | 3/2014 |
| WO | WO 2014059173 A2 | 4/2014 |
| WO | WO 2014059255 A1 | 4/2014 |
| WO | WO-2014/065596 A1 | 5/2014 |
| WO | WO 2014065596 A1 | 5/2014 |
| WO | WO 2014066505 A1 | 5/2014 |
| WO | WO 2014068346 A2 | 5/2014 |
| WO | WO 2014070887 A1 | 5/2014 |
| WO | WO 2014071006 A1 | 5/2014 |
| WO | WO 2014071219 A1 | 5/2014 |
| WO | WO 2014071235 A1 | 5/2014 |
| WO | WO 2014072941 A1 | 5/2014 |
| WO | WO 2014081729 A1 | 5/2014 |
| WO | WO 2014081730 A1 | 5/2014 |
| WO | WO 2014081855 A1 | 5/2014 |
| WO | WO-2014/089290 A1 | 6/2014 |
| WO | WO-2014/093479 A1 | 6/2014 |
| WO | WO-2014/093595 A1 | 6/2014 |
| WO | WO-2014/093622 A2 | 6/2014 |
| WO | WO-2014/093635 A1 | 6/2014 |
| WO | WO-2014/093655 A2 | 6/2014 |
| WO | WO-2014/093661 A2 | 6/2014 |
| WO | WO-2014/093694 A1 | 6/2014 |
| WO | WO-2014/093701 A1 | 6/2014 |
| WO | WO-2014/093709 A1 | 6/2014 |
| WO | WO-2014/093712 A1 | 6/2014 |
| WO | WO-2014/093718 A1 | 6/2014 |
| WO | WO-2014/099744 A1 | 6/2014 |
| WO | WO-2014/099750 A2 | 6/2014 |
| WO | WO 2014082644 A1 | 6/2014 |
| WO | WO 2014085261 A1 | 6/2014 |
| WO | WO 2014085593 A1 | 6/2014 |
| WO | WO 2014085830 A2 | 6/2014 |
| WO | WO 2014089212 A1 | 6/2014 |
| WO | WO 2014089290 A1 | 6/2014 |
| WO | WO 2014089348 A1 | 6/2014 |
| WO | WO 2014089513 A1 | 6/2014 |
| WO | WO 2014089533 A2 | 6/2014 |
| WO | WO 2014089541 A2 | 6/2014 |
| WO | WO 2014093479 | 6/2014 |
| WO | WO 2014093595 A1 | 6/2014 |
| WO | WO 2014093622 A2 | 6/2014 |
| WO | WO 2014093635 A1 | 6/2014 |
| WO | WO 2014093655 A2 | 6/2014 |
| WO | WO 2014093661 A2 | 6/2014 |
| WO | WO 2014093694 A1 | 6/2014 |
| WO | WO 2014093701 A1 | 6/2014 |
| WO | WO 2014093709 A1 | 6/2014 |
| WO | WO 2014093712 A1 | 6/2014 |
| WO | WO 2014093718 A1 | 6/2014 |
| WO | WO 2014093736 A1 | 6/2014 |
| WO | WO 2014093768 A1 | 6/2014 |
| WO | WO 2014093852 A1 | 6/2014 |
| WO | WO 2014096972 A2 | 6/2014 |
| WO | WO 2014099750 | 6/2014 |
| WO | WO-2014/113493 A1 | 7/2014 |
| WO | WO 2014113493 A1 | 7/2014 |
| WO | WO 2014124226 A1 | 8/2014 |
| WO | WO 2014127287 A1 | 8/2014 |
| WO | WO 2014128324 A1 | 8/2014 |
| WO | WO 2014128659 A1 | 8/2014 |
| WO | WO 2014130955 A1 | 8/2014 |
| WO | WO-2014/144288 A1 | 9/2014 |
| WO | WO-2014/144592 A2 | 9/2014 |
| WO | WO-2014/144761 A2 | 9/2014 |
| WO | WO-2014/145599 A2 | 9/2014 |
| WO | WO-2014/150624 A1 | 9/2014 |
| WO | WO-2014/152432 A2 | 9/2014 |
| WO | WO 2014131833 A1 | 9/2014 |
| WO | WO 2014143381 A1 | 9/2014 |
| WO | WO 2014144094 A1 | 9/2014 |
| WO | WO 2014144155 A1 | 9/2014 |
| WO | WO 2014144288 A1 | 9/2014 |
| WO | WO 2014144592 A2 | 9/2014 |
| WO | WO 2014144761 A2 | 9/2014 |
| WO | WO 2014145599 A2 | 9/2014 |
| WO | WO 2014150624 A1 | 9/2014 |
| WO | WO 2014152432 A2 | 9/2014 |
| WO | WO 2014153470 A2 | 9/2014 |
| WO | WO-2014/165825 A2 | 10/2014 |
| WO | WO 2014164466 A1 | 10/2014 |
| WO | WO 2014165177 A1 | 10/2014 |
| WO | WO 2014165349 A1 | 10/2014 |
| WO | WO 2014165612 A2 | 10/2014 |
| WO | WO 2014165825 A2 | 10/2014 |
| WO | WO 2014172458 A1 | 10/2014 |
| WO | WO 2014172470 A2 | 10/2014 |
| WO | WO 2014172489 A2 | 10/2014 |
| WO | WO-2014/186585 A2 | 11/2014 |
| WO | WO 2014182700 A1 | 11/2014 |
| WO | WO 2014183071 A2 | 11/2014 |
| WO | WO 2014184143 A1 | 11/2014 |
| WO | WO 2014184741 A1 | 11/2014 |
| WO | WO 2014184744 A1 | 11/2014 |
| WO | WO 2014186585 A2 | 11/2014 |
| WO | WO 2014186686 A2 | 11/2014 |
| WO | WO 2014190181 A1 | 11/2014 |
| WO | WO-2014/191518 A1 | 12/2014 |
| WO | WO-2014/197568 A2 | 12/2014 |
| WO | WO-2014/197748 A2 | 12/2014 |
| WO | WO-2014/204578 A1 | 12/2014 |
| WO | WO-2014/204724 A1 | 12/2014 |
| WO | WO-2014/204725 A1 | 12/2014 |
| WO | WO-2014/204727 A1 | 12/2014 |
| WO | WO-2014/204728 A1 | 12/2014 |
| WO | WO-2014/204729 A1 | 12/2014 |
| WO | WO 2014191128 A1 | 12/2014 |
| WO | WO 2014191518 A1 | 12/2014 |
| WO | WO 2014191521 A2 | 12/2014 |
| WO | WO 2014191525 A1 | 12/2014 |
| WO | WO 2014191527 A1 | 12/2014 |
| WO | WO 2014194190 A1 | 12/2014 |
| WO | WO 2014197568 A2 | 12/2014 |
| WO | WO 2014197748 A2 | 12/2014 |
| WO | WO 2014200659 A1 | 12/2014 |
| WO | WO 2014201015 A2 | 12/2014 |
| WO | WO 2014204578 A1 | 12/2014 |
| WO | WO 2014204723 A1 | 12/2014 |
| WO | WO 2014204724 A1 | 12/2014 |
| WO | WO 2014204725 A1 | 12/2014 |
| WO | WO 2014204726 A1 | 12/2014 |
| WO | WO 2014204727 A1 | 12/2014 |
| WO | WO 2014204728 A1 | 12/2014 |
| WO | WO 2014204729 A1 | 12/2014 |
| WO | WO-2015/006290 A1 | 1/2015 |
| WO | WO-2015/006294 A2 | 1/2015 |
| WO | WO-2015/010114 A1 | 1/2015 |

(56) References Cited

FOREIGN PATENT DOCUMENTS

| | | |
|---|---|---|
| WO | WO-2015/013583 A2 | 1/2015 |
| WO | WO 2015002780 A1 | 1/2015 |
| WO | WO 2015004241 A2 | 1/2015 |
| WO | WO 2015006290 A1 | 1/2015 |
| WO | WO 2015006294 A2 | 1/2015 |
| WO | WO 2015006498 A2 | 1/2015 |
| WO | WO 2015006747 A2 | 1/2015 |
| WO | WO 2015010114 A1 | 1/2015 |
| WO | WO 2015013583 A2 | 1/2015 |
| WO | WO-2015/021426 A1 | 2/2015 |
| WO | WO 2015017866 A1 | 2/2015 |
| WO | WO 2015018503 A1 | 2/2015 |
| WO | WO 2015021353 A1 | 2/2015 |
| WO | WO 2015021426 A1 | 2/2015 |
| WO | WO 2015021990 A1 | 2/2015 |
| WO | WO 2015024017 A2 | 2/2015 |
| WO | WO 2015026883 A1 | 2/2015 |
| WO | WO 2015026885 A1 | 2/2015 |
| WO | WO 2015026886 A1 | 2/2015 |
| WO | WO 2015026887 A1 | 2/2015 |
| WO | WO 2015027134 A1 | 2/2015 |
| WO | WO-2015/035162 A2 | 3/2015 |
| WO | WO 2015030881 A1 | 3/2015 |
| WO | WO 2015031619 A1 | 3/2015 |
| WO | WO 2015031775 A1 | 3/2015 |
| WO | WO 2015033293 A1 | 3/2015 |
| WO | WO 2015034872 A2 | 3/2015 |
| WO | WO 2015035136 A2 | 3/2015 |
| WO | WO 2015035139 A2 | 3/2015 |
| WO | WO 2015035162 A2 | 3/2015 |
| WO | WO 2015040075 A1 | 3/2015 |
| WO | WO 2015040402 A1 | 3/2015 |
| WO | WO-2015/048577 A2 | 4/2015 |
| WO | WO 2015048577 A2 | 4/2015 |
| WO | WO 2015048690 A1 | 4/2015 |
| WO | WO 2015052133 A1 | 4/2015 |
| WO | WO 2015052231 A2 | 4/2015 |
| WO | WO 2015053995 A1 | 4/2015 |
| WO | WO 2015054253 A1 | 4/2015 |
| WO | WO 2015057976 A1 | 4/2015 |
| WO | WO 2015057980 A1 | 4/2015 |
| WO | WO 2015059265 A1 | 4/2015 |
| WO | WO-2015/070083 A1 | 5/2015 |
| WO | WO 2015065964 A1 | 5/2015 |
| WO | WO 2015066119 A1 | 5/2015 |
| WO | WO 2015066637 A1 | 5/2015 |
| WO | WO 2015070083 A1 | 5/2015 |
| WO | WO 2015070212 A1 | 5/2015 |
| WO | WO 2015071474 A2 | 5/2015 |
| WO | WO 2015073683 A2 | 5/2015 |
| WO | WO 2015073867 A1 | 5/2015 |
| WO | WO 2015073990 A1 | 5/2015 |
| WO | WO 2015075056 A1 | 5/2015 |
| WO | WO 2015075154 A2 | 5/2015 |
| WO | WO 2015075195 A1 | 5/2015 |
| WO | WO 2015077290 A2 | 5/2015 |
| WO | WO 2015077318 A1 | 5/2015 |
| WO | WO-2015/089351 A1 | 6/2015 |
| WO | WO-2015/089354 A1 | 6/2015 |
| WO | WO-2015/089486 A2 | 6/2015 |
| WO | WO 2015079056 A1 | 6/2015 |
| WO | WO 2015079057 A2 | 6/2015 |
| WO | WO 2015086795 A1 | 6/2015 |
| WO | WO 2015086798 A2 | 6/2015 |
| WO | WO 2015086798 A3 | 6/2015 |
| WO | WO 2015088643 A1 | 6/2015 |
| WO | WO 2015089077 A2 | 6/2015 |
| WO | WO 2015089077 A3 | 6/2015 |
| WO | WO 2015089277 A1 | 6/2015 |
| WO | WO 2015089351 A1 | 6/2015 |
| WO | WO 2015089354 A1 | 6/2015 |
| WO | WO 2015089364 A1 | 6/2015 |
| WO | WO 2015089364 A9 | 6/2015 |
| WO | WO 2015089406 A1 | 6/2015 |
| WO | WO 2015089419 A2 | 6/2015 |
| WO | WO 2015089427 A1 | 6/2015 |
| WO | WO 2015089462 A1 | 6/2015 |
| WO | WO 2015089465 A1 | 6/2015 |
| WO | WO 2015089473 A1 | 6/2015 |
| WO | WO 2015089473 A9 | 6/2015 |
| WO | WO 2015089486 A2 | 6/2015 |
| WO | WO 2015095804 A1 | 6/2015 |
| WO | WO 2015099850 A1 | 7/2015 |
| WO | WO 2015100929 A1 | 7/2015 |
| WO | WO 2015103153 A1 | 7/2015 |
| WO | WO 2015105928 A1 | 7/2015 |
| WO | WO 2015108993 A1 | 7/2015 |
| WO | WO 2015112790 A2 | 7/2015 |
| WO | WO 2015112896 A2 | 7/2015 |
| WO | WO 2015113063 A1 | 7/2015 |
| WO | WO 2015115903 A1 | 8/2015 |
| WO | WO 2015116686 A1 | 8/2015 |
| WO | WO 2015117041 A1 | 8/2015 |
| WO | WO 2015121454 A1 | 8/2015 |
| WO | WO 2015122967 A1 | 8/2015 |
| WO | WO 2015123339 A1 | 8/2015 |
| WO | WO 2015126927 A2 | 8/2015 |
| WO | WO 2015127428 A1 | 8/2015 |
| WO | WO 2015127439 A1 | 8/2015 |
| WO | WO 2015131101 A1 | 9/2015 |
| WO | WO 2015134812 A1 | 9/2015 |
| WO | WO 2015136001 A1 | 9/2015 |
| WO | WO 2015138510 A1 | 9/2015 |
| WO | WO 2015138739 A2 | 9/2015 |
| WO | WO 2015138855 A1 | 9/2015 |
| WO | WO 2015138870 A2 | 9/2015 |
| WO | WO 2015139008 A1 | 9/2015 |
| WO | WO 2015139139 A1 | 9/2015 |
| WO | WO 2015143046 A2 | 9/2015 |
| WO | WO 2015148670 A1 | 10/2015 |
| WO | WO 2015148680 A1 | 10/2015 |
| WO | WO 2015148761 A1 | 10/2015 |
| WO | WO 2015148860 A1 | 10/2015 |
| WO | WO 2015148863 A2 | 10/2015 |
| WO | WO 2015153760 A2 | 10/2015 |
| WO | WO 2015153780 A1 | 10/2015 |
| WO | WO 2015153789 A1 | 10/2015 |
| WO | WO 2015153791 A1 | 10/2015 |
| WO | WO 2015153940 A1 | 10/2015 |
| WO | WO 2015155341 A1 | 10/2015 |
| WO | WO 2015155686 A2 | 10/2015 |
| WO | WO 2015157070 A2 | 10/2015 |
| WO | WO 2015157534 A1 | 10/2015 |
| WO | WO 2015159068 A1 | 10/2015 |
| WO | WO 2015159086 A1 | 10/2015 |
| WO | WO 2015159087 A1 | 10/2015 |
| WO | WO 2015160683 A1 | 10/2015 |
| WO | WO 2015161276 A2 | 10/2015 |
| WO | WO-2016/028682 A1 | 2/2016 |
| WO | WO-2016/057821 A2 | 4/2016 |
| WO | WO-2016/081923 A2 | 5/2016 |
| WO | WO-2016/106236 A1 | 6/2016 |
| WO | WO-2016/166340 A1 | 10/2016 |
| WO | WO-2016/205711 A1 | 12/2016 |
| WO | WO-2016/205749 A1 | 12/2016 |
| WO | WO-2016/205759 A1 | 12/2016 |
| WO | WO-2017/064546 A1 | 4/2017 |
| WO | WO-2017/066588 A2 | 4/2017 |
| WO | WO-2017/099494 A1 | 6/2017 |
| WO | WO-2018/106693 A1 | 6/2018 |

OTHER PUBLICATIONS

Mondragon et al., Anti-Transcription Factor RNA Aptamers as Potential Therapeutics, Nucleic Acid Ther. 26(1):29-43 (2016).
Kundert et al., Controlling CRISPR-Cas9 with ligand-activated and ligand-deactivated sgRNAs. Nat Commun 10:2127, (2019).
Zhao et al., Development of aptamer-based inhibitors for CRISPR/Cas system, Nucleic Acids Res., pp. 1-15 (2020).
European Extended Search Report dated May 24, 2018, cited in EP18159400.3, 8 pages.

(56) References Cited

OTHER PUBLICATIONS

Cho et al., "Targeted genome engineering in human cells with the Cas9 RNA-guided endonuclease", Nature Biotechnology, 31, 3 (2013), 230.
U.S. Appl. No. 61/613,373, filed Mar. 20, 2012.
U.S. Appl. No. 61/625,420, filed Apr. 17, 2012.
U.S. Appl. No. 61/652,086, filed May 25, 2012, Jinek.
U.S. Appl. No. 61/716,256, filed Oct. 19, 2012, Jinek.
U.S. Appl. No. 61/717,324, filed Oct. 23, 2012, Cho et al.
U.S. Appl. No. 61/734,256, filed Dec. 6, 2012, Chen et al.
U.S. Appl. No. 61/735,876, filed Dec. 11, 2012, Blake Wiedenheft, et al.
U.S. Appl. No. 61/736,527, filed Dec. 12, 2012, Zhang, F. et al.
U.S. Appl. No. 61/738,355, filed Dec. 17, 2012, George M. Church.
U.S. Appl. No. 61/757,640, filed Jan. 28, 2013, Jinek.
U.S. Appl. No. 61/758,624, filed Jan. 30, 2013, Chen et al.
U.S. Appl. No. 61/761,046, filed Feb. 5, 2013, Knight et al.
U.S. Appl. No. 61/779,169, filed Mar. 13, 2013, Prashant Mali.
U.S. Appl. No. 61/794,422, filed Mar. 15, 2013, Knight et al.
U.S. Appl. No. 61/799,531, filed Mar. 15, 2013, Blake Wiedenheft, et al.
U.S. Appl. No. 61/803,599, filed Mar. 20, 2013, Kim et al.
U.S. Appl. No. 61/837,481, filed Jun. 20, 2013, Cho et al.
U.S. Appl. No. 62/010,879, filed Jun. 11, 2014, Zhang et al.
U.S. Appl. No. 60/010,888, filed Jun. 11, 2014, Zhang et al.
U.S. Appl. No. 61/915,150, filed Dec. 12, 2013, Zhang et al.
International Preliminary Report on Patentability cited in PCT/US2014/064663, dated May 10, 2016, 8 pages.
Altschul et al., "Gapped BLAST and PSI-BLAST: a new generation of protein database search programs," (1997) Nuc. Acids Res. 25:3389-3402.
Altschul et al., "Basic Local Alignment Search Tool," (1990) J. Mol. Biol. 215:403-410.
Ambati et al., "Diffusion of High Molecular Weight Compounds through Sclera," (2000) Invest. Ophthalmol. Vis. Sci. 41:1181-1185.
Ames et al, A eubacterial riboswitch class that senses the coenzyme tetrahydrofolate. Chem Biol. 2010;17(7):681-5.
Anders et al., "Structural Basis of PAM-dependent target DNA recognition by the Cas9 endonclease" Nature, Sep. 2014 25:513 (7519): 569-573 doi: 10.1038/nature13579.
Andreas S., et al., Enhanced Efficiency Through Nuclear Localization Signal Fusion on Phage C31-Integrase: Activity Comparison With Cre and FLPe Recombinase in Mammalian Cells, Nucleic Acic Research, 2002, vol. 30, No. 11, 2299-2306.
Barker et al., Increased DNA microarray hybridization specificity using sscDNA targets, BMC Genomics, Apr. 22, 2005, 2005, 6:57, 8 pages.
Bedell et at, In vivo genome editing using a high-efficiency TALEN system. Nature. Nov. 1, 2012;491(7422):114-8.
Bhagwat, DNA-cytosine deaminases: from antibody maturation to antiviral defense. DNA Repair (Arnst). Jan. 2004;3(1)85-9.
Deveau et al., "Phage response to CRISPR-encoded resistance in *Streptococcus thermophilus*," J Bacteriol., Feb. 2008, 190(4):1390-400.
Doyon et al., Enhancing zinc-finger-nuclease activity with improved obligate heterodimeric architectures. Nat Methods. Jan. 2011;8(1):74-9. Doi: 10.1038/nmeth.1539. Epub Dec. 5, 2010.
Horvath et al., CRISPR/Cas, the immune system of bacteria and archaea. Science. Jan. 8, 2010;327(5962): 167-70. doi: 10.1126/science.1179555.
Feng et al., Efficient genome editing in plants using a CRISPR/Cas system, Cell Research (2013) 33:12290-1232 doi: 10.1038/cr.2013.114; published online Aug. 20, 2013.
Kappel et al., Regulating gene expression in transgenic animals. Curr Opin Biotechnol. Oct. 1992;3(5):548-53.
Maguire et al., "Age-dependent effects of RPE65 gene therapy for Leber's congenital amaurosis: a phase 1 dose-escalation trial", The Lancet, vol. 374, No. 9701, Nov. 7, 2009, pp. 1597-1605.
Narayanan et al., Clamping down on weak terminal base pairs: oligonucleotides with molecular caps as fidelity-enhancing elements at the 5'- and 3'-terminal residues. Nucleic Acids Res. May 20, 2004;32(9):2901-11. Print 2004.
Niewoehner et al. Evolution of CRISPR RNA recognition and processing by Cas6 endonuclease: Nucleic Acids Research Advance Access published Oct. 22, 2013. Nucleic Acids Research, 2013, 1-13. doi:10.1093/nar/gkt922.
Perez-Pinera et al., RNA-guided gene activation by CRISPR-Cas9-based transcription factors. Nat Methods. Oct. 2013;10(10):973-6. doi: 10.1038/nmeth.2600. Epub Jul. 25, 2013.
Ramakrishna et al., "Surrogate reporter-based emichment of cells containing RNA-guided Cas9 nuclease-induced mutations," Nat Commun. Feb. 26, 2014; 5:3378.
Ramirez et al., Engineered zinc finger nickases induce homology-directed repair with reduced mutagenic effects. Nucleic Acids Res. Jul. 2012;40(12):5560-8. doi: 10.1093/nar/gksl79. Epub Feb. 28, 2012.
Rebar et al., "Zinc finger phage: affinity selection of fingers with new DNA-binding specificities," Science, 263:671-673 (1994).
Reynaud et al., What role for AID: mutator, or assembler of the immunoglobulin mutasome? Nat Immunol. Jul. 2003;4(7):631-8.
Roth et al., A riboswitch selective for the queuosine precursor preQ1 contains an unusually small aptamer domain. Nat Struct Mol Biol. Apr. 2007;14(4):308-17. Epub Mar. 25, 2007.
Schleifman et al., "Triplex-Mediated Gene Modification," Methods of Mol. Biol., 435:175-90 (2008).
Shan, Genome editing in rice and wheat using the CRISPR/Cas system, Nature Protocols 9, 2395-2410 (2014) doi:10.1038/nprot.2014.157.
Suess et al., A theophylline responsive riboswitch based on helix slipping controls gene expression in vivo. Nucleic Acids Res. Mar. 5, 2004;32(4):1610-4.
Thompson et al., Cellular uptake mechanisms and endosomal trafficking of supercharged proteins. Chem Biol. Jul. 27, 2012;19(7):831-43. doi: 10.1016/j.chembiol.2012.06.014.
Wadia et al, Transducible TAT-HA fusogenic peptide enhances escape of TAT-fusion proteins after lipid raft macropinocytosis. Nat Med. Mar. 2004;10(3):310-52. Epub Feb. 8, 2004.
Wang et al, Genetic screens in human cells using the CRISPR-Cas9 system. Science. Jan. 3, 2014;343(6166):80-4, doi: 10.1126/science.1246981. Epub Dec. 12, 2013.
Winkler et al, Thiamine derivatives bind messenger RNAs directly to regulate bacterial gene expression. Nature. Oct. 31, 2002;419(6910):952-6. Epub Oct. 16, 2002.
Yu, Z et al. Highly Efficient Genome Modifications Mediated by CRISPR/Cas9 in *Drosophila*. Jul. 5, 2013. Genetics. abstract; 113.153825.
Yarris L. Programmable DNA Scissors Found for Bacterial Immune System. Berkeley Lab News Center. http://newscenter.lbl.gov/feature-stories/2012/06/28/programmable-dna-scissors/[6/29/2013 6:45:51 PM] Jun. 28, 2012.
2013 Runners-Up. Genetic microsurgery for the masses, Science. 2013;342(6165): 1434-5.
Adrian et al., Targeted SAINT-O-Somes for improved intracellular delivery of siRNA and cytotoxic drugs into endothelial cells. J Control Release. 2010;144(3):341-9.
Aguilera et al., Systemic in vivo distribution of activatable cell penetrating peptides is superior to that of cell penetrating peptides. Integr Biol (Camb). 2009; 1(5-6):371-81.
Aihara et al., A conformational switch controls the DNA cleavage activity of lambda integrase. Mol Cell. 2003;12(1):187-98.
Akinc et al., A combinatorial library of lipid-like materials for delivery of RNAi therapeutics. Nat Biotechnol. 2008;26(5):561-9.
Akopian et al., Chimeric recombinases with designed DNA sequence recognition. Proc Natl Acad Sci USA. 2003;100(15):8688-91.
Al-Attar et al., Clustered Regularly Interspaced Short Palindromic Repeats (CRISPRs): The Hallmark of an Ingenious Antiviral Defense Mechanism in Prokaryotes, Biol Chem. (2011) vol. 392 Issue 4, pp. 277-289.
Alexandrov et al., Signatures of mutational processes in human cancer. Nature. 2013;500(7463):415-21.
Ali et al., Novel genetic abnormalities in Bernard-Soulier syndrome in India. Ann Hematol. 2014;93(3):381-4.

(56) References Cited

OTHER PUBLICATIONS

Allen et al, Liposomal drug delivery systems: from concept to clinical applications. Adv Drug Deliv Rev. 2013;65(1):3648.
Alnylam Pharmaceuticals. Developing an RNAi Therapeutic for Liver Disease sociated with Alpha-1-Antitrypsin Deficiency. Nov. 12, 2012.
Al-Taei et al., Intracellular traffic and fate of protein transduction domains HIV-1 TAT peptide and octaarginine. Implications for their utilization as drug delivery vectors. Bioconjug Chem. Jan.-Feb. 2006;17(1):90-100.
Alton, et al. A randomised, double-blind, placebo-controlled phase IIB clinical trial of repeated application of gene therapy in patients with cystic fibrosis.Thorax 2013;00:1-3. doi:10.1136/thoraxjnl-2013-203309. Published on Mar. 22, 2013 as 10.1136/thoraxjnl-2013-203309.
Atschul, Generalized Affine Gap Costs for Protein Sequence Alignment, Proteins: Structure, Function, and Genetics, Computer Applications in the Biosciences, 1998 32( ):88-96.
Ambati et al., "Diffusion of High Molecular Weight Compounds through Sclera," (2000) Invest. hthalmol. Vis. Sci. 41:1181-1185.
Ambati et al., Transscleral Delivery of Bioactive Protein to the Choroid and Retina (2000) Invest. Ophthalmol. Vis. Sci. 41:1186-1191.
An Chung-Il et al: "Artificial control of gene expression in mammalian cells by modulating RNA interference through aptamer-small molecule interaction". RNA. Cold Spring Harbor Laboratory Press. US vol. 12. No. 5. 2006 * pp. 710-716.
Anders et al., "Structural Basis of PAM-dependent target DNA recognition by the Cas9 endoncleas" Nature, 2014, doi: 10.1038/nature13579.
Andreas S., et al., Enhanced Efficiency Through Nuclear Localization Signal Fusion on Phage C31-Integrase: Activity Comparison With Cre and FLPe Recombinase in Mammalian Cells, Nucleic Acids Research.
Ansari et al, Rioactivators: Transcription activation by non-coding RNA, Grit Rev Biochem Mol Biol. 2009; 44(1): 50-61.
Antonarakis S E and Beckmann J S . Mendelian disorders deserve more attention. Nature Reviews. Genetics. vol. 7. 2006. pp. 277-282. www.nature.com/reviews/genetics.
Arimondo et al., "Exploring the Cellular Activity ofCamptothecin-Triple-Helix-Forming Oligonucleotide Coniugates," Mol. Cell. Biol., 26(1 ):324-33 (2006).
Arnould et al., "Engineering of Large Numbers of Highly Specific Homing Endonucleases that Induce Recombination on Novel DNA Targets," J. Mol. Biol., 355:443-58 (2006).
Arnould et al., "The I-CreI meganuclease and its engineered derivatives: applications from cell modification to gene therapy," PEDS, 24:27-31 (2011).
Arnold et al., Mutants of Tn3 resolvase which do not require accessory binding sites for ombination activity. EMBO J. Mar. 1, 1999;18(5):1407-14.
Aslanidis et al., "Ligation-independent cloning of PCR products (LIC-PCR)," Nucleic Acids Res., Oct. 25, 1990;18(20):6069-74.
Asuri, et al., Directed Evolution of Adeno-Associated Virus for Enhanced Gene Delivery and Gene Targeting in Human Pluripotent Stem Cells, Molecular Therapy (2012) vol. 20, No. 2, p. 329-338.
Auer et al., Highly efficient CRISPR/Case9-mediated known-in in zebrafish by homology-independent DNA repair, Genome Res., 2014,24:142-153.
Baala et al., "Pleiotropic Effects of CEP900 (NPHP6) Mutations Extend to Meckel Syndrome," Am J Hum Genet. 81, 170-179, 2007.
Bacman, Specific elimination of mutant mitochondrial genomes in patient-derived cells by mitoTALENsNature Medicine 19,1111-1113 (2013) doi:10.1038/nm.3261.
Bae et al., "Human zinc fingers as building blocks in the construction of artificial transcription factors," Nat. Biotechnol., 21:275-280 (2003).
Bae S. et al: "Cas-OFFinder: a fast and versatile algorithm that searches for potential off-target sites Cas9 RNA-guided endonucleases", BioInformatics, vol. 30, No. 10, Jan. 24, 204, pp. 1473-1475.

Bainbridge et al., "Effect of Gene Therapy on Visual Function in Leber's Congentia) Amaurosis," N Engl J Med. 358, 2231-2239, 2008.
Baker, "Gene Editing at CRISPR Speed," Nature Biotechnology 32( 4 ):309-312 (Apr. 4, 2014).
Banaszewska, et al., Proprotein Convertase Subtilisin/Kexin Type 9: A New Target Molecule for Gene Therapy, Cellular & Molecular Biology Letters (2012) vol. 17, p. 228-2390.
Baron-Benhamou et al., "Using the A-N Peptide to Tether Proteins to RNAs," Methods Mole Biol., Jan. 2004, 257:135-153.
Barrangou et al., CRISPR provides acquired resistance against viruses in prokaryotes. Science. Mar. 23, 2007;315(5819):1709-12.
Barrangou, RNA-Mediated Programmable DNA Cleavage, Nature Biotechnology (2012) vol. 30, No. 9, p. 836-838.
Basha et al., Influence of cationic lipid composition on gene silencing properties of lipid nanoparticle formulations of siRNA in antigen-presenting cells. Mol Ther. 2011;19(12):2186-200. doi: 10.1038/mt.2011.190. Epub Oct. 4, 2011.
Bassett et al., "Highly efficient targeted mutagenesis of Drosophila with the CRISPR/Cas9 system," Cell Reports, 2013, 4:220-228.
Bassett, A.R. and Liu, J.-L., "CRISPR/Cas9 and Genome Editing in Drosophila," Journal of Genetics and Genomics, 2014, vol. 41, pp. 7-19 (including supplementary materials).
Batey et al., Structure of a natural guanine-responsive riboswitch complexed with the metabolite hypoxanthine. Nature. Nov. 18, 2004;432(7015):411-5.
Beerli et al., "Engineering polydactyl zinc-finger transcription factors," Nat. Biotechnol., 20:135-14(2002).
Beerli et al., "Toward controlling gene expression at will: specific regulation of the erbB-2/HER-2 promoter by using polydactyl zinc finger proteins constructed from modular building blocks," PNAS USA, 1998,95:14628-14633.
Belhaj et al., "Plant genome editing made easy: targeted mutagenesis in model and crop plants using the CRISPR/Cas system," Plant Methods, 2013, 9:39, 10 pages.
Bennett, J., 2003, "Immune response following intraocular delivery of recombinant viral vectors" Gene Therapy, vol. 10, p. 977-982.
Berg, "Proposed structure for the zinc-binding domains from transcription factor II1A and related proteins," Proc. Natl. Acad. Sci. USA, 85:99-102 (1988).
Bergemann, J. et al., Excision of specific DNA-sequences from integrated retroviral vectors via site-specific recombination, Nucleic Acids Res. 1995, 23:4451-4456 (Nov. 11, 1995).
Beumer et at, Efficient gene targeting in Drosophila with zinc-finger nucleases. Genetics. Apr. 2006;172(4):2391-403.
Bhagwat, DNA-cytosine deaminases: from antibody maturation to antiviral defense. DNA Repair (Arnst). Jan. 5, 2004;3(1):85-9.
Bibikova et al, Targeted chromosomal cleavage and mutagenesis in Drosophila using zinc-finger nucleases. Genetics. 2002;161(3):1169-75.
Bibikova et al., "Enhancing gene targeting with designed zinc finger nucleases," Science, 2003; 300(5620):764.
Bibikova et al., Stimulation of homologous recombination through targeted cleavage by chimeric nucleases. Mol Cell Biol. Jan. 2001;21(1):289-97.
Bikard D. and Marraffini L. A. *Control of gene expression by CRISPR-Cas systems*. F1000Prime Reports 2013, 5:47 (doi:10. 12703/P5-47) (http://f1000.eom/prime/reports/b/5/47).
Bikard et al., "Programmable repression and activation of bacterial gene expression using an engineered CRISPR-Cas system," Nucleic Acid Res., Jun. 2013 41(15):7429-7437.
Bikard, et al., CRISPR Interference Can Prevent natural Transformation and Virulence Acquisition During In Vivo Bacterial Infection, Cell Host&. Microbe (2012) vol. 12, p. 177-186.
Bitinaite et al., "FoKI dimerization is required for DNA cleavage," Proc. Natl. Acad. Sci. USA, 1998, 95:10570-10575.
Blackburn et al., "The CRISPR System-Keeping Zebrafish Gene Targeting Fresh," Zebrafish, 2013, 10(1):116-118.
Bloom et al. Inactivation of hepatitis B virus replication in cultured cells and in vivo with engineered Transcription Activator-Like Effector Nucleases, Molecular Therapy accepted article preview online Jul. 25, 2013; doi:10.1038/mt.2013.170.

(56) References Cited

OTHER PUBLICATIONS

Boch et al., "Breaking the code of DNA binding specificity of TAL-type III lectors," Science, Dec. 11, 2009 ;326(5959): 1509-12.
Boch, et al., Xanthomonas AvrBs3 Family-Type III Effectors: Discovery and Function, Annu. Rev. Phytopathol. (2010) vol. 48, p. 419-436.
Boch, TALEs of genome targeting. Nat Biotechnol. Feb. 2011;29(2):135-6.
Bogdanove et al. (2010) Curr. Opin. Plant Biol. 13:394-401. TAL effectors: finding plant genes for disease and defense.
Briggs et al., "Iterative capped assembly: rapid and scalable synthesis of repeat-module DNA such a TAL effectors from individual monomers," Nucleic Acids Res., Aug. 2012;40(15):e117.
Briner, Alexandra E. et al., Guide RNA Functional Modules Direct Cas9 Activity and Orthogonality, Molecular Cell (Oct. 23, 2014) vol. 56, p. 333-339.
Brown et al., Serine recombinases as tools for genome engineering. Methods. Apr. 2011;53(4):372-9. doi: 10.1016/j.ymeth.2010.12.031. Epub Dec. 30, 2010.
Brunetti-Pierri N and Lee B—Gene therapy for inborn errors of liver metabolism. Molecular Genetics and Metabolism 86 (2005) 13-24. www.elsevier.com/locate/ymgme. Available online Sep. 9, 2005.
Bulyk et al., Exploring the DNA-binding specificities of zinc fingers with DNA microarrays. Proc Natl Acad Sci U S A. Jun. 19, 2001;98(13):7158-63. Epub Jun. 12, 2001.
Burgess, "A CRISPR genome-editing tool," Nature Reviews Genetics 14, 80-81 (Feb. 2013).
Burke et al., Activating mutations of Tn3 resolvase marking interfaces important in recombination catalysis and its regulation. Mol Microbial. Feb. 2004;51(4):937-48.
Buskirk et al, Directed evolution of ligand dependence: small-molecule-activated protein splicing. Proc Natl Acad Sci USA. Jul. 20, 2004;101(29):10505-10. Epub Jul. 9, 2004.
Cade et al., Highly efficient generation of heritable zebrafish gene mutations using homo- and heterodimeric TALENs. Nucleic Acids Res. Sep. 2012;40(16):8001-10.
Cain A. K. and Boinett C. J. A CRISPRr view of genome sequences. www.nature.com/reviews/micro. 226. Apr. 2013. vol. 11.
Cain C. *CRISPR model building*. SciBX: Science-Business exchange. Cain, C. SciBX 6(19); doi:10.1038/scibx.2013.455.
Caldecott, "Single-strand break repair and genetic disease" Nature Reviews Genetics 9, 619-631 (Aug. 2008).
Cameron, Recent advances in transgenic technology. Mol Biotechnol. Jun. 1997;7(3):253-65.
Cargill et al., Characterization of single-nucleotide polymorphisms in coding regions of human genes. Nat Genet. Jul. 1999;22(3):231-8.
Caron et al., Intracellular delivery of a Tat-eGFP fusion protein into muscle cells. Mol Ther. Mar. 2001;3(3):310-8.
Carroll et al., Gene targeting in *Drosophila* and Caenorhabditis elegans with zinc-finger nucleases. Methods Mol Biol. 2008;435:63-77.
Carroll et al., Progress and prospects: zinc-finger nucleases as gene therapy agents. Gene Ther. Nov. 2008;15(22):1463-8. doi: 10.1038/gt.2008.145.
Carroll et al., "Design, construction and in vitro testing of zinc finger nucleases," Nat. Protoc., 1:1329-41 (2006).
Carroll, "Staying on target with CRISPR-Case," Nat Biotechnol., 2013, 31(9):807-809.
Carroll, A CRISPR Approach to Gene Targeting, Molecular Therapy (2012) vol. 20, No. 9, p. 1658-1660 0.
Cathomen and Joung, "Zinc-finger nucleases: the next generation emerges," Mol. Ther., 2008, 16:1200-1207.
Centlivre et al. *Preclinical In Vivo Evaluation of the Safety of a MultishRNA-based Gene erapy Against HIV-1*. Molecular Therapy—Nucleic Acids (2013) 2, e120; doi:10.1038/mtna.2013.48. www.nature.com/mtna.
Cermak et al., Efficient design and assembly of custom TALEN and other TAL effector-based structs for DNA targeting. Nucleic Acids Res. Jul. 2011;39(12):e82. Doi: 10.1093/nar/gkr218.
Chaikind et al., "Targeted DNA Methylation Using an Artificially Bisected M.HhaI Fused to Zinc Fingers," PLoS ONE, 7(9):E44852 pp. 1-11 (2012).
Chang et al., "Genome editing with RNA-guided Cas9 nuclease in zebrafish embryos," Cell Res., 2013,23:465-472.
Chang et al., Modification of DNA ends can decrease end joining relative to homologous recombination in mammalian cells. Proc Natl Acad Sci USA. Jul. 1987;84(14):4959-63.
Charpentier E. et al: "Rewriting a genome". Biotechnology. Mar. 7, 2013 (Mar. 7, 2013). pp. 50-51. XP055178492.
Chavez et al., Therapeutic applications of the ΦDC31 integrase system. Curr Gene Ther. Oct. 2011;11(5):375-81. Review.
Chelico et al., Biochemical basis of immunological and retroviral responses to DNA-targeted cytosine deamination by activation-induced cytidine deaminase and APOBEC3G. J Biol Chem. Oct. 9, 2000;284(41):27761-5.
Chen et al, Fusion protein linkers: property, design and functionality. Adv Drug Deliv Rev. Oct. 2013;65(10):1357-69.
Chen et al., "Cut Site Selection by the Two Nuclease Domains of the Cas9 RNA-guided Endonuclease," J Biol Chem. May 9, 2014; 289(19):13284-94.
Chen et al., "Dynamic imaging of genomic loci in living human cells by an optimized CRISPR/Cas system," Cell, 2013,155(7):1479-1491.
Chen et al., "Efficient genome editing in Caenorhabditis elegans by CRISPR-targeted homologous recombination," Nucleic Acids Res., 2013, 41(20):e193, 6 pages.
Chen et al., "Induced DNA demethylation by targeting Ten-Eleven Translocation 2 to the human ICAM-1 promoter," Nucleic Acids Research, doi:10.1093/nar/gkt1019 (Nov. 4, 2013).
Chen F. et al. High-frequency genome editing using ssDNA oligonucleotides with zinc-finger nucleases. Nature Methods, Advance Online Publication. Published Online Jul. 17, 2011; DOI:10.1038/NMETH.1653.
Chesnoy et al, Structure and function of lipid-DNA complexes for gene delivery. Annu Rev Biophys Biomol Struct. 2000;29:27-47.
Chipev et al., A leucine—proline mutation in the HI subdomain of keratin 1 causes epidermolytic hyperkeratosis. Cell. Sep. 4, 1992;70(5):821-8.
Chiu et al., "Transgene-free genome editing in Caenorhabditis elegans using CRISPR-Cas," Genetic, Nov. 2013, 195(3):1167-71.
Cho et al., "Analysis of off-target effects of CRISPR/Case-derived RNA-guided endonucleases and nickases," Genome Res., 2014,24:132-141.
Cho et al., "Targeted genome engineering in human cells with the Cas9 RNA-guided endonuclease," Nat Biotechnol., 2013, 31:230-232.
Choo and Klug, "Toward a code for the interactions of zinc fingers with DNA: selection of radomized fingers displayed on phage," Proc. Natl. Acad. Sci. USA, 91:11163-11167 (1994).
Choulika, A. et al., Transfer of single gene-containing long terminal repeats into the genome of mammalian cells by a retroviral vector carrying the ere gene and the loxP site, J. Virol. 1996,70:1792-1798 (Mar. 1996).
Christian et al, Targeting G with TAL effectors: a comparison of activities of TALENs constructed with NN and NK repeat variable di-residues. PLoS One. 2012;7(9):e45383. doi: 10.1371/journal.pone.0045383.
Christian et al., Targeting DNA double-strand breaks with TAL effector nucleases. Genetics. Oct. 2010;186(2):757-61. Doi: 10.1534/genetics.110.120717.
Chylinski et al, The tracrRNA and Cas9 families of type II CRISPR-Cas immunity systems. RNA Biol. May 2013; 10(5);726-37. doi: 10.4161/ma.24321.
Chylinski et al., "Classification and evolution of type II CRISPR-Cas systems," Nucleic Acids Res. 2014;42(10):6091-105.
Cideciyan et al., Proc Natl Acad Sci USA. 105,15112-15117, 2008.
Cobb et al., Directed evolution: an evolving and enabling synthetic biology tool. Curr Opin Chern Biol. Aug. 2012;16(3-4):285-91. doi:10.1016/j.cbpa.2012.05.186.

(56) References Cited

OTHER PUBLICATIONS

Cobb, et al., Directed Evolution as a Powerful Synthetic Biology Tool, Methods. Mar. 15, 2013; 60(1): 81-90. doi:10.1016/j.ymeth.2012.03.009.

Cole-Strauss et al., Correction of the mutation responsible for sickle cell anemia by an RNA-DNA oligonucleotide. Science. Sep. 6, 1996;273(5280): 1386-9.

Colletier et al., Protein encapsulation in liposomes: efficiency depends on interactions between protein and phospholipid bilayer. BMC Biotechnol. May 10, 2002;2:9.

Cong et al, Multiplex genome engineering using CRISPR/Cas systems. Science. Feb. 15, 2013;339(6121):819-23. doi: 10.1126/science.1231143. Epub Jan. 3, 2013.

Cong et al., Comprehensive interrogation of natural TALE DNA-binding modules and transcriptional repressor domains. Nat Commun. Jul. 24, 2012;3:968. doi: 10.1038/ncomms1962.

Conklin, "Sculpting genomes with a hammer and chisel," Nature Methods, 2013, 10(9):839-840.

Connor, "Scientific split—the human genome breakthrough dividing former colleagues," The Independent, Friday Apr. 25, 2014, available at http://www.independent.co.uk/news/science/scientific-split-the-human-genome-breathrough-dividing-former-colleagues-9300456.html.

Conticello The AID/APOBEC family of nucleic acid mutators. Genome Biol. 2008;9(6):229. doi: 10.1186/gb-2008-9-6-229 Epub Jun. 17, 2008.

Coppieters et al., Hum Mutat 31, E1709-E1766, 2010.

Cornu et al., DNA-binding specificity is a major determinant of the activity and toxicity of zincfinger nucleases. Mol Ther. Feb. 2008;16(2):352-8. Epub Nov. 20, 2007.

Cradick et al, Zinc-finger nucleases as a novel therapeutic strategy for targeting hepatitis B virus DNAs. Mol Ther. May 2010;18(5):947-54. Doi: 10.1038/mt.2010.20. Epub Feb. 16, 2010.

Cradick et al., CRISPR/Cas9 systems targeting β-globin and CCR5 genes have substantial off-target activity. Nucleic Acids Res. Nov. 1, 2013;41(20):9584-92. doi: 10.1093/nar/gkt714. Epub Aug. 11, 2013.

CRISPR in the Lab: A Practical Guide [online]. Addgene. Sep. 4, 2014. Retrieved on Dec. 4, 2014. Retrieved from the Internet: <URL: https://www.addgene.org/CRISPR/guide/>.

Cristea et al. In vivo Cleavage of Transgene Donors Promotes Nuclease-Mediated Targeted Integration. Mar. 2013. Biotechnol. Bioeng. 2013;110: 871-880. Article first published online Oct. 23, 2012 in Wiley Online Library (http://onlinelibrary.wiley.com/doi/10.1002/bit.24733/abstract) DOI 10.1002/bit.24733.

Cronican et al., A Class of Human Proteins That Deliver Functional Proteins Into Mammalian cells In Vitro and In Vivo, Biol. Jul. 2p, 2011; 18(7):833-8. doi: 10.1016/j.chembiol.2011.07.003.

Cronican et al., Potent delivery of functional proteins into mammalian cells in vitro and in vivo using a supercharged protein. ACS Chem Biol. Aug. 20, 2010;5(8):747-52. doi: 10.1021/cb1001153.

Cui et al., Targeted integration in rat and mouse embryos with zinc-finger nucleases. Nat Biotechnol. Jan. 2011,29(1):64-7. Doi: 10.1038/nbt.1731. Epub Dec. 12, 2010.

Dadachova E, et al. (2012) *Pre-Clinical Evaluation of a 213Bi-Labeled 2556 Antibody to HIV-1 gp41 Glycoprotein in HIV-1 Mouse Models as a Reagent for HIV Eradication*. PLoS ONE 7(3):e31866. doi:10.1371/journal.pone.0031866.

Dahlem el at, Simple methods for generating and detecting locus-specific mutations induced with TALENs in the zebrafish genome. PLoS Genet. 2012;8(8):e1002861. doi: 10.1371/journal.pgen.1002861.

Dalkara et al. In Vivo-Directed Evolution of a New Adeno-Associated Virus for Therapeutic Outer Retinal Gene Delivery from the Vitreous. Sci Transl Med 5,189ra76 (2013);DOI: 10.1126/scitranslmed.3005708.

Damian Mand Porteus M H . A Crisper Look at Genome Editing:RNA-guided Genome Modification. www.moleculartherapy.org vol. 21 No. 4 Apr. 2013. doi:10.1038/mt.2013.46.

Datsenko, Kirill A. et al., Molecular Memory of Prior Infections Activates the CRISPR/Cas Adaptive Bacterial Immunity System, Nature Communications, Jul. 10, 2012, DOI:10.1038/ncomms1937.

Davis, "Transcriptional regulation by MAP kinases," Mol Reprod Dev., Dec. 1995:42(4):459-67.

De Souza N. Missing the target? Nature Methods. vol. 10 No. 8. 2013 . p. 701.

De Souza N: "Primer: genome editing with engineered nucleases". Nature Methods. Jan. 1, 2012 (Jan. 1, 2012). pp. 27-27.

De Souza, "RNA-guided gene editing," Nat Methods, Mar. 2013, 10(3): 189.

Deltcheva E. et al., "CRISPR RNA maturation by trans-encoded small RNA and host factor Rnase III," Nature, 2011, vol. 471 (7340), pp. 602-607.

Den Hollander et al., "Mutations in the CEP290 (NPHP6) Gene are a Frequent Cause of Leber Congenital Amaurosis," Am J Hum Genet. 79(3): 556-561, 2006.

Den Hollander et al., "Lighting a candle in the dark: advances in genetics and gene therapy of recessive retinal dystrophies," J Clin Invest 120: 3042-3053, 2010.

Den Hollander et al., "Leber congenital amaurosis: Genes, proteins and disease mechanisms", Research Prog Retin Eye Res. 27(4): 391-419, 2008.

Dicarlo et al., Genome engineering in *Saccharomyces cerevisiae* using CRISPR-Cas systems. Nucleic Acids Res. Apr. 2013;41(7):4336-43. doi: 10.1093/nar/gkt135. Epub Mar. 4, 2013.

Dickinson et al., "Engineering the Caenorhabditis elegans genome using Cas9-triggered homologou recombination," Nat Methods., Oct. 2013, 10(10): 1028-34.

Didigu et al, *Simultaneous zinc-finger nuclease editing of the HIV coreceptors ccr5 and cxcr4 protects CD4+ T cells from HIV-1 infection*, From bloodjournal.hematologylibrary.org at Harvard Libraries on Jan. 7, 2014. BLOOD 2014 123: 61-69.

Dimond P. F. *CRISPR/Cas Comes of Age—Almost*. Insight & Intelligence™ : 2013 (vol. 33, No. 15) 2012 Genetic Engineering & Biotechnology News. http://www.genengnews.com/keywordsandtools/print/1/32246/.

Ding et al, A TALEN genome-editing system for generating human stem cell-based disease models. Cell Stem Cell. Feb. 7, 2013;12(2):238-51. Doi: 10.1016/j.stem.2012.11.011.

Ding et al., "Enhanced efficiency of human pluripotent stem cell genome editing through replacing TALENs with CRISPRs," Cell Stem Cell., Apr. 4, 2013,12(4):393-4 (Author Manuscript).

Dingwall, et al., Abstract: A Polypeptide Domain That Specifies Migration of Nucleoplasmin Into the Nucleus, Cell (1982) vol. 2, p. 449-58.

Dixon et al., Reengineering orthogonally selective riboswitches. Proc Natl Acad Sci USA. Feb. 16, 2010;107(7):2830-5. doi: 10.1073/pnas.0911209107.

Douglas, Janet. Choosing a Viral Vector System. Slide 1—IBC_Presentation-Choosing-a-Viral-Vector-System.pdf. http://www.ohsu.edu/xd/about/services/integrity/upload/IBC_Pr . . . .

Doyon et al, Heritable targeted gene disruption in zebrafish using designed zinc-finger nucleases. Nat Biotechnol. Jun. 2008;26(6):702-8. Doi: 10.1038/nbtl409. Epub May 25, 2008.

Dyon et al., Enhancing zinc-finger-nuclease activity with improved obligate heterodimeric architectures. Nat Methods. Jan. 2011;8(1):74-9. Doi: 10.1038/nmeth.l539. Epub Dec. 5, 2010.

Dupuis et al. CRISPR-Cas and restriction-modification systems are compatible and increase phage resistance. Nature Communications. 4:2087 . DOI: 10.1038/ncomms3087 .www.nature.com/naturecommunications.

Ebina & Koyanagi, Harnessing the CRISPRjCas9 system to disrupt latent HIV-1 provirus. Sientific Reports. 3 : 2510. DOI: 10.1 038/srep0251 0.

Edwards et al., Crystal structures of the thi-box riboswitch bound to thiamine pyrophosphate analogs reveal adaptive RNA-small molecule recognition. Structure. Sep. 2006;14(9):1459-68.

Edwards et al., Structural basis for recognition of S-adenosylhomocysteine by riboswitches. RNA. Nov. 2010,16(11):2144-55. doi: 10.1261/rna.2341610.

(56) References Cited

OTHER PUBLICATIONS

Eisenschmidt et al., "Developing a programmed restriction endonuclease for highly specific DNA cleavage," Nucleic Acids Res., 33(22):7039-47 (2005).
Ellington et al., In vitro selection of RNA molecules that bind specific ligands. Nature. Aug. 30, 1990;346(6287):818-22.
Ellis, et al., Zinc-Finger Nuclease-Mediated Gene Correction using Single AA V Vector Transduction and Enhanced by Food and Drug Administration-Approved Drugs, Gene Therapy (20 13) vol. 20, p. 35-42.
Ellis, Macromolecular Crowding: Obvious But Underappreciated, TRENDS in Biochemical Sciences (2001) vol. 26, No. 10, p. 597-604.
Elrod-Erickson et al., "High-resolution structures of variant Zif268-DNA complexes: implications for understanding zinc finger-DNA recognition," Structure, 6:451 (1998).
Engler et al. (2008) PLoS One 3, e3647. "A one pot, one step, precision cloning method with high throughput capability."
Engler et al. (2009) PLoS One 4, e5553. "Golden gate shuffling: a one-pot DNA shuffling method based on type lis restriction enzymes."
Enyeart, P.J., et al., Biotechnological applications of mobile group II introns and their reverse transcriptases: gene targeting, RNA-seq, and non-coding RNA analysis, Mobile DNA 2014, 5:2 (Jan. 13, 2014).
Estrada-Cuzcano et al., "IQCB1 Mutations in Patients with Leber Congential Amaurosis," Invest Ophthalmol. Vis Sci. 52(2): 834-9, 2011.
Esvelt et al, Genome-scale engineering for systems and synthetic biology. Mol Syst Biol. 2013;9:641. doi: 10.1038/msb.2012.66.
Esvelt et al., A system for the continuous directed evolution of biomolecules. Nature. Apr. 28, 2011;472(7344):499-503. doi: 10.1038/nature09929.
Esvelt et al., Orthogonal Cas9 proteins for RNA-guided gene regulation and editing. Nat Methods. Nov. 2013,10(11):1116-21. doi: 10.1038/nmeth.2681.
Farzadfard F. et al. Tunable and Multi-Functional Eukaryotic Transcription Factors Based on CRISPR/Cas. ACS Synth. Biol., Just Accepted Manuscript • DOI: 10.1021/sb40008lr • Publication Date (Web): Aug. 26, 2013. Downloaded from http://pubs.acs.org on Sep. 3, 2013.
Fink, TL et al. Plasmid size up to 20 kbp does not limit effective in vivo lung gene transfer using compacted DNA nanoparticles. Gene Therapy (2006) 13, 1048-1051. www.nature.com/gt.
Fonfara et al., "Phylogeny ofCas9 determines functional exchangeability of dual-RNA and Cas9 among orthologous type II CRISPR-Cas systems." Nucleic Acids Res., Feb. 2014, 42(4):2577-90.
Friedland et al., "Heritable genome editing in C. elegans via a CRISPR-Cas9 system," Nature Methods 10(8): 741-743,2013 (Author Manuscript).
Friedrich M. J. Seeing is Believing: Gene Therapy Shows Promise for Ocular Disorders. JAMA Oct. 13, 2010—vol. 304, No. 14 (Reprinted):1543-1545 (doi:10.1001/jama.2010.1412) http://jama.ama-assn.org/cgi/content/full/304/14/1543.
Fut et l, High-frequency off-target mutagenesis induced by CRISPR-Cas nucleases in human cells. Nat Biotechnol. Sep. 2013;31(9):822-6. doi: 10.1038/nbt.2623.
Fu et al., Improving CRISPR-Cas nuclease specificity using truncated guide RNAs. Nat Biotechnol. Mar. 2014,32(3):279-84. doi: 10.1038/nbt.2808.
Fuchs et al., Polyarginine as a multifunctional fusion tag. Protein Sci. Jun. 2005;I4(6): 1538-44.
Fujita, Efficient isolation of specific genomic regions and identification of associated proteins by engineered DNA-binding molecule-mediated chromatin immunoprecipitation (enChIP) using CRISPR, Sep. 13, 2013;439(1):132-6. doi: 10.1016/j.bbrc.2013.08.013.
Fujisawa et al, Disease-associated mutations in CIAS1 induce cathepsin B-dependent rapid cell death of human THP-1 monocytic cells. Blood. Apr. 1, 2007;109(7):2903-11.
Gabriel et al., "An unbiased genome-wide analysis of zinc-finger nuclease specificity," Nat Biotechnol., 2011, 29:816-823.

Gaj et al., Structure-guided reprogramming of serine recombinase DNA sequence specificity. Proc Natl Acad Sci US A Jan. 11, 2011;108(2):498-503. doi: 10.1073/pnas.1014214108.
Gaj et al. ZFN, TALEN, and CRISPR/Cas-based methods for genome engineering. Trends Biotechnol. May 9, 2013. vol 31, No. 7, pp. 397-405. Especially abstract, p. 399 col. 1 para 2, p. 8 col. 1 para 2, p. 399 fig 1c,d; p. 401 table 1, p. 405 box 2.
Gallo et al, A novel pathogenic PSEN1 mutation in a family with Alzheimer's disease: phenotypical and neuropathological features. J Alzheimers Dis. 2011;25(3):425-31. doi: 10.3233/JAD-2011-110185.
Gao et al., Crystal structure of a TALE protein reveals an extended N-terminal DNA binding region. Cell Res. Dec. 2012;22(12): 1716-20. doi: 10.1038/cr.2012.156.
Garneau, et al., The CRISPR-Cas Bacterial Immune Systems Cleaves Bacteriophage and Plasmid DNA, Nature (2010) 468:67-71.
Gascón et al. "Non-Viral Delivery Systems in Gene Therapy" Non-Viral Delivery Systems in Gene Therapy. http://cdn.intechopen.com/pdfs/43162/InTech-Non_viral_delive...http://dx.doi.org/10.5772/52704 - 3/7/13.
Gasiunas el al., RNA-dependent DNA endonuclease Cas9 of the CRISPR system: Holy Grail of genome editing? Trends Microbiol. Nov. 2013;21(11):562-7. doi: 10.1016/j.tim.2013.09.001.
Gasiunas et al., Cas9-crRNA ribonucleoprotein complex mediates specific DNA cleavage for adaptive immunity in bacteria. Proc Natl Acad Sci USA. Sep. 25, 2012;109(39):E2579-86.
Geißler et al., "Transcriptional Activators of Human Genes with Programmable DNA-Specificity," PLoS ONE, 6:e19509 (2011).
Gerber et al, RNA editing by base deamination: more enzymes, more targets, new mysteries. Trends Biochem Sci. Jun. 2001;26(6):376-84.
Gilbert et al: "CRISPR-Mediated Modular RNA-Guided Regulation of Transcription in Eukaryotes" CELL. vol. 154. No. 2. Jul. 1, 2013 (Jul. 1, 2013). pp. 442-451. XP055115843. ISSN: 0092-8674. DOI: 10.1016/ j. cell. 2013.06.044 abstract.
Gilleron et al, Image-based analysis of lipid nanoparticle-mediated siRNA delivery, intracellular trafficking and endosomal escape. Nat Biotechnol. Jul. 2013;31(7):638-46. doi: 10.1038/nbt.2612.
Goldfarb, et al., Synthetic Peptides as Nuclear Localization Signals, Nature (1986) vol. 322, p. 641-644.
Gordley et al, Evolution of programmable zinc finger-recombinases with activity in human cells. J Mol Biol. Mar. 30, 2007;367(3):802-13.
Grau & Posch. TALENOffer:genome-wide TALEN off-target prediction. Vol. 29 No. 22 2013, pp. 2931-2932. Doi:10.1093/BioInformatics/btt501.
Gratz et al., "CRISPR/Cas9-mediated genome engineering and the promise of designer flies on demand," Fly (Austin), Oct.-Dec. 2013, 7(4):249-55.
Gratz et al., "Genome engineering of *Drosophila* with the CRISPR RNA-guided Cas9 nuclease," Genetics, 2013, 194(4):1029-35.
Grens, "Enzyme Improves Crispr A smaller Cas9 protein enables in vivo genome engineering via viral vectors," The Scientist, Apr. 1, 2015, available at: http://www.thescientist.com/?articlcs.view/articleNo/42580/title/Enzyrne-Inproves-CRISPR/.
Griesenbach et al. Gene therapy for cystic fibrosis:an example for lung gene therapy. Gene Therapy (2004) 11, S43-S50.
Grizot et al., "Generation of redesigned homing endonucleases comprising DNA-binding domains derived from two different scaffolds," Nucl Acids Res., 38:2006-18 (2010).
Grundy et al., The L box regulon: lysine sensing by leader RNAs of bacterial lysine biosynthesis genes. Proc Natl Acad Sci USA. Oct. 14, 2003;100(21): 12057-62.
Gu et al., "R gene expression induced by a type-III effector triggers disease resistance in rice," Nature, Jun. 23, 2005;435(7045): 1122-5.
Guilinger et al., "Fusion of catalytically inactive Cas9 to FokI nuclease improves the specificity of genome modification," Nat Biotechnol., Apr. 2014, 32(6):577-583.
Guilinger et al., Broad specificity profiling of TALENs results in engineered nucleases with proved DNA-cleavage specificity. Nat Methods. Apr. 2014;11(4):429-35. doi: 1038/nmeth.2845.

(56) References Cited

OTHER PUBLICATIONS

Guo et al, Directed evolution of an enhanced and highly efficient Fold cleavage domain for zinc finger nucleases. J Mol Biol. Jul. 2, 2010;400(I):96-107. doi: 10.1016/jjmb.2010.04.060.
Guo et aL, Protein tolerance to random amino acid change. J Gene Med. Mar.-Apr. 2002;4(2):195-204.
Guo et al., Structure of Cre recombinase complexed with DNA in a site-specific recombination synapse. Nature. Sep. 4, 1997;389(6646):40-6.
Guo et el., "Hydroxylation of 5-Methyl cytosine by TETl Promotes Active DNA Demethylation in the Adult Brain," Cell, 145:423-434 (2011).
Gupta et al., Zinc finger protein-dependent and -independent contributions to the in vivo offtarget activity of zinc finger nucleases. Nucleic Acids Res. Jan. 2011;39(1 ):381-92.
Gustafsson, et al., Codon Bias and Heterologous Protein Expression, TRENDS in Biotechnology (2004) vol. 22, No. 7, p. 346-353.
Hadjiargyrou M and Delihas N. The Intertwining of Transposable Elements and Non-Coding RNAs. Int. J. Mol. Sci. 2013, 14, 13307-13328; doi:10.3390/ijms140713307. www.mdpi.com/journal/ijms.
Hafez M and Hausner G. *Homing endonucleases: DNA scissors on a mission.* Genome 55: 536-569 (2012) doi:10.1139/G2012-049. Published at www.nrcresearchpress.com/gen on Aug. 14, 2012.
Haft et al., PLoS Computational Biology 2005,1(6): e60.
Hale et al., Essential Features and Rational Design of CR1SPR RNAs That Function With the Cas RAMP Module Complex to Cleave RNAs, Molecular Cell, (2012) val. 45, Issue 3, 292-302.
Hale et al., RNA-guided RNA cleavage by a CRISPR RNA-Cas protein complex. Cell. Nov. 25, 2009;139(5):945-56. doi: 10.1016/j.cell.2009.07.040.
Hampel et al., Evidence for preorganization of the glmS ribozyme ligand binding pocket. Biochemistry. 2006; 45(25):7861-71.
Handel et al., Expanding or restricting the target site repertoire of zinc-finger nucleases: the inter-domain linker as a major determinant of target site selectivity. Mol Ther. Jan. 2009;17(1):104-11.
Handel, et al, Versatile and Efficient Genome Editing in Human Cells by Combining Zinc-Finger Nucleases With Adena-Associated Viral-Vectors, Human Gene Therapy (2012) vol. 23, p. 321-329.
Harikrishna et aI., "Constructions and Function of Fusion Enzymes of the Human Cytochrome P450scc System," DNA and Cell Biology, 12(5):371-379 (1993).
Hartung et al., Correction of metabolic, craniofacial, and neurologic abnormalities in MPS I mice treated at birth with adena-associated virus vector transducing the human alpha-L-iduronidase gene. Mol Ther. Jun. 2004;9(6):866-75.
Hartung et al., Cre mutants with altered DNA binding properties. J Biol Chern. Sep. 4, 1998;273(36):22884-91.
Hasadsri et al., Functional protein delivery into neurons using polymeric nanoparticles. J Biol Chern. Mar. 13, 2009;284(11):6972-81. doi: 10.1074/jbc.M805956200.
Hatoum-Aslan, et al. 'Mature clustered, regularly interspaced, short palindromic repeats RNA 5,9, 14 (crRNA) length is measured by a ruler mechanism anchored at the precursor processing site.' Proceedings of the National Academy of Sciences. vol. 108, No. 52. pp. 21218-21222. (2011).
Haurwitz et al. Csy4 relies on an unusual catalytic dyad to position and cleave CRISPR RNA. The EMBO Journal Peer Review Process File—EMBO-2011-80101.
Haurwitz, The CRISPR endoribonuclease Csy4 utilizes unusual sequenceand structure-specific mechanisms to recognize and process crRNAs, Thesis. May 8, 2012, University of California, Berkeley, pp. 1-120.
He et al., "Tet-Mediated Formation of 5-Carboxylcytosine and Its Excision by TDG in Mammalian DNA," Science, 333:1303-1307 (2011).
Heigwer et al., E-CRISP: fast CRISPR target site identification, 2014 Nat Methods 11(2): 122-3, doi: 10.1038/nmeth.2812.

Heigwer & Boutros. E-TALEN: a web tool to design TALENs for genome engineering. Nucleic Acids Research, 2013, vol. 41, No. 20 e190. doi:10.1093/nar/gkt789.
Heintze et al. *A CRISPR CASe for high-throughput silencing*, http://www.frontiersin.org/. Percpective Article. Oct. 7, 2013 doi:10.3389/fgene.2013.00193.
Heitz et al, Twenty years of cell-penetrating peptides: from molecular mechanisms to therapeutics. Br J Pharmacol. May 2009;157(2):195-206.
Helou et al., "Mutation analysis ofNPHP6/CEP290 in patients with Joubert syndrome and Senior-Loken Syndrome," J Med Genet. 44: 657-663, 2007.
Herbers et al. (1992) Nature 356:172-174. "Race-specificity of plant resistance to bacterial spot disease determined by repetitive motifs in a bacterial avirulence protein."
Hibbitt, et al., RNAi-Mediated Knockdown of HMG CoA Reductase Enhances Gene Expression From Physiologically Regulated Low-Density Lipoprotein Receptor Therapeutic Vectors In Vivo, Gene Therapy (2012) vol. 19, p. 463-467.
Hildebrand MS, et al. Recent advances in the molecular genetics of epilepsy. J. Med. Genet. 2013;00:1-9. doi:10.1136/jmedgenet-2012-101448. Downloaded from jmg.bmj.com on Mar. 6, 2013. http://jmg.bmj.com.ezp-prod1.hul.harvard.edu/content/early/201.
Hill et al., Functional analysis of conserved histidines in ADP-glucose pyrophosphorylase from *Escherichia coli*.Biochem Biophys Res Commun. Mar. 17, 1998;244(2):573-7.
Hirano et al., Site-specific recombinases as tools for heterologous gene integration. Appl Microbial Biotechnol. Oct. 2011;92(2):227-39. doi: 10.1007/s00253-011-3519-5. Epub Aug. 7, 2011. Review.
Hockemeyer et al., Efficient targeting of expressed and silent genes in human ESCs and iPSCs using zinc-finger nucleases. Nat Biotechnol. Sep. 2009;27(9):851-7. doi: 10.1038/nbt.1562. Epub Aug. 13, 2009.
Hockemeyer et al., Genetic engineering of human pluripotent cells using TALE nucleases. Nat Biotechnol. Jul. 7, 2011;29(8):731-4. doi: 10.1038/nbt.1927.
Hoffman L R. and Ramsey B. W. Cystic Fibrosis Therapeutics the Road Ahead. CHEST:143:1:Jan. 2013 (Downloaded From: http://journal.publications.chestnet.org/by a Francis A Countway User on May 3, 2013).
Holden et al, Crystal structure of the anti-viral APOBEC3G catalytic domain and functional implications. Nature. Nov. 6, 2008;456(7218):121-4. doi: 10.1038/nature07357. Epub Oct. 12, 2008.
Holkers et al. Differential integrity ofT ALE nuclease genes following adenoviral and lentiviral vector gene transfer into human cells. Nucleic Acids Res Dec. 28, 2012 vol 41 No 5 pp. e631-14. Especially p. 2 col. 2 para 2, p. 3 col. 2 para 3, p. 5 col. 2 para 2, p. 9 col. 2 para 2 and para 3, p. 10 col. 2 para 4, p. 13 col. 1 para 1.
Hope et al., Cationic lipids, phosphatidylethanolamine and the intracellular delivery of polymeric, nucleic acid-based drugs (review). Mol Membr Biol. Jan.-Mar. 1998;15(1):1-14.
Horii et al., "Generation of an ICF Syndrome Model by Efficient Genome Editing of Human Induce Pluripotent Stem Cells using the CRISPR System," Int J Mol Sci., 2013,14:19774-19781.
Horvath, et al., RNA-Guided Genome Editing a Ia carte, Cell Research, Cell Research (2013) vol. 23: 733-734.
Hou et al., "Efficient genome engineering in human pluripotent stem cells using Cas9 from Neisseria meningitidis," Proc Natl Acad Sci USA, Sep. 24, 2013,110(39): 15644-9.
Houdebine, The methods to generate transgenic animals and to control transgene expression. J Biotechnol. Sep. 25, 2002;98(2-3):145-60.
Housden et al. "Cas9-Based Genome Editing in *Drosophila*" (2014)Methods in Enzymology, vol. 546, pp. 415-439.
Hsu et al., Development and Applications of CRISPR-Cas9 for Genome Engineering, Cell, Jun. 5, 2014, vol. 157, Iss. 6, pp. 1262-1278.
Hsu et al., DNA targeting specificity of RNA-guided Cas9 nucleases. Nat Biotechnol. Sep. 2013;31(9):827-32. doi: 10.1038/nbt.2647. Epub Jul. 21, 2013.

(56) References Cited

OTHER PUBLICATIONS

Huang et al., Heritable gene targeting in zebrafish using customized TALENs. Nat Biotechnol. Aug. 5, 2011;29(8):699-700. doi: 10.1038/nbt.1939.
Huang et al., Long-range pseudoknot interactions dictate the regulatory response in the tetrahydrofolate riboswitch. Proc Natl Acad Sci USA. Sep. 6, 2011;108(36):14801-6. doi: 10.1073/pnas.1111701108. Epub Aug. 22, 2011.
Humbert et al., Targeted gene therapies: tools, applications, optimization. Crit Rev Biochem Mol Biol. May-Jun. 2012;47(3):264-81. doi: 10.3109/10409238.2012.658112.
Hurt et al., Highly specific zinc finger proteins obtained by directed domain shuffling and cell-based selection. Proc Natl Acad Sci US A. Oct. 14, 2003;100(21):12271-6. Epub Oct. 3, 2003.
Hwang et al., "Heritable and Precise Zebrafish Genome Editing Using a CRISPR-Cas System," PLoS One, 2013, 8(7):e68708, 9 pages.
Hwang et al: "Efficient genome editing in zebrafish using a CRISPR-Cas System" Nature Biotechnology. vol. 31. Mo. 3. Jan. 29, 2013 (Jan. 29, 2013). pp. 227-229. XP055086625. ISSN: 1087-0156. DOI: 10.1038/nbt.2501.
Ikediobi et al., Mutation analysis of 24 known cancer genes in the NCI-60 cell line set. Mol Cancer Ther. Nov. 2006;5(11):2606-12. Epub Nov. 6, 2006.
Irrthum et al., Congenital hereditary lymphedema caused by a mutation that inactivates VEGFR3 tyrosine kinase. Am J Hum Genet. Aug. 2000;67(2):295-301. Epub Jun. 9, 2000.
Isalan et al., "A rapid, generally applicable method to engineer zinc fingers illustrated by targeting the HIV-1 promoter," Nat. Biotechnol., 19:656-660 (2001).
Ishino et al., "Nucleotide sequence of the iap gene, responsible for alkaline phosphatase isozyme 132 conversion in *Escherichia coli*, and identification of the gene product," J Bacteriol., Dec. 1987,169(12):5429-33.
Ito et al., "Tet Proteins Can Convert 5-Methylcytosine to 5-Formylcytosine and 5-Carboxylcytosine," Science, 333:1300-1303 (2011).
Iyer et al., "Prediction of novel families of enzymes involved in oxidative and other complex modifications of bases in nucleic acids," Cell Cycle, Jun. 1, 2009, 8(11): 1698-710.
Jacob Howard J., Next-Generation Sequencing for Clinical Diagnostics. The New England Journal of Medicine. DOI: 10.1056/NEJMe1310846. Published on Oct. 2, 2013, at NEJM.org.
Jamieson et al., "In vitro selection of zinc fingers with altered DNA-binding specificity," Biochemistry, 33:5689-5695 (1994).
Jansen et al, Backbone and nucleobase contacts to glucosamine-6-phosphate in the gImS ribozyme. Nat Struct Mol Biol. Jun. 2006;13(6):517-23. Epub May 14, 2006.
Jansen et al., "Identification of genes that are associated with DNA repeats in prokaryotes," Mol Microbiol., Mar. 2002, 43(6): 1565-75.
Janssen et al, Mouse Models of K-ras-Initiated Carcinogenesis, Biochimicia et Biophysica Acta (2005) vol. 1756, p. 145-154.
Jenkins et al., Comparison of a preQ1 riboswitch aptamer in metabolite-bound and free states with implications for gene regulation. J Biol Chem. Jul. 15, 2011;286(28):24626-37. doi: 1074/jbc.M111.230375. Epub May 18, 2011.
Jiang et al, RNA-guided editing of bacterial genomes using CRISPR-Cas systems. Nat Biotechnol. Mar. 2013,319(3):233-9. doi: 10.1038/nbt.2508. Epub Jan. 29, 2013.
Jiang et al., "CRISPR-assisted editing of bacterial genomes," Nat Biotechnol., 2013, 31:233-239 (Author Manuscript).
Jiang & Weeks—Demonstration of CRISPR/Cas9/sgRNA-mediated targeted gene modification in *Arabidopsis*,tobacco, sorghum and rice. Nucleic Acids Research, 2013, vol. 41, No. 20 e188. doi:10.1093/nar/gkt780.
Jinek et al, A Programmable Dual-RNA-Guided DNA Endonuclease in Adaptive Bacterial Immunity, Science (2012) vol. 337, p. 816-821.
Jinek et al., RNA-programmed genome editing in human cells. Elife. Jan. 29, 2013;2:e00471. doi: 10.7554/eLife.00471.

Jinek et al., Structures of Cas9 endonucleases reveal RNA-mediated conformational activation. Science. Mar. 14, 2014;343(6176):1247997. doi: 10.1126/science.1247997. Epub Feb. 6, 2014.
Jore et al., Structural basis for CRISPR RNA-guided DNA recognition by Cascade, Nat Struct Mol Biol. May 2011;18(5):529-36. doi: 10.1038/nsmb.2019. Epub Apr. 3, 2011.
Joung et al ,TALENs: a widely applicable technology for targeted genome editing. Nat Rev Mol Cell Biol. Jan. 2013;14(1):49-55. doi: 10.1038/nrm3486. Epub Nov. 21, 2012.
Joung et al., A bacterial two-hybrid selection system for studying protein-DNA and protein-protein interactions, Proc Natl Acad Sci USA Jun. 20, 2000;97(13):7382-7.
Joung et al., Genome editing with modularly assembled zinc-finger nucleases, Nat. Methods, 7:91-9 (2010).
Kåhrström Christina Tobin, . Giving CRISPR the slip. Nature Reviews Microbiology | AOP, published online Jan. 3, 2013; doi:10.1038/nrmicro2958.
Kaiser et al, Gene therapy. Putting the fingers on gene repair. Science. Dec. 23, 2005;310(5756):1894-6.
Kandavelou et al., Targeted manipulation of mammalian genomes using designed zinc finger.
Kang et al., Structural Insights into riboswitch control of the biosynthesis of queuosine, a modified nucleotide found in the anticodon of tRNA Mol Cell. Mar. 27, 2009;33(6):784-90. doi: 10.1016/j.molcel.2009.02.019. Epub Mar. 12, 2009.
Karpenshif et al., From yeast to mammals: recent advances in genetic control of homologous recombination. DNA Repair (Anst). Oct. 1, 2012;11(10):781-8. doi: 10.1016/j.dnarep.2012.07.001. Epub Aug. 11, 2012. Review.
Karvelis et al., "crRNA and tracrRNA guide Cas9-mediated DNA interference in *Streptococcus thermophilus*," RNA Biol., 2013,10(5):841-851.
Katic and Großhans, "Targeted heritable mutation and gene conversion by Cas9-CRISPR in Caenorhabditis elegans," Genetics, Nov. 2013, 195(3): 1173-6.
Kaur et al., 2009, Current Gene Therapy, vol. 9. p. 434-458.
Kay et al. (2007) Science 318:648-651. "A bacterial effector acts as a plant transcription factor and induces a cell size regulator."
Keyer-Bibens et al., "Tethering of proteins to RNAs by bacteriophage proteins," Biol Cell, 2008, 0:125-138.
Kilbride et al., Determinants of product topology in a hybrid Cre-Tn3 resolvase site-specific recombination system. J Mol Biol. Jan. 13, 2006;355(2):185-95. Epub Nov. 9, 2005.
Kim et al., A library of TAL effector nucleases spanning the human genome. Nat Biotechnol. Mar. 2013;31(3):251-8. Doi: 10.1038/nbt.2517. Epub Feb. 17, 2013.
Kim et al., Highly efficient RNA-guided genome editing in human cells via delivery of purified Cas9 ribonucleoproteins. Genome Res. Jun. 2014;24(6):1012-9. doi: 10.1101/gr.171322.113. Epub Apr. 2, 2014.
Kim et al., Hybrid restriction enzymes: zinc finger fusions to Fok I cleavage domain. Proc Natl Acad Sci US A. Feb. 6, 1996;93(3):1156-60.
Kim et al., TALENs and ZFNs are associated with different mutationsignatures. Nat Methods. Mar. 2013;10(3):185. doi: 10.1038/nmeth.2364. Epub Feb. 10, 2013.
Kim et al., Targeted genome editing in human cells with zinc finger nucleases constructed via modular assembly. Genome Res. Jul. 2009;19(7):1279-88. doi: 10.1101/gr.089417.108. Epub May 21, 2009.
Kim and Kim, "A guide to genome engineering with programmable nucleases," Nature Rev Genetic 15,321-334(2014).
Klauser et al, An engineered small RNA-mediated genetic switch based on a ribozyme expression platform. Nucleic Acids Res. May 1, 2013;41(10):5542-52. doi: 10.1093/nar/gIct253. Epub Apr. 12, 2013.
Klein et al, Cocrystal structure of a class I preQ1 riboswitch reveals a pseudoknot recognizing an essential hypermodified nucleobase. Nat Struct Mol Biol. Mar. 2009;16(3):343-4. doi: 10.1038/nsmb.1563.Epub Feb. 22, 2009.
Klug et al., Zinc fingers: a novel protein fold for nucleic acid recognition. Cold Spring Harb Symp Quant Biol. 1987;52:473-82.

(56) References Cited

OTHER PUBLICATIONS

Klug, "Co-chairman's remarks: protein designs for the specific recognition of DNA," Gene, 135:83-92 (1993).
Kodama et al., "The Features and Shortcomings for Gene Delivery of Current Non-Viral Carriers" 2006, Current Medicinal Chemistry, vol. 13, p. 2155-2161.
Koenekoop et al., "Genetic testing for retinal dystrophies and dysfunctions: benefits, dilemmas and solutions" Clin Experiment Ophthalmol. 35(5): 473-485, 2007.
Koike-Yusa et al., "Genome-wide recessive genetic screening in mammalian cells with a lentiviral CRISPR-guide RNA library," Nat Biotechnol., Mar. 2014, 32(3):267-73.
Kondo and Ueda, "Highly improved gene targeting by germline-specific Cas9 expression in *Drosophila*," Genetics, Nov. 2013, 195(3):715-21.
Konermann et al., "Optical control of mammalian endogenous transcription and epigenetic states," Nature. Aug. 22, 2013; 500(7463):472-6. (Author Manuscript).
Koomneef, et al., Apolipoprotein B Knockdown by AAV-Delivered shRNA Lowers Plasma Cholesterol in Mice, Molecular Therapy (2011) vol. 19, No. 4, p. 731-740.
Kosuri et al. (2010) Nat. Biotechnol. 28:1295-1299. "Scalable gene synthesis by selective amplification of DNA pools from high-fidelity microchips."
Krishna et al, Structural classification of zinc fingers: survey and summary. Nucleic Acids Res. Jan. 15, 2003;31(2):532-50.
Kumar et al., Structural and functional consequences of the mutation of a conserved arginine residue in alphaA and alphaB crystallins. J Biol Chem. Aug. 20, 1999;274(34):24137-41.
Kundu et al., Leucine to proline substitution by SNP at position 197 in Caspase-9 gene expression leads to neuroblastoma: a BioInformatics analysis. 3 Biotech. 2013; 3:225-34.
Kwon et al., Chemical basis of glycine riboswitch cooperativity. RNA Jan. 2008;14(1):25-34. Epub Nov. 27, 2007.
Lambowitz and Zimmerly, Group II introns: mobile ribozymes that invade DNA, Cold Spring Harb Perspect Biol. 2011; 3:a003616 (Aug. 1, 2011).
Lavergne et al., Defects in type HA von Willebrand disease: a cysteine 509 to arginine substitution in the mature von Willebrand factor disrupts a disulphide loop involved in the interaction with platelet glycoprotein ib-IX. Br J Haematol. Sep. 1992;82(1):66-72.
Lawrence et al., Supercharging proteins can impart unusual resilience. J Am Chem Soc. Aug. 22, 2007;129(33):10110-2. Epub Aug. 1, 2007.
Lamb & Barbas. Directed evolution of the TALE N-terminal domain for recognition of all 50 bases. Nucleic Acids Research, 2013, vol. 41, No. 21 9779-9785. doi:10.1093/nar/gkt754.
Lazar et al., Transforming growth factor alpha: mutation of aspartic acid 47 and leucine 48 results in different biological activities. Mol Cell Biol. Mar. 1988;8(3):1247-52.
Lee et al, PIK3CA gene is frequently mutated in breast carcinomas and hepatocellular carcinomas. Oncogene. Feb. 17, 2005;24(8):1477-80.
Lee et al. RNA—protein analysis using a conditional CRISPR nuclease. www.pnas.org/cgi/doi/10.1073/pnas.1302807110. PNAS Early Edition (Feb. 14, 2013).
Lee et al., "Three-dimensional solution structure of a single zinc finger DNA-binding domain," Science, 245:635-637 (1989).
Lee et al., An allosteric self-splicing ribozyme triggered by a bacterial second messenger. Science. Aug. 13, 2010;329(5993):845-8. doi: 10.1126/science.1190713.
Lei et al., Efficient targeted gene disruption in Xenopus embryos using engineered transcription activator-like effector nucleases (TALENs). Proc Natl Acad Sci USA. Oct. 23, 2012;109(43):17484-9. Doi: 10.1073/pnas.l215421109. Epub Oct. 8, 2012.
Lei S. Qi et al: "Repurposing CRISPR as an RNA-Guided Platform for Sequence-Specific Control of Gene Expression". CELL, vo 1. 152. No. 5. Feb. 1, 2013 (Feb. 1, 2013). pp. 1173-1183. XP055068548. ISSN: 0092-8674. DOI: 10.1016/j. ce 11 . 2013.02.022 the whole document.

Leman, AR et al. The Replication Forie Understanding the Eukaryotic Replication Machinery and the Challenges to Genome Duplication. Genes. Jan. 29, 2013. vol. 4; pp. 1-32; figure 1; DOI: 10.3390/genes4010001.
Lenk et at, Pathogenic mechanism of the FIG4 mutation responsible for Charcot-Marie-Tooth disease CMT4J. PLoS Genet. Jun. 2011;7(6):e1002104. doi: 10.1371/journal.pgen.1002104. Epub Jun. 2, 2011.
Lewis et al, Codon 129 polymorphism of the human prion protein influences the kinetics of amyloid formation. J Gen Virol. Aug. 2006;87(Pt 8):2443-9.
Lewis et al., A serum-resistant cytofectin for cellular delivery of antisense oligodeoxynucleotides and plasmid DNA. Proc Natl Acad Sci USA. Apr. 16, 1996;93(8):3176-81.
Lewis, et al., The c-myc and PyMT Oncogenes Induce Different Tumor Types in a Somatic Mouse Model for Pancreatic Cancer, Genes & Development (2003) vol. 17, p. 3127-3138.
Li et al, Modularly assembled designer TAL effector nucleases for targeted gene knockout and gene replacement in eukaryotes. Nucleic Acids Res. Aug. 2011;39(14):6315-25. doi: 10.1093/nar/gkr188. Epub Mar. 31, 2011.
Li, Multiplex and homologous recombination-mediated genome editing in *Arabidopsis* and Nicotia benthamiana using guide RNA and Cas9, Nature Biotechnology 31, 688-691 (2013) doi:10.1038/nbt.2654.
Li et al. Genetic correction using engineered nucleases for gene therapy applications. Develop. Growth Differ. (2013)doi: 10.1111/dgd.12107.
Li et al., "Heritable gene targeting in the mouse and rat using a CRISPR-Cas system," Nat Biotechnol, Aug. 2013, 31(8):681-3.
Li et al., "Simultaneous generation and germline transmission of multiple gene mutations in rat using CRISPRR-Cas systems," Nat Biotechnol., Aug. 2013, 31(8):684-6.
Li et al., TAL nucleases (TALNs): hybrid proteins composed of TAL effectors and FokI DNA-cleavage domain. Nucleic Acids Res. Jan. 2011;39(1):359-72. doi: 10.1093/nar/gkq704. Epub Aug. 10, 2010.
Li, "Mechanisms and functions of DNA mismatch repair" Cell Research (2008) 18:85-98.
Li, H. et al., In vivo genome editing restores haemostasis in a mouse model of haemophilia, Nature 2011; 475:217-221 (Jul. 14, 2011) doi: 10.1038/nature10177.
Littink et al.,"A Novel Nonsense Mutation in CEP290 Induces Exon Skipping and Leads to a Relatively Mild Retinal Phenotype," Invest Ophthalmol Vis Sci 51, 3646-3652, 2010.
Liu el al., Cell-penetrating peptide-mediated delivery of TALEN proteins via bioconjugation for genome engineering. PLoS One. Jan. 20, 2014;9(1):e85755. doi: 10.1371/journal.pone.0085755. eCollection 2014.
Liu et aL, Design of polydactyl zinc-finger proteins for unique addressing within complex genomes. Proc Nall Acad Sci USA. May 27, 1997;94(11):5525-30.
Liu et al., Fast Colorimetric Sensing of Adenosine and Cocaine Based on a General Sensor Design Involving Aptamers and Nanoparticles. Angew Chern. 2006;118(1):96-100.
Liu et al., "Validated Zinc Finger Protein Designs for Alll6 GNN DNA Triplet Targets," J. Biol. Chem., 277:3850-56 (2002).
Lo et al., "Precise and Heritable Genome Editing in Evolutionarily Diverse Nematodes Using TALEN s and CRISPR/Cas9 to Engineer Insertions and Delections," Genetics, 2013, 195:3 31-348.
Lombardo, et al., Gene Editing in Human Stem Cells Using Zinc Finger Nucleases and Integrase-Defective Lentiviral Vector Delivery, Nature Biotechnology (2007) vol. 25, No. 11, p. I 298-1306.
Lukacs, G L and. Verkman, A.S. CFTR: folding, misfolding and correcting the DF508 conformational defect. Trends in Molecular Medicine Feb. 2012, vol. 18, No. 2 pp. 81-91.
Lundberg et al., Delivery of short interfering RNA using endosomolytic cell-penetrating peptide FASEB I Sep. 2007;21(11):2664-71. Epub Apr. 26, 2007.
Ma et al., A Guide RNA Sequence Design Platform for the CRISPR/Cas9 System for Model Organism Genomes 11 Biomed Research International vol. 31. No. 3. Nov. 2013 (Nov. 2013) pp. 822-824. XP055118861 ISSN: 2314-6133. DOI:10.186/1748-7188-6-26.

(56) References Cited

OTHER PUBLICATIONS

Mabaera et al., "Developmental- and differentiation-specific patterns of human γ- and β-globin promoter DNA methylation," Blood, 110(4):1343-52 (2007).
Maeder et al, CRISPR RNA-guided activation of endogenous human genes. Nat Methods. Oct. 2013;10(10):977-9. doi: 10.1038/nmeth.2598. Epub Jul. 25, 2013.
Maeder et al, Rapid "open-source" engineering of customized zinc-finger nucleases for highly efficient gene modification. Mol Cell. Jul. 25, 2008;31(2):294-301. doi:10.1016/j.molcel.2008.06.016.
Maeder et al, Robust, synergistic regulation of human gene expression using TALE activators. Nat Methods. Mar. 2013;10(3):243-5. doi: 10.1038/nmeth.2366. Epub Feb. 10, 2013.
Maeder et al., "Oligomerized pool engineering (OPEN): an 'open-source' protocol for making customized zinc-finger arrays," Nat Protoc., 2009;4(10):1471-501.
Maeder et al., "Targeted DNA demethylation and activation of endogenous genes using programmable TALE-TET1 fusion proteins," Nat. Biotech. 31:1137-1142 (2013).
Maguire et al., "Age-dependent effects of RPE65 gene therapy for Leber's congenital amaurosis: a phase 1 dose-escalation trial", The Lancet, vol. 374, No. 9701, Nov. 7, 2009, pp. 1597-160.
Maguire et al., N Engl J Med. 358: 2240-2248, 2008.
Mahfouz et al., De novo-engineered transcription activator-like effector (TALE) hybrid nuclease with novel DNA binding specificity creates double-strand breaks. Proc Natl Acad Sci USA. Feb. 8, 2011;108(6):2623-8. doi: 10.1073/pnas.1019533108. Epub Jan. 24, 2011.
Majumdar et al., "Targeted Gene Knock in and Sequence Modulation Mediated by a Psoralen-linked Triplex-forming Oligonucleotide," J Biol Chem., 283(17):11244-52 (2008).
Mak et al., The crystal structure of TAL effector PthXo1 bound to its DNA target. Science. Feb. 10, 2012;335(6069):716-9. doi: 10.1126/science.1216211. Epub Jan. 5, 2012.
Makarova et al., "A putative RNA-interference-based immune system in prokaryotes: computational 153 analysis of the predicted enzymatic machinery, functional analogies with eukaryotic RNAi, and hypothetical mechanisms of action," Biol. Direct, 2006, 1:7, 26 pages.
Makarova et al., "Unification of Cas protein families and a simple scenario for the origin and evolution of CRISPR-Cas systems," Biol. Direct, 2011, 6:38,27 pages.
Makarova et al., Evolution and Classification of the CRISPR-CAS Systems, Nature Reviews Microbiology (2011) vol. 9, No. 6, p. 467-477.
Mali P. et al: "RNA-Guided Human Genome Engineering via Cas9". SCIENCE, vol. 339. No. 6121. Jan. 3, 2013 (Jan. 3, 2013). pp. 823-826. XP055111247. ISSN: 0036-8075. DOI: 10.1126jscience.1232033 the whole document.
Mali, P. et al., "Cas9 as a Versatile Tool for Engineering Biology," Nature Methods, 2013, vol. 10 (10), pp. 957-963.
Malina et al., "Repurposing CRISPR/CAS9 for in situ functional assays," Genes & Development 27:2602-2614, 2013.
Mandal et al, Adenine riboswitches and gene activation by disruption of a transcription terminator. Nat Struct Mol Biol. Jan. 2004;11(1):29-35. Epub Dec. 29, 2003.
Mandal et al., A glycine-dependent riboswitch that uses cooperative binding to control gene expression. Science. Oct. 8, 2004;306(5694):275-9.
Mndell and Barbas III, "Zinc Finger Tools: custom DNA-binding domains for transcription factors and nucleases," Nucl Acids Res., 34:W516-523 (2006).
Mani et al., Design, engineering, and characterization of zinc finger nucleases. Biochem Biophys Res Commun. Sep. 23, 2005;335(2):447-57.
Manica, Schleper et al. Unexpectedly broad target recognition of the CRISPR-mediated virus defence system in the archaeon Sulfolobus solfataricus. Nucleic Acids Research, 2013, vol. 41, No. 22 10509-10517. doi:10.1093/nar/gkt767.
Mao et al., Application of the CRISPR-Cas System for Efficient Genome Engineering in Plants, Mol Plant. Nov. 2013; 6(6): 2008-2011. Published online Aug. 20, 2013. doi: 10.1093/mp/sst121.
Marois et al. (2002)Mol. Plant-Microbe Interact. 15:637-646. The Xanthomonas type Ill effector protein AvrBs3 modulates plant gene expression and induces cell hypertrophy in the susceptible host.
Marraffini and Sontheimer, "Self vs. non-self discrimination during CRISPR RNA-directed immunity," Nature, 2010, 463(7280):568-571 (Author Manuscript).
Marteijn et al., "Understanding nucleotide excision repair and its roles in cancer and ageing" Nature Reviews Molecular Cell Biology 15, 465-481 (2014).
Marx, Vivien. Genome-editing tools storm ahead. vol. 9 No.11, Nov. 2012, Nature Methods pp. 1055-1059.
Mashiko et al., "Generation of mutant mice by pronuclear injection of circular plasmid expressing Cas9 and single guided RNA," Sci Reports, 2013,3(3355):1-6.
Mastroianni, M et al., Group II Intron-Based Gene Targeting Reactions in Eukaryotes, Plos One, 2008, 3:e3121 (Sep. 1, 2008).
McGarty, "CRISPRs and Cancer," White Paper No. 111, Apr. 2014, 22 pages.
McNaughton et al Mammalian cell penetration, siRNA transfection, and DNA transfection by supercharged proteins PNAS vol. 106 No. 15, 6111-6116.
Meckler et al., Quantitative analysis of TALE-DNA interactions suggests polarity effects. Nucleic Acids Res. Apr. 2013;41(7):4118-28. doi: 10.1093/nar/gkt085. Epub Feb. 13, 2013.
Mendenhall et al., "Locus-specific editing of histone modifications at endogenous enhancers," Nature Biotechnology, doi:10.1038/nbt.2701 (Sep. 8, 2013).
Meng et al., Profiling the DNA-binding specificities of engineered Cys2His2 zinc finger domains using a rapid cell-based method. Nucleic Acids Res. 2007;35(11):e81. Epub May 30, 2007.
Meng et al., Targeted gene inactivation in zebrafish using engineered zinc-finger nucleases. Nat Biotechnol. Jun. 2008;26(6):695-701. doi: 10.1038/nbt1398. Epub May 25, 2008.
Meshorer and Misteli, "Chromatin in pluripotent embryonic stem cells and differentiation" Nature Reviews Molecular Cell Biology 7, 540-546 (Jul. 2006).
Meyer et al. Cell-Specific Aptamers as Emerging Therapeutics. Journal of Nucleic Acids vol 2011, Article ID 904750,18 pages. doi:10.4061/2011/904750.
Meyer et al., Breathing life into polycations: functionalization with pH-responsive endosomolytic peptides and polyethylene glycol enables siRNA delivery. JAm Chem Soc. Mar. 19, 2008;130(11):3272-3. doi: 10.1021/ja710344v. Epub Feb. 21, 2008.
Meyer et al., Confirmation of a second natural preQ1 aptamer class in Streptococcaceae bacteria. RNA. Apr. 2008;14(4):685-95. doi: 10.1261/rna.937308. Epub Feb. 27, 2008.
Miao & Qu—Targeted mutagenesis in rice using CRISPR-Cas system. Cell Research (2013) 23:1233-1236. doi:10.1038/cr.2013.123; published online Sep. 3, 2013.
Midoux et al, Chemical vectors for gene delivery: a current review on polymers, peptides and lipids containing histidine or imidazole as nucleic acids carriers. Br J Pharmacol. May 2009;157(2):166-78. doi:10.1111/j.1476-5381.2009.00288.x.
Miller et al, An improved zinc-finger nuclease architecture for highly specific genome editing. Nat Biotechnol. Jul. 2007;25(7):778-85. Epub Jul. 1, 2007.
Miller, et al., A Tale Nuclease Architecture for Efficient Genome Editing Nature Biotechnology (20111) vol. 29, No. 2, p. 143-150.
Minoretti et al, A W148R mutation in the human FOXD4 gene segregating with dilated cardiomyopathy, obsessive-compulsive disorder, and suicidality. Int J Mot Med. Mar. 2007;19(3):369-72.
Minton, How Can Biochemical Reactions Within Cells Differ From Use in Test Tubes? Journal of Cell Science (2006) vol. 119, p. 2863-2869.
Mojica et al., Short motif sequences determine the targets of the prokaryotic CRISPR defence system (Supplementary data. Fig. S1) 11 Microbiology vol. 155. No. 3. Mar. 1, 2009 (Mar. 1, 2009 pp. 733-740 XP055118633 ISSN: 1350-0872. DOI: 10.1099/mic.0.023960-0.

(56) References Cited

OTHER PUBLICATIONS

Mojica et al., "Biological significance of a family of regularly spaced repeats in the genomes of Archaea, Bacteria and mitochondria," Mol Microbiol., Apr. 2000, 36(1):244-6.
Moldt et al., 2011, Molecular Therapy, vol. 19, No. 8, p. 1499-1510.
Montange et al., Structure of the S-adenosylmethionine riboswitch regulatory mRNA element. Naure. Jun. 29, 2006;441(7097): 1172-5.
Moore et al., Improved somatic mutagenesis in zebrafish using transcription activator-like effector nucleases (TALENs). PloS One. 2012;7(5):e37877. Doi: 10.1371/journal.pone.0037877. Epub May 24, 2012.
Mootz et al, Protein splicing triggered by a small molecule. J Am Chcm Soc. Aug. 7, 2002;124(31):9044-5.
Mootz et al., Conditional protein splicing: a new tool to control protein structure and function in vitro and in vivo. J Am Chem Soc. Sep. 3, 2003;125(35):10561-9.
Morbitzer et al., Assembly of custom TALE-type DNA binding domains by modular cloning. Nucleic Acids Res. Jul. 2011;39(13):5790-9. doi: 10.1093/nar/gkrl51. Epub Mar. 18, 2011.
Morgan, W.F. et al., Inducible Expression and Cytogenetic Effects of the EcoRI Restriction Endonuclease in Chinese Hamster Ovary Cells, Mol. Cell. Biol. 1988, 8:4204-4211 (Oct. 1988).
Morris et al , A peptide carrier for the delivery of biologically active proteins into mammalian cell. Nat Biotechnol. Dec. 2001;19(12):1173-6.
Moscou et al., A simple cipher governs DNA recognition by TAL effectors. Science. Dec. 11, 2009;326(5959): 1501. doi: 10.1126/science.1178817.
Mukhopadyay, "On the Same Wavelength," ASBMBTODAY (Aug. 2014), available at http://www.asbmb.org/asbmbtoday/201408/features/doudna.
Mullins et at, Transgenesis in nonmurine species. Hypertension. Oct. 1993;22(4):630-3.
Murakami et al. (2010) Proteins 78:3386-3395. "The repeat domain of the type III effector protein PthA shows a TPR-like structure and undergoes conformational changes upon DNA interaction."
Mussolino and Cathomen, "RNA guides genome engineering," Nat Biotechnol., 2013, 31(3):208-209.
Mussolino et al., A novel TALE nuclease scaffold enables high genome editing activity in combination with low toxicity. Nucleic Acids Res. Nov. 2011;39(21):9283-93. Doi: 10.1093/nar/gkr597. Epub Aug. 3, 2011.
Mussolino et al., TALE nucleases: tailored genome engineering made easy. Curr Opin Biotechnol. Oct. 2012:23(5):644-50. doi: 10.1016/j.copbio.2012.01.013. Epub Feb. 17, 2012.
Musunuru, Kiran . Genome editing of human pluripotent stem cells to generate human cellular disease models. Disease Models & Mechanisms 6, 896-904 (2013) doi:10.1242/dmm.012054.
Nekrasov, Targeted mutagenesis in the model plant *Nicotiana benthamiana* using Cas9 RNA-guided endonuclease, Nature Biotechnology 31,691-693 (2013) doi:10.1038/nbt.2655.
Nahvi et al., Coenzyme B12 riboswitches are widespread genetic control elements in prokaryotes. Nucleic Acids Res. Jan. 2, 2004;32(1):143-50.
Nakamura, et al., Codon Usage Tabulated From International DNA Sequence Databases: Status for the Year 2000, Nucleic Acids Research (2000) vol. 28, No. 1, p. 292.
Navaratnam et al., An overview of cytidine deaminases. Int J Hematol. Apr. 2006;83(3):195-200.
Needleman and Wunsch "A General Method Applicable to the Search for Similarities in the Amino Acid Sequence of Two Proteins" (1970) J. Mol. Biol. 48:444-453.
Neel et al., Riboswitches: Classification, function and in silico approach, International Journal of Pharma Sciences and Research. 2010;1(9):409-420.
Ni et al., Nucleic acid aptamers: clinical applications and promising new horizons. Curr Med Chern. 2011;18(27):4206-14. Review.
Niewoehner et al. Evolution of CRISPR RNA recognition and processing by Cas6 endonucleases. Nucleic Acids Research Advance Access published Oct. 22, 2013. Nucleic Acid Research, 2013, 1-13. doi:10.1093/nar/gkt922.
Nishimasu et al., Crystal structure of Cas9 in complex with guide RNA and target DNA. Cell. Feb. 27, 2014;156(5):935-49. doi: 10.1016/j.cell.2014.02.001. Epub Feb. 13, 2014.
Nissim et al., Multiplexed and Programmable Regulation of Gene Networks with an Integrated RNA and CRISPR/Cas Toolkit in Human Cells, Molecular Cell, May 22, 2014, vol. 54, pp. 689-710.
Niu et al., "Generation of gene-modified cynomolgus monkey via Cas9/RNA-mediated gene targeting in one-cell embryos," Cell, 2014, 156:836-843.
Nomura et al, Synthetic mammalian riboswitcbes based on guanine aptazyme. Chem Commun (Camb). Jul. 21, 2012;48(57):7215-7. doi: 10.1039/c2cc33140c. Epub Jun. 13, 2012.
Nomura, et al., Low-Density Lipoprotein Receptor Gene Therapy Using Helper-Dependent Adenovirus Produces Long-Term Protection Against Atherosclerosis in a Mouse Model of Familial Hypercholesterolemia. Gene Therapy (2004) vol. II, p. 1540-1548.
Noris et al, A phenylalanine-55 to serine amino-acid substitution in the human glycoprotein IX leucine-rich repeat is associated with Bernard-Soulier syndrome. Br I Haematol. May 1997;97(2):312-20.
Oakland et al. Advances in Cell and Gene-based Therapies for Cystic Fibrosis Lung Disease. www.moleculartherapy.org vol. 20 No. 6, 1108-1115 Jun. 2012 (advance online publication 28 (Feb. 2012. doi:10.1038/mt.2012.32).
O'Connell et al, Programmable RNA recognition and cleavage by CRISPR/Cas9. Nature. Sep. 28, 2014. doi: 10.1038/nature13769.
Orlando et al., "Zinc-finger nuclease-driven targeted integration into mammalian genomes using donors with limited chromosomal homology," Nucleic Acids Res., Aug. 2010;38(15):e152, 15 pages.
Osborn et al., TALEN-based gene correction for epidermolysis bullosa. Mol Ther. Jun. 2013;21(6):1151-9. doi: 10.1038/mt.2013.56. Epub Apr. 2, 2013.
Ousterout Reading Frame Correction by Targeted Genome Editing Restores Dystrophin Expression in Cells From Duchenne Muscular Dystrophy Patients. Molecular Therapy.2013. doi:10.1038/mt.2013.111.
Pabo et al., Design and selection of novel Cys2His2 zinc finger proteins. Annu Rev Biochem. 2001;70:313-40.
Padegimas et al. Optimization of hCFTR Lung Expression in Mice Using DNA Nanoparticles. Molecular Therapy vol. 20 No. 1, 63-72 Jan. 2012.
Palpant NJ andDudzinski D . *Zinc finger nucleases: looking toward translation*. Gene Therapy (2013) 20, 121-127; doi:10.1038/gt.2012.2; published online Feb. 9, 2012.
Pan et al., Biological and biomedical applications of engineered nucleases. Mol Biotechnol. Sep. 2013;55(1):54-62. doi: 10.1007/s12033-012-9613-9.
Pandey et al.—Endogenous factor VIII synthesis from the intron 22—inverted F8 locus may modulate the immunogenicity of replacement therapy for hemophilia A. vol. 19. No. 10. Oct. 2013 nature medicine (published online Sep. 15, 2013; doi:10.1038/nm.3270).
Pandika et al., "Jennifer Doudna, CRISPR Code Killer" Jan. 7, 2014 http://www.ozy.com/rising-stars/jennifer-doudna-crispr-code-killer/4690.
Pattanayak el at, Revealing off-target cleavage specificities of zinc-finger nucleases by in vitro selection. Nat Methods. Aug. 7, 2011;8(9):765-70. doi: 10.1038/nmeth.1670.
Patanayak et al, Determining the specificities of TALENs, Cas9, and other genome-editing zymes. Methods Enzymol. 2014;546:47-78. doi: 10.1016/B978-0-12-801185-0.00003-9.
Pattanayak et al, High-throughput profiling of off-target DNA cleavage reveals RNA-programmed Cas9 nuclease specificity. Nat Biotechnol. Sep. 2013;31(9):839-43. doi: 1038/nbt.2673. Epub Aug. 11, 2013.
Patterson, Stacey S. et al., Codon Optimization of Bacterial Luciferase (lux) for Expression in Mammalian Cells, J. Ind. Microbio. Biotechnology (2005) vol. 32, p. 115-123.
Pavletich et al., Zinc finger-DNA recognition: crystal structure of a Zif268-DNA complex at 2.1 A. Science. May 10, 1991;252(5007):809-17.

(56) References Cited

OTHER PUBLICATIONS

Pearson and Lipman, "Improved Tools for Biological Sequence Comparison" (1998) Proc. Nat'l. Acad. Sci. USA 85:2444.

Peart et al. Non-mRNA 3 end formation: how the other half lives. WIREs RNA 2013. doi: 10.1002/wrna.1174. 2013 John Wiley & Sons, Ltd. wires.wiley.com/rna.

Peck et al., Directed evolution of a small-molecule-triggered intein with improved splicing properties in mammalian cells. Chern Biol. May 27, 2011;18(5):619-30. doi:10.1016/j.chembiol.2011.02.014.

Pennisi et al, The CRISPR craze. Science. Aug. 23, 2013;341(6148):833-6. doi: 10.1126/science.341.6148.833.

Pennisi et al, The tale of the TALEs. Science. Dec. 14, 2012;338(6113):1408-11. doi: 10.1126/science.338.6113.1408.

Perez et al, Establishment of HIV-1 resistance in CD4+ T cells by genome editing using zinc-finger nucleases. Nat Biotechnol. Jul. 2008;26(7):808-16. Doi: 10.1038/nbt1410. Epub Jun. 29, 2008.

Perez-Pinera et al., Advances in targeted genome editing. Curr Opin Chem Biol. Aug. 2012;16(3-4):268-77. doi: 10.1016/j.cbpa.2012.06.007. Epub Jul. 20, 2012.

Perez-Pinera, Synergistic and tunable human gene activation by combinations of synthetic transcription factors Nature Methods 10, 239-242 (2013) doi:10.1038/nmeth.2361.

Perrault et al., "Spectrum of NPHP6/CEP290 mutations in Leber congenital amaurosis and delineation of the associated phenotype" Hum Mutat. 28(4):4 16, 2007.

Petek et al., Frequent endonuclease cleavage at off-target locations in vivo. Mol Ther. May 2010;18(5):983-6. Doi: 10.1038/mt.2010.35. Epub Mar. 9, 2010.

Pham et al., Reward versus risk: DNA cytidine deaminases triggering immunity and disease. Biochemistry. Mar. 1, 2005;44(8):2703-15.

Phillips, The challenge of gene therapy and DNA delivery. J Pharm Pharmacol. Sep. 2001;53(9):1169-74.

Pichavant et al. Current Status of Pharmaceutical and Genetic Therapeutic Approaches to Treat DMD. published online Apr. 5, 2011. www.moleculartherapy.org vol. 19 No. 5, 830-840 May 2011. doi:10.1038/mt.2011.59.

Pingoud and Silva, "Precision genome surgery," Nat. Biotechnol., 25:743-744 (2007).

Platt et al., "CRISPR-Cas9 Knockin Mice for Genome Editing and Cancer Modeling," Cell, 159(2):440-455 (2014).

Poller et aL, A leucine-to-proline substitution causes a defective alpha 1-antichymotrypsin allele associated with familial obstructive lung disease. Genomics. Sep. 1993;17(3):740-3.

Porteus & Baltimore, "Chimeric nucleases stimulate gene targeting in human cells," Science. May 2003;300(5620):763.

Porteus M H and Fischer A. Engineering the immune system to cure genetic diseases, HIV,and cancer. Current Opinion in Immunology 2012, 24:576-579. http://dx.doi.org/10.1016/j.coi.2012.09.004.

Porteus M H., et al., Gene Targeting Using Zinc Finger Nucleases, Nature Biotechnology (2005) vol. 23, No. 8, p. 967-973.

Porteus, Design and testing of zinc finger nucleases for use in mammalian cells. Methods Mol Biol. 2008;435:47-61. doi: 10.1007/978-1-59745-232-8_4.

Pougach, Ksenia et al., Transcription, Processing and Function of CRISPR Cassettes in Escherichia coli, Mol. Microbiol, Sep. 2010, 77(6), p. 1367-1379.

Prickett M., and Jain M. Gene therapy in cystic fibrosis. Translational Research. vol. 161, No. 4. Apr. 2013. pp. 255-264.

Proudfoot et al., Zinc finger recombinases with adaptable DNA sequence specificity. PLoS One. Apr. 29, 2011;6(4):e19537. doi: 10.1371/journal.pone.0019537.

Puchta and Fauser et al., "Synthetic nucleases for genome engineering in plants: prospects for a bright future," Plant J. Jun. 2014; 78(5):727-41.

Putney et al., Improving protein therapeutics with sustained-release formulations. Nat Biotechnol. Feb. 1998;16(2):153-7.

Qi et al, Engineering naturally occurring trans-acting non-coding RNAs to sense molecular signals. Nucleic Acids Res. Jul. 2012;40(12):5775-86. doi: 10.1093/nar/gks168. Epub Mar. 1, 2012.

Qi, L. et al., "RNA Processing Enables Predictable Programming of Gene Expression," Nature Biotechnology, 2012, vol. 30(10), pp. 1002-1007 (including Supplementary Information).

Ralph et al. Silencing mutant SOD1 using RNAi protects against neurodegeneration and extends survival in an ALS model. Nature Medicine. vol. 11. No. 4. Apr. 2005. pp. 429-433. Published online at http://www.nature.com/naturemedicine/.

Ramakrishna et al, Gene disruption by cell-penetrating peptide-mediated delivery of Cas9 protein and guide RNA, Genome Res. published online Apr. 2, 2014, pp. 1-20 plus figures.

Ramakrishna et al., "Surrogate reporter-based enrichment of cells containing RNA-guided Cas9 nuclease-induced mutations," Nat Commun. Feb. 26, 2014; 5:3378.

Ramalingam et al., "A CRISPR way to engineer the human genome," Genome Biol., 2013, 14:107, 4 pages.

Ramirez et al., Unexpected failure rates for modular assembly of engineered zinc fingers. Nat Methods. May 2008;5(5):374-5. Doi: 10.1038/nmeth0508-374.

Ran et al., "In vivo genome editing using Staphylococcus aureus Cas9," Nature 520, 186-191 (Apr. 9, 2015) doi: 10.1 038/nature 14299 (Published online Apr. 1, 2015).

Ran, F A et al. Double Nicking by RNA-Guided CRISPR Cas9 for Enhanced Genome Editing Specificity. Cell. Sep. 12, 2013. vol. 154; pp. 1380-1389. DOI: 10.1016/j.cell.2013.08.021.

Rand, Tim A. et al., Argonaute2 Cleaves the Anti-Guide Strand of siRNA During RISC Activation, Cell (2005) vol. 123, p. 621-629.

Raymond, C.S. and Soriano, P., "High-Efficiency FLP and PhiC31 Site-Specific combination in Mammalian Cells," PLoS One, 2007, vol. 2(1), p. el62.

Rebar, Edward J. et al., Induction of Angiogenesis in a Mouse Model Using Engineered Transcription Factors, Nature Medicine (Dec. 2002) vol. 8, No. 12, p. 1427-1432.

Reeks et al. CRISPR interference: a structural perspective. Biochem. J. (2013) 453,155-166 (Printed in Great Britain) doi:10.1042/BJ20130316.

Regalado, A., "Who Owns the Biggest Biotech Discovery of the Century?," MIT Technology Review, Dec. 4, 2014, http://www.technologyreview.com/featuredstory/532796/who-owns-the-biggest-biotech-discovery-of-the-century/.

Reiss, B. et al., RecA protein stimulates homologous recombination in plants, Proc. Natl. Acad. Sci U.S.A. 1996, 93:3094-3098 (Apr. 2, 1996).

Reynaud et al., "Optimized gene editing technology for Drosophila melanogaster using germ line-specific Cas9," Proc Natl Acad Sci USA, Nov. 19, 2013,110(47):19012-7.

Reyon et al., FLASH assembly ofTALENs for high-throughput genome editing. Nat Biotechnol. May 2012;30(5):460-5. doi: 10.1038/nbt.2170.

Reyon et al, Current Protocols in Molecular Biology Engineering Designer Transcription Activator-Like Effector Nucleases (TALENs), Curr Protoc Mol Bio. Oct. 2012; 0 12: Unit 12-15 doi:10.1002/0471142727.mb1215s100.

Rho, Mina et al. 'Diverse CRISPRs Evolving in Human Microbiomes.' PLoS Genetics. vol. 8, No. 6. 1-14 pp. 1-12. Jun. 2012. entire document.

Rodenhiser and Mann, "Epigenetics and human disease: translating basic biology into clinical applications," CMAJ, 174(3):341-348 (2006).

Rohde et al., "BISMA—Fast and accurate bisulfite sequencing data analysis of individual clones from unique and repetitive sequences," BMC BioInformatics, 11:2301 12 pages (2010).

Romer et al. {2007) Science 318:645-648. "Plant pathogen recognition mediated by promoter activation of the pepper Bs3 resistance gene."

Rothman, J., "Mechanisms of intracellular protein transport," Nature, 372:55-63 (1994).

Rusk, "CRISPRs and epigenome editing," Nature Methods, 2014, 11(1):28.

Sage et al., Proliferation of functional hair cells in vivo in the absence of the retinoblastoma protein. Science. Feb. 18, 2005;307(5712): 1114-8. Epub Jan. 13, 2005.

(56) References Cited

OTHER PUBLICATIONS

Sahay et al. Efficiency of siRNA delivery by lipid nanoparticles is limited by endocytic recycling. Nature Biotechnology. Advance Online Publication. Published online Jun. 23, 2013; doi:10.1038/nbt.2614.

Saleh-Gohari et al., Conservative homologous recombination preferentially repairs DNA double-strand breaks in the S phase of the cell cycle in human cells. Nucleic Acids Res. Jul. 13, 2004;32(12):3683-8. Print 2004.

Samal et al, Cationic polymers and their therapeutic potential. Chem Soc Rev. Nov. 7, 2012;41(21):7147-94. doi: 10.1039/c2cs35094g. Epub Aug. 10, 20120.

Samson et al. Corrigendum: A CRISPR/Cas system mediates bacterial innate immune evasion and virulence Nature 501, 262 (Sep. 12, 2013) doi:10.1038/nature12498 Published online Aug. 21, 2013.

Sander et al., Targeted gene disruption in somatic zebrafish cells using engineered TALENs. Nat Biotechnol. Aug. 5, 2011;29(8):697-8. doi: 10.1038/nbt.1934.

Sander et al., CRISPR-Cas systems for editing, regulating and targeting genomes. Nat Biotechnol. Apr. 2014;32(4):347-55. doi: 10.1038/nbt.2842. Epub Mar. 2, 2014.

Sander et al., In silico abstraction of zinc finger nuclease cleavage profiles reveals an expanded landscape of off-target sites. Nucleic Acids Res. Oct. 2013;41(19):e181. doi: 10.1093/nar/gkt716. Eub Aug. 14, 2013.

Saders et al., Use of a Macromolecular Crowding Agent to Dissect Interactions and Define Functions in Transcriptional Activation by a DNA-Tracking Protein: Bacteriophage T4 Gene 45 Protein and Late Transcription, PNAS (1994) vol. 91, p. 7703-7707.

Sanders, UC Berkeley Jan. 7, 2013 Press Release, available at http://newscenter.berkeley.edu/2013/01/07/cheap-and-easy-technique-to-snip-dna-could-revolutionize-gene-therapy/.

Sang, Prospects for transgenesis in the chick. Mech Dev. Sep. 2004;121(9):1179-86.

Sanjana et al, A transcription activator-like effector toolbox for genome engineering, Nature Protocols, 2012, p. 171-192.

Santiago et al, Targeted gene knockout in mammalian cells by using engineered zinc-finger nucleases. Proc Natl Acad Sci U S A. Apr. 15, 20085;105(15):5809-14. doi: 10.1073/pnas.080094010i ub Mar. 21, 2008.

Sapranauskas et al, The *Streptococcus thermophilus* CRISPR/Cas system provides immunity in *Escherichia coli*. Nucleic Acids Res. Nov. 2011;39(21):9275-82. doi: 10.1093/nar/glcr606. Epub Aug. 3, 2011.

Sashital et al, Mechanism of foreign DNA selection in a bacterial adaptive immune system. Mol Cell Jun. 8, 2012;46(5):606-15. doi: 10.1016/j.mokel.2012.03.020. Epub Apr. 19, 2012.

Sauer, B. et al., Site-specific DNA recombination in mammalian cells by the Cre recombinase of bacteriophage PI, Proc. Natl. Acad. Sci. U.S.A. 1988, 85:5166-5170 (Jul. 1988).

Scholze & Bach, "TAL effectors are remote controls for gene activation," J. Curr. Opin. Microbial, 14:47-53 (2011).

Schomack et al., "Gene-for-gene-mediated recognition of nuclear-targeted AvrBs3-like bacterial effector proteins," J Plant Physiol., Feb. 2006;163(3):256-72.

Schonthal, "Regulation of gene expression by serine/threonine protein phosphatases," Semin Cancer Biol., Aug. 1995;6(4):239-48.

Schramm, Laura et al., Recruitment of RNA Polymerase III to Its Target Promoters, Genes & Development (2002) vol. 16, p. 2593-2620.

Schriefer et al., Low pressure DNA shearing: a method for random DNA sequence analysis. Nucleic Acids Res. Dec. 25, 1990;18(24):7455-6.

Schwank et al., Functional repair of CFTR by CRISPR/Cas9 in intestinal stem cell organoids of cystic fibrosis patients. Cell Stem Cell. Dec. 5, 2013; 13(6):653-8. doi: 10.1016/j.stem.2013.11.002.

Schwarze, In vivo protein transduction: delivery of a biologically active protein into the mouse, Science, vol. 285, Sep. 3, 1999 pp. 1569-1572.

Seed et al. A bacteriophage encodes its own CRISPR/Cas adaptive response to evade host innate immunity. Feb. 28, 2013. vol. 494 . Nature . pp. 489-494 doi:10.1038/nature11927.

Segal et al, Toward controlling gene expression at will: selection and design of zinc finger domains recognizing each of the 5'-GNN-3' DNA target sequences. Proc Natl Acad Sci U S A.

Sells et al, Delivery of protein into cells using polycationic liposomes. Bioteclmiques. Jul. 1995;19(1):72-6, 78.

Semenov A et al., Interference by clustered regularly interspaced short palindromic repeat (CRISPR) RNA is governed by a seed sequence. Proc Natl Acad Sci USA. Jun. 21, 2011;108(25):10098-103. doi: 10.1073/pnas.1104144108. Epub Jun. 6, 2011.

Semple et al, Rational design of cationic lipids for siRNA delivery. Nat Biotechnol. Feb. 2010;28(2):172-6. doi: 10.1038/nbt.1602. Epub Jan. 17, 2010.

Serganov et al., Coenzyme recognition and gene regulation by a flavin mononucleotide riboswitch. Nature. Mar. 12, 2009;458(7235):233-7. doi: 10.1038/nature07642. Epub Jan. 25, 2009.

Serganov et al., Structural basis for discriminative regulation of gene expression by adenineand guanine-sensing mRNAs. Chern Biol. Dec. 2004;11(12):1729-41.

Shaikh et al., Chimeras of the Flp and Cre recombinases: tests of the mode of cleavage by Flp and Cre. J Mol Biol. Sep. 8, 2000;302(1):27-48.

Shalem et al., Genome-scale CRISPR-Cas9 knockout screening in human cells. Science. Jan. 3, 2014;343(6166):84-7. doi: 10.1126/science.I247005. Epub Dec. 12, 2013.

Shanks, P., "Crispr Opportunities . . . For What? And For Whom?," Biopolitical Times, Jan. 4, 2014, http://www.biopoliticaltimes.org/article.php?id=8235.

Shao et al. Structure of the Cmr2-Cmr3 Subcomplex of the Cmr RNA Silencing Complex. Structure 21, 376-384, Mar. 5, 2013. Elsevier.

Shen et al., "Efficient genome modification by CRISPR-Cas9 nickase with minimal off-target effects," Nat Methods, 2014, 11(4):399-402.

Shen, et al., Generation of Gene-Modified Mice via Cas9/RNA-Mediated Gene Targeting, Cell Research (2013) vol. 23, p. 720-723.

Sheridan, First CRISPR-Cas patent opens race to stake out intellectual property. Nat Biotechnol. 2014;32(7):599-601.

Sheridan, Gene therapy finds its niche. Nat Biotechnol. Feb. 2011;29(2):121-8. doi: 10.1038/nbt.1769.

Shimizu et al., Adding fingers to an engineered zinc finger nuclease can reduce activity. Biochemistry. Jun. 7, 2011;50(22):5033-41. doi: 10.1021/bi200393g. Epub May 11, 2011.

Sidi Chen et al., "Genome-wide CRISPR Screen in a Mouse Model of Tumor Growth and Metastasis," Cell160, 1-15 (2015).

Siebert et al. An improved PCR method for walking in uncloned genomic DNA. Nucleic Acids Research, 1995, vol. 23, No. 6 pp. 1087-1088, especially, p. 1087.

Silva et al., "Meganucleases and Other Tools for Targeted Genome Engineering: Perspectives and Challenges for Gene Therapy," Current Gene Therapy, 11:11-27 (2011).

Silver, P., "How Proteins Enter the Nucleus," Cell, 64:489-497 (1991).

Simon et al., "Sequence-specific DNA cleavage mediated by bipyridine polyamide conjugates," Nucl. Acids Res., 36(11):3531-8 (2008).

Smith and Waterman, "Comparison of Biosequences" (1981) Adv. Appl. Math. 2:482.

Sontheimer Erik, Project 7: Establishing RNA-Directed DNA Targeting in Eukaryotic Cells; Project dates: Nov. 16, 2011 to Dec. 31, 2012 (Feb. 4, 2012).

Staals et al. Structure and Activity of the RNA-Targeting Type III-B CRISPR-Cas Complex of Thermus thermophilus. Molecular Cell 52, 135-145, Oct. 10, 2013 Elsevier. http://dx.doi.org/10.1016/j.molcel.2013.09.013.

Sternberg SH et al., "DNA interrogation by the CRISPR RNA-guided endonuclease CAS9" Nature 2014 (doi: 10.1038/nature13011).

Stoddard,"Homing endonuclease structure and function," Q. Rev. Biophys., 38:49-95 (2005).

Stolfi et al., "Tissue-specific genome editing in Ciona embryos by CRISPR/Cas9," Development (2014) 141, 4115-4120 doi: 10.1242/dev.114488.

(56) References Cited

OTHER PUBLICATIONS

Stone, "Leber Congenital Amaurosis—A Model for Efficient Genetic Testing of Heterogenous Disorders: LXIV Edward Jackson Memorial Lecture" Am J Ophthalmol. 144(6): 791-811, 2007.

Sudarsan et al., An mRNA structure in bacteria that controls gene expression by binding lysine. Genes Dev. Nov. 1, 2003;17(21):2688-97.

Sudarsan et al., Riboswitches in eubacteria sense the second messenger cyclic di-GMP. Science. Jul. 18, 2008;321(5887):411-3. doi: 10.1126/science.1159519.

Suess et al., A theophylline responsive riboswitch based on helix slipping controls gene expression vivo. Nucleic Acids Res. Mar. 5, 2004;32(4):1610-4.

Sugimoto et al., "Thermodynamic parameters to predict stability of RNA/DNA hybrid duplexes," Biochemistry, 1995,34:11211-11216.

Sugimoto et al., "Thermodynamics-structure relationship of single mismatches in RNA/DNA duplexes," Biochemistry, Sep. 19, 2000, 39(37):11270-81.

Sugio et al., "Two type III effector genes of Xanthomonas oryzae pv. oryzae control the induction of the host genes OsTFIIAgamma1 and OsTFX1 during bacterial blight of rice," Proc Natl Acad Sci USA, Jun. 19, 2007;104(25):10720-5.

Sun et al., Optimized TAL effector nucleases (TALENs) for use in treatment of sickle cell disease. Mol Biosyst. Apr. 2012;8(4): 1255-63. doi: 10.1039/c2mb05461 b. Epub Feb. 3, 2012.

Swiech et al., "In vivo interrogation of gene function in the mammalian brain using CRISPR-Cas9," Nature Biotechnology 33, 102-106 (2015).

Szczepek et al., Structure-based redesign of the dimerization interface reduces the toxicity of zinc-finger nucleases. Nat Biotechnol. Jul. 2007;25(7):786-93. Epub Jul. 1, 2007.

Tahiliani et al., "Conversion of 5-Methyl cytosine to 5-Hydroxymethylcytosine in Mammalian DNA by MLL Partner TET1," Science, 324:930-935 (2009).

Tahashi et al., 2012, Frontiers in Bioscience, vol. S4, p. 133-141.

Tan et al., "Efficient nonmeiotic allele introgression in livestock using custom endonucleases," Proc Natl Acad Sci USA, Oct. 8, 2013,110(41): 16526-31.

Tan et al., "Zinc-finger protein-targeted gene regulation: Genomewide single-gene specificity," PNAS 100:11997-12002 (2003).

Tebas et al., Gene editing of CCR5 in autologous CD4 T cells of persons infected with HIV. N Engl J Med. Mar. 6, 2014;370(10):901-10. doi: 10.1056/NEJMoa1300662.

Terns and Terns, "CRISPR-based adaptive immune systems," Curr Opin Microbiol., 2011, 14:321-327.

Tessarollo et al., Targeted mutation in the neurotrophin-3 gene results in loss of muscle sensor neurons. Proc Natl Acad Sci USA. Dec. 6, 1994;91(25):11844-8.

Tesson et al., Knockout rats generated by embryo microinjection of TALENs. Nat Biotechnol. Aug. 5, 2011;29(8):695-6. doi: 10.1038/nbt.1940.

The Delivery Problem, Nature Biotechnology, 2006, vol. 24(3), pp. 305-306.

Thermo Fisher Scientific—How Cationic Lipid Mediated Transfection Works, retrieved from the internet Aug. 27, 2015: 2 pages.

Thomas et al., "Progress and Problems with the Use of Viral Vectors for Gene Therapy," 2003, Nature Reviews/ Genetics, vol. 4, p. 346-358.

Thompson et al, Cellular uptake mechanisms and endosomal trafficking of supercharged protein. Chem Biol. Jul. 27, 2012;19(7):831-43. doi: 10.1016/j.chembiol.2012.06.014.

Thompson et al, Engineering and identifying supercharged proteins for macromolecule delivery into mammalian cells. Methods Enzymol. 2012;503:293-319. doi: 10.1016/B978-0-12¬396962-0.00012-4.

Thorpe et al, Functional correction of episomal mutations with short DNA fragments and RNA-DNA oligonucleotides. J Gene Med. Mar.-Apr3 2002;4(2):195-204.

Tiley, LS et al. The VP16 Transcription Activation Domain is Functional When Targeted to a Promoter-Proximal RNA Sequence. Genes and Development. 1992. vol. 6; pp. 2077-2087; abstract; p. 2077, first column, first paragraph.

Ting Li et al: High-efficiency TALEN-based gene editing-produces disease-resistant rice 11 Nature Biotechnology vol. 30. No. 5. May 7, 2012 (May 1, 2012) pp. 390-392. XP055086834 ISSN: 1087-0156. DOI: 10.1038/nbt.2199.

Tolia, Niraj H. et al., Slicer and the Argonautes, Nature Chemical Biology (2007) vol. 3, No. 1, p. 36-43.

Trafton, A. Editing the Genome With High Precision [online], MIT News office. Jan. 3, 2013 [retrieved on Dec. 4, 2014). Retrieved from the Internet: <URL:http:/1newsoffice.Trafton.edut2013/editing-the-genome-with-high-precision-01 03 >; pp. 1-3; p. 3, third paragraph.

Trausch et al., The structure of a tetrahydrofolate-sensing riboswitch reveals two ligand binding sites in a single aptamer. Structure. Oct. 12, 2011;19(10):1413-23. doi: 10.1016/j.str.2011.06.019. Epub Sep. 8, 2011.

Tsai et al., Dimeric CRISPR RNA-guided FokI nucleases for highly specific genome editing. Nat Biotechnol. Jun. 2014;32(6):569-76. doi: 10.1038/nbt.2908. Epub Apr. 25, 2014.

Turan et al., Site-specific recombinases: from tag-and-target- to tag-and-exchange-based genomic modifications. FASEB J. Dec. 2011;25(12):4088-107. doi: 10.1096/fj.11-186940. Epub Sep. 2, 2011. Review.

Tzur et al., "Heritable Custom Genomic Modifications in Caenorhabditis elegans via a CRISPR-Cas9 System," Genetics, 2013,195:1181-1185.

University of Berkeley Press Release—Cheap and easy technique to snip DNA could revolutionize gene therapy, Jan. 7, 2013, p. 1-3.

Uri Ben-David . *Flowing through the CRISPR-CAScade: Will genome editing boost cell therapies*? Molecular and Cellular Therapies 2013, 1:3.

Urnov et al., Genome editing with engineered zinc finger nucleases. Nat Rev Genet. Sep. 2010; 11:(9):636-46. doi: 10.1038/nrg2842.

Urnov et al., Highly efficient endogenous human gene correction using designed zinc-finger nucleases. Nature. Jun. 2, 2005;435(7042):646-51. Epub Apr. 3, 2005.

Valente et al., "Mutations in CEP290, which encodes a centrosomal protein, cause pleiotropic forms of Joubert syndrome" Nat Genet. 38: 623-625, 2006.

Van der Oost, New Tool for Genome Surgery, Science (Feb. 15, 2013) vol. 336, p. 768-768.

Van den Brulle et al., "A novel solid phase technology for high-throughput gene synthesis," BioTechniques, 45(3):340-343 (2008).

Van Duyne et al., Teaching Cre to follow directions. Proc Natl Acad Sci US A. Jan. 6, 2009;106(1):4-5. doi: 10.1073/pnas.0811624106. Epub Dec. 31, 2008.

Van Leeuwen et al. Linker length and composition influence the flexibility of Oct-1 DNA binding. EMBO J Apr. 15, 1997 vol. 2043-2053. Especialty abstract, p. 2043 col. 2 para 2, p. 2044 fig 1B.

Van Putten et al. Low dystrophin levels increase survival and improve muscle pathology and function in dystrophin/utrophin double-knockout mice. The FASEB Journal article fj.12-224170. Published online Mar. 4, 2013.

Vanamee et al., FokI requires two specific DNA sites for cleavage. J Mol Biol. May 25, 2001;309(1):69-78.

Villalobos et al., Gene Designer: a synthetic biology tool for constructing artificial DNA segments; BMC BioInformatics, vol. 7, No. 285, pp. 1-8, 2006.

Vitreschak et al., Regulation of the vitamin B 12 metabolism and transport in bacteria by a conserved RNA structural element. RNA. Sep. 2003;9(9):1084-97.

Voytas, et al., DNA Binding Made Easy, Science (2009) vol. 326, p. 1491-492.

Waaigers et al., "CRISPR/Cas9-Targeted Mutagenesis in Caenorhabditis elegans," Genetics, 2013, 15:1187-1191.

Wacey et al., Disentangling the perturbational effects of amino acid substitutions in the DNA-binding domain of p53. Hum Genet. Jan. 1999;104(1):15-22.

Wadia et al, Transducible TAT-HA fusogenic peptide enhances escape of TAT-fusion proteins after lipid raft macropinocytosis. Nat Med. Mar. 2004;10(3):310-5. Epub Feb. 8, 2004.

(56) References Cited

OTHER PUBLICATIONS

Wadia et al., Modulation of cellular function by TAT mediated transduction of full length proteins. Curr Protein Pept Sci. Apr. 2003;4(2):97-104.
Wah et al., Structure ofFokI has implications for DNA cleavage. Proc Natl Acad Sci U S A. Sep. 1, 1998;95(18):10564-9.
Walsh and Hochedlinger. *A variant CRISPR-Cas9 system adds versatility to genome engineering.* 15514-15515. PNAS. Sep. 24, 2013. Vol. 110. No. 39. ww.pnas.org/cgi/doi/10.1073/pnas.1314697110.
Wang et al, Genetic screens in human cells using the CRISPR-Cas9 system. Science. Jan. 3, 2014;343(6166):80-4. doi: 10.1126/science.l246981. Epub Dec. 12, 2013.
Wang et al, One-step generation of mice carrying mutations in multiple genes by CRISPR/Cas-mediated genome engineering. Cell. May 9, 2013;153(4):910-8. doi: 10.1016rice11.2013.04.025. Epub May 2, 2013.
Wang et al., Riboswitches that sense S-adenosylhomocysteine and activate genes involved in coenzyme recycling. Mol Cell. Mar. 28, 2008;29(6):691-702. doi: 10.1016/j.moke1.2008.01.012.
Wang et al., "The CRISPR/Cas system mediates efficient genome engineering in Bombyx mori," Cell Res., Dec. 2013, 23(12):1414-6.
Wang et al., Efficient genome editing in zebrafish using a CRISPR-Cas system. Nat Biotechnol. Mar. 2013;31(3):227-9. doi: 10.1038/nbt.2501. Epub Jan. 29, 2013.
Wang et al., Targeted gene addition to a predetermined site in the human genome using a ZFN-based nicking enzyme. Genome Res. Jul. 2012;22(7):1316-26. doi: 10.1101/gr.I22879.111. Epub 112 Mar. 20, 2012.
Weber et al., Assembly of designer TAL effectors by Golden Gate cloning. PLoS One. 2011;6(5):e19722. doi:10.1371/journal.pone.0019722. Epub May 19, 2011.
Weinberg et al., The aptamer core of SAM-IV riboswitches mimics the ligand-binding site of SAM-I riboswitches. RNA. May 2008;14(5):822-8. doi: 10.1261/rna.988608. Epub Mar. 27, 2008.
Weinberger et al., Disease-causing mutations C277R and C277Y modify gating of human CIC-1 chloride channels in myotonia congenita. J Physiol. Aug. 1, 2012;590(Pt 15):3449-64. doi: 0.1113/jphysio1.2012.232785. Epub May 28, 2012.
Westra et al. The CRISPRs, They Are A-Changin': How Prokaryotes Generate Adaptive Immunity. Annu. Rev. Genet. 2012. 46:311-39. doi:10.1146/annurev-genet-110711-155447.
Westra, Brouns et al. (2013) *TypeI-E CRISPR-Cas Systems Discriminate Target from Non-Target DNA through Base Pairing-Independent PAM Recognition*. PLoS Genet 9(9): e1003742. doi:10.1371/journal.pgen.1003742.
Wiedenheft et al., "RNA-guided genetic silencing systems in bacteria and archaea" 482 Nature 331-338 (Feb. 16, 2012).
Wilusz et al. *3 ' end processing of a long nuclear-retained non-coding RNA yields a tRNA-like cytoplasmic RNA*. Cell. Nov. 28, 2008; 135(5): 919-932. doi:10.1016/j.cell.2008.10.012.
Winkler et al., Control of gene expression by a natural metabolite-responsive ribozyme. Nature. Mar. 18, 2004;428(6980):281-6.
Winkler et al., An mRNA structure that controls gene expression by binding S-adenosylmethionine. Nat Struct Biol.Sep. 2003;10(9):701-7. Epub Aug. 10, 2003.
Wirt S.E. and Porteus M.H. Development of nuclease-mediated site-specific genome modification. Current Opinion in Immunology 2012, 24:609-616. http://dx.doi.Org/10.1016/j.coi.2012.08.005.
Wolfe et al., Analysis of zinc fingers optimized via phage display: evaluating the utility of a recognition code. J Mol Biol. Feb. 5, 1999;285(5):1917-34.
Wong et al., "Detection of aberrant p16 methylation in the plasma and serum of liver cancer patients," Cancer Res. 59:71-73 (1999)—copy provided with IDS of Dec. 19, 2013.
Wood et al., Targeted genome editing across species using ZFNs and TALENs. Science. Jul. 15, 2011;333(6040):307. doi: 10.1126/science.1207773. Epub Jun. 23, 2011.
Wright et al., "Standardized reagents and protocols for engineering zinc finger nucleases by modular assembly," Nat Protoc., 2006;1(3): 1637-52.
Written Opinion in WO/2015070083 dated May 14, 2015.
Wu et al, Correction of a genetic disease in mouse via use of CRISPR-Cas9. Cell Stem Cell. Dec. 5, 2013;13(6):659-62. doi: 10.1016/j.stem.2013.10.016.
Wu et al., "Custom-designed zinc finger nucleases: What is next?" Cell. Mol. Life Sci., 64:2933-44 (20070.
Wu X et al. Genome-wide binding of the CRISPR endonuclease Cas9 in mammalian cells. 2014. Nature Biotechnology. doi.10.1038/nbt.2889 pp. 1-9.
Xiao A et al., "CasOT: a genome-wide Cas9/gRNA off-target searching tool" 2014 BioInformatics PubMed PMID: 24389662.
Xie, RNA-Guided Genome Editing in Plants Using a CRISPR-CAS System, Molecular Plant, vol. 6., Issue 6, p. 1975-1983, Nov. 2013.
Xu et al. *A Zebrafish Embryo Culture System Defines Factors that Promote Vertebrate Myogenesis across Species*. Cell 155, 909-921, Nov. 7, 2013.Elsevier Inc. http://dx.doi.org/10.1016/j.celL2013.10.023.
Xu et al., "Cytosine methylation targetted to pre-determined sequences," Nat Genet., Dec. 1997;17(4):376-8.
Xu et al., "Genome-wide Regulation of 5hmC, 5mC, and Gene Expression by Tetl Hydroxylase in Mouse Embryonic Stem Cells," Mol. Cell, 42:451-464 (2011).
Yang et al. Clinical Whole-Exome Sequencing for the Diagnosis of Mendelian Disorders. N Engl J Med 2013. DOI: 10.1056/NEJMoa1306555. Oct. 2, 2013.
Yang et al., "Os8N3 is a host disease-susceptibility gene for bacterial blight of rice," Proc Natl Acad Sci USA, Jul. 5, 2006;103(27):10503-8.
Yang Hui et al: "One Step Generation of Mice Carrying Reporter and Conditional Alleles by CRISPR/CAS-Mediated Genome Engineering", Cell, vol. 154, No. 6, Sep. 2013, pp. 1370-1379.
Yang, Luhan et al.Optimization of Scarless Human Stem Cell Genome Editing. Supplementary Information (Published online Jul. 31, 2013 Nucleic Acids Research, 2013, vol. 41, No. 19 9049-9061 doi:10.1093/nar/gkt555.
Yanover et aL, Extensive protein and DNA backbone sampling improves structure-based specificity prediction for C2H2 zinc fingers. Nucleic Acids Res. Jun. 2011;39(11):4564-76. doi: 10.1093/nar/gkr048. Epub Feb. 22, 2011.
Yarris L. Programmable DNA Scissors Found for Bacterial Immune System. Berkeley Lab News Center. http://newscenter.lbl.gov/feature-stories/2012/06/28/programmable-dna-scissors/[Jun. 29, 2013 6:45:51 PM] Jun. 28, 2012.
Yazaki et al, Hereditary systemic amyloidosis associated with a new apolipoprotein All stop codon mutation Stop78Arg. Kidney Int. Jul. 2003;64(1):11-6.
Yeager, "Genome Editing in a FLASH," BioTechniques, Apr. 4, 2012, 2 pages http://www.biotechniques.com/news/Genome-Editing-in-a-FLASH/biotechniques-3 293 67 .html.
Yin et al., Genome editing with Cas9 in adult mice corrects a disease mutation and phenotype. Nat Biotechnol. Jun. 2014;32(6):551-3. doi: 10.1038/nbt.2884. Epub Mar. 30, 2014.
Zelphati et al, Intracellular delivery of proteins with a new lipid-mediated delivery system. J Biol Chem. Sep. 14, 2001;276(37):35103-10. Epub Jul. 10, 2001.
Zetsche et al. "A split-Cas9 architecture for inducible genome editing and transcription modulation," Nature biotechnology, 33(2): 139-142 (2015).
Zhang et aL, Conditional gene manipulation: Cre-ating a new biological era. J Zhejiang Univ Sci Jul. 13, 2012;13(7):511-24. doi: 10.1631/jzus.B1200042. Review.
Zhang et al. (CRISPR/Cas9 for genome editing: progress, implications and challenges, Hum Mol Genet. Sep. 15, 2014;23(R 1 ):R40-6).
Zhang et al., "Tet1 is a DNA-binding protein that modulates DNA methylation and gene transcription via hydroxylation of 5-methylcytosine," Cell Res. 20:1390-1393 (2010).
Zhang et al., Efficient construction of sequence-specific TAL effectors for modulating mammalian transcription. Nat Biotechnol. Feb. 2011;29(2):149-53. doi: 10.1038/nbt.1775. Epub Jan. 19, 2011.

(56) References Cited

OTHER PUBLICATIONS

Zhang Feng, Genome Engineering Using TALEs. Third Rock Venture. Nov. 12, 2012.
Zhen Anjie and Kitchen Scott. Stem-Cell-Based Gene Therapy for HIV Infection. Viruses 2014, 6, 1-12; doi:10.3390/v6010001, ISSN 1999-4915, www.mdpi.coin/journal/viruses. Review.
Zhou et al. Alteration of substrate specificities of thermophilic alpha/beta hydro lases through domain swapping and domain interface optimization. Acta Biochim Biophys Sin Dec. 2012 Vo144 No .12 pp. 965-973. Especially abstract.
Zhou et al., "High-throughput screening of a CRISPR/Cas9 library for functional genomics" Nature. May 22, 2014;509(7501):487-91. doi: 10.1038/nature13166. Epub Apr. 9, 2014.
Zimmermann et al, Molecular interactions and metal binding in the theophylline-binding core of au RNA aptamer. RNA. May 2000;6(5):659-67.
Zorko et al, Cell-penetrating peptides: mechanism and kinetics of cargo delivery. Adv Drug Deliv Rev. Feb. 28, 2005;57(4):529-45. Epub Jan. 22, 2005.
Zou et al., Gene targeting of a disease-related gene in human induced pluripotent stem and embryonic stem cells. Cell Stem Cell. Jul. 2, 2009;5(1):97-110. doi: 10.1016/j.stem.2009.05.023. Epu Jun. 18, 2009.
Cheng et al., "Multiplexed activation of endogenous genes by CRISPR-on, an RNA-guided transcriptional activator system" Cell Research, 23:1163-1171 (2013).
Gilbert et al., "A novel short hairpin RNA (shRNA) expression system promotes Sox9-dependent gene silencing" Plasmid, 62:50-55 (2009).
International Search Report and Written Opinion for International Application No. PCT/US2014/064663, dated Mar. 3, 2015.
Larson et al., "CRISPR interference (CRISPRi) for sequence-specific control of gene expression" Nature Protocols, 8(11):2196 (2013).
Mali et al., "CAS9 transcriptional activators for target specificity screening and paired nickases for cooperative genome engineering" Nature Biotechnology, 31(9):833-838 (2013).
Qi et al., "Repurposing CRISPR as an RNA-Guided Platform for Sequence-Specific Control of Gene Expression" Cell Press, 152(5):1173-1183 (2013).
Translation of Japanese Office Action cited in Application No. 2016-553250 dated Aug. 22, 2018 (9 pages).
Grounds of Opposition in European Patent No. 3,066,201, dated Dec. 7, 2018 (38 pages).
"Sequence of a Cas9 protein from *Staphylococcus aureus*" GenBank: CCK74173.1, dated Jan. 21, 2015 (2 pages).
Chylinski et al., "Classification and evolution of type II CRISPR-Cas systems." Nucleic Acids Res. 2014,42(10):6091-105. Supplementary Table S1 (76 pages).
Bouard et al., "Viral vectors: from virology to transgene expression" Brit. J. of Pharma. 157:153-165 (2009).
Joglekar et al., "Integrase-defective Lentiviral Vectors as a Delivery Platform for Targeted Modification of Adenosine Deaminase Locus" Molecular Therapy 21(9): 1705-1717 (2013).
Arguments in Support of Opposition of European Patent No. 3,066,201, dated Dec. 2018 (9 pages).
Pfeifer et al., "Delivery of the Cre recombinase by a self-deleting lentiviral vector: Efficient gene targeting in vivo" PNAS 98(20):11450-11455 (Sep. 25, 2001).
Zhang et al., "A suicidal zinc finger nuclease expression coupled with a surrogate reporter for efficient genome engineering" Biotechnol. Letters, published Oct. 4, 2014 (7 pages).
Silver and Livingston, "Self-Excising Retroviral Vectors Encoding the Cre Recombinase Overcome Cre-Mediated Cellular Toxicity" Molecular Cell 8:233-243 (Jul. 2001).
Bondy-Denomy et al., "Bacteriophage genes that inactivate the CRISPR/Cas bacterial immune system", NATURE, Jan. 17, 2013, 493(7432), pp. 429-432.
Examination Report issued in Canadian Application No. 2,930,015 dated Dec. 29, 2020, 6 pages.

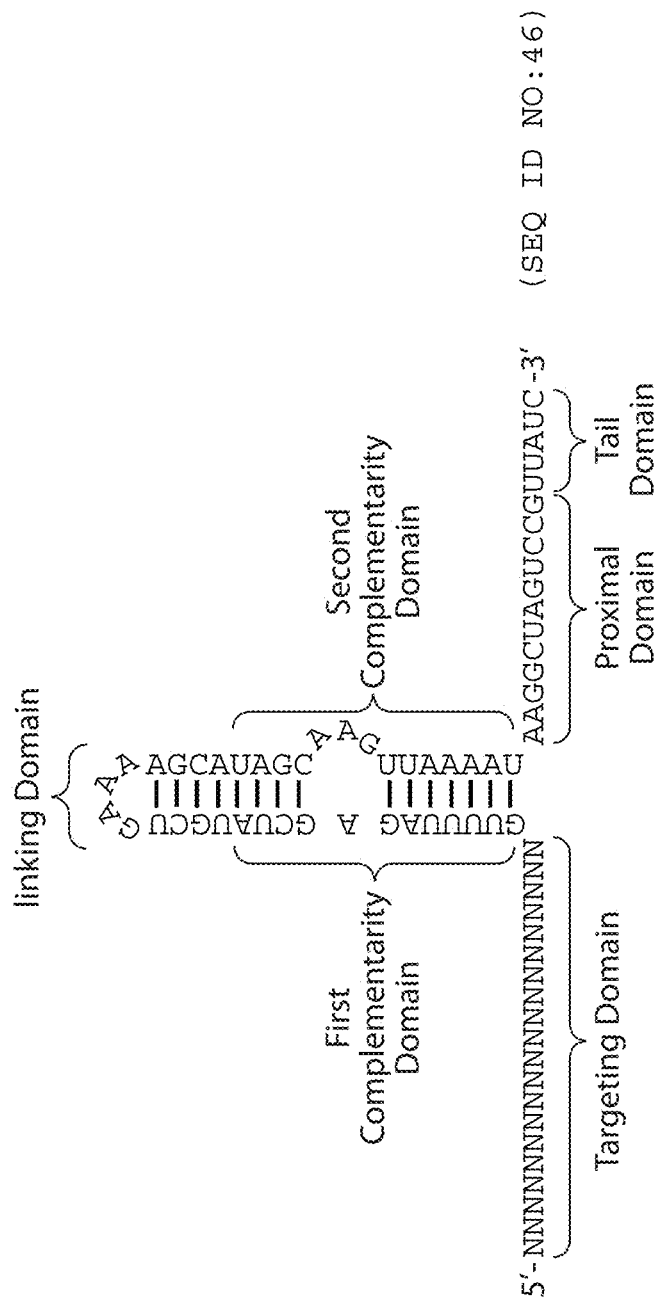

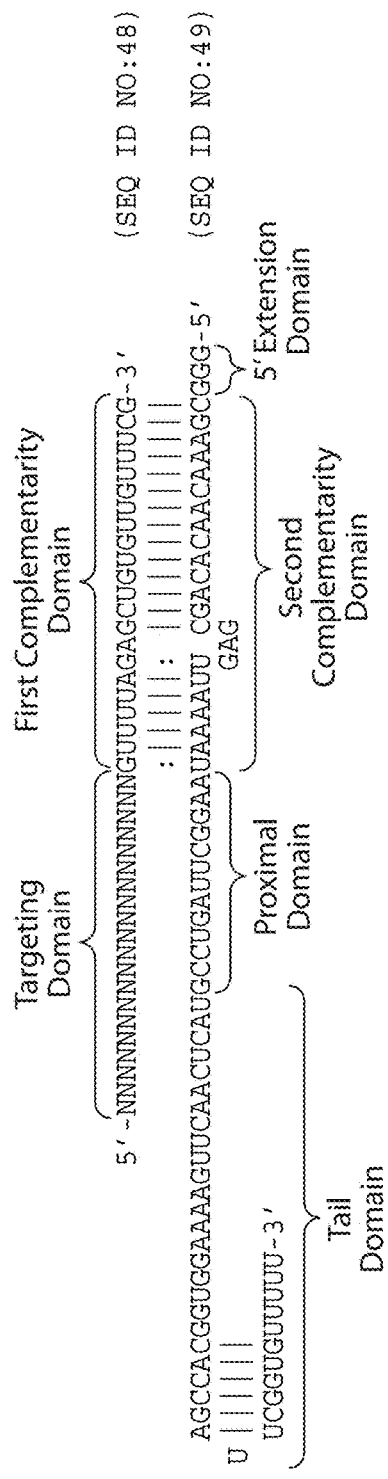

```
CLUSTAL format alignment by MAFFT (v7.058b)
                                                                                    Y SM        KKPYSIGLDIGTNSVGWAVVTDDYKVPAKKMKVLGNTDKSHIEKNLLGALLFDSGNTAED
SP        DKKYSIGLDIGTNSVGWAVITDEYKVPSKKFKVLGNTDRHSIKKNLIGALLFDSGETAEA
ST        TKPYSIGLDIGTNSVGWAVTTDNYKVPSKKMKVLGNTSKKYIKKNLLGVLLFDSGITAEG
LI        KKPYTIGLDIGTNSVGWAVLTDQYDLVKRKMKIAGDSEKKQIKKNFWGVRLFDEGQTAAD
           *::****************  **::.  :*::*:  *::::  *. ****.* **
Motif:    -K-Y*IGLDIGTNSVGWAV-TD*Y-*---*K*K*-G**-*--I*KN*--G--LFD-G-TA--

SM        RRLKRTARRRYTRRRNRILYLQEIFSEEMGKVDDSFFHRLEDSFLVTEDKRGERHPIFGN
SP        TRLKRTARRRYTRRKNRICYLQEIFSNEMAKVDDSFFHRLEESFLVEEDKKHERHPIFGN
ST        RRLKRTARRRYTRRRNRILYLQEIFSTEMATLDDAFFQRLDDSFLVPDDKRDSKYPIFGN
LI        RRMARTARRRIERRRNRISYLQGIFAEEMSKTDANFFCRLSDSFYVDNEKRNSRHPFFAT
          ::  ******   *:***: *** **  **.  *   ** **..**:.*  . :*::
Motif:    -R*-RTARRR--RR*NRI-YLQ-IF*-EM---D--FF-RL-*SF-V-K--P*F--

SM        LEEEVKYHENFPTIYHLRQYLADNPEKVDLRLVYLALAHIIKFRGHFLIEGKFDTRNNDV
SP        IVDEVAYHEKYPTIYHLRKKLVDSTDKADLRLIYLALAHMIKFRGHFLIEGDLNPDNSDV
ST        LVEEKAYHDEFPTIYHLRKYLADSTKKADLRLVYLALAHMIKYRGHFLIEGEFNSKNNDI
LI        IEEEVEYHKNYPTIYHLREELVNSSEKADLRLVYLALAHIIKYRGNFLIEGALDTQNTSV
          : :*  ** :.********: *:.. .*.********:**:**:*****.   : .*
Motif:    *--*E--YH-**PTIYHLR*-L-*--K-DLRL*YLALAH*IK*RGNFLIEG-**-N--*
```

Fig. 2

```
SM      QRLFQEFLAVYDNTFENSS------LQEQNVQVEEILTDKISKSAKKDRVLKLFPNEKSN
SP      DKLFIQLVQTYNQLFEENP------INASGVDAKAILSARLSKSRRLENLIAQLPGEKKN
ST      QKNFQDFLDTYNAIFESDL------SLENSKQLEEIVKDKISKLEKKDRILKLFPGEKNS
LI      DGIYKQFIQTYNQVFASGIEDGSLKKLEDNKDVAKILVEKVTRKEKLERILKLYPGEKSA
         :  . :::. *: .           .       *  .  :    : ::  . *.*.
Motif:  *---*-*****--Y*--f-------------*------I*--*****-*:-**--P-EK--

SM      GRFAEFLKLIVGNQADFKKHFELEEKAPLQFSKDTYEEELEVLLAQIGDNYAELFLSAKK
SP      GLFGNLIALSLGLTPNFKSNFDLAEDAKLQLSKDTYDDDLDNLLAQIGDQYADLFLAAKN
ST      GIFSEFLKLIVGNQADFRKCFNLDEKASLHFSKESYDEDLETLLGYIGDDYSDVFLKAKK
LI      GMFAQFISLIVGSKGNFQKPFFDLIEKSDIECAKDSYEEDLESLLALIGDEYAELFVAAKN
        * *.:.: *  :  . *:. *  ** *  *.:.**:: .* *  .: **.
Motif:  G-F-***-L-*G----*F*--F*L-E*---*KY*L*-LL--IGD*Y****F*-AK*

SM      LYDSILLSGILTVTDVGTKAPLSASMIQRYNEHQMDLAQLKQFIRQKLSDKYNEVFSDVS
SP      LSDAILLSDILRVNTEITKAPLSASMIKRYDEHHQDLTLLKALVRQQLPEKYKEIFFDQS
ST      LYDAILLSGFLTVTDNETEAPLSSAMIKRYNEHKEDLALLKEYIRNISLKTYNEVFKDDT
LI      AYSAVVLSSIITVAETETNAKLSASMIERFDTHEEDLGELKAFIKLHLPKHYEIFSNTE
         . : *** :: * :   * ** ** :: . :**  * . *. : ..  *  * .
Motif:  ---***LS-**-V----T*A-LS**MI*R**-H--DL--LK---*------Y*E*F*---

SM      KDGYAGYIDGKTNQEAFYKYLKGLLNKIEGSSGYFLDKIEREDFLRKQRTFDNGSIPHQIH
SP      KNGYAGYIDGGASQEEFYKFIKPILEKMDGTEELLVKLNREDLLRKQRTFDNGSIPHQIH
ST      KNGYAGYIDGKTNQEDFYVVLKKLLAEFEGADYFLEKIDREDFLRKQRTFDNGSIPYQIH
LI      KHGYAGYIDGKTKQADFYKYMKMTLENIEGADYFIAKIEKENFLRKQRTFDNGAIPHQLH
        *.********  .*: **  :*  *   .*:: :*::*:..:**********:**:*:*
Motif:  K-GYAGYIDG-*-Q--FY-K--L-*G*---K*E**LRKQRTFDNG*IP*Q*H
```

Fig. 2 (Continued)

```
SM      LQEMRAIIRRQAEFYPFLADNQDRIEKLLTFRIPYYVGPLARGKSDFAWLSRKSADKITP
SP      LGELHAILRRQEDFYPFLKDNREKIEKILTFRIPYYVGPLARGNSRFAWMTRKSEETITP
ST      LQEMRAILDKQAKFYPFLAKNKERIEKILTFRIPYYVGPLARGNSDFAWSIRKRNEKITP
LI      LEELEAILHQQAKYYPFLKENYDKIKSLVTFRIPYFVGPLANGQSEFAWLTRKADGEIRP
         *  **:   *  :*****  .: :::*.:*********.   ***  ** .*    *
Motif:  L-E*-AI*--*Q---*YPFL--N-**I*-**TFRIPY*VGPLA-G*S-FAW--RK----I-P SM      WNFDEIVDKESSAEAFINRMTNYDLYLPNQKVLPKHSLLYEKFTVYNELTKVKYTE-QG
SP      WNFEEVVDKGASAQSFIERMTNFDKNLPNEKVLPKHSLLYEYFTVYNELTKVKYVTEGMR
ST      WNFEDVIDKESSAEAFINRMTSFDLYLPEEKVLPKHSLLYETFNVYNELTKVRFIAESMR
LI      WNIEEKVDFGKSAVDFIEKMTNKDTYLPKENVLPKHSLCYQKYLVYNELTKVRYIND-QG
        **: : :* ..** *** :** :*  **::****** *   .*********: : 
Motif:  WN****-*D---SA--FI**MT--D--LP***VLPKHSL-Y*-*-VYNELTKV**--*---

SM      KTAFFDANMKQEIFDGVFKVYRKVTKDKLMDFLEKEFDEFRIVDLTGLDKENKVFNASYG
SP      KPAFLSGEQKKAIVDLLFKTNRKVTVKQLKEDYFKKIECFDSVEISGVEDR---FNASLG
ST      DYQFLDSKQKKDIVRLYFKDKRKVTDKDIIEYL-HAIYGYDGIELKGIEKQ---FNSSLS
LI      KTSYFSGQEKEQIFNDLFKQKRVKKKDLELFL-RNMSHVESPTIEGLEDS---FNSSYS
         :  :    :: *.: * *  *.  : ::  :     :      :    ***  .
Motif:  ----*--*-K*-I-----FK--RKV----*----*------*--G**------FN*S--

SM      TYHDLCKIL-DKDFLDNSKNEKILEDIVLTLTLFEDREMIRKRLENYSDLLTKEQVKKLE
SP      TYHDLLKIIKDKDFLDNEENEDILEDIVLTLTLFEDREMIEERLKTYAHLFDDKVMKQLK
ST      TYHDLLNIINDKEFLDDSSNEAIIEEIIHTLTIFEDREMIKQRLSKFENIFDKSVLKKLS
LI      TYHDLLKVGIKQEILDNPVNTEMLENIVKILTVFEDKRMIKEQLQQFSDVLDGVVLKKLE
        *****    :    :**   .    **: .**:****.  :      :   *: : 
Motif:  TYHDL-----*LD*--N--**E*I*--LT*FED*-MI-L---*--*K*L--
```

Fig. 2 (Continued)

```
SM      RRHYTGWGRLSAELIHGIRNKESRKTILDYLIDDGNSRNFMQLINDDALSFKEEIAKAQ
SP      RRRYTGWGRLSRKLINGIRDKQSGKTILDFLKSDGFANRNFMQLIHDDSLTFKEDIQKAQ
ST      RRHYTGWGKLSAKLINGIRDEKSGNTILDYLIDDGISNRNFMQLIHDDALSFKKIQKAQ
LI      RRHYTGWGRLSAKLLMGIRDKQSHLTILDYLMNDDGLNRNLMQLINDSNLSFKSIIEKEQ
        **:******.**  **:  **********:*******:******:* ****:   *
Motif:  RR*YTGWG*LS--L*-GIR***S--TILD*L--D---NRN*MQLI*D--L*FK---I-K-Q ┌────────────────┐
                                                        │  B  │
                                                        └──┬─────────────┘
                                                           │
                                                           ▼
SM      VIGETD--NLNQVVSDIAGSPAIKKGILQSLKIVDELVKIMG-HQPEN┌IVVEMARENQFT
SP      VSGQGD--SLHEHIANLAGSPAIKKGILQTVKVVDELVKVMGRHKPEN│IVIEMARENQTT
ST      IIGDEDKGNIKEVVKSLPGSPAIKKGILGSIKIVDELVKVMGGRKPES│IVVEMARENQYT
LI      VTTADK--DIQSIVADLAGSPAIKKGILQSLKIVDELVSVMG-YPPQT│IVVEMARENQTT
        :   .   .:  :  * ***********. *:******.:**    *└**:*********
Motif:  *------*--*-GSPAIKKGILQ**K*VDELV-**MG---P*--[IV*EMARENQ-T SM      NQGRRNSQQRLKGLTDSIKEFGSQILKEH------PVENSQLQNDRLFLYYLQNGRDMYT
SP      QKGQKNSRERMKRIEEGIKELGSQILKEH------PVENTQLQNEKLYLYLYLQNGRDMYV
SP      NQGKSNSQQRLKLEKSILKELGSKILKENIPAKLSKIDNNALQNDRLYLYLYLQNGKDMYT
LI      GKGKNNSRPRYKSLEKAIKEFGSQILKEH------PTDNQELRNNRLYLYLYLQNGKDMYT
         :*: **:     * :* :**:**:****.     **  :  :**:** .******:**:
Motif:  --*G---NS*-R-K-*----*KE*GS*ILKE*-------*N--L*N**L*LYYLQNG*DMY- ┌────────────────┐
                                                        │  G  │
                                                        └──┬─────────────┘
                                                           │
                                                           ▼
SM      GEELDIDYLSQY┌DIDHIIPQAFIKDNSIDNRVLTSSKENRGKSDDVPSKDVVRKMKSYWS
SP      DQELDINRLSDY│DVDHIVPQSFLKDDSIDNKVLTRSDKNRGKSDNVPSEEVVKKMKNYWR
ST      GDDLDIDRLSNY│DIDHIIPQAFLKDNSIDNKVLVSSASNRGKSDDVPSLEVVKKRKTFWY
LI      GQDLDIHNLSNY│DIDHIVPQSFITDNSIDNLVLTSSAGNREKGDDVPPLEIVRKRKVFWE
         ::* *:  **:└**:**:**:*: .:****  **..: **: .*:**  * *:*: :*
Motif:  --**LDI--LS*-YD*DHI*PQ-F*-D*SIDN-VL--S--NR-K-D*VP--***K-**W-
```

Fig. 2 (Continued)

```
SM      KLLSAKLITQRKFDNLTKAERGGLTDDDKAGFIKRQLVETRQITKHVARILDERFNTETD
SP      QLLNAKLITQRKFDNLTKAERGGLSELDKAGFIKRQLVETRQITKHVAQILDSRMNTKYD
ST      QLLKSKLISQRKFDNLTKAERGGLSPEDKAGFIQRQLVETRQITKHVARLLDEKFNNKKD
LI      KLYQGNLMSKRKFDYLTKAERGGLTEADKARFIHRQLVETRQITKNVANILHQRFNYEKD
        :.* .:..:*::***.*****       *    **  * ::******:**: .:: .: *
Motif:  *L----*L***RKFD-LTKAERGGL*---DKA-FI*RQLVETRQITK*VA-*L--**N-*-D SM      ENNKKIRQVKIVTLKSNLVSNFRKEFELYKVREINDYHHAHDAYLNAVIGKALLGVYPQL
SP      ENDKLIREVKVITLKSKLVSDFRKDFQFYKVREINNYHHAHDAYLNAVVGTALIKKYPKL
ST      ENNRAVRTVKIITTLKSTLVSQFRKDFELYKVREINDFHHAHDAYLNAVVASALLKKYPKL
LI      DHGNTMKQVRIVTLKSALVSQFRKQFQLYKVRDVNDYHHAHDAYLNGVVANTLLKVYPQL
        :. .  : *::* ***:***:***:*: ****::*:.*********.*:...**  **:*
Motif:  *.*---*-V***TLKS-LVS-FRK*FLYKV*N**HHAHDAYLN-V*---*L---YP*L SM      EPEFVYGDYPHFHGHKE------NK-ATAKKFFYSNIMNFFKKDDVRTD-----------
SP      ESEFVYGDYKVYDYKVYDVRKMIAKSEQEIGK-ATAKYFFYSNIMNFFKTEITLANGEIRKRPLI
ST      EPEFVYGDYPKYNSFRE------RKSATEKVYFYSNIMNIFKKSISLADGRVIERPLI
LI      EPEFVYGDYHQFDWFKA------NK-ATAKKQFYTNIMLFFAQKDRIID----------
        *.********     .:      .* * ::: **:***::*. :: 
Motif:  E-EFVYGDY---*----*------K-AT-K--FY*NIM-*F----*-----------

SM      ----KNGEIIWKKDEHISNIKKVLSYPQVNIVKKVEEQTGGFSKE---------SILPK
SP      ETNGETGEIVWDKGRDFATVRKVLSMPQVNIVKKTEVQTGGFSKE---------SILPK
ST      EVNEETGESVWNKESDLATVRRVLSYPQVNVVKKVEEQNHGLDRGKPKGLFNANLSSKPK
LI      ----ENGEILWDK-KYLDTVKKVMSYRQMNIVKKTEIQKGEFSKA---------TIKPK
            : *  *.* : :  .*:: ::. * *:***.*  : *.   
Motif:  ----*-GE-*W-K---*-----**V*M--Q*N*VKK-E-Q--*--------*--PK
```

Fig. 2 (Continued)

```
SM      GNSDK-LIPRKTKKFYWDTKKYGGFDSPIVAYSILVIADIEKGKSKKLKTVKALVGVTIM
SP      RNSDK-LIARKKD---WDPKKYGGFDSPTVAYSVLVVAKVEKGKSKKLKSVKELLGITIM
ST      PNSNENLVGAKEY---LDPKKYGGYAGISNSFTVLVKGTIEKGAKKKITNVLEFQGISIL
LI      GNSSK-LIPRKTN---WDPMKYGGLDSPNMAYAVVI--EYAKGKN-KLVFEKKIIRVTIM
        **:.:  *     *    *  ****  .   : ::::::  .     :  : :*: **:
Motif:  -NS-*-L*--K-----D---KYGG------------KG----K*-----*--**I*

SM      EKMTFERDPVAFLERKGYRNVQEENIIKLPKYSLFKLENGRKRLLAS------ARELQK
SP      ERSSFEKNPIDFLEAKGYKEVKKDLIIKLPKYSLFELENGRKRMLAS------AGELQK
ST      DRINYRKDKLNFLLEKGYKDI--ELIIELPKYSLFELSDGSRRMLASILSTNNKRGEIHK
LI      ERKAFEKDEKAFLEEQGYRQP--KVLAKLPKYTLYECEEGRRRMLAS------ANEAQK
         :  :::  . ** :.**::      . : :****:*:   * ::*:**      *  :*
Motif:  *--*--*-----FL----*GY**------*-*LPKY*L**----*G--*R*LAS------E--*K SM      GNEIVLPNHLGTLLYHAKNIHKV------DEPKHLDYVDKHKDEFKELLDVVSNFSKKYT
SP      GNELALPSKYVNFLIYLASHYEKLKGSPEDNEQKQL-FVEQHKHYLDEIIEQISEFSKRVI
ST      GNQIFLSQKFVKLLIYHAKRISNT------INENHRKYVENHKKEFEELFYILEFNENYV
LI      GNQQVLPNHLVTLLHHAANCEVS------DGKSLDYIESNREMFAELLAHVSEFAKRYT
        **:   : :  ::: :  :    .:          .:         **:  :* *:  *
Motif:  GN*--L--*----*L*--A-----*-----*---**-**--*-*-E**-**-*F*----

SM      LAEGNLEKIKELYAQNNGEDLKELASSFI------NLLTFTAIGAPATFKFFDKNIDR
SP      LADANLDKVLSAYNKHRDKPIREQAENII-----HLFTLTNLGAPAAFKYFDTTIDR
ST      GAKKNGKLLNSAFQSWQNHSIDELCSSFIGPTGSERKGLFELTSRGSAADFEFLGVKIPR
LI      LAEANLNKINQLFEQNKEGDIKAIAQSFV------DLMAFNAMGAPASFKFETTIER
         *  * :: . ::    .   :   :*.           :  * .:*.*::    * *
Motif:  -A--N---*----*------L*---G*--A-F***--.-*--I-R Fig. 2 (Continued)
```

```
SM  KR-YTSTTEILNATLIHQSITGLYETRIDLNKLGGD      (SEQ ID NO:1)
SP  KR-YTSTKEVLDATLIHQSITGLYETRIDLSQLGGD      (SEQ ID NO:2)
ST  YRDYTPSSLLKDATLIHQSVTGLYETRIDLAKLGEG      (SEQ ID NO:3)
LI  KR-YNNLKELLNSTIIYQSITGLYESRKRLD----D      (SEQ ID NO:4)
     *  .   : ::*:*:******:*******  *    .

Motif: -R-Y-----*-**T*I*QS*TGLYE*R--L------
```

Fig. 2 (Continued)

Alignment of the N terminal RucV-like Domains disclosed in Chylinski et al. (excluding sequence outliers).
(CLUSTAL format alignment by MAFFT (v7.058b))

```
1    DIGTNSVGWAVT  (SEQ ID NO:54)
12   DIGTNSVGWAVT  (SEQ ID NO:55)
3    DVGTNSVGWAVT  (SEQ ID NO:56)
20   DVGTNSVGWAVT  (SEQ ID NO:57)
15   DMGTNSVGWAVT  (SEQ ID NO:58)
4    DVGTSSVGWAVT  (SEQ ID NO:59)
7    DIGTASVGWAVT  (SEQ ID NO:60)
6    DVGTGSVGWAVT  (SEQ ID NO:61)
9    DIGTNSVGWAVV  (SEQ ID NO:62)
10   DIGTNSVGWAVI  (SEQ ID NO:63)
11   DIGTNSVGWAVL  (SEQ ID NO:64)
42   DLGTNSVGWAVV  (SEQ ID NO:65)
48   DLGTNSIGWAI-  (SEQ ID NO:66)
43   DLGTNSIGWALV  (SEQ ID NO:67)
2    DIGTNSVGWCVT  (SEQ ID NO:68)
14   DIGTNSVGYAVT  (SEQ ID NO:69)
5    DMGTGSLGWAVT  (SEQ ID NO:70)
16   DIGTSSVGWAAI  (SEQ ID NO:71)
8    DLGTGSVGWAVV  (SEQ ID NO:72)
22   DLGVGSVGWAII  (SEQ ID NO:73)
23   DLGIASIGWAII  (SEQ ID NO:74)
24   DLGIASVGWAIV  (SEQ ID NO:75)
25   DLGVASVGWSIV  (SEQ ID NO:76)
26   DIGIASVGWAIL  (SEQ ID NO:77)
28   DLGISSVGWSVI  (SEQ ID NO:78)
32   DIGIASVGWSVI  (SEQ ID NO:79)
33   DLGISIGWAVI   (SEQ ID NO:80)
39   DVGIGSIGWAVI  (SEQ ID NO:81)
34   DLGVGSIGFAIV  (SEQ ID NO:82)
47   DIGYASIGWAVI  (SEQ ID NO:83)
50   DTGTNSLGWAIV  (SEQ ID NO:84)
49   DLGTNSIGWCLL  (SEQ ID NO:85)
18   DIGTDSLGWAVF  (SEQ ID NO:86)
41   DIGSNSIGFAVV  (SEQ ID NO:87)
45   DLGVGSIGVAVA  (SEQ ID NO:88)
     DLGIASCGWGVV
```

Fig. 3A

| | | |
|---|---|---|
| 21 | DLGIASVGWCLT | (SEQ ID NO:89) |
| 27 | DIGIGSVGVGIL | (SEQ ID NO:90) |
| 29 | DIGITSVGYGLI | (SEQ ID NO:91) |
| 30 | DIGITSVGFGII | (SEQ ID NO:92) |
| 31 | DVGITSTGYAVL | (SEQ ID NO:93) |
| 40 | DLGITSFGYAIL | (SEQ ID NO:94) |
| 17 | DIGNASVGWSAF | (SEQ ID NO:95) |
| 19 | DVGTNSCGWVAM | (SEQ ID NO:96) |
| 35 | DVGERSIGLAAV | (SEQ ID NO:97) |
| 36 | DVGLNSVGLAAV | (SEQ ID NO:98) |
| 37 | DVGLMSVGLAAI | (SEQ ID NO:99) |
| 38 | DVGTFSVGLAAI | (SEQ ID NO:100) |
| 13 | DIGTGSVGYACM | (SEQ ID NO:101) |
| 44 | DLGTTSIGFAHI | (SEQ ID NO:102) |
| 46 | DLGTNSIGSSVR | (SEQ ID NO:103) |
| | * * * * | |

Fig. 3A (Continued)

Alignment of the N terminal RucV-like Domains disclosed in Chylinski et al.
(CLUSTAL format alignment by MAFFT (v7.058b))

| | | |
|---|---|---|
| 1 | D----IGTNSVGWAVT | (SEQ ID NO:104) |
| 12 | D----IGTNSVGWAVT | (SEQ ID NO:105) |
| 3 | D----VGTNSVGWAVT | (SEQ ID NO:106) |
| 20 | D----VGTNSVGWAVT | (SEQ ID NO:107) |
| 15 | D----MGTNSVGWAVT | (SEQ ID NO:108) |
| 4 | D----VGTSSVGWAVT | (SEQ ID NO:109) |
| 7 | D----IGTASVGWAVT | (SEQ ID NO:110) |
| 6 | D----VGTGSVGWAVT | (SEQ ID NO:111) |
| 9 | D----IGTNSVGWAVV | (SEQ ID NO:112) |
| 10 | D----IGTNSVGWAVI | (SEQ ID NO:113) |
| 52 | D----IGTNSIGWAVI | (SEQ ID NO:114) |
| 11 | D----IGTNSVGWAVI | (SEQ ID NO:115) |
| 42 | D----LGTNSVGWAVL | (SEQ ID NO:116) |
| 48 | D----LGTNSIGMAVV | (SEQ ID NO:117) |
| 43 | D----LGTNSIGWAI- | (SEQ ID NO:118) |
| 2 | D----LGTNSIGMALV | (SEQ ID NO:119) |
| 14 | D----IGTNSVGWCVT | (SEQ ID NO:120) |
| 5 | D----IGTNSVGYAVT | (SEQ ID NO:121) |
| 16 | D----MGTGSLGWAVT | (SEQ ID NO:122) |
| 8 | D----IGTSSVGWAAI | (SEQ ID NO:123) |
| 22 | D----LGTGSVGWAVV | (SEQ ID NO:124) |
| 23 | D----LGVGSVGWAIV | (SEQ ID NO:125) |
| 24 | D----LGIASIGWAII | (SEQ ID NO:126) |
| 68 | D----LGIASVGWAIV | (SEQ ID NO:127) |
| 25 | D----LGIASVGWAVV | (SEQ ID NO:128) |
| 26 | D----LGVASVGWSIV | (SEQ ID NO:129) |
| 66 | D----IGIASVGWAIL | (SEQ ID NO:130) |
| 59 | D----IGIASVGWAVL | (SEQ ID NO:131) |
| 61 | D----IGIASVGWAVI | (SEQ ID NO:132) |
| 64 | D----IGIASIGWAII | (SEQ ID NO:133) |
| 62 | D----VGIASVGWAVI | (SEQ ID NO:134) |
| 67 | D----IGIASVGWAL- | (SEQ ID NO:135) |
| 32 | D----IGIASVGWAMV | (SEQ ID NO:136) |
| 28 | D----LGISSVGWSVI | (SEQ ID NO:137) |
| 63 | D----IGITSVGWAVI | (SEQ ID NO:138) |

Fig. 3B

| | | |
|---|---|---|
| 33 | D-----VGIGSIGWAVI | (SEQ ID NO:139) |
| 57 | D-----LGISSLGWAIV | (SEQ ID NO:140) |
| 39 | D-----LGVGSIGFAIV | (SEQ ID NO:141) |
| 34 | D-----IGYASIGWAVI | (SEQ ID NO:142) |
| 50 | D-----LGTNSIGWCLL | (SEQ ID NO:143) |
| 54 | D-----LGTNSIGWGLL | (SEQ ID NO:144) |
| 47 | D-----TGTNSLGWAIV | (SEQ ID NO:145) |
| 49 | D-----IGTDSLGWAVF | (SEQ ID NO:146) |
| 51 | D-----LGSTSLGWAIF | (SEQ ID NO:147) |
| 58 | D-----LGISSIGWAFS | (SEQ ID NO:148) |
| 21 | D-----LGIASVGWCLT | (SEQ ID NO:149) |
| 45 | D-----LGIASCGWGVV | (SEQ ID NO:150) |
| 18 | D-----LGSNSIGFAVV | (SEQ ID NO:151) |
| 65 | D-----IGTTSIGFSVI | (SEQ ID NO:152) |
| 29 | D-----IGITSVGYGLI | (SEQ ID NO:153) |
| 30 | D-----IGITSVGFGII | (SEQ ID NO:154) |
| 44 | D-----LGTTSIGFAHI | (SEQ ID NO:155) |
| 27 | D-----IGIGSVGVGIL | (SEQ ID NO:156) |
| 41 | D-----LGVGSIGVAVA | (SEQ ID NO:157) |
| 31 | D-----VGITSTGYAVL | (SEQ ID NO:158) |
| 40 | D-----LGITSFGYAIL | (SEQ ID NO:159) |
| 53 | D-----IGTSSIGWWLY | (SEQ ID NO:160) |
| 55 | D-----LGSNSLGWFVT | (SEQ ID NO:161) |
| 56 | D-----LGANSLGWFVV | (SEQ ID NO:162) |
| 17 | D-----IGNASVGWSAF | (SEQ ID NO:163) |
| 19 | D-----VGTNSCGWVAM | (SEQ ID NO:164) |
| 35 | D-----VGERSIGLAAV | (SEQ ID NO:165) |
| 36 | D-----VGLNSVGLAAV | (SEQ ID NO:166) |
| 37 | D-----VGLMSVGLAAI | (SEQ ID NO:167) |
| 38 | D-----VGTFSVGLAAI | (SEQ ID NO:168) |
| 13 | D-----IGTGSVGYACM | (SEQ ID NO:169) |
| 46 | D-----LGTNSIGSSVR | (SEQ ID NO:170) |
| 60 | DIGLRIGITSCGWSI- | (SEQ ID NO:171) |
| 69 | D-----MGAKYTGVFYA | (SEQ ID NO:172) |
| 73 | D-----LGGKNTGFFSF | (SEQ ID NO:173) |
| 74 | D-----LGVKNTGVFSA | (SEQ ID NO:174) |
| 70 | D-----LGAKFTGVALY | (SEQ ID NO:175) |
| 71 | D-----LGGKFTGVCLS | (SEQ ID NO:176) |
| 72 | D-----LGGTYTGTFIT | (SEQ ID NO:177) |
|   | *       *      * |  |

Fig. 3B (Continued)

Alignment of the HNH-like Domains disclosed in Chylinski et al.
(CLUSTAL format alignment by MAFFT (v7.058b))

```
1    YDIDHIYPRS-LTKD------DSF-DNLVLCERTAN    (SEQ ID NO:178)
2    -DIDHIYPRSKVIKD------DSF-DNLVLVLKNEN    (SEQ ID NO:179)
3    -DRDHIYPQS-KIKD------DSI-DNLVLVNKTYN    (SEQ ID NO:180)
4    -DIDHIYPRS-KIKD------DSI-TNRVLVEKDIN    (SEQ ID NO:181)
6    -DIDHIYPQS-KIKD------DSI-SNRVLVCSSCN    (SEQ ID NO:182)
5    -DIDHIYPQS-KTMD------DSL-NNRVLVKKNYN    (SEQ ID NO:183)
7    -DQDHIYPKS-KIYD------DSL-ENRVLVKKNLN    (SEQ ID NO:184)
8    -QIDHIVPQS-LVKD------DSF-DNRVLVVPSEN    (SEQ ID NO:185)
9    -DIDHIIPQA-FIKD------NSI-DNRVLTSSKEN    (SEQ ID NO:186)
12   -DIDHIIPQA-FLKD------NSI-DNKVLVSSASN    (SEQ ID NO:187)
16   -DIDHIIPQA-YTKD------NSL-DNRVLVSNITN    (SEQ ID NO:188)
11   -DIDHIVPQS-FITD------NSI-DNLVLTSSAGN    (SEQ ID NO:189)
10   -DVDHIVPQS-FLKD------DSI-DNKVLTRSDKN    (SEQ ID NO:190)
14   -NIDHIYPQS-MVKD------DSL-DNKVLVQSEIN    (SEQ ID NO:191)
18   -DIDHILPQS-LIKD------DSL-DNRVLVNATIN    (SEQ ID NO:192)
19   -DIDHILPQS-FIKD------DSL-ENRVLVKKAVN    (SEQ ID NO:193)
13   -EVDHIFPRS-FIKD------DSI-DNKVLVIKKMN    (SEQ ID NO:194)
15   -EVDHIFPRS-YIKD------DSF-ENKVLVYREEN    (SEQ ID NO:195)
17   -DIDHIIPQA-VTQN------DSI-DNRVLVARAEN    (SEQ ID NO:196)
22   -EIDHIIPYS-ISFD------DSS-SNKLLVLAESN    (SEQ ID NO:197)
24   -EIDHIIPYS-LCFD------DSS-ANKVLVHKQSN    (SEQ ID NO:198)
32   -DIDHIIPYS-RSMD------DSY-SNKVLVLSGEN    (SEQ ID NO:199)
63   -DIDHIIPYS-KSMD------DSF-NNKVLCLAERN    (SEQ ID NO:200)
59   -EIDHIIPYS-RSFD------DSY-MNKVLVFTKQN    (SEQ ID NO:201)
65   -QIDHIYPYS-RSMD------DSY-MNKVLVLTDEN    (SEQ ID NO:202)
64   -EIDHIIPFS-RSFD------DSL-SNKILVLGSEN    (SEQ ID NO:203)
68   -EIDHALPFS-RTWD------DSF-NNKVLVLGSEN    (SEQ ID NO:204)
69   -EIDHALPFS-RTWD------DSY-NNKVLVLASEN    (SEQ ID NO:205)
28   -EIDHIIPIS-ISLD------DSF-NNKVLVLSKAN    (SEQ ID NO:206)
30   -EVDHIIPIS-ISLD------DSI-TNKVLVTHREN    (SEQ ID NO:207)
62   -QVDHALPYS-RSYD------DSK-NNKVLVLTHEN    (SEQ ID NO:208)
27   -EVDHIIPLS-ITFD------DSL-ANKVLVYATAN    (SEQ ID NO:209)
26   -EIDHIIPRS-ISFD------DAR-SNKVLVYRSEN    (SEQ ID NO:210)
```

Fig. 4A

| | | |
|---|---|---|
| 29 | -EVDHIIPRS-VSFD-----NSY-HNKVLVKQSEN | (SEQ ID NO:211) |
| 67 | -DIDHILPYS-ITFD-----DSF-RNKVLVTSQEN | (SEQ ID NO:212) |
| 58 | -EIDHILPRS-RSAD-----DSF-ANKVLCLARAN | (SEQ ID NO:213) |
| 51 | -EIEHLLPFS-LTLD-----DSM-ANKTVCFRQAN | (SEQ ID NO:214) |
| 55 | -DIDHILPFS-VSLD-----DSA-ANKVVCLREAN | (SEQ ID NO:215) |
| 57 | -DIDHLIPFS-ISWD-----DSA-ANKVVCMRYAN | (SEQ ID NO:216) |
| 56 | -DIDHILPVA-MTLD-----DSP-ANKIICMRYAN | (SEQ ID NO:217) |
| 54 | -DVDHILPYS-RTLD-----DSF-PNRTLCLREAN | (SEQ ID NO:218) |
| 52 | -EIEHILPFS-RTLD-----DSL-NNRTVAMRRAN | (SEQ ID NO:219) |
| 31 | -EVDHIIPYS-ISWD-----DSY-TNKVLTSAKCN | (SEQ ID NO:220) |
| 45 | -QVDHILPWS-RFGD-----DSY-LNKTLCTARSN | (SEQ ID NO:221) |
| 53 | -QVDHILPFS-KTLD-----DSF-ANKVLAQHDAN | (SEQ ID NO:222) |
| 60 | -QIDHAFPLS-RSLD-----DSQ-SNKVLCLTSSN | (SEQ ID NO:223) |
| 21 | -DIDHIVPRS-ISFD-----DSF-SNLVIVNKLDN | (SEQ ID NO:224) |
| 23 | -EIEHIIPYS-MSYD-----NSQ-ANKILTEKAEN | (SEQ ID NO:225) |
| 25 | -EIDHVIPYS-KSAD-----DSW-FNKLLIVKKSTN | (SEQ ID NO:226) |
| 49 | -EMDHILPYS-RSLD-----NGW-HNRVLVHGKDN | (SEQ ID NO:227) |
| 33 | -EVDHIVPYS-LILD-----NTI-NNKALVYAEEN | (SEQ ID NO:228) |
| 42 | -EIEHVIPQS-LYFD-----DSF-SNKVICEAEVN | (SEQ ID NO:229) |
| 43 | -DIEHIIPQA-RLFD-----DSF-SNKTLEARSVN | (SEQ ID NO:230) |
| 44 | -EIEHIVPKA-RVFD-----DSF-SNKTLTFHRIN | (SEQ ID NO:231) |
| 20 | -DKDHIIPQS-MKKD-----DSIINNLVLVNKNAN | (SEQ ID NO:232) |
| 66 | -EVEHIWPRS-RSFD-----NSP-RNKTLCRKDVN | (SEQ ID NO:233) |
| 61 | -IVNHIIPYN-RSFD-----DTY-HNRVLTLTETK | (SEQ ID NO:234) |
| 46 | -DMEHTIPKS-ISFD-----NSD-QNLTLCESYYN | (SEQ ID NO:235) |
| 47 | -DIEHTIPRS-AGGD-----STK-MNLTLCSSRFN | (SEQ ID NO:236) |
| 48 | -DIEHTIPRS-ISQD-----NSQ-MNKTLCSLKFN | (SEQ ID NO:237) |
| 50 | -DIDHVIPLA-RGGR-----DSL-DNMVLCQSDAN | (SEQ ID NO:238) |
| 39 | -DIEHLFPIA-ESED-----NGR-NNLVISHSACN | (SEQ ID NO:239) |
| 41 | -DVDHIFPPRD-DTAD-----NSY-GNKVVAHRQCN | (SEQ ID NO:240) |
| 40 | -DIEHIVPQS-LGGL-----STD-YNTIVTLKSVN | (SEQ ID NO:241) |
| 35 | -ELDHIVPRT-DGGS-----NRH-ENLAITCGACN | (SEQ ID NO:242) |
| 36 | -EMDHIVPRKGVGST-----NTR-TNFAAVCAECN | (SEQ ID NO:243) |
| 37 | -EMDHIVPRKGVGST-----NTR-VNLAAACAACN | (SEQ ID NO:244) |
| 38 | -EMDHIVPRAGOGST-----NTR-ENLVAVCHRCN | (SEQ ID NO:245) |
| 70 | -EIDHILPRS-LIKDARGIVFNAE-PNLLIYASSRGN | (SEQ ID NO:246) |
| 71 | -EIDHIIPRS-LTGRTKKTVFNSE-ANLIYCSSKGN | (SEQ ID NO:247) |
| 73 | -EIDHIIPRS-LTLKKSESIYNSE-VNLIFVSAQGN | (SEQ ID NO:248) |

Fig. 4A (Continued)

```
72  -EIDHIYPRS-LSKKHFGVIFNSE-VNLIYCSSQGN   (SEQ ID NO:249)
74  -EIDHILPRS-HTLKIYGTVFNPE-GNLIYVHQKCN   (SEQ ID NO:250)
75  -ELDHIIPRS-HKKY---GTLNDE-ANLICVTRGDN   (SEQ ID NO:251)
34  -ELEHIVPHS-FRQS-----NAL-SSLVLTWPGVN    (SEQ ID NO:252)
     :*    *                .         :
```

Fig. 4A (Continued)

Alignment of the HNH-like Domains disclosed in Chylinski et al.(excluding sequence outliers).
(CLUSTAL format alignment by MAFFT (v7.058b))

```
1    YDIDHIYPRS-LTKDDS-FDNLVLCERTAN    (SEQ ID NO:253)
2    -DIDHIYPRSKVIKDDS-FDNLVLVLKNEN    (SEQ ID NO:254)
3    -DRDHIYPQS-KIKDDS-IDNLVLVNKTYN    (SEQ ID NO:255)
4    -DIDHIYPRS-KIKDDS-ITNRVLVEKDIN    (SEQ ID NO:256)
6    -DIDHIYPQS-KIKDDS-ISNRVLVCSSCN    (SEQ ID NO:257)
5    -DIDHIYPQS-KTMDDS-LNNRVLVKKNYN    (SEQ ID NO:258)
7    -DQDHIYPKS-KIYDDS-LENRVLVKKNLN    (SEQ ID NO:259)
8    -QIDHIVPQS-LVKDDS-FDNRVLVVPSEN    (SEQ ID NO:260)
9    -DIDHIIPQA-FIKDNS-IDNRVLTSSKEN    (SEQ ID NO:261)
12   -DIDHIIPQA-FLKDNS-IDNKVLVSSASN    (SEQ ID NO:262)
16   -DIDHIIPQA-YTKDNS-LDNRVLVSNITN    (SEQ ID NO:263)
11   -DIDHIVPQS-FITDNS-IDNLVLTSSAGN    (SEQ ID NO:264)
10   -DVDHIVPQS-FLKDDS-IDNKVLTRSDKN    (SEQ ID NO:265)
14   -NIDHIYPQS-MVKDDS-LDNKVLVQSEIN    (SEQ ID NO:266)
18   -DIDHILPQS-LIKDDS-LDNRVLVNATIN    (SEQ ID NO:267)
19   -DIDHILPQS-FIKDDS-LENRVLVKKAVN    (SEQ ID NO:268)
13   -EVDHIFPRS-FIKDDS-IDNKVLVLIKKMN   (SEQ ID NO:269)
15   -EVDHIIPRS-YIKDDS-FENKVLVYREEN    (SEQ ID NO:270)
17   -DIDHIIPQA-VTQNDS-IDNRVLVARAEN    (SEQ ID NO:271)
21   -DIDHIVPRS-ISFDDS-FSNLVIVNKLDN    (SEQ ID NO:272)
22   -EIDHIIPYS-ISFDDS-SSNKLLVLAESN    (SEQ ID NO:273)
24   -EIDHIIPYS-LCFDDS-SANKVLVHKQSN    (SEQ ID NO:274)
28   -EIDHIIPIS-ISLDDS-INNKVLVLSKAN    (SEQ ID NO:275)
30   -EVDHIIPIS-ISLDDS-ITNKVLVTHREN    (SEQ ID NO:276)
27   -EVDHILPLS-ITFDDS-LANKVLVYATAN    (SEQ ID NO:277)
26   -EIDHIIPRS-ISFDDA-RSNKVLVYRSEN    (SEQ ID NO:278)
29   -EVDHIIPRS-VSFDNS-YHNKVLVKQSEN    (SEQ ID NO:279)
31   -EVDHIIPYS-ISWDDS-YTNKVLTSAKCN    (SEQ ID NO:280)
32   -DIDHIIPYS-RSMDDS-YSNKVLVLSGEN    (SEQ ID NO:281)
23   -EIEHIIPYS-MSYDNS-QANKILTEKAEN    (SEQ ID NO:282)
33   -EVDHIVPYS-LILDNT-INNKALVYAEEN    (SEQ ID NO:283)
25   -EIDHILPYS-KSADDS-WFNKLLVKKSTN    (SEQ ID NO:284)
49   -EMDHILPYS-RSLDNG-WHNRVLVHGKDN    (SEQ ID NO:285)
42   -EIEHVIPQS-LYFDDS-FSNKVICEAEVN    (SEQ ID NO:286)
43   -DIEHIIPQA-RLFDDS-FSNKTLEARSVN    (SEQ ID NO:287)
```

Fig. 4B

```
44 -EIEHIVPKA-RVFDDS-FSNKTLTFHRIN          (SEQ ID NO:288)
20 -DKDHIIPQS-MKKDDSIINNLVLVNKNAN          (SEQ ID NO:289)
45 -QVDHILPWS-RFGDDS-YLNKTLCTARSN          (SEQ ID NO:290)
50 -DIDHVIPLA-RGGRDS-LDNMVLCQSDAN          (SEQ ID NO:291)
46 -DMEHTIPKS-ISFDNS-DQNLTLCESYYN          (SEQ ID NO:292)
47 -DIEHTIPRS-AGGDST-KMNLTLCSSRFN          (SEQ ID NO:293)
48 -DIEHTIPRS-ISQDNS-QMNKTLCSLKFN          (SEQ ID NO:294)
39 -DIEHLFPIA-ESEDNG-RNNLVISHSACN          (SEQ ID NO:295)
41 -DVDHIFPRD-DTADNS-YGNKVVAHRQCN          (SEQ ID NO:296)
40 -DIEHIVPQS-LGGLST-DYNTIVTLKSVN          (SEQ ID NO:297)
35 -ELDHIVPRT-DGGSNR-HENLAITCGACN          (SEQ ID NO:298)
36 -EMDHIVPRKGVGSTNT-RTNFAAVCAECN          (SEQ ID NO:299)
37 -EMDHIVPRKGVGSTNT-RVNLAAACAACN          (SEQ ID NO:300)
38 -EMDHIVPRAGQGSTNT-RENLVAVCHRCN          (SEQ ID NO:301)
34 -ELEHIVPHS-FRQSNA-LSSLVLTWPGVN          (SEQ ID NO:302)
      ::  *     *            .  .
```

Fig. 4B (Continued)

Sequence alignment between SpCas9 and NmCas9

```
                                                         Y
NmCas9   MAAFKPNSINYILGL DIGIASVGWAMV EIDEEENPIRLID-------------LGVRVFE
SpCas9   ------MDKKYSIGL DIGTNSVGWAVI TDEYKVPSKKFKVLGNTDRHSIKKNLIGALLFD
         ---------*Y-*GL DIG--SVGWA** |--*-*----**----------------*G--*F*

NmCas9   RAEVPKTGDSLAMARRLARSVRRLTRRAHRLLRTRRLLKREGVLQAA-------------
SpCas9   SGET-------AEATRLKRTARRYTRRKNRICYLQEIFSNEMAKVDDSFFHRLEESFLV
         --E--------A-A-RL-R*-RR---RR--R*---*-**--E------------------

NmCas9   ---------------NFDENGLIKSLPNTPWQLRAAALDRK---LTPLEWSAVLLHLIKHR
SpCas9   EEDKKHERHPIFGNIVDEVAYHEKYP-TIYHLRKKLVDSTDKADLRLI-YLALAHMIKFR
         ----------------DE----*--P-T **LR---*D--------L-----L-H*IK-R

NmCas9   GYLSQRKNE----------------------------GETA---------DKEL---
SpCas9   GHFLIEGDLNPDNSDVDKLFIQLVQTYNQLFEENPINASGVDAKAILSARLSKSRRLENL
         G**----*-----------------------------G--A----------*-L---

NmCas9   -----GALLKGVAGNAHALQTG---DFRTPAE------LAL--NKFEKESGHIRNQ-RSD
SpCas9   IAQLPGEKKNGLFGNLIALSLGLTPNFKSNFDLAEDAKLQLSKDTYDDDLDNLLAQIGDQ
         -----G---*G*-GN--AL--G----*F**-*------L-L--*-*-**-*----*---*

NmCas9   YSHTFSR----------------------------------------------KDLQA
SpCas9   YADLFLAAKNLSDAILLSDILRVNTEITKAPLSASMIKRYDEHHQDLTLLKALVRQQLPE
         Y*--F-------------------------------------------------**L--

NmCas9   ELILLFEKQKEFGN-PHVSGGLK--------------EGIETL---------LMTQRPA
SpCas9   KYKEIFFDQSKNGYAGYIDGGASQEEFYKFIKPILEKMDGTEELLVKLNREDLLRKQRTF
         *---*F--Q-*-G---**-GG---------------*G-E-L---------L--QR--

NmCas9   LSGDAV-QKMLGH-------CTFEPAEP---------------KAAKNTYTAERFIWL
SpCas9   DNGSIPQIHLGELHAILRRQEDFYPFLKDNREKIEKILTFRIPYYVGPLARGNSRFAWM
         --G----Q--LG----------F-P------------------*----RF-W*

NmCas9   TKLNNLRILEQGSERPLTD-------TERATLMDEPY------RKSKLTYAQAR------
SpCas9   TRKSEETITPWNFEEVVDKGASAQSFIERMTNFDKNLPNEKVLPKHSLLYEYFTVYNELT
         T*--**--I-----E---*---------ER-T-*D*--------K--L-Y---------

NmCas9   ----KLLGLEDTAFFKGLRY-------GKDN-------------------------AEA
SpCas9   KVKYVTEGMRKPAFLSGEQKKAIVDLLFKTNRKVTVKQLKEDYFKKIECFDSVEISGVED
         -------G*----AF*-G-*------------*------------------------E-

NmCas9   STLMEMKAYHAISRALEKEGLKDKKSPLNLSPELQDEIGTAFSLFKTDEDITGRLKDRIQ
SpCas9   RFNASLGTYHDLLKIIKDKDFLDNEE----NEDILEDIVLTLTLFEDREMIEERLKTYAH
         ------*-*YH-*-*-**-*-*-D**-------**-**I--***LF*--E-I--RLK---*

NmCas9   P--EILEALLKHISFDKFVQISLKALRRIVPLMEQGKRYDEACAE----IYGDHYGKKNT
SpCas9   LFDDKVMKQLKRRRYTGWGRLSRKLI--------NGIRDKQSGKTILDFLKSDGFANRNF
         ---*-*---LK*---*--*-**S-K-*--------*G-R--**-------*--D-*-**N-

NmCas9   EEKI------Y--------------LPPIPADEIRNPVVLRALSQARKVINGVVRRYG-
SpCas9   MQLIHDDSLTFKEDIQKAQVSGQGDSLHEHIANLAGSPAIKKGILQTVKVVDELVKVGR
         -*-I--------------------L----A*----P-*-*-*-Q*-KV**-*V*--G-

NmCas9   -SPAR IHIETARE VGKSFKDRKEIEKRQEENRKDREKAAAKFREYFPNF----VGEPKSK
SpCas9   HKPEN IVIEMARE NQTTQKGQKNSRER-------MKRIEEGIKELGSQILKEHPVENTQL
         --P-- I-IE-ARE N---*-K-*K*---*R-----------**-----**E---**------E-
       B                      G
NmCas9   DILKLRLYEQQHGKCLYSGKEINLGRLNEKGYV EIDHALPFSRTWDDSFNNKVLVLGSEN
SpCas9   QNEKLYLYLQNGRDMYVDQELDINRLSD---Y DVDHIVPQSFLKDDSIDNKVLTRSDKN
         *--KL-LY--Q-G*-*Y--*E***  RL-*---- **DH-*P-S---DDS**NKVL----*N

NmCas9   QNKGNQTPYEYFNGKDNSREWQEFKA-RVET-SRFP-RSKKQRILLQKFDEDGFKERNLN
SpCas9   RGKSDNVPSEEVVKKM-KNYWRQLLNAKLITQRKFDNLTKAERGGLSELDKAGFIKRQLV
         * K--P-E----K-----W-----T--F----*K-R--L-**D*-GF-*R-L-
```

Fig. 5

```
NmCas9   DTRYVNRFLCQFVADRMRLTGKGKKRVF------ASNGQITNLLRGFWGLRKVRAENDRH
SpCas9   ETRQITKHVAQILDSRMNTKYDENDKLIREVKVITLKSKLVSDFRKDFQFYKVREINNYH
         *TR-*-*-*-Q**--RM------*-***-------*-*-**---*R--*-*-KVR--N*-H

NmCas9    HALDAVV VACSTVAMQQKI---TRFVRYKEMNAFDGKTID----KETGEVLHQKTHFPQP
SpCas9  B HAHDAYL NAVVGTALIKKYPKLESEFVYGDYKVYDVRKMIAKSEQEIGKATAKYFFYSNI
         HH-AD-*-A----A*-*K---------Y-*-*-D-*-*-----*E-G*---*---*-*-

NmCas9   WEFFAQEVMIRVFGKPDGKPE-----------FEEADTLEKLRTLLAEKLSSRPEAVHEY
SpCas9   MNFFKTEITLA-NGEIRKRPLIETNGETGEIVWDKGRDFATVRKVLS-----MPQ-----
         -*FF--E*-*---G*----P-----------***---*--*R-*L*------P*-----

NmCas9   VTPLFVSRAPNRKMSGQGHMETVKSAKRLDEGVSVLRVPLTQLKLKDLEKMVN--REREP
SpCas9   -------------------VNIVKKTEVQTGGFSKES----ILPKRNSDKLIARKKDWDP
         --------------------VK-----G-S--------L--**-*K----*P

NmCas9   KLYEALKARLEAHKDDPAKAFAEPFYKYDKAGNRTQQVKAVR---VEQVQKTGVWVRNH-
SpCas9   KKYGGFD--------SPTVAYSVLVVAKVEKGK-SKKLKSVKELLGITIMERSSFEKNPI
         K-Y--*---------P*-A**--------*-G*-****K*V*------*-*----*-*N--

NmCas9   -----NGIAD-------------------NATMVRVDVFEKGDKYYLVPIY--------
SpCas9   DFLEAKGYKEVKKDLIIKLPKYSLFELENGRKRMLASAGELQKGNELALPSKYVNFLYLA
         ------*G--*-----------------*--*------KG--L---Y-------

NmCas9   -SWQVAKGILPDRAVVQGKDEEDWQLIDDS------FNFKFSLHPNDLVEVI--------
SpCas9   SHYEKLKGSPEDNEQKQLFVEQHKHYLDEIIEQISEFSKRVILADANLDKVLSAYNKHRD
         --**--KG---D----Q---E*--*-D*-------F--*--L----*L-*V*-------

NmCas9   ------------------TKKARMFGYFASCHRGTGNINIRIHDLDHKIGKNGILEGIGV
SpCas9   KPIREQAENIIHLFTLTNLGAPAAFKYFDTTIDRKRYTS-TKEVLDATLIHQSI------
         ------------------F-YF-*------------LD--*-**-I------

NmCas9   KTALSFQKYQIDELGKEIRPCRLKKRPPVR    (SEQ ID NO:6)
SpCas9   -TGLYETRIDLSQLGGD-------------    (SEQ ID NO:7)
         -T-L---*-**-*LG-*-------------
```

Percent Identity Matrix - created by Clustal2.1

Fig. 5 (Continued)

Sequence of the NmCas9 ORF with dual NLS and HA tags

```
atg[gtgcctaagaagaagagaaaggtgg]ctgccttcaaacctaattcaatcaactacatcctcggcctcgat    R
atcggcatcgcatccgtcggctgggcgatggtagaaattgacgaagaagaaaaccccatccgcctgattgat
ttgggcgtgcgcgtatttgagcgtgccgaagtaccgaaaacaggcgactcccttgccatggcaaggcgttttg
gcgcgcagtgttcgccgcctgacccgccgtcgcgccaccgcctgcttcggacccgccgcctattgaaacgc
gaaggcgtattacaagccgccaattttgacgaaaacggcttgattaaatccttaccgaatacaccatggcaa
cttcgcgcagccgcattagaccgcaaactgacgcctttagagtggtcggcagtcttgttgcatttaatcaaa
catcgcggctatttatcgcaacggaaaaacgagggcgaaactgccgataaggagcttggcgctttgcttaaa
ggcgtagccggcaatgcccatgccttacagacaggcgatttccgcacaccggccgaattggctttaaataaa
tttgagaaagaaagcggccatatccgcaatcagcgcagcgattattcgcatacgttcagccgcaaagattta
caggcggagctgattttgctgtttgaaaaacaaaagaatttggcaatccgcatgtttcaggcggccttaaa
gaaggtattgaaaccctactgatgacgcaacgccctgccctgtccggcgatgccgttcaaaaaatgttgggg
cattgcaccttcgaaccggcagagccgaaagccgctaaaacacctacacagccgaacgtttcatctggctg
accaagctgaacaacctgcgtattttagagcaaggcagcgagcggccattgaccgataccgaacgcgccacg
cttatggacgagccatacagaaaatccaaactgacttacgcacaagcccgtaagctgctgggtttagaagat
accgcctttttcaaaggcttgcgctatggtaaagacaatgccgaagcctcaacattgatggaaatgaaggcc
taccatgccatcagccgtgcactggaaaagaaggattgaaagacaaaaaatccccattaaacctttctccc
gaattacaagacgaaatcggcacggcattctccctgttcaaaaccgatgaagacattacaggccgtctgaaa
gaccgtatacagcccgaaatcttagaagcgctgttgaaacacatcagcttcgataagttcgtccaatttcc
ttgaaagcattgcgccgaattgtgcctctaatggaacaaggcaaacgttacgatgaagcctgcgccgaaatc
tacggagaccattacggcaagaagaatacggaagaaaagatttatctgccgccgattccgccgacgaaatc
cgcaacccgtcgtcttgcgcgccttatctcaagcacgtaaggtcattaacggcgtggtacgccgttacggc
tccccagctcgtatccatattgaaactgcaagggaagtaggtaaatcgtttaaagaccgcaaagaaattgag
aaacgccaagaagaaaaccgcaaagaccgggaaaaagccgccgccaaattccgagagtatttccccaatttt
gtcggagaacccaaatccaaagatattctgaaactgcgcctgtacgagcaacaacacggcaaatgcctgtat
tcgggcaaagaaatcaacttaggccgtctgaacgaaaaaggctatgtcgaaatcgaccatgccctgccgttc
tcgcgcacatgggacgacagtttcaacaataaagtactggtattgggcagcgaaaaccaaaacaaaggcaat
caaaccccttacgaatacttcaacggcaaagacaacagccgcgaatggcaggaatttaaagcgcgtgtcgaa
accagccgtttcccgcgcagtaaaaaacaacggattctgctgcaaaaattcgatgaagacggctttaaagaa
cgcaatctgaacgacacgcgctacgtcaaccgtttcctgtgtcaatttgttgccgaccgtatgcggctgaca
ggtaaaggcaagaaacgtgtctttgcatccaacggacaaattaccaatctgttgcgcggcttttggggattg
cgcaaagtgcgtgcggaaaacgaccgccatcacgccttggacgccgtcgtcgttgcctgctcgaccgttgcc
atgcagcagaaaattacccgttttgtacgctataaagagatgaacgcgtttgacggtaaaaccatagacaaa
gaaacaggagaagtgctgcatcaaaaaacacacttcccacaaccttgggaattttcgcacaagaagtcatg
attcgcgtcttcggcaaaccggacggcaaacccgaattcgaagaagccgatacctagaaaaactgcgcacg
ttgcttgccgaaaaattatcatctcgccccgaagccgtacacgaatacgttacgccactgtttgtttcacgc
gcgcccaatcggaagatgagcgggcaagggcatatggagaccgtcaaatccgccaaacgactggacgaaggc
gtcagcgtgttgcgcgtaccgctgacacagttaaaactgaaagacttggaaaaaatggtcaatcgggagcgc
gaacctaagctatacgaagcactgaaagcacggctggaagcacataagacgatcctgccaaagcctttgcc
gagccgttttacaaatacgataaagcaggcaaccgcacccaacaggtaaaagccgtacgcgtagagcaagta
cagaaaaccggcgtatgggtgcgcaaccataacggtattgccgacaacgcaaccatggtgcgcgtagatgtg
tttgagaaaggcgacaagtattatctggtaccgatttacagttggcaggtagcgaaagggattttgccggat
agggctgttgtacaaggaaaagatgaagaagattggcaacttattgatgatagtttcaactttaaattctca
ttacaccctaatgatttagtcgaggttataacaaaaaaagctagaatgtttggttactttgccagctgccat
cgaggcacaggtaatatcaatatacgcattcatgatcttgatcataaaattggcaaaatggaatactggaa
ggtatcggcgtcaaaaccgccctttcattccaaaaataccaaattgacgaactgggcaaagaaatcagacca
tgccgtctgaaaaaacgccgcctgtccgt[tacccatacgatgttccagattacgct][gcagctccagcagcg]
[aagaaaagaagctggat]taa                              G                    O
                                                         (SEQ ID NO:303)
```

R: SV40 NLS, G: HA tag, O: synthetic NLS (1); all else NmCas9

SEQUENCE LISTING

<160> NUMBER OF SEQ ID NOS: 1510

<210> SEQ ID NO 1
<211> LENGTH: 1344

```
<212> TYPE: PRT
<213> ORGANISM: Streptococcus mutans

<400> SEQUENCE: 1

Lys Lys Pro Tyr Ser Ile Gly Leu Asp Ile Gly Thr Asn Ser Val Gly
1               5                   10                  15

Trp Ala Val Val Thr Asp Asp Tyr Lys Val Pro Ala Lys Lys Met Lys
            20                  25                  30

Val Leu Gly Asn Thr Asp Lys Ser His Ile Glu Lys Asn Leu Leu Gly
        35                  40                  45

Ala Leu Leu Phe Asp Ser Gly Asn Thr Ala Glu Asp Arg Arg Leu Lys
    50                  55                  60

Arg Thr Ala Arg Arg Arg Tyr Thr Arg Arg Asn Arg Ile Leu Tyr
65                  70                  75                  80

Leu Gln Glu Ile Phe Ser Glu Glu Met Gly Lys Val Asp Asp Ser Phe
                85                  90                  95

Phe His Arg Leu Glu Asp Ser Phe Leu Val Thr Glu Asp Lys Arg Gly
            100                 105                 110

Glu Arg His Pro Ile Phe Gly Asn Leu Glu Glu Val Lys Tyr His
        115                 120                 125

Glu Asn Phe Pro Thr Ile Tyr His Leu Arg Gln Tyr Leu Ala Asp Asn
    130                 135                 140

Pro Glu Lys Val Asp Leu Arg Leu Val Tyr Leu Ala Leu Ala His Ile
145                 150                 155                 160

Ile Lys Phe Arg Gly His Phe Leu Ile Glu Gly Lys Phe Asp Thr Arg
                165                 170                 175

Asn Asn Asp Val Gln Arg Leu Phe Gln Glu Phe Leu Ala Val Tyr Asp
            180                 185                 190

Asn Thr Phe Glu Asn Ser Ser Leu Gln Glu Gln Asn Val Gln Val Glu
        195                 200                 205

Glu Ile Leu Thr Asp Lys Ile Ser Lys Ser Ala Lys Lys Asp Arg Val
    210                 215                 220

Leu Lys Leu Phe Pro Asn Glu Lys Ser Asn Gly Arg Phe Ala Glu Phe
225                 230                 235                 240

Leu Lys Leu Ile Val Gly Asn Gln Ala Asp Phe Lys Lys His Phe Glu
                245                 250                 255

Leu Glu Glu Lys Ala Pro Leu Gln Phe Ser Lys Asp Thr Tyr Glu Glu
            260                 265                 270

Glu Leu Glu Val Leu Leu Ala Gln Ile Gly Asp Asn Tyr Ala Glu Leu
        275                 280                 285

Phe Leu Ser Ala Lys Lys Leu Tyr Asp Ser Ile Leu Leu Ser Gly Ile
    290                 295                 300

Leu Thr Val Thr Asp Val Gly Thr Lys Ala Pro Leu Ser Ala Ser Met
305                 310                 315                 320

Ile Gln Arg Tyr Asn Glu His Gln Met Asp Leu Ala Gln Leu Lys Gln
                325                 330                 335

Phe Ile Arg Gln Lys Leu Ser Asp Lys Tyr Asn Glu Val Phe Ser Asp
            340                 345                 350

Val Ser Lys Asp Gly Tyr Ala Gly Tyr Ile Asp Gly Lys Thr Asn Gln
        355                 360                 365

Glu Ala Phe Tyr Lys Tyr Leu Lys Gly Leu Leu Asn Lys Ile Glu Gly
    370                 375                 380

Ser Gly Tyr Phe Leu Asp Lys Ile Glu Arg Glu Asp Phe Leu Arg Lys
385                 390                 395                 400
```

```
Gln Arg Thr Phe Asp Asn Gly Ser Ile Pro His Gln Ile His Leu Gln
                405                 410                 415
Glu Met Arg Ala Ile Ile Arg Arg Gln Ala Glu Phe Tyr Pro Phe Leu
            420                 425                 430
Ala Asp Asn Gln Asp Arg Ile Glu Lys Leu Leu Thr Phe Arg Ile Pro
        435                 440                 445
Tyr Tyr Val Gly Pro Leu Ala Arg Gly Lys Ser Asp Phe Ala Trp Leu
    450                 455                 460
Ser Arg Lys Ser Ala Asp Lys Ile Thr Pro Trp Asn Phe Asp Glu Ile
465                 470                 475                 480
Val Asp Lys Glu Ser Ser Ala Glu Ala Phe Ile Asn Arg Met Thr Asn
            485                 490                 495
Tyr Asp Leu Tyr Leu Pro Asn Gln Lys Val Leu Pro Lys His Ser Leu
        500                 505                 510
Leu Tyr Glu Lys Phe Thr Val Tyr Asn Glu Leu Thr Lys Val Lys Tyr
    515                 520                 525
Lys Thr Glu Gln Gly Lys Thr Ala Phe Phe Asp Ala Asn Met Lys Gln
530                 535                 540
Glu Ile Phe Asp Gly Val Phe Lys Val Tyr Arg Lys Val Thr Lys Asp
545                 550                 555                 560
Lys Leu Met Asp Phe Leu Glu Lys Glu Phe Asp Glu Phe Arg Ile Val
            565                 570                 575
Asp Leu Thr Gly Leu Asp Lys Glu Asn Lys Val Phe Asn Ala Ser Tyr
        580                 585                 590
Gly Thr Tyr His Asp Leu Cys Lys Ile Leu Asp Lys Asp Phe Leu Asp
    595                 600                 605
Asn Ser Lys Asn Glu Lys Ile Leu Glu Asp Ile Val Leu Thr Leu Thr
610                 615                 620
Leu Phe Glu Asp Arg Glu Met Ile Arg Lys Arg Leu Glu Asn Tyr Ser
625                 630                 635                 640
Asp Leu Leu Thr Lys Glu Gln Val Lys Lys Leu Glu Arg His His Tyr
            645                 650                 655
Thr Gly Trp Gly Arg Leu Ser Ala Glu Leu Ile His Gly Ile Arg Asn
        660                 665                 670
Lys Glu Ser Arg Lys Thr Ile Leu Asp Tyr Leu Ile Asp Asp Gly Asn
    675                 680                 685
Ser Asn Arg Asn Phe Met Gln Leu Ile Asn Asp Asp Ala Leu Ser Phe
690                 695                 700
Lys Glu Glu Ile Ala Lys Ala Gln Val Ile Gly Glu Thr Asp Asn Leu
705                 710                 715                 720
Asn Gln Val Val Ser Asp Ile Ala Gly Ser Pro Ala Ile Lys Lys Gly
            725                 730                 735
Ile Leu Gln Ser Leu Lys Ile Val Asp Glu Leu Val Lys Ile Met Gly
        740                 745                 750
His Gln Pro Glu Asn Ile Val Val Glu Met Ala Arg Glu Asn Gln Phe
    755                 760                 765
Thr Asn Gln Gly Arg Arg Asn Ser Gln Arg Leu Lys Gly Leu Thr
770                 775                 780
Asp Ser Ile Lys Glu Phe Gly Ser Gln Ile Leu Lys Glu His Pro Val
785                 790                 795                 800
Glu Asn Ser Gln Leu Gln Asn Asp Arg Leu Phe Leu Tyr Tyr Leu Gln
            805                 810                 815
```

```
Asn Gly Arg Asp Met Tyr Thr Gly Glu Leu Asp Ile Asp Tyr Leu
                820                 825                 830

Ser Gln Tyr Asp Ile Asp His Ile Ile Pro Gln Ala Phe Ile Lys Asp
            835                 840                 845

Asn Ser Ile Asp Asn Arg Val Leu Thr Ser Ser Lys Glu Asn Arg Gly
850                 855                 860

Lys Ser Asp Asp Val Pro Ser Lys Asp Val Val Arg Lys Met Lys Ser
865                 870                 875                 880

Tyr Trp Ser Lys Leu Leu Ser Ala Lys Leu Ile Thr Gln Arg Lys Phe
                885                 890                 895

Asp Asn Leu Thr Lys Ala Glu Arg Gly Gly Leu Thr Asp Asp Asp Lys
                900                 905                 910

Ala Gly Phe Ile Lys Arg Gln Leu Val Glu Thr Arg Gln Ile Thr Lys
            915                 920                 925

His Val Ala Arg Ile Leu Asp Glu Arg Phe Asn Thr Glu Thr Asp Glu
            930                 935                 940

Asn Asn Lys Lys Ile Arg Gln Val Lys Ile Val Thr Leu Lys Ser Asn
945                 950                 955                 960

Leu Val Ser Asn Phe Arg Lys Glu Phe Glu Leu Tyr Lys Val Arg Glu
                965                 970                 975

Ile Asn Asp Tyr His His Ala His Asp Ala Tyr Leu Asn Ala Val Ile
                980                 985                 990

Gly Lys Ala Leu Leu Gly Val Tyr Pro Gln Leu Glu Pro Glu Phe Val
            995                 1000                1005

Tyr Gly Asp Tyr Pro His Phe His Gly His Lys Glu Asn Lys Ala
            1010                1015                1020

Thr Ala Lys Lys Phe Phe Tyr Ser Asn Ile Met Asn Phe Phe Lys
            1025                1030                1035

Lys Asp Asp Val Arg Thr Asp Lys Asn Gly Glu Ile Ile Trp Lys
            1040                1045                1050

Lys Asp Glu His Ile Ser Asn Ile Lys Lys Val Leu Ser Tyr Pro
            1055                1060                1065

Gln Val Asn Ile Val Lys Lys Val Glu Glu Gln Thr Gly Gly Phe
            1070                1075                1080

Ser Lys Glu Ser Ile Leu Pro Lys Gly Asn Ser Asp Lys Leu Ile
            1085                1090                1095

Pro Arg Lys Thr Lys Lys Phe Tyr Trp Asp Thr Lys Lys Tyr Gly
            1100                1105                1110

Gly Phe Asp Ser Pro Ile Val Ala Tyr Ser Ile Leu Val Ile Ala
            1115                1120                1125

Asp Ile Glu Lys Gly Lys Ser Lys Lys Leu Lys Thr Val Lys Ala
            1130                1135                1140

Leu Val Gly Val Thr Ile Met Glu Lys Met Thr Phe Glu Arg Asp
            1145                1150                1155

Pro Val Ala Phe Leu Glu Arg Lys Gly Tyr Arg Asn Val Gln Glu
            1160                1165                1170

Glu Asn Ile Ile Lys Leu Pro Lys Tyr Ser Leu Phe Lys Leu Glu
            1175                1180                1185

Asn Gly Arg Lys Arg Leu Leu Ala Ser Ala Arg Glu Leu Gln Lys
            1190                1195                1200

Gly Asn Glu Ile Val Leu Pro Asn His Leu Gly Thr Leu Leu Tyr
            1205                1210                1215
```

```
His Ala Lys Asn Ile His Lys Val Asp Glu Pro Lys His Leu Asp
1220                1225                1230

Tyr Val Asp Lys His Lys Asp Glu Phe Lys Glu Leu Leu Asp Val
1235                1240                1245

Val Ser Asn Phe Ser Lys Lys Tyr Thr Leu Ala Glu Gly Asn Leu
1250                1255                1260

Glu Lys Ile Lys Glu Leu Tyr Ala Gln Asn Asn Gly Glu Asp Leu
1265                1270                1275

Lys Glu Leu Ala Ser Ser Phe Ile Asn Leu Leu Thr Phe Thr Ala
1280                1285                1290

Ile Gly Ala Pro Ala Thr Phe Lys Phe Phe Asp Lys Asn Ile Asp
1295                1300                1305

Arg Lys Arg Tyr Thr Ser Thr Thr Glu Ile Leu Asn Ala Thr Leu
1310                1315                1320

Ile His Gln Ser Ile Thr Gly Leu Tyr Glu Thr Arg Ile Asp Leu
1325                1330                1335

Asn Lys Leu Gly Gly Asp
1340

<210> SEQ ID NO 2
<211> LENGTH: 1367
<212> TYPE: PRT
<213> ORGANISM: Streptococcus pyogenes

<400> SEQUENCE: 2

Asp Lys Lys Tyr Ser Ile Gly Leu Asp Ile Gly Thr Asn Ser Val Gly
1               5                   10                  15

Trp Ala Val Ile Thr Asp Glu Tyr Lys Val Pro Ser Lys Lys Phe Lys
                20                  25                  30

Val Leu Gly Asn Thr Asp Arg His Ser Ile Lys Lys Asn Leu Ile Gly
            35                  40                  45

Ala Leu Leu Phe Asp Ser Gly Glu Thr Ala Glu Ala Thr Arg Leu Lys
        50                  55                  60

Arg Thr Ala Arg Arg Arg Tyr Thr Arg Arg Lys Asn Arg Ile Cys Tyr
65                  70                  75                  80

Leu Gln Glu Ile Phe Ser Asn Glu Met Ala Lys Val Asp Asp Ser Phe
                85                  90                  95

Phe His Arg Leu Glu Glu Ser Phe Leu Val Glu Glu Asp Lys Lys His
            100                 105                 110

Glu Arg His Pro Ile Phe Gly Asn Ile Val Asp Glu Val Ala Tyr His
        115                 120                 125

Glu Lys Tyr Pro Thr Ile Tyr His Leu Arg Lys Lys Leu Val Asp Ser
    130                 135                 140

Thr Asp Lys Ala Asp Leu Arg Leu Ile Tyr Leu Ala Leu Ala His Met
145                 150                 155                 160

Ile Lys Phe Arg Gly His Phe Leu Ile Glu Gly Asp Leu Asn Pro Asp
                165                 170                 175

Asn Ser Asp Val Asp Lys Leu Phe Ile Gln Leu Val Gln Thr Tyr Asn
            180                 185                 190

Gln Leu Phe Glu Glu Asn Pro Ile Asn Ala Ser Gly Val Asp Ala Lys
        195                 200                 205

Ala Ile Leu Ser Ala Arg Leu Ser Lys Ser Arg Arg Leu Glu Asn Leu
    210                 215                 220
```

```
Ile Ala Gln Leu Pro Gly Glu Lys Lys Asn Gly Leu Phe Gly Asn Leu
225                 230                 235                 240

Ile Ala Leu Ser Leu Gly Leu Thr Pro Asn Phe Lys Ser Asn Phe Asp
                245                 250                 255

Leu Ala Glu Asp Ala Lys Leu Gln Leu Ser Lys Asp Thr Tyr Asp Asp
            260                 265                 270

Asp Leu Asp Asn Leu Leu Ala Gln Ile Gly Asp Gln Tyr Ala Asp Leu
        275                 280                 285

Phe Leu Ala Ala Lys Asn Leu Ser Asp Ala Ile Leu Leu Ser Asp Ile
290                 295                 300

Leu Arg Val Asn Thr Glu Ile Thr Lys Ala Pro Leu Ser Ala Ser Met
305                 310                 315                 320

Ile Lys Arg Tyr Asp Glu His His Gln Asp Leu Thr Leu Leu Lys Ala
                325                 330                 335

Leu Val Arg Gln Gln Leu Pro Glu Lys Tyr Lys Glu Ile Phe Phe Asp
            340                 345                 350

Gln Ser Lys Asn Gly Tyr Ala Gly Tyr Ile Asp Gly Gly Ala Ser Gln
        355                 360                 365

Glu Glu Phe Tyr Lys Phe Ile Lys Pro Ile Leu Glu Lys Met Asp Gly
370                 375                 380

Thr Glu Glu Leu Leu Val Lys Leu Asn Arg Glu Asp Leu Leu Arg Lys
385                 390                 395                 400

Gln Arg Thr Phe Asp Asn Gly Ser Ile Pro His Gln Ile His Leu Gly
                405                 410                 415

Glu Leu His Ala Ile Leu Arg Arg Gln Glu Asp Phe Tyr Pro Phe Leu
            420                 425                 430

Lys Asp Asn Arg Glu Lys Ile Glu Lys Ile Leu Thr Phe Arg Ile Pro
        435                 440                 445

Tyr Tyr Val Gly Pro Leu Ala Arg Gly Asn Ser Arg Phe Ala Trp Met
450                 455                 460

Thr Arg Lys Ser Glu Glu Thr Ile Thr Pro Trp Asn Phe Glu Glu Val
465                 470                 475                 480

Val Asp Lys Gly Ala Ser Ala Gln Ser Phe Ile Glu Arg Met Thr Asn
                485                 490                 495

Phe Asp Lys Asn Leu Pro Asn Glu Lys Val Leu Pro Lys His Ser Leu
            500                 505                 510

Leu Tyr Glu Tyr Phe Thr Val Tyr Asn Glu Leu Thr Lys Val Lys Tyr
        515                 520                 525

Val Thr Glu Gly Met Arg Lys Pro Ala Phe Leu Ser Gly Glu Gln Lys
        530                 535                 540

Lys Ala Ile Val Asp Leu Leu Phe Lys Thr Asn Arg Lys Val Thr Val
545                 550                 555                 560

Lys Gln Leu Lys Glu Asp Tyr Phe Lys Lys Ile Glu Cys Phe Asp Ser
                565                 570                 575

Val Glu Ile Ser Gly Val Glu Asp Arg Phe Asn Ala Ser Leu Gly Thr
            580                 585                 590

Tyr His Asp Leu Leu Lys Ile Ile Lys Asp Lys Asp Phe Leu Asp Asn
        595                 600                 605

Glu Glu Asn Glu Asp Ile Leu Glu Asp Ile Val Leu Thr Leu Thr Leu
        610                 615                 620

Phe Glu Asp Arg Glu Met Ile Glu Glu Arg Leu Lys Thr Tyr Ala His
625                 630                 635                 640
```

```
Leu Phe Asp Asp Lys Val Met Lys Gln Leu Lys Arg Arg Tyr Thr
            645                 650                 655
Gly Trp Gly Arg Leu Ser Arg Lys Leu Ile Asn Gly Ile Arg Asp Lys
        660                 665                 670
Gln Ser Gly Lys Thr Ile Leu Asp Phe Leu Lys Ser Asp Gly Phe Ala
        675                 680                 685
Asn Arg Asn Phe Met Gln Leu Ile His Asp Asp Ser Leu Thr Phe Lys
    690                 695                 700
Glu Asp Ile Gln Lys Ala Gln Val Ser Gly Gln Gly Asp Ser Leu His
705                 710                 715                 720
Glu His Ile Ala Asn Leu Ala Gly Ser Pro Ala Ile Lys Lys Gly Ile
                725                 730                 735
Leu Gln Thr Val Lys Val Val Asp Glu Leu Val Lys Val Met Gly Arg
                740                 745                 750
His Lys Pro Glu Asn Ile Val Ile Glu Met Ala Arg Glu Asn Gln Thr
            755                 760                 765
Thr Gln Lys Gly Gln Lys Asn Ser Arg Glu Arg Met Lys Arg Ile Glu
        770                 775                 780
Glu Gly Ile Lys Glu Leu Gly Ser Gln Ile Leu Lys Glu His Pro Val
785                 790                 795                 800
Glu Asn Thr Gln Leu Gln Asn Glu Lys Leu Tyr Leu Tyr Tyr Leu Gln
                805                 810                 815
Asn Gly Arg Asp Met Tyr Val Asp Gln Glu Leu Asp Ile Asn Arg Leu
                820                 825                 830
Ser Asp Tyr Asp Val Asp His Ile Val Pro Gln Ser Phe Leu Lys Asp
            835                 840                 845
Asp Ser Ile Asp Asn Lys Val Leu Thr Arg Ser Asp Lys Asn Arg Gly
        850                 855                 860
Lys Ser Asp Asn Val Pro Ser Glu Glu Val Val Lys Lys Met Lys Asn
865                 870                 875                 880
Tyr Trp Arg Gln Leu Leu Asn Ala Lys Leu Ile Thr Gln Arg Lys Phe
                885                 890                 895
Asp Asn Leu Thr Lys Ala Glu Arg Gly Gly Leu Ser Glu Leu Asp Lys
            900                 905                 910
Ala Gly Phe Ile Lys Arg Gln Leu Val Glu Thr Arg Gln Ile Thr Lys
        915                 920                 925
His Val Ala Gln Ile Leu Asp Ser Arg Met Asn Thr Lys Tyr Asp Glu
            930                 935                 940
Asn Asp Lys Leu Ile Arg Glu Val Lys Val Ile Thr Leu Lys Ser Lys
945                 950                 955                 960
Leu Val Ser Asp Phe Arg Lys Asp Phe Gln Phe Tyr Lys Val Arg Glu
                965                 970                 975
Ile Asn Asn Tyr His His Ala His Asp Ala Tyr Leu Asn Ala Val Val
                980                 985                 990
Gly Thr Ala Leu Ile Lys Lys Tyr Pro Lys Leu Glu Ser Glu Phe Val
            995                 1000                1005
Tyr Gly Asp Tyr Lys Val Tyr Asp Val Arg Lys Met Ile Ala Lys
        1010                1015                1020
Ser Glu Gln Glu Ile Gly Lys Ala Thr Ala Lys Tyr Phe Phe Tyr
        1025                1030                1035
Ser Asn Ile Met Asn Phe Phe Lys Thr Glu Ile Thr Leu Ala Asn
        1040                1045                1050
```

```
Gly Glu Ile Arg Lys Arg Pro Leu Ile Glu Thr Asn Gly Glu Thr
        1055                1060                1065

Gly Glu Ile Val Trp Asp Lys Gly Arg Asp Phe Ala Thr Val Arg
        1070                1075                1080

Lys Val Leu Ser Met Pro Gln Val Asn Ile Val Lys Lys Thr Glu
        1085                1090                1095

Val Gln Thr Gly Gly Phe Ser Lys Glu Ser Ile Leu Pro Lys Arg
        1100                1105                1110

Asn Ser Asp Lys Leu Ile Ala Arg Lys Lys Asp Trp Asp Pro Lys
        1115                1120                1125

Lys Tyr Gly Gly Phe Asp Ser Pro Thr Val Ala Tyr Ser Val Leu
        1130                1135                1140

Val Val Ala Lys Val Glu Lys Gly Lys Ser Lys Lys Leu Lys Ser
        1145                1150                1155

Val Lys Glu Leu Leu Gly Ile Thr Ile Met Glu Arg Ser Ser Phe
        1160                1165                1170

Glu Lys Asn Pro Ile Asp Phe Leu Glu Ala Lys Gly Tyr Lys Glu
        1175                1180                1185

Val Lys Lys Asp Leu Ile Ile Lys Leu Pro Lys Tyr Ser Leu Phe
        1190                1195                1200

Glu Leu Glu Asn Gly Arg Lys Arg Met Leu Ala Ser Ala Gly Glu
        1205                1210                1215

Leu Gln Lys Gly Asn Glu Leu Ala Leu Pro Ser Lys Tyr Val Asn
        1220                1225                1230

Phe Leu Tyr Leu Ala Ser His Tyr Glu Lys Leu Lys Gly Ser Pro
        1235                1240                1245

Glu Asp Asn Glu Gln Lys Gln Leu Phe Val Glu Gln His Lys His
        1250                1255                1260

Tyr Leu Asp Glu Ile Ile Glu Gln Ile Ser Glu Phe Ser Lys Arg
        1265                1270                1275

Val Ile Leu Ala Asp Ala Asn Leu Asp Lys Val Leu Ser Ala Tyr
        1280                1285                1290

Asn Lys His Arg Asp Lys Pro Ile Arg Glu Gln Ala Glu Asn Ile
        1295                1300                1305

Ile His Leu Phe Thr Leu Thr Asn Leu Gly Ala Pro Ala Ala Phe
        1310                1315                1320

Lys Tyr Phe Asp Thr Thr Ile Asp Arg Lys Arg Tyr Thr Ser Thr
        1325                1330                1335

Lys Glu Val Leu Asp Ala Thr Leu Ile His Gln Ser Ile Thr Gly
        1340                1345                1350

Leu Tyr Glu Thr Arg Ile Asp Leu Ser Gln Leu Gly Gly Asp
        1355                1360                1365

<210> SEQ ID NO 3
<211> LENGTH: 1387
<212> TYPE: PRT
<213> ORGANISM: Streptococcus thermophilus

<400> SEQUENCE: 3

Thr Lys Pro Tyr Ser Ile Gly Leu Asp Ile Gly Thr Asn Ser Val Gly
1               5                   10                  15

Trp Ala Val Thr Thr Asp Asn Tyr Lys Val Pro Ser Lys Lys Met Lys
                20                  25                  30

Val Leu Gly Asn Thr Ser Lys Lys Tyr Ile Lys Lys Asn Leu Leu Gly
        35                  40                  45
```

```
Val Leu Leu Phe Asp Ser Gly Ile Thr Ala Glu Gly Arg Arg Leu Lys
 50                  55                  60

Arg Thr Ala Arg Arg Tyr Thr Arg Arg Asn Arg Ile Leu Tyr
 65                  70                  75                  80

Leu Gln Glu Ile Phe Ser Thr Glu Met Ala Thr Leu Asp Asp Ala Phe
                     85                  90                  95

Phe Gln Arg Leu Asp Asp Ser Phe Leu Val Pro Asp Asp Lys Arg Asp
                100                 105                 110

Ser Lys Tyr Pro Ile Phe Gly Asn Leu Val Glu Glu Lys Ala Tyr His
                115                 120                 125

Asp Glu Phe Pro Thr Ile Tyr His Leu Arg Lys Tyr Leu Ala Asp Ser
130                 135                 140

Thr Lys Lys Ala Asp Leu Arg Leu Val Tyr Leu Ala Leu Ala His Met
145                 150                 155                 160

Ile Lys Tyr Arg Gly His Phe Leu Ile Glu Gly Glu Phe Asn Ser Lys
                165                 170                 175

Asn Asn Asp Ile Gln Lys Asn Phe Gln Asp Phe Leu Asp Thr Tyr Asn
                180                 185                 190

Ala Ile Phe Glu Ser Asp Leu Ser Leu Glu Asn Ser Lys Gln Leu Glu
                195                 200                 205

Glu Ile Val Lys Asp Lys Ile Ser Lys Leu Glu Lys Lys Asp Arg Ile
                210                 215                 220

Leu Lys Leu Phe Pro Gly Glu Lys Asn Ser Gly Ile Phe Ser Glu Phe
225                 230                 235                 240

Leu Lys Leu Ile Val Gly Asn Gln Ala Asp Phe Arg Lys Cys Phe Asn
                245                 250                 255

Leu Asp Glu Lys Ala Ser Leu His Phe Ser Lys Glu Ser Tyr Asp Glu
                260                 265                 270

Asp Leu Glu Thr Leu Leu Gly Tyr Ile Gly Asp Asp Tyr Ser Asp Val
                275                 280                 285

Phe Leu Lys Ala Lys Lys Leu Tyr Asp Ala Ile Leu Leu Ser Gly Phe
                290                 295                 300

Leu Thr Val Thr Asp Asn Glu Thr Glu Ala Pro Leu Ser Ser Ala Met
305                 310                 315                 320

Ile Lys Arg Tyr Asn Glu His Lys Glu Asp Leu Ala Leu Leu Lys Glu
                325                 330                 335

Tyr Ile Arg Asn Ile Ser Leu Lys Thr Tyr Asn Glu Val Phe Lys Asp
                340                 345                 350

Asp Thr Lys Asn Gly Tyr Ala Gly Tyr Ile Asp Gly Lys Thr Asn Gln
                355                 360                 365

Glu Asp Phe Tyr Val Tyr Leu Lys Lys Leu Leu Ala Glu Phe Glu Gly
                370                 375                 380

Ala Asp Tyr Phe Leu Glu Lys Ile Asp Arg Glu Asp Phe Leu Arg Lys
385                 390                 395                 400

Gln Arg Thr Phe Asp Asn Gly Ser Ile Pro Tyr Gln Ile His Leu Gln
                405                 410                 415

Glu Met Arg Ala Ile Leu Asp Lys Gln Ala Lys Phe Tyr Pro Phe Leu
                420                 425                 430

Ala Lys Asn Lys Glu Arg Ile Glu Lys Ile Leu Thr Phe Arg Ile Pro
                435                 440                 445

Tyr Tyr Val Gly Pro Leu Ala Arg Gly Asn Ser Asp Phe Ala Trp Ser
450                 455                 460
```

```
Ile Arg Lys Arg Asn Glu Lys Ile Thr Pro Trp Asn Phe Glu Asp Val
465                 470                 475                 480

Ile Asp Lys Glu Ser Ser Ala Glu Ala Phe Ile Asn Arg Met Thr Ser
            485                 490                 495

Phe Asp Leu Tyr Leu Pro Glu Glu Lys Val Leu Pro Lys His Ser Leu
        500                 505                 510

Leu Tyr Glu Thr Phe Asn Val Tyr Asn Glu Leu Thr Lys Val Arg Phe
            515                 520                 525

Ile Ala Glu Ser Met Arg Asp Tyr Gln Phe Leu Asp Ser Lys Gln Lys
        530                 535                 540

Lys Asp Ile Val Arg Leu Tyr Phe Lys Asp Lys Arg Lys Val Thr Asp
545                 550                 555                 560

Lys Asp Ile Ile Glu Tyr Leu His Ala Ile Tyr Gly Tyr Asp Gly Ile
                565                 570                 575

Glu Leu Lys Gly Ile Glu Lys Gln Phe Asn Ser Ser Leu Ser Thr Tyr
            580                 585                 590

His Asp Leu Leu Asn Ile Ile Asn Asp Lys Glu Phe Leu Asp Asp Ser
        595                 600                 605

Ser Asn Glu Ala Ile Ile Glu Glu Ile Ile His Thr Leu Thr Ile Phe
    610                 615                 620

Glu Asp Arg Glu Met Ile Lys Gln Arg Leu Ser Lys Phe Glu Asn Ile
625                 630                 635                 640

Phe Asp Lys Ser Val Leu Lys Lys Leu Ser Arg Arg His Tyr Thr Gly
                645                 650                 655

Trp Gly Lys Leu Ser Ala Lys Leu Ile Asn Gly Ile Arg Asp Glu Lys
            660                 665                 670

Ser Gly Asn Thr Ile Leu Asp Tyr Leu Ile Asp Gly Ile Ser Asn
        675                 680                 685

Arg Asn Phe Met Gln Leu Ile His Asp Asp Ala Leu Ser Phe Lys Lys
    690                 695                 700

Lys Ile Gln Lys Ala Gln Ile Ile Gly Asp Glu Asp Lys Gly Asn Ile
705                 710                 715                 720

Lys Glu Val Val Lys Ser Leu Pro Gly Ser Pro Ala Ile Lys Lys Gly
                725                 730                 735

Ile Leu Gln Ser Ile Lys Ile Val Asp Glu Leu Val Lys Val Met Gly
            740                 745                 750

Gly Arg Lys Pro Glu Ser Ile Val Val Glu Met Ala Arg Glu Asn Gln
        755                 760                 765

Tyr Thr Asn Gln Gly Lys Ser Asn Ser Gln Gln Arg Leu Lys Arg Leu
    770                 775                 780

Glu Lys Ser Leu Lys Glu Leu Gly Ser Lys Ile Leu Lys Glu Asn Ile
785                 790                 795                 800

Pro Ala Lys Leu Ser Lys Ile Asp Asn Asn Ala Leu Gln Asn Asp Arg
                805                 810                 815

Leu Tyr Leu Tyr Tyr Leu Gln Asn Gly Lys Asp Met Tyr Thr Gly Asp
            820                 825                 830

Asp Leu Asp Ile Asp Arg Leu Ser Asn Tyr Asp Ile Asp His Ile Ile
        835                 840                 845

Pro Gln Ala Phe Leu Lys Asp Asn Ser Ile Asp Asn Lys Val Leu Val
    850                 855                 860

Ser Ser Ala Ser Asn Arg Gly Lys Ser Asp Asp Val Pro Ser Leu Glu
865                 870                 875                 880
```

-continued

```
Val Val Lys Lys Arg Lys Thr Phe Trp Tyr Gln Leu Leu Lys Ser Lys
            885                 890                 895

Leu Ile Ser Gln Arg Lys Phe Asp Asn Leu Thr Lys Ala Glu Arg Gly
        900                 905                 910

Gly Leu Ser Pro Glu Asp Lys Ala Gly Phe Ile Gln Arg Gln Leu Val
        915                 920                 925

Glu Thr Arg Gln Ile Thr Lys His Val Ala Arg Leu Leu Asp Glu Lys
    930                 935                 940

Phe Asn Asn Lys Lys Asp Glu Asn Asn Arg Ala Val Arg Thr Val Lys
945                 950                 955                 960

Ile Ile Thr Leu Lys Ser Thr Leu Val Ser Gln Phe Arg Lys Asp Phe
            965                 970                 975

Glu Leu Tyr Lys Val Arg Glu Ile Asn Asp Phe His His Ala His Asp
        980                 985                 990

Ala Tyr Leu Asn Ala Val Val Ala  Ser Ala Leu Leu Lys  Lys Tyr Pro
        995                 1000                1005

Lys Leu Glu Pro Glu Phe Val  Tyr Gly Asp Tyr Pro  Lys Tyr Asn
    1010                1015                1020

Ser Phe Arg Glu Arg Lys Ser  Ala Thr Glu Lys Val  Tyr Phe Tyr
    1025                1030                1035

Ser Asn Ile Met Asn Ile Phe  Lys Lys Ser Ile Ser  Leu Ala Asp
    1040                1045                1050

Gly Arg Val Ile Glu Arg Pro  Leu Ile Glu Val Asn  Glu Glu Thr
    1055                1060                1065

Gly Glu Ser Val Trp Asn Lys  Glu Ser Asp Leu Ala  Thr Val Arg
    1070                1075                1080

Arg Val Leu Ser Tyr Pro Gln  Val Asn Val Val Lys  Lys Val Glu
    1085                1090                1095

Glu Gln Asn His Gly Leu Asp  Arg Gly Lys Pro Lys  Gly Leu Phe
    1100                1105                1110

Asn Ala Asn Leu Ser Ser Lys  Pro Lys Pro Asn Ser  Asn Glu Asn
    1115                1120                1125

Leu Val Gly Ala Lys Glu Tyr  Leu Asp Pro Lys Lys  Tyr Gly Gly
    1130                1135                1140

Tyr Ala Gly Ile Ser Asn Ser  Phe Thr Val Leu Val  Lys Gly Thr
    1145                1150                1155

Ile Glu Lys Gly Ala Lys Lys  Lys Ile Thr Asn Val  Leu Glu Phe
    1160                1165                1170

Gln Gly Ile Ser Ile Leu Asp  Arg Ile Asn Tyr Arg  Lys Asp Lys
    1175                1180                1185

Leu Asn Phe Leu Leu Glu Lys  Gly Tyr Lys Asp Ile  Glu Leu Ile
    1190                1195                1200

Ile Glu Leu Pro Lys Tyr Ser  Leu Phe Glu Leu Ser  Asp Gly Ser
    1205                1210                1215

Arg Arg Met Leu Ala Ser Ile  Leu Ser Thr Asn Asn  Lys Arg Gly
    1220                1225                1230

Glu Ile His Lys Gly Asn Gln  Ile Phe Leu Ser Gln  Lys Phe Val
    1235                1240                1245

Lys Leu Leu Tyr His Ala Lys  Arg Ile Ser Asn Thr  Ile Asn Glu
    1250                1255                1260

Asn His Arg Lys Tyr Val Glu  Asn His Lys Lys Glu  Phe Glu Glu
    1265                1270                1275
```

```
Leu Phe Tyr Tyr Ile Leu Glu Phe Asn Glu Asn Tyr Val Gly Ala
    1280                1285                1290

Lys Lys Asn Gly Lys Leu Leu Asn Ser Ala Phe Gln Ser Trp Gln
    1295                1300                1305

Asn His Ser Ile Asp Glu Leu Cys Ser Ser Phe Ile Gly Pro Thr
    1310                1315                1320

Gly Ser Glu Arg Lys Gly Leu Phe Glu Leu Thr Ser Arg Gly Ser
    1325                1330                1335

Ala Ala Asp Phe Glu Phe Leu Gly Val Lys Ile Pro Arg Tyr Arg
    1340                1345                1350

Asp Tyr Thr Pro Ser Ser Leu Leu Lys Asp Ala Thr Leu Ile His
    1355                1360                1365

Gln Ser Val Thr Gly Leu Tyr Glu Thr Arg Ile Asp Leu Ala Lys
    1370                1375                1380

Leu Gly Glu Gly
    1385

<210> SEQ ID NO 4
<211> LENGTH: 1333
<212> TYPE: PRT
<213> ORGANISM: Listeria innocua

<400> SEQUENCE: 4

Lys Lys Pro Tyr Thr Ile Gly Leu Asp Ile Gly Thr Asn Ser Val Gly
1               5                   10                  15

Trp Ala Val Leu Thr Asp Gln Tyr Asp Leu Val Lys Arg Lys Met Lys
            20                  25                  30

Ile Ala Gly Asp Ser Glu Lys Lys Gln Ile Lys Lys Asn Phe Trp Gly
        35                  40                  45

Val Arg Leu Phe Asp Glu Gly Gln Thr Ala Ala Asp Arg Arg Met Ala
    50                  55                  60

Arg Thr Ala Arg Arg Arg Ile Glu Arg Arg Arg Asn Arg Ile Ser Tyr
65                  70                  75                  80

Leu Gln Gly Ile Phe Ala Glu Glu Met Ser Lys Thr Asp Ala Asn Phe
                85                  90                  95

Phe Cys Arg Leu Ser Asp Ser Phe Tyr Val Asp Asn Glu Lys Arg Asn
            100                 105                 110

Ser Arg His Pro Phe Phe Ala Thr Ile Glu Glu Glu Val Glu Tyr His
        115                 120                 125

Lys Asn Tyr Pro Thr Ile Tyr His Leu Arg Glu Glu Leu Val Asn Ser
    130                 135                 140

Ser Glu Lys Ala Asp Leu Arg Leu Val Tyr Leu Ala Leu Ala His Ile
145                 150                 155                 160

Ile Lys Tyr Arg Gly Asn Phe Leu Ile Glu Gly Ala Leu Asp Thr Gln
                165                 170                 175

Asn Thr Ser Val Asp Gly Ile Tyr Lys Gln Phe Ile Gln Thr Tyr Asn
            180                 185                 190

Gln Val Phe Ala Ser Gly Ile Glu Asp Gly Ser Leu Lys Lys Leu Glu
        195                 200                 205

Asp Asn Lys Asp Val Ala Lys Ile Leu Val Lys Val Thr Arg Lys
    210                 215                 220

Glu Lys Leu Glu Arg Ile Leu Lys Leu Tyr Pro Gly Glu Lys Ser Ala
225                 230                 235                 240
```

```
Gly Met Phe Ala Gln Phe Ile Ser Leu Ile Val Gly Ser Lys Gly Asn
                245                 250                 255

Phe Gln Lys Pro Phe Asp Leu Ile Glu Lys Ser Asp Ile Glu Cys Ala
            260                 265                 270

Lys Asp Ser Tyr Glu Glu Asp Leu Glu Ser Leu Leu Ala Leu Ile Gly
        275                 280                 285

Asp Glu Tyr Ala Glu Leu Phe Val Ala Ala Lys Asn Ala Tyr Ser Ala
    290                 295                 300

Val Val Leu Ser Ser Ile Ile Thr Val Ala Glu Thr Glu Thr Asn Ala
305                 310                 315                 320

Lys Leu Ser Ala Ser Met Ile Glu Arg Phe Asp Thr His Glu Glu Asp
                325                 330                 335

Leu Gly Glu Leu Lys Ala Phe Ile Lys Leu His Leu Pro Lys His Tyr
            340                 345                 350

Glu Glu Ile Phe Ser Asn Thr Glu Lys His Gly Tyr Ala Gly Tyr Ile
        355                 360                 365

Asp Gly Lys Thr Lys Gln Ala Asp Phe Tyr Lys Tyr Met Lys Met Thr
    370                 375                 380

Leu Glu Asn Ile Glu Gly Ala Asp Tyr Phe Ile Ala Lys Ile Glu Lys
385                 390                 395                 400

Glu Asn Phe Leu Arg Lys Gln Arg Thr Phe Asp Asn Gly Ala Ile Pro
                405                 410                 415

His Gln Leu His Leu Glu Glu Leu Glu Ala Ile Leu His Gln Gln Ala
            420                 425                 430

Lys Tyr Tyr Pro Phe Leu Lys Glu Asn Tyr Asp Lys Ile Lys Ser Leu
        435                 440                 445

Val Thr Phe Arg Ile Pro Tyr Phe Val Gly Pro Leu Ala Asn Gly Gln
    450                 455                 460

Ser Glu Phe Ala Trp Leu Thr Arg Lys Ala Asp Gly Glu Ile Arg Pro
465                 470                 475                 480

Trp Asn Ile Glu Glu Lys Val Asp Phe Gly Lys Ser Ala Val Asp Phe
                485                 490                 495

Ile Glu Lys Met Thr Asn Lys Asp Thr Tyr Leu Pro Lys Glu Asn Val
            500                 505                 510

Leu Pro Lys His Ser Leu Cys Tyr Gln Lys Tyr Leu Val Tyr Asn Glu
        515                 520                 525

Leu Thr Lys Val Arg Tyr Ile Asn Asp Gln Gly Lys Thr Ser Tyr Phe
    530                 535                 540

Ser Gly Gln Glu Lys Glu Gln Ile Phe Asn Asp Leu Phe Lys Gln Lys
545                 550                 555                 560

Arg Lys Val Lys Lys Lys Asp Leu Glu Leu Phe Leu Arg Asn Met Ser
                565                 570                 575

His Val Glu Ser Pro Thr Ile Glu Gly Leu Glu Asp Ser Phe Asn Ser
            580                 585                 590

Ser Tyr Ser Thr Tyr His Asp Leu Leu Lys Val Gly Ile Lys Gln Glu
        595                 600                 605

Ile Leu Asp Asn Pro Val Asn Thr Glu Met Leu Glu Asn Ile Val Lys
    610                 615                 620

Ile Leu Thr Val Phe Glu Asp Lys Arg Met Ile Lys Glu Gln Leu Gln
625                 630                 635                 640

Gln Phe Ser Asp Val Leu Asp Gly Val Val Leu Lys Lys Leu Glu Arg
                645                 650                 655
```

```
Arg His Tyr Thr Gly Trp Gly Arg Leu Ser Ala Lys Leu Leu Met Gly
            660                 665                 670

Ile Arg Asp Lys Gln Ser His Leu Thr Ile Leu Asp Tyr Leu Met Asn
        675                 680                 685

Asp Asp Gly Leu Asn Arg Asn Leu Met Gln Leu Ile Asn Asp Ser Asn
690                 695                 700

Leu Ser Phe Lys Ser Ile Ile Glu Lys Glu Gln Val Thr Thr Ala Asp
705                 710                 715                 720

Lys Asp Ile Gln Ser Ile Val Ala Asp Leu Ala Gly Ser Pro Ala Ile
                725                 730                 735

Lys Lys Gly Ile Leu Gln Ser Leu Lys Ile Val Asp Glu Leu Val Ser
            740                 745                 750

Val Met Gly Tyr Pro Pro Gln Thr Ile Val Val Glu Met Ala Arg Glu
        755                 760                 765

Asn Gln Thr Thr Gly Lys Gly Lys Asn Asn Ser Arg Pro Arg Tyr Lys
770                 775                 780

Ser Leu Glu Lys Ala Ile Lys Glu Phe Gly Ser Gln Ile Leu Lys Glu
785                 790                 795                 800

His Pro Thr Asp Asn Gln Glu Leu Arg Asn Asn Arg Leu Tyr Leu Tyr
                805                 810                 815

Tyr Leu Gln Asn Gly Lys Asp Met Tyr Thr Gly Gln Asp Leu Asp Ile
            820                 825                 830

His Asn Leu Ser Asn Tyr Asp Ile Asp His Ile Val Pro Gln Ser Phe
        835                 840                 845

Ile Thr Asp Asn Ser Ile Asp Asn Leu Val Leu Thr Ser Ser Ala Gly
850                 855                 860

Asn Arg Glu Lys Gly Asp Val Pro Pro Leu Glu Ile Val Arg Lys
865                 870                 875                 880

Arg Lys Val Phe Trp Glu Lys Leu Tyr Gln Gly Asn Leu Met Ser Lys
                885                 890                 895

Arg Lys Phe Asp Tyr Leu Thr Lys Ala Glu Arg Gly Gly Leu Thr Glu
            900                 905                 910

Ala Asp Lys Ala Arg Phe Ile His Arg Gln Leu Val Glu Thr Arg Gln
        915                 920                 925

Ile Thr Lys Asn Val Ala Asn Ile Leu His Gln Arg Phe Asn Tyr Glu
930                 935                 940

Lys Asp Asp His Gly Asn Thr Met Lys Gln Val Arg Ile Val Thr Leu
945                 950                 955                 960

Lys Ser Ala Leu Val Ser Gln Phe Arg Lys Gln Phe Gln Leu Tyr Lys
                965                 970                 975

Val Arg Asp Val Asn Asp Tyr His His Ala His Asp Ala Tyr Leu Asn
            980                 985                 990

Gly Val Val Ala Asn Thr Leu Leu Lys Val Tyr Pro Gln Leu Glu Pro
        995                 1000                1005

Glu Phe Val Tyr Gly Asp Tyr His Gln Phe Asp Trp Phe Lys Ala
        1010                1015                1020

Asn Lys Ala Thr Ala Lys Lys Gln Phe Tyr Thr Asn Ile Met Leu
        1025                1030                1035

Phe Phe Ala Gln Lys Asp Arg Ile Ile Asp Glu Asn Gly Glu Ile
        1040                1045                1050

Leu Trp Asp Lys Lys Tyr Leu Asp Thr Val Lys Lys Val Met Ser
        1055                1060                1065
```

```
Tyr Arg Gln Met Asn Ile Val Lys Lys Thr Glu Ile Gln Lys Gly
        1070            1075                1080

Glu Phe Ser Lys Ala Thr Ile Lys Pro Lys Gly Asn Ser Ser Lys
    1085                1090                1095

Leu Ile Pro Arg Lys Thr Asn Trp Asp Pro Met Lys Tyr Gly Gly
    1100                1105                1110

Leu Asp Ser Pro Asn Met Ala Tyr Ala Val Val Ile Glu Tyr Ala
    1115                1120                1125

Lys Gly Lys Asn Lys Leu Val Phe Glu Lys Lys Ile Ile Arg Val
    1130                1135                1140

Thr Ile Met Glu Arg Lys Ala Phe Glu Lys Asp Glu Lys Ala Phe
    1145                1150                1155

Leu Glu Glu Gln Gly Tyr Arg Gln Pro Lys Val Leu Ala Lys Leu
    1160                1165                1170

Pro Lys Tyr Thr Leu Tyr Glu Cys Glu Glu Gly Arg Arg Arg Met
    1175                1180                1185

Leu Ala Ser Ala Asn Glu Ala Gln Lys Gly Asn Gln Gln Val Leu
    1190                1195                1200

Pro Asn His Leu Val Thr Leu Leu His His Ala Ala Asn Cys Glu
    1205                1210                1215

Val Ser Asp Gly Lys Ser Leu Asp Tyr Ile Glu Ser Asn Arg Glu
    1220                1225                1230

Met Phe Ala Glu Leu Leu Ala His Val Ser Glu Phe Ala Lys Arg
    1235                1240                1245

Tyr Thr Leu Ala Glu Ala Asn Leu Asn Lys Ile Asn Gln Leu Phe
    1250                1255                1260

Glu Gln Asn Lys Glu Gly Asp Ile Lys Ala Ile Ala Gln Ser Phe
    1265                1270                1275

Val Asp Leu Met Ala Phe Asn Ala Met Gly Ala Pro Ala Ser Phe
    1280                1285                1290

Lys Phe Phe Glu Thr Thr Ile Glu Arg Lys Arg Tyr Asn Asn Leu
    1295                1300                1305

Lys Glu Leu Leu Asn Ser Thr Ile Ile Tyr Gln Ser Ile Thr Gly
    1310                1315                1320

Leu Tyr Glu Ser Arg Lys Arg Leu Asp Asp
    1325                1330

<210> SEQ ID NO 5
<211> LENGTH: 96
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: a, c, u, g, unknown or other

<400> SEQUENCE: 5
nnnnnnnnnn nnnnnnnnnn guuuuagagc uagaaauagc aaguuaaaau aaggcuaguc    60
cguuaucaac uugaaaaagu ggcaccgagu cggugc                              96

<210> SEQ ID NO 6
<211> LENGTH: 1082
<212> TYPE: PRT
<213> ORGANISM: Neisseria meningitidis
```

<400> SEQUENCE: 6

```
Met Ala Ala Phe Lys Pro Asn Ser Ile Asn Tyr Ile Leu Gly Leu Asp
1               5                   10                  15

Ile Gly Ile Ala Ser Val Gly Trp Ala Met Val Glu Ile Asp Glu Glu
            20                  25                  30

Glu Asn Pro Ile Arg Leu Ile Asp Leu Gly Val Arg Val Phe Glu Arg
        35                  40                  45

Ala Glu Val Pro Lys Thr Gly Asp Ser Leu Ala Met Ala Arg Arg Leu
50                  55                  60

Ala Arg Ser Val Arg Arg Leu Thr Arg Arg Ala His Arg Leu Leu
65                  70                  75                  80

Arg Thr Arg Arg Leu Leu Lys Arg Glu Gly Val Leu Gln Ala Ala Asn
                85                  90                  95

Phe Asp Glu Asn Gly Leu Ile Lys Ser Leu Pro Asn Thr Pro Trp Gln
            100                 105                 110

Leu Arg Ala Ala Ala Leu Asp Arg Lys Leu Thr Pro Leu Glu Trp Ser
        115                 120                 125

Ala Val Leu Leu His Leu Ile Lys His Arg Gly Tyr Leu Ser Gln Arg
130                 135                 140

Lys Asn Glu Gly Glu Thr Ala Asp Lys Glu Leu Gly Ala Leu Leu Lys
145                 150                 155                 160

Gly Val Ala Gly Asn Ala His Ala Leu Gln Thr Gly Asp Phe Arg Thr
                165                 170                 175

Pro Ala Glu Leu Ala Leu Asn Lys Phe Glu Lys Glu Ser Gly His Ile
            180                 185                 190

Arg Asn Gln Arg Ser Asp Tyr Ser His Thr Phe Ser Arg Lys Asp Leu
        195                 200                 205

Gln Ala Glu Leu Ile Leu Leu Phe Glu Lys Gln Lys Glu Phe Gly Asn
210                 215                 220

Pro His Val Ser Gly Gly Leu Lys Glu Gly Ile Glu Thr Leu Leu Met
225                 230                 235                 240

Thr Gln Arg Pro Ala Leu Ser Gly Asp Ala Val Gln Lys Met Leu Gly
                245                 250                 255

His Cys Thr Phe Glu Pro Ala Glu Pro Lys Ala Ala Lys Asn Thr Tyr
            260                 265                 270

Thr Ala Glu Arg Phe Ile Trp Leu Thr Lys Leu Asn Asn Leu Arg Ile
        275                 280                 285

Leu Glu Gln Gly Ser Glu Arg Pro Leu Thr Asp Thr Glu Arg Ala Thr
290                 295                 300

Leu Met Asp Glu Pro Tyr Arg Lys Ser Lys Leu Thr Tyr Ala Gln Ala
305                 310                 315                 320

Arg Lys Leu Leu Gly Leu Glu Asp Thr Ala Phe Phe Lys Gly Leu Arg
                325                 330                 335

Tyr Gly Lys Asp Asn Ala Glu Ala Ser Thr Leu Met Glu Met Lys Ala
            340                 345                 350

Tyr His Ala Ile Ser Arg Ala Leu Glu Lys Glu Gly Leu Lys Asp Lys
        355                 360                 365

Lys Ser Pro Leu Asn Leu Ser Pro Glu Leu Gln Asp Glu Ile Gly Thr
370                 375                 380

Ala Phe Ser Leu Phe Lys Thr Asp Glu Asp Ile Thr Gly Arg Leu Lys
385                 390                 395                 400
```

-continued

```
Asp Arg Ile Gln Pro Glu Ile Leu Glu Ala Leu Leu Lys His Ile Ser
                405                 410                 415
Phe Asp Lys Phe Val Gln Ile Ser Leu Lys Ala Leu Arg Arg Ile Val
            420                 425                 430
Pro Leu Met Glu Gln Gly Lys Arg Tyr Asp Glu Ala Cys Ala Glu Ile
        435                 440                 445
Tyr Gly Asp His Tyr Gly Lys Lys Asn Thr Glu Glu Lys Ile Tyr Leu
    450                 455                 460
Pro Pro Ile Pro Ala Asp Glu Ile Arg Asn Pro Val Val Leu Arg Ala
465                 470                 475                 480
Leu Ser Gln Ala Arg Lys Val Ile Asn Gly Val Val Arg Arg Tyr Gly
                485                 490                 495
Ser Pro Ala Arg Ile His Ile Glu Thr Ala Arg Glu Val Gly Lys Ser
            500                 505                 510
Phe Lys Asp Arg Lys Glu Ile Glu Lys Arg Gln Glu Glu Asn Arg Lys
        515                 520                 525
Asp Arg Glu Lys Ala Ala Ala Lys Phe Arg Glu Tyr Phe Pro Asn Phe
    530                 535                 540
Val Gly Glu Pro Lys Ser Lys Asp Ile Leu Lys Leu Arg Leu Tyr Glu
545                 550                 555                 560
Gln Gln His Gly Lys Cys Leu Tyr Ser Gly Lys Glu Ile Asn Leu Gly
                565                 570                 575
Arg Leu Asn Glu Lys Gly Tyr Val Glu Ile Asp His Ala Leu Pro Phe
            580                 585                 590
Ser Arg Thr Trp Asp Asp Ser Phe Asn Asn Lys Val Leu Val Leu Gly
        595                 600                 605
Ser Glu Asn Gln Asn Lys Gly Asn Gln Thr Pro Tyr Glu Tyr Phe Asn
    610                 615                 620
Gly Lys Asp Asn Ser Arg Glu Trp Gln Glu Phe Lys Ala Arg Val Glu
625                 630                 635                 640
Thr Ser Arg Phe Pro Arg Ser Lys Lys Gln Arg Ile Leu Leu Gln Lys
                645                 650                 655
Phe Asp Glu Asp Gly Phe Lys Glu Arg Asn Leu Asn Asp Thr Arg Tyr
            660                 665                 670
Val Asn Arg Phe Leu Cys Gln Phe Val Ala Asp Arg Met Arg Leu Thr
        675                 680                 685
Gly Lys Gly Lys Lys Arg Val Phe Ala Ser Asn Gly Gln Ile Thr Asn
    690                 695                 700
Leu Leu Arg Gly Phe Trp Gly Leu Arg Lys Val Arg Ala Glu Asn Asp
705                 710                 715                 720
Arg His His Ala Leu Asp Ala Val Val Val Ala Cys Ser Thr Val Ala
                725                 730                 735
Met Gln Gln Lys Ile Thr Arg Phe Val Arg Tyr Lys Glu Met Asn Ala
            740                 745                 750
Phe Asp Gly Lys Thr Ile Asp Lys Glu Thr Gly Glu Val Leu His Gln
        755                 760                 765
Lys Thr His Phe Pro Gln Pro Trp Glu Phe Phe Ala Gln Glu Val Met
    770                 775                 780
Ile Arg Val Phe Gly Lys Pro Asp Gly Lys Pro Glu Phe Glu Glu Ala
785                 790                 795                 800
Asp Thr Leu Glu Lys Leu Arg Thr Leu Leu Ala Glu Lys Leu Ser Ser
                805                 810                 815
```

Arg Pro Glu Ala Val His Glu Tyr Val Thr Pro Leu Phe Val Ser Arg
                820                 825                 830

Ala Pro Asn Arg Lys Met Ser Gly Gln Gly His Met Glu Thr Val Lys
            835                 840                 845

Ser Ala Lys Arg Leu Asp Glu Gly Val Ser Val Leu Arg Val Pro Leu
        850                 855                 860

Thr Gln Leu Lys Leu Lys Asp Leu Glu Lys Met Val Asn Arg Glu Arg
865                 870                 875                 880

Glu Pro Lys Leu Tyr Glu Ala Leu Lys Ala Arg Leu Glu Ala His Lys
                885                 890                 895

Asp Asp Pro Ala Lys Ala Phe Ala Glu Pro Phe Tyr Lys Tyr Asp Lys
            900                 905                 910

Ala Gly Asn Arg Thr Gln Gln Val Lys Ala Val Arg Val Glu Gln Val
        915                 920                 925

Gln Lys Thr Gly Val Trp Val Arg Asn His Asn Gly Ile Ala Asp Asn
930                 935                 940

Ala Thr Met Val Arg Val Asp Val Phe Glu Lys Gly Asp Lys Tyr Tyr
945                 950                 955                 960

Leu Val Pro Ile Tyr Ser Trp Gln Val Ala Lys Gly Ile Leu Pro Asp
                965                 970                 975

Arg Ala Val Val Gln Gly Lys Asp Glu Glu Asp Trp Gln Leu Ile Asp
            980                 985                 990

Asp Ser Phe Asn Phe Lys Phe Ser Leu His Pro Asn Asp Leu Val Glu
        995                 1000                1005

Val Ile Thr Lys Lys Ala Arg Met Phe Gly Tyr Phe Ala Ser Cys
    1010                1015                1020

His Arg Gly Thr Gly Asn Ile Asn Ile Arg Ile His Asp Leu Asp
    1025                1030                1035

His Lys Ile Gly Lys Asn Gly Ile Leu Glu Gly Ile Gly Val Lys
    1040                1045                1050

Thr Ala Leu Ser Phe Gln Lys Tyr Gln Ile Asp Glu Leu Gly Lys
    1055                1060                1065

Glu Ile Arg Pro Cys Arg Leu Lys Lys Arg Pro Val Arg
    1070                1075                1080

<210> SEQ ID NO 7
<211> LENGTH: 1368
<212> TYPE: PRT
<213> ORGANISM: Streptococcus pyogenes

<400> SEQUENCE: 7

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
115                 120                 125

His Glu Lys Tyr Pro Thr Ile Tyr His Leu Arg Lys Lys Leu Val Asp
130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
                180                 185                 190

Asn Gln Leu Phe Glu Glu Asn Pro Ile Asn Ala Ser Gly Val Asp Ala
                195                 200                 205

Lys Ala Ile Leu Ser Ala Arg Leu Ser Lys Ser Arg Arg Leu Glu Asn
210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
                260                 265                 270

Asp Asp Leu Asp Asn Leu Leu Ala Gln Ile Gly Asp Gln Tyr Ala Asp
                275                 280                 285

Leu Phe Leu Ala Ala Lys Asn Leu Ser Asp Ala Ile Leu Leu Ser Asp
                290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
                340                 345                 350

Asp Gln Ser Lys Asn Gly Tyr Ala Gly Tyr Ile Asp Gly Gly Ala Ser
                355                 360                 365

Gln Glu Glu Phe Tyr Lys Phe Ile Lys Pro Ile Leu Glu Lys Met Asp
                370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
                420                 425                 430

Leu Lys Asp Asn Arg Glu Lys Ile Glu Lys Ile Leu Thr Phe Arg Ile
                435                 440                 445

Pro Tyr Tyr Val Gly Pro Leu Ala Arg Gly Asn Ser Arg Phe Ala Trp
450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
                500                 505                 510

Leu Leu Tyr Glu Tyr Phe Thr Val Tyr Asn Glu Leu Thr Lys Val Lys
515                 520                 525

```
Tyr Val Thr Glu Gly Met Arg Lys Pro Ala Phe Leu Ser Gly Glu Gln
            530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
    610                 615                 620

Leu Phe Glu Asp Arg Glu Met Ile Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
    690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
    770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Lys
        835                 840                 845

Asp Asp Ser Ile Asp Asn Lys Val Leu Thr Arg Ser Asp Lys Asn Arg
    850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
    930                 935                 940
```

-continued

```
Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
            965                 970                 975

Glu Ile Asn Asn Tyr His His Ala His Asp Ala Tyr Leu Asn Ala Val
        980                 985                 990

Val Gly Thr Ala Leu Ile Lys Lys Tyr Pro Lys Leu Glu Ser Glu Phe
        995                 1000                1005

Val Tyr Gly Asp Tyr Lys Val Tyr Asp Val Arg Lys Met Ile Ala
    1010                1015                1020

Lys Ser Glu Gln Glu Ile Gly Lys Ala Thr Ala Lys Tyr Phe Phe
    1025                1030                1035

Tyr Ser Asn Ile Met Asn Phe Phe Lys Thr Glu Ile Thr Leu Ala
    1040                1045                1050

Asn Gly Glu Ile Arg Lys Arg Pro Leu Ile Glu Thr Asn Gly Glu
    1055                1060                1065

Thr Gly Glu Ile Val Trp Asp Lys Gly Arg Asp Phe Ala Thr Val
    1070                1075                1080

Arg Lys Val Leu Ser Met Pro Gln Val Asn Ile Val Lys Lys Thr
    1085                1090                1095

Glu Val Gln Thr Gly Gly Phe Ser Lys Glu Ser Ile Leu Pro Lys
    1100                1105                1110

Arg Asn Ser Asp Lys Leu Ile Ala Arg Lys Lys Asp Trp Asp Pro
    1115                1120                1125

Lys Lys Tyr Gly Gly Phe Asp Ser Pro Thr Val Ala Tyr Ser Val
    1130                1135                1140

Leu Val Val Ala Lys Val Glu Lys Gly Lys Ser Lys Lys Leu Lys
    1145                1150                1155

Ser Val Lys Glu Leu Leu Gly Ile Thr Ile Met Glu Arg Ser Ser
    1160                1165                1170

Phe Glu Lys Asn Pro Ile Asp Phe Leu Glu Ala Lys Gly Tyr Lys
    1175                1180                1185

Glu Val Lys Lys Asp Leu Ile Ile Lys Leu Pro Lys Tyr Ser Leu
    1190                1195                1200

Phe Glu Leu Glu Asn Gly Arg Lys Arg Met Leu Ala Ser Ala Gly
    1205                1210                1215

Glu Leu Gln Lys Gly Asn Glu Leu Ala Leu Pro Ser Lys Tyr Val
    1220                1225                1230

Asn Phe Leu Tyr Leu Ala Ser His Tyr Glu Lys Leu Lys Gly Ser
    1235                1240                1245

Pro Glu Asp Asn Glu Gln Lys Gln Leu Phe Val Glu Gln His Lys
    1250                1255                1260

His Tyr Leu Asp Glu Ile Ile Glu Gln Ile Ser Glu Phe Ser Lys
    1265                1270                1275

Arg Val Ile Leu Ala Asp Ala Asn Leu Asp Lys Val Leu Ser Ala
    1280                1285                1290

Tyr Asn Lys His Arg Asp Lys Pro Ile Arg Glu Gln Ala Glu Asn
    1295                1300                1305

Ile Ile His Leu Phe Thr Leu Thr Asn Leu Gly Ala Pro Ala Ala
    1310                1315                1320

Phe Lys Tyr Phe Asp Thr Thr Ile Asp Arg Lys Arg Tyr Thr Ser
    1325                1330                1335
```

-continued

```
Thr Lys Glu Val Leu Asp Ala Thr Leu Ile His Gln Ser Ile Thr
    1340                1345                1350

Gly Leu Tyr Glu Thr Arg Ile Asp Leu Ser Gln Leu Gly Gly Asp
        1355                1360                1365

<210> SEQ ID NO 8
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Ile, Val, Met, Leu or Thr
<220> FEATURE:
<221> NAME/KEY: MOD_RES
<222> LOCATION: (4)..(4)
<223> OTHER INFORMATION: Thr, Ile, Val, Ser, Asn, Tyr, Glu or Leu
<220> FEATURE:
<221> NAME/KEY: MOD_RES
<222> LOCATION: (5)..(5)
<223> OTHER INFORMATION: Asn, Ser, Gly, Ala, Asp, Thr, Arg, Met or Phe
<220> FEATURE:
<221> NAME/KEY: MOD_RES
<222> LOCATION: (6)..(6)
<223> OTHER INFORMATION: Ser, Tyr, Asn or Phe
<220> FEATURE:
<221> NAME/KEY: MOD_RES
<222> LOCATION: (7)..(7)
<223> OTHER INFORMATION: Val, Ile, Leu, Cys, Thr or Phe
<220> FEATURE:
<221> NAME/KEY: MOD_RES
<222> LOCATION: (9)..(9)
<223> OTHER INFORMATION: Trp, Phe, Val, Tyr, Ser or Leu
<220> FEATURE:
<221> NAME/KEY: MOD_RES
<222> LOCATION: (10)..(10)
<223> OTHER INFORMATION: Ala, Ser, Cys, Val or Gly
<220> FEATURE:
<221> NAME/KEY: MOD_RES
<222> LOCATION: (11)..(11)
<223> OTHER INFORMATION: Val, Ile, Leu, Ala, Met or His
<220> FEATURE:
<221> NAME/KEY: MOD_RES
<222> LOCATION: (12)..(12)
<223> OTHER INFORMATION: Any amino acid or is absent

<400> SEQUENCE: 8

Asp Xaa Gly Xaa Xaa Xaa Xaa Gly Xaa Xaa Xaa Xaa
1               5                   10

<210> SEQ ID NO 9
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Ile, Val, Met, Leu or Thr
<220> FEATURE:
<221> NAME/KEY: MOD_RES
<222> LOCATION: (4)..(4)
<223> OTHER INFORMATION: Thr, Ile, Val, Ser, Asn, Tyr, Glu or Leu
<220> FEATURE:
<221> NAME/KEY: MOD_RES
<222> LOCATION: (5)..(5)
<223> OTHER INFORMATION: Asn, Ser, Gly, Ala, Asp, Thr, Arg, Met or Phe
<220> FEATURE:
<221> NAME/KEY: MOD_RES
<222> LOCATION: (7)..(7)
```

```
<223> OTHER INFORMATION: Val, Ile, Leu, Cys, Thr or Phe
<220> FEATURE:
<221> NAME/KEY: MOD_RES
<222> LOCATION: (9)..(9)
<223> OTHER INFORMATION: Trp, Phe, Val, Tyr, Ser or Leu
<220> FEATURE:
<221> NAME/KEY: MOD_RES
<222> LOCATION: (10)..(10)
<223> OTHER INFORMATION: Ala, Ser, Cys, Val or Gly
<220> FEATURE:
<221> NAME/KEY: MOD_RES
<222> LOCATION: (11)..(11)
<223> OTHER INFORMATION: Val, Ile, Leu, Ala, Met or His
<220> FEATURE:
<221> NAME/KEY: MOD_RES
<222> LOCATION: (12)..(12)
<223> OTHER INFORMATION: Any amino acid or is absent

<400> SEQUENCE: 9

Asp Xaa Gly Xaa Xaa Ser Xaa Gly Xaa Xaa Xaa Xaa
1               5                   10

<210> SEQ ID NO 10
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Thr, Ile, Val, Ser, Asn, Tyr, Glu or Leu
<220> FEATURE:
<221> NAME/KEY: MOD_RES
<222> LOCATION: (5)..(5)
<223> OTHER INFORMATION: Asn, Ser, Gly, Ala, Asp, Thr, Arg, Met or Phe
<220> FEATURE:
<221> NAME/KEY: MOD_RES
<222> LOCATION: (11)..(11)
<223> OTHER INFORMATION: Val, Ile, Leu, Ala, Met or His
<220> FEATURE:
<221> NAME/KEY: MOD_RES
<222> LOCATION: (12)..(12)
<223> OTHER INFORMATION: Any amino acid or is absent

<400> SEQUENCE: 10

Asp Ile Gly Xaa Xaa Ser Val Gly Trp Ala Xaa Xaa
1               5                   10

<210> SEQ ID NO 11
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Any non-polar alkyl amino acid or a hydroxyl
      amino acid

<400> SEQUENCE: 11

Asp Ile Gly Thr Asn Ser Val Gly Trp Ala Val Xaa
1               5                   10

<210> SEQ ID NO 12
<211> LENGTH: 8
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Val or His
<220> FEATURE:
<221> NAME/KEY: MOD_RES
<222> LOCATION: (3)..(3)
<223> OTHER INFORMATION: Ile, Leu or Val
<220> FEATURE:
<221> NAME/KEY: MOD_RES
<222> LOCATION: (5)..(5)
<223> OTHER INFORMATION: Met or Thr

<400> SEQUENCE: 12

Ile Xaa Xaa Glu Xaa Ala Arg Glu
1               5

<210> SEQ ID NO 13
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Ile, Leu or Val

<400> SEQUENCE: 13

Ile Val Xaa Glu Met Ala Arg Glu
1               5

<210> SEQ ID NO 14
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: His or Leu
<220> FEATURE:
<221> NAME/KEY: MOD_RES
<222> LOCATION: (7)..(7)
<223> OTHER INFORMATION: Arg or Val
<220> FEATURE:
<221> NAME/KEY: MOD_RES
<222> LOCATION: (8)..(8)
<223> OTHER INFORMATION: Glu or Val

<400> SEQUENCE: 14

His His Ala Xaa Asp Ala Xaa Xaa
1               5

<210> SEQ ID NO 15
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

His His Ala His Asp Ala Tyr Leu
1               5
```

```
<210> SEQ ID NO 16
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Lys or Pro
<220> FEATURE:
<221> NAME/KEY: MOD_RES
<222> LOCATION: (4)..(4)
<223> OTHER INFORMATION: Val, Leu, Ile or Phe
<220> FEATURE:
<221> NAME/KEY: MOD_RES
<222> LOCATION: (5)..(5)
<223> OTHER INFORMATION: Gly, Ala or Ser
<220> FEATURE:
<221> NAME/KEY: MOD_RES
<222> LOCATION: (6)..(6)
<223> OTHER INFORMATION: Leu, Ile, Val or Phe
<220> FEATURE:
<221> NAME/KEY: MOD_RES
<222> LOCATION: (7)..(26)
<223> OTHER INFORMATION: Any amino acid and this region may encompass
      5-20 residues wherein some positions may be absent
<220> FEATURE:
<221> NAME/KEY: MOD_RES
<222> LOCATION: (29)..(29)
<223> OTHER INFORMATION: Asp, Glu, Asn or Gln
<220> FEATURE:
<223> OTHER INFORMATION: See specification as filed for detailed
      description of substitutions and preferred embodiments

<400> SEQUENCE: 16

Lys Xaa Tyr Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Thr Asp Xaa Tyr
            20                  25                  30

<210> SEQ ID NO 17
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Asp, Glu, Gln or Asn
<220> FEATURE:
<221> NAME/KEY: MOD_RES
<222> LOCATION: (2)..(2)
<223> OTHER INFORMATION: Leu, Ile, Arg, Gln, Val, Met or Lys
<220> FEATURE:
<221> NAME/KEY: MOD_RES
<222> LOCATION: (3)..(3)
<223> OTHER INFORMATION: Asp or Glu
<220> FEATURE:
<221> NAME/KEY: MOD_RES
<222> LOCATION: (5)..(5)
<223> OTHER INFORMATION: Ile, Val, Thr, Ala or Leu
<220> FEATURE:
<221> NAME/KEY: MOD_RES
<222> LOCATION: (6)..(6)
<223> OTHER INFORMATION: Val, Tyr, Ile, Leu, Phe or Trp
<220> FEATURE:
<221> NAME/KEY: MOD_RES
<222> LOCATION: (8)..(8)
<223> OTHER INFORMATION: Gln, His, Arg, Lys, Tyr, Ile, Leu, Phe or Trp
<220> FEATURE:
<221> NAME/KEY: MOD_RES
<222> LOCATION: (9)..(9)
```

```
<223> OTHER INFORMATION: Ser, Ala, Asp, Thr or Lys
<220> FEATURE:
<221> NAME/KEY: MOD_RES
<222> LOCATION: (10)..(10)
<223> OTHER INFORMATION: Phe, Leu, Val, Lys, Tyr, Met, Ile, Arg, Ala,
      Glu, Asp or Gln
<220> FEATURE:
<221> NAME/KEY: MOD_RES
<222> LOCATION: (11)..(11)
<223> OTHER INFORMATION: Leu, Arg, Thr, Ile, Val, Ser, Cys, Tyr, Lys,
      Phe or Gly
<220> FEATURE:
<221> NAME/KEY: MOD_RES
<222> LOCATION: (12)..(12)
<223> OTHER INFORMATION: Lys, Gln, Tyr, Thr, Phe, Leu, Trp, Met, Ala,
      Glu, Gly or Ser
<220> FEATURE:
<221> NAME/KEY: MOD_RES
<222> LOCATION: (13)..(13)
<223> OTHER INFORMATION: Asp, Ser, Asn, Arg, Leu or Thr
<220> FEATURE:
<221> NAME/KEY: MOD_RES
<222> LOCATION: (14)..(14)
<223> OTHER INFORMATION: Asp, Asn or Ser
<220> FEATURE:
<221> NAME/KEY: MOD_RES
<222> LOCATION: (15)..(15)
<223> OTHER INFORMATION: Ser, Ala, Thr, Gly or Arg
<220> FEATURE:
<221> NAME/KEY: MOD_RES
<222> LOCATION: (16)..(16)
<223> OTHER INFORMATION: Ile, Leu, Phe, Ser, Arg, Tyr, Gln, Trp, Asp,
      Lys or His
<220> FEATURE:
<221> NAME/KEY: MOD_RES
<222> LOCATION: (17)..(17)
<223> OTHER INFORMATION: Asp, Ser, Ile, Asn, Glu, Ala, His, Phe, Leu,
      Gln, Met, Gly, Tyr or Val
<220> FEATURE:
<221> NAME/KEY: MOD_RES
<222> LOCATION: (19)..(19)
<223> OTHER INFORMATION: Lys, Leu, Arg, Met, Thr or Phe
<220> FEATURE:
<221> NAME/KEY: MOD_RES
<222> LOCATION: (20)..(20)
<223> OTHER INFORMATION: Val, Leu, Ile, Ala or Thr
<220> FEATURE:
<221> NAME/KEY: MOD_RES
<222> LOCATION: (21)..(21)
<223> OTHER INFORMATION: Leu, Ile, Val or Ala
<220> FEATURE:
<221> NAME/KEY: MOD_RES
<222> LOCATION: (22)..(22)
<223> OTHER INFORMATION: Thr, Val, Cys, Glu, Ser or Ala
<220> FEATURE:
<221> NAME/KEY: MOD_RES
<222> LOCATION: (23)..(23)
<223> OTHER INFORMATION: Arg, Phe, Thr, Trp, Glu, Leu, Asn, Cys, Lys,
      Val, Ser, Gln, Ile, Tyr, His or Ala
<220> FEATURE:
<221> NAME/KEY: MOD_RES
<222> LOCATION: (24)..(24)
<223> OTHER INFORMATION: Ser, Pro, Arg, Lys, Asn, Ala, His, Gln, Gly or
      Leu
<220> FEATURE:
<221> NAME/KEY: MOD_RES
<222> LOCATION: (25)..(25)
<223> OTHER INFORMATION: Asp, Gly, Thr, Asn, Ser, Lys, Ala, Ile, Glu,
      Leu, Gln, Arg or Tyr
<220> FEATURE:
<221> NAME/KEY: MOD_RES
<222> LOCATION: (26)..(26)
<223> OTHER INFORMATION: Lys, Val, Ala, Glu, Tyr, Ile, Cys, Leu, Ser,
      Thr, Gly, Lys, Met, Asp or Phe

<400> SEQUENCE: 17

Xaa Xaa Xaa His Xaa Xaa Pro Xaa Xaa Xaa Xaa Xaa Xaa Xaa Xaa Xaa
1               5                   10                  15
```

```
Xaa Asn Xaa Xaa Xaa Xaa Xaa Xaa Xaa Xaa Asn
            20                  25

<210> SEQ ID NO 18
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Asp or Glu
<220> FEATURE:
<221> NAME/KEY: MOD_RES
<222> LOCATION: (2)..(2)
<223> OTHER INFORMATION: Leu, Ile, Arg, Gln, Val, Met or Lys
<220> FEATURE:
<221> NAME/KEY: MOD_RES
<222> LOCATION: (3)..(3)
<223> OTHER INFORMATION: Asp or Glu
<220> FEATURE:
<221> NAME/KEY: MOD_RES
<222> LOCATION: (5)..(5)
<223> OTHER INFORMATION: Ile, Val, Thr, Ala or Leu
<220> FEATURE:
<221> NAME/KEY: MOD_RES
<222> LOCATION: (6)..(6)
<223> OTHER INFORMATION: Val, Tyr, Ile, Leu, Phe or Trp
<220> FEATURE:
<221> NAME/KEY: MOD_RES
<222> LOCATION: (8)..(8)
<223> OTHER INFORMATION: Gln, His, Arg, Lys, Tyr, Ile, Leu, Phe or Trp
<220> FEATURE:
<221> NAME/KEY: MOD_RES
<222> LOCATION: (10)..(10)
<223> OTHER INFORMATION: Phe, Leu, Val, Lys, Tyr, Met, Ile, Arg, Ala,
      Glu, Asp or Gln
<220> FEATURE:
<221> NAME/KEY: MOD_RES
<222> LOCATION: (11)..(11)
<223> OTHER INFORMATION: Leu, Arg, Thr, Ile, Val, Ser, Cys, Tyr, Lys,
      Phe or Gly
<220> FEATURE:
<221> NAME/KEY: MOD_RES
<222> LOCATION: (12)..(12)
<223> OTHER INFORMATION: Lys, Gln, Tyr, Thr, Phe, Leu, Trp, Met, Ala,
      Glu, Gly or Ser
<220> FEATURE:
<221> NAME/KEY: MOD_RES
<222> LOCATION: (16)..(16)
<223> OTHER INFORMATION: Ile, Leu, Phe, Ser, Arg, Tyr, Gln, Trp, Asp,
      Lys or His
<220> FEATURE:
<221> NAME/KEY: MOD_RES
<222> LOCATION: (17)..(17)
<223> OTHER INFORMATION: Asp, Ser, Ile, Asn, Glu, Ala, His, Phe, Leu,
      Gln, Met, Gly, Tyr or Val
<220> FEATURE:
<221> NAME/KEY: MOD_RES
<222> LOCATION: (22)..(22)
<223> OTHER INFORMATION: Thr, Val, Cys, Glu, Ser or Ala
<220> FEATURE:
<221> NAME/KEY: MOD_RES
<222> LOCATION: (23)..(23)
<223> OTHER INFORMATION: Arg, Phe, Thr, Trp, Glu, Leu, Asn, Cys, Lys,
      Val, Ser, Gln, Ile, Tyr, His or Ala
<220> FEATURE:
<221> NAME/KEY: MOD_RES
<222> LOCATION: (24)..(24)
<223> OTHER INFORMATION: Ser, Pro, Arg, Lys, Asn, Ala, His, Gln, Gly or
      Leu
<220> FEATURE:
<221> NAME/KEY: MOD_RES
<222> LOCATION: (25)..(25)
```

```
<223> OTHER INFORMATION: Asp, Gly, Thr, Asn, Ser, Lys, Ala, Ile, Glu,
      Leu, Gln, Arg or Tyr
<220> FEATURE:
<221> NAME/KEY: MOD_RES
<222> LOCATION: (26)..(26)
<223> OTHER INFORMATION: Lys, Val, Ala, Glu, Tyr, Ile, Cys, Leu, Ser,
      Thr, Gly, Lys, Met, Asp or Phe

<400> SEQUENCE: 18

Xaa Xaa Xaa His Xaa Xaa Pro Xaa Ser Xaa Xaa Xaa Asp Asp Ser Xaa
1               5                   10                  15

Xaa Asn Lys Val Leu Xaa Xaa Xaa Xaa Xaa Asn
            20                  25

<210> SEQ ID NO 19
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Asp or Glu
<220> FEATURE:
<221> NAME/KEY: MOD_RES
<222> LOCATION: (3)..(3)
<223> OTHER INFORMATION: Asp or Glu
<220> FEATURE:
<221> NAME/KEY: MOD_RES
<222> LOCATION: (8)..(8)
<223> OTHER INFORMATION: Gln, His, Arg, Lys, Tyr, Ile, Leu or Trp
<220> FEATURE:
<221> NAME/KEY: MOD_RES
<222> LOCATION: (10)..(10)
<223> OTHER INFORMATION: Phe, Leu, Val, Lys, Tyr, Met, Ile, Arg, Ala,
      Glu, Asp or Gln
<220> FEATURE:
<221> NAME/KEY: MOD_RES
<222> LOCATION: (11)..(11)
<223> OTHER INFORMATION: Leu, Arg, Thr, Ile, Val, Ser, Cys, Tyr, Lys,
      Phe or Gly
<220> FEATURE:
<221> NAME/KEY: MOD_RES
<222> LOCATION: (12)..(12)
<223> OTHER INFORMATION: Lys, Gln, Tyr, Thr, Phe, Leu, Trp, Met, Ala,
      Glu, Gly or Ser
<220> FEATURE:
<221> NAME/KEY: MOD_RES
<222> LOCATION: (16)..(16)
<223> OTHER INFORMATION: Ile, Leu, Phe, Ser, Arg, Tyr, Gln, Trp, Asp,
      Lys or His
<220> FEATURE:
<221> NAME/KEY: MOD_RES
<222> LOCATION: (17)..(17)
<223> OTHER INFORMATION: Asp, Ser, Ile, Asn, Glu, Ala, His, Phe, Leu,
      Gln, Met, Gly, Tyr or Val
<220> FEATURE:
<221> NAME/KEY: MOD_RES
<222> LOCATION: (23)..(23)
<223> OTHER INFORMATION: Arg, Phe, Thr, Trp, Glu, Leu, Asn, Cys, Lys,
      Val, Ser, Gln, Ile, Tyr, His or Ala
<220> FEATURE:
<221> NAME/KEY: MOD_RES
<222> LOCATION: (24)..(24)
<223> OTHER INFORMATION: Ser, Pro, Arg, Lys, Asn, Ala, His, Gln, Gly or
      Leu
<220> FEATURE:
<221> NAME/KEY: MOD_RES
<222> LOCATION: (25)..(25)
<223> OTHER INFORMATION: Asp, Gly, Thr, Asn, Ser, Lys, Ala, Ile, Glu,
      Leu, Gln, Arg or Tyr
<220> FEATURE:
<221> NAME/KEY: MOD_RES
<222> LOCATION: (26)..(26)
```

```
<223> OTHER INFORMATION: Lys, Val, Ala, Glu, Tyr, Ile, Cys, Leu, Ser,
      Thr, Gly, Lys, Met, Asp or Phe

<400> SEQUENCE: 19

Xaa Val Xaa His Ile Val Pro Xaa Ser Xaa Xaa Xaa Asp Asp Ser Xaa
1               5                   10                  15

Xaa Asn Lys Val Leu Thr Xaa Xaa Xaa Xaa Asn
            20                  25

<210> SEQ ID NO 20
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Ile or Val
<220> FEATURE:
<221> NAME/KEY: MOD_RES
<222> LOCATION: (6)..(6)
<223> OTHER INFORMATION: Ile or Val
<220> FEATURE:
<221> NAME/KEY: MOD_RES
<222> LOCATION: (9)..(9)
<223> OTHER INFORMATION: Ala or Ser
<220> FEATURE:
<221> NAME/KEY: MOD_RES
<222> LOCATION: (11)..(11)
<223> OTHER INFORMATION: Ile or Leu
<220> FEATURE:
<221> NAME/KEY: MOD_RES
<222> LOCATION: (12)..(12)
<223> OTHER INFORMATION: Lys or Thr
<220> FEATURE:
<221> NAME/KEY: MOD_RES
<222> LOCATION: (14)..(14)
<223> OTHER INFORMATION: Asp or Asn
<220> FEATURE:
<221> NAME/KEY: MOD_RES
<222> LOCATION: (19)..(19)
<223> OTHER INFORMATION: Arg, Lys or Leu
<220> FEATURE:
<221> NAME/KEY: MOD_RES
<222> LOCATION: (22)..(22)
<223> OTHER INFORMATION: Thr or Val
<220> FEATURE:
<221> NAME/KEY: MOD_RES
<222> LOCATION: (23)..(23)
<223> OTHER INFORMATION: Ser or Arg
<220> FEATURE:
<221> NAME/KEY: MOD_RES
<222> LOCATION: (25)..(25)
<223> OTHER INFORMATION: Lys, Asp or Ala
<220> FEATURE:
<221> NAME/KEY: MOD_RES
<222> LOCATION: (26)..(26)
<223> OTHER INFORMATION: Glu, Lys, Gly or Asn

<400> SEQUENCE: 20

Asp Xaa Asp His Ile Xaa Pro Gln Xaa Phe Xaa Xaa Asp Xaa Ser Ile
1               5                   10                  15

Asp Asn Xaa Val Leu Xaa Xaa Ser Xaa Xaa Asn
            20                  25

<210> SEQ ID NO 21
<211> LENGTH: 73
<212> TYPE: PRT
<213> ORGANISM: Artificial Sequence
<220> FEATURE:
```

-continued

```
<223> OTHER INFORMATION: Description of Artificial Sequence: Synthetic
      polypeptide
<220> FEATURE:
<221> NAME/KEY: MOD_RES
<222> LOCATION: (8)..(8)
<223> OTHER INFORMATION: Lys or Arg
<220> FEATURE:
<221> NAME/KEY: MOD_RES
<222> LOCATION: (12)..(12)
<223> OTHER INFORMATION: Val or Thr
<220> FEATURE:
<221> NAME/KEY: MOD_RES
<222> LOCATION: (13)..(13)
<223> OTHER INFORMATION: Gly or Asp
<220> FEATURE:
<221> NAME/KEY: MOD_RES
<222> LOCATION: (14)..(14)
<223> OTHER INFORMATION: Glu, Gln or Asp
<220> FEATURE:
<221> NAME/KEY: MOD_RES
<222> LOCATION: (15)..(15)
<223> OTHER INFORMATION: Glu or Asp
<220> FEATURE:
<221> NAME/KEY: MOD_RES
<222> LOCATION: (19)..(19)
<223> OTHER INFORMATION: Asp, Asn or His
<220> FEATURE:
<221> NAME/KEY: MOD_RES
<222> LOCATION: (20)..(20)
<223> OTHER INFORMATION: Tyr, Arg or Asn
<220> FEATURE:
<221> NAME/KEY: MOD_RES
<222> LOCATION: (23)..(23)
<223> OTHER INFORMATION: Gln, Asp or Asn
<220> FEATURE:
<221> NAME/KEY: MOD_RES
<222> LOCATION: (25)..(64)
<223> OTHER INFORMATION: Any amino acid and this region may encompass
      15-40 residues wherein some positions may be absent
<220> FEATURE:
<221> NAME/KEY: MOD_RES
<222> LOCATION: (67)..(67)
<223> OTHER INFORMATION: Gly or Glu
<220> FEATURE:
<221> NAME/KEY: MOD_RES
<222> LOCATION: (69)..(69)
<223> OTHER INFORMATION: Ser or Gly
<220> FEATURE:
<221> NAME/KEY: MOD_RES
<222> LOCATION: (71)..(71)
<223> OTHER INFORMATION: Asp or Asn
<220> FEATURE:
<223> OTHER INFORMATION: See specification as filed for detailed
      description of substitutions and preferred embodiments

<400> SEQUENCE: 21

Leu Tyr Tyr Leu Gln Asn Gly Xaa Asp Met Tyr Xaa Xaa Xaa Xaa Leu
1               5                   10                  15

Asp Ile Xaa Xaa Leu Ser Xaa Tyr Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Asn Arg Xaa Lys Xaa Asp Xaa Val Pro
65                  70

<210> SEQ ID NO 22
<211> LENGTH: 4107
<212> TYPE: DNA
<213> ORGANISM: Artificial Sequence
```

<220> FEATURE:
<223> OTHER INFORMATION: Description of Artificial Sequence: Synthetic polynucleotide

<400> SEQUENCE: 22

```
atggataaaa agtacagcat cgggctggac atcggtacaa actcagtggg gtgggccgtg      60
attacggacg agtacaaggt accctccaaa aaatttaaag tgctgggtaa cacgacaga     120
cactctataa agaaaaatct tattggagcc ttgctgttcg actcaggcga dacagccgaa     180
gccacaaggt tgaagcggac cgccaggagg cggtatacca ggagaaagaa ccgcatatgc     240
tacctgcaag aaatcttcag taacgagatg gcaaaggttg acgatagctt tttccatcgc     300
ctggaagaat cctttcttgt tgaggaagac aagaagcacg aacggcaccc catctttggc     360
aatattgtcg acgaagtggc atatcacgaa agtacccga ctatctacca cctcaggaag     420
aagctggtgg actctaccga taaggcggac ctcagactta tttatttggc actcgcccac     480
atgattaaat ttagaggaca tttcttgatc gagggcgacc tgaacccgga caacagtgac     540
gtcgataagc tgttcatcca acttgtgcag acctacaatc aactgttcga agaaaaccct     600
ataaatgctt caggagtcga cgctaaagca atcctgtccg cgcgcctctc aaaatctaga     660
agacttgaga atctgattgc tcagttgccc ggggaaaaga aaaatggatt gtttggcaac     720
ctgatcgccc tcagtctcgg actgacccca aatttcaaaa gtaacttcga cctggccgaa     780
gacgctaagc tccagctgtc caaggacaca tacgatgacg acctcgacaa tctgctggcc     840
cagattgggg atcagtacgc cgatctcttt ttggcagcaa agaacctgtc cgacgccatc     900
ctgttgagcg atatccttga gagtgaacac gaaattacta agcacccct tagcgcatct     960
atgatcaagc ggtacgacga gcatcatcag gatctgaccc tgctgaaggc tcttgtgagg    1020
caacagctcc ccgaaaaata caaggaaatc ttctttgacc agagcaaaaa cggctacgct    1080
ggctatatag atggtggggc cagtcaggag gaattctata aattcatcaa gcccattctc    1140
gagaaaatgg acggcacaga ggagttgctg gtcaaactta acaggagga cctgctgcgg    1200
aagcagcgga ccttttgacaa cgggtctatc ccccaccaga ttcatctggg cgaactgcac    1260
gcaatcctga ggaggcagga ggattttttat ccttttctta aagataaccg cgagaaaata    1320
gaaaagattc ttacattcag gatcccgtac tacgtgggac ctctcgcccg gggcaattca    1380
cggtttgcct ggatgacaag gaagtcagag gagactatta caccttggaa cttcgaagaa    1440
gtggtggaca agggtgcatc tgcccagtct ttcatcgagc ggatgacaaa ttttgacaag    1500
aacctcccta atgagaaggt gctgcccaaa cattctctgc tctacagtta ctttaccgtc    1560
tacaatgaac tgactaaagt caagtacgtc accgagggaa tgaggaagcc ggcattcctt    1620
agtggagaac agaagaaggc gattgtagac ctgttgttca gaccaacag gaaggtgact    1680
gtgaagcaac ttaaagaaga ctactttaag aagatcgaat gttttgacag tgtggaaatt    1740
tcagggggtg aagaccgctt caatgcgtca ttggggactt accatgatct tctcaagatc    1800
ataaaggaca aagacttcct ggacaacgaa gaaaatgagg atattctcga agacatcgtc    1860
ctcaccctga ccctgttcga agacagggaa atgatagaag agcgcttgaa aacctatgcc    1920
cacctcttcg acgataaagt tatgaagcag ctgaagcgca ggagatacac aggatgggga    1980
agattgtcaa ggaagctgat caatggaatt agggataaac agagtggcaa gaccatactg    2040
gatttcctca aatctgatgg cttcgccaat aggaacttca tgcaactgat tcacgatgac    2100
tctcttacct tcaaggagga cattcaaaag gctcaggtga cgggcagggg agactcccctt    2160
catgaacaca tcgcgaattt ggcaggttcc cccgctatta aaagggcat ccttcaaact    2220
```

```
gtcaaggtgg tggatgaatt ggtcaaggta atgggcagac ataagccaga aaatattgtg    2280
atcgagatgg cccgcgaaaa ccagaccaca cagaagggcc agaaaaatag tagagagcgg    2340
atgaagagga tcgaggaggg catcaaagag ctgggatctc agattctcaa agaacacccc    2400
gtagaaaaca cacagctgca gaacgaaaaa ttgtacttgt actatctgca gaacggcaga    2460
gacatgtacg tcgaccaaga acttgatatt aatagactgt ccgactatga cgtagaccat    2520
atcgtgcccc agtccttcct gaaggacgac tccattgata caaagtctt gacaagaagc    2580 gacaagaaca ggggtaaaag tgataatgtg cctagcgagg aggtggtgaa aaaaatgaag    2640
aactactggc gacagctgct taatgcaaag ctcattacac aacggaagtt cgataatctg    2700
acgaaagcag agagaggtgg cttgtctgag ttggacaagg cagggtttat taagcggcag    2760
ctggtggaaa ctaggcagat cacaaagcac gtggcgcaga ttttggacag ccggatgaac    2820
acaaaatacg acgaaaatga taaactgata cgagaggtca agttatcac gctgaaaagc    2880 aagctggtgt ccgattttcg gaaagacttc cagttctaca agttcgcga gattaataac    2940 taccatcatg ctcacgatgc gtacctgaac gctgttgtcg ggaccgcctt gataaagaag    3000
tacccaaagc tggaatccga gttcgtatac ggggattaca agtgtacga tgtgaggaaa    3060 atgatagcca agtccgagca ggagattgga aaggccacag ctaagtactt cttttattct    3120
aacatcatga atttttttaa gacgaaaatt accctggcca acggagagat cagaaagcgg    3180
ccccttatag agacaaatgg tgaaacaggt gaaatcgtct gggataaggg cagggatttc    3240
gctactgtga ggaaggtgct gagtatgcca caggtaaata tcgtgaaaaa aaccgaagta    3300
cagaccggag gattttccaa ggaaagcatt ttgcctaaaa gaaactcaga caagctcatc    3360
gcccgcaaga agattgggga ccctaagaaa tacgggggat ttgactcacc caccgtagcc    3420
tattctgtgc tggtggtagc taaggtggaa aaaggaaagt ctaagaagct gaagtccgtg    3480
aaggaactct gggaatcac tatcatgaaa agatcatcct ttgaaaagaa ccctatcgat    3540
ttcctggagg ctaagggtta caaggaggtc aagaaagacc tcatcattaa actgccaaaa    3600
tactctctct tcgagctgga aaatggcagg aagagaatgt tggccagcgc cggagagctg    3660
caaaagggaa acgagcttgc tctgccctcc aaatatgtta attttctcta tctcgcttcc    3720
cactatgaaa agctgaaagg tctcccgaa gataacgagc agaagcagct gttcgtcgaa    3780
cagcacaagc actatctgga tgaaataatc gaacaaataa gcgagttcag caaaagggtt    3840
atcctggcgg atgctaattt ggacaaagta ctgtctgctt ataacaagca ccgggataag    3900
cctattaggg aacaagccga gaatataatt cacctcttta cactcacgaa tctcggagcc    3960
cccgccgcct tcaaatactt tgatacgact atcgaccgga acggtatac cagtaccaaa    4020 gaggtcctcg atgccaccct catccaccag tcaattactg gcctgtacga acacggatc    4080 gacctctctc aactgggcgg cgactag                                         4107
```

<210> SEQ ID NO 23
<211> LENGTH: 1368
<212> TYPE: PRT
<213> ORGANISM: Streptococcus pyogenes

<400> SEQUENCE: 23

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

```
Lys Val Leu Gly Asn Thr Asp Arg His Ser Ile Lys Lys Asn Leu Ile
         35                  40                  45
Gly Ala Leu Leu Phe Asp Ser Gly Glu Thr Ala Glu Ala Thr Arg Leu
 50                  55                  60
Lys Arg Thr Ala Arg Arg Tyr Thr Arg Arg Lys Asn Arg Ile Cys
 65                  70                  75                  80
Tyr Leu Gln Glu Ile Phe Ser Asn Glu Met Ala Lys Val Asp Asp Ser
                 85                  90                  95
Phe Phe His Arg Leu Glu Glu Ser Phe Leu Val Glu Glu Asp Lys Lys
                100                 105                 110
His Glu Arg His Pro Ile Phe Gly Asn Ile Val Asp Glu Val Ala Tyr
                115                 120                 125
His Glu Lys Tyr Pro Thr Ile Tyr His Leu Arg Lys Lys Leu Val Asp
                130                 135                 140
Ser Thr Asp Lys Ala Asp Leu Arg Leu Ile Tyr Leu Ala Leu Ala His
145                 150                 155                 160
Met Ile Lys Phe Arg Gly His Phe Leu Ile Glu Gly Asp Leu Asn Pro
                165                 170                 175
Asp Asn Ser Asp Val Asp Lys Leu Phe Ile Gln Leu Val Gln Thr Tyr
                180                 185                 190
Asn Gln Leu Phe Glu Glu Asn Pro Ile Asn Ala Ser Gly Val Asp Ala
                195                 200                 205
Lys Ala Ile Leu Ser Ala Arg Leu Ser Lys Ser Arg Arg Leu Glu Asn
                210                 215                 220
Leu Ile Ala Gln Leu Pro Gly Glu Lys Lys Asn Gly Leu Phe Gly Asn
225                 230                 235                 240
Leu Ile Ala Leu Ser Leu Gly Leu Thr Pro Asn Phe Lys Ser Asn Phe
                245                 250                 255
Asp Leu Ala Glu Asp Ala Lys Leu Gln Leu Ser Lys Asp Thr Tyr Asp
                260                 265                 270
Asp Asp Leu Asp Asn Leu Leu Ala Gln Ile Gly Asp Gln Tyr Ala Asp
                275                 280                 285
Leu Phe Leu Ala Ala Lys Asn Leu Ser Asp Ala Ile Leu Leu Ser Asp
                290                 295                 300
Ile Leu Arg Val Asn Thr Glu Ile Thr Lys Ala Pro Leu Ser Ala Ser
305                 310                 315                 320
Met Ile Lys Arg Tyr Asp Glu His His Gln Asp Leu Thr Leu Leu Lys
                325                 330                 335
Ala Leu Val Arg Gln Gln Leu Pro Glu Lys Tyr Lys Glu Ile Phe Phe
                340                 345                 350
Asp Gln Ser Lys Asn Gly Tyr Ala Gly Tyr Ile Asp Gly Gly Ala Ser
                355                 360                 365
Gln Glu Glu Phe Tyr Lys Phe Ile Lys Pro Ile Leu Glu Lys Met Asp
                370                 375                 380
Gly Thr Glu Glu Leu Leu Val Lys Leu Asn Arg Glu Asp Leu Leu Arg
385                 390                 395                 400
Lys Gln Arg Thr Phe Asp Asn Gly Ser Ile Pro His Gln Ile His Leu
                405                 410                 415
Gly Glu Leu His Ala Ile Leu Arg Arg Gln Glu Asp Phe Tyr Pro Phe
                420                 425                 430
Leu Lys Asp Asn Arg Glu Lys Ile Glu Lys Ile Leu Thr Phe Arg Ile
                435                 440                 445
```

```
Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
    610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
    690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
    770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Lys
        835                 840                 845

Asp Asp Ser Ile Asp Asn Lys Val Leu Thr Arg Ser Asp Lys Asn Arg
    850                 855                 860
```

```
Gly Lys Ser Asp Asn Val Pro Ser Glu Glu Val Lys Met Lys
865                 870                 875                 880

Asn Tyr Trp Arg Gln Leu Leu Asn Ala Lys Leu Ile Thr Gln Arg Lys
            885                 890                 895

Phe Asp Asn Leu Thr Lys Ala Glu Arg Gly Gly Leu Ser Glu Leu Asp
                900                 905                 910

Lys Ala Gly Phe Ile Lys Arg Gln Leu Val Glu Thr Arg Gln Ile Thr
            915                 920                 925

Lys His Val Ala Gln Ile Leu Asp Ser Arg Met Asn Thr Lys Tyr Asp
        930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
                980                 985                 990

Val Gly Thr Ala Leu Ile Lys Lys Tyr Pro Lys Leu Glu Ser Glu Phe
            995                 1000                1005

Val Tyr Gly Asp Tyr Lys Val Tyr Asp Val Arg Lys Met Ile Ala
    1010                1015                1020

Lys Ser Glu Gln Glu Ile Gly Lys Ala Thr Ala Lys Tyr Phe Phe
    1025                1030                1035

Tyr Ser Asn Ile Met Asn Phe Phe Lys Thr Glu Ile Thr Leu Ala
    1040                1045                1050

Asn Gly Glu Ile Arg Lys Arg Pro Leu Ile Glu Thr Asn Gly Glu
    1055                1060                1065

Thr Gly Glu Ile Val Trp Asp Lys Gly Arg Asp Phe Ala Thr Val
    1070                1075                1080

Arg Lys Val Leu Ser Met Pro Gln Val Asn Ile Val Lys Lys Thr
    1085                1090                1095

Glu Val Gln Thr Gly Gly Phe Ser Lys Glu Ser Ile Leu Pro Lys
    1100                1105                1110

Arg Asn Ser Asp Lys Leu Ile Ala Arg Lys Lys Asp Trp Asp Pro
    1115                1120                1125

Lys Lys Tyr Gly Gly Phe Asp Ser Pro Thr Val Ala Tyr Ser Val
    1130                1135                1140

Leu Val Val Ala Lys Val Glu Lys Gly Lys Ser Lys Lys Leu Lys
    1145                1150                1155

Ser Val Lys Glu Leu Leu Gly Ile Thr Ile Met Glu Arg Ser Ser
    1160                1165                1170

Phe Glu Lys Asn Pro Ile Asp Phe Leu Glu Ala Lys Gly Tyr Lys
    1175                1180                1185

Glu Val Lys Lys Asp Leu Ile Ile Lys Leu Pro Lys Tyr Ser Leu
    1190                1195                1200

Phe Glu Leu Glu Asn Gly Arg Lys Arg Met Leu Ala Ser Ala Gly
    1205                1210                1215

Glu Leu Gln Lys Gly Asn Glu Leu Ala Leu Pro Ser Lys Tyr Val
    1220                1225                1230

Asn Phe Leu Tyr Leu Ala Ser His Tyr Glu Lys Leu Lys Gly Ser
    1235                1240                1245

Pro Glu Asp Asn Glu Gln Lys Gln Leu Phe Val Glu Gln His Lys
    1250                1255                1260
```

| | | | | | | | | | | | |
|---|---|---|---|---|---|---|---|---|---|---|---|
|His|Tyr|Leu|Asp|Glu|Ile|Ile|Glu|Gln|Ile|Ser|Glu|Phe|Ser|Lys|
| |1265| | | |1270| | | |1275| | |

Arg Val Ile Leu Ala Asp Ala Asn Leu Asp Lys Val Leu Ser Ala
    1280             1285             1290

Tyr Asn Lys His Arg Asp Lys Pro Ile Arg Glu Gln Ala Glu Asn
    1295             1300             1305

Ile Ile His Leu Phe Thr Leu Thr Asn Leu Gly Ala Pro Ala Ala
    1310             1315             1320

Phe Lys Tyr Phe Asp Thr Thr Ile Asp Arg Lys Arg Tyr Thr Ser
    1325             1330             1335

Thr Lys Glu Val Leu Asp Ala Thr Leu Ile His Gln Ser Ile Thr
    1340             1345             1350

Gly Leu Tyr Glu Thr Arg Ile Asp Leu Ser Gln Leu Gly Gly Asp
    1355             1360             1365

<210> SEQ ID NO 24
<211> LENGTH: 3249
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 24

```
atggccgcct tcaagcccaa ccccatcaac tacatcctgg gcctggacat cggcatcgcc    60
agcgtgggct gggccatggt ggagatcgac gaggacgaga ccccatctg cctgatcgac    120
ctgggtgtgc gcgtgttcga gcgcgctgag gtgcccaaga ctggtgacag tctggctatg    180
gctcgccggc ttgctcgctc tgttcggcgc cttactcgcc ggcgcgctca ccgccttctg    240
cgcgctcgcc gcctgctgaa gcgcgagggt gtgctgcagg ctgccgactt cgacgagaac    300
ggcctgatca gagcctgcc caacactcct tggcagctgc gcgctgccgc tctggaccgc    360
aagctgactc ctctggagtg gagcgccgtg ctgctgcacc tgatcaagca ccgcggctac    420
ctgagccagc gcaagaacga gggcgagacc gccgacaagg agctgggtgc tctgctgaag    480
ggcgtggccg acaacgccca cgccctgcag actggtgact ccgcactcc tgctgagctg    540
gccctgaaca gttcgagaa ggagagcggc cacatccgca accagcgcgg cgactacagc    600
cacaccttca gccgcaagga cctgcaggcc gagctgatcc tgctgttcga aagcagaag    660
gagttcggca accccacgt gagcggcggc ctgaaggagg gcatcgagac cctgctgatg    720
acccagcgcc ccgccctgag cggcgacgcc gtgcagaaga tgctgggcca ctgcaccttc    780
gagccagccg agcccaaggc cgccaagaac acctacaccg ccgagcgctt catctggctg    840
accaagctga caacctgcg catcctggag cagggcagcg agcgcccct gaccgacacc    900
gagcgcgcca ccctgatgga cgagccctac cgcaagagca agctgaccta cgcccaggcc    960
cgcaagctgc tgggtctgga ggacaccgcc ttcttcaagg gcctgcgcta cggcaaggac   1020
aacgccgagg ccagcaccct gatggagatg aaggcctacc acgccatcag ccgcgccctg   1080
gagaaggagg gcctgaagga caagaagagt cctctgaacc tgagccccga gctgcaggac   1140
gagatcggca ccgccttcag cctgttcaag accgacgagg acatcaccgg ccgcctgaag   1200
gaccgcatcc agcccgagat cctggaggcc ctgctgaagc acatcagctt cgacaagttc   1260
gtgcagatca gcctgaaggc cctgcgccgc atcgtgcccc tgatggagca gggcaagcgc   1320
tacgacgagg cctgcgccga gatctacggc gaccactacg caagaagaa caccgaggag   1380
```

-continued

```
aagatctacc tgcctcctat ccccgccgac gagatccgca accccgtggt gctgcgcgcc    1440
ctgagccagg cccgcaaggt gatcaacggc gtggtgcgcc gctacggcag ccccgcccgc    1500
atccacatcg agaccgcccg cgaggtgggc aagagcttca aggaccgcaa ggagatcgag    1560
aagcgccagg aggagaaccg caaggaccgc gagaaggccg ccgccaagtt ccgcgagtac    1620
ttccccaact tcgtgggcga gcccaagagc aaggacatcc tgaagctgcg cctgtacgag    1680
cagcagcacg gcaagtgcct gtacagcggc aaggagatca acctgggccg cctgaacgag    1740
aagggctacg tggagatcga ccacgccctg cccttcagcc gcacctggga cgacagcttc    1800
aacaacaagg tgctggtgct gggcagcgag aaccagaaca agggcaacca gacccccctac    1860 gagtacttca acggcaagga caacagccgc gagtggcagg agttcaaggc ccgcgtggag    1920
accagccgct tcccccgcag caagaagcag cgcatcctgc tgcagaagtt cgacgaggac    1980
ggcttcaagg agcgcaacct gaacgacacc cgctacgtga accgcttcct gtgccagttc    2040
gtggccgacc gcatgcgcct gaccggcaag ggcaagaagc gcgtgttcgc cagcaacggc    2100
cagatcacca acctgctgcg cggcttctgg ggcctgcgca aggtgcgcgc cgagaacgac    2160
cgccaccacg ccctggacgc cgtggtggtg gcctgcagca ccgtggccat gcagcagaag    2220
atcacccgct tcgtgcgcta aaggagatg aacgccttcg acggtaaaac catcgacaag    2280
gagaccggcg aggtgctgca ccagaagacc cacttccccc agccctggga gttcttcgcc    2340
caggaggtga tgatccgcgt gttcggcaag cccgacggca agcccgagtt cgaggaggcc    2400 gacaccccg agaagctgcg caccctgctg gccgagaagc tgagcagccg ccctgaggcc    2460
gtgcacgagt acgtgactcc tctgttcgtg agccgcgccc ccaaccgcaa gatgagcggt    2520
cagggtcaca tggagaccgt gaagagcgcc aagcgcctgg acgagggcgt gagcgtgctg    2580
cgcgtgcccc tgacccagct gaagctgaag gacctggaga agatggtgaa ccgcgagcgc    2640
gagcccaagc tgtacgaggc cctgaaggcc gccctgagg cccacaagga cgaccccgcc    2700
aaggccttcg ccgagcccctt ctacaagtac gacaaggccg gcaaccgcac ccagcaggtg    2760
aaggccgtgc gcgtggagca ggtgcagaag accggcgtgt gggtgcgcaa ccacaacggc    2820
atcgccgaca cgccaccat ggtgcgcgtg acgtgttcg agaagggcga caagtactac    2880
ctggtgccca tctacagctg gcaggtggcc aagggcatcc tgcccgaccg cgccgtggtg    2940
cagggcaagg acgaggagga ctggcagctg atcgacgaca gcttcaactt caagttcagc    3000 ctgcaccca cgacctggt ggaggtgatc accaagaagg cccgcatgtt cggctacttc    3060
gccagctgcc accgcggcac cggcaacatc aacatccgca tccacgacct ggaccacaag    3120
atcggcaaga acggcatcct ggagggcatc ggcgtgaaga ccgccctgag cttccagaag    3180
taccagatcg acgagctggg caaggagatc cgcccctgcc gcctgaagaa gcgccctcct    3240
gtgcgctaa                                                            3249
```

<210> SEQ ID NO 25
<211> LENGTH: 1082
<212> TYPE: PRT
<213> ORGANISM: Neisseria meningitidis

<400> SEQUENCE: 25

```
Met Ala Ala Phe Lys Pro Asn Pro Ile Asn Tyr Ile Leu Gly Leu Asp
1               5                   10                  15

Ile Gly Ile Ala Ser Val Gly Trp Ala Met Val Glu Ile Asp Glu Asp
            20                  25                  30
```

```
Glu Asn Pro Ile Cys Leu Ile Asp Leu Gly Val Arg Val Phe Glu Arg
         35                  40                  45

Ala Glu Val Pro Lys Thr Gly Asp Ser Leu Ala Met Ala Arg Arg Leu
 50                  55                  60

Ala Arg Ser Val Arg Arg Leu Thr Arg Arg Ala His Arg Leu Leu
 65                  70                  75                  80

Arg Ala Arg Arg Leu Leu Lys Arg Glu Gly Val Leu Gln Ala Ala Asp
                     85                  90                  95

Phe Asp Glu Asn Gly Leu Ile Lys Ser Leu Pro Asn Thr Pro Trp Gln
                100                 105                 110

Leu Arg Ala Ala Ala Leu Asp Arg Lys Leu Thr Pro Leu Glu Trp Ser
                115                 120                 125

Ala Val Leu Leu His Leu Ile Lys His Arg Gly Tyr Leu Ser Gln Arg
                130                 135                 140

Lys Asn Glu Gly Glu Thr Ala Asp Lys Glu Leu Gly Ala Leu Leu Lys
145                 150                 155                 160

Gly Val Ala Asp Asn Ala His Ala Leu Gln Thr Gly Asp Phe Arg Thr
                    165                 170                 175

Pro Ala Glu Leu Ala Leu Asn Lys Phe Glu Lys Glu Ser Gly His Ile
                180                 185                 190

Arg Asn Gln Arg Gly Asp Tyr Ser His Thr Phe Ser Arg Lys Asp Leu
                195                 200                 205

Gln Ala Glu Leu Ile Leu Leu Phe Glu Lys Gln Lys Glu Phe Gly Asn
210                 215                 220

Pro His Val Ser Gly Leu Lys Glu Gly Ile Glu Thr Leu Leu Met
225                 230                 235                 240

Thr Gln Arg Pro Ala Leu Ser Gly Asp Ala Val Gln Lys Met Leu Gly
                245                 250                 255

His Cys Thr Phe Glu Pro Ala Glu Pro Lys Ala Ala Lys Asn Thr Tyr
                260                 265                 270

Thr Ala Glu Arg Phe Ile Trp Leu Thr Lys Leu Asn Asn Leu Arg Ile
                275                 280                 285

Leu Glu Gln Gly Ser Glu Arg Pro Leu Thr Asp Thr Glu Arg Ala Thr
290                 295                 300

Leu Met Asp Glu Pro Tyr Arg Lys Ser Lys Leu Thr Tyr Ala Gln Ala
305                 310                 315                 320

Arg Lys Leu Leu Gly Leu Glu Asp Thr Ala Phe Phe Lys Gly Leu Arg
                325                 330                 335

Tyr Gly Lys Asp Asn Ala Glu Ala Ser Thr Leu Met Glu Met Lys Ala
                340                 345                 350

Tyr His Ala Ile Ser Arg Ala Leu Glu Lys Glu Gly Leu Lys Asp Lys
                355                 360                 365

Lys Ser Pro Leu Asn Leu Ser Pro Glu Leu Gln Asp Glu Ile Gly Thr
370                 375                 380

Ala Phe Ser Leu Phe Lys Thr Asp Glu Asp Ile Thr Gly Arg Leu Lys
385                 390                 395                 400

Asp Arg Ile Gln Pro Glu Ile Leu Glu Ala Leu Leu Lys His Ile Ser
                405                 410                 415

Phe Asp Lys Phe Val Gln Ile Ser Leu Lys Ala Leu Arg Arg Ile Val
                420                 425                 430

Pro Leu Met Glu Gln Gly Lys Arg Tyr Asp Glu Ala Cys Ala Glu Ile
                435                 440                 445
```

```
Tyr Gly Asp His Tyr Gly Lys Lys Asn Thr Glu Glu Lys Ile Tyr Leu
450                 455                 460
Pro Pro Ile Pro Ala Asp Glu Ile Arg Asn Pro Val Val Leu Arg Ala
465                 470                 475                 480
Leu Ser Gln Ala Arg Lys Val Ile Asn Gly Val Val Arg Arg Tyr Gly
            485                 490                 495
Ser Pro Ala Arg Ile His Ile Glu Thr Ala Arg Glu Val Gly Lys Ser
            500                 505                 510
Phe Lys Asp Arg Lys Glu Ile Glu Lys Arg Gln Glu Glu Asn Arg Lys
        515                 520                 525
Asp Arg Glu Lys Ala Ala Lys Phe Arg Glu Tyr Phe Pro Asn Phe
530                 535                 540
Val Gly Glu Pro Lys Ser Lys Asp Ile Leu Lys Leu Arg Leu Tyr Glu
545                 550                 555                 560
Gln Gln His Gly Lys Cys Leu Tyr Ser Gly Lys Glu Ile Asn Leu Gly
                565                 570                 575
Arg Leu Asn Glu Lys Gly Tyr Val Glu Ile Asp His Ala Leu Pro Phe
            580                 585                 590
Ser Arg Thr Trp Asp Asp Ser Phe Asn Asn Lys Val Leu Val Leu Gly
        595                 600                 605
Ser Glu Asn Gln Asn Lys Gly Asn Gln Thr Pro Tyr Glu Tyr Phe Asn
610                 615                 620
Gly Lys Asp Asn Ser Arg Glu Trp Gln Glu Phe Lys Ala Arg Val Glu
625                 630                 635                 640
Thr Ser Arg Phe Pro Arg Ser Lys Lys Gln Arg Ile Leu Leu Gln Lys
                645                 650                 655
Phe Asp Glu Asp Gly Phe Lys Glu Arg Asn Leu Asn Asp Thr Arg Tyr
            660                 665                 670
Val Asn Arg Phe Leu Cys Gln Phe Val Ala Asp Arg Met Arg Leu Thr
        675                 680                 685
Gly Lys Gly Lys Lys Arg Val Phe Ala Ser Asn Gly Gln Ile Thr Asn
690                 695                 700
Leu Leu Arg Gly Phe Trp Gly Leu Arg Lys Val Arg Ala Glu Asn Asp
705                 710                 715                 720
Arg His His Ala Leu Asp Ala Val Val Val Ala Cys Ser Thr Val Ala
                725                 730                 735
Met Gln Gln Lys Ile Thr Arg Phe Val Arg Tyr Lys Glu Met Asn Ala
            740                 745                 750
Phe Asp Gly Lys Thr Ile Asp Lys Glu Thr Gly Glu Val Leu His Gln
        755                 760                 765
Lys Thr His Phe Pro Gln Pro Trp Glu Phe Phe Ala Gln Glu Val Met
770                 775                 780
Ile Arg Val Phe Gly Lys Pro Asp Gly Lys Pro Glu Phe Glu Glu Ala
785                 790                 795                 800
Asp Thr Pro Glu Lys Leu Arg Thr Leu Leu Ala Glu Lys Leu Ser Ser
                805                 810                 815
Arg Pro Glu Ala Val His Glu Tyr Val Thr Pro Leu Phe Val Ser Arg
            820                 825                 830
Ala Pro Asn Arg Lys Met Ser Gly Gln Gly His Met Glu Thr Val Lys
        835                 840                 845
Ser Ala Lys Arg Leu Asp Glu Gly Val Ser Val Leu Arg Val Pro Leu
850                 855                 860
```

```
Thr Gln Leu Lys Leu Lys Asp Leu Glu Lys Met Val Asn Arg Glu Arg
865                 870                 875                 880

Glu Pro Lys Leu Tyr Glu Ala Leu Lys Ala Arg Leu Glu Ala His Lys
                885                 890                 895

Asp Asp Pro Ala Lys Ala Phe Ala Glu Pro Phe Tyr Lys Tyr Asp Lys
            900                 905                 910

Ala Gly Asn Arg Thr Gln Gln Val Lys Ala Val Arg Val Glu Gln Val
        915                 920                 925

Gln Lys Thr Gly Val Trp Val Arg Asn His Asn Gly Ile Ala Asp Asn
    930                 935                 940

Ala Thr Met Val Arg Val Asp Val Phe Glu Lys Gly Asp Lys Tyr Tyr
945                 950                 955                 960

Leu Val Pro Ile Tyr Ser Trp Gln Val Ala Lys Gly Ile Leu Pro Asp
                965                 970                 975

Arg Ala Val Val Gln Gly Lys Asp Glu Glu Asp Trp Gln Leu Ile Asp
            980                 985                 990

Asp Ser Phe Asn Phe Lys Phe Ser Leu His Pro Asn Asp Leu Val Glu
        995                 1000                1005

Val Ile Thr Lys Lys Ala Arg Met Phe Gly Tyr Phe Ala Ser Cys
    1010                1015                1020

His Arg Gly Thr Gly Asn Ile Asn Ile Arg Ile His Asp Leu Asp
    1025                1030                1035

His Lys Ile Gly Lys Asn Gly Ile Leu Glu Gly Ile Gly Val Lys
    1040                1045                1050

Thr Ala Leu Ser Phe Gln Lys Tyr Gln Ile Asp Glu Leu Gly Lys
    1055                1060                1065

Glu Ile Arg Pro Cys Arg Leu Lys Lys Arg Pro Pro Val Arg
    1070                1075                1080

<210> SEQ ID NO 26
<211> LENGTH: 1053
<212> TYPE: PRT
<213> ORGANISM: Staphylococcus aureus

<400> SEQUENCE: 26

Met Lys Arg Asn Tyr Ile Leu Gly Leu Asp Ile Gly Ile Thr Ser Val
1                   5                   10                  15

Gly Tyr Gly Ile Ile Asp Tyr Glu Thr Arg Asp Val Ile Asp Ala Gly
                20                  25                  30

Val Arg Leu Phe Lys Glu Ala Asn Val Glu Asn Asn Glu Gly Arg Arg
            35                  40                  45

Ser Lys Arg Gly Ala Arg Arg Leu Lys Arg Arg Arg Arg His Arg Ile
    50                  55                  60

Gln Arg Val Lys Lys Leu Leu Phe Asp Tyr Asn Leu Leu Thr Asp His
65                  70                  75                  80

Ser Glu Leu Ser Gly Ile Asn Pro Tyr Glu Ala Arg Val Lys Gly Leu
                85                  90                  95

Ser Gln Lys Leu Ser Glu Glu Phe Ser Ala Ala Leu Leu His Leu
            100                 105                 110

Ala Lys Arg Arg Gly Val His Asn Val Asn Glu Val Glu Glu Asp Thr
        115                 120                 125

Gly Asn Glu Leu Ser Thr Lys Glu Gln Ile Ser Arg Asn Ser Lys Ala
    130                 135                 140
```

```
Leu Glu Glu Lys Tyr Val Ala Glu Leu Gln Leu Arg Leu Lys Lys
145                 150                 155                 160

Asp Gly Glu Val Arg Gly Ser Ile Asn Arg Phe Lys Thr Ser Asp Tyr
                165                 170                 175

Val Lys Glu Ala Lys Gln Leu Leu Lys Val Gln Lys Ala Tyr His Gln
                180                 185                 190

Leu Asp Gln Ser Phe Ile Asp Thr Tyr Ile Asp Leu Leu Glu Thr Arg
                195                 200                 205

Arg Thr Tyr Tyr Glu Gly Pro Gly Glu Gly Ser Pro Phe Gly Trp Lys
                210                 215                 220

Asp Ile Lys Glu Trp Tyr Glu Met Leu Met Gly His Cys Thr Tyr Phe
225                 230                 235                 240

Pro Glu Glu Leu Arg Ser Val Lys Tyr Ala Tyr Asn Ala Asp Leu Tyr
                245                 250                 255

Asn Ala Leu Asn Asp Leu Asn Asn Leu Val Ile Thr Arg Asp Glu Asn
                260                 265                 270

Glu Lys Leu Glu Tyr Tyr Glu Lys Phe Gln Ile Ile Glu Asn Val Phe
                275                 280                 285

Lys Gln Lys Lys Lys Pro Thr Leu Lys Gln Ile Ala Lys Glu Ile Leu
290                 295                 300

Val Asn Glu Glu Asp Ile Lys Gly Tyr Arg Val Thr Ser Thr Gly Lys
305                 310                 315                 320

Pro Glu Phe Thr Asn Leu Lys Val Tyr His Asp Ile Lys Asp Ile Thr
                325                 330                 335

Ala Arg Lys Glu Ile Ile Glu Asn Ala Glu Leu Leu Asp Gln Ile Ala
                340                 345                 350

Lys Ile Leu Thr Ile Tyr Gln Ser Ser Glu Asp Ile Gln Glu Glu Leu
                355                 360                 365

Thr Asn Leu Asn Ser Glu Leu Thr Gln Glu Glu Ile Glu Gln Ile Ser
370                 375                 380

Asn Leu Lys Gly Tyr Thr Gly Thr His Asn Leu Ser Leu Lys Ala Ile
385                 390                 395                 400

Asn Leu Ile Leu Asp Glu Leu Trp His Thr Asn Asp Asn Gln Ile Ala
                405                 410                 415

Ile Phe Asn Arg Leu Lys Leu Val Pro Lys Lys Val Asp Leu Ser Gln
                420                 425                 430

Gln Lys Glu Ile Pro Thr Thr Leu Val Asp Asp Phe Ile Leu Ser Pro
                435                 440                 445

Val Val Lys Arg Ser Phe Ile Gln Ser Ile Lys Val Ile Asn Ala Ile
                450                 455                 460

Ile Lys Lys Tyr Gly Leu Pro Asn Asp Ile Ile Ile Glu Leu Ala Arg
465                 470                 475                 480

Glu Lys Asn Ser Lys Asp Ala Gln Lys Met Ile Asn Glu Met Gln Lys
                485                 490                 495

Arg Asn Arg Gln Thr Asn Glu Arg Ile Glu Glu Ile Ile Arg Thr Thr
                500                 505                 510

Gly Lys Glu Asn Ala Lys Tyr Leu Ile Glu Lys Ile Lys Leu His Asp
                515                 520                 525

Met Gln Glu Gly Lys Cys Leu Tyr Ser Leu Glu Ala Ile Pro Leu Glu
                530                 535                 540

Asp Leu Leu Asn Asn Pro Phe Asn Tyr Glu Val Asp His Ile Ile Pro
545                 550                 555                 560
```

-continued

Arg Ser Val Ser Phe Asp Asn Ser Phe Asn Asn Lys Val Leu Val Lys
                565                 570                 575

Gln Glu Glu Asn Ser Lys Lys Gly Asn Arg Thr Pro Phe Gln Tyr Leu
                580                 585                 590

Ser Ser Ser Asp Ser Lys Ile Ser Tyr Glu Thr Phe Lys Lys His Ile
                595                 600                 605

Leu Asn Leu Ala Lys Gly Lys Gly Arg Ile Ser Lys Thr Lys Lys Glu
                610                 615                 620

Tyr Leu Leu Glu Glu Arg Asp Ile Asn Arg Phe Ser Val Gln Lys Asp
625                 630                 635                 640

Phe Ile Asn Arg Asn Leu Val Asp Thr Arg Tyr Ala Thr Arg Gly Leu
                645                 650                 655

Met Asn Leu Leu Arg Ser Tyr Phe Arg Val Asn Asn Leu Asp Val Lys
                660                 665                 670

Val Lys Ser Ile Asn Gly Gly Phe Thr Ser Phe Leu Arg Arg Lys Trp
                675                 680                 685

Lys Phe Lys Lys Glu Arg Asn Lys Gly Tyr Lys His His Ala Glu Asp
                690                 695                 700

Ala Leu Ile Ile Ala Asn Ala Asp Phe Ile Phe Lys Glu Trp Lys Lys
705                 710                 715                 720

Leu Asp Lys Ala Lys Lys Val Met Glu Asn Gln Met Phe Glu Glu Lys
                725                 730                 735

Gln Ala Glu Ser Met Pro Glu Ile Glu Thr Glu Gln Glu Tyr Lys Glu
                740                 745                 750

Ile Phe Ile Thr Pro His Gln Ile Lys His Ile Lys Asp Phe Lys Asp
                755                 760                 765

Tyr Lys Tyr Ser His Arg Val Asp Lys Lys Pro Asn Arg Glu Leu Ile
                770                 775                 780

Asn Asp Thr Leu Tyr Ser Thr Arg Lys Asp Asp Lys Gly Asn Thr Leu
785                 790                 795                 800

Ile Val Asn Asn Leu Asn Gly Leu Tyr Asp Lys Asp Asn Asp Lys Leu
                805                 810                 815

Lys Lys Leu Ile Asn Lys Ser Pro Glu Lys Leu Leu Met Tyr His His
                820                 825                 830

Asp Pro Gln Thr Tyr Gln Lys Leu Lys Leu Ile Met Glu Gln Tyr Gly
                835                 840                 845

Asp Glu Lys Asn Pro Leu Tyr Lys Tyr Tyr Glu Glu Thr Gly Asn Tyr
                850                 855                 860

Leu Thr Lys Tyr Ser Lys Lys Asp Asn Gly Pro Val Ile Lys Lys Ile
865                 870                 875                 880

Lys Tyr Tyr Gly Asn Lys Leu Asn Ala His Leu Asp Ile Thr Asp Asp
                885                 890                 895

Tyr Pro Asn Ser Arg Asn Lys Val Val Lys Leu Ser Leu Lys Pro Tyr
                900                 905                 910

Arg Phe Asp Val Tyr Leu Asp Asn Gly Val Tyr Lys Phe Val Thr Val
                915                 920                 925

Lys Asn Leu Asp Val Ile Lys Lys Glu Asn Tyr Tyr Glu Val Asn Ser
                930                 935                 940

Lys Cys Tyr Glu Glu Ala Lys Lys Leu Lys Lys Ile Ser Asn Gln Ala
945                 950                 955                 960

Glu Phe Ile Ala Ser Phe Tyr Asn Asn Asp Leu Ile Lys Ile Asn Gly
                965                 970                 975

Glu Leu Tyr Arg Val Ile Gly Val Asn Asn Asp Leu Leu Asn Arg Ile
            980             985                 990

Glu Val Asn Met Ile Asp Ile Thr  Tyr Arg Glu Tyr Leu  Glu Asn Met
        995              1000                 1005

Asn Asp  Lys Arg Pro Pro Arg  Ile Ile Lys Thr Ile  Ala Ser Lys
    1010             1015                 1020

Thr Gln  Ser Ile Lys Lys Tyr  Ser Thr Asp Ile Leu  Gly Asn Leu
    1025             1030                 1035

Tyr Glu  Val Lys Ser Lys Lys  His Pro Gln Ile Ile  Lys Lys Gly
    1040             1045                 1050

<210> SEQ ID NO 27
<211> LENGTH: 104
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(20)
<223> OTHER INFORMATION: a, c, u, g, unknown or other

<400> SEQUENCE: 27
nnnnnnnnnn nnnnnnnnnn guuuuagagc uaugcugaaa agcauagcaa guuaaaauaa      60
ggcuaguccg uuaucaacuu gaaaaagugg caccgagucg gugc                      104

<210> SEQ ID NO 28
<211> LENGTH: 106
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(20)
<223> OTHER INFORMATION: a, c, u, g, unknown or other

<400> SEQUENCE: 28
nnnnnnnnnn nnnnnnnnnn guuuuagagc uaugcuggaa acagcauagc aaguuaaaau      60
aaggcuaguc cguuaucaac uugaaaaagu ggcaccgagu cggugc                    106

<210> SEQ ID NO 29
<211> LENGTH: 116
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(20)
<223> OTHER INFORMATION: a, c, u, g, unknown or other

<400> SEQUENCE: 29
nnnnnnnnnn nnnnnnnnnn guuuuagagc uaugcuguuu uggaaacaaa acagcauagc      60
aaguuaaaau aaggcuaguc cguuaucaac uugaaaaagu ggcaccgagu cggugc         116

<210> SEQ ID NO 30
<211> LENGTH: 96
<212> TYPE: RNA
<213> ORGANISM: Artificial Sequence
<220> FEATURE:

```
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: a, c, u, g, unknown or other

<400> SEQUENCE: 30
nnnnnnnnnn nnnnnnnnnn guauuagagc uagaaauagc aaguuaauau aaggcuaguc    60
cguuaucaac uugaaaaagu ggcaccgagu cggugc                              96

<210> SEQ ID NO 31
<211> LENGTH: 96
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: a, c, u, g, unknown or other

<400> SEQUENCE: 31
nnnnnnnnnn nnnnnnnnnn guuuagagc uagaaauagc aaguuuaaau aaggcuaguc     60
cguuaucaac uugaaaaagu ggcaccgagu cggugc                              96

<210> SEQ ID NO 32
<211> LENGTH: 116
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(20)
<223> OTHER INFORMATION: a, c, u, g, unknown or other

<400> SEQUENCE: 32
nnnnnnnnnn nnnnnnnnnn guauuagagc uaugcuguau uggaaacaau acagcauagc    60
aaguuaauau aaggcuaguc cguuaucaac uugaaaaagu ggcaccgagu cggugc       116

<210> SEQ ID NO 33
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 33
aaggcuaguc cguuaucaac uugaaaaagu ggcaccgagu cggugcu                  47

<210> SEQ ID NO 34
<211> LENGTH: 49
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 34
aaggcuaguc cguuaucaac uugaaaaagu ggcaccgagu cgguggugc                49

<210> SEQ ID NO 35
```

```
<211> LENGTH: 51
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 35
aaggcuaguc cguuaucaac uugaaaaagu ggcaccgagu cggugcggau c          51

<210> SEQ ID NO 36
<211> LENGTH: 31
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 36
aaggcuaguc cguuaucaac uugaaaaagu g                                31

<210> SEQ ID NO 37
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 37
aaggcuaguc cguuauca                                               18

<210> SEQ ID NO 38
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 38
aaggcuaguc cg                                                     12

<210> SEQ ID NO 39
<211> LENGTH: 4
<212> TYPE: PRT
<213> ORGANISM: Unknown
<220> FEATURE:
<223> OTHER INFORMATION: Description of Unknown:
      "DEAH" motif peptide

<400> SEQUENCE: 39

Asp Glu Ala His
1

<210> SEQ ID NO 40
<211> LENGTH: 4
<212> TYPE: PRT
<213> ORGANISM: Unknown
<220> FEATURE:
<223> OTHER INFORMATION: Description of Unknown:
      "DEAD" motif peptide

<400> SEQUENCE: 40

Asp Glu Ala Asp
1
```

```
<210> SEQ ID NO 41
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Any amino acid
<220> FEATURE:
<221> NAME/KEY: MOD_RES
<222> LOCATION: (5)..(8)
<223> OTHER INFORMATION: Any amino acid
<220> FEATURE:
<221> NAME/KEY: MOD_RES
<222> LOCATION: (10)..(13)
<223> OTHER INFORMATION: Any amino acid

<400> SEQUENCE: 41

Cys Xaa Xaa Cys Xaa Xaa Xaa Xaa His Xaa Xaa Xaa Xaa Cys
1               5                   10

<210> SEQ ID NO 42
<211> LENGTH: 42
<212> TYPE: RNA
<213> ORGANISM: Streptococcus pyogenes
<220> FEATURE:
<221> NAME/KEY: modified_base
<222> LOCATION: (1)..(20)
<223> OTHER INFORMATION: a, c, u, g, unknown or other

<400> SEQUENCE: 42
nnnnnnnnnn nnnnnnnnnn guuuuagagc uaugcuguuu ug                           42

<210> SEQ ID NO 43
<211> LENGTH: 85
<212> TYPE: RNA
<213> ORGANISM: Streptococcus pyogenes

<400> SEQUENCE: 43
ggaaccauuc aaaacagcau agcaaguuaa aauaaggcua guccguuauc aacuugaaaa        60
aguggcaccg agucggugcu uuuuu                                              85

<210> SEQ ID NO 44
<211> LENGTH: 62
<212> TYPE: RNA
<213> ORGANISM: Streptococcus pyogenes
<220> FEATURE:
<221> NAME/KEY: modified_base
<222> LOCATION: (1)..(20)
<223> OTHER INFORMATION: a, c, u, g, unknown or other

<400> SEQUENCE: 44
nnnnnnnnnn nnnnnnnnnn guuuuagagc uagaaauagc aaguuaaaau aaggcuaguc        60
cg                                                                      62

<210> SEQ ID NO 45
<211> LENGTH: 102
<212> TYPE: RNA
<213> ORGANISM: Streptococcus pyogenes
<220> FEATURE:
<221> NAME/KEY: modified_base
<222> LOCATION: (1)..(20)
<223> OTHER INFORMATION: a, c, u, g, unknown or other
```

```
<400> SEQUENCE: 45
nnnnnnnnnn nnnnnnnnnn guuuuagagc uagaaauagc aaguuaaaau aaggcuaguc      60
cguuaucaac uugaaaaagu ggcaccgagu cggugcuuuu uu                        102

<210> SEQ ID NO 46
<211> LENGTH: 75
<212> TYPE: RNA
<213> ORGANISM: Streptococcus pyogenes
<220> FEATURE:
<221> NAME/KEY: modified_base
<222> LOCATION: (1)..(20)
<223> OTHER INFORMATION: a, c, u, g, unknown or other

<400> SEQUENCE: 46
nnnnnnnnnn nnnnnnnnnn guuuuagagc uaugcugaaa agcauagcaa guuaaaauaa      60
ggcuaguccg uuauc                                                      75

<210> SEQ ID NO 47
<211> LENGTH: 87
<212> TYPE: RNA
<213> ORGANISM: Streptococcus pyogenes
<220> FEATURE:
<221> NAME/KEY: modified_base
<222> LOCATION: (1)..(20)
<223> OTHER INFORMATION: a, c, u, g, unknown or other

<400> SEQUENCE: 47
nnnnnnnnnn nnnnnnnnnn guuuuagagc uaugcuguuu uggaaacaaa acagcauagc      60
aaguuaaaau aaggcuaguc cguuauc                                         87

<210> SEQ ID NO 48
<211> LENGTH: 42
<212> TYPE: RNA
<213> ORGANISM: Streptococcus thermophilus
<220> FEATURE:
<221> NAME/KEY: modified_base
<222> LOCATION: (1)..(20)
<223> OTHER INFORMATION: a, c, u, g, unknown or other

<400> SEQUENCE: 48
nnnnnnnnnn nnnnnnnnnn guuuuagagc uguguuguuu cg                        42

<210> SEQ ID NO 49
<211> LENGTH: 78
<212> TYPE: RNA
<213> ORGANISM: Streptococcus thermophilus

<400> SEQUENCE: 49
gggcgaaaca acacagcgag uuaaaauaag gcuaguccg uacucaacuu gaaaaggugg       60
caccgauucg guguuuuu                                                   78

<210> SEQ ID NO 50
<211> LENGTH: 42
<212> TYPE: RNA
<213> ORGANISM: Streptococcus pyogenes
<220> FEATURE:
<221> NAME/KEY: modified_base
<222> LOCATION: (1)..(20)
<223> OTHER INFORMATION: a, c, u, g, unknown or other

<400> SEQUENCE: 50
nnnnnnnnnn nnnnnnnnnn guuuuagagc uaugcuguuu ug                        42
```

<210> SEQ ID NO 51
<211> LENGTH: 42
<212> TYPE: RNA
<213> ORGANISM: Streptococcus thermophilus
<220> FEATURE:
<221> NAME/KEY: modified_base
<222> LOCATION: (1)..(20)
<223> OTHER INFORMATION: a, c, u, g, unknown or other

<400> SEQUENCE: 51
nnnnnnnnnn nnnnnnnnnn guuuuagagc uguguuguuu cg        42

<210> SEQ ID NO 52
<211> LENGTH: 85
<212> TYPE: RNA
<213> ORGANISM: Streptococcus pyogenes

<400> SEQUENCE: 52
gaaccauuca aaacagcaua gcaaguuaaa auaaggcuag uccguuauca acuugaaaaa        60
guggcaccga gucggugcuu uuuuu        85

<210> SEQ ID NO 53
<211> LENGTH: 78
<212> TYPE: RNA
<213> ORGANISM: Streptococcus thermophilus

<400> SEQUENCE: 53
gggcgaaaca acacagcgag uuaaaauaag gcuuaguccg uacucaacuu gaaaaggugg        60
caccgauucg guguuuuu        78

<210> SEQ ID NO 54
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Asp Ile Gly Thr Asn Ser Val Gly Trp Ala Val Thr
1               5                   10

<210> SEQ ID NO 55
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Asp Ile Gly Thr Asn Ser Val Gly Trp Ala Val Thr
1               5                   10

<210> SEQ ID NO 56
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Asp Val Gly Thr Asn Ser Val Gly Trp Ala Val Thr
1               5                   10

<210> SEQ ID NO 57
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Asp Val Gly Thr Asn Ser Val Gly Trp Ala Val Thr
1               5                   10

<210> SEQ ID NO 58
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Asp Met Gly Thr Asn Ser Val Gly Trp Ala Val Thr
1               5                   10

<210> SEQ ID NO 59
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Asp Val Gly Thr Ser Ser Val Gly Trp Ala Val Thr
1               5                   10

<210> SEQ ID NO 60
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Asp Ile Gly Thr Ala Ser Val Gly Trp Ala Val Thr
1               5                   10

<210> SEQ ID NO 61
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Asp Val Gly Thr Gly Ser Val Gly Trp Ala Val Thr
1               5                   10

<210> SEQ ID NO 62
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 62

Asp Ile Gly Thr Asn Ser Val Gly Trp Ala Val Val
1               5                   10

<210> SEQ ID NO 63
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Asp Ile Gly Thr Asn Ser Val Gly Trp Ala Val Ile
1               5                   10

<210> SEQ ID NO 64
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Asp Ile Gly Thr Asn Ser Val Gly Trp Ala Val Leu
1               5                   10

<210> SEQ ID NO 65
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Asp Leu Gly Thr Asn Ser Ile Gly Trp Ala Val Val
1               5                   10

<210> SEQ ID NO 66
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Asp Leu Gly Thr Asn Ser Ile Gly Trp Ala Ile
1               5                   10

<210> SEQ ID NO 67
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Asp Leu Gly Thr Asn Ser Ile Gly Trp Ala Leu Val
1               5                   10

<210> SEQ ID NO 68
<211> LENGTH: 12
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Asp Ile Gly Thr Asn Ser Val Gly Trp Cys Val Thr
1               5                   10

<210> SEQ ID NO 69
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Asp Ile Gly Thr Asn Ser Val Gly Tyr Ala Val Thr
1               5                   10

<210> SEQ ID NO 70
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Asp Met Gly Thr Gly Ser Leu Gly Trp Ala Val Thr
1               5                   10

<210> SEQ ID NO 71
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Asp Ile Gly Thr Ser Ser Val Gly Trp Ala Ala Ile
1               5                   10

<210> SEQ ID NO 72
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Asp Leu Gly Thr Gly Ser Val Gly Trp Ala Val Val
1               5                   10

<210> SEQ ID NO 73
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 73

Asp Leu Gly Val Gly Ser Val Gly Trp Ala Ile Val
1               5                   10

<210> SEQ ID NO 74
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Asp Leu Gly Ile Ala Ser Ile Gly Trp Ala Ile Ile
1               5                   10

<210> SEQ ID NO 75
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Asp Leu Gly Ile Ala Ser Val Gly Trp Ala Ile Val
1               5                   10

<210> SEQ ID NO 76
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Asp Leu Gly Val Ala Ser Val Gly Trp Ser Ile Val
1               5                   10

<210> SEQ ID NO 77
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Asp Ile Gly Ile Ala Ser Val Gly Trp Ala Ile Leu
1               5                   10

<210> SEQ ID NO 78
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Asp Leu Gly Ile Ser Ser Val Gly Trp Ser Val Ile
1               5                   10

<210> SEQ ID NO 79
<211> LENGTH: 12
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Asp Ile Gly Ile Ala Ser Val Gly Trp Ser Val Ile
1               5                   10

<210> SEQ ID NO 80
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Asp Val Gly Ile Gly Ser Ile Gly Trp Ala Val Ile
1               5                   10

<210> SEQ ID NO 81
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Asp Leu Gly Val Gly Ser Ile Gly Phe Ala Ile Val
1               5                   10

<210> SEQ ID NO 82
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Asp Ile Gly Tyr Ala Ser Ile Gly Trp Ala Val Ile
1               5                   10

<210> SEQ ID NO 83
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Asp Thr Gly Thr Asn Ser Leu Gly Trp Ala Ile Val
1               5                   10

<210> SEQ ID NO 84
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 84

Asp Leu Gly Thr Asn Ser Ile Gly Trp Cys Leu Leu
1               5                   10

<210> SEQ ID NO 85
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Asp Ile Gly Thr Asp Ser Leu Gly Trp Ala Val Phe
1               5                   10

<210> SEQ ID NO 86
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Asp Ile Gly Ser Asn Ser Ile Gly Phe Ala Val Val
1               5                   10

<210> SEQ ID NO 87
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Asp Leu Gly Val Gly Ser Ile Gly Val Ala Val Ala
1               5                   10

<210> SEQ ID NO 88
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Asp Leu Gly Ile Ala Ser Cys Gly Trp Gly Val Val
1               5                   10

<210> SEQ ID NO 89
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Asp Leu Gly Ile Ala Ser Val Gly Trp Cys Leu Thr
1               5                   10

<210> SEQ ID NO 90
<211> LENGTH: 12

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Asp Ile Gly Ile Gly Ser Val Gly Val Gly Ile Leu
1               5                   10

<210> SEQ ID NO 91
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Asp Ile Gly Ile Thr Ser Val Gly Tyr Gly Leu Ile
1               5                   10

<210> SEQ ID NO 92
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Asp Ile Gly Ile Thr Ser Val Gly Phe Gly Ile Ile
1               5                   10

<210> SEQ ID NO 93
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Asp Val Gly Ile Thr Ser Thr Gly Tyr Ala Val Leu
1               5                   10

<210> SEQ ID NO 94
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Asp Leu Gly Ile Thr Ser Phe Gly Tyr Ala Ile Leu
1               5                   10

<210> SEQ ID NO 95
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 95

Asp Ile Gly Asn Ala Ser Val Gly Trp Ser Ala Phe
1               5                   10

<210> SEQ ID NO 96
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Asp Val Gly Thr Asn Ser Cys Gly Trp Val Ala Met
1               5                   10

<210> SEQ ID NO 97
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Asp Val Gly Glu Arg Ser Ile Gly Leu Ala Ala Val
1               5                   10

<210> SEQ ID NO 98
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Asp Val Gly Leu Asn Ser Val Gly Leu Ala Ala Val
1               5                   10

<210> SEQ ID NO 99
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Asp Val Gly Leu Met Ser Val Gly Leu Ala Ala Ile
1               5                   10

<210> SEQ ID NO 100
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Asp Val Gly Thr Phe Ser Val Gly Leu Ala Ala Ile
1               5                   10

<210> SEQ ID NO 101
<211> LENGTH: 12
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Asp Ile Gly Thr Gly Ser Val Gly Tyr Ala Cys Met
1               5                   10

<210> SEQ ID NO 102
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Asp Leu Gly Thr Thr Ser Ile Gly Phe Ala His Ile
1               5                   10

<210> SEQ ID NO 103
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Asp Leu Gly Thr Asn Ser Ile Gly Ser Ser Val Arg
1               5                   10

<210> SEQ ID NO 104
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Asp Ile Gly Thr Asn Ser Val Gly Trp Ala Val Thr
1               5                   10

<210> SEQ ID NO 105
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Asp Ile Gly Thr Asn Ser Val Gly Trp Ala Val Thr
1               5                   10

<210> SEQ ID NO 106
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 106

Asp Val Gly Thr Asn Ser Val Gly Trp Ala Val Thr
1               5                   10

<210> SEQ ID NO 107
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Asp Val Gly Thr Asn Ser Val Gly Trp Ala Val Thr
1               5                   10

<210> SEQ ID NO 108
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Asp Met Gly Thr Asn Ser Val Gly Trp Ala Val Thr
1               5                   10

<210> SEQ ID NO 109
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Asp Val Gly Thr Ser Ser Val Gly Trp Ala Val Thr
1               5                   10

<210> SEQ ID NO 110
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Asp Ile Gly Thr Ala Ser Val Gly Trp Ala Val Thr
1               5                   10

<210> SEQ ID NO 111
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Asp Val Gly Thr Gly Ser Val Gly Trp Ala Val Thr
1               5                   10

<210> SEQ ID NO 112
<211> LENGTH: 12

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Asp Ile Gly Thr Asn Ser Val Gly Trp Ala Val Val
1               5                   10

<210> SEQ ID NO 113
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Asp Ile Gly Thr Asn Ser Val Gly Trp Ala Val Ile
1               5                   10

<210> SEQ ID NO 114
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Asp Ile Gly Thr Asn Ser Ile Gly Trp Ala Val Ile
1               5                   10

<210> SEQ ID NO 115
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Asp Ile Gly Thr Asn Ser Val Gly Trp Ala Val Leu
1               5                   10

<210> SEQ ID NO 116
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Asp Leu Gly Thr Asn Ser Ile Gly Trp Ala Val Val
1               5                   10

<210> SEQ ID NO 117
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 117

Asp Leu Gly Thr Asn Ser Ile Gly Trp Ala Ile
1               5                   10

<210> SEQ ID NO 118
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Asp Leu Gly Thr Asn Ser Ile Gly Trp Ala Leu Val
1               5                   10

<210> SEQ ID NO 119
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Asp Ile Gly Thr Asn Ser Val Gly Trp Cys Val Thr
1               5                   10

<210> SEQ ID NO 120
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Asp Ile Gly Thr Asn Ser Val Gly Tyr Ala Val Thr
1               5                   10

<210> SEQ ID NO 121
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Asp Met Gly Thr Gly Ser Leu Gly Trp Ala Val Thr
1               5                   10

<210> SEQ ID NO 122
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Asp Ile Gly Thr Ser Ser Val Gly Trp Ala Ala Ile
1               5                   10

<210> SEQ ID NO 123
<211> LENGTH: 12

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Asp Leu Gly Thr Gly Ser Val Gly Trp Ala Val Val
1               5                   10

<210> SEQ ID NO 124
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Asp Leu Gly Val Gly Ser Val Gly Trp Ala Ile Val
1               5                   10

<210> SEQ ID NO 125
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Asp Leu Gly Ile Ala Ser Ile Gly Trp Ala Ile Ile
1               5                   10

<210> SEQ ID NO 126
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Asp Leu Gly Ile Ala Ser Val Gly Trp Ala Ile Val
1               5                   10

<210> SEQ ID NO 127
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Asp Leu Gly Ile Ala Ser Val Gly Trp Ala Val Val
1               5                   10

<210> SEQ ID NO 128
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 128

Asp Leu Gly Val Ala Ser Val Gly Trp Ser Ile Val
1               5                   10

<210> SEQ ID NO 129
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Asp Ile Gly Ile Ala Ser Val Gly Trp Ala Ile Leu
1               5                   10

<210> SEQ ID NO 130
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Asp Ile Gly Ile Ala Ser Val Gly Trp Ala Val Leu
1               5                   10

<210> SEQ ID NO 131
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Asp Ile Gly Ile Ala Ser Ile Gly Trp Ala Val Ile
1               5                   10

<210> SEQ ID NO 132
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Asp Ile Gly Ile Ala Ser Val Gly Trp Ala Ile Ile
1               5                   10

<210> SEQ ID NO 133
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Asp Val Gly Ile Ala Ser Val Gly Trp Ala Val Ile
1               5                   10

<210> SEQ ID NO 134
<211> LENGTH: 11
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Asp Ile Gly Ile Ala Ser Val Gly Trp Ala Leu
1               5                   10

<210> SEQ ID NO 135
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Asp Ile Gly Ile Ala Ser Val Gly Trp Ala Met Val
1               5                   10

<210> SEQ ID NO 136
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Asp Ile Gly Ile Ala Ser Val Gly Trp Ser Val Ile
1               5                   10

<210> SEQ ID NO 137
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Asp Leu Gly Ile Ser Ser Val Gly Trp Ser Val Ile
1               5                   10

<210> SEQ ID NO 138
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Asp Ile Gly Ile Thr Ser Val Gly Trp Ala Val Ile
1               5                   10

<210> SEQ ID NO 139
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 139

Asp Val Gly Ile Gly Ser Ile Gly Trp Ala Val Ile
1               5                   10

<210> SEQ ID NO 140
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Asp Leu Gly Ile Ser Ser Leu Gly Trp Ala Ile Val
1               5                   10

<210> SEQ ID NO 141
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Asp Leu Gly Val Gly Ser Ile Gly Phe Ala Ile Val
1               5                   10

<210> SEQ ID NO 142
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Asp Ile Gly Tyr Ala Ser Ile Gly Trp Ala Val Ile
1               5                   10

<210> SEQ ID NO 143
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Asp Leu Gly Thr Asn Ser Ile Gly Trp Cys Leu Leu
1               5                   10

<210> SEQ ID NO 144
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Asp Leu Gly Thr Asn Ser Ile Gly Trp Gly Leu Leu
1               5                   10

<210> SEQ ID NO 145
<211> LENGTH: 12

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Asp Thr Gly Thr Asn Ser Leu Gly Trp Ala Ile Val
1               5                   10

<210> SEQ ID NO 146
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Asp Ile Gly Thr Asp Ser Leu Gly Trp Ala Val Phe
1               5                   10

<210> SEQ ID NO 147
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Asp Leu Gly Ser Thr Ser Leu Gly Trp Ala Ile Phe
1               5                   10

<210> SEQ ID NO 148
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Asp Ile Gly Ile Ser Ser Ile Gly Trp Ala Phe Ser
1               5                   10

<210> SEQ ID NO 149
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Asp Leu Gly Ile Ala Ser Val Gly Trp Cys Leu Thr
1               5                   10

<210> SEQ ID NO 150
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 150

Asp Leu Gly Ile Ala Ser Cys Gly Trp Gly Val Val
1               5                   10

<210> SEQ ID NO 151
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Asp Ile Gly Ser Asn Ser Ile Gly Phe Ala Val Val
1               5                   10

<210> SEQ ID NO 152
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Asp Ile Gly Thr Thr Ser Ile Gly Phe Ser Val Ile
1               5                   10

<210> SEQ ID NO 153
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Asp Ile Gly Ile Thr Ser Val Gly Tyr Gly Leu Ile
1               5                   10

<210> SEQ ID NO 154
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Asp Ile Gly Ile Thr Ser Val Gly Phe Gly Ile Ile
1               5                   10

<210> SEQ ID NO 155
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Asp Leu Gly Thr Thr Ser Ile Gly Phe Ala His Ile
1               5                   10

<210> SEQ ID NO 156
<211> LENGTH: 12
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Asp Ile Gly Ile Gly Ser Val Gly Val Gly Ile Leu
1               5                   10

<210> SEQ ID NO 157
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

Asp Leu Gly Val Gly Ser Ile Gly Val Ala Val Ala
1               5                   10

<210> SEQ ID NO 158
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Asp Val Gly Ile Thr Ser Thr Gly Tyr Ala Val Leu
1               5                   10

<210> SEQ ID NO 159
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Asp Leu Gly Ile Thr Ser Phe Gly Tyr Ala Ile Leu
1               5                   10

<210> SEQ ID NO 160
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Asp Ile Gly Thr Ser Ser Ile Gly Trp Trp Leu Tyr
1               5                   10

<210> SEQ ID NO 161
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 161

Asp Leu Gly Ser Asn Ser Leu Gly Trp Phe Val Thr
1               5                   10

<210> SEQ ID NO 162
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Asp Leu Gly Ala Asn Ser Leu Gly Trp Phe Val Val
1               5                   10

<210> SEQ ID NO 163
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Asp Ile Gly Asn Ala Ser Val Gly Trp Ser Ala Phe
1               5                   10

<210> SEQ ID NO 164
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Asp Val Gly Thr Asn Ser Cys Gly Trp Val Ala Met
1               5                   10

<210> SEQ ID NO 165
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

Asp Val Gly Glu Arg Ser Ile Gly Leu Ala Ala Val
1               5                   10

<210> SEQ ID NO 166
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Asp Val Gly Leu Asn Ser Val Gly Leu Ala Ala Val
1               5                   10

<210> SEQ ID NO 167
<211> LENGTH: 12

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

Asp Val Gly Leu Met Ser Val Gly Leu Ala Ala Ile
1               5                   10

<210> SEQ ID NO 168
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

Asp Val Gly Thr Phe Ser Val Gly Leu Ala Ala Ile
1               5                   10

<210> SEQ ID NO 169
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

Asp Ile Gly Thr Gly Ser Val Gly Tyr Ala Cys Met
1               5                   10

<210> SEQ ID NO 170
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170

Asp Leu Gly Thr Asn Ser Ile Gly Ser Ser Val Arg
1               5                   10

<210> SEQ ID NO 171
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

Asp Ile Gly Leu Arg Ile Gly Ile Thr Ser Cys Gly Trp Ser Ile
1               5                   10                  15

<210> SEQ ID NO 172
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 172

Asp Met Gly Ala Lys Tyr Thr Gly Val Phe Tyr Ala
1               5                   10

<210> SEQ ID NO 173
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

Asp Leu Gly Gly Lys Asn Thr Gly Phe Phe Ser Phe
1               5                   10

<210> SEQ ID NO 174
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Asp Leu Gly Val Lys Asn Thr Gly Val Phe Ser Ala
1               5                   10

<210> SEQ ID NO 175
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

Asp Leu Gly Ala Lys Phe Thr Gly Val Ala Leu Tyr
1               5                   10

<210> SEQ ID NO 176
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

Asp Leu Gly Gly Lys Phe Thr Gly Val Cys Leu Ser
1               5                   10

<210> SEQ ID NO 177
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 177

Asp Leu Gly Gly Thr Tyr Thr Gly Thr Phe Ile Thr
1               5                   10

<210> SEQ ID NO 178
<211> LENGTH: 28

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

Tyr Asp Ile Asp His Ile Tyr Pro Arg Ser Leu Thr Lys Asp Asp Ser
1               5                   10                  15

Phe Asp Asn Leu Val Leu Cys Glu Arg Thr Ala Asn
            20                  25

<210> SEQ ID NO 179
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

Asp Ile Asp His Ile Tyr Pro Arg Ser Lys Val Ile Lys Asp Asp Ser
1               5                   10                  15

Phe Asp Asn Leu Val Leu Val Leu Lys Asn Glu Asn
            20                  25

<210> SEQ ID NO 180
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 180

Asp Arg Asp His Ile Tyr Pro Gln Ser Lys Ile Lys Asp Asp Ser Ile
1               5                   10                  15

Asp Asn Leu Val Leu Val Asn Lys Thr Tyr Asn
            20                  25

<210> SEQ ID NO 181
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 181

Asp Ile Asp His Ile Tyr Pro Arg Ser Lys Ile Lys Asp Asp Ser Ile
1               5                   10                  15

Thr Asn Arg Val Leu Val Glu Lys Asp Ile Asn
            20                  25

<210> SEQ ID NO 182
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

Asp Ile Asp His Ile Tyr Pro Gln Ser Lys Ile Lys Asp Asp Ser Ile
1               5                   10                  15
```

```
Ser Asn Arg Val Leu Val Cys Ser Ser Cys Asn
            20                  25
```

```
<210> SEQ ID NO 183
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183
```

```
Asp Ile Asp His Ile Tyr Pro Gln Ser Lys Thr Met Asp Asp Ser Leu
1               5                   10                  15

Asn Asn Arg Val Leu Val Lys Lys Asn Tyr Asn
            20                  25
```

```
<210> SEQ ID NO 184
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184
```

```
Asp Gln Asp His Ile Tyr Pro Lys Ser Lys Ile Tyr Asp Asp Ser Leu
1               5                   10                  15

Glu Asn Arg Val Leu Val Lys Lys Asn Leu Asn
            20                  25
```

```
<210> SEQ ID NO 185
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185
```

```
Gln Ile Asp His Ile Val Pro Gln Ser Leu Val Lys Asp Asp Ser Phe
1               5                   10                  15

Asp Asn Arg Val Leu Val Val Pro Ser Glu Asn
            20                  25
```

```
<210> SEQ ID NO 186
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 186
```

```
Asp Ile Asp His Ile Ile Pro Gln Ala Phe Ile Lys Asp Asn Ser Ile
1               5                   10                  15

Asp Asn Arg Val Leu Thr Ser Ser Lys Glu Asn
            20                  25
```

```
<210> SEQ ID NO 187
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 187

Asp Ile Asp His Ile Ile Pro Gln Ala Phe Leu Lys Asp Asn Ser Ile
1               5                   10                  15

Asp Asn Lys Val Leu Val Ser Ser Ala Ser Asn
            20                  25

<210> SEQ ID NO 188
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 188

Asp Ile Asp His Ile Ile Pro Gln Ala Tyr Thr Lys Asp Asn Ser Leu
1               5                   10                  15

Asp Asn Arg Val Leu Val Ser Asn Ile Thr Asn
            20                  25

<210> SEQ ID NO 189
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 189

Asp Ile Asp His Ile Val Pro Gln Ser Phe Ile Thr Asp Asn Ser Ile
1               5                   10                  15

Asp Asn Leu Val Leu Thr Ser Ser Ala Gly Asn
            20                  25

<210> SEQ ID NO 190
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 190

Asp Val Asp His Ile Val Pro Gln Ser Phe Leu Lys Asp Asp Ser Ile
1               5                   10                  15

Asp Asn Lys Val Leu Thr Arg Ser Asp Lys Asn
            20                  25

<210> SEQ ID NO 191
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 191

Asn Ile Asp His Ile Tyr Pro Gln Ser Met Val Lys Asp Asp Ser Leu
1               5                   10                  15

Asp Asn Lys Val Leu Val Gln Ser Glu Ile Asn
            20                  25

<210> SEQ ID NO 192

```
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 192

Asp Ile Asp His Ile Leu Pro Gln Ser Leu Ile Lys Asp Asp Ser Leu
1               5                   10                  15

Asp Asn Arg Val Leu Val Asn Ala Thr Ile Asn
            20                  25

<210> SEQ ID NO 193
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 193

Asp Ile Asp His Ile Leu Pro Gln Ser Phe Ile Lys Asp Asp Ser Leu
1               5                   10                  15

Glu Asn Arg Val Leu Val Lys Lys Ala Val Asn
            20                  25

<210> SEQ ID NO 194
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 194

Glu Val Asp His Ile Phe Pro Arg Ser Phe Ile Lys Asp Asp Ser Ile
1               5                   10                  15

Asp Asn Lys Val Leu Val Ile Lys Lys Met Asn
            20                  25

<210> SEQ ID NO 195
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 195

Glu Val Asp His Ile Ile Pro Arg Ser Tyr Ile Lys Asp Asp Ser Phe
1               5                   10                  15

Glu Asn Lys Val Leu Val Tyr Arg Glu Glu Asn
            20                  25

<210> SEQ ID NO 196
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 196

Asp Ile Asp His Ile Ile Pro Gln Ala Val Thr Gln Asn Asp Ser Ile
1               5                   10                  15
```

Asp Asn Arg Val Leu Val Ala Arg Ala Glu Asn
            20                  25

<210> SEQ ID NO 197
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 197

Glu Ile Asp His Ile Ile Pro Tyr Ser Ile Ser Phe Asp Asp Ser Ser
1               5                   10                  15

Ser Asn Lys Leu Leu Val Leu Ala Glu Ser Asn
            20                  25

<210> SEQ ID NO 198
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 198

Glu Ile Asp His Ile Ile Pro Tyr Ser Leu Cys Phe Asp Asp Ser Ser
1               5                   10                  15

Ala Asn Lys Val Leu Val His Lys Gln Ser Asn
            20                  25

<210> SEQ ID NO 199
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 199

Asp Ile Asp His Ile Ile Pro Tyr Ser Arg Ser Met Asp Asp Ser Tyr
1               5                   10                  15

Ser Asn Lys Val Leu Val Leu Ser Gly Glu Asn
            20                  25

<210> SEQ ID NO 200
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 200

Asp Ile Asp His Ile Ile Pro Tyr Ser Lys Ser Met Asp Asp Ser Phe
1               5                   10                  15

Asn Asn Lys Val Leu Cys Leu Ala Glu Glu Asn
            20                  25

<210> SEQ ID NO 201
<211> LENGTH: 27
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 201

Glu Ile Asp His Ile Tyr Pro Tyr Ser Arg Ser Phe Asp Asp Ser Tyr
1               5                   10                  15

Met Asn Lys Val Leu Val Phe Thr Lys Gln Asn
            20                  25

<210> SEQ ID NO 202
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 202

Gln Ile Asp His Ile Tyr Pro Tyr Ser Arg Ser Met Asp Asp Ser Tyr
1               5                   10                  15

Met Asn Lys Val Leu Val Leu Thr Asp Glu Asn
            20                  25

<210> SEQ ID NO 203
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 203

Glu Ile Asp His Ile Ile Pro Phe Ser Arg Ser Phe Asp Asp Ser Leu
1               5                   10                  15

Ser Asn Lys Ile Leu Val Leu Gly Ser Glu Asn
            20                  25

<210> SEQ ID NO 204
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 204

Glu Ile Asp His Ala Leu Pro Phe Ser Arg Thr Trp Asp Asp Ser Phe
1               5                   10                  15

Asn Asn Lys Val Leu Val Leu Gly Ser Glu Asn
            20                  25

<210> SEQ ID NO 205
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 205

Glu Ile Asp His Ala Leu Pro Phe Ser Arg Thr Trp Asp Asp Ser Phe
1               5                   10                  15

Asn Asn Lys Val Leu Val Leu Ala Ser Glu Asn
            20                  25
```

<210> SEQ ID NO 206
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 206

Glu Ile Asp His Ile Ile Pro Ile Ser Ile Ser Leu Asp Asp Ser Ile
1               5                   10                  15

Asn Asn Lys Val Leu Val Leu Ser Lys Ala Asn
            20                  25

<210> SEQ ID NO 207
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 207

Glu Val Asp His Ile Ile Pro Ile Ser Ile Ser Leu Asp Asp Ser Ile
1               5                   10                  15

Thr Asn Lys Val Leu Val Thr His Arg Glu Asn
            20                  25

<210> SEQ ID NO 208
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 208

Gln Val Asp His Ala Leu Pro Tyr Ser Arg Ser Tyr Asp Asp Ser Lys
1               5                   10                  15

Asn Asn Lys Val Leu Val Leu Thr His Glu Asn
            20                  25

<210> SEQ ID NO 209
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 209

Glu Val Asp His Ile Leu Pro Leu Ser Ile Thr Phe Asp Asp Ser Leu
1               5                   10                  15

Ala Asn Lys Val Leu Val Tyr Ala Thr Ala Asn
            20                  25

<210> SEQ ID NO 210
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 210

Glu Ile Asp His Ile Ile Pro Arg Ser Ile Ser Phe Asp Asp Ala Arg
1               5                   10                  15

Ser Asn Lys Val Leu Val Tyr Arg Ser Glu Asn
            20                  25

<210> SEQ ID NO 211
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 211

Glu Val Asp His Ile Ile Pro Arg Ser Val Ser Phe Asp Asn Ser Tyr
1               5                   10                  15

His Asn Lys Val Leu Val Lys Gln Ser Glu Asn
            20                  25

<210> SEQ ID NO 212
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 212

Asp Ile Asp His Ile Leu Pro Tyr Ser Ile Thr Phe Asp Asp Ser Phe
1               5                   10                  15

Arg Asn Lys Val Leu Val Thr Ser Gln Glu Asn
            20                  25

<210> SEQ ID NO 213
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 213

Glu Ile Asp His Ile Leu Pro Arg Ser Arg Ser Ala Asp Asp Ser Phe
1               5                   10                  15

Ala Asn Lys Val Leu Cys Leu Ala Arg Ala Asn
            20                  25

<210> SEQ ID NO 214
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 214

Glu Ile Glu His Leu Leu Pro Phe Ser Leu Thr Leu Asp Asp Ser Met
1               5                   10                  15

Ala Asn Lys Thr Val Cys Phe Arg Gln Ala Asn
            20                  25

<210> SEQ ID NO 215

```
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 215

Asp Ile Asp His Ile Leu Pro Phe Ser Val Ser Leu Asp Asp Ser Ala
1               5                   10                  15

Ala Asn Lys Val Val Cys Leu Arg Glu Ala Asn
            20                  25

<210> SEQ ID NO 216
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 216

Asp Ile Asp His Leu Ile Pro Phe Ser Ile Ser Trp Asp Asp Ser Ala
1               5                   10                  15

Ala Asn Lys Val Val Cys Met Arg Tyr Ala Asn
            20                  25

<210> SEQ ID NO 217
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 217

Asp Ile Asp His Ile Leu Pro Val Ala Met Thr Leu Asp Asp Ser Pro
1               5                   10                  15

Ala Asn Lys Ile Ile Cys Met Arg Tyr Ala Asn
            20                  25

<210> SEQ ID NO 218
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 218

Asp Val Asp His Ile Leu Pro Tyr Ser Arg Thr Leu Asp Asp Ser Phe
1               5                   10                  15

Pro Asn Arg Thr Leu Cys Leu Arg Glu Ala Asn
            20                  25

<210> SEQ ID NO 219
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 219

Glu Ile Glu His Ile Leu Pro Phe Ser Arg Thr Leu Asp Asp Ser Leu
1               5                   10                  15
```

Asn Asn Arg Thr Val Ala Met Arg Arg Ala Asn
            20                  25

<210> SEQ ID NO 220
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 220

Glu Val Asp His Ile Ile Pro Tyr Ser Ile Ser Trp Asp Asp Ser Tyr
1               5                   10                  15

Thr Asn Lys Val Leu Thr Ser Ala Lys Cys Asn
            20                  25

<210> SEQ ID NO 221
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 221

Gln Val Asp His Ile Leu Pro Trp Ser Arg Phe Gly Asp Asp Ser Tyr
1               5                   10                  15

Leu Asn Lys Thr Leu Cys Thr Ala Arg Ser Asn
            20                  25

<210> SEQ ID NO 222
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 222

Gln Val Asp His Ile Leu Pro Phe Ser Lys Thr Leu Asp Ser Phe
1               5                   10                  15

Ala Asn Lys Val Leu Ala Gln His Asp Ala Asn
            20                  25

<210> SEQ ID NO 223
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 223

Gln Ile Asp His Ala Phe Pro Leu Ser Arg Ser Leu Asp Asp Ser Gln
1               5                   10                  15

Ser Asn Lys Val Leu Cys Leu Thr Ser Ser Asn
            20                  25

<210> SEQ ID NO 224
<211> LENGTH: 27
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 224

Asp Ile Asp His Ile Val Pro Arg Ser Ile Ser Phe Asp Ser Phe
1               5                   10                  15

Ser Asn Leu Val Ile Val Asn Lys Leu Asp Asn
            20                  25

<210> SEQ ID NO 225
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 225

Glu Ile Glu His Ile Ile Pro Tyr Ser Met Ser Tyr Asp Asn Ser Gln
1               5                   10                  15

Ala Asn Lys Ile Leu Thr Glu Lys Ala Glu Asn
            20                  25

<210> SEQ ID NO 226
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 226

Glu Ile Asp His Val Ile Pro Tyr Ser Lys Ser Ala Asp Asp Ser Trp
1               5                   10                  15

Phe Asn Lys Leu Leu Val Lys Lys Ser Thr Asn
            20                  25

<210> SEQ ID NO 227
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 227

Glu Met Asp His Ile Leu Pro Tyr Ser Arg Ser Leu Asp Asn Gly Trp
1               5                   10                  15

His Asn Arg Val Leu Val His Gly Lys Asp Asn
            20                  25

<210> SEQ ID NO 228
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 228

Glu Val Asp His Ile Val Pro Tyr Ser Leu Ile Leu Asp Asn Thr Ile
1               5                   10                  15

Asn Asn Lys Ala Leu Val Tyr Ala Glu Glu Asn
            20                  25
```

<210> SEQ ID NO 229
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 229

Glu Ile Glu His Val Ile Pro Gln Ser Leu Tyr Phe Asp Asp Ser Phe
1               5                   10                  15

Ser Asn Lys Val Ile Cys Glu Ala Glu Val Asn
            20                  25

<210> SEQ ID NO 230
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 230

Asp Ile Glu His Ile Ile Pro Gln Ala Arg Leu Phe Asp Asp Ser Phe
1               5                   10                  15

Ser Asn Lys Thr Leu Glu Ala Arg Ser Val Asn
            20                  25

<210> SEQ ID NO 231
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 231

Glu Ile Glu His Ile Val Pro Lys Ala Arg Val Phe Asp Asp Ser Phe
1               5                   10                  15

Ser Asn Lys Thr Leu Thr Phe His Arg Ile Asn
            20                  25

<210> SEQ ID NO 232
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 232

Asp Lys Asp His Ile Ile Pro Gln Ser Met Lys Lys Asp Asp Ser Ile
1               5                   10                  15

Ile Asn Asn Leu Val Leu Val Asn Lys Asn Ala Asn
            20                  25

<210> SEQ ID NO 233
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 233

Glu Val Glu His Ile Trp Pro Arg Ser Arg Ser Phe Asp Asn Ser Pro
1               5                   10                  15

Arg Asn Lys Thr Leu Cys Arg Lys Asp Val Asn
            20                  25

<210> SEQ ID NO 234
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 234

Ile Val Asn His Ile Ile Pro Tyr Asn Arg Ser Phe Asp Asp Thr Tyr
1               5                   10                  15

His Asn Arg Val Leu Thr Leu Thr Glu Thr Lys
            20                  25

<210> SEQ ID NO 235
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 235

Asp Met Glu His Thr Ile Pro Lys Ser Ile Ser Phe Asp Asn Ser Asp
1               5                   10                  15

Gln Asn Leu Thr Leu Cys Glu Ser Tyr Tyr Asn
            20                  25

<210> SEQ ID NO 236
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 236

Asp Ile Glu His Thr Ile Pro Arg Ser Ala Gly Gly Asp Ser Thr Lys
1               5                   10                  15

Met Asn Leu Thr Leu Cys Ser Ser Arg Phe Asn
            20                  25

<210> SEQ ID NO 237
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 237

Asp Ile Glu His Thr Ile Pro Arg Ser Ile Ser Gln Asp Asn Ser Gln
1               5                   10                  15

Met Asn Lys Thr Leu Cys Ser Leu Lys Phe Asn
            20                  25

<210> SEQ ID NO 238
```

```
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 238

Asp Ile Asp His Val Ile Pro Leu Ala Arg Gly Gly Arg Asp Ser Leu
1               5                   10                  15

Asp Asn Met Val Leu Cys Gln Ser Asp Ala Asn
            20                  25

<210> SEQ ID NO 239
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 239

Asp Ile Glu His Leu Phe Pro Ile Ala Glu Ser Glu Asp Asn Gly Arg
1               5                   10                  15

Asn Asn Leu Val Ile Ser His Ser Ala Cys Asn
            20                  25

<210> SEQ ID NO 240
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 240

Asp Val Asp His Ile Phe Pro Arg Asp Asp Thr Ala Asp Asn Ser Tyr
1               5                   10                  15

Gly Asn Lys Val Val Ala His Arg Gln Cys Asn
            20                  25

<210> SEQ ID NO 241
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 241

Asp Ile Glu His Ile Val Pro Gln Ser Leu Gly Gly Leu Ser Thr Asp
1               5                   10                  15

Tyr Asn Thr Ile Val Thr Leu Lys Ser Val Asn
            20                  25

<210> SEQ ID NO 242
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 242

Glu Leu Asp His Ile Val Pro Arg Thr Asp Gly Gly Ser Asn Arg His
1               5                   10                  15
```

```
Glu Asn Leu Ala Ile Thr Cys Gly Ala Cys Asn
            20                  25

<210> SEQ ID NO 243
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 243

Glu Met Asp His Ile Val Pro Arg Lys Gly Val Gly Ser Thr Asn Thr
1               5                   10                  15

Arg Thr Asn Phe Ala Ala Val Cys Ala Glu Cys Asn
            20                  25

<210> SEQ ID NO 244
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 244

Glu Met Asp His Ile Val Pro Arg Lys Gly Val Gly Ser Thr Asn Thr
1               5                   10                  15

Arg Val Asn Leu Ala Ala Ala Cys Ala Ala Cys Asn
            20                  25

<210> SEQ ID NO 245
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 245

Glu Met Asp His Ile Val Pro Arg Ala Gly Gln Gly Ser Thr Asn Thr
1               5                   10                  15

Arg Glu Asn Leu Val Ala Val Cys His Arg Cys Asn
            20                  25

<210> SEQ ID NO 246
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 246

Glu Ile Asp His Ile Leu Pro Arg Ser Leu Ile Lys Asp Ala Arg Gly
1               5                   10                  15

Ile Val Phe Asn Ala Glu Pro Asn Leu Ile Tyr Ala Ser Ser Arg Gly
            20                  25                  30

Asn

<210> SEQ ID NO 247
<211> LENGTH: 33
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 247

Glu Ile Asp His Ile Ile Pro Arg Ser Leu Thr Gly Arg Thr Lys Lys
1               5                   10                  15

Thr Val Phe Asn Ser Glu Ala Asn Leu Ile Tyr Cys Ser Ser Lys Gly
            20                  25                  30

Asn

<210> SEQ ID NO 248
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 248

Glu Ile Asp His Ile Ile Pro Arg Ser Leu Thr Leu Lys Lys Ser Glu
1               5                   10                  15

Ser Ile Tyr Asn Ser Glu Val Asn Leu Ile Phe Val Ser Ala Gln Gly
            20                  25                  30

Asn

<210> SEQ ID NO 249
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 249

Glu Ile Asp His Ile Tyr Pro Arg Ser Leu Ser Lys Lys His Phe Gly
1               5                   10                  15

Val Ile Phe Asn Ser Glu Val Asn Leu Ile Tyr Cys Ser Ser Gln Gly
            20                  25                  30

Asn

<210> SEQ ID NO 250
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 250

Glu Ile Asp His Ile Leu Pro Arg Ser His Thr Leu Lys Ile Tyr Gly
1               5                   10                  15

Thr Val Phe Asn Pro Glu Gly Asn Leu Ile Tyr Val His Gln Lys Cys
            20                  25                  30

Asn

<210> SEQ ID NO 251
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 251

Glu Leu Asp His Ile Ile Pro Arg Ser His Lys Lys Tyr Gly Thr Leu
1               5                   10                  15

Asn Asp Glu Ala Asn Leu Ile Cys Val Thr Arg Gly Asp Asn
            20                  25                  30

<210> SEQ ID NO 252
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 252

Glu Leu Glu His Ile Val Pro His Ser Phe Arg Gln Ser Asn Ala Leu
1               5                   10                  15

Ser Ser Leu Val Leu Thr Trp Pro Gly Val Asn
            20                  25

<210> SEQ ID NO 253
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 253

Tyr Asp Ile Asp His Ile Tyr Pro Arg Ser Leu Thr Lys Asp Asp Ser
1               5                   10                  15

Phe Asp Asn Leu Val Leu Cys Glu Arg Thr Ala Asn
            20                  25

<210> SEQ ID NO 254
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 254

Asp Ile Asp His Ile Tyr Pro Arg Ser Lys Val Ile Lys Asp Asp Ser
1               5                   10                  15

Phe Asp Asn Leu Val Leu Val Leu Lys Asn Glu Asn
            20                  25

<210> SEQ ID NO 255
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 255

Asp Arg Asp His Ile Tyr Pro Gln Ser Lys Ile Lys Asp Asp Ser Ile
1               5                   10                  15

Asp Asn Leu Val Leu Val Asn Lys Thr Tyr Asn
            20                  25

<210> SEQ ID NO 256
```

```
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 256

Asp Ile Asp His Ile Tyr Pro Arg Ser Lys Ile Lys Asp Asp Ser Ile
1               5                   10                  15

Thr Asn Arg Val Leu Val Glu Lys Asp Ile Asn
            20                  25

<210> SEQ ID NO 257
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 257

Asp Ile Asp His Ile Tyr Pro Gln Ser Lys Ile Lys Asp Asp Ser Ile
1               5                   10                  15

Ser Asn Arg Val Leu Val Cys Ser Ser Cys Asn
            20                  25

<210> SEQ ID NO 258
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 258

Asp Ile Asp His Ile Tyr Pro Gln Ser Lys Thr Met Asp Asp Ser Leu
1               5                   10                  15

Asn Asn Arg Val Leu Val Lys Lys Asn Tyr Asn
            20                  25

<210> SEQ ID NO 259
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 259

Asp Gln Asp His Ile Tyr Pro Lys Ser Lys Ile Tyr Asp Asp Ser Leu
1               5                   10                  15

Glu Asn Arg Val Leu Val Lys Lys Asn Leu Asn
            20                  25

<210> SEQ ID NO 260
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 260

Gln Ile Asp His Ile Val Pro Gln Ser Leu Val Lys Asp Asp Ser Phe
1               5                   10                  15
```

Asp Asn Arg Val Leu Val Val Pro Ser Glu Asn
            20                  25

<210> SEQ ID NO 261
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 261

Asp Ile Asp His Ile Ile Pro Gln Ala Phe Ile Lys Asp Asn Ser Ile
1               5                   10                  15

Asp Asn Arg Val Leu Thr Ser Ser Lys Glu Asn
            20                  25

<210> SEQ ID NO 262
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 262

Asp Ile Asp His Ile Ile Pro Gln Ala Phe Leu Lys Asp Asn Ser Ile
1               5                   10                  15

Asp Asn Lys Val Leu Val Ser Ser Ala Ser Asn
            20                  25

<210> SEQ ID NO 263
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 263

Asp Ile Asp His Ile Ile Pro Gln Ala Tyr Thr Lys Asp Asn Ser Leu
1               5                   10                  15

Asp Asn Arg Val Leu Val Ser Asn Ile Thr Asn
            20                  25

<210> SEQ ID NO 264
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 264

Asp Ile Asp His Ile Val Pro Gln Ser Phe Ile Thr Asp Asn Ser Ile
1               5                   10                  15

Asp Asn Leu Val Leu Thr Ser Ser Ala Gly Asn
            20                  25

<210> SEQ ID NO 265
<211> LENGTH: 27
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 265

Asp Val Asp His Ile Val Pro Gln Ser Phe Leu Lys Asp Asp Ser Ile
1               5                   10                  15

Asp Asn Lys Val Leu Thr Arg Ser Asp Lys Asn
            20                  25

<210> SEQ ID NO 266
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 266

Asn Ile Asp His Ile Tyr Pro Gln Ser Met Val Lys Asp Asp Ser Leu
1               5                   10                  15

Asp Asn Lys Val Leu Val Gln Ser Glu Ile Asn
            20                  25

<210> SEQ ID NO 267
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 267

Asp Ile Asp His Ile Leu Pro Gln Ser Leu Ile Lys Asp Asp Ser Leu
1               5                   10                  15

Asp Asn Arg Val Leu Val Asn Ala Thr Ile Asn
            20                  25

<210> SEQ ID NO 268
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 268

Asp Ile Asp His Ile Leu Pro Gln Ser Phe Ile Lys Asp Asp Ser Leu
1               5                   10                  15

Glu Asn Arg Val Leu Val Lys Lys Ala Val Asn
            20                  25

<210> SEQ ID NO 269
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 269

Glu Val Asp His Ile Phe Pro Arg Ser Phe Ile Lys Asp Asp Ser Ile
1               5                   10                  15

Asp Asn Lys Val Leu Val Ile Lys Lys Met Asn
            20                  25
```

<210> SEQ ID NO 270
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 270

Glu Val Asp His Ile Ile Pro Arg Ser Tyr Ile Lys Asp Asp Ser Phe
1               5                   10                  15

Glu Asn Lys Val Leu Val Tyr Arg Glu Glu Asn
            20                  25

<210> SEQ ID NO 271
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 271

Asp Ile Asp His Ile Ile Pro Gln Ala Val Thr Gln Asn Asp Ser Ile
1               5                   10                  15

Asp Asn Arg Val Leu Val Ala Arg Ala Glu Asn
            20                  25

<210> SEQ ID NO 272
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 272

Asp Ile Asp His Ile Val Pro Arg Ser Ile Ser Phe Asp Asp Ser Phe
1               5                   10                  15

Ser Asn Leu Val Ile Val Asn Lys Leu Asp Asn
            20                  25

<210> SEQ ID NO 273
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 273

Glu Ile Asp His Ile Ile Pro Tyr Ser Ile Ser Phe Asp Asp Ser Ser
1               5                   10                  15

Ser Asn Lys Leu Leu Val Leu Ala Glu Ser Asn
            20                  25

<210> SEQ ID NO 274
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 274

Glu Ile Asp His Ile Ile Pro Tyr Ser Leu Cys Phe Asp Asp Ser Ser
1               5                   10                  15

Ala Asn Lys Val Leu Val His Lys Gln Ser Asn
            20                  25

<210> SEQ ID NO 275
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 275

Glu Ile Asp His Ile Ile Pro Ile Ser Ile Ser Leu Asp Asp Ser Ile
1               5                   10                  15

Asn Asn Lys Val Leu Val Leu Ser Lys Ala Asn
            20                  25

<210> SEQ ID NO 276
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 276

Glu Val Asp His Ile Ile Pro Ile Ser Ile Ser Leu Asp Asp Ser Ile
1               5                   10                  15

Thr Asn Lys Val Leu Val Thr His Arg Glu Asn
            20                  25

<210> SEQ ID NO 277
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 277

Glu Val Asp His Ile Leu Pro Leu Ser Ile Thr Phe Asp Asp Ser Leu
1               5                   10                  15

Ala Asn Lys Val Leu Val Tyr Ala Thr Ala Asn
            20                  25

<210> SEQ ID NO 278
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 278

Glu Ile Asp His Ile Ile Pro Arg Ser Ile Ser Phe Asp Asp Ala Arg
1               5                   10                  15

Ser Asn Lys Val Leu Val Tyr Arg Ser Glu Asn
            20                  25

<210> SEQ ID NO 279

```
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 279

Glu Val Asp His Ile Ile Pro Arg Ser Val Ser Phe Asp Asn Ser Tyr
1               5                   10                  15

His Asn Lys Val Leu Val Lys Gln Ser Glu Asn
            20                  25

<210> SEQ ID NO 280
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 280

Glu Val Asp His Ile Ile Pro Tyr Ser Ile Ser Trp Asp Asp Ser Tyr
1               5                   10                  15

Thr Asn Lys Val Leu Thr Ser Ala Lys Cys Asn
            20                  25

<210> SEQ ID NO 281
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 281

Asp Ile Asp His Ile Ile Pro Tyr Ser Arg Ser Met Asp Asp Ser Tyr
1               5                   10                  15

Ser Asn Lys Val Leu Val Leu Ser Gly Glu Asn
            20                  25

<210> SEQ ID NO 282
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 282

Glu Ile Glu His Ile Ile Pro Tyr Ser Met Ser Tyr Asp Asn Ser Gln
1               5                   10                  15

Ala Asn Lys Ile Leu Thr Glu Lys Ala Glu Asn
            20                  25

<210> SEQ ID NO 283
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 283

Glu Val Asp His Ile Val Pro Tyr Ser Leu Ile Leu Asp Asn Thr Ile
1               5                   10                  15
```

```
Asn Asn Lys Ala Leu Val Tyr Ala Glu Glu Asn
            20                  25

<210> SEQ ID NO 284
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 284

Glu Ile Asp His Val Ile Pro Tyr Ser Lys Ser Ala Asp Asp Ser Trp
1               5                   10                  15

Phe Asn Lys Leu Leu Val Lys Lys Ser Thr Asn
            20                  25

<210> SEQ ID NO 285
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 285

Glu Met Asp His Ile Leu Pro Tyr Ser Arg Ser Leu Asp Asn Gly Trp
1               5                   10                  15

His Asn Arg Val Leu Val His Gly Lys Asp Asn
            20                  25

<210> SEQ ID NO 286
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 286

Glu Ile Glu His Val Ile Pro Gln Ser Leu Tyr Phe Asp Asp Ser Phe
1               5                   10                  15

Ser Asn Lys Val Ile Cys Glu Ala Glu Val Asn
            20                  25

<210> SEQ ID NO 287
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 287

Asp Ile Glu His Ile Ile Pro Gln Ala Arg Leu Phe Asp Asp Ser Phe
1               5                   10                  15

Ser Asn Lys Thr Leu Glu Ala Arg Ser Val Asn
            20                  25

<210> SEQ ID NO 288
<211> LENGTH: 27
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 288

Glu Ile Glu His Ile Val Pro Lys Ala Arg Val Phe Asp Asp Ser Phe
1               5                   10                  15

Ser Asn Lys Thr Leu Thr Phe His Arg Ile Asn
            20                  25

<210> SEQ ID NO 289
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 289

Asp Lys Asp His Ile Ile Pro Gln Ser Met Lys Lys Asp Asp Ser Ile
1               5                   10                  15

Ile Asn Asn Leu Val Leu Val Asn Lys Asn Ala Asn
            20                  25

<210> SEQ ID NO 290
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 290

Gln Val Asp His Ile Leu Pro Trp Ser Arg Phe Gly Asp Asp Ser Tyr
1               5                   10                  15

Leu Asn Lys Thr Leu Cys Thr Ala Arg Ser Asn
            20                  25

<210> SEQ ID NO 291
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 291

Asp Ile Asp His Val Ile Pro Leu Ala Arg Gly Gly Arg Asp Ser Leu
1               5                   10                  15

Asp Asn Met Val Leu Cys Gln Ser Asp Ala Asn
            20                  25

<210> SEQ ID NO 292
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 292

Asp Met Glu His Thr Ile Pro Lys Ser Ile Ser Phe Asp Asn Ser Asp
1               5                   10                  15

Gln Asn Leu Thr Leu Cys Glu Ser Tyr Tyr Asn
            20                  25
```

<210> SEQ ID NO 293
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 293

Asp Ile Glu His Thr Ile Pro Arg Ser Ala Gly Gly Asp Ser Thr Lys
1               5                   10                  15

Met Asn Leu Thr Leu Cys Ser Ser Arg Phe Asn
            20                  25

<210> SEQ ID NO 294
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 294

Asp Ile Glu His Thr Ile Pro Arg Ser Ile Ser Gln Asp Asn Ser Gln
1               5                   10                  15

Met Asn Lys Thr Leu Cys Ser Leu Lys Phe Asn
            20                  25

<210> SEQ ID NO 295
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 295

Asp Ile Glu His Leu Phe Pro Ile Ala Glu Ser Glu Asp Asn Gly Arg
1               5                   10                  15

Asn Asn Leu Val Ile Ser His Ser Ala Cys Asn
            20                  25

<210> SEQ ID NO 296
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 296

Asp Val Asp His Ile Phe Pro Arg Asp Asp Thr Ala Asp Asn Ser Tyr
1               5                   10                  15

Gly Asn Lys Val Val Ala His Arg Gln Cys Asn
            20                  25

<210> SEQ ID NO 297
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 297

Asp Ile Glu His Ile Val Pro Gln Ser Leu Gly Gly Leu Ser Thr Asp
1               5                   10                  15

Tyr Asn Thr Ile Val Thr Leu Lys Ser Val Asn
            20                  25

<210> SEQ ID NO 298
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 298

Glu Leu Asp His Ile Val Pro Arg Thr Asp Gly Gly Ser Asn Arg His
1               5                   10                  15

Glu Asn Leu Ala Ile Thr Cys Gly Ala Cys Asn
            20                  25

<210> SEQ ID NO 299
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 299

Glu Met Asp His Ile Val Pro Arg Lys Gly Val Gly Ser Thr Asn Thr
1               5                   10                  15

Arg Thr Asn Phe Ala Ala Val Cys Ala Glu Cys Asn
            20                  25

<210> SEQ ID NO 300
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 300

Glu Met Asp His Ile Val Pro Arg Lys Gly Val Gly Ser Thr Asn Thr
1               5                   10                  15

Arg Val Asn Leu Ala Ala Ala Cys Ala Ala Cys Asn
            20                  25

<210> SEQ ID NO 301
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 301

Glu Met Asp His Ile Val Pro Arg Ala Gly Gln Gly Ser Thr Asn Thr
1               5                   10                  15

Arg Glu Asn Leu Val Ala Val Cys His Arg Cys Asn
            20                  25

<210> SEQ ID NO 302

```
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 302

Glu Leu Glu His Ile Val Pro His Ser Phe Arg Gln Ser Asn Ala Leu
1               5                   10                  15

Ser Ser Leu Val Leu Thr Trp Pro Gly Val Asn
            20                  25

<210> SEQ ID NO 303
<211> LENGTH: 3333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 303
atggtgccta agaagaagag aaaggtggct gccttcaaac ctaattcaat caactacatc      60
ctcggcctcg atatcggcat cgcatccgtc ggctgggcga tggtagaaat tgacgaagaa     120
gaaaacccca tccgcctgat tgatttgggc gtgcgcgtat ttgagcgtgc cgaagtaccg     180
aaaacaggcg actcccttgc catggcaagg cgtttggcgc gcagtgttcg ccgcctgacc     240
cgccgtcgcg cccaccgcct gcttcggacc cgccgcctat tgaaacgcga aggcgtatta     300
caagccgcca attttgacga aaacggcttg attaaatcct taccgaatac accatggcaa     360
cttcgcgcag ccgcattaga ccgcaaactg acgcctttag agtggtcggc agtcttgttg     420
catttaatca acatcgcgg ctattatcg caacggaaaa acgagggcga aactgccgat     480
aaggagcttg gcgctttgct taaggcgta gccggcaatg cccatgcctt acagacaggc     540
gatttccgca caccggccga attggcttta aataaatttg agaaagaaag cggccatatc     600
cgcaatcagc gcagcgatta ttcgcatacg ttcagccgca agatttaca ggcggagctg     660 atttttgctgt ttgaaaaaca aaaagaattt ggcaatccgc atgtttcagg cggccttaaa     720
gaaggtattg aaaccctact gatgacgcaa cgccctgccc tgtccggcga tgccgttcaa     780
aaaatgttgg gcattgcac cttcgaaccg gcagagccga aagccgctaa aaacacctac     840
acagccgaac gtttcatctg gctgaccaag ctgaacaacc tgcgtatttt agagcaaggc     900
agcgagcggc cattgaccga taccgaacgc gccacgctta tggacgagcc atacagaaaa     960
tccaaactga cttacgcaca agcccgtaag ctgctgggtt tagaagatac cgccttttc    1020 aaaggcttgc gctatggtaa agacaatgcc gaagcctcaa cattgatgga atgaaggcc    1080 taccatgcca tcagccgtgc actggaaaaa gaaggattga agacaaaaa atccccatta    1140 aacctttctc ccgaattaca agacgaaatc ggcacggcat tctccctgtt caaaaccgat    1200
gaagacatta caggccgtct gaaagaccgt atacagcccg aaatcttaga agcgctgttg    1260
aaacacatca gcttcgataa gttcgtccaa atttccttga agcattgcg ccgaattgtg    1320 cctctaatgg aacaaggcaa acgttacgat gaagcctgcg ccgaaatcta cggagaccat    1380
tacggcaaga gaatacgga agaaaagatt tatctgccgc cgattccgc cgacgaaatc    1440 cgcaaccccg tcgtcttgcg cgccttatct caagcacgta aggtcattaa cggcgtggta    1500
cgccgttacg gctccccagc tcgtatccat attgaaactg caagggaagt aggtaaatcg    1560
tttaaagacc gcaaagaaat tgagaaacgc caagaagaaa accgcaaaga ccgggaaaaa    1620
```

-continued

```
gccgccgcca aattccgaga gtatttcccc aattttgtcg gagaacccaa atccaaagat    1680
attctgaaac tgcgcctgta cgagcaacaa cacggcaaat gcctgtattc gggcaaagaa    1740
atcaacttag gccgtctgaa cgaaaaaggc tatgtcgaaa tcgaccatgc cctgccgttc    1800
tcgcgcacat gggacgacag tttcaacaat aaagtactgg tattgggcag cgaaaaccaa    1860
aacaaaggca atcaaacccc ttacgaatac ttcaacggca agacaacag ccgcgaatgg     1920 caggaattta agcgcgtgt cgaaccagc cgtttcccgc gcagtaaaaa acaacggatt      1980
ctgctgcaaa aattcgatga agacggcttt aaagaacgca atctgaacga cacgcgctac   2040
gtcaaccgtt tcctgtgtca atttgttgcc gaccgtatgc ggctgacagg taaaggcaag   2100
aaacgtgtct ttgcatccaa cggacaaatt accaatctgt tgcgcggctt tggggattg    2160 cgcaaagtgc gtgcggaaaa cgaccgccat cacgccttgg acgccgtcgt cgttgcctgc   2220
tcgaccgttg ccatgcagca gaaaattacc cgttttgtac gctataaaga gatgaacgcg   2280
tttgacggta aaaccataga caagaaaaca ggagaagtgc tgcatcaaaa aacacacttc   2340
ccacaacctt gggaattttt cgcacaagaa gtcatgattc gcgtcttcgg caaaccggac   2400
ggcaaacccg aattcgaaga agccgatacc ctagaaaaac tgcgcacgtt gcttgccgaa   2460
aaattatcat ctcgccccga agccgtacac gaatacgtta cgccactgtt tgtttcacgc   2520
gcgcccaatc ggaagatgag cgggcaaggg catatggaga ccgtcaaatc cgccaaacga   2580
ctggacgaag gcgtcagcgt gttgcgcgta ccgctgacac agttaaaact gaaagacttg   2640
gaaaaaatgg tcaatcggga gcgcgaacct aagctatacg aagcactgaa agcacggctg   2700
gaagcacata aagacgatcc tgccaaagcc tttgccgagc cgttttacaa atacgataaa   2760
gcaggcaacc gcacccaaca ggtaaaagcc gtacgcgtag agcaagtaca gaaaaccggc   2820
gtatgggtgc gcaaccataa cggtattgcc gacaacgcaa ccatggtgcg cgtagatgtg   2880
tttgagaaag gcgacaagta ttatctggta ccgatttaca gttggcaggt agcgaaaggg   2940
attttgccgg atagggctgt tgtacaagga aaagatgaag aagattggca acttattgat   3000
gatagtttca actttaaatt ctcattacac cctaatgatt tagtcgaggt tataacaaaa   3060
aaagctagaa tgtttggtta ctttgccagc tgccatcgag gcacaggtaa tatcaatata   3120
cgcattcatg atcttgatca taaaattggc aaaaatggaa tactggaagg tatcggcgtc   3180
aaaaccgccc tttcattcca aaaataccaa attgacgaac tgggcaaaga aatcagacca   3240
tgccgtctga aaaaacgccc gcctgtccgt tacccatacg atgttccaga ttacgctgca   3300
gctccagcag cgaagaaaaa gaagctggat taa                                3333
```

<210> SEQ ID NO 304
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 304
gcccuccuau ucgauag                                                    17

<210> SEQ ID NO 305
<211> LENGTH: 17
<212> TYPE: RNA
<213> ORGANISM: Artificial Sequence

```
<220> FEATURE:
<223> OTHER INFORMATION: Description of Artificial Sequence: Synthetic
      oligonucleotide

<400> SEQUENCE: 305
gccugaaacg aaccgcu                                                      17

<210> SEQ ID NO 306
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 306
gccacuaucg aauagga                                                      17

<210> SEQ ID NO 307
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 307
gcacuaauuc cguugga                                                      17

<210> SEQ ID NO 308
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 308
gaacggcacc ccaucuu                                                      17

<210> SEQ ID NO 309
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 309
ggugcccucc uauucgauag                                                   20

<210> SEQ ID NO 310
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 310
gcccauauga uaaaguuccg                                                   20

<210> SEQ ID NO 311
<211> LENGTH: 20
<212> TYPE: RNA
<213> ORGANISM: Artificial Sequence
<220> FEATURE:
```

<223> OTHER INFORMATION: Description of Artificial Sequence: Synthetic
      oligonucleotide

<400> SEQUENCE: 311
gcccacggaa cuuuaucaua                                              20

<210> SEQ ID NO 312
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 312
uccgagcggu ucguuuc                                                 17

<210> SEQ ID NO 313
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 313
aacgaaccgc ucggaga                                                 17

<210> SEQ ID NO 314
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 314
cgccacuauc gaauagg                                                 17

<210> SEQ ID NO 315
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 315
aucggcacua auuccgu                                                 17

<210> SEQ ID NO 316
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 316
uuucgccacu aucgaau                                                 17

<210> SEQ ID NO 317
<211> LENGTH: 17
<212> TYPE: RNA
<213> ORGANISM: Artificial Sequence

```
<220> FEATURE:
<223> OTHER INFORMATION: Description of Artificial Sequence: Synthetic
      oligonucleotide

<400> SEQUENCE: 317
auucgauagu ggcgaaa                                                        17

<210> SEQ ID NO 318
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 318
uaguggcgaa acggcag                                                        17

<210> SEQ ID NO 319
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 319
ccguuucgcc acuaucgaau                                                     20

<210> SEQ ID NO 320
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 320
gacaucggca cuaauuccgu                                                     20

<210> SEQ ID NO 321
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 321
cucgccugaa acgaaccgcu                                                     20

<210> SEQ ID NO 322
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 322
uucuccgagc gguucguuuc                                                     20

<210> SEQ ID NO 323
<211> LENGTH: 20
<212> TYPE: RNA
<213> ORGANISM: Artificial Sequence
<220> FEATURE:
```

<223> OTHER INFORMATION: Description of Artificial Sequence: Synthetic
       oligonucleotide

<400> SEQUENCE: 323
ugaaacgaac cgcucggaga                                          20

<210> SEQ ID NO 324
<211> LENGTH: 20
<212> TYPE: RNA
<213> ORGANISM: Artificial Sequence
<220> FEATURE:
<223> OTHER INFORMATION: Description of Artificial Sequence: Synthetic
       oligonucleotide

<400> SEQUENCE: 324
uuucgccacu aucgaauagg                                          20

<210> SEQ ID NO 325
<211> LENGTH: 20
<212> TYPE: RNA
<213> ORGANISM: Artificial Sequence
<220> FEATURE:
<223> OTHER INFORMATION: Description of Artificial Sequence: Synthetic
       oligonucleotide

<400> SEQUENCE: 325
ucggcacuaa uuccguugga                                          20

<210> SEQ ID NO 326
<211> LENGTH: 20
<212> TYPE: RNA
<213> ORGANISM: Artificial Sequence
<220> FEATURE:
<223> OTHER INFORMATION: Description of Artificial Sequence: Synthetic
       oligonucleotide

<400> SEQUENCE: 326
cgauaguggc gaaacggcag                                          20

<210> SEQ ID NO 327
<211> LENGTH: 20
<212> TYPE: RNA
<213> ORGANISM: Artificial Sequence
<220> FEATURE:
<223> OTHER INFORMATION: Description of Artificial Sequence: Synthetic
       oligonucleotide

<400> SEQUENCE: 327
uucgccacua ucgaauagga                                          20

<210> SEQ ID NO 328
<211> LENGTH: 20
<212> TYPE: RNA
<213> ORGANISM: Artificial Sequence
<220> FEATURE:
<223> OTHER INFORMATION: Description of Artificial Sequence: Synthetic
       oligonucleotide

<400> SEQUENCE: 328 acuguauac cuucuccgag                                           20

<210> SEQ ID NO 329
<211> LENGTH: 20
<212> TYPE: RNA
<213> ORGANISM: Artificial Sequence

```
<220> FEATURE:
<223> OTHER INFORMATION: Description of Artificial Sequence: Synthetic
      oligonucleotide

<400> SEQUENCE: 329
cggcacuaau uccguuggau                                              20

<210> SEQ ID NO 330
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 330
ccuauucgau aguggcgaaa                                              20

<210> SEQ ID NO 331
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 331
cccauaugau aaaguuccgu                                              20

<210> SEQ ID NO 332
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 332
gaaagaaucg ucaacuu                                                 17

<210> SEQ ID NO 333
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 333
gagccaagua gauuaaccuc                                              20

<210> SEQ ID NO 334
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 334
gauaaaaagu auucuau                                                 17

<210> SEQ ID NO 335
<211> LENGTH: 20
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 335
gauucuuuuu aaucgaauga                                              20

<210> SEQ ID NO 336
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 336
ggaaggacuc uuccaaa                                                 17

<210> SEQ ID NO 337
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 337
ggaccugagg uuaaucuacu                                              20

<210> SEQ ID NO 338
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 338
gggcacuuuc ucauuga                                                 17

<210> SEQ ID NO 339
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 339
gguuaugaca gcccauccaa                                              20

<210> SEQ ID NO 340
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 340
guccucuucg acaagga                                                 17

<210> SEQ ID NO 341
<211> LENGTH: 17
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 341
guccuuccuu gucgaag                                                    17

<210> SEQ ID NO 342
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 342
guuucuuguc cucuucgaca                                                 20

<210> SEQ ID NO 343
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 343
aaacauagua gaugagg                                                    17

<210> SEQ ID NO 344
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 344
aaagaaagaa ucgucaacuu                                                 20

<210> SEQ ID NO 345
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 345
aaagaaauuu aaggugu                                                    17

<210> SEQ ID NO 346
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 346
aacaccuuaa auuucuuuga                                                 20

<210> SEQ ID NO 347
<211> LENGTH: 17
<212> TYPE: RNA
<213> ORGANISM: Artificial Sequence
<220> FEATURE:
```

<223> OTHER INFORMATION: Description of Artificial Sequence: Synthetic
      oligonucleotide

<400> SEQUENCE: 347
aagaaauuua agguguu                                                     17

<210> SEQ ID NO 348
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 348
aagaggacaa gaaacaugaa                                                  20

<210> SEQ ID NO 349
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 349
aauuuuuagc aaugaga                                                     17

<210> SEQ ID NO 350
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 350
accuuaaauu ucuuuga                                                     17

<210> SEQ ID NO 351
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 351
accuucaaag aaauuua                                                     17

<210> SEQ ID NO 352
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 352
acggaacuuu aucauau                                                     17

<210> SEQ ID NO 353
<211> LENGTH: 17
<212> TYPE: RNA
<213> ORGANISM: Artificial Sequence

```
<220> FEATURE:
<223> OTHER INFORMATION: Description of Artificial Sequence: Synthetic
      oligonucleotide

<400> SEQUENCE: 353
acuauguuuc caaagau                                                    17

<210> SEQ ID NO 354
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 354
agaaauuuaa gguguug                                                    17

<210> SEQ ID NO 355
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 355
agaaauuuuu agcaaugaga                                                 20

<210> SEQ ID NO 356
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 356
agaguccuuc cuugucgaag                                                 20

<210> SEQ ID NO 357
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 357
aggacaagaa acaugaa                                                    17

<210> SEQ ID NO 358
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 358
agguacuuug uauucau                                                    17

<210> SEQ ID NO 359
<211> LENGTH: 20
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 359
aguaccuuca aagaaauuua                                                     20

<210> SEQ ID NO 360
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 360
agucaacuag cuuuuuucug                                                     20

<210> SEQ ID NO 361
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 361
aguugacuca acugauaaag                                                     20

<210> SEQ ID NO 362
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 362
auaugauaaa guuccgu                                                        17

<210> SEQ ID NO 363
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 363
aucuacuaug uuuccaaaga                                                     20

<210> SEQ ID NO 364
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 364
auggauaaaa aguauucuau                                                     20

<210> SEQ ID NO 365
<211> LENGTH: 17
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 365
auuaaaaaga aucuuau                                                  17

<210> SEQ ID NO 366
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 366
caaagaaauu uaagguguug                                               20

<210> SEQ ID NO 367
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 367
caacuagcuu uuucug                                                   17

<210> SEQ ID NO 368
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 368
caacugauaa agcggaccug                                               20

<210> SEQ ID NO 369
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 369
caaggaagga cucuuccaaa                                               20

<210> SEQ ID NO 370
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 370
caaugagaaa gugccca                                                  17

<210> SEQ ID NO 371
<211> LENGTH: 17
<212> TYPE: RNA
<213> ORGANISM: Artificial Sequence
<220> FEATURE:
```

-continued

```
<223> OTHER INFORMATION: Description of Artificial Sequence: Synthetic
      oligonucleotide

<400> SEQUENCE: 371
cacggaacuu uaucaua                                                        17

<210> SEQ ID NO 372
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 372
cacuaauucc guuggau                                                        17

<210> SEQ ID NO 373
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 373
cauaugauaa aguuccg                                                        17

<210> SEQ ID NO 374
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 374
caugaacggc accccaucuu                                                     20

<210> SEQ ID NO 375
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 375
ccaaguagau uaaccuc                                                        17

<210> SEQ ID NO 376
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 376
cccacggaac uuuaucauau                                                     20

<210> SEQ ID NO 377
<211> LENGTH: 20
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 377
ccgugggcac uuucucauug                                                   20

<210> SEQ ID NO 378
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 378
ccucaaugag aaagugccca                                                   20

<210> SEQ ID NO 379
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 379
ccugagguua aucuacu                                                      17

<210> SEQ ID NO 380
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 380
cgauucuuuc uuucaccguu                                                   20

<210> SEQ ID NO 381
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 381
cgugggcacu uucucauuga                                                   20

<210> SEQ ID NO 382
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 382
cuacuauguu uccaaagaug                                                   20

<210> SEQ ID NO 383
<211> LENGTH: 17
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 383
cuauguuucc aaagaug                                                    17

<210> SEQ ID NO 384
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 384
cugaggugau aaaucgu                                                    17

<210> SEQ ID NO 385
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 385
cugauaaagc ggaccug                                                    17

<210> SEQ ID NO 386
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 386
cuuguaagua acauauu                                                    17

<210> SEQ ID NO 387
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 387
cuuguccucu ucgacaagga                                                 20

<210> SEQ ID NO 388
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 388
cuuuggaaac auaguagaug                                                 20

<210> SEQ ID NO 389
<211> LENGTH: 17
<212> TYPE: RNA
<213> ORGANISM: Artificial Sequence
<220> FEATURE:
```

-continued

```
<223> OTHER INFORMATION: Description of Artificial Sequence: Synthetic
      oligonucleotide

<400> SEQUENCE: 389
uacuauguuu ccaaaga                                                        17

<210> SEQ ID NO 390
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 390
uaugacagcc cauccaa                                                        17

<210> SEQ ID NO 391
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 391
uauucuauug guuuagacau                                                     20

<210> SEQ ID NO 392
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 392
ucaaagaaau uuaagguguu                                                     20

<210> SEQ ID NO 393
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 393
ucgauuaaaa agaaucuuau                                                     20

<210> SEQ ID NO 394
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 394
ucuacuaugu uuccaaagau                                                     20

<210> SEQ ID NO 395
<211> LENGTH: 17
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 395
ucuauugguu uagacau                                                    17

<210> SEQ ID NO 396
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 396
ucuuguccuc uucgaca                                                    17

<210> SEQ ID NO 397
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 397
ucuuuuuaau cgaauga                                                    17

<210> SEQ ID NO 398
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 398
ugaagguacu uuguauucau                                                 20

<210> SEQ ID NO 399
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 399
ugacucaacu gauaaag                                                    17

<210> SEQ ID NO 400
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 400
ugaggugaua aaucguu                                                    17

<210> SEQ ID NO 401
<211> LENGTH: 17
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 401
uggaaacaua guagaug                                                     17

<210> SEQ ID NO 402
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 402
uggaaacaua guagaugagg                                                  20

<210> SEQ ID NO 403
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 403
ugggcacuuu cucauug                                                     17

<210> SEQ ID NO 404
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 404
uguauaccuu cuccgag                                                     17

<210> SEQ ID NO 405
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 405
uucaaagaaa uuuaaggugu                                                  20

<210> SEQ ID NO 406
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 406
uucugaggug auaaaucguu                                                  20

<210> SEQ ID NO 407
<211> LENGTH: 17
<212> TYPE: RNA
<213> ORGANISM: Artificial Sequence
<220> FEATURE:
```

<223> OTHER INFORMATION: Description of Artificial Sequence: Synthetic
oligonucleotide

<400> SEQUENCE: 407
uucuuucuuu caccguu                                                  17

<210> SEQ ID NO 408
<211> LENGTH: 20
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 408
uuucugaggu gauaaaucgu                                               20

<210> SEQ ID NO 409
<211> LENGTH: 20
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 409
uuucuuguaa guaacauauu                                               20

<210> SEQ ID NO 410
<211> LENGTH: 17
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 410
gcgucgcuau acgggcu                                                  17

<210> SEQ ID NO 411
<211> LENGTH: 17
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 411
ggcgucgcua uacgggc                                                  17

<210> SEQ ID NO 412
<211> LENGTH: 17
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 412
ucgaaaaacg gguacgc                                                  17

<210> SEQ ID NO 413
<211> LENGTH: 17
<212> TYPE: RNA
<213> ORGANISM: Artificial Sequence

```
<220> FEATURE:
<223> OTHER INFORMATION: Description of Artificial Sequence: Synthetic
      oligonucleotide

<400> SEQUENCE: 413
cgcucggaua agaaccg                                                        17

<210> SEQ ID NO 414
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 414
cgucgcuaua cgggcug                                                        17

<210> SEQ ID NO 415
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 415
gauaagcguc gugcgca                                                        17

<210> SEQ ID NO 416
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 416
cggguaauug ugcgauc                                                        17

<210> SEQ ID NO 417
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 417
gaucgcgaaa agcgaac                                                        17

<210> SEQ ID NO 418
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 418
gcgacggcuu cgccaau                                                        17

<210> SEQ ID NO 419
<211> LENGTH: 17
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 419
uaaccuuauc gucgaac                                                    17

<210> SEQ ID NO 420
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 420
agcggauaac ggcgccu                                                    17

<210> SEQ ID NO 421
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 421
aagaggcguc gcuauac                                                    17

<210> SEQ ID NO 422
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 422
aagcgucgug cgcaugg                                                    17

<210> SEQ ID NO 423
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 423
cggauguugg cuagcgc                                                    17

<210> SEQ ID NO 424
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 424
cgaucucgac aaucuac                                                    17

<210> SEQ ID NO 425
<211> LENGTH: 17
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 425
ucgacauccg aguuguc                                                         17

<210> SEQ ID NO 426
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 426
gagugcgguc ccuacga                                                         17

<210> SEQ ID NO 427
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 427
cgcggaaacu uaucaac                                                         17

<210> SEQ ID NO 428
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 428
aucuuaaugc cgucgua                                                         17

<210> SEQ ID NO 429
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 429
cucaaucguu caucgag                                                         17

<210> SEQ ID NO 430
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 430
uccgccugcu cacguau                                                         17

<210> SEQ ID NO 431
<211> LENGTH: 17
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 431
ucaccuguuc gacgaua                                                      17

<210> SEQ ID NO 432
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 432
gcucaucgcu cguaaaa                                                      17

<210> SEQ ID NO 433
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 433
gcucggauaa gaaccga                                                      17

<210> SEQ ID NO 434
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 434
uaucuuaaug ccgucgu                                                      17

<210> SEQ ID NO 435
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 435
cggcggagcg agucaag                                                      17

<210> SEQ ID NO 436
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 436
ucgcggaaac uuaucaa                                                      17

<210> SEQ ID NO 437
<211> LENGTH: 17
<212> TYPE: RNA
```

<213> ORGANISM: Artificial Sequence
<220> FEATURE:
<223> OTHER INFORMATION: Description of Artificial Sequence: Synthetic oligonucleotide

<400> SEQUENCE: 437
cgauuuaaug cgucacu                                               17

<210> SEQ ID NO 438
<211> LENGTH: 17
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 438
ucgcucguaa aaaggac                                               17

<210> SEQ ID NO 439
<211> LENGTH: 17
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 439
gacccgaaaa aguacgg                                               17

<210> SEQ ID NO 440
<211> LENGTH: 17
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 440
gccgucggga uuuagag                                               17

<210> SEQ ID NO 441
<211> LENGTH: 17
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 441
aaagaggcgu cgcuaua                                               17

<210> SEQ ID NO 442
<211> LENGTH: 17
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 442
cgcauaccuu acuaugu                                               17

<210> SEQ ID NO 443
<211> LENGTH: 17
<212> TYPE: RNA
<213> ORGANISM: Artificial Sequence

```
<220> FEATURE:
<223> OTHER INFORMATION: Description of Artificial Sequence: Synthetic
      oligonucleotide

<400> SEQUENCE: 443
cgaaccgaga guugccu                                                    17

<210> SEQ ID NO 444
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 444
ggaacucucg guucgca                                                    17

<210> SEQ ID NO 445
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 445
uggccgaaaa cggaugu                                                    17

<210> SEQ ID NO 446
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 446
cgcgucuagc accuccu                                                    17

<210> SEQ ID NO 447
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 447
ucaccgucgc gaagucc                                                    17

<210> SEQ ID NO 448
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 448
uauuaaacgu cagcucg                                                    17

<210> SEQ ID NO 449
<211> LENGTH: 17
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 449
cgcucguaaa aaggacu                                                   17

<210> SEQ ID NO 450
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 450
uuccgccugc ucacgua                                                   17

<210> SEQ ID NO 451
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 451
cuagugagag cgcuaua                                                   17

<210> SEQ ID NO 452
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 452
cgucguaauc agauaaa                                                   17

<210> SEQ ID NO 453
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 453
cugaucgcac aauuacc                                                   17

<210> SEQ ID NO 454
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 454
ucgcauaccu uacuaug                                                   17

<210> SEQ ID NO 455
<211> LENGTH: 17
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 455
cgccggagag cuucaaa                                                  17

<210> SEQ ID NO 456
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 456
gcuggggacg auugucg                                                  17

<210> SEQ ID NO 457
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 457
cgccucaagg aagucga                                                  17

<210> SEQ ID NO 458
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 458
cuuauagcgc ucucacu                                                  17

<210> SEQ ID NO 459
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 459
uucugucgag aucuccg                                                  17

<210> SEQ ID NO 460
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 460
cauauugcga aucuugc                                                  17

<210> SEQ ID NO 461
<211> LENGTH: 17
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 461
gggccgggac uucgcga                                                    17

<210> SEQ ID NO 462
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 462
uaaacccaua cgugagc                                                    17

<210> SEQ ID NO 463
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 463
uuuacgacuu ccucgcu                                                    17

<210> SEQ ID NO 464
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 464
gcgcauacaa caagcac                                                    17

<210> SEQ ID NO 465
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 465
gcagguuaua uugacgg                                                    17

<210> SEQ ID NO 466
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 466
uuuucgcgau caucuua                                                    17

<210> SEQ ID NO 467
<211> LENGTH: 17
<212> TYPE: RNA
<213> ORGANISM: Artificial Sequence
<220> FEATURE:
```

<223> OTHER INFORMATION: Description of Artificial Sequence: Synthetic
oligonucleotide

<400> SEQUENCE: 467
ucguauggga uaagggc                                                17

<210> SEQ ID NO 468
<211> LENGTH: 17
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 468
auaaucccgu gauggau                                                17

<210> SEQ ID NO 469
<211> LENGTH: 17
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 469
acgauacacu ucuacca                                                17

<210> SEQ ID NO 470
<211> LENGTH: 17
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 470
caguugcuga cggacua                                                17

<210> SEQ ID NO 471
<211> LENGTH: 17
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 471
gaacgauaag cugauuc                                                17

<210> SEQ ID NO 472
<211> LENGTH: 17
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 472
ucuaaauccg gacaacu                                                17

<210> SEQ ID NO 473
<211> LENGTH: 17
<212> TYPE: RNA

```
<213> ORGANISM: Artificial Sequence
<220> FEATURE:
<223> OTHER INFORMATION: Description of Artificial Sequence: Synthetic
      oligonucleotide

<400> SEQUENCE: 473
cagcggacuu ucgacaa                                                    17

<210> SEQ ID NO 474
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 474
caugggacgu cacaaac                                                    17

<210> SEQ ID NO 475
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 475
cagguuuucu agccguc                                                    17

<210> SEQ ID NO 476
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 476
ccgcuucaau gaucaaa                                                    17

<210> SEQ ID NO 477
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 477
uagccaacau ccguuuu                                                    17

<210> SEQ ID NO 478
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 478
ggaggauugc aucgcua                                                    17

<210> SEQ ID NO 479
<211> LENGTH: 17
<212> TYPE: RNA
<213> ORGANISM: Artificial Sequence
```

<220> FEATURE:
<223> OTHER INFORMATION: Description of Artificial Sequence: Synthetic
      oligonucleotide

<400> SEQUENCE: 479
caugcaauuc gccuaag                                                17

<210> SEQ ID NO 480
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 480
aaguggcgug gaugcga                                                17

<210> SEQ ID NO 481
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 481 cguauggau aagggcc                                                 17

<210> SEQ ID NO 482
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 482
gacaggugaa aucguau                                                17

<210> SEQ ID NO 483
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 483
gaaccgagag uucccuc                                                17

<210> SEQ ID NO 484
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 484
aaaucgaucu ucuaccc                                                17

<210> SEQ ID NO 485
<211> LENGTH: 17
<212> TYPE: RNA
<213> ORGANISM: Artificial Sequence
<220> FEATURE:

```
<223> OTHER INFORMATION: Description of Artificial Sequence: Synthetic
      oligonucleotide

<400> SEQUENCE: 485
aaugggacgc uaaauac                                                      17

<210> SEQ ID NO 486
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 486
uaaagugcuu acacgcu                                                      17

<210> SEQ ID NO 487
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 487
uacgcagguu auauuga                                                      17

<210> SEQ ID NO 488
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 488
auucugucga gaucucc                                                      17

<210> SEQ ID NO 489
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 489 gauucgucg agaucuc                                                       17

<210> SEQ ID NO 490
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 490
gccucucuaa aucccga                                                      17

<210> SEQ ID NO 491
<211> LENGTH: 17
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 491
ugcaucgcua agguuuu                                                    17

<210> SEQ ID NO 492
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 492
gcaguugcug acggacu                                                    17

<210> SEQ ID NO 493
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 493
cgggauuaua ugaaacu                                                    17

<210> SEQ ID NO 494
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 494
acccauacgu gagcagg                                                    17

<210> SEQ ID NO 495
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 495
agggguccca cauagua                                                    17

<210> SEQ ID NO 496
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 496
agccaccgua cuuuuuc                                                    17

<210> SEQ ID NO 497
<211> LENGTH: 17
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 497 auugggaua acgauua                                                    17

<210> SEQ ID NO 498
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 498
ugacaauguu ccaagcg                                                   17

<210> SEQ ID NO 499
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 499
ggugucggac uucagaa                                                   17

<210> SEQ ID NO 500
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 500
ucuccgcuua gaaaggc                                                   17

<210> SEQ ID NO 501
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 501
uguaaccuuu cgccuca                                                   17

<210> SEQ ID NO 502
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 502
acagguuucc ggacaag                                                   17

<210> SEQ ID NO 503
<211> LENGTH: 17
<212> TYPE: RNA
<213> ORGANISM: Artificial Sequence
<220> FEATURE:
```

<223> OTHER INFORMATION: Description of Artificial Sequence: Synthetic
      oligonucleotide

<400> SEQUENCE: 503
ugggacccga aaaagua                                                    17

<210> SEQ ID NO 504
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 504
uucauauaau cccguga                                                    17

<210> SEQ ID NO 505
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 505
cacagguuuc cggacaa                                                    17

<210> SEQ ID NO 506
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 506
auaguaaggu augcgaa                                                    17

<210> SEQ ID NO 507
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 507
aacugucacu uugcggu                                                    17

<210> SEQ ID NO 508
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 508
uuacuaugug ggacccc                                                    17

<210> SEQ ID NO 509
<211> LENGTH: 17
<212> TYPE: RNA

```
<213> ORGANISM: Artificial Sequence
<220> FEATURE:
<223> OTHER INFORMATION: Description of Artificial Sequence: Synthetic
      oligonucleotide

<400> SEQUENCE: 509
augcggcugg agcgccg                                                    17

<210> SEQ ID NO 510
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 510
uaagacggaa aucacuc                                                    17

<210> SEQ ID NO 511
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 511
cgccacuugc auuuaua                                                    17

<210> SEQ ID NO 512
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 512
ccccaucgac uuccuug                                                    17

<210> SEQ ID NO 513
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 513
gccucaagga agucgau                                                    17

<210> SEQ ID NO 514
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 514
uugaucaguc gaaaaac                                                    17

<210> SEQ ID NO 515
<211> LENGTH: 17
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 515
ucgggauuua gagaggc                                                    17

<210> SEQ ID NO 516
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 516
caaugagucc ccuuguc                                                    17

<210> SEQ ID NO 517
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 517
ucagguuuuc uagccgu                                                    17

<210> SEQ ID NO 518
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 518
gaccggaggg uuuucaa                                                    17

<210> SEQ ID NO 519
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 519
aagccaccgu acuuuuu                                                    17

<210> SEQ ID NO 520
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 520
cuguucuccg cuuagaa                                                    17

<210> SEQ ID NO 521
<211> LENGTH: 17
<212> TYPE: RNA
<213> ORGANISM: Artificial Sequence
<220> FEATURE:
```

<223> OTHER INFORMATION: Description of Artificial Sequence: Synthetic
      oligonucleotide

<400> SEQUENCE: 521
aucauugaag cggauaa                                                        17

<210> SEQ ID NO 522
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 522
uucgccagcc aucaaaa                                                        17

<210> SEQ ID NO 523
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 523
gccggagagc uucaaaa                                                        17

<210> SEQ ID NO 524
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 524
agaacgauaa gcugauu                                                        17

<210> SEQ ID NO 525
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 525
gcacagguuu ccggaca                                                        17

<210> SEQ ID NO 526
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 526
ucgccagcca ucaaaaa                                                        17

<210> SEQ ID NO 527
<211> LENGTH: 17
<212> TYPE: RNA

```
<213> ORGANISM: Artificial Sequence
<220> FEATURE:
<223> OTHER INFORMATION: Description of Artificial Sequence: Synthetic
      oligonucleotide

<400> SEQUENCE: 527
aagguaugcg aaagguu                                                    17

<210> SEQ ID NO 528
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 528
ggcaauacuu uuucguu                                                    17

<210> SEQ ID NO 529
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 529
gaggaaguug ucgauaa                                                    17

<210> SEQ ID NO 530
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 530
cugacguuua auaaauc                                                    17

<210> SEQ ID NO 531
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 531
aaacccgccu uucuaag                                                    17

<210> SEQ ID NO 532
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 532
uauaaaugca aguggcg                                                    17

<210> SEQ ID NO 533
<211> LENGTH: 17
<212> TYPE: RNA
<213> ORGANISM: Artificial Sequence
```

<220> FEATURE:
<223> OTHER INFORMATION: Description of Artificial Sequence: Synthetic
      oligonucleotide

<400> SEQUENCE: 533
ccacuacuuu gacuguc                                                    17

<210> SEQ ID NO 534
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 534
gagaguuccc ucgggcc                                                    17

<210> SEQ ID NO 535
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 535
uauagguuug uacuaac                                                    17

<210> SEQ ID NO 536
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 536
cauuacgaga aguugaa                                                    17

<210> SEQ ID NO 537
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 537
guauguugau caggaac                                                    17

<210> SEQ ID NO 538
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 538
cguauuucgu auucauu                                                    17

<210> SEQ ID NO 539
<211> LENGTH: 17
<212> TYPE: RNA
<213> ORGANISM: Artificial Sequence
<220> FEATURE:

-continued

<223> OTHER INFORMATION: Description of Artificial Sequence: Synthetic
     oligonucleotide

<400> SEQUENCE: 539
ugagggugau cuaaauc                                                  17

<210> SEQ ID NO 540
<211> LENGTH: 17
<212> TYPE: RNA
<213> ORGANISM: Artificial Sequence
<220> FEATURE:
<223> OTHER INFORMATION: Description of Artificial Sequence: Synthetic
     oligonucleotide

<400> SEQUENCE: 540
ccucaaggaa gucgaug                                                  17

<210> SEQ ID NO 541
<211> LENGTH: 17
<212> TYPE: RNA
<213> ORGANISM: Artificial Sequence
<220> FEATURE:
<223> OTHER INFORMATION: Description of Artificial Sequence: Synthetic
     oligonucleotide

<400> SEQUENCE: 541
gaaaucguau gggauaa                                                  17

<210> SEQ ID NO 542
<211> LENGTH: 17
<212> TYPE: RNA
<213> ORGANISM: Artificial Sequence
<220> FEATURE:
<223> OTHER INFORMATION: Description of Artificial Sequence: Synthetic
     oligonucleotide

<400> SEQUENCE: 542
uggaguaauc guuucuu                                                  17

<210> SEQ ID NO 543
<211> LENGTH: 17
<212> TYPE: RNA
<213> ORGANISM: Artificial Sequence
<220> FEATURE:
<223> OTHER INFORMATION: Description of Artificial Sequence: Synthetic
     oligonucleotide

<400> SEQUENCE: 543
ugcuauacuu agaaggc                                                  17

<210> SEQ ID NO 544
<211> LENGTH: 17
<212> TYPE: RNA
<213> ORGANISM: Artificial Sequence
<220> FEATURE:
<223> OTHER INFORMATION: Description of Artificial Sequence: Synthetic
     oligonucleotide

<400> SEQUENCE: 544
ccggagagcu ucaaaag                                                  17

<210> SEQ ID NO 545
<211> LENGTH: 17
<212> TYPE: RNA

```
<213> ORGANISM: Artificial Sequence
<220> FEATURE:
<223> OTHER INFORMATION: Description of Artificial Sequence: Synthetic
      oligonucleotide

<400> SEQUENCE: 545
agacagguga aaucgua                                                    17

<210> SEQ ID NO 546
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 546
gagcuaguua aggucau                                                    17

<210> SEQ ID NO 547
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 547
gaguucccuc gggccag                                                    17

<210> SEQ ID NO 548
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 548
cuuucaacuu cucguaa                                                    17

<210> SEQ ID NO 549
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 549
agaguucccu cgggcca                                                    17

<210> SEQ ID NO 550
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 550
agaucgggaa augauug                                                    17

<210> SEQ ID NO 551
<211> LENGTH: 17
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 551
ugaggcgaaa gguuaca                                                    17

<210> SEQ ID NO 552
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 552
uggcccgagg gaacucu                                                    17

<210> SEQ ID NO 553
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 553
guuucucguu cugcaau                                                    17

<210> SEQ ID NO 554
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 554
acgccacuug cauuuau                                                    17

<210> SEQ ID NO 555
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 555
cacuacuagg acagaau                                                    17

<210> SEQ ID NO 556
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 556
aucuacugcg aaagcag                                                    17

<210> SEQ ID NO 557
<211> LENGTH: 17
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 557
gucgggauuu agagagg                                                    17

<210> SEQ ID NO 558
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 558
ccuagcugau gccaauc                                                    17

<210> SEQ ID NO 559
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 559
uucuccgcuu agaaagg                                                    17

<210> SEQ ID NO 560
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 560
acugaggugc agaccgg                                                    17

<210> SEQ ID NO 561
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 561
ugcaugcuau acuuaga                                                    17

<210> SEQ ID NO 562
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 562
cugaggugca gaccgga                                                    17

<210> SEQ ID NO 563
<211> LENGTH: 17
<212> TYPE: RNA
```

<213> ORGANISM: Artificial Sequence
<220> FEATURE:
<223> OTHER INFORMATION: Description of Artificial Sequence: Synthetic
      oligonucleotide

<400> SEQUENCE: 563
augcccuuuu ugauggc                                                17

<210> SEQ ID NO 564
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 564
auucaccaau ccaucac                                                17

<210> SEQ ID NO 565
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 565
ugggaccccu ggcccga                                                17

<210> SEQ ID NO 566
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 566
uuucaacuuc ucguaau                                                17

<210> SEQ ID NO 567
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 567
guauuucgua uucauuc                                                17

<210> SEQ ID NO 568
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 568
aguggaugag cuaguua                                                17

<210> SEQ ID NO 569
<211> LENGTH: 17
<212> TYPE: RNA
<213> ORGANISM: Artificial Sequence -continued
<220> FEATURE:
<223> OTHER INFORMATION: Description of Artificial Sequence: Synthetic
      oligonucleotide

<400> SEQUENCE: 569
gaguaugccc uuuuuga                                                        17

<210> SEQ ID NO 570
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 570
aucaaacgac ucagaag                                                        17

<210> SEQ ID NO 571
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 571
cauucucuuc guuaucc                                                        17

<210> SEQ ID NO 572
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 572
auacacuucu accaagg                                                        17

<210> SEQ ID NO 573
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 573
gacuuccuug aggcgaa                                                        17

<210> SEQ ID NO 574
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 574
accccaaucc uuuuuga                                                        17

<210> SEQ ID NO 575
<211> LENGTH: 17
<212> TYPE: RNA
<213> ORGANISM: Artificial Sequence
<220> FEATURE:

```
<223> OTHER INFORMATION: Description of Artificial Sequence: Synthetic
      oligonucleotide

<400> SEQUENCE: 575
ugaaucgucc uucaaaa                                                         17

<210> SEQ ID NO 576
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 576
uacccucuuu gaagauc                                                         17

<210> SEQ ID NO 577
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 577
ucugaacuug acaaggc                                                         17

<210> SEQ ID NO 578
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 578
cgauugucuu ugaggaa                                                         17

<210> SEQ ID NO 579
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 579
ggacauguau guugauc                                                         17

<210> SEQ ID NO 580
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 580
cgcauacaac aagcaca                                                         17

<210> SEQ ID NO 581
<211> LENGTH: 17
<212> TYPE: RNA
```

<213> ORGANISM: Artificial Sequence
<220> FEATURE:
<223> OTHER INFORMATION: Description of Artificial Sequence: Synthetic
      oligonucleotide

<400> SEQUENCE: 581
ucgauuacaa uguuuuc                                                    17

<210> SEQ ID NO 582
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 582
cguccuucaa aaaggau                                                    17

<210> SEQ ID NO 583
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 583
cuuacuaagc ugcaauu                                                    17

<210> SEQ ID NO 584
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 584
aagaaacgau uacucca                                                    17

<210> SEQ ID NO 585
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 585
caacuuuugc cacuacu                                                    17

<210> SEQ ID NO 586
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 586
cuauucuguc cuaguag                                                    17

<210> SEQ ID NO 587
<211> LENGTH: 17
<212> TYPE: RNA
<213> ORGANISM: Artificial Sequence

```
<220> FEATURE:
<223> OTHER INFORMATION: Description of Artificial Sequence: Synthetic
      oligonucleotide

<400> SEQUENCE: 587
cugcauaaag uuccuau                                                        17

<210> SEQ ID NO 588
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 588
gugggacccc uggcccg                                                        17

<210> SEQ ID NO 589
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 589
guaugcggac uuauuuu                                                        17

<210> SEQ ID NO 590
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 590
ccuaagugga uuugaug                                                        17

<210> SEQ ID NO 591
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 591
gauuuucuaa agagcga                                                        17

<210> SEQ ID NO 592
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 592
gggcagccag aucuuaa                                                        17

<210> SEQ ID NO 593
<211> LENGTH: 17
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 593
caaauugcag cuuagua                                                    17

<210> SEQ ID NO 594
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 594
ugaaaucgua ugggaua                                                    17

<210> SEQ ID NO 595
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 595
uuuacucuua ccaaccu                                                    17

<210> SEQ ID NO 596
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 596
gaugcuccuu uaagauc                                                    17

<210> SEQ ID NO 597
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 597
cucucaguau gucagau                                                    17

<210> SEQ ID NO 598
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 598
aaauacuuga augcggc                                                    17

<210> SEQ ID NO 599
<211> LENGTH: 17
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 599
acuuaacuaa agcugag                                                  17

<210> SEQ ID NO 600
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 600
cgaacaggag auaggca                                                  17

<210> SEQ ID NO 601
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 601
gauucaccaa uccauca                                                  17

<210> SEQ ID NO 602
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 602
uuugaucagu cgaaaaa                                                  17

<210> SEQ ID NO 603
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 603
cuuaaaggag cauccug                                                  17

<210> SEQ ID NO 604
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 604
ccuuuugauc auugaag                                                  17

<210> SEQ ID NO 605
<211> LENGTH: 17
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 605
ugagcuaguu aagguca                                                        17

<210> SEQ ID NO 606
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 606
aaacauugua aucgaga                                                        17

<210> SEQ ID NO 607
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 607
ccagauuggc aucagcu                                                        17

<210> SEQ ID NO 608
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 608 aauugggauau uuuccac                                                       17

<210> SEQ ID NO 609
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 609
ucaaacagac uauacuu                                                        17

<210> SEQ ID NO 610
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 610
ccacaucaaa uccacuu                                                        17

<210> SEQ ID NO 611
<211> LENGTH: 17
<212> TYPE: RNA
<213> ORGANISM: Artificial Sequence
<220> FEATURE:
```

<223> OTHER INFORMATION: Description of Artificial Sequence: Synthetic
      oligonucleotide

<400> SEQUENCE: 611
ggauauacaa aaggcac                                                    17

<210> SEQ ID NO 612
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 612
aaucuacugg cacaaau                                                    17

<210> SEQ ID NO 613
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 613
ucaguauguc agauagg                                                    17

<210> SEQ ID NO 614
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 614
aguuaaguau gucacug                                                    17

<210> SEQ ID NO 615
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 615
aaguucgacu uaaaauu                                                    17

<210> SEQ ID NO 616
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 616
uucuguucgu uaucuuc                                                    17

<210> SEQ ID NO 617
<211> LENGTH: 17
<212> TYPE: RNA

```
<213> ORGANISM: Artificial Sequence
<220> FEATURE:
<223> OTHER INFORMATION: Description of Artificial Sequence: Synthetic
      oligonucleotide

<400> SEQUENCE: 617
gaggguauua aagaacu                                                        17

<210> SEQ ID NO 618
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 618
guuaaguaug ucacuga                                                        17

<210> SEQ ID NO 619
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 619
gcuuaacugu cacuuug                                                        17

<210> SEQ ID NO 620
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 620
agauuuguca cagcuug                                                        17

<210> SEQ ID NO 621
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 621
agacuugaca cuucuca                                                        17

<210> SEQ ID NO 622
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 622
ccagacaguc aaaguag                                                        17

<210> SEQ ID NO 623
<211> LENGTH: 17
<212> TYPE: RNA
<213> ORGANISM: Artificial Sequence
```

<220> FEATURE:
<223> OTHER INFORMATION: Description of Artificial Sequence: Synthetic
      oligonucleotide

<400> SEQUENCE: 623
ccccuuuuga agcucuc                                                        17

<210> SEQ ID NO 624
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 624
uuaucaguuu cgcauuu                                                        17

<210> SEQ ID NO 625
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 625
aaaucaaacg acucaga                                                        17

<210> SEQ ID NO 626
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 626
aaucgauucu uccaaaa                                                        17

<210> SEQ ID NO 627
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 627
uucccgaucu ucaaaga                                                        17

<210> SEQ ID NO 628
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 628
gucagucaaa gaauuau                                                        17

<210> SEQ ID NO 629
<211> LENGTH: 17
<212> TYPE: RNA
<213> ORGANISM: Artificial Sequence
<220> FEATURE:

```
<223> OTHER INFORMATION: Description of Artificial Sequence: Synthetic
      oligonucleotide

<400> SEQUENCE: 629
gauuugucac agcuugg                                                    17

<210> SEQ ID NO 630
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 630
gaaaccaaug gggagac                                                    17

<210> SEQ ID NO 631
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 631
agguuaaaga gucauca                                                    17

<210> SEQ ID NO 632
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 632 agagguauu aaagaac                                                     17

<210> SEQ ID NO 633
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 633
acagaauagg caacugu                                                    17

<210> SEQ ID NO 634
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 634
uuucacgauu gucuuug                                                    17

<210> SEQ ID NO 635
<211> LENGTH: 17
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 635
guccuucaaa aaggauu                                                      17

<210> SEQ ID NO 636
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 636
augcuuugug auuuggc                                                      17

<210> SEQ ID NO 637
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 637
ugagaagugu caagucu                                                      17

<210> SEQ ID NO 638
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 638
uaaagauaag gacuucc                                                      17

<210> SEQ ID NO 639
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 639
uuucucguuc ugcaauu                                                      17

<210> SEQ ID NO 640
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 640
ccauugguuu caauuaa                                                      17

<210> SEQ ID NO 641
<211> LENGTH: 17
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 641
auccaucuuc ucuaaua                                                       17

<210> SEQ ID NO 642
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 642
uaauacugag auuacca                                                       17

<210> SEQ ID NO 643
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 643
uucaccuguc ucccccau                                                      17

<210> SEQ ID NO 644
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 644
auagauuugu cacagcu                                                       17

<210> SEQ ID NO 645
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 645
cuugucugaa cuugaca                                                       17

<210> SEQ ID NO 646
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 646
cuuaacuaaa gcugaga                                                       17

<210> SEQ ID NO 647
<211> LENGTH: 17
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 647
cagucaaaga auuauug                                                  17

<210> SEQ ID NO 648
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 648
aaauucacgu auuuaga                                                  17

<210> SEQ ID NO 649
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 649
uagauuuguc acagcuu                                                  17

<210> SEQ ID NO 650
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 650
uaauacuuug uccagau                                                  17

<210> SEQ ID NO 651
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 651
acucacuuuc uagcuuc                                                  17

<210> SEQ ID NO 652
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 652
ccuuuaauug aaaccaa                                                  17

<210> SEQ ID NO 653
<211> LENGTH: 17
<212> TYPE: RNA
```

<213> ORGANISM: Artificial Sequence
<220> FEATURE:
<223> OTHER INFORMATION: Description of Artificial Sequence: Synthetic
      oligonucleotide

<400> SEQUENCE: 653
uacuccaugg aauuuug                                                  17

<210> SEQ ID NO 654
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 654
gucaaaauac uugaaug                                                  17

<210> SEQ ID NO 655
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 655
acuuaaaauu ugguguc                                                  17

<210> SEQ ID NO 656
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 656
cucuauuacc uacaaaa                                                  17

<210> SEQ ID NO 657
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 657
cucuuuaacc uucaaag                                                  17

<210> SEQ ID NO 658
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 658
cuuuacuaug uugacuu                                                  17

<210> SEQ ID NO 659
<211> LENGTH: 17
<212> TYPE: RNA
<213> ORGANISM: Artificial Sequence

```
<220> FEATURE:
<223> OTHER INFORMATION: Description of Artificial Sequence: Synthetic
      oligonucleotide

<400> SEQUENCE: 659
caacaugcuu ugugauu                                                    17

<210> SEQ ID NO 660
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 660
aauuggagau caguaug                                                    17

<210> SEQ ID NO 661
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 661
cauuuuguag guaauag                                                    17

<210> SEQ ID NO 662
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 662
gacugacuuc aguuucu                                                    17

<210> SEQ ID NO 663
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 663
acuaaagcug agagggg                                                    17

<210> SEQ ID NO 664
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 664
aaaagcgaac aggagau                                                    17

<210> SEQ ID NO 665
<211> LENGTH: 17
<212> TYPE: RNA
<213> ORGANISM: Artificial Sequence
<220> FEATURE:
```

<223> OTHER INFORMATION: Description of Artificial Sequence: Synthetic
      oligonucleotide

<400> SEQUENCE: 665
aacccuauaa augcaag                                                        17

<210> SEQ ID NO 666
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 666
acccauauua gagaaga                                                        17

<210> SEQ ID NO 667
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 667
guauuucuua augagug                                                        17

<210> SEQ ID NO 668
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 668
uauguugacu ugggggca                                                       17

<210> SEQ ID NO 669
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 669
caaaaggcac agguuuc                                                        17

<210> SEQ ID NO 670
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 670
uuucccgauc uucaaag                                                        17

<210> SEQ ID NO 671
<211> LENGTH: 17
<212> TYPE: RNA

```
<213> ORGANISM: Artificial Sequence
<220> FEATURE:
<223> OTHER INFORMATION: Description of Artificial Sequence: Synthetic
      oligonucleotide

<400> SEQUENCE: 671
uuacccucuu ugaagau                                                  17

<210> SEQ ID NO 672
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 672
uauuagagaa gauggau                                                  17

<210> SEQ ID NO 673
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 673
uuaacuaaag cugagag                                                  17

<210> SEQ ID NO 674
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 674
aguuaagcaa uugaaag                                                  17

<210> SEQ ID NO 675
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 675
aaagucaaaa uuggugu                                                  17

<210> SEQ ID NO 676
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 676
uucaaacaac ugauuau                                                  17

<210> SEQ ID NO 677
<211> LENGTH: 17
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 677
guggcaaaag uugagaa                                                     17

<210> SEQ ID NO 678
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 678
uaaaguaaac ugugcuu                                                     17

<210> SEQ ID NO 679
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 679
cauugucacu uuucccu                                                     17

<210> SEQ ID NO 680
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 680
uuccuuugaa aacccuc                                                     17

<210> SEQ ID NO 681
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 681
aacucacuuu cuagcuu                                                     17

<210> SEQ ID NO 682
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 682
acugccugag aaauaua                                                     17

<210> SEQ ID NO 683
<211> LENGTH: 17
<212> TYPE: RNA
<213> ORGANISM: Artificial Sequence
<220> FEATURE:
```

<223> OTHER INFORMATION: Description of Artificial Sequence: Synthetic
      oligonucleotide

<400> SEQUENCE: 683
caugcuuugu gauuugg                                                      17

<210> SEQ ID NO 684
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 684
aguggcaaaa guugaga                                                      17

<210> SEQ ID NO 685
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 685
cuguuugagu uagaaaa                                                      17

<210> SEQ ID NO 686
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 686
uagaaaaugg ccgaaaa                                                      17

<210> SEQ ID NO 687
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 687
uuuacuaugu ugacuug                                                      17

<210> SEQ ID NO 688
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 688
auuaccuaca aaaugga                                                      17

<210> SEQ ID NO 689
<211> LENGTH: 17
<212> TYPE: RNA

```
<213> ORGANISM: Artificial Sequence
<220> FEATURE:
<223> OTHER INFORMATION: Description of Artificial Sequence: Synthetic
      oligonucleotide

<400> SEQUENCE: 689
gaaagugagu uugugua                                                17

<210> SEQ ID NO 690
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 690
uccaucuucu cuaauau                                                17

<210> SEQ ID NO 691
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 691
cuuuaauuga aaccaau                                                17

<210> SEQ ID NO 692
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 692
ucagucaaag aauuauu                                                17

<210> SEQ ID NO 693
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 693
aaucaaacga cucagaa                                                17

<210> SEQ ID NO 694
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 694
ugucccuucc auuuugu                                                17

<210> SEQ ID NO 695
<211> LENGTH: 17
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 695
uuuaauugaa accaaug                                                    17

<210> SEQ ID NO 696
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 696
uaaauucuug ucaaagu                                                    17

<210> SEQ ID NO 697
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 697
uuguauaucc ucuuuga                                                    17

<210> SEQ ID NO 698
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 698
cuuuaauuau cuuuagg                                                    17

<210> SEQ ID NO 699
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 699
aaaugaagaa cuauugg                                                    17

<210> SEQ ID NO 700
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 700
ucuuuacuau guugacu                                                    17

<210> SEQ ID NO 701
<211> LENGTH: 17
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 701
ccggagagaa gaaaaau                                                    17

<210> SEQ ID NO 702
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 702
aaucauagag caaauuu                                                    17

<210> SEQ ID NO 703
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 703
cccggagaga agaaaaa                                                    17

<210> SEQ ID NO 704
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 704
uuaccuacaa aauggaa                                                    17

<210> SEQ ID NO 705
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 705
ucucaggcag uugcuga                                                    17

<210> SEQ ID NO 706
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 706
uccuucaaaa aggauug                                                    17

<210> SEQ ID NO 707
<211> LENGTH: 17
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 707
uucaauucua uaaaguu                                                    17

<210> SEQ ID NO 708
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 708
ugguaagagu aaacaaa                                                    17

<210> SEQ ID NO 709
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 709
ucaauucuau aaaguua                                                    17

<210> SEQ ID NO 710
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 710
gaaaucacuc uggcaaa                                                    17

<210> SEQ ID NO 711
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 711 acuccucaa aauucca                                                     17

<210> SEQ ID NO 712
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 712
uuaucacuau uccuuuu                                                    17

<210> SEQ ID NO 713
<211> LENGTH: 17
<212> TYPE: RNA
<213> ORGANISM: Artificial Sequence
```

<220> FEATURE:
<223> OTHER INFORMATION: Description of Artificial Sequence: Synthetic
      oligonucleotide

<400> SEQUENCE: 713
cacuuuaaag ucaaaau                                                      17

<210> SEQ ID NO 714
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 714
auauuagaga agaugga                                                      17

<210> SEQ ID NO 715
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 715
cccauuuuuc uucucuc                                                      17

<210> SEQ ID NO 716
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 716
aaaaaaacag ucgagag                                                      17

<210> SEQ ID NO 717
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 717
uuaugaaaca guuaaag                                                      17

<210> SEQ ID NO 718
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 718
aagaaaaaug gguuguu                                                      17

<210> SEQ ID NO 719
<211> LENGTH: 17
<212> TYPE: RNA
<213> ORGANISM: Artificial Sequence
<220> FEATURE:

-continued

```
<223> OTHER INFORMATION: Description of Artificial Sequence: Synthetic
      oligonucleotide

<400> SEQUENCE: 719 ccauuuucu ucucucc                                                    17

<210> SEQ ID NO 720
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 720
cauaguaaag aaaacug                                                   17

<210> SEQ ID NO 721
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 721
auaagagaca agcaaag                                                   17

<210> SEQ ID NO 722
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 722
gaugaagaga auagaag                                                   17

<210> SEQ ID NO 723
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 723
ggcuggagcg ccgaggu                                                   17

<210> SEQ ID NO 724
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 724
auuuccuuau auuucuc                                                   17

<210> SEQ ID NO 725
<211> LENGTH: 17
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 725
cagaauaggc aacugua                                                  17

<210> SEQ ID NO 726
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 726
uaugaauuuc uuuaaga                                                  17

<210> SEQ ID NO 727
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 727 agaaaugaa gaacuau                                                   17

<210> SEQ ID NO 728
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 728
uuacaaggaa guaaaaa                                                  17

<210> SEQ ID NO 729
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 729
agagaagaug gauggga                                                  17

<210> SEQ ID NO 730
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 730
aaaacugagg ugcagac                                                  17

<210> SEQ ID NO 731
<211> LENGTH: 17
<212> TYPE: RNA
<213> ORGANISM: Artificial Sequence
```

<220> FEATURE:
<223> OTHER INFORMATION: Description of Artificial Sequence: Synthetic
      oligonucleotide

<400> SEQUENCE: 731
uaucuuuaau uaucuuu                                                     17

<210> SEQ ID NO 732
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 732
agaauaaaag aaguauu                                                     17

<210> SEQ ID NO 733
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 733
augaagagaa uagaaga                                                     17

<210> SEQ ID NO 734
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 734
aaagauaauu aaagaua                                                     17

<210> SEQ ID NO 735
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 735
uauacuuaga aggcagg                                                     17

<210> SEQ ID NO 736
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 736
caaagaggau auacaaa                                                     17

<210> SEQ ID NO 737
<211> LENGTH: 20
<212> TYPE: RNA
<213> ORGANISM: Artificial Sequence
<220> FEATURE:

```
<223> OTHER INFORMATION: Description of Artificial Sequence: Synthetic
      oligonucleotide

<400> SEQUENCE: 737
cagucgaaaa acggguacgc                                              20

<210> SEQ ID NO 738
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 738
cacgcucgga uaagaaccga                                              20

<210> SEQ ID NO 739
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 739
uaagauaagc gucgugcgca                                              20

<210> SEQ ID NO 740
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 740
cgcucaccug uucgacgaua                                              20

<210> SEQ ID NO 741
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 741
gauaagcguc gugcgcaugg                                              20

<210> SEQ ID NO 742
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 742
cgauucuguc gagaucuccg                                              20

<210> SEQ ID NO 743
<211> LENGTH: 20
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 743
agaggcgucg cuauacgggc                                                 20

<210> SEQ ID NO 744
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 744
uuaaagaggc gucgcuauac                                                 20

<210> SEQ ID NO 745
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 745
aggcgucgcu auacgggcug                                                 20

<210> SEQ ID NO 746
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 746
cgcuuuucgc gaucaucuua                                                 20

<210> SEQ ID NO 747
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 747
agagcgacgg cuucgccaau                                                 20

<210> SEQ ID NO 748
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 748
ugaagcggau aacggcgccu                                                 20

<210> SEQ ID NO 749
<211> LENGTH: 20
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 749
acacgcucgg auaagaaccg                                                    20

<210> SEQ ID NO 750
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 750
gaggcgucgc uauacgggcu                                                    20

<210> SEQ ID NO 751
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 751
gaugaucgcg aaaagcgaac                                                    20

<210> SEQ ID NO 752
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 752
uaagggccgg gacuucgcga                                                    20

<210> SEQ ID NO 753
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 753 cguauggga cgcuaaauac                                                     20

<210> SEQ ID NO 754
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 754
cuccggguaa uugugcgauc                                                    20

<210> SEQ ID NO 755
<211> LENGTH: 20
<212> TYPE: RNA
<213> ORGANISM: Artificial Sequence
<220> FEATURE:
```

<223> OTHER INFORMATION: Description of Artificial Sequence: Synthetic
oligonucleotide

<400> SEQUENCE: 755
ugucgcggaa acuuaucaac                                               20

<210> SEQ ID NO 756
<211> LENGTH: 20
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 756
cgcuagccaa cauccguuuu                                               20

<210> SEQ ID NO 757
<211> LENGTH: 20
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 757
aaugagugcg gucccuacga                                               20

<210> SEQ ID NO 758
<211> LENGTH: 20
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 758
uacgcagguu auauugacgg                                               20

<210> SEQ ID NO 759
<211> LENGTH: 20
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 759
ugacgaucuc gacaaucuac                                               20

<210> SEQ ID NO 760
<211> LENGTH: 20
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 760
guuaaagagg cgucgcuaua                                               20

<210> SEQ ID NO 761
<211> LENGTH: 20
<212> TYPE: RNA

<213> ORGANISM: Artificial Sequence
<220> FEATURE:
<223> OTHER INFORMATION: Description of Artificial Sequence: Synthetic
      oligonucleotide

<400> SEQUENCE: 761
cgacgucgua aucagauaaa                                               20

<210> SEQ ID NO 762
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 762
ucauaaccuu aucgucgaac                                               20

<210> SEQ ID NO 763
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 763
gcuuaucuua augccgucgu                                               20

<210> SEQ ID NO 764
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 764
aaacggaugu uggcuagcgc                                               20

<210> SEQ ID NO 765
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 765
uugucgacau ccgaguuguc                                               20

<210> SEQ ID NO 766
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 766
cagcucaauc guucaucgag                                               20

<210> SEQ ID NO 767
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 767
gaucgauuua augcgucacu                                               20

<210> SEQ ID NO 768
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 768
cuuaucuuaa ugccgucgua                                               20

<210> SEQ ID NO 769
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 769
ugacggcgga gcgagucaag                                               20

<210> SEQ ID NO 770
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 770
cuagccgucg ggauuuagag                                               20

<210> SEQ ID NO 771
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 771
ucaucgcucg uaaaaaggac                                               20

<210> SEQ ID NO 772
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 772
cgagaacgau aagcugauuc                                               20

<210> SEQ ID NO 773
<211> LENGTH: 20
<212> TYPE: RNA
<213> ORGANISM: Artificial Sequence
<220> FEATURE:

<223> OTHER INFORMATION: Description of Artificial Sequence: Synthetic
oligonucleotide

<400> SEQUENCE: 773
augcgaaccg agaguuccccu                                              20

<210> SEQ ID NO 774
<211> LENGTH: 20
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 774
uaagcucauc gcucguaaaa                                               20

<210> SEQ ID NO 775
<211> LENGTH: 20
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 775
uugucgcgga aacuuaucaa                                               20

<210> SEQ ID NO 776
<211> LENGTH: 20
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 776
ucgauucugu cgagaucucc                                               20

<210> SEQ ID NO 777
<211> LENGTH: 20
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 777
ugucgcgucu agcaccuccu                                               20

<210> SEQ ID NO 778
<211> LENGTH: 20
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 778
ugggacccga aaaaguacgg                                               20

<210> SEQ ID NO 779
<211> LENGTH: 20
<212> TYPE: RNA

```
<213> ORGANISM: Artificial Sequence
<220> FEATURE:
<223> OTHER INFORMATION: Description of Artificial Sequence: Synthetic
      oligonucleotide

<400> SEQUENCE: 779
ggccuaguga gagcgcuaua                                                    20

<210> SEQ ID NO 780
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 780
ggauaaaccc auacgugagc                                                    20

<210> SEQ ID NO 781
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 781
ccgucgggau uuagagaggc                                                    20

<210> SEQ ID NO 782
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 782
uuuuccgccu gcucacguau                                                    20

<210> SEQ ID NO 783
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 783
caucgcucgu aaaaaggacu                                                    20

<210> SEQ ID NO 784
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 784
aaccuuauag cgcucucacu                                                    20

<210> SEQ ID NO 785
<211> LENGTH: 20
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 785
aucgacuucc uugaggcgaa                                                    20

<210> SEQ ID NO 786
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 786
cgaucagguu uucuagccgu                                                    20

<210> SEQ ID NO 787
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 787
cgucguauuu cguauucauu                                                    20

<210> SEQ ID NO 788
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 788
ucgaagccac cguacuuuuu                                                    20

<210> SEQ ID NO 789
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 789
ugcgaaccga gaguucccuc                                                    20

<210> SEQ ID NO 790
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 790
uagcgccgga gagcuucaaa                                                    20

<210> SEQ ID NO 791
<211> LENGTH: 20
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 791
aaccugaucg cacaauuacc                                                    20

<210> SEQ ID NO 792
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 792
ggguacgcag guuauauuga                                                    20

<210> SEQ ID NO 793
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 793
gagggaacuc ucgguucgca                                                    20

<210> SEQ ID NO 794
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 794
acgagaacga uaagcugauu                                                    20

<210> SEQ ID NO 795
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 795
cccgccucuc uaaaucccga                                                    20

<210> SEQ ID NO 796
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 796
cgggcugggg acgauugucg                                                    20

<210> SEQ ID NO 797
<211> LENGTH: 20
<212> TYPE: RNA
```

<213> ORGANISM: Artificial Sequence
<220> FEATURE:
<223> OTHER INFORMATION: Description of Artificial Sequence: Synthetic
      oligonucleotide

<400> SEQUENCE: 797
cguaaacccg ccuuucuaag                                           20

<210> SEQ ID NO 798
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 798
cauauaaucc cgugauggau                                           20

<210> SEQ ID NO 799
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 799
uucgauucug ucgagaucuc                                           20

<210> SEQ ID NO 800
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 800
cgaagccacc guacuuuuuc                                           20

<210> SEQ ID NO 801
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 801
ccgaagaaac gauuacucca                                           20

<210> SEQ ID NO 802
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 802
gucguauuuc guauucauuc                                           20

<210> SEQ ID NO 803
<211> LENGTH: 20
<212> TYPE: RNA
<213> ORGANISM: Artificial Sequence

```
<220> FEATURE:
<223> OTHER INFORMATION: Description of Artificial Sequence: Synthetic
      oligonucleotide

<400> SEQUENCE: 803
agcgccggag agcuucaaaa                                                   20

<210> SEQ ID NO 804
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 804
uucucaccgu cgcgaagucc                                                   20

<210> SEQ ID NO 805
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 805
ugaucuaaau ccggacaacu                                                   20

<210> SEQ ID NO 806
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 806
gaucagguuu ucuagccguc                                                   20

<210> SEQ ID NO 807
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 807
gguucgccag ccaucaaaaa                                                   20

<210> SEQ ID NO 808
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 808
uucgccucaa ggaagucgau                                                   20

<210> SEQ ID NO 809
<211> LENGTH: 20
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 809
ucgccuaagu ggauuugaug                                                    20

<210> SEQ ID NO 810
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 810
ugguucgcca gccaucaaaa                                                    20

<210> SEQ ID NO 811
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 811
ucgccucaag gaagucgaug                                                    20

<210> SEQ ID NO 812
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 812
accgagaguu cccucgggcc                                                    20

<210> SEQ ID NO 813
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 813
auaggaggau ugcaucgcua                                                    20

<210> SEQ ID NO 814
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 814
gccgucggga uuuagagagg                                                    20

<210> SEQ ID NO 815
<211> LENGTH: 20
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 815
caauaaagug cuuacacgcu                                              20

<210> SEQ ID NO 816
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 816 auuuccgcc ugcucacgua                                               20

<210> SEQ ID NO 817
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 817 gaacccauc gacuuccuug                                               20

<210> SEQ ID NO 818
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 818
gcgccggaga gcuucaaaag                                              20

<210> SEQ ID NO 819
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 819
acgauacacu ucuaccaagg                                              20

<210> SEQ ID NO 820
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 820
aaauggccga aaacggaugu                                              20

<210> SEQ ID NO 821
<211> LENGTH: 20
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 821
uagcaugcaa uucgccuaag                                                     20

<210> SEQ ID NO 822
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 822
uaagcgcaua caacaagcac                                                     20

<210> SEQ ID NO 823
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 823
uuucgccuca aggaagucga                                                     20

<210> SEQ ID NO 824
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 824
ugaaugcggc uggagcgccg                                                     20

<210> SEQ ID NO 825
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 825
gugcaaugag uccccuuguc                                                     20

<210> SEQ ID NO 826
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 826 ugcaagguggc guggaugcga                                                    20

<210> SEQ ID NO 827
<211> LENGTH: 20
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 827
aagcagcgga cuucgacaa                                                  20

<210> SEQ ID NO 828
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 828
uaaacccaua cgugagcagg                                                 20

<210> SEQ ID NO 829
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 829
cccuauaaau gcaaguggcg                                                 20

<210> SEQ ID NO 830
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 830
uuucgcauac cuuacuaugu                                                 20

<210> SEQ ID NO 831
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 831
gcguuaucag uuucgcauuu                                                 20

<210> SEQ ID NO 832
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 832
ggucauggga cgucacaaac                                                 20

<210> SEQ ID NO 833
<211> LENGTH: 20
<212> TYPE: RNA
```

<213> ORGANISM: Artificial Sequence
<220> FEATURE:
<223> OTHER INFORMATION: Description of Artificial Sequence: Synthetic oligonucleotide

<400> SEQUENCE: 833
cgagaguucc cucgggccag                                        20

<210> SEQ ID NO 834
<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 834
uucuuuacga cuuccucgcu                                        20

<210> SEQ ID NO 835
<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 835
caaacgauac acuucuacca                                        20

<210> SEQ ID NO 836
<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 836
accuuacuau gugggacccc                                        20

<210> SEQ ID NO 837
<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 837
gauugcaucg cuaagguuuu                                        20

<210> SEQ ID NO 838
<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 838
cuuucgcaua ccuuacuaug                                        20

<210> SEQ ID NO 839
<211> LENGTH: 20
<212> TYPE: RNA
<213> ORGANISM: Artificial Sequence -continued

```
<220> FEATURE:
<223> OTHER INFORMATION: Description of Artificial Sequence: Synthetic
      oligonucleotide

<400> SEQUENCE: 839
uugaucauug aagcggauaa                                                 20

<210> SEQ ID NO 840
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 840
cucgauuuuc uaaagagcga                                                 20

<210> SEQ ID NO 841
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 841
ucgaaguucg acuuaaaauu                                                 20

<210> SEQ ID NO 842
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 842
aggcaguugc ugacggacua                                                 20

<210> SEQ ID NO 843
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 843
uauccgcuuc aaugaucaaa                                                 20

<210> SEQ ID NO 844
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 844
gacugggacc cgaaaaagua                                                 20

<210> SEQ ID NO 845
<211> LENGTH: 20
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 845
ccgagaguuc ccucgggcca                                              20

<210> SEQ ID NO 846
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 846
gcaugcuaua cuuagaaggc                                              20

<210> SEQ ID NO 847
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 847
aaucguaugg gauaagggcc                                              20

<210> SEQ ID NO 848
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 848
guccuuacua agcugcaauu                                              20

<210> SEQ ID NO 849
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 849
uguucuccgc uuagaaaggc                                              20

<210> SEQ ID NO 850
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 850
cgaccuuuaa uugaaaccaa                                              20

<210> SEQ ID NO 851
<211> LENGTH: 20
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 851
aaaucguaug ggauaagggc                                               20

<210> SEQ ID NO 852
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 852
gaacauauug cgaaucuugc                                               20

<210> SEQ ID NO 853
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 853
gagcugacgu uuaauaaauc                                               20

<210> SEQ ID NO 854
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 854
cuuaacuguc acuuugcggu                                               20

<210> SEQ ID NO 855
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 855
auuaaaucga ucuucuaccc                                               20

<210> SEQ ID NO 856
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 856
ggcacagguu uccggacaag                                               20

<210> SEQ ID NO 857
<211> LENGTH: 20
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 857
cacauaguaa gguaugcgaa                                                    20

<210> SEQ ID NO 858
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 858
aguaagguau gcgaaagguu                                                    20

<210> SEQ ID NO 859
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 859
ccauggagua aucguuucuu                                                    20

<210> SEQ ID NO 860
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 860
cggguauuuc uuaaugagug                                                    20

<210> SEQ ID NO 861
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 861
uaugugggac cccuggcccg                                                    20

<210> SEQ ID NO 862
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 862
ccuuguaacc uuucgccuca                                                    20

<210> SEQ ID NO 863
<211> LENGTH: 20
<212> TYPE: RNA
<213> ORGANISM: Artificial Sequence
<220> FEATURE:
```

-continued

<223> OTHER INFORMATION: Description of Artificial Sequence: Synthetic
      oligonucleotide

<400> SEQUENCE: 863
uccacgccac uugcauuuau                                                    20

<210> SEQ ID NO 864
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 864
ucccauuacg agaaguugaa                                                    20

<210> SEQ ID NO 865
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 865
auuggugucg gacuucagaa                                                    20

<210> SEQ ID NO 866
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 866
aguuucauau aaucccguga                                                    20

<210> SEQ ID NO 867
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 867
ggugaaaucg uaugggauaa                                                    20

<210> SEQ ID NO 868
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 868
auuauugggg auaacgauua                                                    20

<210> SEQ ID NO 869
<211> LENGTH: 20
<212> TYPE: RNA

```
-continued

<213> ORGANISM: Artificial Sequence
<220> FEATURE:
<223> OTHER INFORMATION: Description of Artificial Sequence: Synthetic
      oligonucleotide

<400> SEQUENCE: 869
ucacgggauu auaugaaacu                                                   20

<210> SEQ ID NO 870
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 870
aagugacaau guuccaagcg                                                   20

<210> SEQ ID NO 871
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 871
gcgaaaagcg aacaggagau                                                   20

<210> SEQ ID NO 872
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 872
ggagacaggu gaaaucguau                                                   20

<210> SEQ ID NO 873
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 873
accuuucaac uucucguaau                                                   20

<210> SEQ ID NO 874
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 874
gcagaccgga ggguuuucaa                                                   20

<210> SEQ ID NO 875
<211> LENGTH: 20
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 875
ugccacuacu aggacagaau                                               20

<210> SEQ ID NO 876
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 876
ccacgccacu ugcauuuaua                                               20

<210> SEQ ID NO 877
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 877
auuuauuaaa cgucagcucg                                               20

<210> SEQ ID NO 878
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 878
aaccuuucaa cuucucguaa                                               20

<210> SEQ ID NO 879
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 879
cgaaaaucaa acgacucaga                                               20

<210> SEQ ID NO 880
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 880
ucuuugauca gucgaaaaac                                               20

<210> SEQ ID NO 881
<211> LENGTH: 20
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 881
cgguaaauuc uugucaaagu                                                   20

<210> SEQ ID NO 882
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 882
augugggacc ccuggcccga                                                   20

<210> SEQ ID NO 883
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 883
cggauagauu ugucacagcu                                                   20

<210> SEQ ID NO 884
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 884
ucgacuuaaa auuuggguguc                                                  20

<210> SEQ ID NO 885
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 885
cauccuagcu gaugccaauc                                                   20

<210> SEQ ID NO 886
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 886
cauccacuac uuugacuguc                                                   20

<210> SEQ ID NO 887
<211> LENGTH: 20
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 887
aggcacaggu uuccggacaa                                               20

<210> SEQ ID NO 888
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 888
gccagggguc ccacauagua                                               20

<210> SEQ ID NO 889
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 889
ucguaaagua aacugugcuu                                               20

<210> SEQ ID NO 890
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 890
caggcaguug cugacggacu                                               20

<210> SEQ ID NO 891
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 891
cugauucacc aauccaucac                                               20

<210> SEQ ID NO 892
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 892
ugccuauucu guccuaguag                                               20

<210> SEQ ID NO 893
<211> LENGTH: 20
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 893
gaugagcuag uuaaggucau                                                     20

<210> SEQ ID NO 894
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 894
aguaugcccu uuugauggc                                                      20

<210> SEQ ID NO 895
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 895
gggagacagg ugaaaucgua                                                     20

<210> SEQ ID NO 896
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 896
gauugaaucg uccuucaaaa                                                     20

<210> SEQ ID NO 897
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 897
cuguucuccg cuuagaaagg                                                     20

<210> SEQ ID NO 898
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 898
aagaucuacu gcgaaagcag                                                     20

<210> SEQ ID NO 899
<211> LENGTH: 20
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 899
uugucugaac uugacaaggc                                               20

<210> SEQ ID NO 900
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 900
ugcggcugga gcgccgaggu                                               20

<210> SEQ ID NO 901
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 901
cauguauguu gaucaggaac                                               20

<210> SEQ ID NO 902
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 902
gacaaucuac uggcacaaau                                               20

<210> SEQ ID NO 903
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 903
ccuugaggcg aaagguuaca                                               20

<210> SEQ ID NO 904
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 904
gcuuaauacu uuguccagau                                               20

<210> SEQ ID NO 905
<211> LENGTH: 20
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 905
aggugaaauc guaugggaua                                                   20

<210> SEQ ID NO 906
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 906
aaggcacagg uuuccggaca                                                   20

<210> SEQ ID NO 907
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 907
aucguccuuc aaaaaggauu                                                   20

<210> SEQ ID NO 908
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 908
cagcugcaua aaguuccuau                                                   20

<210> SEQ ID NO 909
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 909
gaucuuaaag gagcauccug                                                   20

<210> SEQ ID NO 910
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 910
guaccuuuug aucauugaag                                                   20

<210> SEQ ID NO 911
<211> LENGTH: 20
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 911
ugaagaucgg gaaaugauug                                                     20

<210> SEQ ID NO 912
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 912
ugccaaauug cagcuuagua                                                     20

<210> SEQ ID NO 913
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 913
ggaugagcua guuaagguca                                                     20

<210> SEQ ID NO 914
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 914
cgauuccuuu gaaaacccuc                                                     20

<210> SEQ ID NO 915
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 915
cuucuguucu ccgcuuagaa                                                     20

<210> SEQ ID NO 916
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 916
uuugaggaag uugucgauaa                                                     20

<210> SEQ ID NO 917
<211> LENGTH: 20
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 917
ucaaaauacu ugaaugcggc                                                   20

<210> SEQ ID NO 918
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 918
acugggcagc cagaucuuaa                                                   20

<210> SEQ ID NO 919
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 919
gauagauuug ucacagcuug                                                   20

<210> SEQ ID NO 920
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 920
ccuugagaag ugucaagucu                                                   20

<210> SEQ ID NO 921
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 921
aucucgauua caauguuuuc                                                   20

<210> SEQ ID NO 922
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 922
ucacgauugu cuuugaggaa                                                   20

<210> SEQ ID NO 923
<211> LENGTH: 20
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 923
cuggaguaug cccuuuuuga                                              20

<210> SEQ ID NO 924
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 924
aaaguuucuc guucugcaau                                              20

<210> SEQ ID NO 925
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 925
uuguuuacuc uuaccaaccu                                              20

<210> SEQ ID NO 926
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 926
aagcgcauac aacaagcaca                                              20

<210> SEQ ID NO 927
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 927
aaucguccuu caaaaaggau                                              20

<210> SEQ ID NO 928
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 928
ugcaauuggg uauuuuccac                                              20

<210> SEQ ID NO 929
<211> LENGTH: 20
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 929
cucucaguau gucagauagg                                                      20

<210> SEQ ID NO 930
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 930
ugcuucuguu cguuaucuuc                                                      20

<210> SEQ ID NO 931
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 931
ggauagauuu gucacagcuu                                                      20

<210> SEQ ID NO 932
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 932
uguaccccaa uccuuuuuga                                                      20

<210> SEQ ID NO 933
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 933
uggcuugucu gaacuugaca                                                      20

<210> SEQ ID NO 934
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 934
aagggacaug uauguugauc                                                      20

<210> SEQ ID NO 935
<211> LENGTH: 20
<212> TYPE: RNA
<213> ORGANISM: Artificial Sequence
<220> FEATURE:
```

<223> OTHER INFORMATION: Description of Artificial Sequence: Synthetic
      oligonucleotide

<400> SEQUENCE: 935
gauuucaccu gucuccccau                                                    20

<210> SEQ ID NO 936
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 936
uuaggcaaua cuuuuucguu                                                    20

<210> SEQ ID NO 937
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 937
uaacucucag uaugucagau                                                    20

<210> SEQ ID NO 938
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 938
guuccccuuu ugaagcucuc                                                    20

<210> SEQ ID NO 939
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 939
ucaguaugcg gacuuauuuu                                                    20

<210> SEQ ID NO 940
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 940
ucucaacuuu ugccacuacu                                                    20

<210> SEQ ID NO 941
<211> LENGTH: 20
<212> TYPE: RNA

```
<213> ORGANISM: Artificial Sequence
<220> FEATURE:
<223> OTHER INFORMATION: Description of Artificial Sequence: Synthetic
      oligonucleotide

<400> SEQUENCE: 941
gauuauaggu uuguacuaac                                               20

<210> SEQ ID NO 942
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 942
gaccuuuaau ugaaaccaau                                               20

<210> SEQ ID NO 943
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 943
aggaaucgau ucuuccaaaa                                               20

<210> SEQ ID NO 944
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 944
cuuuaagacg gaaaucacuc                                               20

<210> SEQ ID NO 945
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 945
aaguuucucg uucugcaauu                                               20

<210> SEQ ID NO 946
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 946
gugcaacaug cuuugugauu                                               20

<210> SEQ ID NO 947
<211> LENGTH: 20
<212> TYPE: RNA
<213> ORGANISM: Artificial Sequence
```

<220> FEATURE:
<223> OTHER INFORMATION: Description of Artificial Sequence: Synthetic
      oligonucleotide

<400> SEQUENCE: 947
auugaaacca augggagac                                                      20

<210> SEQ ID NO 948
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 948
acuccagaca gucaaaguag                                                     20

<210> SEQ ID NO 949
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 949
aauugcaugc uauacuuaga                                                     20

<210> SEQ ID NO 950
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 950
aacucaaaca gacuauacuu                                                     20

<210> SEQ ID NO 951
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 951
gauuacucca uggaauuuug                                                     20

<210> SEQ ID NO 952
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 952
ggaaaacauu guaaucgaga                                                     20

<210> SEQ ID NO 953
<211> LENGTH: 20
<212> TYPE: RNA
<213> ORGANISM: Artificial Sequence
<220> FEATURE:

<223> OTHER INFORMATION: Description of Artificial Sequence: Synthetic
      oligonucleotide

<400> SEQUENCE: 953
aguaguggau gagcuaguua                                           20

<210> SEQ ID NO 954
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 954
caggaugcuc cuuuaagauc                                           20

<210> SEQ ID NO 955
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 955
cauugagggu gaucuaaauc                                           20

<210> SEQ ID NO 956
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 956
ccaagacuug acacuucuca                                           20

<210> SEQ ID NO 957
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 957
uccccauugg uuucaauuaa                                           20

<210> SEQ ID NO 958
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 958
auaacuuaac uaaagcugag                                           20

<210> SEQ ID NO 959
<211> LENGTH: 20
<212> TYPE: RNA

```
<213> ORGANISM: Artificial Sequence
<220> FEATURE:
<223> OTHER INFORMATION: Description of Artificial Sequence: Synthetic
      oligonucleotide

<400> SEQUENCE: 959
cccauccauc uucucuaaua                                                      20

<210> SEQ ID NO 960
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 960
gagaacccua uaaaugcaag                                                      20

<210> SEQ ID NO 961
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 961
aaaacugagg ugcagaccgg                                                      20

<210> SEQ ID NO 962
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 962
ggcaaaaaaa cagucgagag                                                      20

<210> SEQ ID NO 963
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 963
aggaaauuca cguauuuaga                                                      20

<210> SEQ ID NO 964
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 964
aagcgaacag gagauaggca                                                      20

<210> SEQ ID NO 965
<211> LENGTH: 20
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 965
ucuuacccuc uuugaagauc                                                      20

<210> SEQ ID NO 966
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 966
cccuggcccg agggaacucu                                                      20

<210> SEQ ID NO 967
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 967
cgaaaucaua gagcaaauuu                                                      20

<210> SEQ ID NO 968
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 968
uucuuugauc agucgaaaaa                                                      20

<210> SEQ ID NO 969
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 969
ugacucuuua accuucaaag                                                      20

<210> SEQ ID NO 970
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 970
aggacagaau aggcaacugu                                                      20

<210> SEQ ID NO 971
<211> LENGTH: 20
<212> TYPE: RNA
<213> ORGANISM: Artificial Sequence
<220> FEATURE:
```

<223> OTHER INFORMATION: Description of Artificial Sequence: Synthetic
      oligonucleotide

<400> SEQUENCE: 971
aguuaauacu gagauuacca                                               20

<210> SEQ ID NO 972
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 972
accuuuaauu gaaaccaaug                                               20

<210> SEQ ID NO 973
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 973
auuccacauc aaauccacuu                                               20

<210> SEQ ID NO 974
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 974
agcuuaucac uauuccuuuu                                               20

<210> SEQ ID NO 975
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 975
uguccagauu ggcaucagcu                                               20

<210> SEQ ID NO 976
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 976
gaaaguuaag uaugucacug                                               20

<210> SEQ ID NO 977
<211> LENGTH: 20
<212> TYPE: RNA

```
<213> ORGANISM: Artificial Sequence
<220> FEATURE:
<223> OTHER INFORMATION: Description of Artificial Sequence: Synthetic
      oligonucleotide

<400> SEQUENCE: 977
aacaugcuuu gugauuuggc                                                   20

<210> SEQ ID NO 978
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 978
cauuucccga ucuucaaaga                                                   20

<210> SEQ ID NO 979
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 979
ccauauuaga gaagauggau                                                   20

<210> SEQ ID NO 980
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 980
uaccucuauu accuacaaaa                                                   20

<210> SEQ ID NO 981
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 981
auagauuugu cacagcuugg                                                   20

<210> SEQ ID NO 982
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 982
gguugguaag aguaaacaaa                                                   20

<210> SEQ ID NO 983
<211> LENGTH: 20
<212> TYPE: RNA
<213> ORGANISM: Artificial Sequence
```

<220> FEATURE:
<223> OTHER INFORMATION: Description of Artificial Sequence: Synthetic
      oligonucleotide

<400> SEQUENCE: 983 ucauucccg aucuucaaag                                              20

<210> SEQ ID NO 984
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 984
acggaaauca cucuggcaaa                                             20

<210> SEQ ID NO 985
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 985
ugaagguuaa agagucauca                                             20

<210> SEQ ID NO 986
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 986
cucuucaaac aacugauuau                                             20

<210> SEQ ID NO 987
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 987
cuucauucuc uucguuaucc                                             20

<210> SEQ ID NO 988
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 988
auacaaaagg cacagguuuc                                             20

<210> SEQ ID NO 989
<211> LENGTH: 20
<212> TYPE: RNA
<213> ORGANISM: Artificial Sequence
<220> FEATURE:

```
<223> OTHER INFORMATION: Description of Artificial Sequence: Synthetic
      oligonucleotide

<400> SEQUENCE: 989
guaguggcaa aaguugagaa                                                    20

<210> SEQ ID NO 990
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 990
agucagucaa agaauuauug                                                    20

<210> SEQ ID NO 991
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 991
gcaacugccu gagaaauaua                                                    20

<210> SEQ ID NO 992
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 992
cuagaaagug aguuugugua                                                    20

<210> SEQ ID NO 993
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 993
gaacauuguc acuuuucccu                                                    20

<210> SEQ ID NO 994
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 994
cccauauuag agaagaugga                                                    20

<210> SEQ ID NO 995
<211> LENGTH: 20
<212> TYPE: RNA
```

<213> ORGANISM: Artificial Sequence
<220> FEATURE:
<223> OTHER INFORMATION: Description of Artificial Sequence: Synthetic
      oligonucleotide

<400> SEQUENCE: 995
caacaugcuu ugugauuugg                                              20

<210> SEQ ID NO 996
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 996 acaugcccu uccauuugu                                                20

<210> SEQ ID NO 997
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 997
cucuuacccu cuuugaagau                                              20

<210> SEQ ID NO 998
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 998
acaaauugga gaucaguaug                                              20

<210> SEQ ID NO 999
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 999
aaacugaggu gcagaccgga                                              20

<210> SEQ ID NO 1000
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1000
uacccggaga gaagaaaaau                                              20

<210> SEQ ID NO 1001
<211> LENGTH: 20
<212> TYPE: RNA
<213> ORGANISM: Artificial Sequence

```
<220> FEATURE:
<223> OTHER INFORMATION: Description of Artificial Sequence: Synthetic
      oligonucleotide

<400> SEQUENCE: 1001
uuaacuaaag cugagagggg                                                     20

<210> SEQ ID NO 1002
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1002
gaagucaguc aaagaauuau                                                     20

<210> SEQ ID NO 1003
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1003
aaaguuaagu augucacuga                                                     20

<210> SEQ ID NO 1004
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1004
ucuauuaccu acaaaaugga                                                     20

<210> SEQ ID NO 1005
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1005
aacuuaacua aagcugagag                                                     20

<210> SEQ ID NO 1006
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1006
aauuaaagau aaggacuucc                                                     20

<210> SEQ ID NO 1007
<211> LENGTH: 20
<212> TYPE: RNA
<213> ORGANISM: Artificial Sequence
<220> FEATURE:
```

<223> OTHER INFORMATION: Description of Artificial Sequence: Synthetic
      oligonucleotide

<400> SEQUENCE: 1007
aguaguggca aaaguugaga                                               20

<210> SEQ ID NO 1008
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1008
agaggauaua caaaaggcac                                               20

<210> SEQ ID NO 1009
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1009
ucuuuucacg auugucuuug                                               20

<210> SEQ ID NO 1010
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1010
caaacccaua uuagagaaga                                               20

<210> SEQ ID NO 1011
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1011
ugugucaaaa uacuugaaug                                               20

<210> SEQ ID NO 1012
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1012
gacaguuaag caauugaaag                                               20

<210> SEQ ID NO 1013
<211> LENGTH: 20
<212> TYPE: RNA

```
<213> ORGANISM: Artificial Sequence
<220> FEATURE:
<223> OTHER INFORMATION: Description of Artificial Sequence: Synthetic
      oligonucleotide

<400> SEQUENCE: 1013
gaagagggua uuaaagaacu                                                   20

<210> SEQ ID NO 1014
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1014
uuccauuuug uagguaauag                                                   20

<210> SEQ ID NO 1015
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1015
gcggaugaag agaauagaag                                                   20

<210> SEQ ID NO 1016
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1016
cuauuaccua caaaauggaa                                                   20

<210> SEQ ID NO 1017
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1017
auugcuuaac ugucacuuug                                                   20

<210> SEQ ID NO 1018
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1018
agucuguuug aguuagaaaa                                                   20

<210> SEQ ID NO 1019
<211> LENGTH: 20
<212> TYPE: RNA
<213> ORGANISM: Artificial Sequence
```

<220> FEATURE:
<223> OTHER INFORMATION: Description of Artificial Sequence: Synthetic
      oligonucleotide

<400> SEQUENCE: 1019
acaaacucac uuucuagcuu                                                      20

<210> SEQ ID NO 1020
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1020
aaaaucaaac gacucagaag                                                      20

<210> SEQ ID NO 1021
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1021
agaagagggu auuaaagaac                                                      20

<210> SEQ ID NO 1022
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1022
caaacucacu uucuagcuuc                                                      20

<210> SEQ ID NO 1023
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1023
uuacccggag agaagaaaaa                                                      20

<210> SEQ ID NO 1024
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1024
auuucucagg caguugcuga                                                      20

<210> SEQ ID NO 1025
<211> LENGTH: 20
<212> TYPE: RNA
<213> ORGANISM: Artificial Sequence
<220> FEATURE:

```
<223> OTHER INFORMATION: Description of Artificial Sequence: Synthetic
      oligonucleotide

<400> SEQUENCE: 1025
aguuagaaaa uggccgaaaa                                              20

<210> SEQ ID NO 1026
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1026
uaacuuaacu aaagcugaga                                              20

<210> SEQ ID NO 1027
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1027
ggacagaaua ggcaacugua                                              20

<210> SEQ ID NO 1028
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1028
aagucaguca aagaauuauu                                              20

<210> SEQ ID NO 1029
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1029
agguuaugaa acaguuaaag                                              20

<210> SEQ ID NO 1030
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1030
uuugacugac uucaguuucu                                              20

<210> SEQ ID NO 1031
<211> LENGTH: 20
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 1031
caacccauuu uucuucucuc                                              20

<210> SEQ ID NO 1032
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1032
ucguccuuca aaaggauug                                               20

<210> SEQ ID NO 1033
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1033
uacuauguug acuuggggca                                              20

<210> SEQ ID NO 1034
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1034
ugcuauacuu agaaggcagg                                              20

<210> SEQ ID NO 1035
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1035
acaacuuccu caaaauucca                                              20

<210> SEQ ID NO 1036
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1036
uuuaaaguca aaauuggugu                                              20

<210> SEQ ID NO 1037
<211> LENGTH: 20
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 1037
cggaugaaga gaauagaaga                                                    20

<210> SEQ ID NO 1038
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1038
cuuuuguaua uccucuuuga                                                    20

<210> SEQ ID NO 1039
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1039
aacccauuuu ucuucucucc                                                    20

<210> SEQ ID NO 1040
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1040
ccauccaucu ucucuaauau                                                    20

<210> SEQ ID NO 1041
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1041
auuagagaag auggauggga                                                    20

<210> SEQ ID NO 1042
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1042
acugauucac caauccauca                                                    20

<210> SEQ ID NO 1043
<211> LENGTH: 20
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 1043
ccuaaagaua auuaaagaua                                                    20

<210> SEQ ID NO 1044
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1044
gggauaagag acaagcaaag                                                    20

<210> SEQ ID NO 1045
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1045
uucuuuacua uguugacuug                                                    20

<210> SEQ ID NO 1046
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1046
gaaaaucaaa cgacucagaa                                                    20

<210> SEQ ID NO 1047
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1047
uuucuuuacu auguugacuu                                                    20

<210> SEQ ID NO 1048
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1048
ccuuaucuuu aauuaucuuu                                                    20

<210> SEQ ID NO 1049
<211> LENGTH: 20
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 1049
aaucacuuua aagucaaaau                                                   20

<210> SEQ ID NO 1050
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1050 agaaaugaa gaacuauugg                                                    20

<210> SEQ ID NO 1051
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1051
guuagaauaa aagaaguauu                                                   20

<210> SEQ ID NO 1052
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1052
caacauagua aagaaaacug                                                   20

<210> SEQ ID NO 1053
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1053
agguuacaag gaaguaaaaa                                                   20

<210> SEQ ID NO 1054
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1054
uaucuuuaau uaucuuuagg                                                   20

<210> SEQ ID NO 1055
<211> LENGTH: 20
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 1055
gagaagaaaa auggguuguu                                                     20

<210> SEQ ID NO 1056
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1056
cauuaugaau uucuuuaaga                                                     20

<210> SEQ ID NO 1057
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1057
uuuucuuuac uauguugacu                                                     20

<210> SEQ ID NO 1058
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1058
auuuucaauu cuauaaaguu                                                     20

<210> SEQ ID NO 1059
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1059
aauauuuccu uauauuucuc                                                     20

<210> SEQ ID NO 1060
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1060
uuuucaauuc uauaaaguua                                                     20

<210> SEQ ID NO 1061
<211> LENGTH: 20
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 1061
uaaagaaaau gaagaacuau                                               20

<210> SEQ ID NO 1062
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1062
aagaaaacug aggugcagac                                               20

<210> SEQ ID NO 1063
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1063
cuucaaagag gauauacaaa                                               20

<210> SEQ ID NO 1064
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1064
ggacaucggg auuacaagcg                                               20

<210> SEQ ID NO 1065
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1065
guaaucccga uguccagccc                                               20

<210> SEQ ID NO 1066

<400> SEQUENCE: 1066

000

<210> SEQ ID NO 1067

<400> SEQUENCE: 1067

000

<210> SEQ ID NO 1068
<211> LENGTH: 20
<212> TYPE: RNA
<213> ORGANISM: Artificial Sequence
<220> FEATURE:
```

<223> OTHER INFORMATION: Description of Artificial Sequence: Synthetic
      oligonucleotide

<400> SEQUENCE: 1068
ggaauuaauc cuuaugaagc                                                    20

<210> SEQ ID NO 1069
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1069
gccuuucacc cuggcuucau                                                    20

<210> SEQ ID NO 1070
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1070
cugcaccugg cuaagcgccg                                                    20

<210> SEQ ID NO 1071
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1071
accgaccauu cugagcugag                                                    20

<210> SEQ ID NO 1072
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1072
ugcugaccga ccauucugag                                                    20

<210> SEQ ID NO 1073
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1073
aacagcaguu ucuucacccu                                                    20

<210> SEQ ID NO 1074
<211> LENGTH: 20
<212> TYPE: RNA

```
<213> ORGANISM: Artificial Sequence
<220> FEATURE:
<223> OTHER INFORMATION: Description of Artificial Sequence: Synthetic
      oligonucleotide

<400> SEQUENCE: 1074
aggauuaauu ccacucagcu                                               20

<210> SEQ ID NO 1075
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1075
uacauucugg ggcuggacau                                               20

<210> SEQ ID NO 1076
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1076
augaagccag ggugaaaggc                                               20

<210> SEQ ID NO 1077

<400> SEQUENCE: 1077

000

<210> SEQ ID NO 1078

<400> SEQUENCE: 1078

000

<210> SEQ ID NO 1079
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1079
cugaaacgac ggagaaggca                                               20

<210> SEQ ID NO 1080
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1080
cggagaaggc acagaaucca                                               20

<210> SEQ ID NO 1081
<211> LENGTH: 20
<212> TYPE: RNA
```

<213> ORGANISM: Artificial Sequence
<220> FEATURE:
<223> OTHER INFORMATION: Description of Artificial Sequence: Synthetic
      oligonucleotide

<400> SEQUENCE: 1081
gagucagaag cugucagagg                                                    20

<210> SEQ ID NO 1082
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1082
gaagaaagau ggcgagguga                                                    20

<210> SEQ ID NO 1083
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1083
gggauuacaa gcgugggua                                                     20

<210> SEQ ID NO 1084
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1084
gauacgcuac ucgcggccug                                                    20

<210> SEQ ID NO 1085
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1085
augaucgacc ucguaguuga                                                    20

<210> SEQ ID NO 1086
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1086
augaaugaua agcgcccccc                                                    20

<210> SEQ ID NO 1087
<211> LENGTH: 20
<212> TYPE: RNA
<213> ORGANISM: Artificial Sequence

```
<220> FEATURE:
<223> OTHER INFORMATION: Description of Artificial Sequence: Synthetic
      oligonucleotide

<400> SEQUENCE: 1087
acgcagaucu guacaacgcc                                                    20

<210> SEQ ID NO 1088
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1088
acuacaagua cucucaccgg                                                    20

<210> SEQ ID NO 1089
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1089
cgccguuguc cagauagaca                                                    20

<210> SEQ ID NO 1090
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1090
ucauugagaa cgccgaacug                                                    20

<210> SEQ ID NO 1091
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1091
uaauaugauc gaccucguag                                                    20

<210> SEQ ID NO 1092
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1092
gcguucucuu ucccgguagu                                                    20

<210> SEQ ID NO 1093
<211> LENGTH: 20
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 1093
ggcgaacugu auaggucau                                                      20

<210> SEQ ID NO 1094
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1094
gcccgaaauc gagacagaac                                                     20

<210> SEQ ID NO 1095
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1095
aucugcugaa ccgcauugaa                                                     20

<210> SEQ ID NO 1096
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1096
ccguucagau uguucacaau                                                     20

<210> SEQ ID NO 1097
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1097
ucggagcucu gguagauagu                                                     20

<210> SEQ ID NO 1098
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1098
gaccaccuug uugcgacugu                                                     20

<210> SEQ ID NO 1099
<211> LENGTH: 20
<212> TYPE: RNA
<213> ORGANISM: Artificial Sequence
```

<220> FEATURE:
<223> OTHER INFORMATION: Description of Artificial Sequence: Synthetic
      oligonucleotide

<400> SEQUENCE: 1099
uuuguaugcc acagcucauc                                                    20

<210> SEQ ID NO 1100
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1100
gggcuuuuua uccacccggu                                                    20

<210> SEQ ID NO 1101
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1101
guugaguacu uuuugauacu                                                    20

<210> SEQ ID NO 1102
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1102
aagaucaaug gcgaacugua                                                    20

<210> SEQ ID NO 1103
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1103
gaaagucaag uccaucaacg                                                    20

<210> SEQ ID NO 1104
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1104
ggucccucau aguagguucu                                                    20

<210> SEQ ID NO 1105
<211> LENGTH: 20
<212> TYPE: RNA
<213> ORGANISM: Artificial Sequence
<220> FEATURE:

-continued

<223> OTHER INFORMATION: Description of Artificial Sequence: Synthetic
      oligonucleotide

<400> SEQUENCE: 1105
ccuauuuccg ggugaacaau                                              20

<210> SEQ ID NO 1106
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1106
cgcagcagau ucaucaggcc                                              20

<210> SEQ ID NO 1107
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1107
cagguuuccc agaaugucgg                                              20

<210> SEQ ID NO 1108
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1108
cgaacagauu aguaaucuga                                              20

<210> SEQ ID NO 1109
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1109
ccagauuguu cacccggaaa                                              20

<210> SEQ ID NO 1110
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1110
aaaucgucca ccaguguggu                                              20

<210> SEQ ID NO 1111
<211> LENGTH: 20
<212> TYPE: RNA

```
<213> ORGANISM: Artificial Sequence
<220> FEATURE:
<223> OTHER INFORMATION: Description of Artificial Sequence: Synthetic
      oligonucleotide

<400> SEQUENCE: 1111
cuucggaugg aaagacauca                                              20

<210> SEQ ID NO 1112
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1112
aaaugccgac uucaucuuua                                              20

<210> SEQ ID NO 1113
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1113
ucaacagauu cuccguccag                                              20

<210> SEQ ID NO 1114
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1114
gcguugauca cuuugaugcu                                              20

<210> SEQ ID NO 1115
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1115
aaggacuaca aguacucuca                                              20

<210> SEQ ID NO 1116
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1116
cuccgcuuga ccacggguga                                              20

<210> SEQ ID NO 1117
<211> LENGTH: 20
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 1117
ggugacaagc acuggaaaac                                                20

<210> SEQ ID NO 1118
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1118
accugaccaa guauagcaaa                                                20

<210> SEQ ID NO 1119
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1119
ggaugaagcu ccgcuugacc                                                20

<210> SEQ ID NO 1120
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1120
ccgcaucagc aagaccaaaa                                                20

<210> SEQ ID NO 1121
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1121
uccagaagga uuuuauuaac                                                20

<210> SEQ ID NO 1122
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1122
uugauaugcu ugaucuggug                                                20

<210> SEQ ID NO 1123
<211> LENGTH: 20
<212> TYPE: RNA
<213> ORGANISM: Artificial Sequence
<220> FEATURE:
```

<223> OTHER INFORMATION: Description of Artificial Sequence: Synthetic
      oligonucleotide

<400> SEQUENCE: 1123
uguauaaauu ugugacuguc                                          20

<210> SEQ ID NO 1124
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1124
cucaccagau caagcauauc                                          20

<210> SEQ ID NO 1125
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1125
ugcagaaggc uuaccaccag                                          20

<210> SEQ ID NO 1126
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1126
uugauguccu cuucguugac                                          20

<210> SEQ ID NO 1127
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1127
cuaaucuguu cgaucucuuc                                          20

<210> SEQ ID NO 1128
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1128
gaccagcacc uuguuguuaa                                          20

<210> SEQ ID NO 1129
<211> LENGTH: 20
<212> TYPE: RNA

<213> ORGANISM: Artificial Sequence
<220> FEATURE:
<223> OTHER INFORMATION: Description of Artificial Sequence: Synthetic
      oligonucleotide

<400> SEQUENCE: 1129
gaagaggaca ucaagggcua                                           20

<210> SEQ ID NO 1130
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1130
uaauaaaauc cuucuggacg                                           20

<210> SEQ ID NO 1131
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1131
uggucccaaa aaagguggac                                           20

<210> SEQ ID NO 1132
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1132
cucuucauag uacuuauaca                                           20

<210> SEQ ID NO 1133
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1133
aaucugcugc gauccuauuu                                           20

<210> SEQ ID NO 1134
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1134
gaacuagaca gguacuggaa                                           20

<210> SEQ ID NO 1135
<211> LENGTH: 20
<212> TYPE: RNA
<213> ORGANISM: Artificial Sequence

```
<220> FEATURE:
<223> OTHER INFORMATION: Description of Artificial Sequence: Synthetic
      oligonucleotide

<400> SEQUENCE: 1135
aaagguuucg uaagagaucu                                                    20

<210> SEQ ID NO 1136
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1136
cccuuuccuu uggccagauu                                                    20

<210> SEQ ID NO 1137
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1137
ucgucuuuuc uuguacuaua                                                    20

<210> SEQ ID NO 1138
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1138
aggaguccua uugcccuuuu                                                    20

<210> SEQ ID NO 1139
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1139
uaugauugac aucacuuacc                                                    20

<210> SEQ ID NO 1140
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1140
uucaccucau acagguuucc                                                    20

<210> SEQ ID NO 1141
<211> LENGTH: 20
<212> TYPE: RNA
<213> ORGANISM: Artificial Sequence
<220> FEATURE:
```

<223> OTHER INFORMATION: Description of Artificial Sequence: Synthetic
      oligonucleotide

<400> SEQUENCE: 1141
cuccaggggg auggccucca                                                    20

<210> SEQ ID NO 1142
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1142
ugaaagcuau caaucugauu                                                    20

<210> SEQ ID NO 1143
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1143
ucaaguacua ugggaacaag                                                    20

<210> SEQ ID NO 1144
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1144
ugaacaaccu ggucaucacc                                                    20

<210> SEQ ID NO 1145
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1145
uuguucagca gguccuccag                                                    20

<210> SEQ ID NO 1146
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1146
accgagagua ucuggaaaac                                                    20

<210> SEQ ID NO 1147
<211> LENGTH: 20
<212> TYPE: RNA

```
<213> ORGANISM: Artificial Sequence
<220> FEATURE:
<223> OTHER INFORMATION: Description of Artificial Sequence: Synthetic
      oligonucleotide

<400> SEQUENCE: 1147
guuuaaaaag gagcgcaaca                                                    20

<210> SEQ ID NO 1148
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1148
cuucaguuuc ugauaugucu                                                    20

<210> SEQ ID NO 1149
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1149
aaacaauugc cucuaagacu                                                    20

<210> SEQ ID NO 1150
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1150 gaaaagauu agcaaccagg                                                     20

<210> SEQ ID NO 1151
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1151
cagggaugaa aacgagaaac                                                    20

<210> SEQ ID NO 1152
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1152
uucagguuag ucagcucuuc                                                    20

<210> SEQ ID NO 1153
<211> LENGTH: 20
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 1153
uugucgaagg acacgcuucu                                              20

<210> SEQ ID NO 1154
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1154
aaaccuuuaa aaagcacauu                                              20

<210> SEQ ID NO 1155
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1155
accaggagaa gggagccccu                                              20

<210> SEQ ID NO 1156
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1156
guacaagaaa agacgauaag                                              20

<210> SEQ ID NO 1157
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1157
gauguucgaa gagaagcagg                                              20

<210> SEQ ID NO 1158
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1158
aaaaggagaa cuacuaugaa                                              20

<210> SEQ ID NO 1159
<211> LENGTH: 20
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 1159
aauuugugac ugucaagaau                                                    20

<210> SEQ ID NO 1160
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1160
gaagcaggcc gaaucuaugc                                                    20

<210> SEQ ID NO 1161
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1161
aggaauggua cgagaugcug                                                    20

<210> SEQ ID NO 1162
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1162
uccgggugaa caaucuggau                                                    20

<210> SEQ ID NO 1163
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1163
agacucggag aaccuacuau                                                    20

<210> SEQ ID NO 1164
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1164
ggacgcacag aagaugauca                                                    20

<210> SEQ ID NO 1165
<211> LENGTH: 20
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 1165
ucacauccag auuguucacc                                                       20

<210> SEQ ID NO 1166
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1166
ggagaaggga gccccuucgg                                                       20

<210> SEQ ID NO 1167
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1167
ccggcaacga gcugucuaca                                                       20

<210> SEQ ID NO 1168
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1168
aaguacucaa ccgacauucu                                                       20

<210> SEQ ID NO 1169
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1169
aaugacaccc uguauaguac                                                       20

<210> SEQ ID NO 1170
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1170
acuguucaag gaggccaacg                                                       20

<210> SEQ ID NO 1171
<211> LENGTH: 20
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 1171
ccgacuucau cuuuaaggag                                                  20

<210> SEQ ID NO 1172
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1172
gaaucugaac uagacaggua                                                  20

<210> SEQ ID NO 1173
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1173
cggguggaua aaaagcccaa                                                  20

<210> SEQ ID NO 1174
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1174
accagagcuc cgaggacauc                                                  20

<210> SEQ ID NO 1175
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1175
ggugguacau cagcagcuuc                                                  20

<210> SEQ ID NO 1176
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1176
ccggaacaca caaccugucc                                                  20

<210> SEQ ID NO 1177
<211> LENGTH: 20
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 1177
gugcuuuuua aagguuucgu                                                 20

<210> SEQ ID NO 1178
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1178
uucacaucca gauuguucac                                                 20

<210> SEQ ID NO 1179
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1179
uuccagagcu uugcuauugc                                                 20

<210> SEQ ID NO 1180
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1180
acaucuuuuc ugaggcgcaa                                                 20

<210> SEQ ID NO 1181
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1181
aaagcugauc aacaaaaguc                                                 20

<210> SEQ ID NO 1182
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1182
gaaucuggau gucaucaaaa                                                 20

<210> SEQ ID NO 1183
<211> LENGTH: 20
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 1183
uauaaguacu augaagagac                                                    20

<210> SEQ ID NO 1184
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1184
caucacuuac cgagaguauc                                                    20

<210> SEQ ID NO 1185
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1185
uaucauuauc gagcuggcua                                                    20

<210> SEQ ID NO 1186
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1186
caaggugcug gucaagcagg                                                    20

<210> SEQ ID NO 1187
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1187
aaaguacuca accgacauuc                                                    20

<210> SEQ ID NO 1188
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1188
auugucgaag gacacgcuuc                                                    20

<210> SEQ ID NO 1189
<211> LENGTH: 20
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 1189
gagugcauaa cgucaaugag                                                    20

<210> SEQ ID NO 1190
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1190
aguaugucgc agagcugcag                                                    20

<210> SEQ ID NO 1191
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1191
gaaaucgucc accagugugg                                                    20

<210> SEQ ID NO 1192
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1192
accaugaucc ucagacauau                                                    20

<210> SEQ ID NO 1193
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1193
cuugacgcuu cucagcucuu                                                    20

<210> SEQ ID NO 1194
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1194
guauaaguac uaugaagaga                                                    20

<210> SEQ ID NO 1195
<211> LENGTH: 20
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 1195
gggguauggg auuauugacu                                               20

<210> SEQ ID NO 1196
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1196
cccacuguau aaguacuaug                                               20

<210> SEQ ID NO 1197
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1197
ucgaaaacgu guuuaagcag                                               20

<210> SEQ ID NO 1198
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1198
agaccaaaaa ggaguaccug                                               20

<210> SEQ ID NO 1199
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1199
uuaaacacgu uuucgaugau                                               20

<210> SEQ ID NO 1200
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1200
gcuugaccac gggugacaga                                               20

<210> SEQ ID NO 1201
<211> LENGTH: 20
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 1201
uuaaacuucc auuugcgccu                                                     20

<210> SEQ ID NO 1202
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1202
augagggacg gagaagcaag                                                     20

<210> SEQ ID NO 1203
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1203
cugacucagg uccaccuuuu                                                     20

<210> SEQ ID NO 1204
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1204
gaaagacauc aaggaauggu                                                     20

<210> SEQ ID NO 1205
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1205
uaaggacauc acagcacgga                                                     20

<210> SEQ ID NO 1206
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1206
aaaaggugga ccugagucag                                                     20

<210> SEQ ID NO 1207
<211> LENGTH: 20
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 1207
aauaugauug acaucacuua                                                   20

<210> SEQ ID NO 1208
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1208
gagaagggag ccccuucgga                                                   20

<210> SEQ ID NO 1209
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1209
gauuauccga acuaccggga                                                   20

<210> SEQ ID NO 1210
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1210
ucaaagaagc caagcagcug                                                   20

<210> SEQ ID NO 1211
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1211
ggugagagua cuuguagucc                                                   20

<210> SEQ ID NO 1212
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1212
accugaacag cgagcugacc                                                   20

<210> SEQ ID NO 1213
<211> LENGTH: 20
<212> TYPE: RNA
<213> ORGANISM: Artificial Sequence
<220> FEATURE:
```

<223> OTHER INFORMATION: Description of Artificial Sequence: Synthetic
      oligonucleotide

<400> SEQUENCE: 1213
gaccgaccau ucugagcuga                                          20

<210> SEQ ID NO 1214
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1214
gcuugaucug gugaggagug                                          20

<210> SEQ ID NO 1215
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1215
ugaccagcac cuuguuguua                                          20

<210> SEQ ID NO 1216
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1216
caagcugcac gauaugcagg                                          20

<210> SEQ ID NO 1217
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1217
uaaagguuuc guaagagauc                                          20

<210> SEQ ID NO 1218
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1218
gcaccuauuu uccagaagag                                          20

<210> SEQ ID NO 1219
<211> LENGTH: 20
<212> TYPE: RNA

```
<213> ORGANISM: Artificial Sequence
<220> FEATURE:
<223> OTHER INFORMATION: Description of Artificial Sequence: Synthetic
      oligonucleotide

<400> SEQUENCE: 1219
aaacgagaaa cuggaauacu                                                 20

<210> SEQ ID NO 1220
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1220
ugaagagauu auccgaacua                                                 20

<210> SEQ ID NO 1221
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1221
ggcugaagaa agauggcgag                                                 20

<210> SEQ ID NO 1222
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1222
guccagaagg auuuuauuaa                                                 20

<210> SEQ ID NO 1223
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1223
gaacagcgag cugacccagg                                                 20

<210> SEQ ID NO 1224
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1224
agaaccuacu augagggacc                                                 20

<210> SEQ ID NO 1225
<211> LENGTH: 20
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 1225
agccaggugc agcagagcug                                                   20

<210> SEQ ID NO 1226
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1226
cuacuaugag ggaccaggag                                                   20

<210> SEQ ID NO 1227
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1227
gaaaaccaga guucaccaau                                                   20

<210> SEQ ID NO 1228
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1228
acaacaaggu gcuggucaag                                                   20

<210> SEQ ID NO 1229
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1229
gcagaccaau gaacgcauug                                                   20

<210> SEQ ID NO 1230
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1230
ggaaaaagcu ggacaaagcc                                                   20

<210> SEQ ID NO 1231
<211> LENGTH: 20
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 1231
uucagauucc aagaucucuu                                                    20

<210> SEQ ID NO 1232
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1232
agcugcagcu ggaacggcug                                                    20

<210> SEQ ID NO 1233
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1233
gauuauggag caguacggcg                                                    20

<210> SEQ ID NO 1234
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1234
agaaucagau ugauagcuuu                                                    20

<210> SEQ ID NO 1235
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1235
uccuccaggg ggauggccuc                                                    20

<210> SEQ ID NO 1236
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1236
gggauuauug acuaugaaac                                                    20

<210> SEQ ID NO 1237
<211> LENGTH: 20
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 1237
ucucacgcaa uagcaaagcu                                                      20

<210> SEQ ID NO 1238
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1238
acguggaaaa caaugaggga                                                      20

<210> SEQ ID NO 1239
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1239
uugacgcuuc ucagcucuuc                                                      20

<210> SEQ ID NO 1240
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1240
gauaucauua ucgagcuggc                                                      20

<210> SEQ ID NO 1241
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1241
guuaauaaaa uccuucugga                                                      20

<210> SEQ ID NO 1242
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1242
caaccugguc aucaccaggg                                                      20

<210> SEQ ID NO 1243
<211> LENGTH: 20
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 1243
gcacauucug aaucuggcca                                                    20

<210> SEQ ID NO 1244
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1244
gguggaccug agucagcaga                                                    20

<210> SEQ ID NO 1245
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1245
auauuaagga caucacagca                                                    20

<210> SEQ ID NO 1246
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1246
cuacauucug gggcuggaca                                                    20

<210> SEQ ID NO 1247
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1247
gcaagagggg agccaggcgc                                                    20

<210> SEQ ID NO 1248
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1248
ccagggauga aaacgagaaa                                                    20

<210> SEQ ID NO 1249
<211> LENGTH: 20
<212> TYPE: RNA
<213> ORGANISM: Artificial Sequence
<220> FEATURE:
```

<223> OTHER INFORMATION: Description of Artificial Sequence: Synthetic
      oligonucleotide

<400> SEQUENCE: 1249
uagccaggug cagcagagcu                                                    20

<210> SEQ ID NO 1250
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1250
gggcuaccgg gugacaagca                                                    20

<210> SEQ ID NO 1251
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1251
ggucaucacc agggaugaaa                                                    20

<210> SEQ ID NO 1252
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1252
gagccaggcg ccugaaacga                                                    20

<210> SEQ ID NO 1253
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1253
gcuacgaaga ggcuaaaaag                                                    20

<210> SEQ ID NO 1254
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1254
ggacaaagcc aagaaaguga                                                    20

<210> SEQ ID NO 1255
<211> LENGTH: 20
<212> TYPE: RNA

<213> ORGANISM: Artificial Sequence
<220> FEATURE:
<223> OTHER INFORMATION: Description of Artificial Sequence: Synthetic
      oligonucleotide

<400> SEQUENCE: 1255
uugggcuuuu uauccacccg                                                   20

<210> SEQ ID NO 1256
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1256
gacuguucaa ggaggccaac                                                   20

<210> SEQ ID NO 1257
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1257
aaaaguacuc aaccgacauu                                                   20

<210> SEQ ID NO 1258
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1258
uaguaaucug aagggguaca                                                   20

<210> SEQ ID NO 1259
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1259
ggccgaaucu augcccgaaa                                                   20

<210> SEQ ID NO 1260
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1260
ucaagcugca cgauaugcag                                                   20

<210> SEQ ID NO 1261
<211> LENGTH: 20
<212> TYPE: RNA
<213> ORGANISM: Artificial Sequence

```
<220> FEATURE:
<223> OTHER INFORMATION: Description of Artificial Sequence: Synthetic
      oligonucleotide

<400> SEQUENCE: 1261
cugaacaacc uggucaucac                                                      20

<210> SEQ ID NO 1262
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1262
ggcacagaau ccagagggug                                                      20

<210> SEQ ID NO 1263
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1263
acgcaauagc aaagcucugg                                                      20

<210> SEQ ID NO 1264
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1264
agagaacgca aaguaccuga                                                      20

<210> SEQ ID NO 1265
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1265
ucaucaccag ggaugaaaac                                                      20

<210> SEQ ID NO 1266
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1266
aaggaguacc ugcuggaaga                                                      20

<210> SEQ ID NO 1267
<211> LENGTH: 20
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 1267
agcagaagaa aaagccuaca                                              20

<210> SEQ ID NO 1268
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1268
acaucacuua ccgagaguau                                              20

<210> SEQ ID NO 1269
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1269
cacagcacgg aaagaaauca                                              20

<210> SEQ ID NO 1270
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1270
agaagaugau caaugagaug                                              20

<210> SEQ ID NO 1271
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1271
aagcugcacg auaugcagga                                              20

<210> SEQ ID NO 1272
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1272
auuguucagc agguccucca                                              20

<210> SEQ ID NO 1273
<211> LENGTH: 20
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 1273
gauauuaagg acaucacagc                                                      20

<210> SEQ ID NO 1274
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1274
cuaugagaag uuccagauca                                                      20

<210> SEQ ID NO 1275
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1275
gaagagauua uccgaacuac                                                      20

<210> SEQ ID NO 1276
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1276
uacacugaaa cagauugcua                                                      20

<210> SEQ ID NO 1277
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1277
aguacaagaa aagacgauaa                                                      20

<210> SEQ ID NO 1278
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1278
cgggauuaca agcgugggu                                                       20

<210> SEQ ID NO 1279
<211> LENGTH: 20
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 1279
ggcuaccggg ugacaagcac                                                    20

<210> SEQ ID NO 1280
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1280
auaucgaccu gcuggagacu                                                    20

<210> SEQ ID NO 1281
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1281
uuaauccuua ugaagccagg                                                    20

<210> SEQ ID NO 1282
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1282
cgagacagaa caggaguaca                                                    20

<210> SEQ ID NO 1283
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1283
gaucaagaag aucaaguacu                                                    20

<210> SEQ ID NO 1284
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1284
gccgacuuca ucuuuaagga                                                    20

<210> SEQ ID NO 1285
<211> LENGTH: 20
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 1285
aagagauuau ccgaacuacc                                                  20

<210> SEQ ID NO 1286
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1286
augaucaaug agaugcagaa                                                  20

<210> SEQ ID NO 1287
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1287
aggccaacgu ggaaaacaau                                                  20

<210> SEQ ID NO 1288
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1288
aucaagaaga ucaaguacua                                                  20

<210> SEQ ID NO 1289
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1289
cacauucuga aucuggccaa                                                  20

<210> SEQ ID NO 1290
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1290
acgacaaaga uaaugacaag                                                  20

<210> SEQ ID NO 1291
<211> LENGTH: 20
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 1291
aaucugaacu agacagguac                                                    20

<210> SEQ ID NO 1292
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1292
gccugaguca gaagcuguca                                                    20

<210> SEQ ID NO 1293
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1293
cgauacuuau aucgaccugc                                                    20

<210> SEQ ID NO 1294
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1294
uaguacaaga aaagacgaua                                                    20

<210> SEQ ID NO 1295
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1295
ccuucggaug gaaagacauc                                                    20

<210> SEQ ID NO 1296
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1296
gauggagaac cagauguucg                                                    20

<210> SEQ ID NO 1297
<211> LENGTH: 20
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 1297
cggcgcuuag ccaggugcag                                                    20

<210> SEQ ID NO 1298
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1298
aguaaucuga agggguacac                                                    20

<210> SEQ ID NO 1299
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1299
cgaccugauu aagaucaaug                                                    20

<210> SEQ ID NO 1300
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1300
agcuaucaau cugauucugg                                                    20

<210> SEQ ID NO 1301
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1301
aaaggaacua cauucugggg                                                    20

<210> SEQ ID NO 1302
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1302
ggccaacgug gaaaacaaug                                                    20

<210> SEQ ID NO 1303
<211> LENGTH: 20
<212> TYPE: RNA
<213> ORGANISM: Artificial Sequence
<220> FEATURE:
```

<223> OTHER INFORMATION: Description of Artificial Sequence: Synthetic
      oligonucleotide

<400> SEQUENCE: 1303
ucuuuaagga guggaaaaag                                          20

<210> SEQ ID NO 1304
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1304
aggaguaccu gcuggaagag                                          20

<210> SEQ ID NO 1305
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1305
ugacuaucua ccagagcucc                                          20

<210> SEQ ID NO 1306
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1306
gugguacauc agcagcuucu                                          20

<210> SEQ ID NO 1307
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1307
aggagauccu ggucaacgaa                                          20

<210> SEQ ID NO 1308
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1308
uguuguuaaa ggaauugucg                                          20

<210> SEQ ID NO 1309
<211> LENGTH: 20
<212> TYPE: RNA

```
<213> ORGANISM: Artificial Sequence
<220> FEATURE:
<223> OTHER INFORMATION: Description of Artificial Sequence: Synthetic
      oligonucleotide

<400> SEQUENCE: 1309
acauugcacc uauuuuccag                                                    20

<210> SEQ ID NO 1310
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1310
gagaacucua aaagggcaa                                                     20

<210> SEQ ID NO 1311
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1311
agagcugacu aaccugaaca                                                    20

<210> SEQ ID NO 1312
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1312
cauacagauu cgaugucuau                                                    20

<210> SEQ ID NO 1313
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1313
uucugaaucu ggccaaagga                                                    20

<210> SEQ ID NO 1314
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1314
ugacucaggu ccaccuuuuu                                                    20

<210> SEQ ID NO 1315
<211> LENGTH: 20
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 1315
aacuguauag ggucaucggg                                                    20

<210> SEQ ID NO 1316
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1316
gaaucagauu gauagcuuuc                                                    20

<210> SEQ ID NO 1317
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1317
uggcuaggga gaagaacagc                                                    20

<210> SEQ ID NO 1318
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1318
uccaggaaga gcugacuaac                                                    20

<210> SEQ ID NO 1319
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1319
cuuugacgua gucgcuuguc                                                    20

<210> SEQ ID NO 1320
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1320
auaaguacua ugaagagacu                                                    20

<210> SEQ ID NO 1321
<211> LENGTH: 20
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 1321
uuccgguuaa uaaaauccuu                                                     20

<210> SEQ ID NO 1322
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1322
ugaagcuggu cccaaaaaag                                                     20

<210> SEQ ID NO 1323
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1323
uagauucggc cugcuucucu                                                     20

<210> SEQ ID NO 1324
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1324
ucaagaagau caaguacuau                                                     20

<210> SEQ ID NO 1325
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1325
auuuuauuaa ccggaaucug                                                     20

<210> SEQ ID NO 1326
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1326
ugggaaaccu guaugaggug                                                     20

<210> SEQ ID NO 1327
<211> LENGTH: 20
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 1327
ucagaaacug aagcugauua                                               20

<210> SEQ ID NO 1328
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1328
aggcuuacca ccagcuggau                                               20

<210> SEQ ID NO 1329
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1329
ugcugcgauc cuauuuccgg                                               20

<210> SEQ ID NO 1330
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1330
auaacgucaa ugagguggaa                                               20

<210> SEQ ID NO 1331
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1331
gaacgcauug aagagauuau                                               20

<210> SEQ ID NO 1332
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1332
uucugucacc cguggucaag                                               20

<210> SEQ ID NO 1333
<211> LENGTH: 20
<212> TYPE: RNA
<213> ORGANISM: Artificial Sequence
```

<220> FEATURE:
<223> OTHER INFORMATION: Description of Artificial Sequence: Synthetic
      oligonucleotide

<400> SEQUENCE: 1333
gcgcaaaugg aaguuuaaaa                                              20

<210> SEQ ID NO 1334
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1334
uaaacacguu uucgaugauc                                              20

<210> SEQ ID NO 1335
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1335
guacuugauc uucuugauca                                              20

<210> SEQ ID NO 1336
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1336
aagucggcau uugcgauaau                                              20

<210> SEQ ID NO 1337
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1337
cgagcugacc caggaagaga                                              20

<210> SEQ ID NO 1338
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1338
ucaagcauau caaggauuuc                                              20

<210> SEQ ID NO 1339
<211> LENGTH: 20
<212> TYPE: RNA
<213> ORGANISM: Artificial Sequence
<220> FEATURE:

<223> OTHER INFORMATION: Description of Artificial Sequence: Synthetic
      oligonucleotide

<400> SEQUENCE: 1339
aggugcuggu caagcaggaa                                                 20

<210> SEQ ID NO 1340
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1340
cucuggaggc caucccccug                                                 20

<210> SEQ ID NO 1341
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1341
acuaugaggg accaggagaa                                                 20

<210> SEQ ID NO 1342
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1342
gagcuccgag gacauccagg                                                 20

<210> SEQ ID NO 1343
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1343
caaaaaggag uaccugcugg                                                 20

<210> SEQ ID NO 1344
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1344
auacccugau ugugaacaau                                                 20

<210> SEQ ID NO 1345
<211> LENGTH: 20
<212> TYPE: RNA

```
<213> ORGANISM: Artificial Sequence
<220> FEATURE:
<223> OTHER INFORMATION: Description of Artificial Sequence: Synthetic
      oligonucleotide

<400> SEQUENCE: 1345
ucuggaagag aaguaugucg                                              20

<210> SEQ ID NO 1346
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1346
auaaggggaa uacccugauu                                              20

<210> SEQ ID NO 1347
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1347
ccagcucgau aaugauauca                                              20

<210> SEQ ID NO 1348
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1348
ggauuauuga cuaugaaaca                                              20

<210> SEQ ID NO 1349
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1349
gagggacgga gaagcaagag                                              20

<210> SEQ ID NO 1350
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1350
cagcucuucc uggauguccu                                              20

<210> SEQ ID NO 1351
<211> LENGTH: 20
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 1351
gaaagaaauc auugagaacg                                              20

<210> SEQ ID NO 1352
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1352
cagcacggaa agaaaucauu                                              20

<210> SEQ ID NO 1353
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1353
gacucggaga accuacuaug                                              20

<210> SEQ ID NO 1354
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1354
aagaugugaa cccgccguug                                              20

<210> SEQ ID NO 1355
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1355
gguggauaaa aagcccaaca                                              20

<210> SEQ ID NO 1356
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1356
ucggggugaa caaugaucug                                              20

<210> SEQ ID NO 1357
<211> LENGTH: 20
<212> TYPE: RNA
<213> ORGANISM: Artificial Sequence
<220> FEATURE:
```

<223> OTHER INFORMATION: Description of Artificial Sequence: Synthetic
      oligonucleotide

<400> SEQUENCE: 1357
uguacaacgc ccugaaugac                                               20

<210> SEQ ID NO 1358
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1358
acuccuguuc ugucucgauu                                               20

<210> SEQ ID NO 1359
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1359
aucuaugccc gaaaucgaga                                               20

<210> SEQ ID NO 1360
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1360
ggaacaagcu gaaugcccau                                               20

<210> SEQ ID NO 1361
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1361
accagguugu ucaggucauu                                               20

<210> SEQ ID NO 1362
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1362
acaaagccaa gaaagugaug                                               20

<210> SEQ ID NO 1363
<211> LENGTH: 20
<212> TYPE: RNA

```
<213> ORGANISM: Artificial Sequence
<220> FEATURE:
<223> OTHER INFORMATION: Description of Artificial Sequence: Synthetic
      oligonucleotide

<400> SEQUENCE: 1363
caaccugcug accgaccauu                                                   20

<210> SEQ ID NO 1364
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1364
aucuggaugu caucaaaaag                                                   20

<210> SEQ ID NO 1365
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1365
ccaucccccu ggaggaccug                                                   20

<210> SEQ ID NO 1366
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1366
ggucggucag cagguuguaa                                                   20

<210> SEQ ID NO 1367
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1367
ugaaagugua ucacgauauu                                                   20

<210> SEQ ID NO 1368
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1368
cuaagauccu gacuaucuac                                                   20

<210> SEQ ID NO 1369
<211> LENGTH: 20
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 1369
uggucaagcg gagcuucauc                                                    20

<210> SEQ ID NO 1370
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1370
cggcaacgag cugucuacaa                                                    20

<210> SEQ ID NO 1371
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1371
agcaggaaga gaacucuaaa                                                    20

<210> SEQ ID NO 1372
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1372
gaaacgaaac cggcagacca                                                    20

<210> SEQ ID NO 1373
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1373
cuugaugucu uuccauccga                                                    20

<210> SEQ ID NO 1374
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1374
ccugauugug aacaaucuga                                                    20

<210> SEQ ID NO 1375
<211> LENGTH: 20
<212> TYPE: RNA
<213> ORGANISM: Artificial Sequence
<220> FEATURE:
```

<223> OTHER INFORMATION: Description of Artificial Sequence: Synthetic
oligonucleotide

<400> SEQUENCE: 1375
uuaucgagcu ggcuagggag                                               20

<210> SEQ ID NO 1376
<211> LENGTH: 20
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1376
cgugauacac uuucagauug                                               20

<210> SEQ ID NO 1377
<211> LENGTH: 20
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1377
aagagauccc aaccacacug                                               20

<210> SEQ ID NO 1378
<211> LENGTH: 20
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1378
uucguaagag aucuuggaau                                               20

<210> SEQ ID NO 1379
<211> LENGTH: 20
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1379
ccugcccaau gauaucauua                                               20

<210> SEQ ID NO 1380
<211> LENGTH: 20
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1380
aucgaccugc uggagacucg                                               20

<210> SEQ ID NO 1381
<211> LENGTH: 20
<212> TYPE: RNA

```
<213> ORGANISM: Artificial Sequence
<220> FEATURE:
<223> OTHER INFORMATION: Description of Artificial Sequence: Synthetic
      oligonucleotide

<400> SEQUENCE: 1381 ugcauugau cagcucucug                                                    20

<210> SEQ ID NO 1382
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1382
uggagcagua cggcgacgag                                                   20

<210> SEQ ID NO 1383
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1383
auuugcgccu cagaaaagau                                                   20

<210> SEQ ID NO 1384
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1384
uguuuuccac guuggccucc                                                   20

<210> SEQ ID NO 1385
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1385
cguuguugua aaaggaggcg                                                   20

<210> SEQ ID NO 1386
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1386
agcacccuca gauuaucaaa                                                   20

<210> SEQ ID NO 1387
<211> LENGTH: 20
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 1387
ucugcgacau acuucucuuc                                                  20

<210> SEQ ID NO 1388
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1388
ggaaugguac gagaugcuga                                                  20

<210> SEQ ID NO 1389
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1389
guaugucgca gagcugcagc                                                  20

<210> SEQ ID NO 1390
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1390
uggucaacga agaggacauc                                                  20

<210> SEQ ID NO 1391
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1391
gguggaagag gacaccggca                                                  20

<210> SEQ ID NO 1392
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1392
uaaucgucug ugauguccag                                                  20

<210> SEQ ID NO 1393
<211> LENGTH: 20
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 1393
uuauccgaac uaccgggaaa                                             20

<210> SEQ ID NO 1394
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1394
aauuguuuug auaauucgag                                             20

<210> SEQ ID NO 1395
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1395
gaccaaaaag gaguaccugc                                             20

<210> SEQ ID NO 1396
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1396
caucaaaaag gagaacuacu                                             20

<210> SEQ ID NO 1397
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1397
agugaauagc aagugcuacg                                             20

<210> SEQ ID NO 1398
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1398
cgacauucug ggaaaccugu                                             20

<210> SEQ ID NO 1399
<211> LENGTH: 20
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 1399
ccgaggagug cauaacguca                                                  20

<210> SEQ ID NO 1400
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1400
aggccugagu cagaagcugu                                                  20

<210> SEQ ID NO 1401
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1401
gcaauagcaa agcucuggaa                                                  20

<210> SEQ ID NO 1402
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1402
accuauuuuc cagaagagcu                                                  20

<210> SEQ ID NO 1403
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1403
ucagcucuuc cuggaugucc                                                  20

<210> SEQ ID NO 1404
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1404
gcaggucgau auaaguaucg                                                  20

<210> SEQ ID NO 1405
<211> LENGTH: 20
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 1405
cuugauaugc uugaucuggu                                                    20

<210> SEQ ID NO 1406
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1406
agugcauaac gucaaugagg                                                    20

<210> SEQ ID NO 1407
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1407
agcuucaguu ucugauaugu                                                    20

<210> SEQ ID NO 1408
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1408
ggcaauuguu uugauaauuc                                                    20

<210> SEQ ID NO 1409
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1409
caacaaggug cuggucaagc                                                    20

<210> SEQ ID NO 1410
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1410
agugauggag aaccagaugu                                                    20

<210> SEQ ID NO 1411
<211> LENGTH: 20
<212> TYPE: RNA
<213> ORGANISM: Artificial Sequence
<220> FEATURE:
```

-continued

<223> OTHER INFORMATION: Description of Artificial Sequence: Synthetic
     oligonucleotide

<400> SEQUENCE: 1411
gggaaagugu cuguauucuc                                              20

<210> SEQ ID NO 1412
<211> LENGTH: 20
<212> TYPE: RNA
<213> ORGANISM: Artificial Sequence
<220> FEATURE:
<223> OTHER INFORMATION: Description of Artificial Sequence: Synthetic
     oligonucleotide

<400> SEQUENCE: 1412
agggaaagug ucuguauucu                                              20

<210> SEQ ID NO 1413
<211> LENGTH: 20
<212> TYPE: RNA
<213> ORGANISM: Artificial Sequence
<220> FEATURE:
<223> OTHER INFORMATION: Description of Artificial Sequence: Synthetic
     oligonucleotide

<400> SEQUENCE: 1413
agaucgaaca gauuaguaau                                              20

<210> SEQ ID NO 1414
<211> LENGTH: 20
<212> TYPE: RNA
<213> ORGANISM: Artificial Sequence
<220> FEATURE:
<223> OTHER INFORMATION: Description of Artificial Sequence: Synthetic
     oligonucleotide

<400> SEQUENCE: 1414
gauuguucag cagguccucc                                              20

<210> SEQ ID NO 1415
<211> LENGTH: 20
<212> TYPE: RNA
<213> ORGANISM: Artificial Sequence
<220> FEATURE:
<223> OTHER INFORMATION: Description of Artificial Sequence: Synthetic
     oligonucleotide

<400> SEQUENCE: 1415
aaucaagcug cacgauaugc                                              20

<210> SEQ ID NO 1416
<211> LENGTH: 20
<212> TYPE: RNA
<213> ORGANISM: Artificial Sequence
<220> FEATURE:
<223> OTHER INFORMATION: Description of Artificial Sequence: Synthetic
     oligonucleotide

<400> SEQUENCE: 1416
guggaaaaca augagggacg                                              20

<210> SEQ ID NO 1417
<211> LENGTH: 20
<212> TYPE: RNA

```
<213> ORGANISM: Artificial Sequence
<220> FEATURE:
<223> OTHER INFORMATION: Description of Artificial Sequence: Synthetic
      oligonucleotide

<400> SEQUENCE: 1417
gccaggcgcc ugaaacgacg                                                   20

<210> SEQ ID NO 1418
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1418
ucgauacuua uaucgaccug                                                   20

<210> SEQ ID NO 1419
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1419
aggauaaugg ccccgugauc                                                   20

<210> SEQ ID NO 1420
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1420
ucauuaucga gcuggcuagg                                                   20

<210> SEQ ID NO 1421
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1421
aaccuacuau gagggaccag                                                   20

<210> SEQ ID NO 1422
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1422
acaaugaggg acggagaagc                                                   20

<210> SEQ ID NO 1423
<211> LENGTH: 20
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 1423
ugaagugaau agcaagugcu                                                   20

<210> SEQ ID NO 1424
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1424
auucucugga ggccaucccc                                                   20

<210> SEQ ID NO 1425
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1425
cugaagaaag auggcgaggu                                                   20

<210> SEQ ID NO 1426
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1426
uggcgaacug uauaggguca                                                   20

<210> SEQ ID NO 1427
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1427
uacuaugagg gaccaggaga                                                   20

<210> SEQ ID NO 1428
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1428
caauuguuuu gauaauucga                                                   20

<210> SEQ ID NO 1429
<211> LENGTH: 20
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 1429
gcugagugga auuaauccuu                                                   20

<210> SEQ ID NO 1430
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1430
cugcugcacc uggcuaagcg                                                   20

<210> SEQ ID NO 1431
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1431
ccagagcucc gaggacaucc                                                   20

<210> SEQ ID NO 1432
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1432
aauugucgaa ggacacgcuu                                                   20

<210> SEQ ID NO 1433
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1433
uauaucgacc ugcuggagac                                                   20

<210> SEQ ID NO 1434
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1434
agcugaucaa caaaaguccc                                                   20

<210> SEQ ID NO 1435
<211> LENGTH: 20
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 1435
agaagaacag caaggacgca                                                     20

<210> SEQ ID NO 1436
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1436
uggagaacca gauguucgaa                                                     20

<210> SEQ ID NO 1437
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1437
agauugcaau cuuuaaccgg                                                     20

<210> SEQ ID NO 1438
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1438
uucucuggag gccauccccc                                                     20

<210> SEQ ID NO 1439
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1439
aaugagggac ggagaagcaa                                                     20

<210> SEQ ID NO 1440
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1440
uccuugauau gcuugaucug                                                     20

<210> SEQ ID NO 1441
<211> LENGTH: 20
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 1441
gggacauugc accuauuuuc                                                     20

<210> SEQ ID NO 1442
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1442
aagugaucaa cgccaucauc                                                     20

<210> SEQ ID NO 1443
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1443
gcugcaccug gcuaagcgcc                                                     20

<210> SEQ ID NO 1444
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1444
ggaacggcug aagaaagaug                                                     20

<210> SEQ ID NO 1445
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1445
ccuugauguc uuuccauccg                                                     20

<210> SEQ ID NO 1446
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1446
ggaggccaac guggaaaaca                                                     20

<210> SEQ ID NO 1447
<211> LENGTH: 20
<212> TYPE: RNA
<213> ORGANISM: Artificial Sequence
<220> FEATURE:
```

<223> OTHER INFORMATION: Description of Artificial Sequence: Synthetic
      oligonucleotide

<400> SEQUENCE: 1447
acggcggguu cacaucuuuu                                                 20

<210> SEQ ID NO 1448
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1448
gaggucgauc auauuauccc                                                 20

<210> SEQ ID NO 1449
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1449
ucgaacagau uaguaaucug                                                 20

<210> SEQ ID NO 1450
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1450
caaugaucug cugaaccgca                                                 20

<210> SEQ ID NO 1451
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1451
ccugacuauc uaccagagcu                                                 20

<210> SEQ ID NO 1452
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1452
acgagaaacu ggaauacuau                                                 20

<210> SEQ ID NO 1453
<211> LENGTH: 20
<212> TYPE: RNA

<213> ORGANISM: Artificial Sequence
<220> FEATURE:
<223> OTHER INFORMATION: Description of Artificial Sequence: Synthetic
      oligonucleotide

<400> SEQUENCE: 1453
cgcaggcguc agacuguuca                                              20

<210> SEQ ID NO 1454
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1454
auuccuugau gucuuuccau                                              20

<210> SEQ ID NO 1455
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1455
ccggcagacc aaugaacgca                                              20

<210> SEQ ID NO 1456
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1456
agaaucugga ugucaucaaa                                              20

<210> SEQ ID NO 1457
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1457
ugcuaaggag auccugguca                                              20

<210> SEQ ID NO 1458
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1458
aguacuugau cuucuugauc                                              20

<210> SEQ ID NO 1459
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1459
auaucauuau cgagcuggcu                                                    20

<210> SEQ ID NO 1460
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1460
aaaucaagcu gcacgauaug                                                    20

<210> SEQ ID NO 1461
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1461
cagagcugca gcuggaacgg                                                    20

<210> SEQ ID NO 1462
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1462
gaacccacug uauaaguacu                                                    20

<210> SEQ ID NO 1463
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1463
ugaucacuuu gaugcucugg                                                    20

<210> SEQ ID NO 1464
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1464
gcugaacaau ccauucaacu                                                    20

<210> SEQ ID NO 1465
<211> LENGTH: 20
<212> TYPE: RNA
<213> ORGANISM: Artificial Sequence
<220> FEATURE:

<223> OTHER INFORMATION: Description of Artificial Sequence: Synthetic
oligonucleotide

<400> SEQUENCE: 1465
caucuuuucu gaggcgcaaa					20

<210> SEQ ID NO 1466
<211> LENGTH: 20
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1466
gccgcaucag caagaccaaa					20

<210> SEQ ID NO 1467
<211> LENGTH: 20
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1467
aucagaaacu gaagcugauu					20

<210> SEQ ID NO 1468
<211> LENGTH: 20
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1468
auccucagac auaucagaaa					20

<210> SEQ ID NO 1469
<211> LENGTH: 20
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1469
acgcaggcgu cagacuguuc					20

<210> SEQ ID NO 1470
<211> LENGTH: 20
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1470
ccuuguuguu aaaggaauug					20

<210> SEQ ID NO 1471
<211> LENGTH: 20
<212> TYPE: RNA

<213> ORGANISM: Artificial Sequence
<220> FEATURE:
<223> OTHER INFORMATION: Description of Artificial Sequence: Synthetic
      oligonucleotide

<400> SEQUENCE: 1471
cucacgcaau agcaaagcuc                                               20

<210> SEQ ID NO 1472
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1472
caaaugccga cuucaucuuu                                               20

<210> SEQ ID NO 1473
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1473
uuauggagca guacggcgac                                               20

<210> SEQ ID NO 1474
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1474
gcuuuuucca cuccuuaaag                                               20

<210> SEQ ID NO 1475
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1475
ucaucgaaaa cguguuuaag                                               20

<210> SEQ ID NO 1476
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1476
ccagggugaa aggccugagu                                               20

<210> SEQ ID NO 1477
<211> LENGTH: 20
<212> TYPE: RNA
<213> ORGANISM: Artificial Sequence

```
<220> FEATURE:
<223> OTHER INFORMATION: Description of Artificial Sequence: Synthetic
      oligonucleotide

<400> SEQUENCE: 1477
gguuaauaaa auccuucugg                                                   20

<210> SEQ ID NO 1478
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1478
acaagguggu caagcuguca                                                   20

<210> SEQ ID NO 1479
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1479
gagaaccuac uaugagggac                                                   20

<210> SEQ ID NO 1480
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1480 caaagggua c aagcaccaug                                                  20

<210> SEQ ID NO 1481
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1481
aacguggaaa acaaugaggg                                                   20

<210> SEQ ID NO 1482
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1482
uucugggaaa ccuguaugag                                                   20

<210> SEQ ID NO 1483
<211> LENGTH: 20
<212> TYPE: RNA
<213> ORGANISM: Artificial Sequence
<220> FEATURE:
```

<223> OTHER INFORMATION: Description of Artificial Sequence: Synthetic
      oligonucleotide

<400> SEQUENCE: 1483
ugagggacgg agaagcaaga                                                    20

<210> SEQ ID NO 1484
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1484
caagacaagc gacuacguca                                                    20

<210> SEQ ID NO 1485
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1485
ggagccaggc gccugaaacg                                                    20

<210> SEQ ID NO 1486
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1486
acaucaacag auucuccguc                                                    20

<210> SEQ ID NO 1487
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1487
ugaacuagac agguacugga                                                    20

<210> SEQ ID NO 1488
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1488
cuacacugaa acagauugcu                                                    20

<210> SEQ ID NO 1489
<211> LENGTH: 20
<212> TYPE: RNA

```
<213> ORGANISM: Artificial Sequence
<220> FEATURE:
<223> OTHER INFORMATION: Description of Artificial Sequence: Synthetic
      oligonucleotide

<400> SEQUENCE: 1489
gacggagaag gcacagaauc                                                    20

<210> SEQ ID NO 1490
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1490
cuuuuugaua cucugagucu                                                    20

<210> SEQ ID NO 1491
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1491
uggacaaagc caagaaagug                                                    20

<210> SEQ ID NO 1492
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1492
auucugucac ccguggucaa                                                    20

<210> SEQ ID NO 1493
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1493
auaguacaag aaaagacgau                                                    20

<210> SEQ ID NO 1494
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1494
ccugaacagc gagcugaccc                                                    20

<210> SEQ ID NO 1495
<211> LENGTH: 20
<212> TYPE: RNA
<213> ORGANISM: Artificial Sequence
```

<220> FEATURE:
<223> OTHER INFORMATION: Description of Artificial Sequence: Synthetic
      oligonucleotide

<400> SEQUENCE: 1495
gaggcaauug uuuugauaau                                              20

<210> SEQ ID NO 1496
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1496
aaucaggucg uuguuguaaa                                              20

<210> SEQ ID NO 1497
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1497
gcaauuguuu ugauaauucg                                              20

<210> SEQ ID NO 1498
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1498
ggcgcaaaug gaaguuuaaa                                              20

<210> SEQ ID NO 1499
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1499
ucgagacaga acaggaguac                                              20

<210> SEQ ID NO 1500
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1500
ccaagcagcu gcugaaagug                                              20

<210> SEQ ID NO 1501
<211> LENGTH: 20
<212> TYPE: RNA
<213> ORGANISM: Artificial Sequence
<220> FEATURE:

<223> OTHER INFORMATION: Description of Artificial Sequence: Synthetic
      oligonucleotide

<400> SEQUENCE: 1501
uggacaucgg gauuacaagc                                                   20

<210> SEQ ID NO 1502
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1502
gaaggcacag aauccagagg                                                   20

<210> SEQ ID NO 1503
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1503
uaaggagauc cuggucaacg                                                   20

<210> SEQ ID NO 1504
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1504
uaaucagguc guuguuguaa                                                   20

<210> SEQ ID NO 1505
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1505
ggauuguuca gcagguccuc                                                   20

<210> SEQ ID NO 1506
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1506
gcauaacguc aaugaggugg                                                   20

<210> SEQ ID NO 1507
<211> LENGTH: 20
<212> TYPE: RNA

```
<213> ORGANISM: Artificial Sequence
<220> FEATURE:
<223> OTHER INFORMATION: Description of Artificial Sequence: Synthetic
      oligonucleotide

<400> SEQUENCE: 1507
ggagacucgg agaaccuacu                                                   20

<210> SEQ ID NO 1508
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1508
ccugagucag aagcugucag                                                   20

<210> SEQ ID NO 1509
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1509
ugcccgaaau cgagacagaa                                                   20

<210> SEQ ID NO 1510
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1510
ggtgagugag ugugugcgug                                                   20
```

CRISPR-RELATED METHODS AND COMPOSITIONS WITH GOVERNING GRNAS

CROSS-REFERENCE TO RELATED APPLICATIONS

The present application is a continuation of U.S. Ser. No. 16/256,615, filed Jan. 24, 2019, which is a continuation of Ser. No. 15/825,616, filed Nov. 29, 2017, now U.S. Pat. No. 10,190,137 issued Jan. 29, 2019, which is a divisional of U.S. Ser. No. 14/536,319, filed Nov. 7, 2014, now U.S. Pat. No. 9,834,791, issued Dec. 5, 2017, which claims the benefit of U.S. Provisional Application No. 61/901,215, filed Nov. 7, 2013, the contents of which are incorporated by reference herein in their entireties.

SEQUENCE LISTING

The instant application contains a Sequence Listing which has been submitted electronically in ASCII format and is hereby incorporated by reference in its entirety. Said ASCII copy, created on Dec. 18, 2014, is named C2159-704110_SL.txt and is 501,350 bytes in size.

FIELD OF THE INVENTION

The invention relates to CRISPR-related methods and components for editing of, or delivery of a payload to, a target nucleic acid sequence.

BACKGROUND OF THE INVENTION

CRISPRs (Clustered Regularly Interspaced Short Palindromic Repeats) evolved in bacteria as an adaptive immune system to defend against viral attack. Upon exposure to a virus, short segments of viral DNA are integrated into the CRISPR locus. RNA is transcribed from a portion of the CRISPR locus that includes the viral sequence. That RNA, which contains sequence complimentary to the viral genome, mediates targeting of a Cas9 protein to to a target sequence in the viral genome. The Cas9 protein cleaves and thereby silences the viral target.

Recently, the CRISPR/Cas system has been adapted for genome editing in eukaryotic cells. The introduction of site-specific double strand breaks (DSBs) allows for target sequence alteration through one of two endogenous DNA repair mechanisms—either non-homologous end-joining (NHEJ) or homology-directed repair (HDR). The CRISPR/Cas system has also been used for gene regulation including transcription repression and activation without altering the target sequence. Targeted gene regulation based on the CRISPR/Cas system uses an enzymatically inactive Cas9 (also known as a catalytically dead Cas9).

Despite the recent advances adapting the CRISPR/Cas system for genome editing in eukaryotic cells, there remains a need for improved regulation and control of these systems for use in eukaryotic cells.

SUMMARY OF THE INVENTION

Disclosed herein are methods and compositions, e.g., a Cas9 molecule complexed with a gRNA molecule, that can be used to target a specific location in a target DNA. Depending on the Cas9 molecule/gRNA molecule complex used in the disclosed methods and compositions, specific editing of a target nucleic acid, or the delivery of a payload, can be effected.

Methods and compositions that use, or include, a nucleic acid, e.g., a DNA, that encodes a Cas9 molecule or a gRNA molecule, can, in addition, use or include a "governing gRNA molecule." The governing gRNA molecule can complex with the Cas9 molecule to inactivate or silence a component of a Cas9 system. In one aspect, the disclosure features a gRNA molecule, referred to herein as a governing gRNA molecule, comprises a targeting domain which targets a component of the Cas9 system. In an embodiment, the governing gRNA molecule targets and silences (1) a nucleic acid that encodes a Cas9 molecule (i.e., a Cas9-targeting gRNA molecule), (2) a nucleic acid that encodes a gRNA molecule (i.e., a gRNA-targeting gRNA molecule), or (3) a nucleic acid sequence engineered into the Cas9 components that is designed with minimal homology to other nucleic acid sequences in the cell to minimize off-target cleavage (i.e., an engineered control sequence-targeting gRNA molecule).

The targeting sequence for the governing gRNA can be selected to increase regulation or control of the Cas9 system and/or to reduce or minimize off-target effects of the system. For example, a governing gRNA can minimize undesirable cleavage, e.g., "recleavage" after Cas9 mediated alteration of a target nucleic acid or off-target cutting of Cas9, by inactivating (e.g., cleaving) a nucleic acid that encodes a Cas9 molecule. In an embodiment, a governing gRNA places temporal or other limit(s) on the level of expression or activity of the Cas9 molecule/gRNA molecule complex. In an embodiment, the governing gRNA reduces off-target or other unwanted activity.

A target sequence for the governing gRNA can be disposed in the control or coding region of the Cas9 encoding sequence. This can be a Cas9 sequence or a non-Cas9 sequence, e.g., a sequence which is selected for, or which results in, reduced or minimized off target effect. The silencing, or inactivation, can be effected by cleaving the targeted nucleic acid sequence or by binding a Cas9 molecule/governing gRNA molecule complex to the targeted nucleic acid sequence.

In an aspect, the disclosure features a gRNA molecule that targets, optionally inactivates, a Cas9 molecule. In an embodiment, the gRNA molecule targets a nucleic acid sequence that encodes the Cas9 molecule. For example, a sequence that encodes the Cas9 molecule can comprise one or more of: a sequence encoding the amino acid sequence of the Cas9 molecule, a sequence encoding the amino acid sequence of the Cas9 molecule comprising non-translated sequence, or a sequence encoding the amino acid sequence of the Cas9 molecule comprising non-transcribed sequence.

In an embodiment, the Cas9 molecule is an eaCas9 molecule. In another embodiment, the Cas9 molecule is an eiCas9 molecule.

In an embodiment, the gRNA is configured to provide a Cas9 molecule-mediated cleavage event in the nucleic acid sequence that encodes the Cas9 molecule. In an embodiment, the gRNA molecule comprises a targeting domain configured to provide a Cas9 molecule-mediated cleavage event in the nucleic acid sequence that encodes the Cas9 molecule.

In an embodiment, the gRNA molecule:
targets the Cas9 molecule-amino acid coding sequence of the nucleic acid sequence;

is configured to provide a Cas9 molecule-mediated cleavage event in the Cas 9 molecule-amino acid coding sequence of the nucleic acid sequence; or comprises a targeting domain configured to provide a Cas9 molecule-mediated cleavage event in the Cas9 molecule-amino acid coding sequence of the nucleic acid sequence.

In an embodiment, the gRNA molecule:
targets a non-coding sequence of the nucleic acid sequence;
is configured to provide a Cas9 molecule-mediated cleavage event in a non-coding sequence of the nucleic acid sequence; or
comprises a targeting domain configured to provide a Cas9 molecule-mediated cleavage event in a non-coding sequence of the nucleic acid sequence.

In an embodiment, the gRNA molecule:
targets an untranslated sequence of the nucleic acid sequence;
is configured to provide a Cas9 molecule-mediated cleavage event in an untranslated sequence of the nucleic acid sequence; or
comprises a targeting domain configured to provide a Cas9 moleucle-mediated cleavage event in an untranslated sequence of the nucleic acid sequence.

In an embodiment, the gRNA molecule:
targets the nucleic acid sequence 5' of the Cas 9 molecule-amino acid coding region;
is configured to provide a Cas9 molecule-mediated cleavage event in the nucleic acid sequence 5' of the Cas9 molecule-coding region; or
comprises a targeting domain configured to provide a Cas9 molecule-mediated cleavage event 5' of the Cas9 molecule-coding region of the nucleic acid sequence.

In an embodiment, the gRNA molecule:
targets the nucleic acid sequence that encodes the Cas9 molecule 3' of the Cas9 molecule-coding region;
is configured to provide a Cas9 molecule-mediated cleavage event in the nucleic acid sequence 3' of the Cas9 molecule-coding region; or
comprises a targeting domain configured to provide a Cas9 molecule-mediated cleavage event 3' of the Cas9 molecule-coding region of the nucleic acid sequence.

In an embodiment, the gRNA molecule:
targets the promoter region of the nucleic acid sequence,
is configured to provide a Cas9 molecule-mediated cleavage event in the promoter region of nucleic acid sequence; or
comprises a targeting domain configured to provide a Cas9 molecule-mediated cleavage event in the promoter region of the nucleic acid sequence, wherein the promoter region is functionally linked to the Cas9 molecule amino acid coding region.

In an embodiment, the gRNA molecule:
targets Cas9 molecule intronic sequence of the nucleic acid sequence;
is configured to provide a Cas9 molecule-mediated cleavage event in Cas9 molecule intronic sequence of the nucleic acid sequence; or
comprises a targeting domain configured to provide a Cas9 molecule-mediated cleavage event in Cas9 molecule intronic sequence of the nucleic acid sequence.

In an embodiment, the Cas9 molecule is a *S. pyogenes* Cas9 molecule. In another embodiment, the Cas9 molecule is a *S. aureus* Cas9 molecule.

In an embodiment, the gRNA molecule is selected from Tables E1-E6. In another embodiment, the gRNA molecule is selected from Tables E7-E12.

In an embodiment, the gRNA is a chimeric gRNA. In another embodiment, the gRNA is a modular gRNA.

In an embodiment, the governing gRNA molecule targets the coding sequence, or a control region, e.g., a promoter, for the Cas9 system component to be negatively regulated. For example, the gRNA can target the coding sequence for Cas9, or a control region, e.g., a promoter, that regulates the expression of the Cas9 coding sequence. In an embodiment, the governing gRNA, e.g., a Cas9-targeting gRNA molecule, or a nucleic acid that encodes it, is introduced separately, e.g., later than the Cas9 molecule or a nucleic acid that encodes it. For example, a first vector, e.g., a viral vector, e.g., an AAV vecvtor, can introduce nucleic acid encoding a Cas9 and one or more gRNAs and a second vector, e.g., a viral vector, e.g., an AAV vecvtor, can introduce a nucleic acid encoding a governing gRNA molecule, e.g., a Cas9-targeting gRNA molecule. The second vector can be introduced after the first. In an embodiment, the governing gRNA, e.g., a Cas9-targeting gRNA molecule, or a nucleic acid that encodes it, can be introduced together, e.g., at the same time or in the same vector, with the Cas9 molecule or a nucleic acid that encodes it, but, e.g., under transcriptional control elements, e.g., a promoter or an enhancer, that are activated at a later time, e.g., such that after a period of time the transcription of Cas9 is silenced. In an embodiment, the transcriptional control element is activated intrinsically. In an embodiment, the transcriptional element is activated via the introduction of an external trigger.

In an aspect, the disclosure features a nucleic acid comprising a sequence that encodes a governing gRNA molecule. In an embodiment, the governing gRNA molecule comprises a Cas9 molecule-targeting gRNA molecule. In an embodiment, the nucleic acid comprises a sequence that encodes a gRNA molecule described herein. In an embodiment, the nucleic acid is purified.

In another aspect, the disclosure features a nucleic acid, e.g., one or more vectors, e.g., one or more viral vectors, e.g., one or more AAV vectors, comprising:
a) a first nucleic acid sequence that encodes a governing gRNA molecule, e.g., a Cas9 molecule-targeting gRNA molecule or a gRNA molecule-targeting gRNA molecule; and
b) a second nucleic acid sequence that encodes a Cas9 molecule, e.g., an eaCas9 or an eiCas9 molecule.

In an embodiment, the governing gRNA molecule comprises a Cas9 molecule-targeting gRNA molecule. In another embodiment, the governing gRNA molecule comprises a gRNA molecule-targeting gRNA molecule.

In an embodiment, the governing gRNA molecule comprises a Cas9 molecule-targeting gRNA molecule and the Cas9 molecule-targeting gRNA molecule targets the second nucleic acid sequence that encodes the Cas9 molecule.

In an embodiment, the Cas9 molecule is an eaCas9 molecule. In another embodiment, the Cas9 molecule is an eiCas9 molecule.

In an embodiment, the gRNA molecule is configured to provide a Cas9 molecule-mediated cleavage event in the second nucleic acid sequence. In an embodiment, the gRNA molecule comprises a targeting domain configured to provide a Cas9 molecule-mediated cleavage event in the second nucleic acid sequence. In an embodiment, the gRNA molecule is a gRNA molecule described herein and targets the second nucleic acid sequence.

In an embodiment, the nucleic acid is purified.

In an embodiment, component a) and component b) are provided on the same nucleic acid, e.g., the same vector, e.g., the same viral vector, e.g., the same AAV vector. In another embodiment, component a) and component b) are provided on different nucleic acids, e.g., different vectors, e.g., different viral vectors, e.g., different AAV vectors.

In an embodiment, the nucleic acid is configured such that a Cas9 molecule-targeting gRNA transcribed from said nucleic acid forms a complex with a Cas9 molecule produced from said nucleic acid.

In an embodiment, said complex is capable of inactivating or silencing, e.g., by cleaving, the nucleic acid sequence that comprises or encodes said Cas9 molecule sequence. In an embodiment, the inactivating comprises cleaving.

In an embodiment, said first nucleic acid sequence is under the control of a first control region, e.g., promoter, and said second nucleic acid sequence is under the control of a second control region, e.g., promoter, and said first and second control regions, e.g., promoters, are different, e.g., one is a constitutive promoter and one is an inducible promoter. In an embodiment, one of the first and second control regions is a constitutive promoter and one is an inducible promoter.

In an embodiment, said first nucleic acid sequence and said second nucleic acid sequence are differentially expressed, e.g., differentially expressed in terms of level of expression or temporally, e.g., the first sequence is expressed later than said second sequence, or the first sequence is expressed at a lower level than said second sequence.

In an embodiment, the nucleic acid further comprises:
  c) a third nucleic acid sequence that encodes a gRNA molecule, e.g., a second gRNA molecule, comprising a targeting domain which is complementary with a target nucleic acid, e.g., wherein the second gRNA does not target b).

In an embodiment, the target nucleic acid is disclosed herein, e.g., a sequence from:
  a gene or pathway described herein, e.g., in Section VIIB, e.g., in Table VII-13, VII-14, VII-15, VII-16, VII-17, VII-18, VII-19, VII-20, VII, 21, VII-22, VII-23, VII-24, IX-1, IX-1A, IX-3, or XII-1, or in Section VIII.

In an embodiment, said first nucleic acid sequence is under the control of a first control region, e.g., promoter,
  said second nucleic acid sequence is under the control of said second control region, e.g., promoter, or a third control region, e.g., promoter,
  said third nucleic acid sequence is under the control of said second control region, e.g., promoter, or said third control region, e.g., promoter, and
  said first control region, e.g., promoter, is different from said second and/or said third control region, e.g., promoter.

In an embodiment, said first nucleic acid sequence and said third nucleic acid sequence are differentially expressed, e.g., differentially expressed in terms of level of expression or temporally, e.g., the first sequence is expressed later than said third sequence, or the first sequence is expressed at a lower level than said third sequence.

In an embodiment, the nucleic acid further comprises a template nucleic acid (referred to interchangeably herein as a swap nucleic acid sequence), e.g., having 5' and 3' flanking region sequences recognized by one or more governing gRNAs.

In an embodiment, the nucleic acid sequence that comprises or encodes the Cas9 molecule sequence or the gRNA molecule sequence (e.g., targeted by the governing gRNA as described herein) further comprises a nucleic acid sequence that is capable of being used as a template nucleic acid, e.g., after being cleaved or excised (e.g., by the method described herein) from the nucleic acid sequence that comprises or encodes the Cas9 molecule sequence or the gRNA molecule sequence, e.g., as a donor DNA for homologous recombination. In an embodiment, a first governing gRNA molecule targets a region 5' of a nucleic acid sequence comprising the template nucleic acid sequence and a second governing gRNA molecule targets a region 3' of the nucleic acid sequence comprising the template nucleic acid sequence. For example, at least two (e.g., two, three, four, five or more) governing gRNAs can be used to produce one or more (e.g., two, three, four or more) template nucleic acids. In another embodiment, a single governing gRNA molecule targets both the regions 5' and 3' of the nucleic acid sequence comprising the template nucleic acid sequence. For example, the region (e.g., targeted by the governing gRNA molecule) 5' of the nucleic acid sequence comprising the template nucleic acid sequence can be the same or substantially the same as the region (e.g., targeted by the governing gRNA molecule) 3' of the nucleic acid sequence comprising the template nucleic acid sequence. In an embodiment, the nucleic acid sequence comprising the template nucleic acid sequence is in a vector, e.g., a vector described herein. In an embodiment, the vector is a viral vector, e.g., an AAV vector.

In an aspect, the disclosure features a vector comprising a nucleic acid described herein. In an embodiment, the vector is a viral vector. In an embodiment, the viral vector, is an AAV rector.

In an aspect, the disclosure features a composition, e.g., a pharmaceutical composition, comprising:
  a) a governing gRNA molecule, e.g., a governing gRNA molecule described herein, or a nucleic acid that encodes a governing gRNA molecule, e.g., a nucleic acid described herein.

In an embodiment, the composition comprises one or more (e.g., 2 or all) of;
  b) a Cas9 molecule, e.g., a Cas9 molecule described herein, or a nucleic acid sequence that encodes the Cas 9 molecule, e.g., a nucleic acid sequence described herein;
  c) a second gRNA molecule or a nucleic acid encoding the second gRNA molecule; or
  d) a template nucleic acid.

In an embodiment, the governing gRNA molecule comprises a Cas9 molecule-targeting gRNA molecule. In an embodiment, the Cas 9 molecule-targeting gRNA comprises a gRNA molecule described herein.

In an embodiment, the gRNA molecule is configured to provide a Cas 9 molecule-mediated cleavage event in the nucleic acid sequence that encodes the Cas 9 molecule.

In an embodiment, the composition comprises a Cas9 molecule-targeting gRNA molecule and a nucleic acid encoding the Cas9 molecule. In another embodiment, the composition comprises a Cas9 molecule-targeting gRNA molecule and the Cas9 molecule.

In an embodiment, the composition further comprises:
  c) a second gRNA molecule or a nucleic acid encoding the second gRNA molecule.

In an embodiment, the second gRNA targets a Cas 9 molecule to a target nucleic acid.

In an embodiment, the composition further comprises:
  d) a template nucleic acid.

In an embodiment, the composition comprises a second gRNA or a nucleic acid encoding the second gRNA.

In an embodiment, the template nucleic acid is configured to mediate repair of a break positioned by the second gRNA.

In an embodiment, each of a), b), c) and d) is present as a nucleic acid and are encoded on the same nucleic acid molecule. In an embodiment, a first sequence selected from a), b), c) and d) is encoded on a first nucleic acid molecule and a second sequence selected from a), b), c), and d) is encoded on a second nucleic acid molecule.

In another aspect, the disclosure features a composition, e.g., a pharmaceutical composition, comprising the nucleic acid described herein. For example, the nucleic acid, e.g., one or more vectors, e.g., one or more viral vectors, e.g., one or more AAV vectors, can comprise:

a) a first nucleic acid sequence that encodes a governing gRNA molecule, e.g., a Cas9-targeting gRNA molecule or a gRNA-targeting gRNA molecule; and b) a second nucleic acid sequence that encodes a Cas9 molecule, e.g., an eaCas9 or an eiCas9 molecule.

In an embodiment, said nucleic acid comprises an AAV vector.

In an aspect, the disclosure features a composition, e.g., a pharmaceutical composition, comprising nucleic acid sequence, e.g., a DNA, that encodes a governing gRNA molecule, e.g., a Cas9-targeting gRNA molecule or a gRNA-targeting gRNA molecule, and one or more of a) a Cas9 molecule,
b) a second Cas9 molecule,
c) a gRNA molecule, and
d) a second gRNA molecule.

In an embodiment, each of a), b), c) and d) present are encoded on the same nucleic acid molecule. In an embodiment, a first sequence selected from a, b, c and d is encoded on a first nucleic acid molecule and a second sequence selected from a, b, c, and d is encoded on a second nucleic acid molecule. In an embodiment, said nucleic acid encodes: a and c; a, c, and d; or a, b, c, and d.

In an aspect, the disclosure features a pharmaceutical preparation comprising:
a gRNA molecule described herein;
a nucleic acid described herein;
a vector described herein; or
a composition described herein.

In an aspect, the disclosure features a cell comprising:
a gRNA molecule described herein;
a nucleic acid described herein;
a vector described herein; or a composition described herein.

In an embodiment, the cell comprises:
a nucleic acid sequence encoding a Cas 9 molecule, wherein a sequence that encodes the Cas9 molecule can comprise one or more of: a sequence encoding the amino acid sequence of the Cas9 molecule, a sequence encoding the amino acid sequence of the Cas9 molecule comprising non-translated sequence, and a sequence encoding the amino acid sequence of the Cas9 molecule comprising non-transcribed sequence; and
a governing gRNA molecule.

In an embodiment, the governing gRNA molecule comprises a gRNA molecule that targets the nucleic acid sequence that encodes the Cas 9 molecule. In an embodiment, the gRNA molecule is a gRNA molecule described herein.

In an embodiment, the cell further comprises a Cas 9 molecule.

In an embodiment, the cell further comprises a second gRNA molecule or a nucleic acid encoding the second gRNA molecule. In an embodiment, the second gRNA targets a Cas9 molecule to a target nucleic acid.

In an embodiment, the cell further comprises a template nucleic acid. In an embodiment, the template nucleic acid is configured to mediate repair of a break in the target nucleic acid positioned by the second gRNA molecule.

In an embodiment, the cell comprises target nucleic acid cleaved by second gRNA molecule mediated targeting of the Cas9 molecule.

In an embodiment, the cell comprises the target nucleic acid that has been cleaved and repaired. In an embodiment, the repair comprises template nucleic acid mediated repair.

In an embodiment, the nucleic acid sequence encoding the Cas9 molecule has not been cleaved. In an embodiment, the nucleic acid sequence encoding the Cas9 molecule can express Cas 9 molecule.

In an embodiment, the nucleic acid sequence encoding the Cas9 molecule has been cleaved by gRNA mediated targeting of Cas 9 molecule. In an embodiment, the cleaved nucleic acid sequence encoding the Cas9 molecule has reduced ability to express Cas9 molecule, as compared to the same molecule not having been cleaved. In an embodiment, the cleaved nucleic acid sequence encoding the Cas9 molecule is substantially incapable of expressing Cas 9 molecule.

In an embodiment, the cell comprises one or both of:
a cleaved nucleic acid sequence encoding the Cas9 molecule; or
a target nucleic acid having a repaired Cas9 molecule-mediated cleavage event.

In an embodiment, the cell is a vertebrate, mammalian, rodent, goat, pig, bird, chicken, turkey, cow, horse, sheep, fish, primate, or human cell.

In another embodiment, the cell is a plant cell. In an embodiment, the plant cell is a monocot or a dicot.

In an embodiment, the cell is a human cell. In an embodiment, the cell is a somatic cell, germ cell, or prenatal cell. In an embodiment, the cell is a zygotic, blastocyst or embryonic cell, a stem cell, a mitotically competent cell, a meiotically competent cell.

In an aspect, the disclosure features a method of altering a cell, e.g., altering the structure, e.g., sequence, of a target nucleic acid of a cell, comprising contacting said cell with the nucleic acid described herein. For example, the nucleic acid, e.g., one or more vectors, e.g., one or more viral vectors, e.g., one or more AAV vectors, can comprise:

a) a first nucleic acid sequence that encodes a governing gRNA molecule, e.g., a Cas9-targeting gRNA molecule or a gRNA-targeting gRNA molecule; and b) a second nucleic acid sequence that encodes a Cas9 molecule, e.g., an eaCas9 or an eiCas9 molecule.

In an embodiment, the cell is a mammalian, primate, or human cell. In an embodiment, the cell is a human cell, e.g., a cell described herein, e.g., in Section VIIA. In an embodiment, the cell is: a somatic cell, germ cell, prenatal cell, e.g., zygotic, blastocyst or embryonic cell, a stem cell, a mitotically competent cell, or a meiotically competent cell. In an embodiment, the target nucleic acid is a chromosomal nucleic acid.

In another aspect, the disclosure features a method of altering a cell, e.g., altering the structure, e.g., sequence, of a target nucleic acid of a cell, comprising contacting the cell with an effective amount of:
a gRNA molecule described herein;
a nucleic acid described herein;
a vector described herein; or
a composition described herein.

In an embodiment, the cell is a vertebrate, mammalian, rodent, goat, pig, bird, chicken, turkey, cow, horse, sheep, fish, primate, or human cell.

In another embodiment, the cell is a plant cell. In an embodiment, the plant cell is a monocot or a dicot.

In an embodiment, the cell is a human cell. In an embodiment, the cell is a somatic cell, germ cell, or prenatal cell. In an embodiment, the cell is a zygotic, blastocyst or embryonic cell, a stem cell, a mitotically competent cell, a meiotically competent cell.

In an embodiment, the subject is a mammal, primate, or human.

In an embodiment, the target nucleic acid is a chromosomal nucleic acid.

In another aspect, the disclosure features a method of treating a subject, e.g., by altering the structure, e.g., altering the sequence, of a target nucleic acid, comprising administering to the subject, an effective amount of the nucleic acid described herein. For example, the nucleic acid, e.g., one or more vectors, e.g., one or more viral vectors, e.g., one or more AAV vectors, can comprise:

a) a first nucleic acid sequence that encodes a governing gRNA molecule, e.g., a Cas9-targeting gRNA molecule or a gRNA-targeting gRNA molecule; and b) a second nucleic acid sequence that encodes a Cas9 molecule, e.g., an eaCas9 or an eiCas9 molecule.

In an embodiment, the subject is a mammalian, primate, or human. In an embodiment, the target nucleic acid is the nucleic acid of a human cell, e.g., a cell described herein, e.g., in Section VIIA. In an embodiment, the target nucleic acid is the nucleic acid of: a somatic cell, germ cell, prenatal cell, e.g., zygotic, blastocyst or embryonic cell, a stem cell, a mitotically competent cell, or a meiotically competent cell. In an embodiment, the target nucleic acid is a chromosomal nucleic acid.

In another aspect, the disclosure features a method of treating a subject, e.g., by altering the structure, e.g., altering the sequence, of a target nucleic acid, in a cell of the subject, comprising contacting the cell or the subject, with an effective amount of the nucleic acid of: a gRNA molecule described herein;

a nucleic acid described herein;
a vector described herein; or
a composition described herein.

In an embodiment, the cell is a vertebrate, mammalian, rodent, goat, pig, bird, chicken, turkey, cow, horse, sheep, fish, primate, or human cell.

In another embodiment, the cell is a plant cell. In an embodiment, the plant cell is a monocot or a dicot.

In an embodiment, the cell is a human cell. In an embodiment, the cell is a somatic cell, germ cell, or prenatal cell. In an embodiment, the cell is a zygotic, blastocyst or embryonic cell, a stem cell, a mitotically competent cell, a meiotically competent cell.

In an embodiment, the subject is a mammal, primate, or human.

In an embodiment, the target nucleic acid is a chromosomal nucleic acid.

In an aspect, the disclosure features a reaction mixture comprising a cell and:

a gRNA molecule described herein;
a nucleic acid described herein;
a vector described herein; or
a composition described herein.

In another aspect, the disclosure features a reaction mixture comprising a composition described herein and a cell, e.g., a cell described herein.

In an aspect, the disclosure features a kit comprising:

a gRNA molecule described herein;
a nucleic acid described herein;
a vector described herein; or
a composition described herein.

In an embodiment, the kit comprises an instruction for using the gRNA molecule, the nucleic acid, the vector, or the composition, in a method described herein.

In another aspect, the disclosure features a composition, e.g., pharmaceutical composition, comprising a governing gRNA molecule described herein.

In an embodiment, the composition further comprises a Cas9 molecule, e.g., an eaCas9 or an eiCas9 molecule. In an embodiment, said Cas9 molecule is an eaCas9 molecule. In an embodiment, said Cas9 molecule is an eiCas9 molecule.

In an embodiment, the composition further comprises a gRNA molecule comprising a targeting domain which is complementary with a target sequence from a target nucleic acid disclosed herein, e.g., a sequence from: a gene or pathway described herein, e.g., in Section VIIB, e.g., in Table VII-13, VII-14, VII-15, VII-16, VII-17, VII-18, VII-19, VII-20, VII-21, VII-22, VII-23, VII-24, IX-1, IX-1A, IX-3, or XII-1, or in Section VIII.

In another aspect, the disclosure features a composition, e.g., pharmaceutical composition, comprising a gRNA molecule described herein.

In an embodiment, the composition further comprises a Cas9 molecule, e.g., an eaCas9 or an eiCas9 molecule. In an embodiment, said Cas9 molecule is an eaCas9 molecule. In another embodiment, said Cas9 molecule is an eiCas9 molecule.

In an embodiment, said composition comprises a payload, e.g., a payload described herein, e.g., in Section VI, e.g., in Table VI-1, VI-2, VI-3, VI-4, VI-5, or VI-6.

In an embodiment, the payload comprises: an epigenetic modifier, e.g., a molecule that modifies DNA or chromatin; component, e.g., a molecule that modifies a histone, e.g., an epigenetic modifier described herein, e.g., in Section VI; a transcription factor, e.g., a transcription factor described herein, e.g., in Section VI; a transcriptional activator domain; an inhibitor of a transcription factor, e.g., an anti-transcription factor antibody, or other inhibitors; a small molecule; an antibody; an enzyme; an enzyme that interacts with DNA, e.g., a helicase, restriction enzyme, ligase, or polymerase; and/or a nucleic acid, e.g., an enzymatically active nucleic acid, e.g., a ribozyme, or an mRNA, siRNA, of antisense oligonucleotide. In an embodiment, the composition further comprises a Cas9 molecule, e.g., an eiCas9, molecule.

In an embodiment, said payload is coupled, e.g., covalently or noncovalently, to a Cas9 molecule, e.g., an eiCas9 molecule. In an embodiment, said payload is coupled to said Cas9 molecule by a linker. In an embodiment, said linker is or comprises a bond that is cleavable under physiological, e.g., nuclear, conditions. In an embodiment, said linker is, or comprises, a bond described herein, e.g., in Section XI. In an embodiment, said linker is, or comprises, an ester bond. In an embodiment, said payload comprises a fusion partner fused to a Cas9 molecule, e.g., an eaCas9 molecule or an eiCas9 molecule.

In an embodiment, said payload is coupled, e.g., covalently or noncovalently, to the gRNA molecule. In an embodiment, said payload is coupled to said gRNA molecule by a linker. In an embodiment, said linker is or comprises a bond that is cleavable under physiological, e.g., nuclear, conditions. In an embodiment, said linker is, or comprises, a bond described herein, e.g., in Section XI. In an embodiment, said linker is, or comprises, an ester bond.

In an embodiment, the composition comprises an eaCas9 molecule. In an embodiment, the composition comprises an eaCas9 molecule which forms a double stranded break in the target nucleic acid.

In an embodiment, the composition comprises an eaCas9 molecule which forms a single stranded break in the target nucleic acid. In an embodiment, said single stranded break is formed in the complementary strand of the target nucleic acid. In an embodiment, said single stranded break is formed in the strand which is not the complementary strand of the target nucleic acid.

In an embodiment, the composition comprises HNH-like domain cleavage activity but having no, or no significant, N-terminal RuvC-like domain cleavage activity. In an embodiment, the composition comprises N-terminal RuvC-like domain cleavage activity but having no, or no significant, HNH-like domain cleavage activity.

In an embodiment, said double stranded break is within 10, 20, 30, 40, 50, 100, 150 or 200 nucleotides of a nucleotide of the target position. In an embodiment, said single stranded break is within 10, 20, 30, 40, 50, 100, 150 or 200 nucleotides of a nucleotide of the target position.

In an embodiment, the composition further comprises a template nucleic acid, e.g., a template nucleic acid described herein, e.g., in Section IV. In an embodiment, the template nucleic acid comprises a nucleotide that corresponds to a nucleotide of the target position.

In an embodiment, said template nucleic acid comprises a nucleotide that corresponds to a nucleotide of the target position from a sequence of: a gene, or a gene from a pathway, described herein, e.g., in Section VIIB, e.g., in Table VII-13, VII-14, VII-15, VII-16, VII-17, VII-18, VII-19, VII-20, VII-21, VII-22, VII-23, VII-24, IX-1, IX-1A, IX-3, or XII-1, or in Section VIII.

In an embodiment, the template nucleic acid is or comprises a fragment of 10 to 500, 10 to 400, 10 to 300, 10 to 200 nucleotides in length from a sequence in: a gene, or a gene from a pathway, described herein, e.g., in Section VIIB, e.g., in Table VII-13, VII-14, VII-15, VII-16, VII-17, VII-18, VII-19, VII-20, VII-21, VII-22, VII-23, VII-24, IX-1, IX-1A, IX-3, or XII-1, or in Section VIII.

In an embodiment, the template nucleic acid is or comprises a fragment of 10 to 500, 10 to 400, 10 to 300, 10 to 200 nucleotides in length, which differs at at least 1 nucleotide, but not more than 5, 10, 20 or 30% of its nucleotides, from a corresponding sequence in: a gene, or a gene from a pathway, described herein, e.g., in Section VIIB, e.g., in Table VII-13, VII-14, VII-15, VII-16, VII-17, VII-18, VII-19, VII-20, VII-21, VII-22, VII-23, VII-24, IX-1, IX-1A, IX-3, or XII-1, or in Section VIII.

In an embodiment, the composition further comprises a second gRNA molecule, e.g., a second gRNA molecule described herein.

In an embodiment, said gRNA molecule and said second gRNA molecule mediate breaks at different sites in the target nucleic acid, e.g., flanking a target position. In an embodiment, said gRNA molecule and said second gRNA molecule are complementary to the same strand of the target. In an embodiment, said gRNA molecule and said second gRNA molecule are complementary to the different strands of the target.

In an embodiment, said Cas9 molecule mediates a double stranded break.

In an embodiment, said gRNA molecule and said second gRNA molecule are configured such that first and second break made by the Cas9 molecule flank a target position. In an embodiment, said double stranded break is within 10, 20, 30, 40, 50, 100, 150 or 200 nucleotides of a nucleotide of the target position.

In an embodiment, the composition further comprises a template nucleic acid. In an embodiment, the template nucleic acid comprises a nucleotide that corresponds to a nucleotide of the target position.

In an embodiment, said template nucleic acid comprises a nucleotide that corresponds to a nucleotide of a target position from a sequence of: a gene, or a gene from a pathway, described herein, e.g., in Section VIIB, e.g., in Table VII-13, VII-14, VII-15, VII-16, VII-17, VII-18, VII-19, VII-20, VII-21, VII-22, VII-23, VII-24, IX-1, IX-1A, IX-3, or XII-1, or in Section VIII.

In an embodiment, the template nucleic acid is a fragment of 10 to 500, 10 to 400, 10 to 300, 10 to 200 nucleotides in length from a sequence in: a gene, or a gene from a pathway, described herein, e.g., in Section VIIB, e.g., in Table VII-13, VII-14, VII-15, VII-16, VII-17, VII-18, VII-19, VII-20, VII-21, VII-22, VII-23, VII-24, IX-1, IX-1A, IX-3, or XII-1, or in Section VIII.

In an embodiment, the template nucleic acid is a fragment of 10 to 500, 10 to 400, 10 to 300, 10 to 200 nucleotides in length, which differs at at least 1 nucleotide, but not more than 5, 10, 20 or 30% of its nucleotides, from a corresponding sequence in: a gene, or a gene from a pathway, described herein, e.g., in Table VII-13, VII-14, VII-15, VII-16, VII-17, VII-18, VII-19, VII-20, VII-21, VII-22, VII-23, VII-24, IX-1, IX-1A, IX-3, or XII-1, or in Section VIII.

In an embodiment, said Cas9 molecule mediates a single stranded break.

In an embodiment, said gRNA molecule and said second gRNA molecule are configured such that a first and second break are formed in the same strand of the nucleic acid target, e.g., in the case of transcribed sequence, the template strand or the non-template strand.

In an embodiment, said first and second break flank a target position.

In an embodiment, one of said first and second single stranded breaks, or both are independently, within 10, 20, 30, 40, 50, 100, 150 or 200 nucleotides of a nucleotide of the target position.

In an embodiment, the composition further comprises a template nucleic acid. In an embodiment, the template nucleic acid comprises a nucleotide that corresponds to a nucleotide of the target position. In an embodiment, said template nucleic acid comprises a nucleotide that corresponds to a nucleotide of the target position from a sequence of: a gene, or a gene from a pathway, described herein, e.g., in Section VIIB, e.g., in Table VII-13, VII-14, VII-15, VII-16, VII-17, VII-18, VII-19, VII-20, VII-21, VII-22, VII-23, VII-24, IX-1, IX-1A, IX-3, or XII-1, or in Section VIII.

In an embodiment, the template nucleic acid is or comprises a fragment of 10 to 500, 10 to 400, 10 to 300, 10 to 200 nucleotides in length from a sequence in: a gene, or a gene from a pathway, described herein, e.g., in Table VII-13, VII-14, VII-15, VII-16, VII-17, VII-18, VII-19, VII-20, VII-21, VII-22, VII-23, VII-24, IX-1, IX-1A, IX-3, or XII-1, or in Section VIII. In an embodiment, the template nucleic acid is or comprises a fragment of 10 to 500, 10 to 400, 10 to 300, 10 to 200 nucleotides in length, which differs at at least 1 nucleotide, but not more than 5, 10, 20 or 30% of its nucleotides, from a corresponding sequence in: a gene, or a gene from a pathway, described herein, e.g., in Section VIIB, e.g., in Table VII-13, VII-14, VII-15, VII-16, VII-17, VII-18, VII-19, VII-20, VII-21, VII-22, VII-23, VII-24, IX-1, IX-1A, IX-3, or XII-1, or in Section VIII.

In an embodiment, said gRNA molecule and said second gRNA molecule are configured such that a first and a second breaks are formed in different strands of the target. In an embodiment, said first and second break flank a target position. In an embodiment, one of said first and second single stranded breaks, or both are independently, within 10, 20, 30, 40, 50, 100, 150 or 200 nucleotides of a nucleotide of the target position.

In an embodiment, the composition further comprises a template nucleic acid. In an embodiment, the template nucleic acid comprises a nucleotide that corresponds to a nucleotide of the target position.

In an embodiment, said template nucleic acid comprises a nucleotide that corresponds to a nucleotide of the target position from a sequence of: a gene, or a gene from a pathway, described herein, e.g., in Section VIIB, e.g., in Table VII-13, VII-14, VII-15, VII-16, VII-17, VII-18, VII-19, VII-20, VII-21, VII-22, VII-23, VII-24, IX-1, IX-1A, IX-3, or XII-1, or in Section VIII.

In an embodiment, the template nucleic acid is or comprises a fragment of 10 to 500, 10 to 400, 10 to 300, 10 to 200 nucleotides in length from a sequence in: a gene, or a gene from a pathway, described herein, e.g., in Section VIIB, e.g., in Table VII-13, VII-14, VII-15, VII-16, VII-17, VII-18, VII-19, VII-20, VII-21, VII-22, VII-23, VII-24, IX-1, IX-1A, IX-3, or XII-1, or in Section VIII.

In an embodiment, the template nucleic acid is or comprises a fragment of 10 to 500, 10 to 400, 10 to 300, 10 to 200 nucleotides in length, which differs at at least 1 nucleotide, but not more than 5, 10, 20 or 30% of its nucleotides, from a corresponding sequence in: a gene, or a gene from a pathway, described herein, e.g., in Section VIIB, e.g., in Table VII-13, VII-14, VII-15, VII-16, VII-17, VII-18, VII-19, VII-20, VII-21, VII-22, VII-23, VII-24, IX-1, IX-1A, IX-3, or XII-1, or in Section VIII.

In an embodiment, the composition comprises a second Cas9 molecule.

In an embodiment, one or both of said Cas9 molecule and said second Cas9 molecule are eiCas9 molecules. In an embodiment, said eiCas9 molecule is coupled to a payload by a linker and said second eiCas9 molecules is coupled to a second payload by a second linker.

In an embodiment, said payload and said second payload are the same. In an embodiment, said payload and said second payload are different. In an embodiment, said linker and said second linker are the same. In an embodiment, said linker and said second linker are different, e.g., have different release properties, e.g., different release rates.

In an embodiment, said payload and said second payload are each described herein, e.g., in Section VI, e.g., in Table VI-1, VI-2, VI-3, VI-4, VI-5, or VI-6. In an embodiment, said payload and said second payload can interact, e.g., they are subunits of a protein.

In an embodiment, one of both of said Cas9 molecule and said second Cas9 molecule are eaCas9 molecules.

In an embodiment, said eaCas9 molecule comprises a first cleavage activity and said second eaCas9 molecule comprises a second cleavage activity. In an embodiment, said cleavage activity and said second cleavage activity are the same, e.g., both are N-terminal RuvC-like domain activity or are both HNH-like domain activity. In an embodiment, said cleavage activity and said second cleavage activity are different, e.g., one is N-terminal RuvC-like domain activity and one is HNH-like domain activity.

In an embodiment, said Cas9 molecule and said second Cas9 molecule are specific for different PAMs, e.g., one is specific for NGG and the other is specific for, e.g., NGGNG, NNAGAAW (W=A or T), or NAAR (R=A or G). In an embodiment, said Cas9 molecule of S. aureus recognizes the sequence motif NNGRR (R=A or G) and directs cleavage of a target nucleic acid sequence 1 to 10, e.g., 3 to 5, base pairs upstream from that sequence. In an embodiment, one of said Cas 9 molecule and said second Cas 9 molecule recognizes an S. aureus PAM. In an embodiment, said Cas9 molecule of N. meningitidis recognizes the sequence motif NNNNGATT and directs cleavage of a target nucleic acid sequence 1 to 10, e.g., 3 to 5, base pairs upstream from that sequence. In an embodiment, one of said Cas 9 molecule and said second Cas 9 molecule recognizes an N. meningitidis PAM.

In an embodiment, said Cas9 molecule and said second Cas9 molecule both mediate double stranded breaks.

In an embodiment, said Cas9 molecule and said second Cas9 molecule are specific for different PAMs, e.g., one is specific for NGG and the other is specific for another PAM, e.g., another PAM described herein. In an embodiment, said gRNA molecule and said second gRNA molecule are configured such that first and second break flank a target position. In an embodiment, one of said first and second double stranded breaks, or both are independently, within 10, 20, 30, 40, 50, 100, 150 or 200 nucleotides of a nucleotide of the target position.

In an embodiment, the composition further comprises a template nucleic acid. In an embodiment, the template nucleic acid comprises a nucleotide that corresponds to a nucleotide of the target position.

In an embodiment, said template nucleic acid comprises a nucleotide that corresponds to a nucleotide of the target position from a sequence of: a gene, or a gene from a pathway, described herein, e.g., in Section VIIB, e.g., in Table VII-13, VII-14, VII-15, VII-16, VII-17, VII-18, VII-19, VII-20, VII-21, VII-22, VII-23, VII-24, IX-1, IX-1A, IX-3, XII-1, or Section VIII.

In an embodiment, the template nucleic acid is or comprises a fragment of 10 to 500, 10 to 400, 10 to 300, 10 to 200 nucleotides in length from a sequence in: a gene, or a gene from a pathway, described herein, e.g., in Section VIIB, e.g., in Table VII-13, VII-14, VII-15, VII-16, VII-17, VII-18, VII-19, VII-20, VII-21, VII-22, VII-23, VII-24, IX-1, IX-1A, IX-3, or XII-1, or in Section VIII.

In an embodiment, the template nucleic acid is or comprises a fragment of 10 to 500, 10 to 400, 10 to 300, 10 to 200 nucleotides in length, which differs at at least 1 nucleotide, but not more than 5, 10, 20 or 30% of its nucleotides, from a corresponding sequence in: a gene, or a gene from a pathway, described herein, e.g., in Section VIIB, e.g., in Table VII-13, VII-14, VII-15, VII-16, VII-17, VII-18, VII-19, VII-20, VII-21, VII-22, VII-23, VII-24, IX-1, IX-1A, IX-3, or XII-1, or in Section VIII.

In an embodiment, one of said Cas9 molecule and said second Cas9 molecule mediates a double stranded break and the other mediates a single stranded break.

In an embodiment, said Cas9 molecule and said second Cas9 molecule are specific for different PAMs, e.g., one is specific for NGG and the other is specific for another PAM, e.g., another PAM described herein. In an embodiment, said gRNA molecule and said second gRNA molecule are configured such that a first and second break flank a target position. In an embodiment, said first and second break flank a target position. In an embodiment, one of said first and second breaks, or both are independently, within 10, 20, 30, 40, 50, 100, 150 or 200 nucleotides of a nucleotide of the target position.

In an embodiment, the composition further comprises a template nucleic acid. In an embodiment, the template nucleic acid comprises a nucleotide that corresponds to a nucleotide of the target position.

In an embodiment, said template nucleic acid comprises a nucleotide that corresponds to a nucleotide of the target position from a sequence of: a gene, or a gene from a pathway, described herein, e.g., in Section VIIB, e.g., in Table VII-13, VII-14, VII-15, VII-16, VII-17, VII-18, VII-19, VII-20, VII-21, VII-22, VII-23, VII-24, IX-1, IX-1A, IX-3, or XII-1, or in Section VIII.

In an embodiment, the template nucleic acid is or comprises a fragment of 10 to 500, 10 to 400, 10 to 300, 10 to 200 nucleotides in length from a sequence in: a gene, or a gene from a pathway, described herein, e.g., in Section VIIB, e.g., in Table VII-13, VII-14, VII-15, VII-16, VII-17, VII-18, VII-19, VII-20, VII-21, VII-22, VII-23, VII-24, IX-1, IX-1A, IX-3, or XII-1, or in Section VIII.

In an embodiment, the template nucleic acid is or comprises a fragment of 10 to 500, 10 to 400, 10 to 300, 10 to 200 nucleotides in length, which differs at at least 1 nucleotide, but not more than 5, 10, 20 or 30% of its nucleotides, from a corresponding sequence in: a gene, or a gene from a pathway, described herein, e.g., in Section VIIB, e.g., in Table VII-13, VII-14, VII-15, VII-16, VII-17, VII-18, VII-19, VII-20, VII-21, VII-22, VII-23, VII-24, IX-1, IX-1A, IX-3, or XII-1, or in Section VIII.

In an embodiment, said Cas9 molecule and said second Cas9 molecule both mediate single stranded breaks.

In an embodiment, said Cas9 molecule and said second Cas9 molecule are specific for different PAMs, e.g., one is specific for NGG and the other is specific for another PAM, e.g., another PAM described herein. In an embodiment, said first and second break flank a target position.

In an embodiment, one of said first and second single stranded breaks, or both are independently, within 10, 20, 30, 40, 50, 100, 150 or 200 nucleotides of a nucleotide of the target position.

In an embodiment, the composition further comprises a template nucleic acid. In an embodiment, the template nucleic acid comprises a nucleotide that corresponds to a nucleotide of the target position.

In an embodiment, said template nucleic acid comprises a nucleotide that corresponds to a nucleotide of the target position from a sequence of: a gene, or a gene from a pathway, described herein, e.g., in Section VIIB, e.g., in Table VII-13, VII-14, VII-15, VII-16, VII-17, VII-18, VII-19, VII-20, VII-21, VII-22, VII-23, VII-24, IX-1, IX-1A, IX-3, or XII-1, or in Section VIII.

In an embodiment, the template nucleic acid is or comprises a fragment of 10 to 500, 10 to 400, 10 to 300, 10 to 200 nucleotides in length from a sequence in: a gene, or a gene from a pathway, described herein, e.g., in Section VIIB, e.g., in Table VII-13, VII-14, VII-15, VII-16, VII-17, VII-18, VII-19, VII-20, VII-21, VII-22, VII-23, VII-24, IX-1, IX-1A, IX-3, or XII-1, or in Section VIII.

In an embodiment, the template nucleic acid is or comprises a fragment of 10 to 500, 10 to 400, 10 to 300, 10 to 200 nucleotides in length, which differs at at least 1 nucleotide, but not more than 5, 10, 20 or 30% of its nucleotides, from a corresponding sequence in: a gene, or a gene from a pathway, described herein, e.g., in Section VIIB, e.g., in Table VII-13, VII-14, VII-15, VII-16, VII-17, VII-18, VII-19, VII-20, VII-21, VII-22, VII-23, VII-24, IX-1, IX-1A, IX-3, or XII-1, or in Section VIII.

In an embodiment, said gRNA molecule, said second gRNA molecule are configured such that a first and second break are in the same strand.

In an embodiment, said Cas9 molecule and said second Cas9 molecule are specific for different PAMs, e.g., one is specific for NGG and the other is specific for another PAM, e.g., another PAM described herein. In an embodiment, said gRNA molecule, said second gRNA molecule are configured such that a first and second break flank a target position. In an embodiment, one of said first and second single stranded breaks, or both are independently, within 10, 20, 30, 40, 50, 100, 150 or 200 nucleotides of a nucleotide of the target position.

In an embodiment, the composition further comprises a template nucleic acid. In an embodiment, the template nucleic acid comprises a nucleotide that corresponds to a nucleotide of the target position.

In an embodiment, said template nucleic acid comprises a nucleotide that corresponds to a nucleotide of the target position from a sequence of: a gene, or a gene from a pathway, described herein, e.g., in Section VIIB, e.g., in Table VII-13, VII-14, VII-15, VII-16, VII-17, VII-18, VII-19, VII-20, VII-21, VII-22, VII-23, VII-24, IX-1, IX-1A, IX-3, or XII-1, or in Section VIII.

In an embodiment, the template nucleic acid is or comprises a fragment of 10 to 500, 10 to 400, 10 to 300, 10 to 200 nucleotides in length from a sequence in: a gene, or a gene from a pathway, described herein, e.g., in Section VIIB, e.g., in Table VII-13, VII-14, VII-15, VII-16, VII-17, VII-18, VII-19, VII-20, VII-21, VII-22, VII-23, VII-24, IX-1, IX-1A, IX-3, or XII-1, or in Section VIII.

In an embodiment, the template nucleic acid is or comprises a fragment of 10 to 500, 10 to 400, 10 to 300, 10 to 200 nucleotides in length, which differs at at least 1 nucleotide, but not more than 5, 10, 20 or 30% of its nucleotides, from a corresponding sequence in: a gene, or a gene from a pathway, described herein, e.g., in Section VIIB, e.g., in Table VII-13, VII-14, VII-15, VII-16, VII-17, VII-18, VII-19, VII-20, VII-21, VII-22, VII-23, VII-24, IX-1, IX-1A, IX-3, or XII-1, or in Section VIII.

In an embodiment, said first and second break are on the different strands.

In an embodiment, said Cas9 molecule and said second Cas9 molecule are specific for different PAMs, e.g., one is specific for NGG and the other is specific for another PAM, e.g., another PAM described herein. In an embodiment, said gRNA molecule, said second gRNA molecule are configured such that a first and second break are on different strands.

In an embodiment, said gRNA molecule, said second gRNA molecule are configured such that a first and second break flank a target position. In an embodiment, said first and second break flank a target position.

In an embodiment, one of said first and second single stranded breaks, or both are independently, within 10, 20, 30, 40, 50, 100, 150 or 200 nucleotides of a nucleotide of the target position.

In an embodiment, the composition further comprises a template nucleic acid. In an embodiment, the template nucleic acid comprises a nucleotide that corresponds to a nucleotide of the target position.

In an embodiment, said template nucleic acid comprises a nucleotide that corresponds to a nucleotide of the target position from a sequence of: a gene, or a gene from a pathway, described herein, e.g., in Section VIIB, e.g., in Table VII-13, VII-14, V11-15, VII-16, VII-17, VII-18, VII- 19, VII-20, VII-21, VII-22, VII-23, VII-24, IX-1, IX-1A, IX-3, or XII-1, or in Section VIII.

In an embodiment, the template nucleic acid is or comprises a fragment of 10 to 500, 10 to 400, 10 to 300, 10 to 200 nucleotides in length from a sequence in: a gene, or a gene from a pathway, described herein, e.g., in Section VIIB, e.g., in Table VII-13, VII-14, V11-15, VII-16, VII-17, VII-18, VII-19, VII-20, VII-21, VII-22, VII-23, VII-24, IX-1, IX-1A, IX-3, or XII-1, or in Section VIII.

In an embodiment, the template nucleic acid is or comprises a fragment of 10 to 500, 10 to 400, 10 to 300, 10 to 200 nucleotides in length, which differs at least 1 nucleotide, but not more than 5, 10, 20 or 30% of its nucleotides, from a corresponding sequence in: a gene, or a gene from a pathway, described herein, e.g., in Section VIIB, e.g., in Table VII-13, VII-14, VII-15, VII-16, VII-17, VII-18, VII-19, VII-20, VII-21, VII-22, VII-23, VII-24, IX-1, IX-1A, IX-3, or XII-1, or Section VIII.

In yet another aspect, the disclosure features a composition, e.g., a pharmaceutical composition, comprising governing gRNA molecule, e.g., a Cas9-targeting gRNA molecule or a gRNA-targeting gRNA molecule, a gRNA molecule and a second gRNA molecule described herein.

In an embodiment, the composition further comprises a nucleic acid, e.g., a DNA or mRNA, that encodes a Cas9 molecule described herein. In an embodiment, the composition further comprises a nucleic acid, e.g., a DNA or RNA, that encodes a second Cas9 molecule described herein. In an embodiment, the composition further comprises a template nucleic acid described herein.

In one aspect, the disclosure features a composition, e.g., a pharmaceutical composition, comprising, nucleic acid sequence, e.g., a DNA, that encodes a governing gRNA molecule, e.g., a Cas9-targeting gRNA molecule or a gRNA-targeting gRNA molecule, and one or more gRNA molecules described herein.

In an embodiment, said nucleic acid comprises a promoter operably linked to the sequence that encodes a gRNA molecule, e.g., a promoter described herein.

In an embodiment, said nucleic acid comprises a second promoter operably linked to the sequence that encodes a second gRNA molecule, e.g., a promoter described herein. In an embodiment, the promoter and second promoter are different promoters. In an embodiment, the promoter and second promoter are the same.

In an embodiment, the nucleic acid further encodes a Cas9 molecule described herein. In an embodiment, the nucleic acid further encodes a second Cas9 molecule described herein.

In an embodiment, said nucleic acid comprises a promoter operably linked to the sequence that encodes a Cas9 molecule, e.g., a promoter described herein.

In an embodiment, said nucleic acid comprises a second promoter operably linked to the sequence that encodes a second Cas9 molecule, e.g., a promoter described herein. In an embodiment, the promoter and second promoter are different promoters. In an embodiment, the promoter and second promoter are the same.

In an embodiment, the composition further comprises a template nucleic acid e.g., a template nucleic acid described herein, e.g., in Section IV.

In another aspect, the disclosure features a composition, e.g., a pharmaceutical composition, comprising nucleic acid sequence that encodes one or more of: a) a Cas9 molecule, b) a second Cas9 molecule, c) a gRNA molecule, d) a second gRNA molecule, and e) a governing gRNA molecule, e.g., a Cas9-targeting gRNA molecule or a gRNA-targeting gRNA molecule.

In an embodiment, each of a), b), c) d) and e) present are encoded on the same nucleic acid molecule.

In an embodiment, a first sequence selected from of a), b), c), d) and e) is encoded on a first nucleic acid molecule and a second sequence selected from a), b), c), d) and e) is encoded on a second nucleic acid molecule.

In an embodiment, said nucleic acid encodes: a), c) and e); a), c), d) and e); or a), b), c), d) and e).

In an embodiment, the composition further comprises a Cas9 molecule, e.g., comprising one or more of the Cas9 molecules wherein said nucleic acid does not encode a Cas9 molecule.

In an embodiment, the composition further comprises an mRNA encoding Cas9 molecule, e.g., comprising one or more mRNAs encoding one or more of the Cas9 molecules wherein said nucleic acid does not encode a Cas9 molecule.

In an embodiment, the composition further comprises a template nucleic acid e.g., a template nucleic acid described herein, e.g., in Section IV.

In yet another aspect, the disclosure features a nucleic acid described herein.

In one aspect, the disclosure features a composition comprising: a) a gRNA molecule (or combination of gRNA molecules, e.g., a gRNA molecule and a second gRNA molecule); b) an eaCas9 molecule (or combination of eaCas9 molecules, e.g., an eaCas9 molecule; and a second eaCas9 molecule); and c) optionally, a template nucleic acid e.g., a template nucleic acid described herein, e.g., in Section IV.

In another aspect, the disclosure features a composition comprising: a) a gRNA molecule (or combination of gRNA molecules, e.g., a gRNA molecule and a second gRNA molecule); b) a nucleic acid, e.g. a DNA or mRNA encoding an eaCas9 molecule (or combination of eaCas9 molecules, e.g., an eaCas9 molecule and a second eaCas9 molecule); c) optionally, a template nucleic acid, e.g., a template nucleic acid described herein, e.g., in Section IV; and d) a governing gRNA molecule, e.g., a Cas9-targeting gRNA molecule.

In yet another aspect, the disclosure features a composition comprising: a) a nucleic acid, e.g., a DNA, which encodes a gRNA molecule (or combination of gRNA molecules, e.g., a gRNA molecule and a second gRNA molecule); b) an eaCas9 molecule (or combination of eaCas9 molecules, e.g., an eaCas9 molecule and a second eaCas9 molecule); c) optionally, a template nucleic acid, e.g., a template nucleic acid described herein, e.g., in Section IV; and d) a governing gRNA molecule, e.g., a gRNA-targeting gRNA molecule.

In still another aspect, the disclosure features a composition comprising: a) nucleic acid, e.g., a DNA, which encodes a gRNA molecule or (or combination of gRNA molecules, e.g., a gRNA molecule and a second gRNA molecule); b) nucleic acid, e.g. a DNA or mRNA encoding eaCas9 molecule or (or combination of eaCas9 molecules, e.g., an eaCas9 molecule and a second eaCas9 molecule) (wherein the gRNA molecule encoding nucleic acid and the eaCas9 molecule encoding nucleic acid can be on the same or different molecules); c) optionally, a template nucleic acid, e.g., a template nucleic acid described herein, e.g., in Section IV; and d) a governing gRNA molecule, e.g., a Cas9-targeting gRNA molecule or a gRNA-targeting gRNA molecule.

In one aspect, the disclosure features a method of altering a cell, e.g., altering the structure, e.g., sequence, of a target nucleic acid of a cell, comprising contacting said cell with:
1) a composition comprising:
   a) a gRNA molecule (or combination of gRNA molecules, e.g., a gRNA molecule and a second gRNA molecule);
   b) an eaCas9 molecule (or combination of eaCas9 molecules, e.g., an eaCas9 molecule; and a second eaCas9 molecule); and
   c) optionally, a template nucleic acid, e.g., a template nucleic acid described herein, e.g., in Section IV;
2) a composition comprising:
   a) a gRNA molecule (or combination of gRNA molecules, e.g., a gRNA molecule and a second gRNA molecule);
   b) a nucleic acid, e.g. a DNA or mRNA encoding an eaCas9 molecule (or combination of eaCas9 molecules, e.g., an eaCas9 molecule and a second eaCas9 molecule); and
   c) optionally, a template nucleic acid, e.g., a template nucleic acid described herein, e.g., in Section IV; and
   d) a governing gRNA molecule, e.g., a Cas9-targeting gRNA molecule;
3) a composition comprising:
   a) a nucleic acid, e.g., a DNA, which encodes a gRNA molecule (or combination of gRNA molecules, e.g., a gRNA molecule and a second gRNA molecule);
   b) an eaCas9 molecule (or combination of eaCas9 molecules, e.g., an eaCas9 molecule and a second eaCas9 molecule); and
   c) optionally, a template nucleic acid, e.g., a template nucleic acid described herein, e.g., in Section IV; and
   d) a governing gRNA molecule, e.g., a Cas9-targeting gRNA molecule or a gRNA-targeting gRNA molecule; and/or
4) a composition comprising:
   a) nucleic acid, e.g., a DNA, which encodes a gRNA molecule (or combination of gRNA molecules, e.g., a gRNA molecule and a second gRNA molecule);
   b) nucleic acid, e.g. a DNA or mRNA encoding eaCas9 molecule (or combination of eaCas9 molecules, e.g., an eaCas9 molecule and a second eaCas9 molecule), (wherein the gRNA molecule encoding nucleic acid and the eaCas9 molecule encoding nucleic acid can be on the same or different molecules); and
   c) optionally, a template nucleic acid, e.g., a template nucleic acid described herein, e.g., in Section IV; and
   d) a governing gRNA molecule, e.g., a Cas9-targeting gRNA molecule or a gRNA-targeting gRNA molecule.

In an embodiment, a gRNA molecule or nucleic acid encoding a gRNA molecule, and an eaCas9 molecule, or nucleic acid encoding an eaCas9 molecule, are delivered in or by, one dosage form, mode of delivery, or formulation.

In an embodiment, a) a gRNA molecule or nucleic acid encoding a gRNA molecule is delivered in or by, a first dosage form, a first mode of delivery, or a first formulation; and b) an eaCas9 molecule, or nucleic acid encoding an eaCas9 molecule, is delivered in or by a second dosage form, second mode of delivery, or second formulation. In an embodiment, a governing gRNA molecule (or a nucleic acide that encodes it), e.g., a Cas9-targeting gRNA molecule or a gRNA-targeting gRNA molecule, is provided in the dosage form that contains the component it inactivates, or in another dosage form, mode of delivery, or formulation.

In an embodiment, the cell is an animal or plant cell. In an embodiment, the cell is a mammalian, primate, or human cell. In an embodiment, the cell is a human cell, e.g., a cell from described herein, e.g., in Section VIIA. In an embodiment, the cell is: a somatic cell, germ cell, prenatal cell, e.g., zygotic, blastocyst or embryonic, blastocyst cell, a stem cell, a mitotically competent cell, a meiotically competent cell. In an embodiment, the cell is a human cell, e.g., a cancer cell or other cell characterized by a disease or disorder.

In an embodiment, the target nucleic acid is a chromosomal nucleic acid. In an embodiment, the target nucleic acid is an organellar nucleic acid. In an embodiment, the target nucleic acid is a mitochondrial nucleic acid. In an embodiment, the target nucleic acid is a chloroplast nucleic acid.

In an embodiment, the cell is a cell of a disease causing organism, e.g., a virus, bacterium, fungus, protozoan, or parasite.

In an embodiment, the target nucleic acid is the nucleic acid of a disease causing organism, e.g., of a disease causing organism, e.g., a virus, bacterium, fungus, protozoan, or parasite.

In an embodiment, said method comprises: modulating the expression of a gene or inactivating a disease organism.

In an embodiment, said cell is a cell characterized by unwanted proliferation, e.g., a cancer cell. In an embodiment, said cell is a cell characterized by an unwanted genomic component, e.g., a viral genomic component. In an embodiment, the cell is a cell described herein, e.g., in Section IIA. In an embodiment, a control or structural sequence of at least, 2 3, 4, 5 or 6 or more genes is altered.

In an embodiment, the target nucleic acid is a rearrangement, a rearrangement that comprises a kinase gene, or a rearrangement that comprises a tumor suppressor gene. In an embodiment, the targent nucleic acid comprises a kinase gene or a tumor suppressor gene.

In an embodiment, the method comprises cleaving a target nucleic acid within 10, 20, 30, 40, 50, 100, 150 or 200 nucleotides of a nucleotide of the target position. In an embodiment, said composition comprises a template nucleic acid.

In an embodiment, the template nucleic acid comprises a nucleotide that corresponds to a nucleotide of the target position.

In an embodiment, said template nucleic acid comprises a nucleotide that corresponds to a nucleotide of the target position from a sequence of: a gene, or a gene from a pathway, described herein, e.g., in Section VIIB, e.g., in Table VII-13, VII-14, VII-15, VII-16, VII-17, VII-18, VII-19, VII-20, VII-21, VII-22, VII-23, VII-24, IX-1, IX-1A, IX-3, or XII-1, or in Section VIII.

In an embodiment, the template nucleic acid is or comprises a fragment of 10 to 500, 10 to 400, 10 to 300, 10 to 200 nucleotides in length from a sequence in: a gene, or a gene from a pathway, described herein, e.g., in Section VIIB, e.g., in Table VII-13, VII-14, VII-15, VII-16, VII-17, VII-18, VII-19, VII-20, VII-21, VII-22, VII-23, VII-24, IX-1, IX-1A, IX-3, or XII-1, or in Section VIII.

In an embodiment, the template nucleic acid is or comprises a fragment of 10 to 500, 10 to 400, 10 to 300, 10 to 200 nucleotides in length, which differs at at least 1 nucleotide, but not more than 5, 10, 20 or 30% of its nucleotides, from a corresponding sequence in: a gene, or a gene from a pathway, described herein, e.g., in Section VIIB, e.g., in Table VII-13, VII-14, VII-15, VII-16, VII-17, VII-18, VII-19, VII-20, VII-21, VII-22, VII-23, VII-24, IX-1, IX-1A, IX-3, or XII-1, or in Section VIII.

In an embodiment,
   a) a control region, e.g., a cis-acting or tans-acting control region, of a gene is cleaved;

b) the sequence of a control region, e.g., a cis-acting or trans-acting control region, of a gene is altered, e.g., by an alteration that modulates, e.g., increases or decreases, expression a gene under control of the control region, e.g., a control sequence is disrupted or a new control sequence is inserted;

c) the coding sequence of a gene is cleaved;

d) the sequence of a transcribed region, e.g., a coding sequence of a gene is altered, e.g., a mutation is corrected or introduced, an alteration that increases expression of or activity of the gene product is effected, e.g., a mutation is corrected; and/or e) the sequence of a transcribed region, e.g., the coding sequence of a gene is altered, e.g., a mutation is corrected or introduced, an alteration that decreases expression of or activity of the gene product is effected, e.g., a mutation is inserted, e.g., the sequence of one or more nucleotides is altered so as to insert a stop codon.

In an embodiment, a control region or transcribed region, e.g., a coding sequence, of at least 2, 3, 4, 5, or 6 or more genes are altered.

In another aspect, the disclosure features a method of treating a subject, e.g., by altering the structure, e.g., altering the sequence, of a target nucleic acid, comprising administering to the subject, an effective amount of:

1) a composition comprising:
a) a gRNA molecule (or combination of gRNA molecules, e.g., a gRNA molecule and a second gRNA molecule);
b) an eaCas9 molecule (or combination of eaCas9 molecules, e.g., an eaCas9 molecule; and a second eaCas9 molecule); and
c) optionally, a template nucleic acid, e.g., a template nucleic acid described herein, e.g., in Section IV;

2) a composition comprising:
a) a gRNA molecule (or combination of gRNA molecules, e.g., a gRNA molecule and a second gRNA molecule);
b) a nucleic acid, e.g. a DNA or mRNA encoding an eaCas9 molecule (or combination of eaCas9 molecules, e.g., an eaCas9 molecule and a second eaCas9 molecule); and
c) optionally, a template nucleic acid, e.g., a template nucleic acid described herein, e.g., in Section IV; and
d) a governing gRNA molecule, e.g., a Cas9-targeting gRNA molecule;

3) a composition comprising:
a) a nucleic acid, e.g., a DNA, which encodes a gRNA molecule (or combination of gRNA molecules, e.g., a gRNA molecule and a second gRNA molecule);
b) an eaCas9 molecule (or combination of eaCas9 molecules, e.g., an eaCas9 molecule and a second eaCas9 molecule); and
c) optionally, a template nucleic acid, e.g., a template nucleic acid described herein, e.g., in Section IV; and
d) a governing gRNA molecule, e.g., a gRNA-targeting gRNA molecule;

and/or 4) a composition comprising:
a) nucleic acid, e.g., a DNA, which encodes a gRNA molecule or (or combination of gRNA molecules, e.g., a gRNA molecule and a second gRNA molecule);
b) nucleic acid, e.g. a DNA or mRNA encoding eaCas9 molecule or (or combination of eaCas9 molecules, e.g., an eaCas9 molecule and a second eaCas9 molecule), (wherein the gRNA molecule encoding nucleic acid and the eaCas9 molecule encoding nucleic acid can be on the same or different molecules); and c) optionally, a template nucleic acid, e.g., a template nucleic acid described herein, e.g., in Section IV; and
d) a governing gRNA molecule, e.g., a Cas9-targeting gRNA molecule or a gRNA-targeting gRNA molecule.

In an embodiment, a gRNA molecule or nucleic acid encoding a gRNA molecule, and an eaCas9 molecule, or nucleic acid encoding an eaCas9 molecule, are delivered in or by one dosage form, mode of delivery, or formulation. In an embodiment, a governing gRNA molecule (or a nucleic acide that encodes it), e.g., a Cas9-targeting gRNA molecule or a gRNA-targeting gRNA molecule, is provided in the dosage form that contains the component it inactivates, or in another dosage form, mode of delivery, or formulation.

In an embodiment, a gRNA molecule or nucleic acid encoding a gRNA molecule is delivered in or by a first dosage form, in a first mode of delivery, or first formulation; and an eaCas9 molecule, or nucleic acid encoding an eaCas9 molecule, is delivered in or by a second dosage form, second mode of delivery, or second formulation. In an embodiment a governing gRNA molecule (or a nucleic acide that encodes it), e.g., a Cas9-targeting gRNA molecule or a gRNA-targeting gRNA molecule, can provided in the dosage form that contains the component it inactivates, or in another dosage form, mode of delivery, or formulation.

In an embodiment, the subject is an animal or plant. In an embodiment, the subject is a mammalian, primate, or human.

In an embodiment, the target nucleic acid is the nucleic acid of a human cell, e.g., a cell described herein, e.g., in Section VIIA. In an embodiment, the target nucleic acid is the nucleic acid of: a somatic cell, germ cell, prenatal cell, e.g., zygotic, blastocyst or embryonic, blasotcyst cell, a stem cell, a mitotically competent cell, a meiotically competent cell.

In an embodiment, the target nucleic acid is a chromosomal nucleic acid. In an embodiment, the target nucleic acid is an organellar nucleic acid. In an embodiment, the nucleic acid is a mitochondrial nucleic acid. In an embodiment, the nucleic acid is a chloroplast nucleic acid.

In an embodiment, the target nucleic acid is the nucleic acid of a disease causing organism, e.g., of a disease causing organism, e.g., a virus, bacterium, fungus, protozoan, or parasite. In an embodiment, said method comprises modulating expression of a gene or inactivating a disease organism.

In an embodiment, the target nucleic acid is the nucleic acid of a cell characterized by unwanted proliferation, e.g., a cancer cell. In an embodiment, said target nucleic acid comprises an unwanted genomic component, e.g., a viral genomic component. In an embodiment, a control or structural sequence of at least, 2 3, 4, 5 or 6 or more genes is altered. In an embodiment, the target nucleic acid is a rearrangement, a rearrangement that comprises a kinase gene, or a rearrangement that comprises a tumor suppressor gene. In an embodiment, the targent nucleic acid comprises a kinase gene or a tumor suppressor gene.

In an embodiment, the method comprises cleaving a target nucleic acid within 10, 20, 30, 40, 50, 100, 150 or 200 nucleotides of a nucleotide of the target position.

In an embodiment, said composition comprises a template nucleic acid. In an embodiment, the template nucleic acid comprises a nucleotide that corresponds to a nucleotide of the target position.

In an embodiment, said template nucleic acid comprises a nucleotide that corresponds to a nucleotide of the target position from a sequence of: a gene, or a gene from a pathway, described herein, e.g., in Section VIIB, e.g., in Table VII-13, VII-14, VII-15, VII-16, VII-17, VII-18, VII-19, VII-20, VII-21, VII-22, VII-23, VII-24, IX-1, IX-1A, IX-3, or XII-1, or in Section VIII.

In an embodiment, the template nucleic acid is or comprises a fragment of 10 to 500, 10 to 400, 10 to 300, 10 to 200 nucleotides in length from a sequence in: a gene, or a gene from a pathway, described herein, e.g., in Section VIIB, e.g., in Table VII-13, VII-14, VII-15, VII-16, VII-17, VII-18, VII-19, VII-20, VII-21, VII-22, VII-23, VII-24, IX-1, IX-1A, IX-3, or XII-1, or in Section VIII.

In an embodiment, the template nucleic acid is or comprises a fragment of 10 to 500, 10 to 400, 10 to 300, 10 to 200 nucleotides in length, which differs at at least 1 nucleotide, but not more than 5, 10, 20 or 30% of its nucleotides, from a corresponding sequence in:

In an embodiment, a) a control region, e.g., a cis-acting or trans-acting control region, of a gene is cleaved;

b) the sequence of a control region, e.g., a cis-acting or trans-acting control region, of a gene is altered, e.g., by an alteration that modulates, e.g., increases or decreases, expression a gene under control of the control region, e.g., a control sequence is disrupted or a new control sequence is inserted;

c) the coding sequence of a gene is cleaved;

d) the sequence of a transcribed region, e.g., a coding sequence of a gene is altered, e.g., a mutation is corrected or introduced, an alteration that increases expression of or activity of the gene product is effected, e.g., a mutation is corrected;

e) the non-coding sequence of a gene or an intergenic region between genes is cleaved; and/or f) the sequence of a transcribed region, e.g., the coding sequence of a gene is altered, e.g., a mutation is corrected or introduced, an alteration that decreases expression of or activity of the gene product is effected, e.g., a mutation is inserted, e.g., the sequence of one or more nucleotides is altered so as to insert a stop codon.

In an embodiment, a control region or transcribed region, e.g., a coding sequence, of at least 2, 3, 4, 5, or 6 or more genes are altered.

In one aspect, the disclosure features a composition comprising: a) a gRNA molecule (or combination of gRNA molecules, e.g., a gRNA molecule and a second gRNA molecule); b) a Cas9 molecule, e.g., an eiCas9 molecule (or combination of Cas9 molecules, e.g., an eiCas9 molecule and a second eiCas9 molecule); and c) a payload coupled, covalently or non-covalently, to a complex of the gRNA molecule and the Cas9 molecule, e.g., coupled to the Cas9 molecule or the gRNA molecule.

In another aspect, the disclosure features a composition comprising: a) a gRNA molecule (or combination of gRNA molecules, e.g., a gRNA molecule and a second gRNA molecule); b) a nucleic acid, e.g. a DNA or mRNA encoding a Cas9 molecule, e.g., an eiCas9 molecule (or combination of Cas9 molecules, e.g., an eiCas9 molecule and a second eiCas9 molecule); and c) a payload which is: coupled, covalently or non-covalently, the gRNA molecule; or a fusion partner with the Cas9 molecule.

In yet another aspect, the disclosure features a composition comprising: a) a nucleic acid, e.g., a DNA, which encodes a gRNA molecule (or combination of gRNA molecules, e.g., a gRNA molecule and a second gRNA molecule); b) a Cas9 molecule, e.g., an eiCas9 molecule (or combination of Cas9 molecules, e.g., an eiCas9 molecule and a second eiCas9 molecule); c) a payload which is coupled, covalently or non-covalently, to the Cas9 molecule; and d) a governing gRNA molecule, e.g., a gRNA-targeting gRNA molecule.

In still another aspect, the disclosure features a composition comprising: a) nucleic acid, e.g., a DNA, which encodes a gRNA molecule or (or combination of gRNA molecules, e.g., a gRNA molecule and a second gRNA molecule); b) nucleic acid, e.g. a DNA or mRNA, encoding a Cas9 molecule, e.g., an eiCas9 molecule (or combination of Cas9 molecules, e.g., an eiCas9 molecule and a second eiCas9 molecule), wherein the gRNA molecule encoding nucleic acid and the eaCas9 molecule encoding nucleic acid can be on the same or different molecules; c) a payload which is a fusion partner with the Cas9 molecule; and d) a governing gRNA molecule, e.g., a Cas9-targeting gRNA molecule or a gRNA-targeting gRNA molecule.

In one aspect, the disclosure features a method of delivering a payload to a cell, e.g., by targeting a payload to target nucleic acid, comprising contacting said cell with:

1) a composition comprising:
a) a gRNA molecule (or combination of gRNA molecules, e.g., a gRNA molecule and a second gRNA molecule);
b) a Cas9 molecule, e.g., an eiCas9 molecule (or combination of Cas9 molecules, e.g., an eiCas9 molecule and a second eiCas9 molecule); and
c) a payload coupled, covalently or non-covalently, to a complex of the gRNA molecule and the Cas9 molecule, e.g., coupled to the Cas9 molecule or the gRNA molecule;

2) a composition comprising:
a) a gRNA molecule (or combination of gRNA molecules, e.g., a gRNA molecule and a second gRNA molecule);
b) a nucleic acid, e.g. a DNA or mRNA encoding a Cas9 molecule, e.g., an eiCas9 molecule (or combination of Cas9 molecules, e.g., an eiCas9 molecule and a second eiCas9 molecule);
c) a payload which is: coupled, covalently or non-covalently, the gRNA molecule; or a fusion partner with the Cas9 molecule;

3) a composition comprising:
a) a nucleic acid, e.g., a DNA, which encodes a gRNA molecule (or combination of gRNA molecules, e.g., a gRNA molecule and a second gRNA molecule);
b) a Cas9 molecule, e.g., an eiCas9 molecule (or combination of Cas9 molecules, e.g., an eiCas9 molecule and a second eiCas9 molecule);
c) a payload which is coupled, covalently or non-covalently, to the Cas9 molecule; and
d) a governing gRNA molecule, e.g., a gRNA-targeting gRNA molecule; and/or 4) a composition comprising:
a) nucleic acid, e.g., a DNA, which encodes a gRNA molecule or (or combination of gRNA molecules, e.g., a gRNA molecule and a second gRNA molecule);
b) nucleic acid, e.g. a DNA or mRNA, encoding a Cas9 molecule, e.g., an eiCas9 molecule (or combination of Cas9 molecules, e.g., an eiCas9 molecule and a second eiCas9 molecule), wherein the gRNA molecule encoding nucleic acid and the eaCas9 molecule encoding nucleic acid can be on the same or different molecules;
c) a payload which is a fusion partner with the Cas9 molecule; and
d) a governing gRNA molecule, e.g., a Cas9-targeting gRNA molecule or a gRNA-targeting gRNA molecule.

In an embodiment, a gRNA molecule or nucleic acid encoding a gRNA molecule, and an eaCas9 molecule, or nucleic acid encoding an eaCas9 molecule, are delivered in or by one dosage form, mode of delivery, or formulation. In an embodiment, a governing gRNA molecule (or a nucleic acide that encodes it), e.g., a Cas9-targeting gRNA molecule or a gRNA-targeting gRNA molecule, is provided in the dosage form that contains the component it inactivates, or in another dosage form, mode of delivery, or formulation.

In an embodiment, a gRNA molecule or nucleic acid encoding a gRNA molecule is delivered in or by a first dosage form, first mode of delivery, or first formulation; and a Cas9 molecule, or nucleic acid encoding a Cas9 molecule, is delivered in or by a second dosage form, second mode of delivery, or second formulation. In an embodiment, a governing gRNA molecule (or a nucleic acide that encodes it), e.g., a Cas9-targeting gRNA molecule or a gRNA-targeting gRNA molecule, is provided in the dosage form that contains the component it inactivates, or in another dosage form, mode of delivery, or formulation.

In an embodiment, the cell is an animal or plant cell. In an embodiment, the cell is a mammalian, primate, or human cell. In an embodiment, the cell is a human cell, e.g., a human cell described herein, e.g., in Section VIIA. In an embodiment, the cell is: a somatic cell, germ cell, prenatal cell, e.g., zygotic, blastocyst or embryonic, blasotcyst cell, a stem cell, a mitotically competent cell, a meiotically competent cell. In an embodiment, the cell is a human cell, e.g., a cancer cell, a cell comprising an unwanted genetic element, e.g., all or part of a viral genome.

In an embodiment, the gRNA mediates targeting of a chromosomal nucleic acid. In an embodiment, the gRNA mediates targeting of a selected genomic signature. In an embodiment, the gRNA mediates targeting of an organellar nucleic acid. In an embodiment, the gRNA mediates targeting of a mitochondrial nucleic acid. In an embodiment, the gRNA mediates targeting of a chloroplast nucleic acid.

In an embodiment, the cell is a cell of a disease causing organism, e.g., a virus, bacterium, fungus, protozoan, or parasite.

In an embodiment, the gRNA mediates targeting of the nucleic acid of a disease causing organism, e.g., of a disease causing organism, e.g., a virus, bacterium, fungus, protozoan, or parasite.

In an embodiment, the payload comprises a payload described herein, e.g., in Section VI.

In an embodiment, said cell is a cell characterized by unwanted proliferation, e.g., a cancer cell. In an embodiment, said cell is characterized by an unwanted genomic component, e.g., a viral genomic component.

In an embodiment, a control or structural sequence of at least 2 3, 4, 5, or 6 or more genes is altered.

In an embodiment, the gRNA targets a selected genomic signature, e.g., a mutation, e.g., a germline or acquired somatic mutation. In an embodiment, the target nucleic acid is a rearrangement, a rearrangement that comprises a kinase gene, or a rearrangement that comprises a tumor suppressor gene. In an embodiment, the targent nucleic acid comprises a kinase gene or a tumor suppressor gene. In an embodiment, the gRNA targets a cancer cell, e.g., a cancer cell disclosed herein, e.g., in Section VIIA. In an embodiment, the gRNA targets a cell which has been infected with a virus.

In another aspect, the disclosure features a method of treating a subject, e.g., by targeting a payload to target nucleic acid, comprising administering to the subject, an effective amount of:
1) a composition comprising:
   a) a gRNA molecule (or combination of gRNA molecules, e.g., a gRNA molecule and a second gRNA molecule);
   b) a Cas9 molecule, e.g., an eiCas9 molecule (or combination of Cas9 molecules, e.g., an eiCas9 molecule and a second eiCas9 molecule); and
   c) a payload coupled, covalently or non-covalently, to a complex of the gRNA molecule and the Cas9 molecule, e.g., coupled to the Cas9 molecule;
2) a composition comprising:
   a) a gRNA molecule (or combination of gRNA molecules, e.g., a gRNA molecule and a second gRNA molecule);
   b) a nucleic acid, e.g. a DNA or mRNA encoding a Cas9 molecule, e.g., an eiCas9 molecule (or combination of Cas9 molecules, e.g., an eiCas9 molecule and a second eiCas9 molecule);
   c) a payload which is:
      coupled, covalently or non-covalently, the gRNA molecule; or
      is a fusion partner with the Cas9 molecule; and
   d) a governing gRNA molecule, e.g., a Cas9-targeting gRNA molecule;
3) a composition comprising:
   a) a nucleic acid, e.g., a DNA, which encodes a gRNA molecule (or combination of gRNA molecules, e.g., a gRNA molecule and a second gRNA molecule);
   b) a Cas9 molecule, e.g., an eiCas9 molecule (or combination of Cas9 molecules, e.g., an eiCas9 molecule and a second eiCas9 molecule); and
   c) a payload which is coupled, covalently or non-covalently, to the Cas9 molecule; and
   d) a governing gRNA molecule, e.g., a gRNA-targeting gRNA molecule; and/or
4) a composition comprising:
   a) a nucleic acid, e.g., a DNA, which encodes a gRNA molecule or (or combination of gRNA molecules, e.g., a gRNA molecule and a second gRNA molecule);
   b) a nucleic acid, e.g. a DNA or mRNA, encoding a Cas9 molecule, e.g., an eiCas9 molecule (or combination of Cas9 molecules, e.g., an eiCas9 molecule and a second eiCas9 molecule), (wherein the gRNA molecule encoding nucleic acid and the eaCas9 molecule encoding nucleic acid can be on the same or different molecules);
   c) a payload which is a fusion partner with the Cas9 molecule; and
   d) a governing gRNA molecule, e.g., a Cas9-targeting gRNA molecule or a gRNA-targeting gRNA molecule.

In an embodiment, a gRNA molecule or nucleic acid encoding a gRNA molecule, and an eaCas9 molecule, or nucleic acid encoding an eaCas9 molecule, are delivered in or by one dosage form, mode of delivery, or formulation. In an embodiment a governing gRNA molecule (or a nucleic acide that encodes it), e.g., a Cas9-targeting gRNA molecule or a gRNA-targeting gRNA molecule, can provided in the dosage form that contains the component it inactivates, or in another dosage form, mode of delivery, or formulation.

In an embodiment, a gRNA molecule or nucleic acid encoding a gRNA molecule is delivered in or by a first dosage, mode of delivery form or formulation; and a Cas9 molecule, or nucleic acid encoding a Cas9 molecule, is delivered in or by a second dosage form, mode of delivery, or formulation. In an embodiment a governing gRNA molecule (or a nucleic acide that encodes it), e.g., a Cas9-targeting gRNA molecule or a gRNA-targeting gRNA molecule, can provided in the dosage form that contains the component it inactivates, or in another dosage form, mode of delivery, or formulation.

In an embodiment, the subject is an animal or plant cell. In an embodiment, the subject is a mammalian, primate, or human cell.

In an embodiment, the gRNA mediates targeting of a human cell, e.g., a human cell described herein, e.g., in Section VIIA. In an embodiment, the gRNA mediates targeting of: a somatic cell, germ cell, prenatal cell, e.g., zygotic, blastocyst or embryonic, blasotcyst cell, a stem cell, a mitotically competent cell, a meiotically competent cell. In an embodiment, the gRNA mediates targeting of a cancer cell or a cell comprising an unwanted genomic element, e.g., all or part of a viral genome. In an embodiment, the gRNA mediates targeting of a chromosomal nucleic acid. In an embodiment, the gRNA mediates targeting of a selected genomic signature. In an embodiment, the gRNA mediates targeting of an organellar nucleic acid. In an embodiment, the gRNA mediates targeting of a mitochondrial nucleic acid. In an embodiment, the gRNA mediates targeting of a chloroplast nucleic acid. In an embodiment, the gRNA mediates targeting of the nucleic acid of a disease causing organism, e.g., of a disease causing organism, e.g., a virus, bacterium, fungus, protozoan, or parasite. In an embodiment, the gRNA targets a cell characterized by unwanted proliferation, e.g., a cancer cell, e.g., a cancer cell from Section VIIA, e.g., from Table VII-11. In an embodiment, the gRNA targets a cell characterized by an unwanted genomic component, e.g., a viral genomic component.

In an embodiment, a control element, e.g., a promoter or enhancer, is targeted. In an embodiment, the target nucleic acid is a rearrangement, a rearrangement that comprises a kinase gene, or a rearrangement that comprises a tumor suppressor gene. In an embodiment, the targent nucleic acid comprises a kinase gene or a tumor suppressor gene. In an embodiment, the gRNA targets a selected genomic signature, e.g., a mutation, e.g., a germline or acquired somatic mutation.

In an embodiment, the gRNA targets a cancer cell. In an embodiment, the gRNA targets a cell which has been infected with a virus.

In an embodiment, at least one eaCas9 molecule and a payload are administered. In an embodiment, the payload comprises a payload described herein, e.g., in Section VI.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In addition, the materials, methods, and examples are illustrative only and not intended to be limiting.

Headings, including numeric and alphabetical headings and subheadings, are for organization and presentation and are not intended to be limiting.

Other features and advantages of the invention will be apparent from the detailed description, drawings, and from the claims.

BRIEF DESCRIPTION OF THE DRAWING

The Figures described below, that together make up the Drawing, are for illustration purposes only, not for limitation.

FIG. 1A-G are representations of several exemplary gRNAs.

FIG. 1A depicts a modular gRNA molecule derived in part (or modeled on a sequence in part) from *Streptococcus pyogenes* (*S. pyogenes*) as a duplexed structure (SEQ ID NOS 42 and 43, respectively, in order of appearance);

FIG. 1B depicts a unimolecular (or chimeric) gRNA molecule derived in part from *S. pyogenes* as a duplexed structure (SEQ ID NO: 44);

FIG. 1C depicts a unimolecular gRNA molecule derived in part from *S. pyogenes* as a duplexed structure (SEQ ID NO: 45);

FIG. 1D depicts a unimolecular gRNA molecule derived in part from *S. pyogenes* as a duplexed structure (SEQ ID NO: 46);

FIG. 1E depicts a unimolecular gRNA molecule derived in part from *S. pyogenes* as a duplexed structure (SEQ ID NO: 47);

FIG. 1F depicts a modular gRNA molecule derived in part from *Streptococcus thermophilus* (*S. thermophilus*) as a duplexed structure (SEQ ID NOS 48 and 49, respectively, in order of appearance);

FIG. 1G depicts an alignment of modular gRNA molecules of *S. pyogenes* and *S. thermophilus* (SEQ ID NOS 50-53, respectively, in order of appearance).

FIG. 2 depicts an alignment of Cas9 sequences from Chylinski et al., RNA BIOL. 2013; 10(5): 726-737. The N-terminal RuvC-like domain is boxed and indicated with a "Y". The other two RuvC-like domains are boxed and indicated with a "B". The HNH-like domain is boxed and indicated by a "G". Sm: *S. nutans* (SEQ ID NO: 1); Sp: *S. pyogenes* (SEQ ID NO: 2); St: *S. thermophilus* (SEQ ID NO: 3); Li: *L. innocua* (SEQ ID NO: 4). Motif: this is a motif based on the four sequences: residues conserved in all four sequences are indicated by single letter amino acid abbreviation; "*" indicates any amino acid found in the corresponding position of any of the four sequences; and "-" indicates any amino acid, e.g., any of the 20 naturally occurring amino acids.

FIG. 3A shows an alignment of the N-terminal RuvC-like domain from the Cas9 molecules disclosed in Chylinski et al. (SEQ ID NOS 54-103, respectively, in order of appearance). The last line of FIG. 3A identifies 3 highly conserved residues.

FIG. 3B shows an alignment of the N-terminal RuvC-like domain from the Cas9 molecules disclosed in Chylinski et al. with sequence outliers removed (SEQ ID NOS 104-177, respectively, in order of appearance). The last line of FIG. 3B identifies 4 highly conserved residues.

FIG. 4A shows an alignment of the HNH-like domain from the Cas9 molecules disclosed in Chylinski et al. (SEQ ID NOS 178-252, respectively, in order of appearance). The last line of FIG. 4A identifies conserved residues.

FIG. 4B shows an alignment of the HNH-like domain from the Cas9 molecules disclosed in Chylinski et al. with sequence outliers removed (SEQ ID NOS 253-302, respectively, in order of appearance). The last line of FIG. 4B identifies 3 highly conserved residues.

FIG. 5 depicts an alignment of Cas9 sequences from *S. pyogenes* and *Neisseria meningitidis* (*N. meningitidis*). The N-terminal RuvC-like domain is boxed and indicated with a "Y". The other two RuvC-like domains are boxed and indicated with a "B". The HNH-like domain is boxed and indicated with a "G". Sp: *S. pyogenes*; Nm: *N. meningitidis*. Motif: this is a motif based on the two sequences: residues conserved in both sequences are indicated by a single amino acid designation; "*" indicates any amino acid found in the corresponding position of any of the two sequences; "-" indicates any amino acid, e.g., any of the 20 naturally occurring amino acids, and "-" indicates any amino acid, e.g., any of the 20 naturally occurring amino acids, or absent.

FIG. 6 shows a nucleic acid sequence encoding Cas9 of *N. meningitidis* (SEQ ID NO: 303). Sequence indicated by an "R" is an SV40 NLS; sequence indicated as "G" is an HA tag; sequence indicated by an "0" is a synthetic NLS sequence. The remaining (unmarked) sequence is the open reading frame (ORF).

DEFINITIONS

Figure 1A:
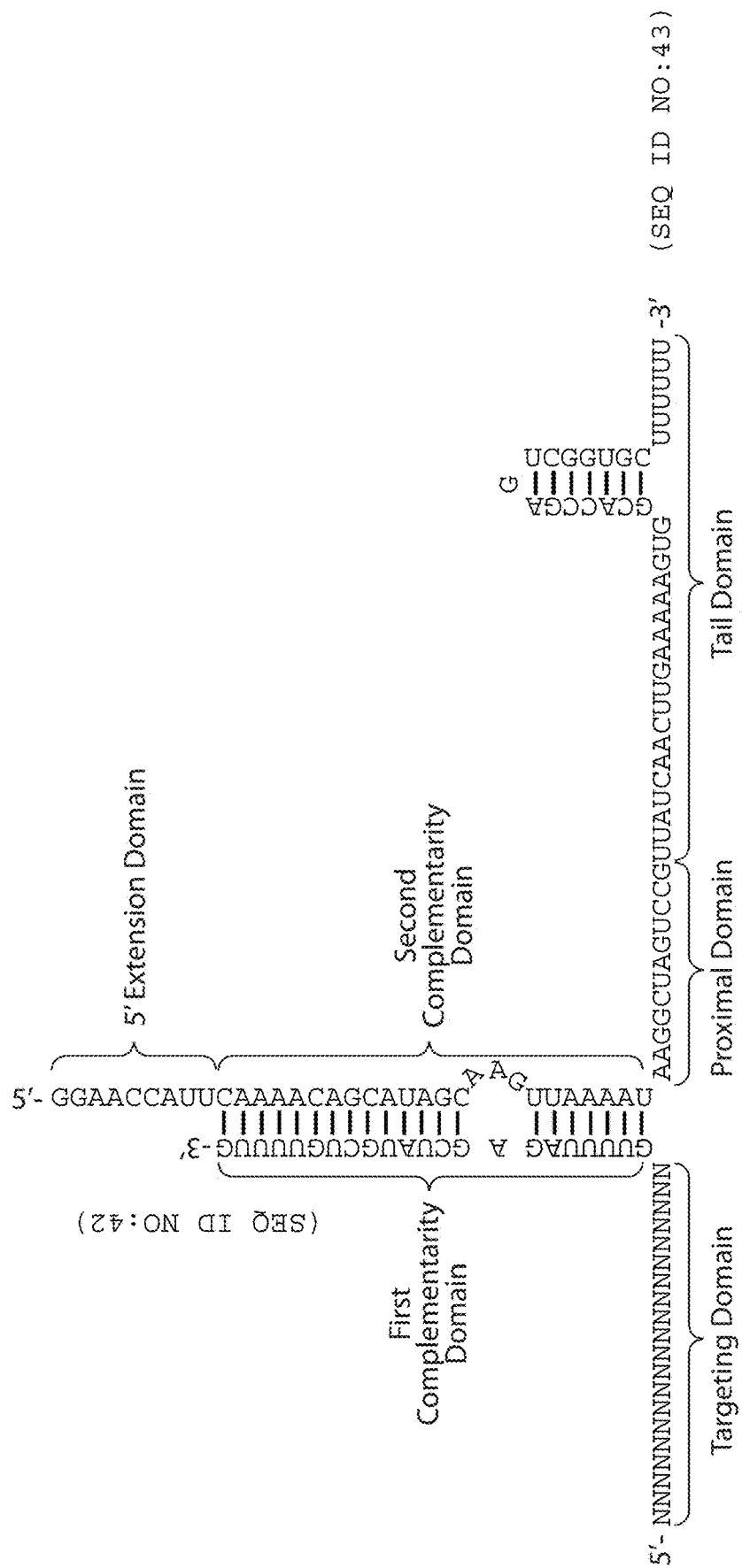

"Governing gRNA molecule", as used herein, refers to a gRNA molecule that can complex with a Cas9 molecule to inactivate or silence a component of the Cas9 system. In an embodiment, the governing gRNA molecule inactivates or silences a nucleic acid that comprises the sequence encoding the Cas9 molecule. In an embodiment, it inactivates or silences the nucleic acid that comprises the sequence encoding the gRNA molecule. In an embodiment, the governing gRNA, e.g., a Cas9-targeting gRNA molecule, or a gRNA targeting gRNA molecule, limits the effect of the Cas9 molecule/gRNA molecule complex-mediated gene targeting. In an embodiment, it places temporal, level of expression, or other limits, on activity of the Cas9 molecule/gRNA molecule complex. In an embodiment, it reduces off-target or other unwanted activity. Governing gRNA molecules can act as to inhibit, e.g., entirely or substantially inhibit, the production of a component of the Cas9 system, e.g., the Cas9 molecule, and thereby limit, or govern, its activity.

The governing gRNA molecule can target any region of the nucleic acid that comprises the sequence encoding the component to be negatively regulated, within or outside the transcribed or translated region of the component, as long as production of the component is reduced.

In an embodiment, a governing gRNA molecule comprises a targeting sequence that is complementary with a target sequence on the nuciec acid on which the sequence encoding the component to be negatively regulated resides.

In an embodiment, a governing gRNA molecule comprises a targeting sequence that is complementary with a sequence of the component to be negatively regulated.

In an embodiment, a Cas9-targeting gRNA molecule can include a targeting sequence that targets the nucleic acid on which the sequence that encodes the Cas9 molecule resides.

In an embodiment, a Cas9-targeting gRNA molecule can include a targeting sequence that targets the Cas9 molecule sequence.

In an embodiment, a gRNA-targeting gRNA molecule can include a targeting sequence that targets the nucleic acid on which the sequence that encodes the gRNA molecule resides.

In an embodiment, a gRNA-targeting gRNA molecule can include a targeting sequence that targets the gRNA molecule sequence.

"Domain", as used herein, is used to describe segments of a protein or nucleic acid. Unless otherwise indicated, a domain is not required to have any specific functional property.

Calculations of "homology" or "sequence identity" between two sequences (the terms are used interchangeably herein) are performed as follows. The sequences are aligned for optimal comparison purposes (e.g., gaps can be introduced in one or both of a first and a second amino acid or nucleic acid sequence for optimal alignment and non-homologous sequences can be disregarded for comparison purposes). The optimal alignment is determined as the best score using the GAP program in the GCG software package with a Blossum 62 scoring matrix with a gap penalty of 12, a gap extend penalty of 4, and a frame shift gap penalty of 5. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein, In an embodiment, amino acid or nucleic acid "identity" is equivalent to amino acid or nucleic acid "homology"). The percent identity between the two sequences is a function of the number of identical positions shared by the sequences.

"Modulator", as used herein, refers to an entity, e.g., a drug, that can alter the activity (e.g., enzymatic activity, transcriptional activity, or translational activity), amount, distribution, or structure of a subject molecule or genetic sequence. In an embodiment, modulation comprises cleavage, e.g., breaking of a covalent or non-covalent bond, or the forming of a covalent or non-covalent bond, e.g., the attachment of a moiety, to the subject molecule. In an embodiment, a modulator alters the, three dimensional, secondary, tertiary, or quaternary structure, of a subject molecule. A modulator can increase, decrease, initiate, or eliminate a subject activity.

"Large molecule", as used herein, refers to a molecule having a molecular weight of at least 2, 3, 5, 10, 20, 30, 40, 50, 60, 70, 80, 90, or 100 kD. Large molecules include proteins, polypeptides, nucleic acids, biologics, and carbohydrates.

"Polypeptide", as used herein, refers to a polymer of amino acids having less than 100 amino acid residues. In an embodiment, it has less than 50, 20, or 10 amino acid residues.

"Reference molecule", e.g., a reference Cas9 molecule or reference gRNA, as used herein, refers to a molecule to which a subject molecule, e.g., a subject Cas9 molecule of subject gRNA molecule, e.g., a modified or candidate Cas9 molecule is compared. For example, a Cas9 molecule can be characterized as having no more than 10% of the nuclease activity of a reference Cas9 molecule. Examples of reference Cas9 molecules include naturally occurring unmodified Cas9 molecules, e.g., a naturally occurring Cas9 molecule such as a Cas9 molecule of *S. pyogenes*, or *S. thermophilus*. In an embodiment, the reference Cas9 molecule is the naturally occurring Cas9 molecule having the closest sequence identity or homology with the Cas9 molecule to which it is being compared. In an embodiment, the reference Cas9 molecule is a sequence, e.g., a naturally occurring or known sequence, which is the parental form on which a change, e.g., a mutation has been made.

"Replacement", or "replaced", as used herein with reference to a modification of a molecule does not require a process limitation but merely indicates that the replacement entity is present.

"Small molecule", as used herein, refers to a compound having a molecular weight less than about 2 kD, e.g., less than about 2 kD, less than about 1.5 kD, less than about 1 kD, or less than about 0.75 kD.

"Subject", as used herein, may mean either a human or non-human animal. The term includes, but is not limited to, mammals (e.g., humans, other primates, pigs, rodents (e.g., mice and rats or hamsters), rabbits, guinea pigs, cows, horses, cats, dogs, sheep, and goats). In an embodiment, the subject is a human. In an embodiment, the subject is poultry.

"Treat", "treating" and "treatment", as used herein, mean the treatment of a disease in a mammal, e.g., in a human, including (a) inhibiting the disease, i.e., arresting or preventing its development; (b) relieving the disease, i.e., causing regression of the disease state; or (c) curing the disease.

"X" as used herein in the context of an amino acid sequence, refers to any amino acid (e.g., any of the twenty natural amino acids) unless otherwise specified.

DETAILED DESCRIPTION

I. gRNA Molecules

A gRNA molecule, as that term is used herein, refers to a nucleic acid that promotes the specific targeting or homing of a gRNA molecule/Cas9 molecule complex to a target nucleic acid. gRNA molecules can be unimolecular (having a single RNA molecule), sometimes referred to herein as "chimeric" gRNAs, or modular (comprising more than one, and typically two, separate RNA molecules). A gRNA molecule comprises a number of domains. The gRNA molecule domains are described in more detail below. Typically, gRNA will incorporate the functions or structure of both crRNA and tracrRNA, e.g., the functions of processed or mature crRNA and of processed or mature tracrRNA. Chimieric or unimolecular gRNA molecules can have a single RNA molecule, e.g., which incorporates both crRNA function or structure and the tracrRNA function or structure. A modular gRNA molecule can comprise a RNA molecule that incorporates the crRNA function or structure another that incorporates the tracrRNA function or structure. Several exemplary gRNA structures, with domains indicated thereon, are provided in FIG. 1. While not wishing to be bound by theory with regard to the three dimensional form, or intra- or inter-strand interactions of an active form of a gRNA, regions of high complementarity are sometimes shown as duplexes in FIG. 1 and other depictions provided herein.

In an embodiment, a unimolecular, or chimeric, gRNA comprises, preferably from 5' to 3':
  a targeting domain, e.g., comprising 15, 16, 17, 18, 19, or 20 nucleotides (which is complementary to a target nucleic acid);
  a first complementarity domain;
  a linking domain;
  a second complementarity domain (which is complementary to the first complementarity domain);
  a proximal domain; and
  optionally, a tail domain.
In an embodiment, a modular gRNA comprises:
  a first strand comprising, preferably from 5' to 3';
    a targeting domain (which is complementary with a target sequence from a target nucleic acid disclosed herein, e.g., a sequence from: a gene or pathway described herein, e.g., in Section VIIB, e.g., in Table VII-13, VII-14, VII-15, VII-16, VII-17, VII-18, VII-19, VII-20, VII-21, VII-22, VII-23, VII-24, IX-1, IX-1A, IX-3, or XII-1, or in Section VIII); and
    a first complementarity domain; and
  a second strand, comprising, preferably from 5' to 3':
    optionally, a 5' extension domain;
    a second complementarity domain; and a proximal domain; and
    optionally, a tail domain.

The domains are discussed briefly below:
1) The Targeting Domain:
FIGS. 1A-1G provide examples of the placement of targeting domains.

The targeting domain comprises a nucleotide sequence that is complementary, e.g., at least 80, 85, 90, or 95% complementary, e.g., fully complementary, to the target sequence on the target nucleic acid. The targeting domain is part of an RNA molecule and will therefore comprise the base uracil (U), while any DNA encoding the gRNA molecule will comprise the base thymine (T). While not wishing to be bound by theory, it is believed that the complementarity of the targeting domain with the target sequence contributes to specificity of the interaction of the gRNA molecule/Cas9 molecule complex with a target nucleic acid. It is understood that in a targeting domain and target sequence pair, the uracil bases in the targeting domain will pair with the adenine bases in the target sequence. In an embodiment, the target domain itself comprises, in the 5' to 3' direction, an optional secondary domain, and a core domain. In an embodiment, the core domain is fully complementary with the target sequence. In an embodiment, the targeting domain is 5 to 50, e.g., 10 to 40, e.g., 10 to 30, e.g., 15 to 30, e.g., 15 to 25 nucleotides in length. In an embodiment, the targeting domain is 15, 16, 17, 18, 19, 20, 21, 22, 23, 24, 25, or 26 nucleotides in length. The strand of the target nucleic acid with which the targeting domain is complementary is referred to herein as the complementary strand. Some or all of the nucleotides of the domain can have a modification, e.g., modification found in Section X herein.

In an embodiment, the targeting domain is 15 nucleotides in length.

In an embodiment, the targeting domain is 16 nucleotides in length.

In an embodiment, the targeting domain is 17 nucleotides in length.

In an embodiment, the targeting domain is 18 nucleotides in length.

In an embodiment, the targeting domain is 19 nucleotides in length.

In an embodiment, the targeting domain is 20 nucleotides in length.

In an embodiment, the targeting domain is 21 nucleotides in length.

In an embodiment, the targeting domain is 22 nucleotides in length.

In an embodiment, the targeting domain is 23 nucleotides in length.

In an embodiment, the targeting domain is 24 nucleotides in length.

In an embodiment, the targeting domain is 25 nucleotides in length.

In an embodiment, the targeting domain is 26 nucleotides in length.

In an embodiment, the targeting domain comprises 15 nucleotides.

In an embodiment, the targeting domain comprises 16 nucleotides.

In an embodiment, the targeting domain comprises 17 nucleotides.

In an embodiment, the targeting domain comprises 18 nucleotides.

In an embodiment, the targeting domain comprises 19 nucleotides.

In an embodiment, the targeting domain comprises 20 nucleotides.

In an embodiment, the targeting domain comprises 21 nucleotides.

In an embodiment, the targeting domain comprises 22 nucleotides.

In an embodiment, the targeting domain comprises 23 nucleotides.

In an embodiment, the targeting domain comprises 24 nucleotides.

In an embodiment, the targeting domain comprises 25 nucleotides.

In an embodiment, the targeting domain comprises 26 nucleotides.

Targeting domains are discussed in more detail below.

2) The First Complementarity Domain:

FIGS. 1A-1G provide examples of first complementarity domains.

The first complementarity domain is complementary with the second complementarity domain, and in an embodiment, has sufficient complementarity to the second complementarity domain to form a duplexed region under at least some physiological conditions. In an embodiment, the first complementarity domain is 5 to 30 nucleotides in length. In an embodiment, the first complementarity domain is 5 to 25 nucleotides in length. In an embodiment, the first complementary domain is 7 to 25 nucleotides in length. In an embodiment, the first complementary domain is 7 to 22 nucleotides in length. In an embodiment, the first complementary domain is 7 to 18 nucleotides in length. In an embodiment, the first complementary domain is 7 to 15 nucleotides in length. In an embodiment, the first complementary domain is 5, 6, 7, 8, 9, 10, 11, 12, 13, 14, 15, 16, 17, 18, 19, 20, 21, 22, 23, 24, or 25 nucleotides in length.

In an embodiment, the first complementarity domain comprises 3 subdomains, which, in the 5' to 3' direction are: a 5' subdomain, a central subdomain, and a 3' subdomain. In an embodiment, the 5' subdomain is 4-9, e.g., 4, 5, 6, 7, 8 or 9 nucleotides in length. In an embodiment, the central subdomain is 1, 2, or 3, e.g., 1, nucleotide in length. In an embodiment, the 3' subdomain is 3 to 25, e.g., 4-22, 4-18, or 4 to 10, or 3, 4, 5, 6, 7, 8, 9, 10, 11, 12, 13, 14, 15, 16, 17, 18, 19, 20, 21, 22, 23, 24, or 25, nucleotides in length.

The first complementarity domain can share homology with, or be derived from, a naturally occurring first complementarity domain. In an embodiment, it has at least 50% homology with a first complementarity domain disclosed herein, e.g., an S. pyogenes, or S. thermophilus, first complementarity domain.

Some or all of the nucleotides of the domain can have a modification, e.g., modification found in Section X herein.

First complementarity domains are discussed in more detail below.

3) The Linking Domain

FIGS. 1B-1E provide examples of linking domains.

A linking domain serves to link the first complementarity domain with the second complementarity domain of a unimolecular gRNA. The linking domain can link the first and second complementarity domains covalently or non-covalently. In an embodiment, the linkage is covalent. In an embodiment, the linking domain covalently couples the first and second complementarity domains, see, e.g., FIGS. 1B-1E. In an embodiment, the linking domain is, or comprises, a covalent bond interposed between the first complementarity domain and the second complementarity domain. Typically, the linking domain comprises one or more, e.g., 2, 3, 4, 5, 6, 7, 8, 9, or 10 nucleotides.

In modular gRNA molecules the two molecules can be associated by virtue of the hybridization of the complementarity domains, see e.g., FIG. 1A.

A wide variety of linking domains are suitable for use in unimolecular gRNA molecules. Linking domains can consist of a covalent bond, or be as short as one or a few nucleotides, e.g., 1, 2, 3, 4, or 5 nucleotides in length.

In an embodiment, a linking domain is 2, 3, 4, 5, 6, 7, 8, 9, 10, 15, 20, or 25 or more nucleotides in length. In an embodiment, a linking domain is 2 to 50, 2 to 40, 2 to 30, 2 to 20, 2 to 10, or 2 to 5 nucleotides in length. In an embodiment, a linking domain shares homology with, or is derived from, a naturally occurring sequence, e.g., the sequence of a tracrRNA that is 5' to the second complementarity domain. In an embodiment, the linking domain has at least 50% homology with a linking domain disclosed herein.

Some or all of the nucleotides of the domain can have a modification, e.g., modification found in Section X herein.

Linking domains are discussed in more detail below.

4) The 5' Extension Domain

In an embodiment, a modular gRNA can comprise additional sequence, 5' to the second complementarity domain, referred to herein as the 5' extension domain, see, e.g., FIG. 1A. In an embodiment, the 5' extension domain is, 2-10, 2-9, 2-8, 2-7, 2-6, 2-5, 2-4 nucleotides in length. In an embodiment, the 5' extension domain is 2, 3, 4, 5, 6, 7, 8, 9, or 10 or more nucleotides in length.

5) The Second Complementarity Domain:

FIGS. 1A-1F provide examples of second complementarity domains.

Figure 1B:
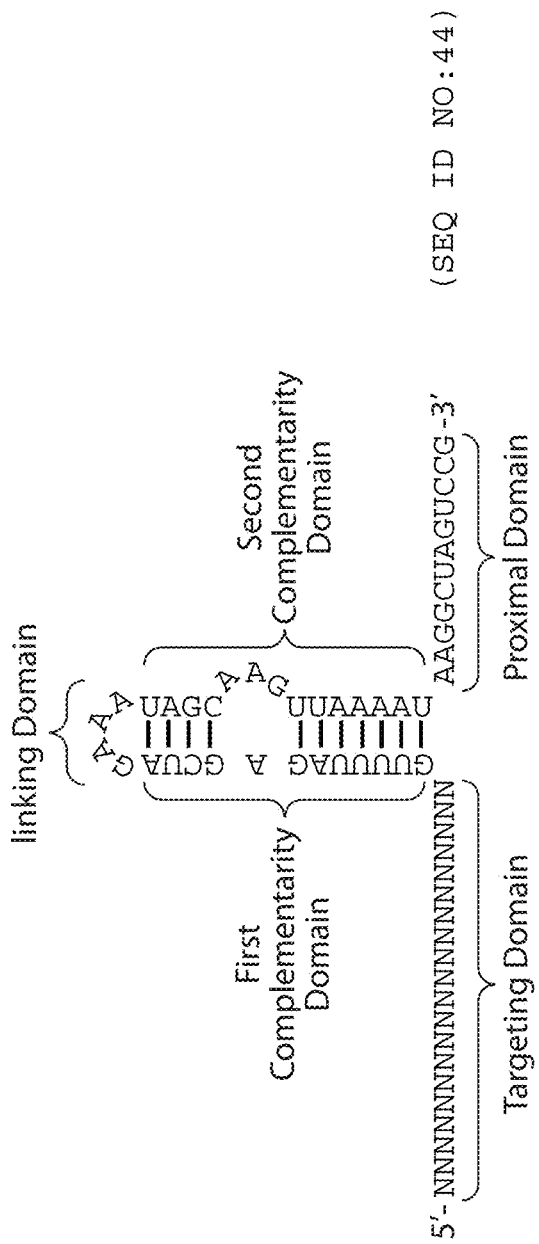
Figure 1C:
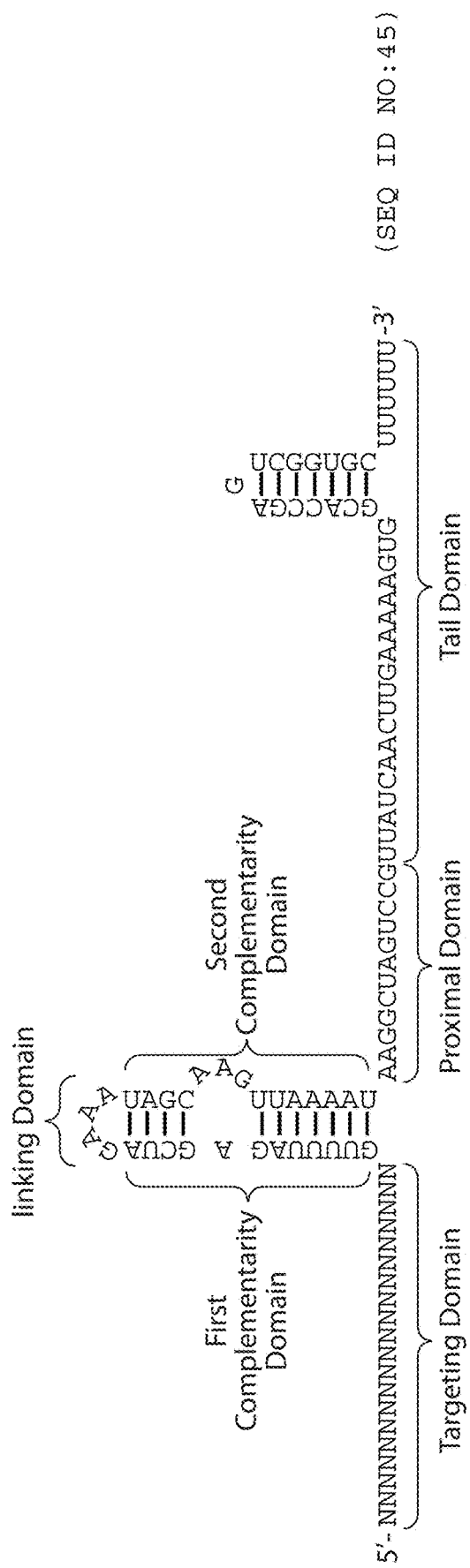
Figure 1E:
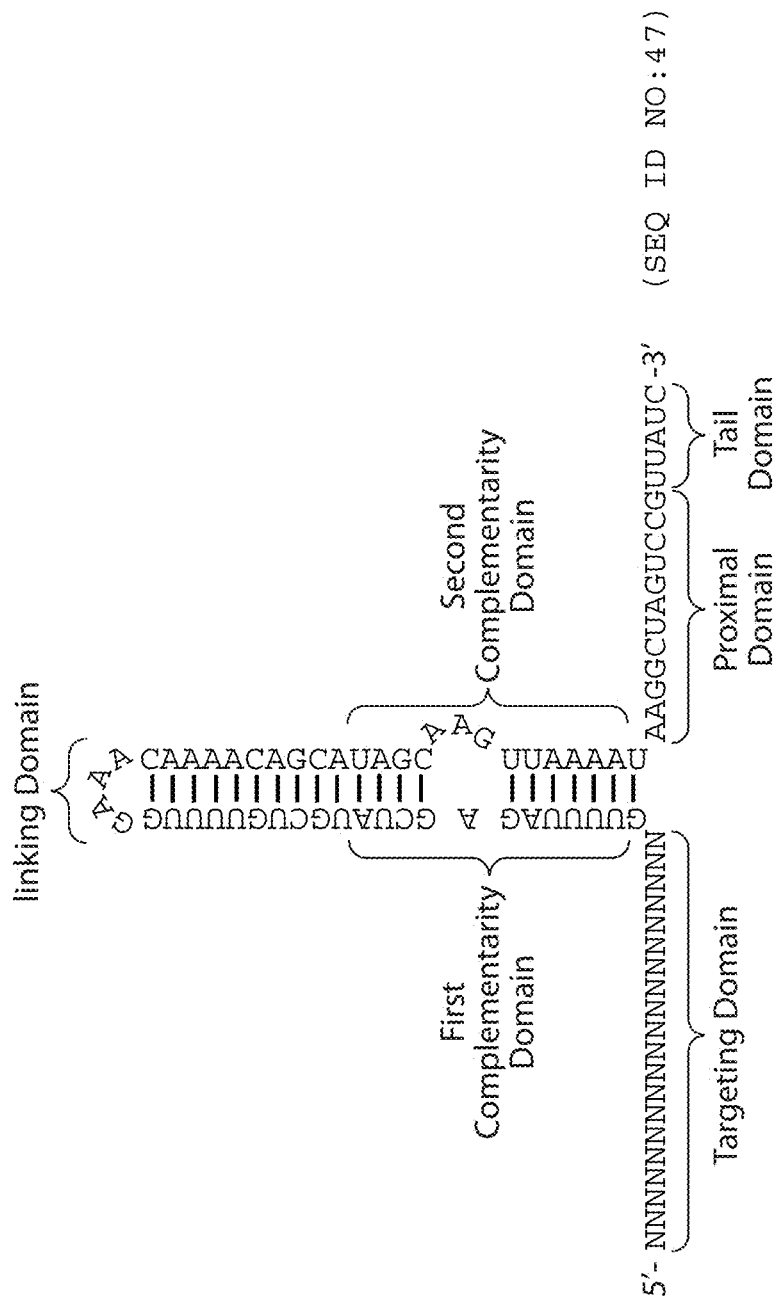

The second complementarity domain is complementary with the first complementarity domain, and in an embodiment, has sufficient complementarity to the second complementarity domain to form a duplexed region under at least some physiological conditions. In an embodiment, e.g., as shown in FIG. 1A or FIG. 1B, the second complementarity domain can include sequence that lacks complementarity with the first complementarity domain, e.g., sequence that loops out from the duplexed region.

In an embodiment, the second complementarity domain is 5 to 27 nucleotides in length. In an embodiment, it is longer than the first complementarity region.

In an embodiment, the second complementary domain is 7 to 27 nucleotides in length. In an embodiment, the second complementary domain is 7 to 25 nucleotides in length. In an embodiment, the second complementary domain is 7 to 20 nucleotides in length. In an embodiment, the second complementary domain is 7 to 17 nucleotides in length. In an embodiment, the complementary domain is 5, 6, 7, 8, 9, 10, 11, 12, 13, 14, 15, 16, 17, 18, 19, 20, 21, 22, 23, 24 or 25 nucleotides in length.

In an embodiment, the second complementarity domain comprises 3 subdomains, which, in the 5' to 3' direction are: a 5' subdomain, a central subdomain, and a 3' subdomain. In an embodiment, the 5' subdomain is 3 to 25, e.g., 4 to 22, 4 to18, or 4 to 10, or 3, 4, 5, 6, 7, 8, 9, 10, 11, 12, 13, 14, 15, 16, 17, 18, 19, 20, 21, 22, 23, 24, or 25 nucleotides in length. In an embodiment, the central subdomain is 1, 2, 3, 4 or 5, e.g., 3, nucleotides in length. In an embodiment, the 3' subdomain is 4 to 9, e.g., 4, 5, 6, 7, 8 or 9 nucleotides in length.

In an embodiment, the 5' subdomain and the 3' subdomain of the first complementarity domain, are respectively, complementary, e.g., fully complementary, with the 3' subdomain and the 5' subdomain of the second complementarity domain.

The second complementarity domain can share homology with or be derived from a naturally occurring second complementarity domain. In an embodiment, it has at least 50% homology with a second complementarity domain disclosed herein, e.g., an *S. pyogenes*, or *S. thermophilus*, first complementarity domain.

Some or all of the nucleotides of the domain can have a modification, e.g., modification found in Section X herein.

6) A Proximal Domain:

FIGS. 1A-1F provide examples of proximal domains.

In an embodiment, the proximal domain is 5 to 20 nucleotides in length. In an embodiment, the proximal domain can share homology with or be derived from a naturally occurring proximal domain. In an embodiment, it has at least 50% homology with a proximal domain disclosed herein, e.g., an *S. pyogenes*, or *S. thermophilus*, proximal domain.

Some or all of the nucleotides of the domain can have a modification, e.g., modification found in Section X herein.

7) A Tail Domain:

FIG. 1A and FIGS. 1C-1F provide examples of tail domains.

As can be seen by inspection of the tail domains in FIG. 1A and FIGS. 1C-1F, a broad spectrum of tail domains are suitable for use in gRNA molecules. In an embodiment, the tail domain is 0 (absent), 1, 2, 3, 4, 5, 6, 7, 8, 9, or 10 nucleotides in length. In an embodiment, the tail domain nucleotides are from or share homology with sequence from the 5' end of a naturally occurring tail domain, see e.g., FIG. 1D or FIG. 1E. In an embodiment, the tail domain includes sequences that are complementary to each other and which, under at least some physiological conditions, form a duplexed region.

In an embodiment, the tail domain is absent or is 1 to 50 nucleotides in length. In an embodiment, the tail domain can share homology with or be derived from a naturally occurring proximal tail domain. In an embodiment, it has at least 50% homology with a tail domain disclosed herein, e.g., an *S. pyogenes*, or *S. thermophilus*, tail domain.

Some or all of the nucleotides of the domain can have a modification, e.g., modification found in Section X herein.

In an embodiment, the tail domain includes nucleotides at the 3' end that are related to the method of in vitro or in vivo transcription. When a T7 promoter is used for in vitro transcription of the gRNA, these nucleotides may be any nucleotides present before the 3' end of the DNA template. When a U6 promoter is used for in vivo transcription, these nucleotides may be the sequence UUUUUU. When alternate pol-III promoters are used, these nucleotides may be various numbers or uracil bases or may include alternate bases.

The domains of gRNA molecules are described in more detail below.

The Targeting Domain

The "targeting domain" of the gRNA is complementary to the "target domain" on the target nucleic acid. The strand of the target nucleic acid comprising the nucleotide sequence complementary to the core domain of the gRNA is referred to herein as the "complementary strand" of the target nucleic acid. Guidance on the selection of targeting domains can be found, e.g., in Fu Y et al., NAT BIOTECHNOL 2014 (doi: 10.1038/nbt.2808) and Sternberg S H et al., NATURE 2014 (doi: 10.1038/nature13011).

In an embodiment, the targeting domain is 15, 16, 17, 18, 19, 20, 21, 22, 23, 24, 25 or 26 nucleotides in length.

In an embodiment, the targeting domain comprises 15, 16, 17, 18, 19, 20, 21, 22, 23, 24, 25 or 26 nucleotides in length.

In an embodiment, the targeting domain is 15 nucleotides in length.

In an embodiment, the targeting domain is 16 nucleotides in length.

In an embodiment, the targeting domain is 17 nucleotides in length.

In an embodiment, the targeting domain is 18 nucleotides in length.

In an embodiment, the targeting domain is 19 nucleotides in length.

In an embodiment, the targeting domain is 20 nucleotides in length.

In an embodiment, the targeting domain is 21 nucleotides in length.

In an embodiment, the targeting domain is 22 nucleotides in length.

In an embodiment, the targeting domain is 23 nucleotides in length.

In an embodiment, the targeting domain is 24 nucleotides in length.

In an embodiment, the targeting domain is 25 nucleotides in length.

In an embodiment, the targeting domain is 26 nucleotides in length.

In an embodiment, the targeting domain comprises 15 nucleotides.

In an embodiment, the targeting domain comprises 16 nucleotides.

In an embodiment, the targeting domain comprises 17 nucleotides.

In an embodiment, the targeting domain comprises 18 nucleotides.

In an embodiment, the targeting domain comprises 19 nucleotides.

In an embodiment, the targeting domain comprises 20 nucleotides.

In an embodiment, the targeting domain comprises 21 nucleotides.

In an embodiment, the targeting domain comprises 22 nucleotides.

In an embodiment, the targeting domain comprises 23 nucleotides.

In an embodiment, the targeting domain comprises 24 nucleotides.

In an embodiment, the targeting domain comprises 25 nucleotides.

In an embodiment, the targeting domain comprises 26 nucleotides.

In an embodiment, the targeting domain is 10+/−5, 20+/−5, 30+/−5, 40+/−5, 50+/−5, 60+/−5, 70+/−5, 80+/−5, 90+/−5, or 100+/−5 nucleotides, in length.

In an embodiment, the targeting domain is 20+/−5 nucleotides in length.

In an embodiment, the targeting domain is 20+/−10, 30+/−10, 40+/−10, 50+/−10, 60+/−10, 70+/−10, 80+/−10, 90+/−10, or 100+/−10 nucleotides, in length.

In an embodiment, the targeting domain is 30+/−10 nucleotides in length.

In an embodiment, the targeting domain is 10 to 100, 10 to 90, 10 to 80, 10 to 70, 10 to 60, 10 to 50, 10 to 40, 10 to 30, 10 to 20 or 10 to 15 nucleotides in length. In an embodiment, the targeting domain is 20 to 100, 20 to 90, 20 to 80, 20 to 70, 20 to 60, 20 to 50, 20 to 40, 20 to 30, or 20 to 25 nucleotides in length.

Typically the targeting domain has full complementarity with the target sequence. In an embodiment the targeting domain has or includes 1, 2, 3, 4, 5, 6, 7 or 8 nucleotides that are not complementary with the corresponding nucleotide of the targeting domain.

In an embodiment, the target domain includes 1, 2, 3, 4 or 5 nucleotides that are complementary with the corresponding nucleotide of the targeting domain within 5 nucleotides of its 5' end. In an embodiment, the target domain includes 1, 2, 3, 4 or 5 nucleotides that are complementary with the corresponding nucleotide of the targeting domain within 5 nucleotides of its 3' end.

In an embodiment, the target domain includes 1, 2, 3, or 4 nucleotides that are not complementary with the corresponding nucleotide of the targeting domain within 5 nucleotides of its 5' end. In an embodiment, the target domain includes 1, 2, 3, or 4 nucleotides that are not complementary with the corresponding nucleotide of the targeting domain within 5 nucleotides of its 3' end.

In an embodiment, the degree of complementarity, together with other properties of the gRNA, is sufficient to allow targeting of a Cas9 molecule to the target nucleic acid.

In an embodiment, the targeting domain comprises two consecutive nucleotides that are not complementary to the target domain ("non-complementary nucleotides"), e.g., two consecutive noncomplementary nucleotides that are within 5 nucleotides of the 5' end of the targeting domain, within 5 nucleotides of the 3' end of the targeting domain, or more than 5 nucleotides away from one or both ends of the targeting domain.

In an embodiment, no two consecutive nucleotides within 5 nucleotides of the 5' end of the targeting domain, within 5 nucleotides of the 3' end of the targeting domain, or within a region that is more than 5 nucleotides away from one or both ends of the targeting domain, are not complementary to the targeting domain.

In an embodiment, there are no noncomplementary nucleotides within 5 nucleotides of the 5' end of the targeting domain, within 5 nucleotides of the 3' end of the targeting domain, or within a region that is more than 5 nucleotides away from one or both ends of the targeting domain.

In an embodiment, the targeting domain nucleotides do not comprise modifications, e.g., modifications of the type provided in Section X. However, in an embodiment, the targeting domain comprises one or more modifications, e.g., modifications that it render it less susceptible to degradation or more bio-compatible, e.g., less immunogenic. By way of example, the backbone of the targeting domain can be modified with a phosphorothioate, or other modification from Section X. In an embodiment, a nucleotide of the targeting domain can comprise a 2' modification (e.g., a modification at the 2' position on ribose), e.g., a 2' acetylation, e.g., a 2' methylation, or other modification from Section X.

In an embodiment, the targeting domain includes 1, 2, 3, 4, 5, 6, 7 or 8 or more modifications. In an embodiment, the targeting domain includes 1, 2, 3, or 4 modifications within 5 nucleotides of its 5' end. In an embodiment, the targeting domain comprises as many as 1, 2, 3, or 4 modifications within 5 nucleotides of its 3' end.

In an embodiment, the targeting domain comprises modifications at two consecutive nucleotides, e.g., two consecutive nucleotides that are within 5 nucleotides of the 5' end of the targeting domain, within 5 nucleotides of the 3' end of the targeting domain, or more than 5 nucleotides away from one or both ends of the targeting domain.

In an embodiment, no two consecutive nucleotides are modified within 5 nucleotides of the 5' end of the targeting domain, within 5 nucleotides of the 3' end of the targeting domain, or within a region that is more than 5 nucleotides away from one or both ends of the targeting domain. In an embodiment, no nucleotide is modified within 5 nucleotides of the 5' end of the targeting domain, within 5 nucleotides of the 3' end of the targeting domain, or within a region that is more than 5 nucleotides away from one or both ends of the targeting domain.

Modifications in the targeting domain can be selected so as to not interfere with targeting efficacy, which can be evaluated by testing a candidate modification in the system described in Section III. gRNA's having a candidate targeting domain having a selected length, sequence, degree of complementarity, or degree of modification, can be evaluated in a system in Section III. The candidate targeting domain can be placed, either alone, or with one or more other candidate changes in a gRNA molecule/Cas9 molecule system known to be functional with a selected target and evaluated.

In an embodiment, all of the modified nucleotides are complementary to and capable of hybridizing to corresponding nucleotides present in the target domain. In an embodiment, 1, 2, 3, 4, 5, 6, 7 or 8 or more modified nucleotides are not complementary to or capable of hybridizing to corresponding nucleotides present in the target domain.

In an embodiment, the targeting domain comprises, preferably in the 5'→3' direction: a secondary domain and a core domain. These domains are discussed in more detail below.

The Core Domain and Secondary Domain of the Targeting Domain

The "core domain" of the targeting domain is complementary to the "core domain target" on the target nucleic acid. In an embodiment, the core domain comprises about 8 to about 13 nucleotides from the 3' end of the targeting domain (e.g., the most 3' 8 to 13 nucleotides of the targeting domain).

In an embodiment, the core domain is 6+/−2, 7+/−2, 8+/−2, 9+/−2, 10+/−2, 11+/−2, 12+/−2, 13+/−2, 14+/−2, 15+/−2, or 16+/−2 nucleotides in length.

In an embodiment, the core domain is 10+/−2 nucleotides in length.

In an embodiment, the core domain is 10+/−4 nucleotides in length.

In an embodiment, the core domain is 6, 7, 8, 9, 10, 11, 12, 13, 14, 15, or 16 nucleotides in length.

In an embodiment, the core domain is 8 to 13, e.g., 8 to 12, 8 to 11, 8 to 10, 8 to 9, 9 to 13, 9 to 12, 9 to 11, or 9 to 10 nucleotides in length.

In an embodiment, the core domain is 6 to 16, e.g., 6 to 15, 6 to 14, 6 to 13, 7 to 14, 7 to 13, 7 to 12, 7 to 11, 7 to 10, 8 to 14, 8 to 13, 8 to 12, 8 to 11, 8 to 10, or 8 to 9 nucleotides in length.

The core domain is complementary with the core domain target. Typically the core domain has exact complementarity with the core domain target. In an embodiment, the core domain can have 1, 2, 3, 4 or 5 nucleotides that are not complementary with the corresponding nucleotide of the core domain. In an embodiment, the degree of complementarity, together with other properties of the gRNA, is sufficient to allow targeting of a Cas9 molecule to the target nucleic acid.

The "secondary domain" of the targeting domain of the gRNA is complementary to the "secondary domain target" of the target nucleic acid.

In an embodiment, the secondary domain is positioned 5' to the core domain.

In an embodiment, the secondary domain is absent or optional.

In an embodiment, if the targeting domain is, or is at least, 26 nucleotides in length and the core domain (counted from the 3' end of the targeting domain) is 8 to 13 nucleotides in length, the secondary domain is 12 to 17 nucleotides in length.

In an embodiment, if the targeting domain is, or is at least, 25 nucleotides in length and the core domain (counted from the 3' end of the targeting domain) is 8 to 13 nucleotides in length, the secondary domain is 12 to 17 nucleotides in length.

In an embodiment, if the targeting domain is, or is at least, 24 nucleotides in length and the core domain (counted from the 3' end of the targeting domain) is 8 to 13 nucleotides in length, the secondary domain is 11 to 16 nucleotides in length.

In an embodiment, if the targeting domain is, or is at least, 23 nucleotides in length and the core domain (counted from the 3' end of the targeting domain) is 8 to 13 nucleotides in length, the secondary domain is 10 to 15 nucleotides in length.

In an embodiment, if the targeting domain is, or is at least, 22 nucleotides in length and the core domain (counted from the 3' end of the targeting domain) is 8 to 13 nucleotides in length, the secondary domain is 9 to 14 nucleotides in length.

In an embodiment, if the targeting domain is, or is at least, 21 nucleotides in length and the core domain (counted from the 3' end of the targeting domain) is 8 to 13 nucleotides in length, the secondary domain is 8 to 13 nucleotides in length.

In an embodiment, if the targeting domain is, or is at least, 20 nucleotides in length and the core domain (counted from the 3' end of the targeting domain) is 8 to 13 nucleotides in length, the secondary domain is 7 to 12 nucleotides in length.

In an embodiment, if the targeting domain is, or is at least, 19 nucleotides in length and the core domain (counted from the 3' end of the targeting domain) is 8 to 13 nucleotides in length, the secondary domain is 6 to 11 nucleotides in length.

In an embodiment, if the targeting domain is, or is at least, 18 nucleotides in length and the core domain (counted from the 3' end of the targeting domain) is 8 to 13 nucleotides in length, the secondary domain is 5 to 10 nucleotides in length.

In an embodiment, if the targeting domain is, or is at least, 17 nucleotides in length and the core domain (counted from the 3' end of the targeting domain) is 8 to 13 nucleotides in length, the secondary domain is 4 to 9 nucleotides in length.

In an embodiment, if the targeting domain is, or is at least, 16 nucleotides in length and the core domain (counted from the 3' end of the targeting domain) is 8 to 13 nucleotides in length, the secondary domain is 3 to 8 nucleotides in length.

In an embodiment, the secondary domain is 0, 1, 2, 3, 4, 5, 6, 7, 8, 9, 10, 11, 12, 13, 14 or 15 nucleotides in length.

The secondary domain is complementary with the secondary domain target. Typically the secondary domain has exact complementarity with the secondary domain target. In an embodiment the secondary domain can have 1, 2, 3, 4 or 5 nucleotides that are not complementary with the corresponding nucleotide of the secondary domain. In an embodiment, the degree of complementarity, together with other properties of the gRNA, is sufficient to allow targeting of a Cas9 molecule to the target nucleic acid.

In an embodiment, the core domain nucleotides do not comprise modifications, e.g., modifications of the type provided in Section X. However, in an embodiment, the core domain comprises one or more modifications, e.g., modifications that it render it less susceptible to degradation or more bio-compatible, e.g., less immunogenic. By way of example, the backbone of the core domain can be modified with a phosphorothioate, or other modification from Section X. In an embodiment, a nucleotide of the core domain can comprise a 2' modification (e.g., a modification at the 2' position on ribose), e.g., a 2'-acetylation, e.g., a 2' methylation, or other modification from Section X. Typically, a core domain will contain no more than 1, 2, or 3 modifications.

Modifications in the core domain can be selected to not interfere with targeting efficacy, which can be evaluated by testing a candidate modification in the system described in Section III. gRNA's having a candidate core domain having a selected length, sequence, degree of complementarity, or degree of modification, can be evaluated in the system described at Section III. The candidate core domain can be placed, either alone, or with one or more other candidate changes in a gRNA molecule/Cas9 molecule system known to be functional with a selected target and evaluated.

In an embodiment, the secondary domain nucleotides do not comprise modifications, e.g., modifications of the type provided in Section X. However, in an embodiment, the secondary domain comprises one or more modifications, e.g., modifications that render it less susceptible to degradation or more bio-compatible, e.g., less immunogenic. By way of example, the backbone of the secondary domain can be modified with a phosphorothioate, or other modification from Section X. In an embodiment, a nucleotide of the secondary domain can comprise a 2' modification (e.g., a modification at the 2' position on ribose), e.g., a 2'-acetylation, e.g., a 2' methylation, or other modification from Section X. Typically, a secondary domain will contain no more than 1, 2, or 3 modifications.

Modifications in the secondary domain can be selected to not interfere with targeting efficacy, which can be evaluated by testing a candidate modification in the system described in Section III. gRNA's having a candidate secondary domain having a selected length, sequence, degree of complementarity, or degree of modification, can be evaluated in the system described at Section III. The candidate secondary domain can be placed, either alone, or with one or more other candidate changes in a gRNA molecule/Cas9 molecule system known to be functional with a selected target and evaluated.

In an embodiment, (1) the degree of complementarity between the core domain and its target, and (2) the degree of complementarity between the secondary domain and its target, may differ. In an embodiment, (1) may be greater than (2). In an embodiment, (1) may be less than (2). In an embodiment, (1) and (2) may be the same, e.g., each may be completely complementary with its target.

In an embodiment, (1) the number of modifications (e.g., modifications from Section X) of the nucleotides of the core domain and (2) the number of modification (e.g., modifications from Section X) of the nucleotides of the secondary domain, may differ. In an embodiment, (1) may be less than (2). In an embodiment, (1) may be greater than (2). In an embodiment, (1) and (2) may be the same, e.g., each may be free of modifications.

The First and Second Complementarity Domains

The first complementarity domain is complementary with the second complementarity domain.

Typically the first domain does not have exact complementarity with the second complementarity domain target. In an embodiment, the first complementarity domain can have 1, 2, 3, 4 or 5 nucleotides that are not complementary with the corresponding nucleotide of the second complementarity domain. In an embodiment, 1, 2, 3, 4, 5 or 6, e.g., 3 nucleotides, will not pair in the duplex, and, e.g., form a non-duplexed or looped-out region. In an embodiment, an unpaired, or loop-out, region, e.g., a loop-out of 3 nucleotides, is present on the second complementarity domain. In an embodiment, the unpaired region begins 1, 2, 3, 4, 5, or 6, e.g., 4, nucleotides from the 5' end of the second complementarity domain.

In an embodiment, the degree of complementarity, together with other properties of the gRNA, is sufficient to allow targeting of a Cas9 molecule to the target nucleic acid.

In an embodiment, the first and second complementarity domains are:

independently, 6+/−2, 7+/−2, 8+/−2, 9+/−2, 10+/−2, 11+/−2, 12+/−2, 13+/−2, 14+/−2, 15+/−2, 16+/−2, 17+/−2, 18+/−2, 19+/−2, or 20+/−2, 21+/−2, 22+/−2, 23+/−2, or 24+/−2 nucleotides in length;

independently, 6, 7, 8, 9, 10, 11, 12, 13, 14, 14, 16, 17, 18, 19, 20, 21, 22, 23, 24, 25, or 26 nucleotides in length; or independently, 5 to 24, 5 to 23, 5 to 22, 5 to 21, 5 to 20, 7 to 18, 9 to 16, or 10 to 14 nucleotides in length.

In an embodiment, the second complementarity domain is longer than the first complementarity domain, e.g., 2, 3, 4, 5, or 6, e.g., 6, nucleotides longer.

In an embodiment, the first and second complementary domains, independently, do not comprise modifications, e.g., modifications of the type provided in Section X.

In an embodiment, the first and second complementary domains, independently, comprise one or more modifications, e.g., modifications that the render the domain less susceptible to degradation or more bio-compatible, e.g., less immunogenic. By way of example, the backbone of the domain can be modified with a phosphorothioate, or other modification from Section X. In an embodiment, a nucleotide of the domain can comprise a 2' modification (e.g., a modification at the 2' position on ribose), e.g., a 2'-acetylation, e.g., a 2' methylation, or other modification from Section X.

In an embodiment, the first and second complementary domains, independently, include 1, 2, 3, 4, 5, 6, 7 or 8 or more modifications. In an embodiment, the first and second complementary domains, independently, include 1, 2, 3, or 4 modifications within 5 nucleotides of its 5' end. In an embodiment, the first and second complementary domains, independently, include as many as 1, 2, 3, or 4 modifications within 5 nucleotides of its 3' end.

In an embodiment, the first and second complementary domains, independently, include modifications at two consecutive nucleotides, e.g., two consecutive nucleotides that are within 5 nucleotides of the 5' end of the domain, within 5 nucleotides of the 3' end of the domain, or more than 5 nucleotides away from one or both ends of the domain. In an embodiment, the first and second complementary domains, independently, include no two consecutive nucleotides that are modified, within 5 nucleotides of the 5' end of the domain, within 5 nucleotides of the 3' end of the domain, or within a region that is more than 5 nucleotides away from one or both ends of the domain. In an embodiment, the first and second complementary domains, independently, include no nucleotide that is modified within 5 nucleotides of the 5' end of the domain, within 5 nucleotides of the 3' end of the domain, or within a region that is more than 5 nucleotides away from one or both ends of the domain.

Modifications in a complementarity domain can be selected to not interfere with targeting efficacy, which can be evaluated by testing a candidate modification in the system described in Section III. gRNA's having a candidate complementarity domain having a selected length, sequence, degree of complementarity, or degree of modification, can be evaluated in the system described in Section III. The candidate complementarity domain can be placed, either alone, or with one or more other candidate changes in a gRNA molecule/Cas9 molecule system known to be functional with a selected target and evaluated.

In an embodiment, the first complementarity domain has at least 60, 70, 80, 85%, 90%, or 95% homology with, or differs by no more than 1, 2, 3, 4, 5, or 6 nucleotides from, a reference first complementarity domain, e.g., a naturally occurring, e.g., an S. pyogenes, or S. thermophilus, first complementarity domain, or a first complementarity domain described herein, e.g., from FIGS. 1A-1F.

In an embodiment, the second complementarity domain has at least 60, 70, 80, 85%, 90%, or 95% homology with, or differs by no more than 1, 2, 3, 4, 5, or 6 nucleotides from, a reference second complementarity domain, e.g., a naturally occurring, e.g., an S. pyogenes, or S. thermophilus, second complementarity domain, or a second complementarity domain described herein, e.g., from FIGS. 1A-1F.

The duplexed region formed by first and second complementarity domains is typically 6, 7, 8, 9, 10, 11, 12, 13, 14, 15, 16, 17, 18, 19, 20, 21 or 22 base pairs in length (excluding any looped out or unpaired nucleotides).

In an embodiment, the first and second complementarity domains, when duplexed, comprise 11 paired nucleotides, for example, in the gRNA sequence (one paired strand underlined, one bolded):

(SEQ ID NO: 5)
NNNNNNNNNNNNNNNNNNNNNNNGUUUUAGAGCUAGAAAUAGCAAGUUAAAAU

AAGGCUAGUCCGUUAUCAACUUGAAAAAGUGGCACCGAGUCGGUGC.

In an embodiment, the first and second complementarity domains, when duplexed, comprise 15 paired nucleotides, for example in the gRNA sequence (one paired strand underlined, one bolded):

(SEQ ID NO: 27)
NNNNNNNNNNNNNNNNNNNNNNNGUUUUAGAGCUAUGCUGAAAAGCAUAGCAA

GUUAAAAUAAGGCUAGUCCGUUAUCAACUUGAAAAAGUGGCACCGAGUCG

GUGC.

In an embodiment the first and second complementarity domains, when duplexed, comprise 16 paired nucleotides, for example in the gRNA sequence (one paired strand underlined, one bolded):

(SEQ ID NO: 28)
NNNNNNNNNNNNNNNNNNNNNNNGUUUUAGAGCUAUGCUGGAAACAGCAUAGC

AAGUUAAAAUAAGGCUAGUCCGUUAUCAACUUGAAAAAGUGGCACCGAGU

CGGUGC.

In an embodiment the first and second complementarity domains, when duplexed, comprise 21 paired nucleotides, for example in the gRNA sequence (one paired strand underlined, one bolded):

(SEQ ID NO: 29)
NNNNNNNNNNNNNNNNNNNNNNNGUUUUAGAGCUAUGCUGUUUUGGAAACAAA

ACAGCAUAGCAAGUUAAAAUAAGGCUAGUCCGUUAUCAACUUGAAAAAGU

GGCACCGAGUCGGUGC.

In an embodiment, nucleotides are exchanged to remove poly-U tracts, for example in the gRNA sequences (exchanged nucleotides underlined):

(SEQ ID NO: 30)
NNNNNNNNNNNNNNNNNNNNNNGUAUUAGAGCUAGAAAUAGCAAGUUAAUAU

AAGGCUAGUCCGUUAUCAACUUGAAAAAGUGGCACCGAGUCGGUGC;

(SEQ ID NO: 31)
NNNNNNNNNNNNNNNNNNNNNNGUUUAAGAGCUAGAAAUAGCAAGUUUAAAU

AAGGCUAGUCCGUUAUCAACUUGAAAAAGUGGCACCGAGUCGGUGC;
and (SEQ ID NO: 32)
NNNNNNNNNNNNNNNNNNNNNNGUAUUAGAGCUAUGCUGUAUUGGAAACAAU

ACAGCAUAGCAAGUUAAUAUAAGGCUAGUCCGUUAUCAACUUGAAAAGU

GGCACCGAGUCGGUGC.

The 5' Extension Domain

In an embodiment, a modular gRNA can comprise additional sequence, 5' to the second complementarity domain. In an embodiment, the 5' extension domain is 2 to 10, 2 to 9, 2 to 8, 2 to 7, 2 to 6, 2 to 5, or 2 to 4 nucleotides in length. In an embodiment, the 5' extension domain is 2, 3, 4, 5, 6, 7, 8, 9, or 10 or more nucleotides in length.

In an embodiment, the 5' extension domain nucleotides do not comprise modifications, e.g., modifications of the type provided in Section X. However, in an embodiment, the 5' extension domain comprises one or more modifications, e.g., modifications that it render it less susceptible to degradation or more bio-compatible, e.g., less immunogenic. By way of example, the backbone of the 5' extension domain can be modified with a phosphorothioate, or other modification from Section X. In an embodiment, a nucleotide of the 5' extension domain can comprise a 2' modification (e.g., a modification at the 2' position on ribose), e.g., a 2'-acetylation, e.g., a 2' methylation, or other modification from Section X.

In an embodiment, the 5' extension domain can comprise as many as 1, 2, 3, 4, 5, 6, 7 or 8 modifications. In an embodiment, the 5' extension domain comprises as many as 1, 2, 3, or 4 modifications within 5 nucleotides of its 5' end, e.g., in a modular gRNA molecule. In an embodiment, the 5' extension domain comprises as many as 1, 2, 3, or 4 modifications within 5 nucleotides of its 3' end, e.g., in a modular gRNA molecule.

In an embodiment, the 5' extension domain comprises modifications at two consecutive nucleotides, e.g., two consecutive nucleotides that are within 5 nucleotides of the 5' end of the 5' extension domain, within 5 nucleotides of the 3' end of the 5' extension domain, or more than 5 nucleotides away from one or both ends of the 5' extension domain. In an embodiment, no two consecutive nucleotides are modified within 5 nucleotides of the 5' end of the 5' extension domain, within 5 nucleotides of the 3' end of the 5' extension domain, or within a region that is more than 5 nucleotides away from one or both ends of the 5' extension domain. In an embodiment, no nucleotide is modified within 5 nucleotides of the 5' end of the 5' extension domain, within 5 nucleotides of the 3' end of the 5' extension domain, or within a region that is more than 5 nucleotides away from one or both ends of the 5' extension domain. Modifications in the 5' extension domain can be selected to not interfere with gRNA molecule efficacy, which can be evaluated by testing a candidate modification in the system described in Section III. gRNAs having a candidate 5' extension domain having a selected length, sequence, degree of complementarity, or degree of modification, can be evaluated in the system described at Section III. The candidate 5' extension domain can be placed, either alone, or with one or more other candidate changes in a gRNA molecule/Cas9 molecule system known to be functional with a selected target and evaluated.

In an embodiment, the 5' extension domain has at least 60, 70, 80, 85, 90 or 95% homology with, or differs by no more than 1, 2, 3, 4, 5, or 6 nucleotides from, a reference 5' extension domain, e.g., a naturally occurring, e.g., an *S. pyogenes*, or *S. thermophilus*, 5' extension domain, or a 5' extension domain described herein, e.g., from FIG. 1A and FIG. 1F.

The Linking Domain

In a unimolecular gRNA molecule the linking domain is disposed between the first and second complementarity domains. In a modular gRNA molecule, the two molecules are associated with one another by the complementarity domains.

In an embodiment, the linking domain is 10+/−5, 20+/−5, 30+/−5, 40+/−5, 50+/−5, 60+/−5, 70+/−5, 80+/−5, 90+/−5, or 100+/−5 nucleotides, in length.

In an embodiment, the linking domain is 20+/−10, 30+/−10, 40+/−10, 50+/−10, 60+/−10, 70+/−10, 80+/−10, 90+/−10, or 100+/−10 nucleotides, in length.

In an embodiment, the linking domain is 10 to 100, 10 to 90, 10 to 80, 10 to 70, 10 to 60, 10 to 50, 10 to 40, 10 to 30, 10 to 20 or 10 to 15 nucleotides in length. In an embodiment, the targeting domain is 20 to 100, 20 to 90, 20 to 80, 20 to 70, 20 to 60, 20 to 50, 20 to 40, 20 to 30, or 20 to 25 nucleotides in length.

In an embodiment, the linking domain is 1, 2, 3, 4, 5, 6, 7, 8, 9, 10, 11, 12, 13, 14, 15, 16 17, 18, 19, or 20 nucleotides in length.

In an embodiment, the linking domain is a covalent bond.

In an embodiment, the linking domain comprises a duplexed region, typically adjacent to or within 1, 2, or 3 nucleotides of the 3' end of the first complementarity domain and/or the 5-end of the second complementarity domain. In an embodiment, the duplexed region can be 20+/−10, 30+/−10, 40, +/−10 or 50+/−10 base pairs in length. In an embodiment, the duplexed region can be 10+/−5, 15+/−5, 20+/−5, or 30+/−5 base pairs in length. In an embodiment, the duplexed region can be 1, 2, 3, 4, 5, 6, 7, 8, 9, 10, 11, 12, 13, 14, or 15 base pairs in length.

Typically the sequences forming the duplexed region have exact complementarity with one another, though in an embodiment as many as 1, 2, 3, 4, 5, 6, 7 or 8 nucleotides are not complementary with the corresponding nucleotides.

In an embodiment, the linking domain nucleotides do not comprise modifications, e.g., modifications of the type provided in Section X. However, in an embodiment the linking domain comprises one or more modifications, e.g., modifications that it render it less susceptible to degradation or more bio-compatible, e.g., less immunogenic. By way of example, the backbone of the linking domain can be modified with a phosphorothioate, or other modification from Section X. In an embodiment, a nucleotide of the linking domain can comprise a 2' modification (e.g., a modification at the 2' position on ribose), e.g., a 2'-acetylation, e.g., a 2' methylation, or other modification from Section X.

In an embodiment, the linking domain can comprise as many as 1, 2, 3, 4, 5, 6, 7 or 8 modifications.

Modifications in a linking domain can be selected to not interfere with targeting efficacy, which can be evaluated by testing a candidate modification in the system described in Section III. gRNA's having a candidate linking domain having a selected length, sequence, degree of complementarity, or degree of modification, can be evaluated a system described in Section III. A candidate linking domain can be placed, either alone, or with one or more other candidate changes in a gRNA molecule/Cas9 molecule system known to be functional with a selected target and evaluated.

In an embodiment, the linking domain has at least 60, 70, 80, 85, 90 or 95% homology with, or differs by no more than 1, 2, 3, 4, 5, or 6 nucleotides from, a reference linking domain, e.g., a linking domain described herein, e.g., from FIG. 1B-1E.

The Proximal Domain

In an embodiment, the proximal domain is 6+/−2, 7+/−2, 8+/−2, 9+/−2, 10+/−2, 11+/−2, 12+/−2, 13+/−2, 14+/−2, 14+/−2, 16+/−2, 17+/−2, 18+/−2, 19+/−2, or 20+/−2 nucleotides in length.

In an embodiment, the proximal domain is 6, 7, 8, 9, 10, 11, 12, 13, 14, 14, 16, 17, 18, 19, or 20 nucleotides in length.

In an embodiment, the proximal domain is 5 to 20, 7, to 18, 9 to 16, or 10 to 14 nucleotides in length.

In an embodiment, the proximal domain nucleotides do not comprise modifications, e.g., modifications of the type provided in Section X. However, in an embodiment, the proximal domain comprises one or more modifications, e.g., modifications that it render it less susceptible to degradation or more bio-compatible, e.g., less immunogenic. By way of example, the backbone of the proximal domain can be modified with a phosphorothioate, or other modification from Section X. In an embodiment, a nucleotide of the proximal domain can comprise a 2' modification (e.g., a modification at the 2' position on ribose), e.g., a 2'-acetylation, e.g., a 2' methylation, or other modification from Section X.

In an embodiment, the proximal domain can comprise as many as 1, 2, 3, 4, 5, 6, 7 or 8 modifications. In an embodiment, the proximal domain comprises as many as 1, 2, 3, or 4 modifications within 5 nucleotides of its 5' end, e.g., in a modular gRNA molecule. In an embodiment, the target domain comprises as many as 1, 2, 3, or 4 modifications within 5 nucleotides of its 3' end, e.g., in a modular gRNA molecule.

In an embodiment, the proximal domain comprises modifications at two consecutive nucleotides, e.g., two consecutive nucleotides that are within 5 nucleotides of the 5' end of the proximal domain, within 5 nucleotides of the 3' end of the proximal domain, or more than 5 nucleotides away from one or both ends of the proximal domain. In an embodiment, no two consecutive nucleotides are modified within 5 nucleotides of the 5' end of the proximal domain, within 5 nucleotides of the 3' end of the proximal domain, or within a region that is more than 5 nucleotides away from one or both ends of the proximal domain. In an embodiment, no nucleotide is modified within 5 nucleotides of the 5' end of the proximal domain, within 5 nucleotides of the 3' end of the proximal domain, or within a region that is more than 5 nucleotides away from one or both ends of the proximal domain.

Modifications in the proximal domain can be selected to not interfere with gRNA molecule efficacy, which can be evaluated by testing a candidate modification in the system described in Section III. gRNA's having a candidate proximal domain having a selected length, sequence, degree of complementarity, or degree of modification, can be evaluated at the system described at Section III. The candidate proximal domain can be placed, either alone, or with one or more other candidate changes in a gRNA molecule/Cas9 molecule system known to be functional with a selected target and evaluated.

In an embodiment, the proximal domain has at least 60%, 70%, 80%, 85%, 90%, or 95% homology with, or differs by no more than 1, 2, 3, 4, 5, or 6 nucleotides from, a reference proximal domain, e.g., a naturally occurring, e.g., an *S. pyogenes*, or *S. thermophilus*, proximal domain, or a proximal domain described herein, e.g., from FIG. 1A-1F.

The Tail Domain

In an embodiment, the tail domain is 10+/−5, 20+/−5, 30+/−5, 40+/−5, 50+/−5, 60+/−5, 70+/−5, 80+/−5, 90+/−5, or 100+/−5 nucleotides, in length.

In an embodiment, the tail domain is 20+/−5 nucleotides in length.

In an embodiment, the tail domain is 20+/−10, 30+/−10, 40+/−10, 50+/−10, 60+/−10, 70+/−10, 80+/−10, 90+/−10, or 100+/−10 nucleotides, in length.

In an embodiment, the tail domain is 25+/−10 nucleotides in length.

In an embodiment, the tail domain is 10 to 100, 10 to 90, 10 to 80, 10 to 70, 10 to 60, 10 to 50, 10 to 40, 10 to 30, 10 to 20 or 10 to 15 nucleotides in length.

In an embodiment, the tail domain is 20 to 100, 20 to 90, 20 to 80, 20 to 70, 20 to 60, 20 to 50, 20 to 40, 20 to 30, or 20 to 25 nucleotides in length.

In an embodiment, the tail domain is 1 to 20, 1 to 1, 1 to 10, or 1 to 5 nucleotides in length.

In an embodiment, the tail domain nucleotides do not comprise modifications, e.g., modifications of the type provided in Section X. However, in an embodiment, the tail domain comprises one or more modifications, e.g., modifications that it render it less susceptible to degradation or more bio-compatible, e.g., less immunogenic. By way of example, the backbone of the tail domain can be modified with a phosphorothioate, or other modification from Section X. In an embodiment, a nucleotide of the tail domain can comprise a 2' modification (e.g., a modification at the 2' position on ribose), e.g., a 2'-acetylation, e.g., a 2' methylation, or other modification from Section X.

In an embodiment, the tail domain can have as many as 1, 2, 3, 4, 5, 6, 7 or 8 modifications. In an embodiment, the target domain comprises as many as 1, 2, 3, or 4 modifications within 5 nucleotides of its 5' end. In an embodiment, the target domain comprises as many as 1, 2, 3, or 4 modifications within 5 nucleotides of its 3' end.

In an embodiment, the tail domain comprises a tail duplex domain, which can form a tail duplexed region. In an embodiment, the tail duplexed region can be 3, 4, 5, 6, 7, 8, 9, 10, 11, or 12 base pairs in length. In an embodiment, a further single stranded domain exists 3' to the tail duplexed domain. In an embodiment, this domain is 3, 4, 5, 6, 7, 8, 9, or 10 nucleotides in length. In an embodiment, it is 4 to 6 nucleotides in length.

In an embodiment, the tail domain has at least 60, 70, 80, or 90% homology with, or differs by no more than 1, 2, 3, 4, 5, or 6 nucleotides from, a reference tail domain, e.g., a naturally occurring, e.g., an *S. pyogenes*, or *S. thermophilus*, tail domain, or a tail domain described herein, e.g., from FIG. 1A and FIGS. 1C-1F.

In an embodiment, the proximal and tail domain, taken together comprise the following sequences:

(SEQ ID NO: 33)
AAGGCUAGUCCGUUAUCAACUUGAAAAAGUGGCACCGAGUCGGUGCU;

```
                                               (SEQ ID NO: 34)
AAGGCUAGUCCGUUAUCAACUUGAAAAAGUGGCACCGAGUCGGUGGUGC;

(SEQ ID NO: 35)
AAGGCUAGUCCGUUAUCAACUUGAAAAAGUGGCACCGAGUCGGUGCGGA

UC;

(SEQ ID NO: 36)
AAGGCUAGUCCGUUAUCAACUUGAAAAAGUG;

(SEQ ID NO: 37)
AAGGCUAGUCCGUUAUCA;
or (SEQ ID NO: 38)
AAGGCUAGUCCG.
```

In an embodiment, the tail domain comprises the 3' sequence UUUUUU, e.g., if a U6 promoter is used for transcription.

In an embodiment, the tail domain comprises the 3' sequence UUUU, e.g., if an H1 promoter is used for transcription.

In an embodiment, tail domain comprises variable numbers of 3' U's depending, e.g., on the termination signal of the pol-III promoter used.

In an embodiment, the tail domain comprises variable 3' sequence derived from the DNA template if a T7 promoter is used.

In an embodiment, the tail domain comprises variable 3' sequence derived from the DNA template, e.g., if in vitro transcription is used to generate the RNA molecule.

In an embodiment, the tail domain comprises variable 3' sequence derived from the DNA template, e.g, if a pol-II promoter is used to drive transcription.

Modifications in the tail domain can be selected to not interfere with targeting efficacy, which can be evaluated by testing a candidate modification in the system described in Section III. gRNA's having a candidate tail domain having a selected length, sequence, degree of complementarity, or degree of modification, can be evaluated in the system described in Section III. The candidate tail domain can be placed, either alone, or with one or more other candidate changes in a gRNA molecule/Cas9 molecule system known to be functional with a selected target and evaluated.

In an embodiment, the tail domain comprises modifications at two consecutive nucleotides, e.g., two consecutive nucleotides that are within 5 nucleotides of the 5' end of the tail domain, within 5 nucleotides of the 3' end of the tail domain, or more than 5 nucleotides away from one or both ends of the tail domain. In an embodiment, no two consecutive nucleotides are modified within 5 nucleotides of the 5' end of the tail domain, within 5 nucleotides of the 3' end of the tail domain, or within a region that is more than 5 nucleotides away from one or both ends of the tail domain. In an embodiment, no nucleotide is modified within 5 nucleotides of the 5' end of the tail domain, within 5 nucleotides of the 3' end of the tail domain, or within a region that is more than 5 nucleotides away from one or both ends of the tail domain.

In an embodiment a gRNA has the following structure:
5' [targeting domain]-[first complementarity domain]-[linking domain]-[second complementarity domain]-[proximal domain]-[tail domain]-3'
wherein,
the targeting domain comprises a core domain and optionally a secondary domain, and is
10 to 50 nucleotides in length;
the first complementarity domain is 5 to 25 nucleotides in length and, in an embodiment has
at least 50, 60, 70, 80, 85, 90, or 95% homology with a reference first
complementarity domain disclosed herein;
the linking domain is 1 to 5 nucleotides in length;
the proximal domain is 5 to 20 nucleotides in length and, in an embodiment has at least 50, 60, 70, 80, 85, 90 or 95% homology with a reference proximal domain disclosed herein;
and
the tail domain is absent or a nucleotide sequence is 1 to 50 nucleotides in length and, in an embodiment has at least 50, 60, 70, 80, 85, 90 or 95% homology with a reference tail domain disclosed herein.

Exemplary Chimeric gRNAs

In an embodiment, a unimolecular, or chimeric, gRNA comprises, preferably from 5' to 3':
- a targeting domain, e.g., comprsing 15, 16, 17, 18, 19 or 20 nucleotides (which is complementary to a target nucleic acid);
- a first complementarity domain;
- a linking domain;
- a second complementarity domain (which is complementary to the first complementarity domain);
- a proximal domain; and
- a tail domain,
wherein,
(a) the proximal and tail domain, when taken together, comprise
at least 15, 18, 20, 25, 30, 31, 35, 40, 45, 49, 50, or 53 nucleotides;
(b) there are at least 15, 18, 20, 25, 30, 31, 35, 40, 45, 49, 50, or 53 nucleotides 3' to the last nucleotide of the second complementarity domain; or
(c) there are at least 16, 19, 21, 26, 31, 32, 36, 41, 46, 50, 51, or 54 nucleotides 3' to the last nucleotide of the second complementarity domain that is complementary to its corresponding nucleotide of the first complementarity domain.

In an embodiment, the sequence from (a), (b), or (c), has at least 60, 75, 80, 85, 90, 95, or 99% homology with the corresponding sequence of a naturally occurring gRNA, or with a gRNA described herein.

In an embodiment, the proximal and tail domain, when taken together, comprise at least 15, 18, 20, 25, 30, 31, 35, 40, 45, 49, 50, or 53 nucleotides.

In an embodiment, there are at least 15, 18, 20, 25, 30, 31, 35, 40, 45, 49, 50, or 53 nucleotides 3' to the last nucleotide of the second complementarity domain.

In an embodiment, there are at least 16, 19, 21, 26, 31, 32, 36, 41, 46, 50, 51, or 54 nucleotides 3' to the last nucleotide of the second complementarity domain that is complementary to its corresponding nucleotide of the first complementarity domain.

In an embodiment, the targeting domain comprises, has, or consists of 16, 17, 18, 19, 20, 21, 22, 23, 24 or 25 nucleotides (e.g., 16, 17, 18, 19, 20, 21, 22, 23, 24 or 25 consecutive nucleotides) having complementarity with the target domain, e.g., the targeting domain is 16, 17, 18, 19, 20, 21, 22, 23, 24 or 25 nucleotides in length.

In an embodiment, the targeting domain comprises, has, or consists of, 16 nucleotides (e.g., 16 consecutive nucleotides) having complementarity with the target domain, e.g., the targeting domain is 16 nucleotides in length.

In an embodiment, the targeting domain comprises, has, or consists of, 17 nucleotides (e.g., 17 consecutive nucleotides) having complementarity with the target domain, e.g., the targeting domain is 17 nucleotides in length.

In an embodiment, the targeting domain comprises, has, or consists of, 18 nucleotides (e.g., 18 consecutive nucleotides) having complementarity with the target domain, e.g., the targeting domain is 18 nucleotides in length.

In an embodiment, the targeting domain comprises, has, or consists of, 19 nucleotides (e.g., 19 consecutive nucleotides) having complementarity with the target domain, e.g., the targeting domain is 19 nucleotides in length.

In an embodiment, the targeting domain comprises, has, or consists of, 20 nucleotides (e.g., 20 consecutive nucleotides) having complementarity with the target domain, e.g., the targeting domain is 20 nucleotides in length.

In an embodiment, the targeting domain comprises, has, or consists of, 21 nucleotides (e.g., 21 consecutive nucleotides) having complementarity with the target domain, e.g., the targeting domain is 21 nucleotides in length.

In an embodiment, the targeting domain comprises, has, or consists of, 22 nucleotides (e.g., 22 consecutive nucleotides) having complementarity with the target domain, e.g., the targeting domain is 22 nucleotides in length.

In an embodiment, the targeting domain comprises, has, or consists of, 23 nucleotides (e.g., 23 consecutive nucleotides) having complementarity with the target domain, e.g., the targeting domain is 23 nucleotides in length.

In an embodiment, the targeting domain comprises, has, or consists of, 24 nucleotides (e.g., 24 consecutive nucleotides) having complementarity with the target domain, e.g., the targeting domain is 24 nucleotides in length.

In an embodiment, the targeting domain comprises, has, or consists of, 25 nucleotides (e.g., 25 consecutive nucleotides) having complementarity with the target domain, e.g., the targeting domain is 25 nucleotides in length.

In an embodiment, the targeting domain comprises, has, or consists of, 26 nucleotides (e.g., 26 consecutive nucleotides) having complementarity with the target domain, e.g., the targeting domain is 26 nucleotides in length. In an embodiment, the targeting domain comprises, has, or consists of, 16 nucleotides (e.g., 16 consecutive nucleotides) having complementarity with the target domain, e.g., the targeting domain is 16 nucleotides in length; and the proximal and tail domain, when taken together, comprise at least 15, 18, 20, 25, 30, 31, 35, 40, 45, 49, 50, or 53 nucleotides.

In an embodiment, the targeting domain comprises, has, or consists of, 16 nucleotides (e.g., 16 consecutive nucleotides) having complementarity with the target domain, e.g., the targeting domain is 16 nucleotides in length; and there are at least 15, 18, 20, 25, 30, 31, 35, 40, 45, 49, 50, or 53 nucleotides 3' to the last nucleotide of the second complementarity domain.

In an embodiment, the targeting domain comprises, has, or consists of, 16 nucleotides (e.g., 16 consecutive nucleotides) having complementarity with the target domain, e.g., the targeting domain is 16 nucleotides in length; and there are at least 16, 19, 21, 26, 31, 32, 36, 41, 46, 50, 51, or 54 nucleotides 3' to the last nucleotide of the second complementarity domain that is complementary to its corresponding nucleotide of the first complementarity domain.

In an embodiment, the targeting domain comprises, has, or consists of, 17 nucleotides (e.g., 17 consecutive nucleotides) having complementarity with the target domain, e.g., the targeting domain is 17 nucleotides in length; and the proximal and tail domain, when taken together, comprise at least 15, 18, 20, 25, 30, 31, 35, 40, 45, 49, 50, or 53 nucleotides. In an embodiment, the targeting domain comprises, has, or consists of, 17 nucleotides (e.g., 17 consecutive nucleotides) having complementarity with the target domain, e.g., the targeting domain is 17 nucleotides in length; and there are at least 15, 18, 20, 25, 30, 31, 35, 40, 45, 49, 50, or 53 nucleotides 3' to the last nucleotide of the second complementarity domain.

In an embodiment, the targeting domain comprises, has, or consists of, 17 nucleotides (e.g., 17 consecutive nucleotides) having complementarity with the target domain, e.g., the targeting domain is 17 nucleotides in length; and there are at least 16, 19, 21, 26, 31, 32, 36, 41, 46, 50, 51, or 54 nucleotides 3' to the last nucleotide of the second complementarity domain that is complementary to its corresponding nucleotide of the first complementarity domain.

In an embodiment, the targeting domain comprises, has, or consists of, 18 nucleotides (e.g., 18 consecutive nucleotides) having complementarity with the target domain, e.g., the targeting domain is 18 nucleotides in length; and the proximal and tail domain, when taken together, comprise at least 15, 18, 20, 25, 30, 31, 35, 40, 45, 49, 50, or 53 nucleotides.

In an embodiment, the targeting domain comprises, has, or consists of, 18 nucleotides (e.g., 18 consecutive nucleotides) having complementarity with the target domain, e.g., the targeting domain is 18 nucleotides in length; and there are at least 15, 18, 20, 25, 30, 31, 35, 40, 45, 49, 50, or 53 nucleotides 3' to the last nucleotide of the second complementarity domain.

In an embodiment, the targeting domain comprises, has, or consists of, 18 nucleotides (e.g., 18 consecutive nucleotides) having complementarity with the target domain, e.g., the targeting domain is 18 nucleotides in length; and there are at least 16, 19, 21, 26, 31, 32, 36, 41, 46, 50, 51, or 54 nucleotides 3' to the last nucleotide of the second complementarity domain that is complementary to its corresponding nucleotide of the first complementarity domain.

In an embodiment, the targeting domain comprises, has, or consists of, 19 nucleotides (e.g., 19 consecutive nucleotides) having complementarity with the target domain, e.g., the targeting domain is 19 nucleotides in length; and the proximal and tail domain, when taken together, comprise at least 15, 18, 20, 25, 30, 31, 35, 40, 45, 49, 50, or 53 nucleotides.

In an embodiment, the targeting domain comprises, has, or consists of, 19 nucleotides (e.g., 19 consecutive nucleotides) having complementarity with the target domain, e.g., the targeting domain is 19 nucleotides in length; and there are at least 15, 18, 20, 25, 30, 31, 35, 40, 45, 49, 50, or 53 nucleotides 3' to the last nucleotide of the second complementarity domain.

In an embodiment, the targeting domain comprises, has, or consists of, 19 nucleotides (e.g., 19 consecutive nucleotides) having complementarity with the target domain, e.g., the targeting domain is 19 nucleotides in length; and there are at least 16, 19, 21, 26, 31, 32, 36, 41, 46, 50, 51, or 54 nucleotides 3' to the last nucleotide of the second complementarity domain that is complementary to its corresponding nucleotide of the first complementarity domain.

In an embodiment, the targeting domaincomprises, has, or consists of, 20 nucleotides (e.g., 20 consecutive nucleotides) having complementarity with the target domain, e.g., the targeting domain is 20 nucleotides in length; and the proximal and tail domain, when taken together, comprise at least 15, 18, 20, 25, 30, 31, 35, 40, 45, 49, 50, or 53 nucleotides.

In an embodiment, the targeting domain comprises, has, or consists of, 20 nucleotides (e.g., 20 consecutive nucleotides) having complementarity with the target domain, e.g., the targeting domain is 20 nucleotides in length; and there are at least 15, 18, 20, 25, 30, 31, 35, 40, 45, 49, 50, or 53 nucleotides 3' to the last nucleotide of the second complementarity domain.

In an embodiment, the targeting domain comprises, has, or consists of, 20 nucleotides (e.g., 20 consecutive nucleotides) having complementarity with the target domain, e.g., the targeting domain is 20 nucleotides in length; and there are at least 16, 19, 21, 26, 31, 32, 36, 41, 46, 50, 51, or 54 nucleotides 3' to the last nucleotide of the second complementarity domain that is complementary to its corresponding nucleotide of the first complementarity domain.

In an embodiment, the targeting domain comprises, has, or consists of, 21 nucleotides (e.g., 21 consecutive nucleotides) having complementarity with the target domain, e.g., the targeting domain is 21 nucleotides in length; and the proximal and tail domain, when taken together, comprise at least 15, 18, 20, 25, 30, 31, 35, 40, 45, 49, 50, or 53 nucleotides.

In an embodiment, the targeting domain comprises, has, or consists of, 21 nucleotides (e.g., 21 consecutive nucleotides) having complementarity with the target domain, e.g., the targeting domain is 21 nucleotides in length; and there are at least 15, 18, 20, 25, 30, 31, 35, 40, 45, 49, 50, or 53 nucleotides 3' to the last nucleotide of the second complementarity domain.

In an embodiment, the targeting domain comprises, has, or consists of, 21 nucleotides (e.g., 21 consecutive nucleotides) having complementarity with the target domain, e.g., the targeting domain is 21 nucleotides in length; and there are at least 16, 19, 21, 26, 31, 32, 36, 41, 46, 50, 51, or 54 nucleotides 3' to the last nucleotide of the second complementarity domain that is complementary to its corresponding nucleotide of the first complementarity domain.

In an embodiment, the targeting domain comprises, has, or consists of, 22 nucleotides (e.g., 22 consecutive nucleotides) having complementarity with the target domain, e.g., the targeting domain is 22 nucleotides in length; and the proximal and tail domain, when taken together, comprise at least 15, 18, 20, 25, 30, 31, 35, 40, 45, 49, 50, or 53 nucleotides.

In an embodiment, the targeting domain comprises, has, or consists of, 22 nucleotides (e.g., 22 consecutive nucleotides) having complementarity with the target domain, e.g., the targeting domain is 22 nucleotides in length; and there are at least 15, 18, 20, 25, 30, 31, 35, 40, 45, 49, 50, or 53 nucleotides 3' to the last nucleotide of the second complementarity domain.

In an embodiment, the targeting domain comprises, has, or consists of, 22 nucleotides (e.g., 22 consecutive nucleotides) having complementarity with the target domain, e.g., the targeting domain is 22 nucleotides in length; and there are at least 16, 19, 21, 26, 31, 32, 36, 41, 46, 50, 51, or 54 nucleotides 3' to the last nucleotide of the second complementarity domain that is complementary to its corresponding nucleotide of the first complementarity domain.

In an embodiment, the targeting domain comprises, has, or consists of, 23 nucleotides (e.g., 23 consecutive nucleotides) having complementarity with the target domain, e.g., the targeting domain is 23 nucleotides in length; and the proximal and tail domain, when taken together, comprise at least 15, 18, 20, 25, 30, 31, 35, 40, 45, 49, 50, or 53 nucleotides.

In an embodiment, the targeting domain comprises, has, or consists of, 23 nucleotides (e.g., 23 consecutive nucleotides) having complementarity with the target domain, e.g., the targeting domain is 23 nucleotides in length; and there are at least 15, 18, 20, 25, 30, 31, 35, 40, 45, 49, 50, or 53 nucleotides 3' to the last nucleotide of the second complementarity domain.

In an embodiment, the targeting domain comprises, has, or consists of, 23 nucleotides (e.g., 23 consecutive nucleotides) having complementarity with the target domain, e.g., the targeting domain is 23 nucleotides in length; and there are at least 16, 19, 21, 26, 31, 32, 36, 41, 46, 50, 51, or 54 nucleotides 3' to the last nucleotide of the second complementarity domain that is complementary to its corresponding nucleotide of the first complementarity domain.

In an embodiment, the targeting domain comprises, has, or consists of, 24 nucleotides (e.g., 24 consecutive nucleotides) having complementarity with the target domain, e.g., the targeting domain is 24 nucleotides in length; and the proximal and tail domain, when taken together, comprise at least 15, 18, 20, 25, 30, 31, 35, 40, 45, 49, 50, or 53 nucleotides.

In an embodiment, the targeting domain comprises, has, or consists of, 24 nucleotides (e.g., 24 consecutive nucleotides) having complementarity with the target domain, e.g., the targeting domain is 24 nucleotides in length; and there are at least 15, 18, 20, 25, 30, 31, 35, 40, 45, 49, 50, or 53 nucleotides 3' to the last nucleotide of the second complementarity domain.

In an embodiment, the targeting domain comprises, has, or consists of, 24 nucleotides (e.g., 24 consecutive nucleotides) having complementarity with the target domain, e.g., the targeting domain is 24 nucleotides in length; and there are at least 16, 19, 21, 26, 31, 32, 36, 41, 46, 50, 51, or 54 nucleotides 3' to the last nucleotide of the second complementarity domain that is complementary to its corresponding nucleotide of the first complementarity domain.

In an embodiment, the targeting domain comprises, has, or consists of, 25 nucleotides (e.g., 25 consecutive nucleotides) having complementarity with the target domain, e.g., the targeting domain is 25 nucleotides in length; and the proximal and tail domain, when taken together, comprise at least 15, 18, 20, 25, 30, 31, 35, 40, 45, 49, 50, or 53 nucleotides.

In an embodiment, the targeting domain has, or consists of, 25 nucleotides (e.g., 25 consecutive nucleotides) having complementarity with the target domain, e.g., the targeting domain is 25 nucleotides in length; and there are at least 15, 18, 20, 25, 30, 31, 35, 40, 45, 49, 50, or 53 nucleotides 3' to the last nucleotide of the second complementarity domain.

In an embodiment, the targeting domain comprises, has, or consists of, 25 nucleotides (e.g., 25 consecutive nucleotides) having complementarity with the target domain, e.g., the targeting domain is 25 nucleotides in length; and there are at least 16, 19, 21, 26, 31, 32, 36, 41, 46, 50, 51, or 54 nucleotides 3' to the last nucleotide of the second complementarity domain that is complementary to its corresponding nucleotide of the first complementarity domain.

In an embodiment, the targeting domain comprises, has, or consists of, 26 nucleotides (e.g., 26 consecutive nucleotides) having complementarity with the target domain, e.g., the targeting domain is 26 nucleotides in length; and the proximal and tail domain, when taken together, comprise at least 15, 18, 20, 25, 30, 31, 35, 40, 45, 49, 50, or 53 nucleotides.

In an embodiment, the targeting domain comprises, has, or consists of, 26 nucleotides (e.g., 26 consecutive nucleotides) having complementarity with the target domain, e.g., the targeting domain is 26 nucleotides in length; and there are at least 15, 18, 20, 25, 30, 31, 35, 40, 45, 49, 50, or 53 nucleotides 3' to the last nucleotide of the second complementarity domain.

In an embodiment, the targeting domain comprises, has, or consists of, 26 nucleotides (e.g., 26 consecutive nucleotides) having complementarity with the target domain, e.g., the targeting domain is 26 nucleotides in length; and there are at least 16, 19, 21, 26, 31, 32, 36, 41, 46, 50, 51, or 54 nucleotides 3' to the last nucleotide of the second complementarity domain that is complementary to its corresponding nucleotide of the first complementarity domain.

Exemplary Modular gRNAs

In an embodiment, a modular gRNA comprises:
a first strand comprising, preferably from 5' to 3';
  a targeting domain, e.g., comprising 15, 16, 17, 18, 19, or 20 nucleotides;
  a first complementarity domain; and
a second strand, comprising, preferably from 5' to 3':
  optionally a 5' extension domain;
  a second complementarity domain;
  a proximal domain; and
  a tail domain,
wherein:
(a) the proximal and tail domain, when taken together, comprise at least 15, 18, 20, 25, 30, 31, 35, 40, 45, 49, 50, or 53 nucleotides;
(b) there are at least 15, 18, 20, 25, 30, 31, 35, 40, 45, 49, 50, or 53 nucleotides 3' to the last nucleotide of the second complementarity domain; or
(c) there are at least 16, 19, 21, 26, 31, 32, 36, 41, 46, 50, 51, or 54 nucleotides 3' to the last nucleotide of the second complementarity domain that is complementary to its corresponding nucleotide of the first complementarity domain.

In an embodiment, the sequence from (a), (b), or (c), has at least 60, 75, 80, 85, 90, 95, or 99% homology with the corresponding sequence of a naturally occurring gRNA, or with a gRNA described herein.

In an embodiment, the proximal and tail domain, when taken together, comprise at least 15, 18, 20, 25, 30, 31, 35, 40, 45, 49, 50, or 53 nucleotides.

In an embodiment, there are at least 15, 18, 20, 25, 30, 31, 35, 40, 45, 49, 50, or 53 nucleotides 3' to the last nucleotide of the second complementarity domain.

In an embodiment, there are at least 16, 19, 21, 26, 31, 32, 36, 41, 46, 50, 51, or 54 nucleotides 3' to the last nucleotide of the second complementarity domain that is complementary to its corresponding nucleotide of the first complementarity domain.

In an embodiment, the targeting domain comprises, has, or consists of, 16, 17, 18, 19, 20, 21, 22, 23, 24, 25, or 26 nucleotides (e.g., 16, 17, 18, 19, 20, 21, 22, 23, 24, 25, or 26 consecutive nucleotides) having complementarity with the target domain, e.g., the targeting domain is 16, 17, 18, 19, 20, 21, 22, 23, 24, 25, or 26 nucleotides in length.

In an embodiment, the targeting domain comprises, has, or consists of, 16 nucleotides (e.g., 16 consecutive nucleotides) having complementarity with the target domain, e.g., the targeting domain is 16 nucleotides in length.

In an embodiment, the targeting domain comprises, has, or consists of, 17 nucleotides (e.g., 17 consecutive nucleotides) having complementarity with the target domain, e.g., the targeting domain is 17 nucleotides in length.

In an embodiment, the targeting domain comprises, has, or consists of, 18 nucleotides (e.g., 18 consecutive nucleotides) having complementarity with the target domain, e.g., the targeting domain is 18 nucleotides in length.

In an embodiment, the targeting domain comprises, has, or consists of, 19 nucleotides (e.g., 19 consecutive nucleotides) having complementarity with the target domain, e.g., the targeting domain is 19 nucleotides in length.

In an embodiment, the targeting domain comprises, has, or consists of, 20 nucleotides (e.g., 20 consecutive nucleotides) having complementarity with the target domain, e.g., the targeting domain is 20 nucleotides in length.

In an embodiment, the targeting domain comprises, has, or consists of, 21 nucleotides (e.g., 21 consecutive nucleotides) having complementarity with the target domain, e.g., the targeting domain is 21 nucleotides in length.

In an embodiment, the targeting domain comprises, has, or consists of, 22 nucleotides (e.g., 22 consecutive nucleotides) having complementarity with the target domain, e.g., the targeting domain is 22 nucleotides in length.

In an embodiment, the targeting domain comprises, has, or consists of, 23 nucleotides (e.g., 23 consecutive nucleotides) having complementarity with the target domain, e.g., the targeting domain is 23 nucleotides in length.

In an embodiment, the targeting domain has, or consists of, 24 nucleotides (e.g., 24 consecutive nucleotides) having complementarity with the target domain, e.g., the targeting domain is 24 nucleotides in length.

In an embodiment, the targeting domain comprises, has, or consists of, 25 nucleotides (e.g., 25 consecutive nucleotides) having complementarity with the target domain, e.g., the targeting domain is 5 nucleotides in length.

In an embodiment, the targeting domain comprises, has, or consists of, 26 nucleotides (e.g., 26 consecutive nucleotides) having complementarity with the target domain, e.g., the targeting domain is 5 nucleotides in length.

In an embodiment, the targeting domain comprises, has, or consists of, 16 nucleotides (e.g., 16 consecutive nucleotides) having complementarity with the target domain, e.g., the targeting domain is 16 nucleotides in length; and the proximal and tail domain, when taken together, comprise at least 15, 18, 20, 25, 30, 31, 35, 40, 45, 49, 50, or 53 nucleotides.

In an embodiment, the targeting domain comprises, has, or consists of, 16 nucleotides (e.g., 16 consecutive nucleotides) having complementarity with the target domain, e.g., the targeting domain is 16 nucleotides in length; and there are at least 15, 18, 20, 25, 30, 31, 35, 40, 45, 49, 50, or 53 nucleotides 3' to the last nucleotide of the second complementarity domain.

In an embodiment, the targeting domai comprises, n has, or consists of, 16 nucleotides (e.g., 16 consecutive nucleotides) having complementarity with the target domain, e.g., the targeting domain is 16 nucleotides in length; and there are at least 16, 19, 21, 26, 31, 32, 36, 41, 46, 50, 51, or 54 nucleotides 3' to the last nucleotide of the second complementarity domain that is complementary to its corresponding nucleotide of the first complementarity domain.

In an embodiment, the targeting domain comprises, has, or consists of, 17 nucleotides (e.g., 17 consecutive nucleotides) having complementarity with the target domain, e.g., the targeting domain is 17 nucleotides in length; and the proximal and tail domain, when taken together, comprise at least 15, 18, 20, 25, 30, 31, 35, 40, 45, 49, 50, or 53 nucleotides.

In an embodiment, the targeting domain comprises, has, or consists of, 17 nucleotides (e.g., 17 consecutive nucleotides) having complementarity with the target domain, e.g., the targeting domain is 17 nucleotides in length; and there are at least 15, 18, 20, 25, 30, 31, 35, 40, 45, 49, 50, or 53 nucleotides 3' to the last nucleotide of the second complementarity domain.

In an embodiment, the targeting domain comprises, has, or consists of, 17 nucleotides (e.g., 17 consecutive nucleotides) having complementarity with the target domain, e.g., the targeting domain is 17 nucleotides in length; and there are at least 16, 19, 21, 26, 31, 32, 36, 41, 46, 50, 51, or 54 nucleotides 3' to the last nucleotide of the second complementarity domain that is complementary to its corresponding nucleotide of the first complementarity domain.

In an embodiment, the targeting domain comprises, has, or consists of, 18 nucleotides (e.g., 18 consecutive nucleotides) having complementarity with the target domain, e.g., the targeting domain is 18 nucleotides in length; and the proximal and tail domain, when taken together, comprise at least 15, 18, 20, 25, 30, 31, 35, 40, 45, 49, 50, or 53 nucleotides. In an embodiment, the targeting domain comprises, has, or consists of, 18 nucleotides (e.g., 18 consecutive nucleotides) having complementarity with the target domain, e.g., the targeting domain is 18 nucleotides in length; and there are at least 15, 18, 20, 25, 30, 31, 35, 40, 45, 49, 50, or 53 nucleotides 3' to the last nucleotide of the second complementarity domain.

In an embodiment, the targeting domain comprises, has, or consists of, 18 nucleotides (e.g., 18 consecutive nucleotides) having complementarity with the target domain, e.g., the targeting domain is 18 nucleotides in length; and there are at least 16, 19, 21, 26, 31, 32, 36, 41, 46, 50, 51, or 54 nucleotides 3' to the last nucleotide of the second complementarity domain that is complementary to its corresponding nucleotide of the first complementarity domain.

In an embodiment, the targeting domain comprises, has, or consists of, 19 nucleotides (e.g., 19 consecutive nucleotides) having complementarity with the target domain, e.g., the targeting domain is 19 nucleotides in length; and the proximal and tail domain, when taken together, comprise at least 15, 18, 20, 25, 30, 31, 35, 40, 45, 49, 50, or 53 nucleotides.

In an embodiment, the targeting domain comprises, has, or consists of, 19 nucleotides (e.g., 19 consecutive nucleotides) having complementarity with the target domain, e.g., the targeting domain is 19 nucleotides in length; and there are at least 15, 18, 20, 25, 30, 31, 35, 40, 45, 49, 50, or 53 nucleotides 3' to the last nucleotide of the second complementarity domain.

In an embodiment, the targeting domain comprises, has, or consists of, 19 nucleotides (e.g., 19 consecutive nucleotides) having complementarity with the target domain, e.g., the targeting domain is 19 nucleotides in length; and there are at least 16, 19, 21, 26, 31, 32, 36, 41, 46, 50, 51, or 54 nucleotides 3' to the last nucleotide of the second complementarity domain that is complementary to its corresponding nucleotide of the first complementarity domain.

In an embodiment, the targeting domain comprises, has, or consists of, 20 nucleotides (e.g., 20 consecutive nucleotides) having complementarity with the target domain, e.g., the targeting domain is 20 nucleotides in length; and the proximal and tail domain, when taken together, comprise at least 15, 18, 20, 25, 30, 31, 35, 40, 45, 49, 50, or 53 nucleotides.

In an embodiment, the targeting domain comprises, has, or consists of, 20 nucleotides (e.g., 20 consecutive nucleotides) having complementarity with the target domain, e.g., the targeting domain is 20 nucleotides in length; and there are at least 15, 18, 20, 25, 30, 31, 35, 40, 45, 49, 50, or 53 nucleotides 3' to the last nucleotide of the second complementarity domain. In an embodiment, the targeting domain comprises, has, or consists of, 20 nucleotides (e.g., 20 consecutive nucleotides) having complementarity with the target domain, e.g., the targeting domain is 20 nucleotides in length; and there are at least 16, 19, 21, 26, 31, 32, 36, 41, 46, 50, 51, or 54 nucleotides 3' to the last nucleotide of the second complementarity domain that is complementary to its corresponding nucleotide of the first complementarity domain.

In an embodiment, the targeting domain comprises, has, or consists of, 21 nucleotides (e.g., 21 consecutive nucleotides) having complementarity with the target domain, e.g., the targeting domain is 21 nucleotides in length; and the proximal and tail domain, when taken together, comprise at least 15, 18, 20, 25, 30, 31, 35, 40, 45, 49, 50, or 53 nucleotides. In an embodiment, the targeting domain comprises, has, or consists of, 21 nucleotides (e.g., 21 consecutive nucleotides) having complementarity with the target domain, e.g., the targeting domain is 21 nucleotides in length; and there are at least 15, 18, 20, 25, 30, 31, 35, 40, 45, 49, 50, or 53 nucleotides 3' to the last nucleotide of the second complementarity domain.

In an embodiment, the targeting domain comprises, has, or consists of, 21 nucleotides (e.g., 21 consecutive nucleotides) having complementarity with the target domain, e.g., the targeting domain is 21 nucleotides in length; and there are at least 16, 19, 21, 26, 31, 32, 36, 41, 46, 50, 51, or 54 nucleotides 3' to the last nucleotide of the second complementarity domain that is complementary to its corresponding nucleotide of the first complementarity domain.

In an embodiment, the targeting domain comprises, has, or consists of, 22 nucleotides (e.g., 22 consecutive nucleotides) having complementarity with the target domain, e.g., the targeting domain is 22 nucleotides in length; and the proximal and tail domain, when taken together, comprise at least 15, 18, 20, 25, 30, 31, 35, 40, 45, 49, 50, or 53 nucleotides.

In an embodiment, the targeting domain comprises, has, or consists of, 22 nucleotides (e.g., 22 consecutive nucleotides) having complementarity with the target domain, e.g., the targeting domain is 22 nucleotides in length; and there are at least 15, 18, 20, 25, 30, 31, 35, 40, 45, 49, 50, or 53 nucleotides 3' to the last nucleotide of the second complementarity domain.

In an embodiment, the targeting domain comprises, has, or consists of, 22 nucleotides (e.g., 22 consecutive nucleotides) having complementarity with the target domain, e.g., the targeting domain is 22 nucleotides in length; and there are at least 16, 19, 21, 26, 31, 32, 36, 41, 46, 50, 51, or 54 nucleotides 3' to the last nucleotide of the second complementarity domain that is complementary to its corresponding nucleotide of the first complementarity domain.

In an embodiment, the targeting domain comprises, has, or consists of, 23 nucleotides (e.g., 23 consecutive nucleotides) having complementarity with the target domain, e.g., the targeting domain is 23 nucleotides in length; and the proximal and tail domain, when taken together, comprise at least 15, 18, 20, 25, 30, 31, 35, 40, 45, 49, 50, or 53 nucleotides.

In an embodiment, the targeting domain comprises, has, or consists of, 23 nucleotides (e.g., 23 consecutive nucleotides) having complementarity with the target domain, e.g., the targeting domain is 23 nucleotides in length; and there are at least 15, 18, 20, 25, 30, 31, 35, 40, 45, 49, 50, or 53 nucleotides 3' to the last nucleotide of the second complementarity domain. In an embodiment, the targeting domain comprises, has, or consists of, 23 nucleotides (e.g., 23 consecutive nucleotides) having complementarity with the target domain, e.g., the targeting domain is 23 nucleotides in length; and there are at least 16, 19, 21, 26, 31, 32, 36, 41, 46, 50, 51, or 54 nucleotides 3' to the last nucleotide of the second complementarity domain that is complementary to its corresponding nucleotide of the first complementarity domain.

In an embodiment, the targeting domain comprises, has, or consists of, 24 nucleotides (e.g., 24 consecutive nucleotides) having complementarity with the target domain, e.g., the targeting domain is 24 nucleotides in length; and the proximal and tail domain, when taken together, comprise at least 15, 18, 20, 25, 30, 31, 35, 40, 45, 49, 50, or 53 nucleotides.

In an embodiment, the targeting domain comprises, has, or consists of, 24 nucleotides (e.g., 24 consecutive nucleotides) having complementarity with the target domain, e.g., the targeting domain is 24 nucleotides in length; and there are at least 15, 18, 20, 25, 30, 31, 35, 40, 45, 49, 50, or 53 nucleotides 3' to the last nucleotide of the second complementarity domain.

In an embodiment, the targeting domain comprises, has, or consists of, 24 nucleotides (e.g., 24 consecutive nucleotides) having complementarity with the target domain, e.g., the targeting domain is 24 nucleotides in length; and there are at least 16, 19, 21, 26, 31, 32, 36, 41, 46, 50, 51, or 54 nucleotides 3' to the last nucleotide of the second complementarity domain that is complementary to its corresponding nucleotide of the first complementarity domain.

In an embodiment, the targeting domain comprises, has, or consists of, 25 nucleotides (e.g., 25 consecutive nucleotides) having complementarity with the target domain, e.g., the targeting domain is 25 nucleotides in length; and the proximal and tail domain, when taken together, comprise at least 15, 18, 20, 25, 30, 31, 35, 40, 45, 49, 50, or 53 nucleotides.

In an embodiment, the targeting domain comprises, has, or consists of, 25 nucleotides (e.g., 25 consecutive nucleotides) having complementarity with the target domain, e.g., the targeting domain is 25 nucleotides in length; and there are at least 15, 18, 20, 25, 30, 31, 35, 40, 45, 49, 50, or 53 nucleotides 3' to the last nucleotide of the second complementarity domain.

In an embodiment, the targeting domain comprises, has, or consists of, 25 nucleotides (e.g., 25 consecutive nucleotides) having complementarity with the target domain, e.g., the targeting domain is 25 nucleotides in length; and there are at least 16, 19, 21, 26, 31, 32, 36, 41, 46, 50, 51, or 54 nucleotides 3' to the last nucleotide of the second complementarity domain that is complementary to its corresponding nucleotide of the first complementarity domain.

In an embodiment, the targeting domain comprises, has, or consists of, 26 nucleotides (e.g., 26 consecutive nucleotides) having complementarity with the target domain, e.g., the targeting domain is 26 nucleotides in length; and the proximal and tail domain, when taken together, comprise at least 15, 18, 20, 25, 30, 31, 35, 40, 45, 49, 50, or 53 nucleotides. In an embodiment, the targeting domain comprises, has, or consists of, 26 nucleotides (e.g., 26 consecutive nucleotides) having complementarity with the target domain, e.g., the targeting domain is 26 nucleotides in length; and there are at least 15, 18, 20, 25, 30, 31, 35, 40, 45, 49, 50, or 53 nucleotides 3' to the last nucleotide of the second complementarity domain.

In an embodiment, the targeting domain comprises, has, or consists of, 26 nucleotides (e.g., 26 consecutive nucleotides) having complementarity with the target domain, e.g., the targeting domain is 26 nucleotides in length; and there are at least 16, 19, 21, 26, 31, 32, 36, 41, 46, 50, 51, or 54 nucleotides 3' to the last nucleotide of the second complementarity domain that is complementary to its corresponding nucleotide of the first complementarity domain.

Methods for Designing gRNAs

Methods for designing gRNAs are described herein, including methods for selecting, designing and validating target domains. Exemplary targeting domains are also provided herein. Targeting Domains discussed herein can be incorporated into the gRNAs described herein.

Methods for selection and validation of target sequences as well as off-target analyses are described, e.g., in Mali et al., 2013 SCIENCE 339(6121): 823-826; Hsu et al., 2013 NAT BIOTECHNOL, 31(9): 827-32; Fu et al., 2014 NAT BIOTECHNOL, doi: 10.1038/nbt.2808. PubMed PMID: 24463574; Heigwer et al., 2014 NAT METHODS 11(2):122-3. doi: 10.1038/nmeth.2812. PubMed PMID: 24481216; Bae et al., 2014 BIOINFORMATICS PubMed PMID: 24463181; Xiao A et al., 2014 BIOINFORMATICS PubMed PMID: 24389662.

For example, a software tool can be used to optimize the choice of gRNA within a user's target sequence, e.g., to minimize total off-target activity across the genome. Off target activity may be other than cleavage. For each possible gRNA choice e.g., using *S. pyogenes* Cas9, the tool can identify all off-target sequences (e.g., preceding either NAG or NGG PAMs) across the genome that contain up to certain number (e.g., 1, 2, 3, 4, 5, 6, 7, 8, 9, or 10) of mismatched base-pairs. The cleavage efficiency at each off-target sequence can be predicted, e.g., using an experimentally-derived weighting scheme. Each possible gRNA is then ranked according to its total predicted off-target cleavage; the top-ranked gRNAs represent those that are likely to have the greatest on-target and the least off-target cleavage. Other functions, e.g., automated reagent design for CRISPR construction, primer design for the on-target Surveyor assay, and primer design for high-throughput detection and quantification of off-target cleavage via next-gen sequencing, can also be included in the tool. Candidate gRNA molecules can be evaluated by art-known methods or as described in Section IV herein.

II. Cas9 Molecules

Cas9 molecules of a variety of species can be used in the methods and compositions described herein. While the *S. pyogenes* and *S. thermophilus* Cas9 molecules are the subject of much of the disclosure herein, Cas9 molecules of, derived from, or based on the Cas9 proteins of other species listed herein can be used as well. In other words, while the much of the description herein uses *S. pyogenes* and *S. thermophilus* Cas9 molecules, Cas9 molecules from the other species can replace them, e.g., *Staphylococcus aureus* and *Neisseria meningitidis* Cas9 molecules. Additional Cas9 species include: *Acidovorax avenae, Actinobacillus pleuropneumoniae, Actinobacillus succinogenes, Actinobacillus suis, Actinomyces* sp., *Cycliphilus denitrificans, Aminomonas paucivorans, Bacillus cereus, Bacillus smithii, Bacillus thuringiensis, Bacteroides* sp., *Blastopirellula marina, Bradyrhizobium* sp., *Brevibacillus laterosporus, Campylobacter coli, Campylobacter jejuni, Campylobacter lari, Candidatus Puniceispirillum, Clostridium cellulolyticum, Clostridium perfringens, Corynebacterium accolens, Corynebacterium diphtheria, Corynebacterium matruchotii,* Dinoroseobacter shibae, *Eubacterium dolichum,* gamma proteobacterium, *Gluconacetobacter diazotrophicus, Haemophilus parainfluenzae, Haemophilus sputorum, Helicobacter canadensis, Helicobacter cinaedi, Helicobacter mustelae, Ilyobacter polytropus, Kingella kingae, Lactobacillus crispatus, List-*

*eria ivanovii, Listeria monocytogenes, Listeriaceae bacterium, Methylocystis* sp., *Methylosinus trichosporium, Mobiluncus mulieris, Neisseria bacilliformis, Neisseria cinerea, Neisseria flavescens, Neisseria lactamica, Neisseria* sp., *Neisseria wadsworthii, Nitrosomonas* sp., *Parvibaculum lavamentivorans, Pasteurella multocida, Phascolarctobacterium succinatutens, Ralstonia syzygii, Rhodopseudomonas palustris, Rhodovulum* sp., *Simonsiella muelleri, Sphingomonas* sp., *Sporolactobacillus vineae, Staphylococcus lugdunensis, Streptococcus* sp., *Subdoligranulum* sp., *Tistrella mobilis, Treponema* sp., or *Verminephrobacter eiseniae*.

A Cas9 molecule, as that term is used herein, refers to a molecule that can interact with a gRNA molecule and, in concert with the gRNA molecule, localize (e.g., target or home) to a site which comprises a target domain and PAM sequence.

In an embodiment, the Cas9 molecule is capable of cleaving a target nucleic acid molecule. A Cas9 molecule that is capable of cleaving a target nucleic acid molecule is referred to herein as an eaCas9 (an enzymatically active Cas9) molecule. In an embodiment, an eaCas9 molecule, comprises one or more of the following activities:

a nickase activity, i.e., the ability to cleave a single strand, e.g., the non-complementary strand or the complementary strand, of a nucleic acid molecule;

a double stranded nuclease activity, i.e., the ability to cleave both strands of a double stranded nucleic acid and create a double stranded break, which in an embodiment is the presence of two nickase activities;

an endonuclease activity;

an exonuclease activity; and a helicase activity, i.e., the ability to unwind the helical structure of a double stranded nucleic acid.

In an embodiment, an enzymatically active Cas9 or an eaCas9 molecule cleaves both DNA strands and results in a double stranded break. In an embodiment, an eaCas9 molecule cleaves only one strand, e.g., the strand to which the gRNA hybridizes to, or the strand complementary to the strand the gRNA hybridizes with. In an embodiment, an eaCas9 molecule comprises cleavage activity associated with an HNH-like domain. In an embodiment, an eaCas9 molecule comprises cleavage activity associated with an N-terminal RuvC-like domain. In an embodiment, an eaCas9 molecule comprises cleavage activity associated with an HNH-like domain and cleavage activity associated with an N-terminal RuvC-like domain. In an embodiment, an eaCas9 molecule comprises an active, or cleavage competent, HNH-like domain and an inactive, or cleavage incompetent, N-terminal RuvC-like domain. In an embodiment, an eaCas9 molecule comprises an inactive, or cleavage incompetent, HNH-like domain and an active, or cleavage competent, N-terminal RuvC-like domain.

In an embodiment, the ability of an eaCas9 molecule to interact with and cleave a target nucleic acid is PAM sequence dependent. A PAM sequence is a sequence in the target nucleic acid. In an embodiment, cleavage of the target nucleic acid occurs upstream from the PAM sequence. EaCas9 molecules from different bacterial species can recognize different sequence motifs (e.g., PAM sequences). In an embodiment, an eaCas9 molecule of *S. pyogenes* recognizes the sequence motif NGG and directs cleavage of a target nucleic acid sequence 1 to 10, e.g., 3 to 5, base pairs upstream from that sequence. See, e.g., Mali et al., SCIENCE 2013; 339(6121): 823-826. In an embodiment, an eaCas9 molecule of *S. thermophilus* recognizes the sequence motif NGGNG and NNAGAAW (W=A or T) and directs cleavage of a core target nucleic acid sequence 1 to 10, e.g., 3 to 5, base pairs upstream from these sequences. See, e.g., Horvath et al., SCIENCE 2010; 327(5962):167-170, and Deveau et al., J BACTERIOL 2008; 190(4): 1390-1400. In an embodiment, an eaCas9 molecule of *S. mutans* recognizes the sequence motif NGG or NAAR (R=A or G) and directs cleavage of a core target nucleic acid sequence 1 to 10, e.g., 3 to 5 base pairs, upstream from this sequence. See, e.g., Deveau et al., J BACTERIOL 2008; 190(4): 1390-1400. In an embodiment, an eaCas9 molecule of *S. aureus* recognizes the sequence motif NNGRR (R=A or G) and directs cleavage of a target nucleic acid sequence 1 to 10, e.g., 3 to 5, base pairs upstream from that sequence. In an embodiment, an eaCas9 molecule of *N. meningitidis* recognizes the sequence motif NNNNGATT and directs cleavage of a target nucleic acid sequence 1 to 10, e.g., 3 to 5, base pairs upstream from that sequence. See, e.g., Hou et al., PNAS EARLY EDITION 2013, 1-6. The ability of a Cas9 molecule to recognize a PAM sequence can be determined, e.g., using a transformation assay described in Jinek et al., SCIENCE 2012, 337:816.

Some Cas9 molecules have the ability to interact with a gRNA molecule, and in conjunction with the gRNA molecule home (e.g., targeted or localized) to a core target domain, but are incapable of cleaving the target nucleic acid, or incapable of cleaving at efficient rates. Cas9 molecules having no, or no substantial, cleavage activity are referred to herein as an eiCas9 (an enzymatically inactive Cas9) molecule. For example, an eiCas9 molecule can lack cleavage activity or have substantially less, e.g., less than 20, 10, 5, 1 or 0.1% of the cleavage activity of a reference Cas9 molecule, as measured by an assay described herein.

Exemplary naturally occurring Cas9 molecules are described in Chylinski et al., RNA Biology 2013; 10:5, 727-737. Such Cas9 molecules include Cas9 molecules of a cluster 1 bacterial family, cluster 2 bacterial family, cluster 3 bacterial family, cluster 4 bacterial family, cluster 5 bacterial family, cluster 6 bacterial family, a cluster 7 bacterial family, a cluster 8 bacterial family, a cluster 9 bacterial family, a cluster 10 bacterial family, a cluster 11 bacterial family, a cluster 12 bacterial family, a cluster 13 bacterial family, a cluster 14 bacterial family, a cluster 15 bacterial family, a cluster 16 bacterial family, a cluster 17 bacterial family, a cluster 18 bacterial family, a cluster 19 bacterial family, a cluster 20 bacterial family, a cluster 21 bacterial family, a cluster 22 bacterial family, a cluster 23 bacterial family, a cluster 24 bacterial family, a cluster 25 bacterial family, a cluster 26 bacterial family, a cluster 27 bacterial family, a cluster 28 bacterial family, a cluster 29 bacterial family, a cluster 30 bacterial family, a cluster 31 bacterial family, a cluster 32 bacterial family, a cluster 33 bacterial family, a cluster 34 bacterial family, a cluster 35 bacterial family, a cluster 36 bacterial family, a cluster 37 bacterial family, a cluster 38 bacterial family, a cluster 39 bacterial family, a cluster 40 bacterial family, a cluster 41 bacterial family, a cluster 42 bacterial family, a cluster 43 bacterial family, a cluster 44 bacterial family, a cluster 45 bacterial family, a cluster 46 bacterial family, a cluster 47 bacterial family, a cluster 48 bacterial family, a cluster 49 bacterial family, a cluster 50 bacterial family, a cluster 51 bacterial family, a cluster 52 bacterial family, a cluster 53 bacterial family, a cluster 54 bacterial family, a cluster 55 bacterial family, a cluster 56 bacterial family, a cluster 57 bacterial family, a cluster 58 bacterial family, a cluster 59 bacterial family, a cluster 60 bacterial family, a cluster 61 bacterial family, a cluster 62 bacterial family, a cluster 63 bacterial family, a cluster 64 bacterial family, a cluster 65 bacterial family, a cluster 66 bacterial family, a cluster 67 bacterial family, a cluster 68 bacterial family, a cluster 69 bacterial family, a cluster 70 bacterial family, a cluster 71 bacterial family, a cluster 72 bacterial family, a cluster 73 bacterial family, a cluster 74 bacterial family, a cluster 75 bacterial family, a cluster 76 bacterial family, a cluster 77 bacterial family, or a cluster 78 bacterial family.

Exemplary naturally occurring Cas9 molecules include a Cas9 molecule of a cluster 1 bacterial family. Examples include a Cas9 molecule of: *S. pyogenes* (e.g., strain SF370, MGAS10270, MGAS10750, MGAS2096, MGAS315, MGAS5005, MGAS6180, MGAS9429, NZ131 and SSI-1), *S. thermophilus* (e.g., strain LMD-9), *S. pseudoporcinus* (e.g., strain SPIN 20026), *S. mutans* (e.g., strain UA159, NN2025), *S. macacae* (e.g., strain NCTC11558), *S. gallolyticus* (e.g., strain UCN34, ATCC BAA-2069), *S. equines* (e.g., strain ATCC 9812, MGCS 124), *S. dysdalactiae* (e.g., strain GGS 124), *S. bovis* (e.g., strain ATCC 700338), *S. anginosus* (e.g., strain F0211), *S. agalactiae* (e.g., strain NEM316, A909), *Listeria monocytogenes* (e.g., strain F6854), *Listeria innocua* (*L. innocua*, e.g., strain Clip11262), *Enterococcus italicus* (e.g., strain DSM 15952), or *Enterococcus faecium* (e.g., strain 1,231,408). Additional exemplary Cas9 molecules are a Cas9 molecule of *Neisseria meningitidis* (Hou et al. PNAS Early Edition 2013, 1-6) and a *S. aureus* Cas9 molecule.

In an embodiment, a Cas9 molecule, e.g., an eaCas9 molecule or eiCas9 molecule, comprises an amino acid sequence:

having 60%, 65%, 70%, 75%, 80%, 85%, 90%, 95%, 96%, 97%, 98%, or 99% homology with;

differs at no more than, 2, 5, 10, 15, 20, 30, or 40% of the amino acid residues when compared with;

differs by at least 1, 2, 5, 10 or 20 amino acids but by no more than 100, 80, 70, 60, 50, 40 or 30 amino acids from; or is identical to;

any Cas9 molecule sequence described herein or a naturally occurring Cas9 molecule sequence, e.g., a Cas9 molecule from a species listed herein or described in Chylinski et al., RNA Biology 2013, 10:5, 727-737; Hou et al. PNAS Early Edition 2013, 1-6. In an embodiment, the Cas9 molecule comprises one or more of the following activities: a nickase activity; a double stranded cleavage activity (e.g., an endonuclease and/or exonuclease activity); a helicase activity; or the ability, together with a gRNA molecule, to localize to a target nucleic acid.

In an embodiment, a Cas9 molecule comprises the amino acid sequence of the consensus sequence of FIG. 2, wherein "*" indicates any amino acid found in the corresponding position in the amino acid sequence of a Cas9 molecule of *S. pyogenes, S. thermophilus, S. mutans* and *L. innocua*, and "-" indicates any amino acid. In an embodiment, a Cas9 molecule differs from the sequence of the consensus sequence disclosed in FIG. 2 by at least 1, but no more than 2, 3, 4, 5, 6, 7, 8, 9, or 10 amino acid residues. In an embodiment, a Cas9 molecule comprises the amino acid sequence of SEQ ID NO:7 of FIG. 5, wherein "*" indicates any amino acid found in the corresponding position in the amino acid sequence of a Cas9 molecule of *S. pyogenes*, or *N. meningitidis*,"-" indicates any amino acid, and "-" indicates any amino acid or absent. In an embodiment, a Cas9 molecule differs from the sequence of SEQ ID NO:6 or 7 by at least 1, but no more than 2, 3, 4, 5, 6, 7, 8, 9, or 10 amino acid residues.

A comparison of the sequence of a number of Cas9 molecules indicate that certain regions are conserved. These are identified below as:

region 1 (residues 1 to 180, or in the case of region 1' residues 120 to 180)

region 2 (residues 360 to 480);

region 3 (residues 660 to 720);

region 4 (residues 817 to 900); and region 5 (residues 900 to 960).

In an embodiment, a Cas9 molecule comprises regions 1-5, together with sufficient additional Cas9 molecule sequence to provide a biologically active molecule, e.g., a Cas9 molecule having at least one activity described herein. In an embodiment, each of regions 1-6, independently, have, 50%, 60%, 70%, 80%, 85%, 90%, 95%, 96%, 97%, 98% or 99% homology with the corresponding residues of a Cas9 molecule described herein, e.g., a sequence from FIG. 2 or from FIG. 5.

In an embodiment, a Cas9 molecule, e.g., an eaCas9 molecule or eiCas9 molecule, comprises an amino acid sequence referred to as region 1:

having 50%, 60%, 70%, 80%, 85%, 90%, 95%, 96%, 97%, 98% or 99% homology with amino acids 1-180 (the numbering is according to the motif sequence in FIG. 2; 52% of residues in the four Cas9 sequences in FIG. 2 are conserved) of the amino acid sequence of Cas9 of *S. pyogenes*;

differs by at least 1, 2, 5, 10 or 20 amino acids but by no more than 90, 80, 70, 60, 50, 40 or 30 amino acids from amino acids 1-180 of the amino acid sequence of Cas9 of *S. pyogenes, S. thermophilus, S. mutans, L. innocua, N. meningitidis*, or *S. aureus*; or is identical to 1-180 of the amino acid sequence of Cas9 of *S. pyogenes, S. thermophilus, S. mutans, L. innocua, N. meningitidis*, or *S. aureus*.

In an embodiment, a Cas9 molecule, e.g., an eaCas9 molecule or eiCas9 molecule, comprises an amino acid sequence referred to as region 1':

having 55%, 60%, 65%, 70%, 75%, 80%, 85%, 90%, 95%, 96%, 97%, 98% or 99% homology with amino acids 120-180 (55% of residues in the four Cas9 sequences in FIG. 2 are conserved) of the amino acid sequence of Cas9 of *S. pyogenes, S. thermophilus, S. mutans* or, *L. innocua, N. meningitidis*, or *S. aureus*;

differs by at least 1, 2, or 5 amino acids but by no more than 35, 30, 25, 20 or 10 amino acids from amino acids 120-180 of the amino acid sequence of Cas9 of *S. pyogenes, S. thermophilus, S. mutans* or, *L. innocua, N. meningitidis*, or *S. aureus*; or is identical to 120-180 of the amino acid sequence of Cas9 of *S. pyogenes, S. thermophilus, S. mutans* or, *L. innocua, N. meningitidis*, or *S. aureus*.

In an embodiment, a Cas9 molecule, e.g., an eaCas9 molecule or eiCas9 molecule, comprises an amino acid sequence referred to as region 2:

having 50%, 55%, 60%, 65%, 70%, 75%, 80%, 85%, 90%, 95%, 96%, 97%, 98% or 99% homology with amino acids 360-480 (52% of residues in the four Cas9 sequences in FIG. 2 are conserved) of the amino acid sequence of Cas9 of *S. pyogenes, S. thermophilus, S. mutans* or, *L. innocua, N. meningitidis*, or *S. aureus*;

differs by at least 1, 2, or 5 amino acids but by no more than 35, 30, 25, 20 or 10 amino acids from amino acids 360-480 of the amino acid sequence of Cas9 of *S. pyogenes, S. thermophilus, S. mutans* or, *L. innocua, N. meningitidis*, or *S. aureus*; or is identical to 360-480 of the amino acid sequence of Cas9 of *S. pyogenes, S. thermophilus, S. mutans* or, *L. innocua, N. meningitidis*, or *S. aureus*.

In an embodiment, a Cas9 molecule, e.g., an eaCas9 molecule or eiCas9 molecule, comprises an amino acid sequence referred to as region 3:

having 55%, 60%, 65%, 70%, 75%, 80%, 85%, 90%, 95%, 96%, 97%, 98% or 99% homology with amino acids 660-720 (56% of residues in the four Cas9 sequences in FIG. 2 are conserved) of the amino acid sequence of Cas9 of *S. pyogenes, S. thermophilus, S. mutans* or, *L. innocua, N. meningitidis,* or *S. aureus;* differs by at least 1, 2, or 5 amino acids but by no more than 35, 30, 25, 20 or 10 amino acids from amino acids 660-720 of the amino acid sequence of Cas9 of *S. pyogenes, S. thermophilus, S. mutans* or, *L. innocua, N. meningitidis,* or *S. aureus;* or is identical to 660-720 of the amino acid sequence of Cas9 of *S. pyogenes, S. thermophilus, S. mutans* or, *L. innocua, N. meningitidis,* or *S. aureus.*

In an embodiment, a Cas9 molecule, e.g., an eaCas9 molecule or eiCas9 molecule, comprises an amino acid sequence referred to as region 4:

having 50%, 55%, 60%, 65%, 70%, 75%, 80%, 85%, 90%, 95%, 96%, 97%, 98% or 99% homology with amino acids 817-900 (55% of residues in the four Cas9 sequences in FIG. 2 are conserved) of the amino acid sequence of Cas9 of *S. pyogenes, S. thermophilus, S. mutans* or, *L. innocua, N. meningitidis,* or *S. aureus;* differs by at least 1, 2, or 5 amino acids but by no more than 35, 30, 25, 20 or 10 amino acids from amino acids 817-900 of the amino acid sequence of Cas9 of *S. pyogenes, S. thermophilus, S. mutans* or, *L. innocua, N. meningitidis,* or *S. aureus;* or is identical to 817-900 of the amino acid sequence of Cas9 of *S. pyogenes, S. thermophilus, S. mutans* or, *L. innocua, N. meningitidis,* or *S. aureus.*

In an embodiment, a Cas9 molecule, e.g., an eaCas9 molecule or eiCas9 molecule, comprises an amino acid sequence referred to as region 5:

having 50%, 55%, 60%, 65%, 70%, 75%, 80%, 85%, 90%, 95%, 96%, 97%, 98% or 99% homology with amino acids 900-960 (60% of residues in the four Cas9 sequences in FIG. 2 are conserved) of the amino acid sequence of Cas9 of *S. pyogenes, S. thermophilus, S. mutans* or, *L. innocua, N. meningitidis,* or *S. aureus;* differs by at least 1, 2, or 5 amino acids but by no more than 35, 30, 25, 20 or 10 amino acids from amino acids 900-960 of the amino acid sequence of Cas9 of *S. pyogenes, S. thermophilus, S. mutans* or, *L. innocua, N. meningitidis,* or *S. aureus;* or is identical to 900-960 of the amino acid sequence of Cas9 of *S. pyogenes, S. thermophilus, S. mutans* or, *L. innocua, N. meningitidis,* or *S. aureus.*

A RuvC-Like Domain and an HNH-Like Domain

In an embodiment, a Cas9 molecule comprises an HNH-like domain and an RuvC-like domain. In an embodiment, cleavage activity is dependent on a RuvC-like domain and an HNH-like domain. A Cas9 molecule, e.g., an eaCas9 or eiCas9 molecule, can comprise one or more of the following domains: a RuvC-like domain and an HNH-like domain. In an embodiment, a cas9 molecule is an eaCas9 molecule and the eaCas9 molecule comprises a RuvC-like domain, e.g., a RuvC-like domain described below, and/or an HNH-like domain, e.g., an HNH-like domain described below. In an embodiment, a Cas9 molecule is an eiCas9 molecule comprising one or more difference in an RuvC-like domain and/or in an HNH-like domain as compared to a reference Cas9 molecule, and the eiCas9 molecule does not cleave a nucleic acid, or cleaves with significantly less efficiency than does wildtype, e.g., when compared with wild type in a cleavage assay, e.g., as described herein, cuts with less than 50, 25, 10, or 1% of the a reference Cas9 molecule, as measured by an assay described herein.

RuvC-Like Domains

In an embodiment, a RuvC-like domain cleaves, a single strand, e.g., the non-complementary strand of the target nucleic acid molecule. A Cas9 molecule can include more than one RuvC-like domain (e.g., one, two, three or more RuvC-like domains). In an embodiment, an RuvC-like domain is at least 5, 6, 7, 8 amino acids in length but not more than 20, 19, 18, 17, 16 or 15 amino acids in length. In an embodiment, the cas9 molecule comprises an N-terminal RuvC-like domain of about 10 to 20 amino acids, e.g., about 15 amino acids in length.

N-Terminal RuvC-Like Domains

Some naturally occurring Cas9 molecules comprise more than one RuvC-like domain, with cleavage being dependent on the N-terminal RuvC-like domain. Accordingly, Cas9 molecules can comprise an N-terminal RuvC-like domain. Exemplary N-terminal RuvC-like domains are described below.

In an embodiment, an eaCas9 molecule comprises an N-terminal RuvC-like domain comprising an amino acid sequence of formula I:

(SEQ ID NO: 8)
D-X1-G-X2-X3-X4-X5-G-X6-X7-X8-X9, wherein,

X1 is selected from I, V, M, L and T (e.g., selected from I, V, and L);

X2 is selected from T, I, V, S, N, Y, E and L (e.g., selected from T, V, and I);

X3 is selected from N, S, G, A, D, T, R, M and F (e.g., A or N);

X4 is selected from S, Y, N and F (e.g., S);

X5 is selected from V, I, L, C, T and F (e.g., selected from V, I and L);

X6 is selected from W, F, V, Y, S and L (e.g., W);

X7 is selected from A, S, C, V and G (e.g., selected from A and S);

X8 is selected from V, I, L, A, M and H (e.g., selected from V, I, M and L); and X9 is selected from any amino acid or is absent (e.g., selected from T, V, I, L, A, F, S, A, Y, M and R, or, e.g., selected from T, V, I, L and A).

In an embodiment, the N-terminal RuvC-like domain differs from a sequence of SEQ ID NO:8, by as many as 1 but no more than 2, 3, 4, or 5 residues.

In embodiment the N-terminal RuvC-like domain is cleavage competent.

In embodiment the N-terminal RuvC-like domain is cleavage incompetent.

In an embodiment, an eaCas9 molecule comprises an N-terminal RuvC-like domain comprising an amino acid sequence of formula II:

(SEQ ID NO: 9)
D-X1-G-X2-X3-S-X5-G-X6-X7-X8-X9, wherein

X1 is selected from I, V, M, L and T (e.g., selected from I, V, and L);

X2 is selected from T, I, V, S, N, Y, E and L (e.g., selected from T, V, and I);

X3 is selected from N, S, G, A, D, T, R, M and F (e.g., A or N);

X5 is selected from V, I, L, C, T and F (e.g., selected from V, I and L);

X6 is selected from W, F, V, Y, S and L (e.g., W);

X7 is selected from A, S, C, V and G (e.g., selected from A and S);

X8 is selected from V, I, L, A, M and H (e.g., selected from V, I, M and L); and X9 is selected from any amino acid or is absent (e.g., selected from T, V, I, L, A, F, S, A, Y, M and R or selected from e.g., T, V, I, L and Δ).

In an embodiment, the N-terminal RuvC-like domain differs from a sequence of SEQ ID NO:9 by as many as 1, but no more than 2, 3, 4, or 5 residues.

In an embodiment, the N-terminal RuvC-like domain comprises an amino acid sequence of formula III:

$$D-I-G-X2-X3-S-V-G-W-A-X8-X9, \quad \text{(SEQ ID NO: 10)}$$

wherein

X2 is selected from T, I, V, S, N, Y, E and L (e.g., selected from T, V, and I);

X3 is selected from N, S, G, A, D, T, R, M and F (e.g., A or N);

X8 is selected from V, I, L, A, M and H (e.g., selected from V, I, M and L); and X9 is selected from any amino acid or is absent (e.g., selected from T, V, I, L, A, F, S, A, Y, M and R or selected from e.g., T, V, I, L and A).

In an embodiment, the N-terminal RuvC-like domain differs from a sequence of SEQ ID NO:10 by as many as 1, but no more than, 2, 3, 4, or 5 residues.

In an embodiment, the N-terminal RuvC-like domain comprises an amino acid sequence of formula III:

$$D-I-G-T-N-S-V-G-W-A-V-X, \quad \text{(SEQ ID NO: 11)}$$

wherein

X is a non-polar alkyl amino acid or a hydroxyl amino acid, e.g., X is selected from V, I, L and T (e.g., the eaCas9 molecule can comprise an N-terminal RuvC-like domain shown in FIG. 2 (depicted as "Y")).

In an embodiment, the N-terminal RuvC-like domain differs from a sequence of SEQ ID NO:11 by as many as 1 but no more than, 2, 3, 4, or 5 residues.

In an embodiment, the N-terminal RuvC-like domain differs from a sequence of an N-terminal RuvC-like domain disclosed herein, e.g., in FIG. 3A or FIG. 5, as many as 1, but no more than 2, 3, 4, or 5 residues. In an embodiment, 1, 2, or all 3 of the highly conserved residues identified in FIG. 3A or FIG. 5 are present.

In an embodiment, the N-terminal RuvC-like domain differs from a sequence of an N-terminal RuvC-like domain disclosed herein, e.g., in FIG. 3B, as many as 1, but no more than 2, 3, 4, or 5 residues. In an embodiment, 1, 2, 3 or all 4 of the highly conserved residues identified in FIG. 3B are present.

Additional RuvC-Like Domains

In addition to the N-terminal RuvC-like domain, a Cas9 molecule, e.g., an eaCas9 molecule, can comprise one or more additional RuvC-like domains. In an embodiment, a Cas9 molecule can comprise two additional RuvC-like domains. Preferably, the additional RuvC-like domain is at least 5 amino acids in length and, e.g., less than 15 amino acids in length, e.g., 5 to 10 amino acids in length, e.g., 8 amino acids in length.

An additional RuvC-like domain can comprise an amino acid sequence:

$$I-X1-X2-E-X3-A-R-E, \quad \text{(SEQ ID NO: 12)}$$

wherein

X1 is V or H,

X2 is I, L or V (e.g., I or V); and

X3 is M or T.

In an embodiment, the additional RuvC-like domain comprises the amino acid sequence:

I-V-X2-E-M-A-R-E (SEQ ID NO:13), wherein

X2 is I, L or V (e.g., I or V) (e.g., the eaCas9 molecule can comprise an additional RuvC-like domain shown in FIG. 2 or FIG. 5 (depicted as "B")).

An additional RuvC-like domain can comprise an amino acid sequence:

$$H-H-A-X1-D-A-X2-X3, \quad \text{(SEQ ID NO: 14)}$$

wherein

X1 is H or L;

X2 is R or V; and

X3 is E or V.

In an embodiment, the additional RuvC-like domain comprises the amino acid sequence:

$$H-H-A-H-D-A-Y-L. \quad \text{(SEQ ID NO: 15)}$$

In an embodiment, the additional RuvC-like domain differs from a sequence of SEQ ID NO:13, 15, 12 or 14 by as many as 1, but no more than 2, 3, 4, or 5 residues.

In an embodiment, the sequence flanking the N-terminal RuvC-like domain is a sequences of formula V:

$$K-X1'-Y-X2'-X3'-X4'-Z-T-D-X9'-Y, \quad \text{(SEQ ID NO: 16)}$$

wherein

X1' is selected from K and P,

X2' is selected from V, L, I, and F (e.g., V, I and L);

X3' is selected from G, A and S (e.g., G),

X4' is selected from L, I, V and F (e.g., L);

X9' is selected from D, E, N and Q; and

Z is an N-terminal RuvC-like domain, e.g., as described above.

HNH-Like Domains

In an embodiment, an HNH-like domain cleaves a single stranded complementary domain, e.g., a complementary strand of a double stranded nucleic acid molecule. In an embodiment, an HNH-like domain is at least 15, 20, 25 amino acids in length but not more than 40, 35 or 30 amino acids in length, e.g., 20 to 35 amino acids in length, e.g., 25 to 30 amino acids in length. Exemplary HNH-like domains are described below.

In an embodiment, an eaCas9 molecule comprises an HNH-like domain having an amino acid sequence of formula VI:

(SEQ ID NO: 17)
X1-X2-X3-H-X4-X5-P-X6-X7-X8-X9-X10-X11-X12-X13-X14-X15-N-X16-X17-X18-X19-X20-X21-X22-X23-N, wherein
X1 is selected from D, E, Q and N (e.g., D and E);
X2 is selected from L, I, R, Q, V, M and K;
X3 is selected from D and E;
X4 is selected from I, V, T, A and L (e.g., A, I and V);
X5 is selected from V, Y, I, L, F and W (e.g., V, I and L);
X6 is selected from Q, H, R, K, Y, I, L, F and W;
X7 is selected from S, A, D, T and K (e.g., S and A);
X8 is selected from F, L, V, K, Y, M, I, R, A, E, D and Q (e.g., F);
X9 is selected from L, R, T, I, V, S, C, Y, K, F and G;
X10 is selected from K, Q, Y, T, F, L, W, M, A, E, G, and S;
X11 is selected from D, S, N, R, L and T (e.g., D);
X12 is selected from D, N and S;
X13 is selected from S, A, T, G and R (e.g., S);
X14 is selected from I, L, F, S, R, Y, Q, W, D, K and H (e.g., I, L and F);
X15 is selected from D, S, I, N, E, A, H, F, L, Q, M, G, Y and V;
X16 is selected from K, L, R, M, T and F (e.g., L, R and K);
X17 is selected from V, L, I, A and T;
X18 is selected from L, I, V and A (e.g., L and I);
X19 is selected from T, V, C, E, S and A (e.g., T and V);
X20 is selected from R, F, T, W, E, L, N, C, K, V, S, Q, I, Y, H and A;
X21 is selected from S, P, R, K, N, A, H, Q, G and L;
X22 is selected from D, G, T, N, S, K, A, I, E, L, Q, R and Y; and
X23 is selected from K, V, A, E, Y, I, C, L, S, T, G, K, M, D and F.

In an embodiment, a HNH-like domain differs from a sequence of SEQ ID NO:17 by at least 1, but no more than, 2, 3, 4, or 5 residues.

In an embodiment, the HNH-like domain is cleavage competent.

In an embodiment, the HNH-like domain is cleavage incompetent.

In an embodiment, an eaCas9 molecule comprises an HNH-like domain comprising an amino acid sequence of formula VII:

(SEQ ID NO: 18)
X1-X2-X3-H-X4-X5-P-X6-S-X8-X9-X10-D-D-S-X14-X15-N-K-V-L-X19-X20-X21-X22-X23-N, wherein
X1 is selected from D and E;
X2 is selected from L, I, R, Q, V, M and K;
X3 is selected from D and E;
X4 is selected from I, V, T, A and L (e.g., A, I and V);
X5 is selected from V, Y, I, L, F and W (e.g., V, I and L);
X6 is selected from Q, H, R, K, Y, I, L, F and W;
X8 is selected from F, L, V, K, Y, M, I, R, A, E, D and Q (e.g., F);
X9 is selected from L, R, T, I, V, S, C, Y, K, F and G;
X10 is selected from K, Q, Y, T, F, L, W, M, A, E, G, and S;
X14 is selected from I, L, F, S, R, Y, Q, W, D, K and H (e.g., I, L and F);
X15 is selected from D, S, I, N, E, A, H, F, L, Q, M, G, Y and V;
X19 is selected from T, V, C, E, S and A (e.g., T and V);
X20 is selected from R, F, T, W, E, L, N, C, K, V, S, Q, I, Y, H and A;
X21 is selected from S, P, R, K, N, A, H, Q, G and L;
X22 is selected from D, G, T, N, S, K, A, I, E, L, Q, R and Y; and
X23 is selected from K, V, A, E, Y, I, C, L, S, T, G, K, M, D and F.

In an embodiment, the HNH-like domain differs from a sequence of SEQ ID NO:18 by 1, 2, 3, 4, or 5 residues.

In an embodiment, an eaCas9 molecule comprises an HNH-like domain comprising an amino acid sequence of formula VII:

(SEQ ID NO: 19)
X1-V-X3-H-I-V-P-X6-S-X8-X9-X10-D-D-S-X14-X15-N-K-V-L-T-X20-X21-X22-X23-N, wherein
X1 is selected from D and E;
X3 is selected from D and E;
X6 is selected from Q, H, R, K, Y, I, L and W;
X8 is selected from F, L, V, K, Y, M, I, R, A, E, D and Q (e.g., F);
X9 is selected from L, R, T, I, V, S, C, Y, K, F and G;
X10 is selected from K, Q, Y, T, F, L, W, M, A, E, G, and S;
X14 is selected from I, L, F, S, R, Y, Q, W, D, K and H (e.g., I, L and F);
X15 is selected from D, S, I, N, E, A, H, F, L, Q, M, G, Y and V;
X20 is selected from R, F, T, W, E, L, N, C, K, V, S, Q, I, Y, H and A;
X21 is selected from S, P, R, K, N, A, H, Q, G and L;
X22 is selected from D, G, T, N, S, K, A, I, E, L, Q, R and Y; and
X23 is selected from K, V, A, E, Y, I, C, L, S, T, G, K, M, D and F.

In an embodiment, the HNH-like domain differs from a sequence of SEQ ID NO:19 by 1, 2, 3, 4, or 5 residues.

In an embodiment, an eaCas9 molecule comprises an HNH-like domain having an amino acid sequence of formula VIII:

(SEQ ID NO: 20)
D-X2-D-H-I-X5-P-Q-X7-F-X9-X10-D-X12-S-I-D-N-X16-V-L-X19-X20-S-X22-X23-N, wherein
X2 is selected from I and V;
X5 is selected from I and V;
X7 is selected from A and S;
X9 is selected from I and L;
X10 is selected from K and T;
X12 is selected from D and N;
X16 is selected from R, K and L; X19 is selected from T and V;
X20 is selected from S and R;
X22 is selected from K, D and A; and
X23 is selected from E, K, G and N (e.g., the eaCas9 molecule can comprise an HNH-like domain as described herein).

In an embodiment, the HNH-like domain differs from a sequence of SEQ ID NO:20 by as many as 1, but no more than 2, 3, 4, or 5 residues.

In an embodiment, an eaCas9 molecule comprises the amino acid sequence of formula IX:

(SEQ ID NO: 21)
L-Y-Y-L-Q-N-G-X1'-D-M-Y-X2'-X3'-X4'-X5'-L-D-I-X6'-

X7'-L-S-X8'-Y-Z-N-R-X9'-K-X10'-D-X11'-V-P, wherein
X1' is selected from K and R;
X2' is selected from V and T;
X3' is selected from G and D;
X4' is selected from E, Q and D;
X5' is selected from E and D;
X6' is selected from D, N and H;
X7' is selected from Y, R and N;
X8' is selected from Q, D and N; X9' is selected from G and E;
X10' is selected from S and G;
X11' is selected from D and N; and
Z is an HNH-like domain, e.g., as described above.

In an embodiment, the eaCas9 molecule comprises an amino acid sequence that differs from a sequence of SEQ ID NO:21 by as many as 1, but no more than 2, 3, 4, or 5 residues.

In an embodiment, the HNH-like domain differs from a sequence of an HNH-like domain disclosed herein, e.g., in FIG. 4A or FIG. 5, as many as 1, but no more than 2, 3, 4, or 5 residues.

In an embodiment, the HNH-like domain differs from a sequence of an HNH-like domain disclosed herein, e.g., in FIG. 4B, by as many as 1, but no more than 2, 3, 4, or 5 residues. In an embodiment, 1, 2, all 3 of the highly conserved residues identified in FIG. 4B are present.

Altered Cas9 Molecules

Naturally occurring Cas9 molecules possess a number of properties, including: nickase activity, nuclease activity (e.g., endonuclease and/or exonuclease activity); helicase activity; the ability to associate functionally with a gRNA molecule; and the ability to target (or localize to) a site on a nucleic acid (e.g., PAM recognition and specificity). In an embodiment, a Cas9 molecules can include all or a subset of these properties. In a typical embodiment, Cas9 molecules have the ability to interact with a gRNA molecule and, in concert with the gRNA molecule, localize to a site in a nucleic acid. Other activities, e.g., PAM specificity, cleavage activity, or helicase activity can vary more widely in Cas9 molecules.

Cas9 molecules with desired properties can be made in a number of ways, e.g., by alteration of a parental, e.g., naturally occurring Cas9 molecules to provide an altered Cas9 molecule having a desired property. For example, one or more mutations or differences relative to a parental Cas9 molecule can be introduced. Such mutations and differences comprise: substitutions (e.g., conservative substitutions or substitutions of non-essential amino acids); insertions; or deletions. In an embodiment, a Cas9 molecule can comprises one or more mutations or differences, e.g., at least 1, 2, 3, 4, 5, 10, 15, 20, 30, 40 or 50 mutations but less than 200, 100, or 80 mutations relative to a reference Cas9 molecule.

In an embodiment, a mutation or mutations do not have a substantial effect on a Cas9 activity, e.g. a Cas9 activity described herein. In an embodiment, a mutation or mutations have a substantial effect on a Cas9 activity, e.g. a Cas9 activity described herein. In an embodiment, exemplary activities comprise one or more of PAM specificity, cleavage activity, and helicase activity. A mutation(s) can be present, e.g., in: one or more RuvC-like domain, e.g., an N-terminal RuvC-like domain; an HNH-like domain; a region outside the RuvC-like domains and the HNH-like domain. In an embodiment, a mutation(s) is present in an N-terminal RuvC-like domain. In an embodiment, a mutation(s) is present in an HNH-like domain. In an embodiment, mutations are present in both an N-terminal RuvC-like domain and an HNH-like domain.

Whether or not a particular sequence, e.g., a substitution, may affect one or more activity, such as targeting activity, cleavage activity, etc, can be evaluated or predicted, e.g., by evaluating whether the mutation is conservative or by the method described in Section III. In an embodiment, a "non-essential" amino acid residue, as used in the context of a Cas9 molecule, is a residue that can be altered from the wild-type sequence of a Cas9 molecule, e.g., a naturally occurring Cas9 molecule, e.g., an eaCas9 molecule, without abolishing or more preferably, without substantially altering a Cas9 activity (e.g., cleavage activity), whereas changing an "essential" amino acid residue results in a substantial loss of activity (e.g., cleavage activity).

In an embodiment, the altered Cas9 molecule is an eaCas9 molecule comprising the fixed amino acid residues of *S. pyogenes* shown in the consensus sequence disclosed in FIG. 2, and has one or more amino acids that differ from the amino acid sequence of *S. pyogenes* (e.g., has a substitution) at one or more residue (e.g., 2, 3, 5, 10, 15, 20, 30, 50, 70, 80, 90, 100, 200 amino acid residues) represented by an "-" in the consensus sequence disclosed in FIG. 2 or SEQ ID NO:7. In an embodiment, the altered Cas9 molecule is an eiCas9 molecule wherein one or more of the fixed amino acid residues of *S. pyogenes* shown in the consensus sequence disclosed in FIG. 2 (e.g., 2, 3, 5, 10, 15, 20, 30, 50, 70, 80, 90, 100, 200 amino acid residues) is mutated.

In an embodiment, the altered Cas9 molecule comprises a sequence in which:

the sequence corresponding to the fixed sequence of the consensus sequence disclosed in FIG. 2 differs at no more than 1, 2, 3, 4, 5, 10, 15, or 20% of the fixed residues in the consensus sequence disclosed in FIG. 2;

the sequence corresponding to the residues identified by "*" in the consensus sequence disclosed in FIG. 2 differ at no more than 1, 2, 3, 4, 5, 10, 15, 20, 25, 30, 35, or 40% of the "*" residues from the corresponding sequence of naturally occurring Cas9 molecule, e.g., an *S. pyogenes* Cas9 molecule; and, the sequence corresponding to the residues identified by "-" in the consensus sequence disclosed in FIG. 2 differ at no more than 5, 10, 15, 20, 25, 30, 35, 40, 45, 55, or 60% of the "-" residues from the corresponding sequence of naturally occurring Cas9 molecule, e.g., an *S. pyogenes* Cas9 molecule.

In an embodiment, the altered Cas9 molecule is an eaCas9 molecule comprising the fixed amino acid residues of *S. thermophilus* shown in the consensus sequence disclosed in FIG. 2, and has one or more amino acids that differ from the amino acid sequence of *S. thermophilus* (e.g., has a substitution) at one or more residue (e.g., 2, 3, 5, 10, 15, 20, 30, 50, 70, 80, 90, 100, 200 amino acid residues) represented by an "-" in the consensus sequence disclosed in FIG. 2. In an embodiment, the altered Cas9 molecule is an eiCas9 molecule wherein one or more of the fixed amino acid residues of *S. thermophilus* shown in the consensus sequence disclosed in FIG. 2 (e.g., 2, 3, 5, 10, 15, 20, 30, 50, 70, 80, 90, 100, 200 amino acid residues) is mutated.

In an embodiment the altered Cas9 molecule comprises a sequence in which:

the sequence corresponding to the fixed sequence of the consensus sequence disclosed in FIG. 2 differs at no more than 1, 2, 3, 4, 5, 10, 15, or 20% of the fixed residues in the consensus sequence disclosed in FIG. 2;

the sequence corresponding to the residues identified by "*" in the consensus sequence disclosed in FIG. 2 differ at no more than 1, 2, 3, 4, 5, 10, 15, 20, 25, 30, 35, or 40% of the "*" residues from the corresponding sequence of naturally occurring Cas9 molecule, e.g., an S. thermophilus Cas9 molecule; and, the sequence corresponding to the residues identified by "-" in the consensus sequence disclosed in FIG. 2 differ at no more than 5, 10, 15, 20, 25, 30, 35, 40, 45, 55, or 60% of the "-" residues from the corresponding sequence of naturally occurring Cas9 molecule, e.g., an S. thermophilus Cas9 molecule.

In an embodiment, the altered Cas9 molecule is an eaCas9 molecule comprising the fixed amino acid residues of S. mutans shown in the consensus sequence disclosed in FIG. 2, and has one or more amino acids that differ from the amino acid sequence of S. mutans (e.g., has a substitution) at one or more residue (e.g., 2, 3, 5, 10, 15, 20, 30, 50, 70, 80, 90, 100, 200 amino acid residues) represented by an "-" in the consensus sequence disclosed in FIG. 2. In an embodiment, the altered Cas9 molecule is an eiCas9 molecule wherein one or more of the fixed amino acid residues of S. mutans shown in the consensus sequence disclosed in FIG. 2 (e.g., 2, 3, 5, 10, 15, 20, 30, 50, 70, 80, 90, 100, 200 amino acid residues) is mutated.

In an embodiment the altered Cas9 molecule comprises a sequence in which:

the sequence corresponding to the fixed sequence of the consensus sequence disclosed in FIG. 2 differs at no more than 1, 2, 3, 4, 5, 10, 15, or 20% of the fixed residues in the consensus sequence disclosed in FIG. 2;

the sequence corresponding to the residues identified by "*" in the consensus sequence disclosed in FIG. 2 differ at no more than 1, 2, 3, 4, 5, 10, 15, 20, 25, 30, 35, or 40% of the "*" residues from the corresponding sequence of naturally occurring Cas9 molecule, e.g., an S. mutans Cas9 molecule; and, the sequence corresponding to the residues identified by "-" in the consensus sequence disclosed in FIG. 2 differ at no more than 5, 10, 15, 20, 25, 30, 35, 40, 45, 55, or 60% of the "-" residues from the corresponding sequence of naturally occurring Cas9 molecule, e.g., an S. mutans Cas9 molecule.

In an embodiment, the altered Cas9 molecule is an eaCas9 molecule comprising the fixed amino acid residues of L. innocula shown in the consensus sequence disclosed in FIG. 2, and has one or more amino acids that differ from the amino acid sequence of L. innocula (e.g., has a substitution) at one or more residue (e.g., 2, 3, 5, 10, 15, 20, 30, 50, 70, 80, 90, 100, 200 amino acid residues) represented by an "-" in the consensus sequence disclosed in FIG. 2. In an embodiment, the altered Cas9 molecule is an eiCas9 molecule wherein one or more of the fixed amino acid residues of L. innocula shown in the consensus sequence disclosed in FIG. 2 (e.g., 2, 3, 5, 10, 15, 20, 30, 50, 70, 80, 90, 100, 200 amino acid residues) is mutated.

In an embodiment the altered Cas9 molecule comprises a sequence in which:

the sequence corresponding to the fixed sequence of the consensus sequence disclosed in FIG. 2 differs at no more than 1, 2, 3, 4, 5, 10, 15, or 20% of the fixed residues in the consensus sequence disclosed in FIG. 2;

the sequence corresponding to the residues identified by "*" in the consensus sequence disclosed in FIG. 2 differ at no more than 1, 2, 3, 4, 5, 10, 15, 20, 25, 30, 35, or 40% of the "*" residues from the corresponding sequence of naturally occurring Cas9 molecule, e.g., an L. innocula Cas9 molecule; and, the sequence corresponding to the residues identified by "-" in the consensus sequence disclosed in FIG. 2 differ at no more than 5, 10, 15, 20, 25, 30, 35, 40, 45, 55, or 60% of the "-" residues from the corresponding sequence of naturally occurring Cas9 molecule, e.g., an L. innocula Cas9 molecule.

In an embodiment, the altered Cas9 molecule, e.g., an eaCas9 molecule or an eiCas9 molecule, can be a fusion, e.g., of two of more different Cas9 molecules, e.g., of two or more naturally occurring Cas9 molecules of different species. For example, a fragment of a naturally occurring Cas9 molecule of one species can be fused to a fragment of a Cas9 molecule of a second species. As an example, a fragment of Cas9 of S. pyogenes comprising an N-terminal RuvC-like domain can be fused to a fragment of Cas9 of a species other than S. pyogenes (e.g., S. thermophilus) comprising an HNH-like domain.

Cas9 Molecules with Altered PAM Recognition or No PAM Recognition

Naturally occurring Cas9 molecules can recognize specific PAM sequences, for example the PAM recognition sequences described above for S. pyogenes, S. thermophilus, S. mutans, S. aureus and N. meningitidis.

In an embodiment, a Cas9 molecule has the same PAM specificities as a naturally occurring Cas9 molecule. In an embodiment, a Cas9 molecule has a PAM specificity not associated with a naturally occurring Cas9 molecule, or a PAM specificity not associated with the naturally occurring Cas9 molecule to which it has the closest sequence homology. For example, a naturally occurring Cas9 molecule can be altered, e.g., to alter PAM recognition, e.g., to alter the PAM sequence that the Cas9 molecule recognizes to decrease off target sites and/or improve specificity; or eliminate a PAM recognition requirement. In an embodiment, a Cas9 molecule can be altered, e.g., to increase length of PAM recognition sequence and/or improve Cas9 specificity to high level of identity to decrease off target sites and increase specificity. In an embodiment, the length of the PAM recognition sequence is at least 4, 5, 6, 7, 8, 9, 10 or 15 amino acids in length. Cas9 molecules that recognize different PAM sequences and/or have reduced off-target activity can be generated using directed evolution. Exemplary methods and systems that can be used for directed evolution of Cas9 molecules are described, e.g., in Esvelt et al., NATURE 2011, 472(7344): 499-503. Candidate Cas9 molecules can be evaluated, e.g., by methods described in Section III.

Non-Cleaving and Modified-Cleavage Cas9 Molecules

In an embodiment, a Cas9 molecule comprises a cleavage property that differs from naturally occurring Cas9 molecules, e.g., that differs from the naturally occurring Cas9 molecule having the closest homology. For example, a Cas9 molecule can differ from naturally occurring Cas9 molecules, e.g., a Cas9 molecule of S. pyogenes, as follows: its ability to modulate, e.g., decreased or increased, cleavage of a double stranded break (endonuclease and/or exonuclease activity), e.g., as compared to a naturally occurring Cas9 molecule (e.g., a Cas9 molecule of *S. pyogenes*); its ability to modulate, e.g., decreased or increased, cleavage of a single strand of a nucleic acid, e.g., a non-complimentary strand of a nucleic acid molecule or a complementary strand of a nucleic acid molecule (nickase activity), e.g., as compared to a naturally occurring Cas9 molecule (e.g., a Cas9 molecule of *S. pyogenes*); or the ability to cleave a nucleic acid molecule, e.g., a double stranded or single stranded nucleic acid molecule, can be eliminated.

Modified Cleavage eaCas9 Molecules

In an embodiment, an eaCas9 molecule comprises one or more of the following activities: cleavage activity associated with an N-terminal RuvC-like domain; cleavage activity associated with an HNH-like domain; cleavage activity associated with an HNH domain and cleavage activity associated with an N-terminal RuvC-like domain.

In an embodiment an eaCas9 molecule comprises an active, or cleavage competent, HNH-like domain (e.g., an HNH-like domain described herein, e.g., SEQ ID NO:17, SEQ ID NO:18, SEQ ID NO:19, SEQ ID NO:20 or SEQ ID NO:21) and an inactive, or cleavage incompetent, N-terminal RuvC-like domain. An exemplary inactive, or cleavage incompetent N-terminal RuvC-like domain can have a mutation of an aspartic acid in an N-terminal RuvC-like domain, e.g., an aspartic acid at position 9 of the consensus sequence disclosed in FIG. 2 or an aspartic acid at position 10 of SEQ ID NO:7, e.g., can be substituted with an alanine. In an embodiment, the eaCas9 differs from wild type in the N-terminal RuvC-like domain and does not cleave the target nucleic acid, or cleaves with significantly less efficiency, e.g., less than 20, 10, 5, 1 or 0.1% of the cleavage activity of a reference Cas9 molecule, e.g., as measured by an assay described herein. The reference Cas9 molecule can by a naturally occurring unmodified Cas9 molecule, e.g., a naturally occurring Cas9 molecule such as a Cas9 molecule of *S. pyogenes*, or *S. thermophilus*. In an embodiment, the reference Cas9 molecule is the naturally occurring Cas9 molecule having the closest sequence identity or homology.

In an embodiment, an eaCas9 molecule comprises an inactive, or cleavage incompetent, HNH domain and an active, or cleavage competent, N-terminal RuvC-like domain (e.g., an HNH-like domain described herein, e.g., SEQ ID NO:8, SEQ ID NO:9, SEQ ID NO:10, SEQ ID NO:11, SEQ ID NO:12, SEQ ID NO:13, SEQ ID NO:14 or SEQ ID NO:15). Exemplary inactive, or cleavage incompetent HNH-like domains can have a mutation at one or more of: a histidine in an HNH-like domain, e.g., a histidine at position 856 of the consensus sequence disclosed in FIG. 2, e.g., can be substituted with an alanine; and one or more asparagines in an HNH-like domain, e.g., an asparagine at position 870 of the consensus sequence disclosed in FIG. 2 and/or at position 879 of the consensus sequence disclosed in FIG. 2, e.g., can be substituted with an alanine. In an embodiment, the eaCas9 differs from wild type in the HNH-like domain and does not cleave the target nucleic acid, or cleaves with significantly less efficiency, e.g., less than 20, 10, 5, 1 or 0.1% of the cleavage activity of a reference Cas9 molecule, e.g., as measured by an assay described herein. The reference Cas9 molecule can by a naturally occurring unmodified Cas9 molecule, e.g., a naturally occurring Cas9 molecule such as a Cas9 molecule of *S. pyogenes*, or *S. thermophilus*. In an embodiment, the reference Cas9 molecule is the naturally occurring Cas9 molecule having the closest sequence identity or homology.

Non-Cleaving eiCas9 Molecules

In an embodiment, the altered Cas9 molecule is an eiCas9 molecule which does not cleave a nucleic acid molecule (either double stranded or single stranded nucleic acid molecules) or cleaves a nucleic acid molecule with significantly less efficiency, e.g., less than 20, 10, 5, 1 or 0.1% of the cleavage activity of a reference Cas9 molecule, e.g., as measured by an assay described herein. The reference Cas9 molecule can by a naturally occurring unmodified Cas9 molecule, e.g., a naturally occurring Cas9 molecule such as a Cas9 molecule of *S. pyogenes, S. thermophilus, S. aureus* or *N. meningitidis*. In an embodiment, the reference Cas9 molecule is the naturally occurring Cas9 molecule having the closest sequence identity or homology. In an embodiment, the eiCas9 molecule lacks substantial cleavage activity associated with an N-terminal RuvC-like domain and cleavage activity associated with an HNH-like domain.

In an embodiment, an eiCas9 molecule comprises an inactive, or cleavage incompetent, N-terminal RuvC-like domain. An exemplary inactive, or cleavage incompetent N-terminal RuvC-like domain can have a mutation of an aspartic acid in an N-terminal RuvC-like domain, e.g., an aspartic acid at position 9 of the consensus sequence disclosed in FIG. 2 or an aspartic acid at position 10 of SEQ ID NO:7, e.g., can be substituted with an alanine.

In an embodiment an eiCas9 molecule comprises an inactive, or cleavage incompetent, HNH domain (e.g., an HNH-like domain described herein, e.g., SEQ ID NO:8, SEQ ID NO:9, SEQ ID NO:10, SEQ ID NO:11, SEQ ID NO:12, SEQ ID NO:13, SEQ ID NO:14 or SEQ ID NO:15). Exemplary inactive, or cleavage incompetent HNH-like domains can have a mutation at one or more of: a histidine in an HNH-like domain, e.g., a histidine at position 856 of the consensus sequence disclosed in FIG. 2, e.g., can be substituted with an alanine; and one or more asparagines in an HNH-like domain, e.g., an asparagine at position 870 of the consensus sequence disclosed in FIG. 2 and/or at position 879 of the consensus sequence disclosed in FIG. 2, e.g., can be substituted with an alanine.

A catalytically inactive Cas9 molecule may be fused with a transcription repressor. An eiCas9 fusion protein complexes with a gRNA and localizes to a DNA sequence specified by gRNA's targeting domain, but, unlike an eaCas9, it will not cleave the target DNA. Fusion of an effector domain, such as a transcriptional repression domain, to an eiCas9 enables recruitment of the effector to any DNA site specified by the gRNA. Site specific targeting of an eiCas9 or an eiCas9 fusion protein to a promoter region of a gene can block RNA polymerase binding to the promoter region, a transcription factor (e.g., a transcription activator) and/or a transcriptional enhancer to inhibit transcription activation. Alternatively, site specific targeting of an eiCas9-fusion to a transcription repressor to a promoter region of a gene can be used to decrease transcription activation.

Transcription repressors or transcription repressor domains that may be fused to an eiCas9 molecule can include Krüppel associated box (KRAB or SKD), the Mad mSIN3 interaction domain (SID) or the ERF repressor domain (ERD).

In another embodiment, an eiCas9 molecule may be fused with a protein that modifies chromatin. For example, an eiCas9 molecule may be fused to heterochromatin protein 1 (HP1), a histone lysine methyltransferase (e.g., SUV39H1, SUV39H2, G9A, ESET/SETDB1, Pr-SET7/8, SUV4-20H1, RIZ1), a histone lysine demethylates (e.g., LSD1/BHC110, SpLsd1/Sw,1/Saf110, Su(var)3-3, JMJD2A/JHDM3A, JMJD2B, JMJD2C/GASC1, JMJD2D, Rphl, JARID1A/RBP2, JAR1D1B/PLU-1, JAR1D1C/SMCX, JARID1D/SMCY, Lid, Jhn2, Jmj2), a histone lysine deacetylases (e.g., HDAC1, HDAC2, HDAC3, HDAC8, Rpd3, Hos1, Cir6, HDAC4, HDAC5, HDAC7, HDAC9, Hdal, Cir3, SIRT1, SIRT2, Sir2, Hst1, Hst2, Hst3, Hst4, HDAC11) and a DNA methylases (DNMT1, DNMT2a/DMNT3b, MET1). An eiCas9-chomatin modifying molecule fusion protein can be used to alter chromatin status to reduce expression a target gene.

The heterologous sequence (e.g., the transcription repressor domain) may be fused to the N- or C-terminus of the eiCas9 protein. In an alternative embodiment, the heterologous sequence (e.g., the transcription repressor domain) may be fused to an internal portion (i.e., a portion other than the N-terminus or C-terminus) of the eiCas9 protein.

The ability of a Cas9 molecule/gRNA molecule complex to bind to and cleave a target nucleic acid can be evaluated, e.g., by the methods described herein in Section III. The activity of a Cas9 molecule, either an eaCas9 or a eiCas9, alone or in a complex with a gRNA molecule may also be evaluated by methods well-known in the art, including, gene expression assays and chromatin-based assays, e.g., chromatin immunoprecipitation (ChiP) and chromatin in vivo assay (CiA).

Nucleic Acids Encoding Cas9 Molecules

Nucleic acids encoding the Cas9 molecules, e.g., an eaCas9 molecule or an eiCas9 molecule are provided herein.

Exemplary nucleic acids encoding Cas9 molecules are described in Cong et al., SCIENCE 2013, 399(6121):819-823; Wang et al., CELL 2013, 153(4):910-918; Mali et al., SCIENCE 2013, 399(6121):823-826; Jinek et al., SCIENCE 2012, 337 (6096):816-821. Another exemplary nucleic acid encoding a Cas9 molecule of *N. meningitidis* is shown in FIG. 6.

In an embodiment, a nucleic acid encoding a Cas9 molecule can be a synthetic nucleic acid sequence. For example, the synthetic nucleic acid molecule can be chemically modified, e.g., as described in Section X. In an embodiment, the Cas9 mRNA has one or more of, e.g., all of the following properties: it is capped, polyadenylated, substituted with κ-methylcytidine and/or pseudouridine.

In addition or alternatively, the synthetic nucleic acid sequence can be codon optimized, e.g., at least one non-common codon or less-common codon has been replaced by a common codon. For example, the synthetic nucleic acid can direct the synthesis of an optimized messenger mRNA, e.g., optimized for expression in a mammalian expression system, e.g., described herein.

In addition, or alternatively, a nucleic acid encoding a Cas9 molecule may comprise a nuclear localization sequence (NLS). Nuclear localization sequences are known in the art.

Provided below is an exemplary codon optimized nucleic acid sequence encoding a Cas9 molecule of *S. pyogenes*.

```
                                        (SEQ ID NO: 22)
ATGGATAAAA AGTACAGCAT CGGGCTGGAC ATCGGTACAA

ACTCAGTGGG GTGGGCCGTG ATTACGGACG AGTACAAGGT

ACCCTCCAAA AAATTTAAAG TGCTGGGTAA CACGGACAGA

CACTCTATAA AGAAAAATCT TATTGGAGCC TTGCTGTTCG

ACTCAGGCGA GACAGCCGAA GCCACAAGGT TGAAGCGGAC

CGCCAGGAGG CGGTATACCA GGAGAAAGAA CCGCATATGC

TACCTGCAAG AAATCTTCAG TAACGAGATG GCAAAGGTTG

ACGATAGCTT TTTCCATCGC CTGGAAGAAT CCTTTCTTGT
```

-continued
```
TGAGGAAGAC AAGAAGCACG AACGGCACCC CATCTTTGGC

AATATTGTCG ACGAAGTGGC ATATCACGAA AAGTACCCGA

CTATCTACCA CCTCAGGAAG AAGCTGGTGG ACTCTACCGA

TAAGGCGGAC CTCAGACTTA TTTATTTGGC ACTCGCCCAC

ATGATTAAAT TTAGAGGACA TTTCTTGATC GAGGGCGACC

TGAACCCGGA CAACAGTGAC GTCGATAAGC TGTTCATCCA

ACTTGTGCAG ACCTACAATC AACTGTTCGA AGAAAACCCT

ATAAATGCTT CAGGAGTCGA CGCTAAAGCA ATCCTGTCCG

CGCGCCTCTC AAAATCTAGA AGACTTGAGA ATCTGATTGC

TCAGTTGCCC GGGGAAAAGA AAAATGGATT GTTTGGCAAC

CTGATCGCCC TCAGTCTCGG ACTGACCCCA AATTTCAAAA

GTAACTTCGA CCTGGCCGAA GACGCTAAGC TCCAGCTGTC

CAAGGACACA TACGATGACG ACCTCGACAA TCTGCTGGCC

CAGATTGGGG ATCAGTACGC CGATCTCTTT TTGGCAGCAA

AGAACCTGTC CGACGCCATC CTGTTGAGCG ATATCTTGAG

AGTGAACACC GAAATTACTA AAGCACCCCT TAGCGCATCT

ATGATCAAGC GGTACGACGA GCATCATCAG GATCTGACCC

TGCTGAAGGC TCTTGTGAGG CAACAGCTCC CCGAAAAATA

CAAGGAAATC TTCTTTGACC AGAGCAAAAA CGGCTACGCT

GGCTATATAG ATGGTGGGGC CAGTCAGGAG GAATTCTATA

AATTCATCAA GCCCATTCTC GAGAAAATGG ACGGCACAGA

GGAGTTGCTG GTCAAACTTA ACAGGGAGGA CCTGCTGCGG

AAGCAGCGGA CCTTTGACAA CGGGTCTATC CCCCACCAGA

TTCATCTGGG CGAACTGCAC GCAATCCTGA GGAGGCAGGA

GGATTTTTAT CCTTTTCTTA AAGATAACCG CGAGAAAATA

GAAAAGATTC TTACATTCAG GATCCCGTAC TACGTGGGAC

CTCTCGCCCG GGGCAATTCA CGGTTTGCCT GGATGACAAG

GAAGTCAGAG GAGACTATTA CACCTTGGAA CTTCGAAGAA

GTGGTGGACA AGGGTGCATC TGCCCAGTCT TTCATCGAGC

GGATGACAAA TTTTGACAAG AACCTCCCTA ATGAGAAGGT

GCTGCCCAAA CATTCTCTGC TCTACGAGTA CTTTACCGTC

TACAATGAAC TGACTAAAGT CAAGTACGTC ACCGAGGGAA

TGAGGAAGCC GGCATTCCTT AGTGGAGAAC AGAAGAAGGC

GATTGTAGAC CTGTTGTTCA AGACCAACAG GAAGGTGACT

GTGAAGCAAC TTAAAGAAGA CTACTTTAAG AAGATCGAAT

GTTTTGACAG TGTGGAAATT TCAGGGGTTG AAGACCGCTT

CAATGCGTCA TTGGGGACTT ACCATGATCT TCTCAAGATC

ATAAAGGACA AAGACTTCCT GGACAACGAA GAAAATGAGG

ATATTCTCGA AGACATCGTC CTCACCCTGA CCCTGTTCGA

AGACAGGGAA ATGATAGAAG AGCGCTTGAA AACCTATGCC

CACCTCTTCG ACGATAAAGT TATGAAGCAG CTGAAGCGCA
```

-continued

```
GGAGATACAC AGGATGGGGA AGATTGTCAA GGAAGCTGAT

CAATGGAATT AGGGATAAAC AGAGTGGCAA GACCATACTG

GATTTCCTCA AATCTGATGG CTTCGCCAAT AGGAACTTCA

TGCAACTGAT TCACGATGAC TCTCTTACCT TCAAGGAGGA

CATTCAAAAG GCTCAGGTGA GCGGGCAGGG AGACTCCCTT

CATGAACACA TCGCGAATTT GGCAGGTTCC CCCGCTATTA

AAAAGGGCAT CCTTCAAACT GTCAAGGTGG TGGATGAATT

GGTCAAGGTA ATGGGCAGAC ATAAGCCAGA AAATATTGTG

ATCGAGATGG CCCGCGAAAA CCAGACCACA CAGAAGGGCC

AGAAAAATAG TAGAGAGCGG ATGAAGAGGA TCGAGGAGGG

CATCAAAGAG CTGGGATCTC AGATTCTCAA AGAACACCCC

GTAGAAAACA CACAGCTGCA GAACGAAAAA TTGTACTTGT

ACTATCTGCA GAACGGCAGA GACATGTACG TCGACCAAGA

ACTTGATATT AATAGACTGT CCGACTATGA CGTAGACCAT

ATCGTGCCCC AGTCCTTCCT GAAGGACGAC TCCATTGATA

ACAAAGTCTT GACAAGAAGC GACAAGAACA GGGGTAAAAG

TGATAATGTG CCTAGCGAGG AGGTGGTGAA AAAAATGAAG

AACTACTGGC GACAGCTGCT TAATGCAAAG CTCATTACAC

AACGGAAGTT CGATAATCTG ACGAAAGCAG AGAGAGGTGG

CTTGTCTGAG TTGGACAAGG CAGGGTTTAT TAAGCGGCAG

CTGGTGGAAA CTAGGCAGAT CACAAAGCAC GTGGCGCAGA

TTTTGGACAG CCGGATGAAC ACAAAATACG ACGAAAATGA

TAAACTGATA CGAGAGGTCA AAGTTATCAC GCTGAAAAGC

AAGCTGGTGT CCGATTTTCG GAAAGACTTC CAGTTCTACA

AAGTTCGCGA GATTAATAAC TACCATCATG CTCACGATGC

GTACCTGAAC GCTGTTGTCG GGACCGCCTT GATAAAGAAG

TACCCAAAGC TGGAATCCGA GTTCGTATAC GGGGATTACA

AAGTGTACGA TGTGAGGAAA ATGATAGCCA AGTCCGAGCA

GGAGATTGGA AAGGCCACAG CTAAGTACTT CTTTTATTCT

AACATCATGA ATTTTTTTAA GACGGAAATT ACCCTGGCCA

ACGGAGAGAT CAGAAAGCGG CCCCTTATAG AGACAAATGG

TGAAACAGGT GAAATCGTCT GGGATAAGGG CAGGGATTTC

GCTACTGTGA GGAAGGTGCT GAGTATGCCA CAGGTAAATA

TCGTGAAAAA AACCGAAGTA CAGACCGGAG GATTTTCCAA

GGAAAGCATT TTGCCTAAAA GAAACTCAGA CAAGCTCATC

GCCCGCAAGA AGATTGGGA CCCTAAGAAA TACGGGGAT

TTGACTCACC CACCGTAGCC TATTCTGTGC TGGTGGTAGC

TAAGGTGGAA AAAGGAAAGT CTAAGAAGCT GAAGTCCGTG

AAGGAACTCT TGGGAATCAC TATCATGGAA AGATCATCCT

TTGAAAAGAA CCCTATCGAT TTCCTGGAGG CTAAGGGTTA
```

```
CAAGGAGGTC AAGAAAGACC TCATCATTAA ACTGCCAAAA

TACTCTCTCT TCGAGCTGGA AAATGGCAGG AAGAGAATGT

TGGCCAGCGC CGGAGAGCTG CAAAAGGGAA ACGAGCTTGC

TCTGCCCTCC AAATATGTTA ATTTTCTCTA TCTCGCTTCC

CACTATGAAA AGCTGAAAGG GTCTCCCGAA GATAACGAGC

AGAAGCAGCT GTTCGTCGAA CAGCACAAGC ACTATCTGGA

TGAAATAATC GAACAAATAA GCGAGTTCAG CAAAAGGGTT

ATCCTGGCGG ATGCTAATTT GGACAAAGTA CTGTCTGCTT

ATAACAAGCA CCGGGATAAG CCTATTAGGG AACAAGCCGA

GAATATAATT CACCTCTTTA CACTCACGAA TCTCGGAGCC

CCCGCCGCCT TCAAATACTT TGATACGACT ATCGACCGGA

AACGGTATAC CAGTACCAAA GAGGTCCTCG ATGCCACCCT

CATCCACCAG TCAATTACTG GCCTGTACGA AACACGGATC

GACCTCTCTC AACTGGGCGG CGACTAG
```

Provided below is the corresponding amino acid sequence of a *S. pyogenes* Cas9 molecule.

(SEQ ID NO: 23)
```
MDKKYSIGLDIGTNSVGWAVITDEYKVPSKKFKVLGNTDRHSIKKNLIGAL
LFDSGETAEATRLKRTARRRYTRRKNRICYLQEIFSNEMAKVDDSFFHRLE
ESFLVEEDKKHERHPIFGNIVDEVAYHEKYPTIYHLRKKLVDSTDKADLRL
IYLALAHMIKFRGHFLIEGDLNPDNSDVDKLFIQLVQTYNQLFEENPINAS
GVDAKAILSARLSKSRRLENLIAQLPGEKKNGLFGNLIALSLGLTPNFKSN
FDLAEDAKLQLSKDTYDDDLDNLLAQIGDQYADLFLAAKNLSDAILLSDIL
RVNTEITKAPLSASMIKRYDEHHQDLTLLKALVRQQLPEKYKEIFFDQSKN
GYAGYIDGGASQEEFYKFIKPILEKMDGTEELLVKLNREDLLRKQRTFDNG
SIPHQIHLGELHAILRRQEDFYPFLKDNREKIEKILTFRIPYYVGPLARGN
SRFAWMTRKSEETITPWNFEEVVDKGASAQSFIERMTNFDKNLPNEKVLPK
HSLLYEYFTVYNELTKVKYVTEGMRKPAFLSGEQKKAIVDLLFKTNRKVTV
KQLKEDYFKKIECFDSVEISGVEDRFNASLGTYHDLLKIIKDKDFLDNEEN
EDILEDIVLTLTLFEDREMIEERLKTYAHLFDDKVMKQLKRRRYTGWGRLS
RKLINGIRDKQSGKTILDFLKSDGFANRNFMQLIHDDSLTFKEDIQKAQVS
GQGDSLHEHIANLAGSPAIKKGILQTVKVVDELVKVMGRHKPENIVIEMAR
ENQTTQKGQKNSRERMKRIEEGIKELGSQILKEHPVENTQLQNEKLYLYYL
QNGRDMYVDQELDINRLSDYDVDHIVPQSFLKDDSIDNKVLTRSDKNRGKS
DNVPSEEVVKKMKNYWRQLLNAKLITQRKFDNLTKAERGGLSELDKAGFIK
RQLVETRQITKHVAQILDSRMNTKYDENDKLIREVKVITLKSKLVSDFRKD
FQFYKVREINNYHHAHDAYLNAVVGTALIKKYPKLESEFVYGDYKVYDVRK
MIAKSEQEIGKATAKYFFYSNIMNFFKTEITLANGEIRKRPLIETNGETGE
IVWDKGRDFATVRKVLSMPQVNIVKKTEVQTGGFSKESILPKRNSDKLIAR
KKDWDPKKYGGFDSPTVAYSVLVVAKVEKGKSKKLKSVKELLGITIMERSS
FEKNPIDFLEAKGYKEVKKDLIIKLPKYSLFELENGRKRMLASAGELQKGN
```

ELALPSKYVNFLYLASHYEKLKGSPEDNEQKQLFVEQHKHYLDEIIEQISE

FSKRVILADANLDKVLSAYNKHRDKPIREQAENIIHLFTLTNLGAPAAFKY

FDTTIDRKRYTSTKEVLDATLIHQSITGLYETRIDLSQLGGD*

Provided below is an exemplary codon optimized nucleic acid sequence encoding a Cas9 molecule of N. meningitidis.

(SEQ ID NO: 24)
ATGGCCGCCTTCAAGCCCAACCCCATCAACTACATCCTGGGCCTGGACATC
GGCATCGCCAGCGTGGGCTGGGCCATGGTGGAGATCGACGAGGACGAGAAC
CCCATCTGCCTGATCGACCTGGGTGTGCGCGTGTTCGAGCGCGCTGAGGTG
CCCAAGACTGGTGACAGTCTGGCTATGGCTCGCCGGCTTGCTCGCTCTGTT
CGGCGCCTTACTCGCCGGCGCGCTCACCGCCTTCTGCGCGCTCGCCGCCTG
CTGAAGCGCGAGGGTGTGCTGCAGGCTGCCGACTTCGACGAGAACGGCCTG
ATCAAGAGCCTGCCCAACACTCCTTGGCAGCTGCGCGCTGCCGCTCTGGAC
CGCAAGCTGACTCCTCTGGAGTGGAGCGCCGTGCTGCTGCACCTGATCAAG
CACCGCGGCTACCTGAGCCAGCGCAAGAACGAGGGCGAGACCGCCGACAAG
GAGCTGGGTGCTCTGCTGAAGGGCGTGGCCGACAACGCCCACGCCCTGCAG
ACTGGTGACTTCCGCACTCCTGCTGAGCTGGCCCTGAACAAGTTCGAGAAG
GAGAGCGGCCACATCCGCAACCAGCGCGGCGACTACAGCCACACCTTCAGC
CGCAAGGACCTGCAGGCCGAGCTGATCCTGCTGTTCGAGAAGCAGAAGGAG
TTCGGCAACCCCCACGTGAGCGGCGGCCTGAAGGAGGGCATCGAGACCCTG
CTGATGACCCAGCGCCCCGCCCTGAGCGGCGACGCCGTGCAGAAGATGCTG
GGCCACTGCACCTTCGAGCCAGCCGAGCCCAAGGCCGCCAAGAACACCTAC
ACCGCCGAGCGCTTCATCTGGCTGACCAAGCTGAACAACCTGCGCATCCTG
GAGCAGGGCAGCGAGCGCCCCCTGACCGACACCGAGCGCGCCACCCTGATG
GACGAGCCCTACCGCAAGAGCAAGCTGACCTACGCCCAGGCCCGCAAGCTG
CTGGGTCTGGAGGACACCGCCTTCTTCAAGGGCCTGCGCTACGGCAAGGAC
AACGCCGAGGCCAGCACCCTGATGGAGATGAAGGCCTACCACGCCATCAGC
CGCGCCCTGGAGAAGGAGGGCCTGAAGGACAAGAAGAGTCCTCTGAACCTG
AGCCCCGAGCTGCAGGACGAGATCGGCACCGCCTTCAGCCTGTTCAAGACC
GACGAGGACATCACCGGCCGCCTGAAGGACCGCATCCAGCCCGAGATCCTG
GAGGCCCTGCTGAAGCACATCAGCTTCGACAAGTTCGTGCAGATCAGCCTG
AAGGCCCTGCGCCGCATCGTGCCCCTGATGGAGCAGGGCAAGCGCTACGAC
GAGGCCTGCGCCGAGATCTACGGCGACCACTACGGCAAGAAGAACACCGAG
GAGAAGATCTACCTGCCTCCTATCCCCGCCGACGAGATCCGCAACCCCGTG
GTGCTGCGCGCCCTGAGCCAGGCCCGCAAGGTGATCAACGGCGTGGTGCGC
CGCTACGGCAGCCCCGCCCGCATCCACATCGAGACCGCCCGCGAGGTGGGC
AAGAGCTTCAAGGACCGCAAGGAGATCGAGAAGCGCCAGGAGGAGAACCGC
AAGGACCGCGAGAAGGCCGCCGCCAAGTTCCGCGAGTACTTCCCCAACTTC
GTGGGCGAGCCCAAGAGCAAGGACATCCTGAAGCTGCGCCTGTACGAGCAG
CAGCACGGCAAGTGCCTGTACAGCGGCAAGGAGATCAACCTGGGCCGCCTG

AACGAGAAGGGCTACGTGGAGATCGACCACGCCCTGCCCTTCAGCCGCACC
TGGGACGACAGCTTCAACAACAAGGTGCTGGTGCTGGGCAGCGAGAACCAG
AACAAGGGCAACCAGACCCCCTACGAGTACTTCAACGGCAAGGACAACAGC
CGCGAGTGGCAGGAGTTCAAGGCCCGCGTGGAGACCAGCCGCTTCCCCCGC
AGCAAGAAGCAGCGCATCCTGCTGCAGAAGTTCGACGAGGACGGCTTCAAG
GAGCGCAACCTGAACGACACCCGCTACGTGAACCGCTTCCTGTGCCAGTTC
GTGGCCGACCGCATGCGCCTGACCGGCAAGGGCAAGAAGCGCGTGTTCGCC
AGCAACGGCCAGATCACCAACCTGCTGCGCGGCTTCTGGGGCCTGCGCAAG
GTGCGCGCCGAGAACGACCGCCACCACGCCCTGGACGCCGTGGTGGTGGCC
TGCAGCACCGTGGCCATGCAGCAGAAGATCACCCGCTTCGTGCGCTACAAG
GAGATGAACGCCTTCGACGGTAAAACCATCGACAAGGAGACCGGCGAGGTG
CTGCACCAGAAGACCCACTTCCCCCAGCCCTGGGAGTTCTTCGCCCAGGAG
GTGATGATCCGCGTGTTCGGCAAGCCCGACGGCAAGCCCGAGTTCGAGGAG
GCCGACACCCCCGAGAAGCTGCGCACCCTGCTGGCCGAGAAGCTGAGCAGC
CGCCCTGAGGCCGTGCACGAGTACGTGACTCCTCTGTTCGTGAGCCGCGCC
CCCAACCGCAAGATGAGCGGTCAGGGTCACATGGAGACCGTGAAGAGCGCC
AAGCGCCTGGACGAGGGCGTGAGCGTGCTGCGCGTGCCCCTGACCCAGCTG
AAGCTGAAGGACCTGGAGAAGATGGTGAACCGCGAGCGCGAGCCCAAGCTG
TACGAGGCCCTGAAGGCCCGCCTGGAGGCCCACAAGGACGACCCCGCCAAG
GCCTTCGCCGAGCCCTTCTACAAGTACGACAAGGCCGGCAACCGCACCCAG
CAGGTGAAGGCCGTGCGCGTGGAGCAGGTGCAGAAGACCGGCGTGTGGGTG
CGCAACCACAACGGCATCGCCGACAACGCCACCATGGTGCGCGTGGACGTG
TTCGAGAAGGGCGACAAGTACTACCTGGTGCCCATCTACAGCTGGCAGGTG
GCCAAGGGCATCCTGCCCGACCGCGCCGTGGTGCAGGGCAAGGACGAGGAG
GACTGGCAGCTGATCGACGACAGCTTCAACTTCAAGTTCAGCCTGCACCCC
AACGACCTGGTGGAGGTGATCACCAAGAAGGCCCGCATGTTCGGCTACTTC
GCCAGCTGCCACCGCGGCACCGGCAACATCAACATCCGCATCCACGACCTG
GACCACAAGATCGGCAAGAACGGCATCCTGGAGGGCATCGGCGTGAAGACC
GCCCTGAGCTTCCAGAAGTACCAGATCGACGAGCTGGGCAAGGAGATCCGC
CCCTGCCGCCTGAAGAAGCGCCCTCCTGTGCGCTAA

Provided below is the corresponding amino acid sequence of a N. meningitidis Cas9 molecule.

(SEQ ID NO: 25)
MAAFKPNPINYILGLDIGIASVGWAMVEIDEDENPICLIDLGVRVFERAEV

PKTGDSLAMARRLARSVRRLTRRRAHRLLRARRLLKREGVLQAADFDENGL

IKSLPNTPWQLRAAALDRKLTPLEWSAVLLHLIKHRGYLSQRKNEGETADK

ELGALLKGVADNAHALQTGDFRTPAELALNKFEKESGHIRNQRGDYSHTFS

RKDLQAELILLFEKQKEFGNPHVSGGLKEGIETLLMTQRPALSGDAVQKML

GHCTFEPAEPKAAKNTYAERFIWLTKLNNLRILEQGSERPLTDTERATLM

DEPYRKSKLTYAQARKLLGLEDTAFFKGLRYGKDNAEASTLMEMKAYHAIS

RALEKEGLKDKKSPLNLSPELQDEIGTAFSLFKTDEDITGRLKDRIQPEIL

-continued

```
EALLKHISFDKFVQISLKALRRIVPLMEQGKRYDEACAEIYGDHYGKKNTE

EKIYLPPIPADEIRNPVVLRALSQARKVINGVVRRYGSPARIHIETAREVG

KSFKDRKEIEKRQEENRKDREKAAAKFREYFPNFVGEPKSKDILKLRLYEQ

QHGKCLYSGKEINLGRLNEKGYVEIDHALPFSRTWDDSFNNKVLVLGSENQ

NKGNQTPYEYFNGKDNSREWQEFKARVETSRFPRSKKQRILLQKFDEDGFK

ERNLNDTRYVNRFLCQFVADRMRLTGKGKKRVFASNGQITNLLRGFWGLRK

VRAENDRHHALDAVVVACSTVAMQQKITRFVRYKEMNAFDGKTIDKETGEV

LHQKTHFPQPWEFFAQEVMIRVFGKPDGKPEFEEADTPEKLRTLLAEKLSS

RPEAVHEYVTPLFVSRAPNRKMSGQGHMETVKSAKRLDEGVSVLRVPLTQL

KLKDLEKMVNREREPKLYEALKARLEAHKDDPAKAFAEPFYKYDKAGNRTQ

QVKAVRVEQVQKTGVWVRNHNGIADNATMVRVDVFEKGDKYYLVPIYSWQV

AKGILPDRAVVQGKDEEDWQLIDDSFNFKFSLHPNDLVEVITKKARMFGYF

ASCHRGTGNINIRIHDLDHKIGKNGILEGIGVKTALSFQKYQIDELGKEIR

PCRLKKRPPVR*
```

Provided below is an amino acid sequence of a *S. aureus* Cas9 molecule.

```
                                        (SEQ ID NO: 26)
MKRNYILGLDIGITSVGYGIIDYETRDVIDAGVRLFKEANVENNEGRRSKR

GARRLKRRRHRIQRVKKLLFDYNLLTDHSELSGINPYEARVKGLSQKLSE

EEFSAALLHLAKRRGVHNVNEVEEDTGNELSTKEQISRNSKALEEKYVAEL

QLERLKKDGEVRGSINRFKTSDYVKEAKQLLKVQKAYHQLDQSFIDTYIDL

LETRRTYYEGPGEGSPFGWKDIKEWYEMLMGHCTYFPEELRSVKYAYNADL

YNALNDLNNLVITRDENEKLEYYEKFQIIENVFKQKKKPTLKQIAKEILVN

EEDIKGYRVTSTGKPEFTNLKVYHDIKDITARKEIIENAELLDQIAKILTI

YQSSEDIQEELTNLNSELTQEEIEQISNLKGYTGTHNLSLKAINLILDELW

HTNDNQIAIFNRLKLVPKKVDLSQQKEIPTTLVDDFILSPVVKRSFIQSIK

VINAIIKKYGLPNDIIIELAREKNSKDAQKMINEMQKRNRQTNERIEEIIR

TTGKENAKYLIEKIKLHDMQEGKCLYSLEAIPLEDLLNNPFNYEVDHIIPR

SVSFDNSFNNKVLVKQEENSKKGNRTPFQYLSSSDSKISYETFKKHILNLA

KGKGRISKTKKEYLLEERDINRFSVQKDFINRNLVDTRYATRGLMNLLRSY

FRVNNLDVKVKSINGGFTSFLRRKWKFKKERNKGYKHHAEDALIIANADFI

FKEWKKLDKAKKVMENQMFEEKQAESMPEIETEQEYKEIFITPHQIKHIKD

FKDYKYSHRVDKKPNRELINDTLYSTRKDDKGNTLIVNNLNGLYDKDNDKL

KKLINKSPEKLLMYHHDPQTYQKLKLIMEQYGDEKNPLYKYYEETGNYLTK

YSKKDNGPVIKKIKYYGNKLNAHLDITDDYPNSRNKVVKLSLKPYRFDVYL

DNGVYKFVTVKNLDVIKKENYYEVNSKCYEEAKKLKKISNQAEFIASFYNN

DLIKINGELYRVIGVNNDLLNRIEVNMIDITYREYLENMNDKRPPRIIKTI

ASKTQSIKKYSTDILGNLYEVKSKKHPQIIKKG*
```

If any of the above Cas9 sequences are fused with a peptide or polypeptide at the C-terminus (e.g., an eiCas9 fused with a transcripon repressor at the C-terminus), it is understood that the stop codon will be removed.

Other Cas Molecules

Various types of Cas molecules can be used to practice the inventions disclosed herein. In an embodiment, Cas molecules of Type II Cas systems are used. In an embodiment, Cas molecules of other Cas systems are used. For example, Type I or Type III Cas molecules may be used. Exemplary Cas molecules (and Cas systems) are described, e.g., in Haft et al., PLoS COMPUTATIONAL BIOLOGY 2005, 1(6): e60 and Makarova et al., NATURE REVIEW MICROBIOLOGY 2011, 9:467-477, the contents of both references are incorporated herein by reference in their entirety. Exemplary Cas molecules (and Cas systems) are also shown in Table II-1.

TABLE II-1

| | Cas Systems | | | | |
|---|---|---|---|---|---|
| Gene name‡ | System type or subtype | Name from Haft et al.§ | Structure of encoded protein (PDB accessions)¶ | Families (and superfamily) of encoded protein#** | Representatives |
| cas1 | Type I<br>Type II<br>Type III | cas1 | 3GOD, 3LFX and 2YZS | COG1518 | SERP2463, SPy1047 and ygbT |
| cas2 | Type I<br>Type II<br>Type III | cas2 | 2IVY, 2I8E and 3EXC | COG1343 and COG3512 | SERP2462, SPy1048, SPy1723 (N-terminal domain) and ygbF |
| cas3' | Type I‡‡ | cas3 | NA | COG1203 | APE1232 and ygcB |
| cas3" | Subtype I-A<br>Subtype I-B | NA | NA | COG2254 | APE1231 and BH0336 |
| cas4 | Subtype I-A<br>Subtype I-B<br>Subtype I-C<br>Subtype | cas4 and csa1 | NA | COG1468 | APE1239 and BH0340 |

TABLE II-1-continued

Cas Systems

| Gene name[‡] | System type or subtype | Name from Haft et al.[§] | Structure of encoded protein (PDB accessions)[¶] | Families (and superfamily) of encoded protein[#**] | Representatives |
|---|---|---|---|---|---|
| | I-D Subtype II-B | | | | |
| cas5 | Subtype I-A Subtype I-B Subtype I-C Subtype I-E | cas5a, cas5d, cas5e, cas5h, cas5p, cas5t and cmx5 | 3KG4 | COG1688 (RAMP) | APE1234, BH0337, devS and ygcI |
| cas6 | Subtype I-A Subtype I-B Subtype I-D Subtype III-A Subtype III-B | cas6 and cmx6 | 3I4H | COG1583 and COG5551 (RAMP) | PF1131 and slr7014 |
| cas6e | Subtype I-E | cse3 | 1WJ9 | (RAMP) | ygcH |
| cas6f | Subtype I-F | csy4 | 2XLJ | (RAMP) | y1727 |
| cas7 | Subtype I-A Subtype I-B Subtype I-C Subtype I-E | csa2, csd2, cse4, csh2, csp1 and cst2 | NA | COG1857 and COG3649 (RAMP) | devR and ygcJ |
| cas8a1 | Subtype I-A[‡‡] | cmx1, cst1, csx8, csx13 and CXXC-CXXC | NA | BH0338-like | LA3191[§§] and PG2018[§§] |
| cas8a2 | Subtype I-A[‡‡] | csa4 and csx9 | NA | PH0918 | AF0070, AF1873, MJ0385, PF0637, PH0918 and SSO1401 |
| cas8b | Subtype I-B[‡‡] | csh1 and TM1802 | NA | BH0338-like | MTH1090 and TM1802 |
| cas8c | Subtype I-C[‡‡] | csd1 and csp2 | NA | BH0338-like | BH0338 |
| cas9 | Type II[‡‡] | csn1 and csx12 | NA | COG3513 | FTN_0757 and SPy1046 |
| cas10 | Type III[‡‡] | cmr2, csm1 and csx11 | NA | COG1353 | MTH326, Rv2823c[§§] and TM1794[§§] |
| cas10d | Subtype I-D[‡‡] | csc3 | NA | COG1353 | slr7011 |
| csy1 | Subtype I-F[‡‡] | csy1 | NA | y1724-like | y1724 |
| csy2 | Subtype I-F | csy2 | NA | (RAMP) | y1725 |
| csy3 | Subtype I-F | csy3 | NA | (RAMP) | y1726 |
| cse1 | Subtype I-E[‡‡] | cse1 | NA | YgcL-like | ygcL |
| cse2 | Subtype I-E | cse2 | 2ZCA | YgcK-like | ygcK |
| csc1 | Subtype I-D | csc1 | NA | Alr1563-like (RAMP) | alr1563 |
| csc2 | Subtype I-D | csc1 and csc2 | NA | COG1337 (RAMP) | slr7012 |
| csa5 | Subtype I-A | csa5 | NA | AF1870 | AF1870, MJ0380, PF0643 and SSO1398 |
| csn2 | Subtype II-A | csn2 | NA | SPy1049-like | SPy1049 |
| csm2 | Subtype III-A[‡‡] | csm2 | NA | COG1421 | MTH1081 and SERP2460 |

TABLE II-1-continued

Cas Systems

| Gene name‡ | System type or subtype | Name from Haft et al.§ | Structure of encoded protein (PDB accessions)¶ | Families (and superfamily) of encoded protein#** | Representatives |
|---|---|---|---|---|---|
| csm3 | Subtype III-A | csc2 and csm3 | NA | COG1337 (RAMP) | MTH1080 and SERP2459 |
| csm4 | Subtype III-A | csm4 | NA | COG1567 (RAMP) | MTH1079 and SERP2458 |
| csm5 | Subtype III-A | csm5 | NA | COG1332 (RAMP) | MTH1078 and SERP2457 |
| csm6 | Subtype III-A | APE2256 and csm6 | 2WTE | COG1517 | APE2256 and SSO1445 |
| cmr1 | Subtype III-B | cmr1 | NA | COG1367 (RAMP) | PF1130 |
| cmr3 | Subtype III-B | cmr3 | NA | COG1769 (RAMP) | PF1128 |
| cmr4 | Subtype III-B | cmr4 | NA | COG1336 (RAMP) | PF1126 |
| cmr5 | Subtype III-B‡‡ | cmr5 | 2ZOP and 2OEB | COG3337 | MTH324 and PF1125 |
| cmr6 | Subtype III-B | cmr6 | NA | COG1604 (RAMP) | PF1124 |
| csb1 | Subtype I-U | GSU0053 | NA | (RAMP) | Balac_1306 and GSU0053 |
| csb2 | Subtype I-U§§ | NA | NA | (RAMP) | Balac_1305 and GSU0054 |
| csb3 | Subtype I-U | NA | NA | (RAMP) | Balac_1303§§ |
| csx17 | Subtype I-U | NA | NA | NA | Btus_2683 |
| csx14 | Subtype I-U | NA | NA | NA | GSU0052 |
| csx10 | Subtype I-U | csx10 | NA | (RAMP) | Caur_2274 |
| csx16 | Subtype III-U | VVA1548 | NA | NA | VVA1548 |
| csaX | Subtype III-U | csaX | NA | NA | SSO1438 |
| csx3 | Subtype III-U | csx3 | NA | NA | AF1864 |
| csx1 | Subtype III-U | csa3, csx1, csx2, DXTHG, NE0113 and TIGR02710 | 1XMX and 2I71 | COG1517 and COG4006 | MJ1666, NE0113, PF1127 and TM1812 |
| csx15 | Unknown | NA | NA | TTE2665 | TTE2665 |
| csf1 | Type U | csf1 | NA | NA | AFE_1038 |
| csf2 | Type U | csf2 | NA | (RAMP) | AFE_1039 |
| csf3 | Type U | csf3 | NA | (RAMP) | AFE_1040 |
| csf4 | Type U | csf4 | NA | NA | AFE_1037 |

III. Functional Analysis of Candidate Molecules

Candidate Cas9 molecules, candidate gRNA molecules, candidate Cas9 molecule/gRNA molecule complexes, can be evaluated by art-known methods or as described herein. For example, exemplary methods for evaluating the endonuclease activity of Cas9 molecule are described, e.g., in Jinek et al., SCIENCE 2012; 337(6096):816-821.

Binding and Cleavage Assay: Testing the Endonuclease Activity of Cas9 Molecule

The ability of a Cas9 molecule/gRNA molecule complex to bind to and cleave a target nucleic acid can be evaluated in a plasmid cleavage assay. In this assay, synthetic or in vitro-transcribed gRNA molecule is pre-annealed prior to the reaction by heating to 95° C. and slowly cooling down to room temperature. Native or restriction digest-linearized plasmid DNA (300 ng (~8 nM)) is incubated for 60 min at 37° C. with purified Cas9 protein molecule (50-500 nM) and gRNA (50-500 nM, 1:1) in a Cas9 plasmid cleavage buffer (20 mM HEPES pH 7.5, 150 mM KCl, 0.5 mM DTT, 0.1 mM EDTA) with or without 10 mM $MgCl_2$. The reactions are stopped with 5×DNA loading buffer (30% glycerol, 1.2% SDS, 250 mM EDTA), resolved by a 0.8 or 1% agarose gel electrophoresis and visualized by ethidium bromide staining. The resulting cleavage products indicate whether the Cas9 molecule cleaves both DNA strands, or only one of the two strands. For example, linear DNA products indicate the cleavage of both DNA strands. Nicked open circular products indicate that only one of the two strands is cleaved.

Alternatively, the ability of a Cas9 molecule/gRNA molecule complex to bind to and cleave a target nucleic acid can be evaluated in an oligonucleotide DNA cleavage assay. In this assay, DNA oligonucleotides (10 pmol) are radiolabeled by incubating with 5 units T4 polynucleotide kinase and ~3-6 pmol (~20-40 mCi) [γ-32P]-ATP in 1×T4 polynucleotide kinase reaction buffer at 37° C. for 30 min, in a 50 µL reaction. After heat inactivation (65° C. for 20 min), reactions are purified through a column to remove unincorporated label. Duplex substrates (100 nM) are generated by annealing labeled oligonucleotides with equimolar amounts of unlabeled complementary oligonucleotide at 95° C. for 3 min, followed by slow cooling to room temperature. For cleavage assays, gRNA molecules are annealed by heating to 95° C. for 30 s, followed by slow cooling to room temperature. Cas9 (500 nM final concentration) is pre-incubated with the annealed gRNA molecules (500 nM) in cleavage assay buffer (20 mM HEPES pH 7.5, 100 mM KCl, 5 mM MgCl2, 1 mM DTT, 5% glycerol) in a total volume of 9 µl. Reactions are initiated by the addition of 1 µl target DNA (10 nM) and incubated for 1 h at 37° C. Reactions are quenched by the addition of 20 µl of loading dye (5 mM EDTA, 0.025% SDS, 5% glycerol in formamide) and heated to 95° C. for 5 min. Cleavage products are resolved on 12% denaturing polyacrylamide gels containing 7 M urea and visualized by phosphorimaging. The resulting cleavage products indicate that whether the complementary strand, the non-complementary strand, or both, are cleaved.

One or both of these assays can be used to evaluate the suitability of a candidate gRNA molecule or candidate Cas9 molecule.

Binding Assay: Testing the Binding of Cas9 Molecule to Target DNA

Exemplary methods for evaluating the binding of Cas9 molecule to target DNA are described, e.g., in Jinek et al., SCIENCE 2012; 337(6096):816-821.

For example, in an electrophoretic mobility shift assay, target DNA duplexes are formed by mixing of each strand (10 nmol) in deionized water, heating to 95° C. for 3 min and slow cooling to room temperature. All DNAs are purified on 8% native gels containing 1×TBE. DNA bands are visualized by UV shadowing, excised, and eluted by soaking gel pieces in DEPC-treated H$_2$O. Eluted DNA is ethanol precipitated and dissolved in DEPC-treated H$_2$O. DNA samples are 5' end labeled with [γ-32P]-ATP using T4 polynucleotide kinase for 30 min at 37° C. Polynucleotide kinase is heat denatured at 65° C. for 20 min, and unincorporated radiolabel is removed using a column. Binding assays are performed in buffer containing 20 mM HEPES pH 7.5, 100 mM KCl, 5 mM MgCl$_2$, 1 mM DTT and 10% glycerol in a total volume of 10 µl. Cas9 protein molecule is programmed with equimolar amounts of pre-annealed gRNA molecule and titrated from 100 pM to 1 µM. Radiolabeled DNA is added to a final concentration of 20 pM. Samples are incubated for 1 h at 37° C. and resolved at 4° C. on an 8% native polyacrylamide gel containing 1×TBE and 5 mM MgCl$_2$. Gels are dried and DNA visualized by phosphorimaging.

IV. Template Nucleic Acids (Genome Editing Approaches)

The terms "template nucleic acid" and "swap nucleic acid" are used interchangeably and have identical meaning in this document and its priority documents.

Mutations in a gene or pathway described herein, e.g., in Section VIIB, e.g., in Table VII-13, VII-14, VII-15, VII-16, VII-17, VII-18, VII-19, VII-20, VII-21, VII-22, VII-23, VII-24, IX-1, IX-1A, IX-3, or XII-1, or in Section VIII, may be corrected using one of the approaches discussed herein. In an embodiment, a mutation in a gene or pathway described herein, e.g., in Section VIIB, e.g., in Table VII-13, VH-14, VII-15, VH-16, VH-17, VII-18, VII-19, VII-20, VII-21, VII-22, VII-23, VII-24, IX-1, IX-1A, IX-3, or XII-1, or in Section VIII, is corrected by homology directed repair (HDR) using a template nucleic acid (see Section IV.1). In an embodiment, a mutation in a gene or pathway described herein, e.g., in Section VIIB, e.g., in Table VII-13, VII-14, VH-15, VII-16, VII-17, VH-18, VII-19, VII-20, VII-21, VII-22, VII-23, VII-24, IX-1, IX-1A, IX-3, or XII-1, or in Section VIII, is corrected by Non-Homologous End Joining (NHEJ) repair using a template nucleic acid (see Section IV.2).

IV.1 HDR Repair and Template Nucleic Acids

As described herein, nuclease-induced homology directed repair (HDR) can be used to alter a target sequence and correct (e.g., repair or edit) a mutation in the genome. While not wishing to be bound by theory, it is believed that alteration of the target sequence occurs by homology-directed repair (HDR) with a donor template or template nucleic acid. For example, the donor template or the template nucleic acid provides for alteration of the target sequence. It is contemplated that a plasmid donor can be used as a template for homologous recombination. It is further contemplated that a single stranded donor template can be used as a template for alteration of the target sequence by alternate methods of homology directed repair (e.g., single strand annealing) between the target sequence and the donor template. Donor template-effected alteration of a target sequence depends on cleavage by a Cas9 molecule. Cleavage by Cas9 can comprise a double strand break or two single strand breaks.

In an embodiment, a mutation can be corrected by either a single double-strand break or two single strand breaks. In an embodiment, a mutation can be corrected by (1) a single double-strand break, (2) two single strand breaks, (3) two double stranded breaks with a break occurring on each side of the target sequence, (4) one double stranded breaks and two single strand breaks with the double strand break and two single strand breaks occurring on each side of the target sequence or (5) four single stranded breaks with a pair of single stranded breaks occurring on each side of the target sequence.

Double Strand Break Mediated Correction

In an embodiment, double strand cleavage is effected by a Cas9 molecule having cleavage activity associated with an HNH-like domain and cleavage activity associated with a RuvC-like domain, e.g., an N-terminal RuvC-like domain, e.g., a wild type Cas9. Such an embodiment requires only a single gRNA.

Single Strand Break Mediated Correction

In an embodiment, two single strand breaks, or nicks, are effected by a Cas9 molecule having nickase activity, e.g., cleavage activity associated with an HNH-like domain or cleavage activity associated with an N-terminal RuvC-like domain. Such an embodiment requires two gRNAs, one for placement of each single strand break. In an embodiment, the Cas9 molecule having nickase activity cleaves the strand to which the gRNA hybridizes, but not the strand that is complementary to the strand to which the gRNA hybridizes. In an embodiment, the Cas9 molecule having nickase activity does not cleave the strand to which the gRNA hybridizes, but rather cleaves the strand that is complementary to the strand to which the gRNA hybridizes.

In an embodiment, the nickase has HNH activity, e.g., a Cas9 molecule having the RuvC activity inactivated, e.g., a Cas9 molecule having a mutation at D10, e.g., the D10A mutation. D10A inactivates RuvC; therefore, the Cas9 nickase has (only) HNH activity and will cut on the strand to which the gRNA hybridizes (e.g., the complementary strand, which does not have the NGG PAM on it). In an embodiment, a Cas9 molecule having an H840, e.g., an H840A, mutation can be used as a nickase. H840A inactivates HNH; therefore, the Cas9 nickase has (only) RuvC activity and cuts on the non-complementary strand (e.g., the strand that has the NGG PAM and whose sequence is identical to the gRNA).

In an embodiment, in which a nickase and two gRNAs are used to position two single strand nicks, one nick is on the + strand and one nick is on the − strand of the target nucleic acid. The PAMs are outwardly facing. The gRNAs can be selected such that the gRNAs are separated by, from about 0-50, 0-100, or 0-200 nucleotides. In an embodiment, there is no overlap between the target sequence that is complementary to the targeting domains of the two gRNAs. In an embodiment, the gRNAs do not overlap and are separated by as much as 50, 100, or 200 nucleotides. In an embodiment, the use of two gRNAs can increase specificity, e.g., by decreasing off-target binding (Ran et al., CELL 2013).

In an embodiment, a single nick can be used to induce HDR. It is contemplated herein that a single nick can be used to increase the ratio of HR to NHEJ at a given cleavage site.

Placement of the Double Strand Break or a Single Strand Break Relative to Target Position The double strand break or single strand break in one of the strands should be sufficiently close to target position such that correction occurs. In an embodiment, the distance is not more than 50, 100, 200, 300, 350 or 400 nucleotides. While not wishing to be bound by theory, it is believed that the break should be sufficiently close to target position such that the break is within the region that is subject to exonuclease-mediated removal during end resection. If the distance between the target position and a break is too great, the mutation may not be included in the end resection and, therefore, may not be corrected, as donor sequence may only be used to correct sequence within the end resection region.

In an embodiment, in which a gRNA (unimolecular (or chimeric) or modular gRNA) and Cas9 nuclease induce a double strand break for the purpose of inducing HDR-mediated correction, the cleavage site is between 0-200 bp (e.g., 0 to 175, 0 to 150, 0 to 125, 0 to 100, 0 to 75, 0 to 50, 0 to 25, 25 to 200, 25 to 175, 25 to 150, 25 to 125, 25 to 100, 25 to 75, 25 to 50, 50 to 200, 50 to 175, 50 to 150, 50 to 125, 50 to 100, 50 to 75, 75 to 200, 75 to 175, 75 to 150, 75 to 125, 75 to 100 bp) away from the target position. In an embodiment, the cleavage site is between 0-100 bp (e.g., 0 to 75, 0 to 50, 0 to 25, 25 to 100, 25 to 75, 25 to 50, 50 to 100, 50 to 75 or 75 to 100 bp) away from the target position.

In an embodiment, in which two gRNAs (independently, unimolecular (or chimeric) or modular gRNA) complexing with Cas9 nickases induce two single strand breaks for the purpose of inducing HDR-mediated correction, the closer nick is between 0-200 bp (e.g., 0 to 175, 0 to 150, 0 to 125, 0 to 100, 0 to 75, 0 to 50, 0 to 25, 25 to 200, 25 to 175, 25 to 150, 25 to 125, 25 to 100, 25 to 75, 25 to 50, 50 to 200, 50 to 175, 50 to 150, 50 to 125, 50 to 100, 50 to 75, 75 to 200, 75 to 175, 75 to 150, 75 to 125, 75 to 100 bp) away from the target position and the two nicks will ideally be within 25-55 bp of each other (e.g., 25 to 50, 25 to 45, 25 to 40, 25 to 35, 25 to 30, 30 to 55, 30 to 50, 30 to 45, 30 to 40, 30 to 35, 35 to 55, 35 to 50, 35 to 45, 35 to 40, 40 to 55, 40 to 50, 40 to 45 bp) and no more than 100 bp away from each other (e.g., no more than 90, 80, 70, 60, 50, 40, 30, 20, 10 or 5 bp away from each other). In an embodiment, the cleavage site is between 0-100 bp (e.g., 0 to 75, 0 to 50, 0 to 25, 25 to 100, 25 to 75, 25 to 50, 50 to 100, 50 to 75 or 75 to 100 bp) away from the target position.

In one embodiment, two gRNAs, e.g., independently, unimolecular (or chimeric) or modular gRNA, are configured to position a double-strand break on both sides of a target position. In an alternate embodiment, three gRNAs, e.g., independently, unimolecular (or chimeric) or modular gRNA, are configured to position a double strand break (i.e., one gRNA complexes with a cas9 nuclease) and two single strand breaks or paired single stranded breaks (i.e., two gRNAs complex with Cas9 nickases) on either side of the target position (e.g., the first gRNA is used to target upstream (i.e., 5') of the target position and the second gRNA is used to target downstream (i.e., 3') of the target position). In another embodiment, four gRNAs, e.g., independently, unimolecular (or chimeric) or modular gRNA, are configured to generate two pairs of single stranded breaks (i.e., two pairs of two gRNAs complex with Cas9 nickases) on either side of the target position (e.g., the first gRNA is used to target upstream (i.e., 5') of the target position and the second gRNA is used to target downstream (i.e., 3') of the target position). The double strand break(s) or the closer of the two single strand nicks in a pair will ideally be within 0-500 bp of the target position (e.g., no more than 450, 400, 350, 300, 250, 200, 150, 100, 50 or 25 bp from the target position). When nickases are used, the two nicks in a pair are within 25-55 bp of each other (e.g., between 25 to 50, 25 to 45, 25 to 40, 25 to 35, 25 to 30, 50 to 55, 45 to 55, 40 to 55, 35 to 55, 30 to 55, 30 to 50, 35 to 50, 40 to 50, 45 to 50, 35 to 45, or 40 to 45 bp) and no more than 100 bp away from each other (e.g., no more than 90, 80, 70, 60, 50, 40, 30, 20 or 10 bp).

In one embodiment, two gRNAs, e.g., independently, unimolecular (or chimeric) or modular gRNA, are configured to position a double-strand break on both sides of a target position. In an alternate embodiment, three gRNAs, e.g., independently, unimolecular (or chimeric) or modular gRNA, are configured to position a double strand break (i.e., one gRNA complexes with a cas9 nuclease) and two single strand breaks or paired single stranded breaks (i.e., two gRNAs complex with Cas9 nickases) on either side of the target position (e.g., the first gRNA is used to target upstream (i.e., 5') of the mutation in a gene or pathway described herein, e.g., in Section VIIB, e.g., in Table VII-13, VII-14, VII-15, VII-16, VII-17, VII-18, VII-19, VII-20, VII-21, VII-22, VII-23, VII-24, IX-1, IX-1A, IX-3, or XII-1, or in Section VIII and the second gRNA is used to target downstream (i.e., 3') of the mutation in a gene or pathway described herein, e.g., in Section VIIB, e.g., in Table VII-13, VII-14, VII-15, VII-16, VII-17, VII-18, VII-19, VII-20, VII-21, VII-22, VII-23, VII-24, IX-1, IX-1A, IX-3, or XII-1, or in Section VIII). In another embodiment, four gRNAs, e.g., independently, unimolecular (or chimeric) or modular gRNA, are configured to generate two pairs of single stranded breaks (i.e., two pairs of two gRNAs complex with Cas9 nickases) on either side of the target position (e.g., the first gRNA is used to target upstream (i.e., 5') of the mutation in a gene or pathway described herein, and the second gRNA is used to target downstream (i.e., 3') of the mutation in a gene or pathway described herein). The double strand break(s) or the closer of the two single strand nicks in a pair will ideally be within 0-500 bp of the target position (e.g., no more than 450, 400, 350, 300, 250, 200, 150, 100, 50 or 25 bp from the target position). When nickases are used, the two nicks in a pair are within 25-55 bp of each other (e.g., between 25 to 50, 25 to 45, 25 to 40, 25 to 35, 25 to 30, 50 to 55, 45 to 55, 40 to 55, 35 to 55, 30 to 55, 30 to 50, 35 to 50, 40 to 50, 45 to 50, 35 to 45, or 40 to 45 bp) and no more than 100 bp away from each other (e.g., no more than 90, 80, 70, 60, 50, 40, 30, 20 or 10 bp).

Length of the Homology Arms

The homology arm should extend at least as far as the region in which end resection may occur, e.g., in order to allow the resected single stranded overhang to find a complementary region within the donor template. The overall length could be limited by parameters such as plasmid size or viral packaging limits. In an embodiment, a homology arm does not extend into repeated elements, e.g., ALU repeats, LINE repeats.

Exemplary homology arm lengths include a least 50, 100, 250, 500, 750 or 1000 nucleotides.

Target position, as used herein, refers to a site on a target nucleic acid (e.g., the chromosome) that is modified by a Cas9 molecule-dependent process. For example, the target position can be a modified Cas9 molecule cleavage of the target nucleic acid and template nucleic acid directed modification, e.g., correction, of the target position. In an embodiment, a target position can be a site between two nucleotides, e.g., adjacent nucleotides, on the target nucleic acid into which one or more nucleotides is added. The target position may comprise one or more nucleotides that are altered, e.g., corrected, by a template nucleic acid. In an embodiment, the target position is within a target sequence (e.g., the sequence to which the gRNA binds). In an embodiment, a target position is upstream or downstream of a target sequence (e.g., the sequence to which the gRNA binds).

A template nucleic acid, as that term is used herein, refers to a nucleic acid sequence which can be used in conjunction with a Cas9 molecule and a gRNA molecule to alter the structure of a target position. The term "template nucleic acid" is synonymous with the term "swap nucleic acid" used in the priority document and herein. The terms "template nucleic acid" and "swap nucleic acid" have exactly the same meaning and can be used interchangeably. In an embodiment, the target nucleic acid is modified to have some or all of the sequence of the template nucleic acid, typically at or near cleavage site(s). In an embodiment, the template nucleic acid is single stranded. In an alternate embodiment, the tempolate nuceic acid is double stranded. In an embodiment, the template nucleic acid is DNA, e.g., double stranded DNA. In an alternate embodiment, the template nucleic acid is single stranded DNA.

In an embodiment, the template nucleic acid alters the structure of the target position by participating in a homology directed repair event. In an embodiment, the template nucleic acid alters the sequence of the target position. In an embodiment, the template nucleic acid results in the incorporation of a modified, or non-naturally occurring, nucleotide into the target nucleic acid.

Typically, the template sequence undergoes a breakage mediated or catalyzed recombination with the target sequence. In an embodiment, the template nucleic acid includes sequence that corresponds to a site on the target sequence that is cleaved by an eaCas9 mediated cleavage event. In an embodiment, the template nucleic acid includes sequence that corresponds to both, a first site on the target sequence that is cleaved in a first Cas9 mediated event, and a second site on the target sequence that is cleaved in a second Cas9 mediated event.

In an embodiment, the template nucleic acid can include sequence which results in an alteration in the coding sequence of a translated sequence, e.g., one which results in the substitution of one amino acid for another in a protein product, e.g., transforming a mutant allele into a wild type allele, transforming a wild type allele into a mutant allele, and/or introducing a stop codon, insertion of an amino acid residue, deletion of an amino acid residue, or a nonsense mutation.

In an embodiment, the template nucleic acid can include sequence which results in an alteration in a non-coding sequence, e.g., an alteration in an exon or in a 5' or 3' non-translated or non-transcribed region. Such alterations include an alteration in a control element, e.g., a promoter, enhancer, and an alteration in a cis-acting or trans-acting control element.

A template nucleic acid having homology with a target position in a gene or pathway described herein, e.g., in Section VIIB, e.g., in Table VII-13, VII-14, VII-15, VII-16, VII-17, VII-18, VII-19, VII-20, VII-21, VII-22, VII-23, VII-24, IX-1, IX-1A, IX-3, or XII-1, or in Section VIII, can be used to alter the structure of a target sequence. The template sequence can be used to alter an unwanted structure, e.g., an unwanted or mutant nucleotide.

The template nucleic acid can include sequence which, when integrated, results in:
decreasing the activity of a positive control element;
increasing the activity of a positive control element;
decreasing the activity of a negative control element;
increasing the activity of a negative control element;
decreasing the expression of a gene;
increasing the expression of a gene;
increasing resistance to a disorder or disease;
increasing resistance to viral entry;
correcting a mutation or altering an unwanted amino acid residue conferring, increasing, abolishing or decreasing a biological property of a gene product, e.g., increasing the enzymatic activity of an enzyme, or increasing the ability of a gene product to interact with another molecule.

The template nucleic acid can include sequence which results in:
a change in sequence of 1, 2, 3, 4, 5, 6, 7, 8, 9, 10, 11, 12 or more nucleotides of the target sequence.

In an embodiment, the template nucleic acid is 20+/−10, 30+/−10, 40+/−10, 50+/−10, 60+/−10, 70+/−10, 80+/−10, 90+/−10, 100+/−10, 110+/−10, 120+/−10, 130+/−10, 140+/−10, 150+/−10, 160+/−10, 170+/−10, 180+/−10, 190+/−10, 200+/−10, 210+/−10, of 220+/−10 nucleotides in length.

In an embodiment, the template nucleic acid is 30+/−20, 40+/−20, 50+/−20, 60+/−20, 70+/−20, 80+/−20, 90+/−20, 100+/−20, 110+/−20, 120+/−20, 130+/−20, 140+/−20, 150+/−20, 160+/−20, 170+/−20, 180+/−20, 190+/−20, 200+/−20, 210+/−20, of 220+/−20 nucleotides in length.

In an embodiment, the template nucleic acid is 10 to 1,000, 20 to 900, 30 to 800, 40 to 700, 50 to 600, 50 to 500, 50 to 400, 50 to 300, 50 to 200, or 50 to 100 nucleotides in length.

A template nucleic acid comprises the following components:

[5' homology arm]-[replacement sequence]-[3' homology arm].

The homology arms provide for recombination into the chromosome, thus replacing the undesired element, e.g., a mutation or signature, with the replacement sequence. In an embodiment, the homology arms flank the most distal cleavage sites.

In an embodiment, the 3' end of the 5' homology arm is the position next to the 5' end of the replacement sequence. In an embodiment, the 5' homology arm can extend at least 10, 20, 30, 40, 50, 100, 200, 300, 400, 500, 600, 700, 800, 900, 1000, 1500, or 2000 nucleotides 5' from the 5' end of the replacement sequence.

In an embodiment, the 5' end of the 3' homology arm is the position next to the 3' end of the replacement sequence. In an embodiment, the 3' homology arm can extend at least 10, 20, 30, 40, 50, 100, 200, 300, 400, 500, 600, 700, 800, 900, 1000, 1500, or 2000 nucleotides 3' from the 3' end of the replacement sequence.

It is contemplated herein that one or both homology arms may be shortened to avoid including certain sequence repeat elements, e.g., Alu repeats, LINE elements. For example, a 5' homology arm may be shortened to avoid a sequence repeat element. In an embodiment, a 3' homology arm may be shortened to avoid a sequence repeat element. In an embodiment, both the 5' and the 3' homology arms may be shortened to avoid including certain sequence repeat elements.

It is contemplated herein that template nucleic acids for correcting a mutation may designed for use as a single-stranded oligonucleotide (ssODN). When using a ssODN, 5' and 3' homology arms may range up to about 200 base pairs (bp) in length, e.g., at least 25, 50, 75, 100, 125, 150, 175, or 200 bp in length. Longer homology arms are also contemplated for ssODNs as improvements in oligonucleotide synthesis continue to be made.

In an embodiment, an ssODN may be used to correct a mutation in a gene or pathway described herein, e.g., in Section VIIB, e.g., in Table VII-13, VII-14, VII-15, VII-16, VII-17, VII-18, VII-19, VII-20, VII-21, VII-22, VII-23, VII-24, IX-1, IX-1A, IX-3, or XII-1, or in Section VIII.

IV.2 NHEJ Approaches for Gene Targeting

As Described Herein, Nuclease-Induced Non-Homologous End-Joining (NHEJ) can be Used to target gene-specific knockouts. Nuclease-induced NHEJ can also be used to remove (e.g., delete) sequence in a gene of interest.

While not wishing to be bound by theory, it is believed that, in an embodiment, the genomic alterations associated with the methods described herein rely on nuclease-induced NHEJ and the error-prone nature of the NHEJ repair pathway. NHEJ repairs a double-strand break in the DNA by joining together the two ends; however, generally, the original sequence is restored only if two compatible ends, exactly as they were formed by the double-strand break, are perfectly ligated. The DNA ends of the double-strand break are frequently the subject of enzymatic processing, resulting in the addition or removal of nucleotides, at one or both strands, prior to rejoining of the ends. This results in the presence of insertion and/or deletion (indel) mutations in the DNA sequence at the site of the NHEJ repair. Two-thirds of these mutations typically alter the reading frame and, therefore, produce a non-functional protein. Additionally, mutations that maintain the reading frame, but which insert or delete a significant amount of sequence, can destroy functionality of the protein. This is locus dependent as mutations in critical functional domains are likely less tolerable than mutations in non-critical regions of the protein.

The indel mutations generated by NHEJ are unpredictable in nature; however, at a given break site certain indel sequences are favored and are over represented in the population, likely due to small regions of microhomology. The lengths of deletions can vary widely; most commonly in the 1-50 bp range, but they can easily reach greater than 100-200 bp. Insertions tend to be shorter and often include short duplications of the sequence immediately surrounding the break site. However, it is possible to obtain large insertions, and in these cases, the inserted sequence has often been traced to other regions of the genome or to plasmid DNA present in the cells.

Because NHEJ is a mutagenic process, it can also be used to delete small sequence motifs as long as the generation of a specific final sequence is not required. If a double-strand break is targeted near to a short target sequence, the deletion mutations caused by the NHEJ repair often span, and therefore remove, the unwanted nucleotides. For the deletion of larger DNA segments, introducing two double-strand breaks, one on each side of the sequence, can result in NHEJ between the ends with removal of the entire intervening sequence. Both of these approaches can be used to delete specific DNA sequences; however, the error-prone nature of NHEJ may still produce indel mutations at the site of repair.

Both double strand cleaving eaCas9 molecules and single strand, or nickase, eaCas9 molecules can be used in the methods and compositions described herein to generate NHEJ-mediated indels. NHEJ-mediated indels targeted to the gene, e.g., a coding region, e.g., an early coding region of a gene of interest can be used to knockout (i.e., eliminate expression of) a gene of interest. For example, early coding region of a gene of interest includes sequence immediately following a transcription start site, within a first exon of the coding sequence, or within 500 bp of the transcription start site (e.g., less than 500, 450, 400, 350, 300, 250, 200, 150, 100 or 50 bp).

Placement of Double Strand or Single Strand Breaks Relative to the Target Position In an embodiment, in which a gRNA and Cas9 nuclease generate a double strand break for the purpose of inducing NHEJ-mediated indels, a gRNA, e.g., a unimolecular (or chimeric) or modular gRNA molecule, is configured to position one double-strand break in close proximity to a nucleotide of the target position. In an embodiment, the cleavage site is between 0-500 bp away from the target position (e.g., less than 500, 400, 300, 200, 100, 50, 40, 30, 25, 20, 15, 10, 9, 8, 7, 6, 5, 4, 3, 2 or 1 bp from the target position).

In an embodiment, in which two gRNAs complexing with Cas9 nickases induce two single strand breaks for the purpose of inducing NHEJ-mediated indels, two gRNAs, e.g., independently, unimolecular (or chimeric) or modular gRNA, are configured to position two single-strand breaks to provide for NHEJ repair a nucleotide of the target position. In an embodiment, the gRNAs are configured to position cuts at the same position, or within a few nucleotides of one another, on different strands, essentially mimicking a double strand break. In an embodiment, the closer nick is between 0-30 bp away from the target position (e.g., less than 30, 25, 20, 15, 10, 9, 8, 7, 6, 5, 4, 3, 2 or 1 bp from the target position), and the two nicks are within 25-55 bp of each other (e.g., between 25 to 50, 25 to 45, 25 to 40, 25 to 35, 25 to 30, 50 to 55, 45 to 55, 40 to 55, 35 to 55, 30 to 55, 30 to 50, 35 to 50, 40 to 50, 45 to 50, 35 to 45, or 40 to 45 bp) and no more than 100 bp away from each other (e.g., no more than 90, 80, 70, 60, 50, 40, 30, 20 or 10 bp). In an embodiment, the gRNAs are configured to place a single strand break on either side of a nucleotide of the target position.

Both double strand cleaving eaCas9 molecules and single strand, or nickase, eaCas9 molecules can be used in the methods and compositions described herein to generate breaks both sides of a target position. Double strand or paired single strand breaks may be generated on both sides of a target position (e.g., of a gene or pathway described herein, e.g., in Section VIIB, e.g., in Table VII-13, VII-14, VII-15, VII-16, VII-17, VII-18, VII-19, VII-20, VII-21, VII-22, VII-23, VII-24, IX-1, IX-1A, IX-3, or XII-1, or in Section VIII, to remove the nucleic acid sequence between the two cuts (e.g., the region between the two breaks is deleted). In one embodiment, two gRNAs, e.g., independently, unimolecular (or chimeric) or modular gRNA, are configured to position a double-strand break on both sides of a target position (e.g., the first gRNA is used to target upstream (i.e., 5') of the mutation in a gene or pathway described herein, and the second gRNA is used to target downstream (i.e., 3') of the mutation in a gene or pathway described herein). In an alternate embodiment, three gRNAs, e.g., independently, unimolecular (or chimeric) or modular gRNA, are configured to position a double strand break (i.e., one gRNA complexes with a cas9 nuclease) and two single strand breaks or paired single stranded breaks (i.e., two gRNAs complex with Cas9 nickases) on either side of a target position (e.g., the first gRNA is used to target upstream (i.e., 5') of the mutation in a gene or pathway described herein, and the second gRNA is used to target downstream (i.e., 3') of the mutation in a gene or pathway described herein). In another embodiment, four gRNAs, e.g., independently, unimolecular (or chimeric) or modular gRNA, are configured to generate two pairs of single stranded breaks (i.e., two pairs of two gRNAs complex with Cas9 nickases) on either side of the target position (e.g., the first gRNA is used to target upstream (i.e., 5') of the mutation in a gene or pathway described herein, and the second gRNA is used to target downstream (i.e., 3') of the mutation in a gene or pathway described herein). The double strand break(s) or the closer of the two single strand nicks in a pair will ideally be within 0-500 bp of the target position (e.g., no more than 450, 400, 350, 300, 250, 200, 150, 100, 50 or 25 bp from the target position). When nickases are used, the two nicks in a pair are within 25-55 bp of each other (e.g., between 25 to 50, 25 to 45, 25 to 40, 25 to 35, 25 to 30, 50 to 55, 45 to 55, 40 to 55, 35 to 55, 30 to 55, 30 to 50, 35 to 50, 40 to 50, 45 to 50, 35 to 45, or 40 to 45 bp) and no more than 100 bp away from each other (e.g., no more than 90, 80, 70, 60, 50, 40, 30, 20 or 10 bp).

IV.3 Targeted Knockdown Unlike CRISPR/Cas-mediated gene knockout, which permanently eliminates expression by mutating the gene at the DNA level, CRISPR/Cas knockdown allows for temporary reduction of gene expression through the use of artificial transcription factors. Mutating key residues in both DNA cleavage domains of the Cas9 protein (e.g. the D10A and H840A mutations) results in the generation of a catalytically inactive Cas9 (eiCas9 which is also known as dead Cas9 or dCas9). A catalytically inactive Cas9 complexes with a gRNA and localizes to the DNA sequence specified by that gRNA's targeting domain, however, it does not cleave the target DNA. Fusion of the dCas9 to an effector domain, e.g., a transcription repression domain, enables recruitment of the effector to any DNA site specified by the gRNA. While it has been show that the eiCas9 itself can block transcription when recruited to early regions in the coding sequence, more robust repression can be achieved by fusing a transcriptional repression domain (for example KRAB, SID or ERD) to the Cas9 and recruiting it to the promoter region of a gene. It is likely that targeting DNAseI hypersensitive regions of the promoter may yield more efficient gene repression or activation because these regions are more likely to be accessible to the Cas9 protein and are also more likely to harbor sites for endogenous transcription factors. Especially for gene repression, it is contemplated herein that blocking the binding site of an endogenous transcription factor would aid in down-regulating gene expression. In another embodiment, an eiCas9 can be fused to a chromatin modifying protein. Altering chromatin status can result in decreased expression of the target gene.

In an embodiment, a gRNA molecule can be targeted to a known transcription response elements (e.g., promoters, enhancers, etc.), a known upstream activating sequences (UAS), and/or sequences of unknown or known function that are suspected of being able to control expression of the target DNA.

CRISPR/Cas-mediated gene knockdown can be used to reduce expression of an unwanted allele or transcript. Contemplated herein are scenarios wherein permanent destruction of the gene is not ideal. In these scenarios, site-specific repression may be used to temporarily reduce or eliminate expression. It is also contemplated herein that the off-target effects of a Cas-repressor may be less severe than those of a Cas-nuclease as a nuclease can cleave any DNA sequence and cause mutations whereas a Cas-repressor may only have an effect if it targets the promoter region of an actively transcribed gene. However, while nuclease-mediated knockout is permanent, repression may only persist as long as the Cas-repressor is present in the cells. Once the repressor is no longer present, it is likely that endogenous transcription factors and gene regulatory elements would restore expression to its natural state.

IV.4 Examples of gRNAs in Genome Editing Methods gRNA molecules as described herein can be used with Cas9 molecules that generate a double strand break or a single strand break to alter the sequence of a target nucleic acid, e.g., a target position or target genetic signature. gRNA molecules useful in these methods are described below.

In an embodiment, the gRNA, e.g., a chimeric gRNA, is configured such that it comprises one or more of the following properties;

a) it can position, e.g., when targeting a Cas9 molecule that makes double strand breaks, a double strand break (i) within 50, 100, 150 or 200 nucleotides of a target position, or (ii) sufficiently close that the target position is within the region of end resection;

b) it has a targeting domain of at least 15, 16, 17, 18, 19 or 20, nucleotides, e.g., a targeting domain of (i) 17, (ii) 18, or (iii) 20 nucleotides; and c)
  (i) the proximal and tail domain, when taken together, comprise at least 15, 18, 20, 25, 30, 31, 35, 40, 45, 49, 50, or 53 nucleotides, e.g., at least 15, 18, 20, 25, 30, 31, 35, 40, 45, 49, 50, or 53 nucleotides from a naturally occurring *S. pyogenes, S. thermophilus, S. aureus*, or *N. meningitidis* tail and proximal domain, or a sequence that differs by no more than 1, 2, 3, 4, 5; 6, 7, 8, 9 or 10 nucleotides therefrom;
  (ii) there are at least 15, 18, 20, 25, 30, 31, 35, 40, 45, 49, 50, or 53 nucleotides 3' to the last nucleotide of the second complementarity domain, e.g., at least 15, 18, 20, 25, 30, 31, 35, 40, 45, 49, 50, or 53 nucleotides from the corresponding sequence of a naturally occurring *S. pyogenes, S. thermophilus, S. aureus*, or *N. meningitidis* gRNA, or a sequence that differs by no more than 1, 2, 3, 4, 5; 6, 7, 8, 9 or 10 nucleotides therefrom;
  (iii) there are at least 16, 19, 21, 26, 31, 32, 36, 41, 46, 50, 51, or 54 nucleotides 3' to the last nucleotide of the second complementarity domain that is complementary to its corresponding nucleotide of the first complementarity domain, e.g., at least 16, 19, 21, 26, 31, 32, 36, 41, 46, 50, 51, or 54 nucleotides from the corresponding sequence of a naturally occurring *S. pyogenes, S. thermophilus, S. aureus*, or *N. meningitidis* gRNA, or a sequence that differs by no more than 1, 2, 3, 4, 5, 6, 7, 8, 9 or 10 nucleotides therefrom;
  iv) the tail domain is at least 10, 15, 20, 25, 30, 35 or 40 nucleotides in length, e.g., it comprises at least 10, 15, 20, 25, 30, 35 or 40 nucleotides from a naturally occurring *S. pyogenes, S. thermophilus, S. aureus*, or *N. meningitidis* tail domain; or, or a sequence that differs by no more than 1, 2, 3, 4, 5, 6, 7, 8, 9 or 10 nucleotides therefrom; or
  (v) the tail domain comprises 15, 20, 25, 30, 35, 40 nucleotides or all of the corresponding portions of a naturally occurring tail domain, e.g., a naturally occurring S. pyogenes, S. thermophilus, S. aureus, or N. meningitidis tail domain.

In an embodiment, the gRNA is configured such that it comprises properties: a and b(i).

In an embodiment, the gRNA is configured such that it comprises properties: a and b(ii).

In an embodiment, the gRNA is configured such that it comprises properties: a and b(iii).

In an embodiment, the gRNA is configured such that it comprises properties: a and c.

In an embodiment, the gRNA is configured such that in comprises properties: a, b, and c.

In an embodiment, the gRNA is configured such that in comprises properties: a(i), b(i), and c(i).

In an embodiment, the gRNA is configured such that in comprises properties: a(i), b(i), and c(ii).

In an embodiment, the gRNA is configured such that in comprises properties: a(i), b(iii), and c(i).

In an embodiment, the gRNA is configured such that in comprises properties: a(i), b(iii), and c(ii).

In an embodiment, the gRNA, e.g., a chimeric gRNA, is configured such that it comprises one or more of the following properties;

a) it can position, e.g., when targeting a Cas9 molecule that makes single strand breaks, a single strand break (i) within 50, 100, 150 or 200 nucleotides of a target position, or (ii) sufficiently close that the target position is within the region of end resection;

b) it has a targeting domain of at least 15, 16, 17, 18, 19, or 20, nucleotides, e.g., a targeting domain of (i) 17, (ii) 18, or (iii) 20 nucleotides; and c)
(i) the proximal and tail domain, when taken together, comprise at least 15, 18, 20, 25, 30, 31, 35, 40, 45, 49, 50, or 53 nucleotides, e.g., at least 15, 18, 20, 25, 30, 31, 35, 40, 45, 49, 50, or 53 nucleotides from a naturally occurring S. pyogenes, S. thermophilus, S. aureus, or N. meningitidis tail and proximal domain, or a sequence that differs by no more than 1, 2, 3, 4, 5, 6, 7, 8, 9 or 10 nucleotides therefrom;

(ii) there are at least 15, 18, 20, 25, 30, 31, 35, 40, 45, 49, 50, or 53 nucleotides 3' to the last nucleotide of the second complementarity domain, e.g., at least 15, 18, 20, 25, 30, 31, 35, 40, 45, 49, 50, or 53 nucleotides from the corresponding sequence of a naturally occurring S. pyogenes, S. thermophilus, S. aureus, or N. meningitidis gRNA, or a sequence that differs by no more than 1, 2, 3, 4, 5, 6, 7, 8, 9 or 10 nucleotides therefrom;

(iii) there are at least 16, 19, 21, 26, 31, 32, 36, 41, 46, 50, 51, or 54 nucleotides 3' to the last nucleotide of the second complementarity domain that is complementary to its corresponding nucleotide of the first complementarity domain, e.g., at least 16, 19, 21, 26, 31, 32, 36, 41, 46, 50, 51, or 54 nucleotides from the corresponding sequence of a naturally occurring S. pyogenes, S. thermophilus, S. aureus, or N. meningitidis gRNA, or a sequence that differs by no more than 1, 2, 3, 4, 5; 6, 7, 8, 9 or 10 nucleotides therefrom;

iv) the tail domain is at least 10, 15, 20, 25, 30, 35 or 40 nucleotides in length, e.g., it comprises at least 10, 15, 20, 25, 30, 35 or 40 nucleotides from a naturally occurring S. pyogenes, S. thermophilus, S. aureus, or N. meningitidis tail domain; or, a sequence that differs by no more than 1, 2, 3, 4, 5, 6, 7, 8, 9 or 10 nucleotides therefrom; or (v) the tail domain comprises 15, 20, 25, 30, 35, 40 nucleotides or all of the corresponding portions of a naturally occurring tail domain, e.g., a naturally occurring S. pyogenes, S. thermophilus, S. aureus, or N. meningitidis tail domain.

In an embodiment, the gRNA is configured such that it comprises properties: a and b(i).

In an embodiment, the gRNA is configured such that it comprises properties: a and b(ii).

In an embodiment, the gRNA is configured such that it comprises properties: a and b(iii).

In an embodiment, the gRNA is configured such that it comprises properties: a and c.

In an embodiment, the gRNA is configured such that in comprises properties: a, b, and c.

In an embodiment, the gRNA is configured such that in comprises properties: a(i), b(i), and c(i).

In an embodiment, the gRNA is configured such that in comprises properties: a(i), b(i), and c(ii).

In an embodiment, the gRNA is configured such that in comprises properties: a(i), b(iii), and c(i).

In an embodiment, the gRNA is configured such that in comprises properties: a(i), b(iii), and c(ii).

In an embodiment, the gRNA is used with a Cas9 nickase molecule having HNH activity, e.g., a Cas9 molecule having the RuvC activity inactivated, e.g., a Cas9 molecule having a mutation at D10, e.g., the D10A mutation.

In an embodiment, the gRNA is used with a Cas9 nickase molecule having RuvC activity, e.g., a Cas9 molecule having the HNH activity inactivated, e.g., a Cas9 molecule having a mutation at H840, e.g., a H840A.

In an embodiment, a pair of gRNAs, e.g., a pair of chimeric gRNAs, comprising a first and a second gRNA, is configured such that they comprises one or more of the following properties;

a) one or both of the gRNAs can position, e.g., when targeting a Cas9 molecule that makes single strand breaks, a single strand break within (i) 50, 100, 150 or 200 nucleotides of a target position, or (ii) sufficiently close that the target position is within the region of end resection;

b) one or both have a targeting domain of at least 17 nucleotides, e.g., a targeting domain of (i) 17 or (ii) 18 nucleotides;

c) one or both:
(i) the proximal and tail domain, when taken together, comprise at least 15, 18, 20, 25, 30, 31, 35, 40, 45, 49, 50, or 53 nucleotides, e.g., at least 15, 18, 20, 25, 30, 31, 35, 40, 45, 49, 50, or 53 nucleotides from a naturally occurring S. pyogenes, S. thermophilus, S. aureus, or N. meningitidis tail and proximal domain, or a sequence that differs by no more than 1, 2, 3, 4, 5, 6, 7, 8, 9 or 10 nucleotides therefrom;

(ii) there are at least 15, 18, 20, 25, 30, 31, 35, 40, 45, 49, 50, or 53 nucleotides 3' to the last nucleotide of the second complementarity domain, e.g., at least 15, 18, 20, 25, 30, 31, 35, 40, 45, 49, 50, or 53 nucleotides from the corresponding sequence of a naturally occurring S. pyogenes, S. thermophilus, S. aureus, or N. meningitidis gRNA, or a sequence that differs by no more than 1, 2, 3, 4, 5, 6, 7, 8, 9 or 10 nucleotides therefrom;

(iii) there are at least 16, 19, 21, 26, 31, 32, 36, 41, 46, 50, 51, or 54 nucleotides 3' to the last nucleotide of the second complementarity domain that is complementary to its corresponding nucleotide of the first complementarity domain, e.g., at least 16, 19, 21, 26, 31, 32, 36, 41, 46, 50, 51, or 54 nucleotides from the corresponding sequence of a naturally occurring S. pyogenes, S.

thermophilus, S. aureus, or N. meningitidis gRNA, or a sequence that differs by no more than 1, 2, 3, 4, 5; 6, 7, 8, 9 or 10 nucleotides therefrom;

iv) the tail domain is at least 10, 15, 20, 25, 30, 35 or 40 nucleotides in length, e.g., it comprises at least 10, 15, 20, 25, 30, 35 or 40 nucleotides from a naturally occurring S. pyogenes, S. thermophilus, S. aureus, or N. meningitidis tail domain; or, or a sequence that differs by no more than 1, 2, 3, 4, 5, 6, 7, 8, 9 or 10 nucleotides therefrom; or (v) the tail domain comprises 15, 20, 25, 30, 35, 40 nucleotides or all of the corresponding portions of a naturally occurring tail domain, e.g., a naturally occurring S. pyogenes, S. thermophilus, S. aureus, or N. meningitidis tail domain;

d) the gRNAs are configured such that, when hybridized to target nucleic acid, they are separated by 0-50, 0-100, 0-200, at least 10, at least 20, at least 30 or at least 50 nucleotides;

e) the breaks made by the first gRNA and second gRNA are on different strands; and f) the PAMs are facing outwards.

In an embodiment, one or both of the gRNAs is configured such that it comprises properties: a and b(i).

In an embodiment, one or both of the gRNAs is configured such that it comprises properties: a and b(ii).

In an embodiment, one or both of the gRNAs is configured such that it comprises properties: a and b(iii).

In an embodiment, one or both of the gRNAs configured such that it comprises properties: a and c.

In an embodiment, one or both of the gRNAs is configured such that in comprises properties: a, b, and c.

In an embodiment, one or both of the gRNAs is configured such that in comprises properties: a(i), b(i), and c(i).

In an embodiment, one or both of the gRNAs is configured such that in comprises properties: a(i), b(i), and c(ii).

In an embodiment, one or both of the gRNAs is configured such that in comprises properties: a(i), b(i), c, and d.

In an embodiment, one or both of the gRNAs is configured such that in comprises properties: a(i), b(i), c, and e.

In an embodiment, one or both of the gRNAs is configured such that in comprises properties: a(i), b(i), c, d, and e.

In an embodiment, one or both of the gRNAs is configured such that in comprises properties: a(i), b(iii), and c(i).

In an embodiment, one or both of the gRNAs is configured such that in comprises properties: a(i), b(iii), and c(ii).

In an embodiment, one or both of the gRNAs is configured such that in comprises properties: a(i), b(iii), c, and d.

In an embodiment, one or both of the gRNAs is configured such that in comprises properties: a(i), b(iii), c, and e.

In an embodiment, one or both of the gRNAs is configured such that in comprises properties: a(i), b(iii), c, d, and e.

In an embodiment, the gRNAs are used with a Cas9 nickase molecule having HNH activity, e.g., a Cas9 molecule having the RuvC activity inactivated, e.g., a Cas9 molecule having a mutation at D10, e.g., the D10A mutation.

In an embodiment, the gRNAs are used with a Cas9 nickase molecule having RuvC activity, e.g., a Cas9 molecule having the HNH activity inactivated, e.g., a Cas9 molecule having a mutation at H840, e.g., a H840A.

V. Constructs/Components

The components, e.g., a Cas9 molecule or gRNA molecule, or both, can be delivered, formulated, or administered in a variety of forms, see, e.g., Table V-1a and Table V-1b. When a component is delivered encoded in DNA the DNA will typically include a control region, e.g., comprising a promoter, to effect expression. Useful promoters for Cas9 molecule sequences include CMV, EF-1a, MSCV, PGK, CAG control promoters. Useful promoters for gRNAs include H1, EF-1a and U6 promoters. Promoters with similar or dissimilar strengths can be selected to tune the expression of components. Sequences encoding a Cas9 molecule can comprise a nuclear localization signal (NLS), e.g., an SV40 NLS. In an embodiment, a promoter for a Cas9 molecule or a gRNA molecule can be, independently, inducible, tissue specific, or cell specific.

Table V-1a and Table V-1b provide examples of how the components can be formulated, delivered, or administered.

TABLE V-1a

| Element | | | |
|---|---|---|---|
| Cas9 Molecule(s) | gRNA molecule(s) | Template Nucleic Acid | Comments |
| DNA | DNA | DNA | In an embodiment, a Cas9 molecule, typically an eaCas9 molecule, and a gRNA are transcribed from DNA. In this embodiment, they are encoded on separate molecules. In an embodiment, the donor template is provided as a separate DNA molecule. A governing gRNA molecule can also be present. It can be encoded on the molecule that encodes the Cas9 molecule or the gRNA molecule or can be on a third nucleic acid molecule. The governing gRNA molecule can be a Cas9-targeting gRNA molecule or a gRNA-targeting gRNA molecule. In an embodiment, both are present. In an embodiment, the governing gRNA molecule is a Cas9-targeting gRNA molecule which targets, by binding and/or cleavage, the sequence that encodes the Cas9 molecule and results in substantial reduction of the production of Cas9 molecule. In an embodiment, the governing gRNA molecule is a gRNA-targeting gRNA molecule which targets, by binding and/or cleavage, the sequence that encodes the gRNA molecule and results in substantial reduction of the production of gRNA molecule. |

TABLE V-1a-continued

| | | Element | |
|---|---|---|---|
| Cas9 Molecule(s) | gRNA molecule(s) | Template Nucleic Acid | Comments |
| DNA | | DNA | In an embodiment, a Cas9 molecule, typically an eaCas9 molecule, and a gRNA are transcribed from DNA. In this embodiment, they are encoded on separate molecules. In this embodiment, the donor template is provided on the same DNA molecule that encodes the gRNA. A governing gRNA molecule can also be present. It can be encoded on the molecule that encodes the Cas9 molecule and the gRNA molecule or can be on a second nucleic acid molecule. The governing gRNA molecule can be a Cas9-targeting gRNA molecule or a gRNA-targeting gRNA molecule. In an embodiment, both are present. In an embodiment, the governing gRNA molecule is a Cas9-targeting gRNA molecule which targets, by binding and/or cleavage, the sequence that encodes the Cas9 molecule and results in substantial reduction of the production of Cas9 molecule. In an embodiment, the governing gRNA molecule is a gRNA-targeting gRNA molecule which targets, by binding and/or cleavage, the sequence that encodes the gRNA molecule and results in substantial reduction of the production of gRNA molecule. |
| | DNA | DNA | In an embodiment, a Cas9 molecule, typically an eaCas9 molecule, and a gRNA are transcribed from DNA, here from a single molecule. In this embodiment, the donor template is provided as a separate DNA molecule. A governing gRNA molecule can also be present. It can be encoded on the molecule that encodes the Cas9 molecule and the gRNA molecule or can be on a second nucleic acid molecule. The governing gRNA molecule can be a Cas9-targeting gRNA molecule or a gRNA-targeting gRNA molecule. In an embodiment, both are present. In an embodiment, the governing gRNA molecule is a Cas9-targeting gRNA molecule which targets, by binding and/or cleavage, the sequence that encodes the Cas9 molecule and results in substantial reduction of the production of Cas9 molecule. In an embodiment, the governing gRNA molecule is a gRNA-targeting gRNA molecule which targets, by binding and/or cleavage, the sequence that encodes the gRNA molecule and results in substantial reduction of the production of gRNA molecule. |
| DNA | DNA | DNA | In an embodiment, a Cas9 molecule, typically an eaCas9 molecule, and a gRNA are transcribed from DNA. In this embodiment, they are encoded on separate molecules. In this embodiment, the donor template is provided on the same DNA molecule that encodes the Cas9. A governing gRNA molecule can also be present. It can be encoded on the molecule that encodes the Cas9 molecule or the gRNA molecule or can be on a third nucleic acid molecule. The governing gRNA molecule can be a Cas9-targeting gRNA molecule or a gRNA-targeting gRNA molecule. In an embodiment, both are present. In an embodiment, the governing gRNA molecule is a Cas9-targeting gRNA molecule which targets, by binding and/or cleavage, the sequence that encodes the Cas9 molecule and results in substantial reduction of the production of Cas9 molecule. In an embodiment, the governing gRNA molecule is a gRNA-targeting gRNA molecule which targets, by binding and/or cleavage, the sequence that encodes the gRNA molecule and results in substantial reduction of the production of gRNA molecule. |
| DNA | RNA | DNA | In an embodiment, a Cas9 molecule, typically an eaCas9 molecule, is transcribed from DNA, and |

TABLE V-1a-continued

| Cas9 Molecule(s) | gRNA molecule(s) | Template Nucleic Acid | Comments |
|---|---|---|---|
| | | | a gRNA is provided as in vitro transcribed or synthesized RNA. In this embodiment, the donor template is provided as a separate DNA molecule. In an embodiment, the gRNA comprises one or more modifications, e.g., as described in Section X. A governing gRNA molecule can also be present. It can be encoded on the molecule that encodes the Cas9 molecule or can be on a second nucleic acid molecule. In an embodiment, the governing gRNA molecule is a Cas9-targeting gRNA molecule which targets, by binding and/or cleavage, the sequence that encodes the Cas9 molecule and results in substantial reduction of the production of Cas9 molecule. |
| DNA | RNA | DNA | In an embodiment, a Cas9 molecule, typically an eaCas9 molecule, is transcribed from DNA, and a gRNA is provided as in vitro transcribed or synthesized RNA. In this embodiment, the donor template is provided on the same DNA molecule that encodes the Cas9. In an embodiment, the gRNA comprises one or more modifications, e.g., as described in Section X. A governing gRNA molecule can also be present. It can be encoded on the molecule that encodes the Cas9 molecule or can be on a second nucleic acid molecule. In an embodiment, the governing gRNA molecule is a Cas9-targeting gRNA molecule which targets, by binding and/or cleavage, the sequence that encodes the Cas9 molecule and results in substantial reduction of the production of Cas9 molecule. |
| mRNA | RNA | DNA | In an embodiment, a Cas9 molecule, typically an eaCas9 molecule, is translated from in vitro transcribed mRNA, and a gRNA is provided as in vitro transcribed or synthesized RNA. In this embodiment, the donor template is provided as a DNA molecule. In an embodiment, the gRNA comprises one or more modifications, e.g., as described in Section X. In an embodiment, the mRNA comprises one or more modifications, e.g., as described in Section X. |
| mRNA | DNA | DNA | In an embodiment, a Cas9 molecule, typically an eaCas9 molecule, is translated from in vitro transcribed mRNA, and a gRNA is transcribed from DNA. In this embodiment, the donor template is provided as a separate DNA molecule. In an embodiment, the mRNA comprises one or more modifications, e.g., as described in Section X. A governing gRNA molecule can also be present. It can be encoded on the molecule that encodes the gRNA molecule or can be on a second nucleic acid molecule. In an embodiment, the governing gRNA molecule is a gRNA-targeting gRNA molecule which targets, by binding and/or cleavage, the sequence that encodes the gRNA molecule and results in substantial reduction of the production of gRNA molecule. |
| mRNA | | DNA | In an embodiment, a Cas9 molecule, typically an eaCas9 molecule, is translated from in vitro transcribed mRNA, and a gRNA is transcribed from DNA. In this embodiment, the donor template is provided on the same DNA molecule that encodes the gRNA. In an embodiment, the mRNA comprises one or more modifications, e.g., as described in Section X. A governing gRNA molecule can also be present. It can be encoded on the molecule that encodes the gRNA molecule or can be on a second nucleic acid molecule. In an embodiment, the governing gRNA molecule is a gRNA-targeting gRNA molecule which targets, by binding and/or cleavage, the sequence that encodes the gRNA molecule and results in substantial reduction of the production of gRNA molecule. |

TABLE V-1a-continued

| | | Element | |
|---|---|---|---|
| Cas9 Molecule(s) | gRNA molecule(s) | Template Nucleic Acid | Comments |
| Protein | DNA | DNA | In an embodiment, a Cas9 molecule, typically an eaCas9 molecule, is provided as a protein, and a gRNA is transcribed from DNA. In this embodiment, the donor template is provided as a separate DNA molecule. A governing gRNA molecule can also be present. It can be encoded on the molecule that encodes the gRNA molecule or can be on a second nucleic acid molecule. In an embodiment the governing gRNA molecule is a gRNA-targeting gRNA molecule which targets, by binding and/or cleavage, the sequence that encodes the gRNA molecule and results in substantial reduction of the production of gRNA molecule. |
| Protein | | DNA | In an embodiment, a Cas9 molecule, typically an eaCas9 molecule, is provided as a protein, and a gRNA is transcribed from DNA. In this embodiment, the donor template is provided on the same DNA molecule that encodes the gRNA. A governing gRNA molecule can also be present. It can be encoded on the molecule that encodes the gRNA molecule or can be on a second nucleic acid molecule. In an embodiment the governing gRNA molecule is a gRNA-targeting gRNA molecule which targets, by binding and/or cleavage, the sequence that encodes the gRNA molecule and results in substantial reduction of the production of gRNA molecule. |
| Protein | RNA | DNA | In an embodiment, an eaCas9 molecule is provided as a protein, and a gRNA is provided as transcribed or synthesized RNA. In this embodiment, the donor template is provided as a DNA molecule. In an embodiment, the gRNA comprises one or more modifications, e.g., as described in Section X. |

TABLE V-1b

| | | Element | |
|---|---|---|---|
| Cas9 Molecule(s) | gRNA molecule(s) | Payload | Comments |
| DNA | DNA | Yes | In this embodiment, a Cas9 molecule, typically an eiCas9 molecule, and a gRNA are transcribed from DNA. Here they are provided on separate molecules. A governing gRNA molecule can also be present. It can be encoded on the molecule that encodes the Cas9 molecule or the gRNA molecule or can be on a third nucleic acid molecule. The governing gRNA molecule can be a Cas9-targeting gRNA or molecule or a gRNA-targeting gRNA molecule. In an embodiment, both are present. In an embodiment, the governing gRNA molecule is a Cas9-targeting gRNA molecule which targets, by binding and/or cleavage, the sequence that encodes the Cas9 molecule and results in substantial reduction of the production of Cas9 molecule. In an embodiment, the governing gRNA molecule is a gRNA-targeting gRNA molecule which targets, by binding and/or cleavage, the sequence that encodes the gRNA molecule and results in substantial reduction of the production of gRNA molecule. |
| | DNA | Yes | Similar to above, but in this embodiment, a Cas9 molecule, typically an eiCas9 molecule, and a gRNA are transcribed from a single molecule. A governing gRNA molecule can also be present. It can be encoded on the molecule that encodes |

TABLE V-1b-continued

| Cas9 Molecule(s) | gRNA molecule(s) | Payload | Comments |
|---|---|---|---|
| | | | the Cas9 molecule or the gRNA molecule or can be on a second nucleic acid molecule. The governing gRNA molecule can be a Cas9-targeting gRNA molecule or a gRNA-targeting gRNA molecule. In an embodiment, both are present. In an embodiment, the governing gRNA molecule is a Cas9-targeting gRNA molecule which targets, by binding and/or cleavage, the sequence that encodes the Cas9 molecule and results in substantial reduction of the production of Cas9 molecule. In an embodiment, the governing gRNA molecule is a gRNA-targeting gRNA molecule which targets, by binding and/or cleavage, the sequence that encodes the gRNA molecule and results in substantial reduction of the production of gRNA molecule. |
| DNA | RNA | Yes | In this embodiment, a Cas9 molecule, typically an eiCas9 molecule, is transcribed from DNA. A gRNA is provided as RNA. In an embodiment, the gRNA comprises one or more modifications, e.g., as described in Section X. A governing gRNA molecule can also be present. It can be encoded on the molecule that encodes the Cas9 molecule or can be on a second nucleic acid molecule. In an embodiment the governing gRNA molecule is a Cas9-targeting gRNA molecule which targets, by binding and/or cleavage, the sequence that encodes the Cas9 molecule and results in substantial reduction of the production of Cas9 molecule. |
| mRNA | RNA | Yes | In this embodiment, a Cas9 molecule, typically an eiCas9 molecule, is provided as encoded in mRNA. A gRNA is provided as RNA. In an embodiment, the gRNA comprises one or more modifications, e.g., as described in Section X. In an embodiment, the mRNA comprises one or more modifications, e.g., as described in section X. |
| Protein | DNA | Yes | In this embodiment a Cas9 molecule, typically an eiCas9 molecule, is provided as a protein. A gRNA is provided encoded in DNA. A governing gRNA molecule can also be present. It can be encoded on the molecule that encodes the gRNA molecule or can be on a second nucleic acid molecule. In an embodiment the governing gRNA molecule is a gRNA-targeting gRNA molecule which targets, by binding and/or cleavage, the sequence that encodes the gRNA molecule and results in substantial reduction of the production of the gRNA molecule. |
| Protein | RNA | Yes | In this embodiment, a Cas9 molecule, typically an eiCas9 molecule, is provided as a protein. A gRNA is provided as RNA. In an embodiment, the gRNA comprises one or more modifications, e.g., as described in Section X. |

In an embodiment, the components of a Cas system are delivered in vivo, e.g., using a method describe herein. In another embodiment, the components a Cas system are delievered ex vivo, e.g., using a method described herein.

Table V-2 summarizes various delivery methods the components of a Cas system, e.g., the Cas9 molecule component and the gRNA molecule component are described herein, e.g., in Table V-2.

TABLE V-2

| Delivery Vector/Mode | | Delivery into Non-Dividing Cells | Duration of Expression | Genome Integration | Type of Molecule Delivered |
|---|---|---|---|---|---|
| Physical (eg, electroporation, particle gun, Calcium Phosphate transfection) | | YES | Transient | NO | Nucleic Acids and Proteins |
| Viral | Retrovirus | NO | Stable | YES | RNA |
| | Lentivirus | YES | Stable | YES/NO with modifications | RNA |
| | Adenovirus | YES | Transient | NO | DNA |
| | Adeno-Associated Virus (AAV) | YES | Stable | NO | DNA |
| | Vaccinia Virus | YES | Very Transient | NO | DNA |
| | Herpes Simplex Virus | YES | Stable | NO | DNA |
| Non-Viral | Cationic Liposomes | YES | Transient | Depends on what is delivered | Nucleic Acids and Proteins |
| | Polymeric Nanoparticles | YES | Transient | Depends on what is delivered | Nucleic Acids and Proteins |
| Biological Non-Viral Delivery Vehicles | Attenuated Bacteria | YES | Transient | NO | Nucleic Acids |
| | Engineered Bacteriophages | YES | Transient | NO | Nucleic Acids |
| | Mammalian Virus-like Particles | YES | Transient | NO | Nucleic Acids |
| | Biological liposomes: Erythrocyte Ghosts and Exosomes | YES | Transient | NO | Nucleic Acids |

DNA-Based Delivery of a Cas9 Molecule and or a gRNA Molecule

DNA encoding Cas9 molecules (e.g., eaCas9 molecules or eiCas9 molecules), gRNA molecules, and/or template nucleic acids, can be administered to subjects or delivered into cells by art-known methods or as described herein. For example, Cas9-encoding and/or gRNA-encoding DNA can be delivered, e.g., by vectors (e.g., viral or non-viral vectors), non-vector based methods (e.g., using naked DNA or DNA complexes), or a combination thereof.

In an embodiment, the DNA includes a nucleic acid that encodes a governing gRNA molecule. The governing gRNA molecule can complex with the Cas9 molecule to inactivate or silence a component of the system, e.g., the nucleic acid that encodes the Cas9 molecule or the nucleic acid that encodes the gRNA molecule. In either case, the governing gRNA, e.g., a Cas9-targeting gRNA molecule, or a gRNA targeting gRNA molecule, limits the effect of the Cas9/gRNA complex mediated gene targeting, and can place temporal limits on activity or reduce off-target activity.

In an embodiment, the Cas9- and/or gRNA-encoding DNA is delivered by a vector (e.g., viral vector/virus or plasmid).

A vector can comprise a sequence that encodes a Cas9 molecule and/or a gRNA molecule. A vector can also comprise a sequence encoding a signal peptide (e.g., for nuclear localization, nucleolar localization, mitochondrial localization), fused, e.g., to a Cas9 molecule sequence. For example, a vector can comprise a nuclear localization sequence (e.g., from SV40) fused to the sequence encoding the Cas9 molecule.

One or more regulatory/control elements, e.g., a promoter, an enhancer, an intron, a polyadenylation signal, a Kozak consensus sequence, internal ribosome entry sites (IRES), a 2A sequence, and a splice acceptor or donor can be included in the vectors. In an embodiment, the promoter is recognized by RNA polymerase II (e.g., a CMV promoter). In an embodiment, the promoter is recognized by RNA polymerase III (e.g., a U6 promoter). In an embodiment, the promoter is a regulated promoter (e.g., inducible promoter). In an embodiment, the promoter is a constitutive promoter. In an embodiment, the promoter is a tissue specific promoter. In an embodiment, the promoter is a viral promoter. In an embodiment, the promoter is a non-viral promoter.

In an embodiment, the vector or delivery vehicle is a viral vector (e.g., for generation of recombinant viruses). In an embodiment, the virus is a DNA virus (e.g., dsDNA or ssDNA virus). In an embodiment, the virus is an RNA virus (e.g., an ssRNA virus). Exemplary viral vectors/viruses include, e.g., retroviruses, lentiviruses, adenovirus, adeno-associated virus (AAV), vaccinia viruses, poxviruses, and herpes simplex viruses. In an embodiment, the viral vector, e.g., an AAV, comprises a sequence that encodes a governing gRNA molecule, e.g., a Cas9-targeting gRNA molecule or a gRNA-targeting gRNA molecule.

In an embodiment, the viral vector has the ability of cell type and/or tissue type recognition. For example, the viral vectors can be pseudotyped with different/alternative viral envelope glycoproteins; engineered with cell type-specific receptors (e.g., genetically modification of viral envelope glycoproteins to incorporate targeting ligands such as peptide ligands, single chain antibodies, growth factors); and/or engineered to have a molecular bridge with dual specificities with one end recognizing viral glycoproteins and the other end recognizing a moiety of the target cell surface (e.g., ligand-receptor, monoclonal antibodies, avidin-biotin and chemical conjugation).

In an embodiment, the viral vector achieves cell type specific expression. For example, tissue-specific promoter can be constructed to restrict expression of the transgene (Cas 9 and gRNA) in only the target cells. The specificity of the vectors can also be mediated by microRNA-dependent control of transgene expression. In an embodiment, the viral vector has increased efficiency of fusion of viral vector and target cell membrane. For example, fusion proteins such as fusion-competent hemagglutin (HA) can be incorporated to increase viral uptake into cells. In an embodiment, the viral vector has the ability of nuclear localization. For example, certain viruses that require the breakdown of the cell wall (during cell division) will not infect non-diving cell. Incorporated nuclear localization peptides into the matrix proteins of the virus allow transduction into non-proliferating cells.

In an embodiment, the virus infects dividing cells. In an embodiment, the virus infects non-dividing cells. In an embodiment, the virus infects both dividing and non-dividing cells. In an embodiment, the virus can integrate into the host genome. In an embodiment, the virus is engineered to have reduced immunity, e.g., in human. In an embodiment, the virus is replication-competent. In an embodiment, the virus is replication-defective, e.g., having one or more coding regions for the genes necessary for additional rounds of virion replication and/or packaging replaced with other genes or deleted. In an embodiment, the virus causes transient expression of the Cas9 molecule and/or the gRNA molecule. In an embodiment, the virus causes long-lasting, e.g., at least 1 week, 2 weeks, 1 month, 2 months, 3 months, 6 months, 9 months, 1 year, 2 years, or permanent expression, of the Cas9 molecule and/or the gRNA molecule. The packaging capacity of the viruses may vary, e.g., from at least about 4 kb to at least about 30 kb, e.g., at least about 5 kb, 10 kb, 15 kb, 20 kb, 25 kb, 30 kb, 35 kb, 40 kb, 45 kb, or 50 kb.

In an embodiment, the Cas9- and/or gRNA-encoding DNA is delivered by a recombinant retrovirus. In an embodiment, the retrovirus (e.g., Moloney murine leukemia virus) comprises a reverse transcriptase, e.g., that allows integration into the host genome. In an embodiment, the retrovirus is replication-competent. In an embodiment, the retrovirus is replication-defective, e.g., having one of more coding regions for the genes necessary for additional rounds of virion replication and packaging replaced with other genes, or deleted.

In an embodiment, the Cas9- and/or gRNA-encoding DNA is delivered by a recombinant lentivirus. For example, the lentivirus is replication-defective, e.g., does not comprise one or more genes required for viral replication.

In an embodiment, the Cas9- and/or gRNA-encoding DNA is delivered by a recombinant adenovirus. In an embodiment, the adenovirus is engineered to have reduced immunity in human.

In an embodiment, the Cas9- and/or gRNA-encoding DNA is delivered by a recombinant AAV. In an embodiment, the AAV can incorporate its genome into that of a host cell, e.g., a target cell as described herein. In an embodiment, the AAV is a self-complementary adeno-associated virus (scAAV), e.g., a scAAV that packages both strands which anneal together to form double stranded DNA. AAV serotypes that may be used in the disclosed methods include, e.g., AAV1, AAV2, modified AAV2 (e.g., modifications at Y444F, Y500F, Y730F and/or S662V), AAV3, modified AAV3 (e.g., modifications at Y705F, Y731F and/or T492V), AAV4, AAV5, AAV6, modified AAV6 (e.g., modifications at S663V and/or T492V), AAV8, AAV 8.2, AAV9, AAV rh 10, and pseudotyped AAV, such as AAV2/8, AAV2/5 and AAV2/6 can also be used in the disclosed methods.

In an embodiment, the Cas9- and/or gRNA-encoding DNA is delivered by a hybrid virus, e.g., a hybrid of one or more of the viruses described herein.

A packaging cell is used to form a virus particle that is capable of infecting a host or target cell. Such a cell includes a 293 cell, which can package adenovirus, and a ψ2 cell or a PA317 cell, which can package retrovirus. A viral vector used in gene therapy is usually generated by a producer cell line that packages a nucleic acid vector into a viral particle. The vector typically contains the minimal viral sequences required for packaging and subsequent integration into a host or target cell (if applicable), with other viral sequences being replaced by an expression cassette encoding the protein to be expressed. For example, an AAV vector used in gene therapy typically only possesses inverted terminal repeat (ITR) sequences from the AAV genome which are required for packaging and gene expression in the host or target cell. The missing viral functions are supplied in trans by the packaging cell line. Henceforth, the viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV.

In an embodiment, the viral vector has the ability of cell type and/or tissue type recognition. For example, the viral vector can be pseudotyped with a different/alternative viral envelope glycoprotein; engineered with a cell type-specific receptor (e.g., genetic modification of the viral envelope glycoproteins to incorporate targeting ligands such as a peptide ligand, a single chain antibodies, a growth factor); and/or engineered to have a molecular bridge with dual specificities with one end recognizing a viral glycoprotein and the other end recognizing a moiety of the target cell surface (e.g., ligand-receptor, monoclonal antibody, avidin-biotin and chemical conjugation).

In an embodiment, the viral vector achieves cell type specific expression. For example, a tissue-specific promoter can be constructed to restrict expression of the transgene (Cas 9 and gRNA) in only the target cell. The specificity of the vector can also be mediated by microRNA-dependent control of transgene expression. In an embodiment, the viral vector has increased efficiency of fusion of the viral vector and a target cell membrane. For example, a fusion protein such as fusion-competent hemagglutin (HA) can be incorporated to increase viral uptake into cells. In an embodiment, the viral vector has the ability of nuclear localization. For example, aviruse that requires the breakdown of the cell wall (during cell division) and therefore will not infect a non-diving cell can be altered to incorporate a nuclear localization peptide in the matrix protein of the virus thereby enabling the transduction of non-proliferating cells. In an embodiment, the Cas9- and/or gRNA-encoding DNA is delivered by a non-viral vector or non-vector based method (e.g., using naked DNA or DNA complexes). For example, the DNA can be delivered, e.g., by organically modified silica or silicate (Ormosil), electroporation, gene gun, sonoporation, magnetofection, lipid-mediated transfection, dendrimers, inorganic nanoparticles, calcium phosphates, or a combination thereof. In an embodiment, the DNA is delivered by an inorganic nanoparticle (e.g., attached to the payload to the surface of the nanoparticle). Exemplary inorganic nanoparticles include, e.g., magnetic nanoparticles (e.g., Fe3MnO2), silica (e.g., can integrate multi-functionality, e.g., conjugate the outer surface of the nanoparticle with a positively charged polymer (e.g., polyethylenimine, polylysine, polyserine) which allows for attachment (e.g., conjugation or entrapment) of payload and internal magnetic component, mesaporous silica nanoparticles with a positive charged polymer loaded with chloroquine to enhance transfection of the non-viral vector in vitro, high density lipoproteins and gold nanoparticles, gold nanoparticles coated with payload which gets released when nanoparticles are exposed to increased temperature by exposure to near infrared light, gold, iron or silver nanoparticles with surface modified with polylysine or another charge polymer to capture the nucleic acid cargo. In an embodiment, the DNA is delivered by an organic nanoparticle (e.g., entrapment of the payload inside the nanoparticle). Exemplary organic nanoparticles include, e.g., SNALP liposomes that contain cationic lipids together with neutral helper lipids which are coated with polyethylene glycol (PEG) and protamine and nucleic acid complex coated with lipid coating.

In an embodiment, the delivery vehicle is a physical vehicle. In an embodiment, the vehicle is low density ultrasound. For example, microbubbles containing payload (e.g., made of biocompatible material such protein, surfactant, or biocompatible polymer or lipid shell) can be used and the microbubbles can be destroyed by a focused ultrasound bean during microvascular transit. In an embodiment, the vehicle is electroporation. For example, naked nucleic acids or proteins can be delivered by electroporation, e.g., into cell suspensions or tissue environment, such as retina and embryonic tissue. In an embodiment, the vehicle is needle or jet injection. For example, naked nucleic acids or protein can be injected into, e.g., muscular, liver, skin, brain or heart tissue.

In an embodiment, the Cas9- and/or gRNA-encoding DNA is delivered by a combination of a vector and a non-vector based method. For example, a virosome comprises a liposome combined with an inactivated virus (e.g., HIV or influenza virus), which can result in more efficient gene transfer, e.g., in a respiratory epithelial cell than either a viral or a liposomal method alone.

In an embodiment, the delivery vehicle is a non-viral vector. In an embodiment, the non-viral vector is an inorganic nanoparticle (e.g., attached to the payload to the surface of the nanoparticle). Exemplary inorganic nanoparticles include, e.g., magnetic nanoparticles (e.g., $Fe_3MnO_2$), or silica. The outer surface of the nanoparticle can be conjugated with a positively charged polymer (e.g., polyethylenimine, polylysine, polyserine) which allows for attachment (e.g., conjugation or entrapment) of payload. In an embodiment, the non-viral vector is an organic nanoparticle (e.g., entrapment of the payload inside the nanoparticle). Exemplary organic nanoparticles include, e.g., SNALP liposomes that contain cationic lipids together with neutral helper lipids which are coated with polyethylene glycol (PEG) and protamine and nucleic acid complex coated with lipid coating.

Exemplary lipids for gene transfer are shown in Table V-3.

TABLE V-3

| Lipids Used for Gene Transfer | | |
|---|---|---|
| Lipid | Abbreviation | Feature |
| 1,2-Dioleoyl-sn-glycero-3-phosphatidylcholine | DOPC | Helper |
| 1,2-Dioleoyl-sn-glycero-3-phosphatidylethanolamine | DOPE | Helper |
| Cholesterol | | Helper |
| N-[1-(2,3-Dioleyloxy)prophyl]N,N,N-trimethylammonium chloride | DOTMA | Cationic |
| 1,2-Dioleoyloxy-3-trimethylammonium-propane | DOTAP | Cationic |
| Dioctadecylamidoglycylspermine | DOGS | Cationic |
| N-(3-Aminopropyl)-N,N-dimethyl-2,3-bis(dodecyloxy)-1-propanaminium bromide | GAP-DLRIE | Cationic |
| Cetyltrimethylammonium bromide | CTAB | Cationic |
| 6-Lauroxyhexyl ornithinate | LHON | Cationic |
| 1-(2,3-Dioleoyloxypropyl)-2,4,6-trimethylpyridinium | 2Oc | Cationic |
| 2,3-Dioleyloxy-N-[2(sperminecarboxamido-ethyl]-N,N-dimethyl-1-propanaminium trifluoroacetate | DOSPA | Cationic |
| 1,2-Dioleyl-3-trimethylammonium-propane | DOPA | Cationic |
| N-(2-Hydroxyethyl)-N,N-dimethyl-2,3-bis(tetradecyloxy)-1-propanaminium bromide | MDRIE | Cationic |
| Dimyristooxypropyl dimethyl hydroxyethyl ammonium bromide | DMRI | Cationic |
| 3β-[N-(N',N'-Dimethylaminoethane)-carbamoyl]cholesterol | DC-Chol | Cationic |
| Bis-guanidium-tren-cholesterol | BGTC | Cationic |
| 1,3-Diodeoxy-2-(6-carboxy-spermyl)-propylamide | DOSPER | Cationic |
| Dimethyloctadecylammonium bromide | DDAB | Cationic |
| Dioctadecylamidoglicylspermidin | DSL | Cationic |
| rac-[(2,3-Dioctadecyloxypropyl)(2-hydroxyethyl)]-dimethylammonium chloride | CLIP-1 | Cationic |
| rac-[2(2,3-Dihexadecyloxypropyl-oxymethyloxy)ethyl]trimethylammonium bromide | CLIP-6 | Cationic |
| Ethyldimyristoylphosphatidylcholine | EDMPC | Cationic |
| 1,2-Distearyloxy-N,N-dimethyl-3-aminopropane | DSDMA | Cationic |

TABLE V-3-continued

Lipids Used for Gene Transfer

| Lipid | Abbreviation | Feature |
| --- | --- | --- |
| 1,2-Dimyristoyl-trimethylammonium propane | DMTAP | Cationic |
| O,O'-Dimyristyl-N-lysyl aspartate | DMKE | Cationic |
| 1,2-Distearoyl-sn-glycero-3-ethylphosphocholine | DSEPC | Cationic |
| N-Palmitoyl D-erythro-sphingosyl carbamoyl-spermine | CCS | Cationic |
| N-t-Butyl-N0-tetradecyl-3-tetradecylaminopropionamidine | diC14-amidine | Cationic |
| Octadecenolyoxy[ethyl-2-heptadecenyl-3 hydroxyethyl] imidazolinium chloride | DOTIM | Cationic |
| N1-Cholesteryloxycarbonyl-3,7-diazanonane-1,9-diamine | CDAN | Cationic |
| 2-(3-[Bis(3-amino-propyl)-amino]propylamino)-N-ditetradecylcarbamoylme-ethyl-acetamide | RPR209120 | Cationic |
| 1,2-dilinoleyloxy-3-dimethylaminopropane | DLinDMA | Cationic |
| 2,2-dilinoleyl-4-dimethylaminoethyl-[1,3]-dioxolane | DLin-KC2-DMA | Cationic |
| dilinoleyl-methyl-4-dimethylaminobutyrate | DLin-MC3-DMA | Cationic |

Exemplary polymers for gene transfer are shown below in Table V-4.

TABLE V-4

Polymers Used for Gene Transfer

| Polymer | Abbreviation |
| --- | --- |
| Poly(ethylene)glycol | PEG |
| Polyethylenimine | PEI |
| Dithiobis(succinimidylpropionate) | DSP |
| Dimethyl-3,3'-dithiobispropionimidate | DTBP |
| Poly(ethylene imine)biscarbamate | PEIC |
| Poly(L-lysine) | PLL |
| Histidine modified PLL | |
| Poly(N-vinylpyrrolidone) | PVP |
| Poly(propylenimine) | PPI |
| Poly(amidoamine) | PAMAM |
| Poly(amidoethylenimine) | SS-PAEI |
| Triethylenetetramine | TETA |
| Poly(β-aminoester) | |
| Poly(4-hydroxy-L-proline ester) | PHP |
| Poly(allylamine) | |
| Poly(α-[4-aminobutyl]-L-glycolic acid) | PAGA |
| Poly(D,L-lactic-co-glycolic acid) | PLGA |
| Poly(N-ethyl-4-vinylpyridinium bromide) | |
| Poly(phosphazene)s | PPZ |
| Poly(phosphoester)s | PPE |
| Poly(phosphoramidate)s | PPA |
| Poly(N-2-hydroxypropylmethacrylamide) | pHPMA |
| Poly (2-(dimethylamino)ethyl methacrylate) | pDMAEMA |
| Poly(2-aminoethyl propylene phosphate) | PPE-EA |
| Chitosan | |
| Galactosylated chitosan | |
| N-Dodacylated chitosan | |
| Histone | |
| Collagen | |
| Dextran-spermine | D-SPM |

In an embodiment, the vehicle has targeting modifications to increase target cell uptake of nanoparticles and liposomes, e.g., cell specific antigens, monoclonal antibodies, single chain antibodies, aptamers, polymers, sugars, and cell penetrating peptides. In an embodiment, the vehicle uses fusogenic and endosome-destabilizing peptides/polymers. In an embodiment, the vehicle undergoes acid-triggered conformational changes (e.g., to accelerate endosomal escape of the cargo). In an embodiment, a stimuli-cleavable polymer is used, e.g., for release in a cellular compartment. For example, disulfide-based cationic polymers that are cleaved in the reducing cellular environment can be used.

In an embodiment, liposomes are used for delivery, e.g., to blood or bone marrow, e.g., as a way of targeting hematopoietic stem cells (HSCs) and progenitors. For example, long-term treatment can be enabled by direct delivery using liposomes for conditions where obtaining HSCs is difficult (e.g., HSCs are not stable or HSCs are rare). These conditions can include, e.g., sickle cell anemia, Fanconi anemia, and aplastic anemia. In an embodiment, liposomes are used for delivery to localized specific tissues, e.g., to liver or lung, via intravenous delivery or via localized injection to target organ or its blood flow. For example, long-term treatment can be enable to concentrate effect in that specific organ or tissue type. These conditions can include urea cycle disorders, alpha-1-anti-trypsin or cystic fibrosis.

In an embodiment, the delivery vehicle is a biological non-viral delivery vehicle. In an embodiment, the vehicle is an attenuated bacterium (e.g., naturally or artificially engineered to be invasive but attenuated to prevent pathogenesis and expressing the transgene (e.g., Listeria monocytogenes, certain Salmonella strains, Bifidobacterium longum, and modified Escherichia coli), bacteria having nutritional and tissue-specific tropism to target specific tissues, bacteria having modified surface proteins to alter target tissue specificity). In an embodiment, the vehicle is a genetically modified bacteriophage (e.g., engineered phages having large packaging capacity, less immunogenic, containing mammalian plasmid maintenance sequences and having incorporated targeting ligands). In an embodiment, the vehicle is a mammalian virus-like particle. For example, modified viral particles can be generated (e.g., by purification of the "empty" particles followed by ex vivo assembly of the virus with the desired cargo). The vehicle can also be engineered to incorporate targeting ligands to alter target tissue specificity. In an embodiment, the vehicle is a biological liposome. For example, the biological liposome is a phospholipid-based particle derived from human cells (e.g., erythrocyte ghosts, which are red blood cells broken down into spherical structures derived from the subject (e.g., tissue targeting can be achieved by attachment of various tissue or cell-specific ligands), or secretory exosomes—subject (i.e., patient) derived membrane-bound nanovescicle (30-100 nm) of endocytic origin (e.g., can be produced from various cell types and can therefore be taken up by cells without the need of for targeting ligands).

In an embodiment, delivery of Cas components by nanoparticles in the bone marrow is an in vivo approach to curing blood and immune diseases.

In an embodiment, the components of a Cas system, e.g., the Cas9 molecule component and the gRNA molecule component described herein is delivered by nucleofection. For example, Nucleofector™ (Lonza Cologne AG) is a transfection technology that can be used for delivery to primary cells and difficult-to-transfect cell lines. It is a non-viral method based on a combination of electrical parameters and cell-type specific solutions. It allows transfected nucleic acids to directly enter the nucleus (e.g., without relying on cell division for the transfer of nucleic acids into the nucleus), providing the ability to transfect non-dividing cells, such as neurons and resting blood cells. In an embodiment, nucleofection is used as an ex vivo delivery method.

In an embodiment, the components of a Cas system, e.g., the Cas9 molecule component and the gRNA molecule component described herein is delivered by methods utilizing endogenous receptor-mediate transporters, e.g., antibody-based molecular Trojan Horses (ArmaGen). Such methods can allow for non-invasive delivery of therapeutics to locations that are otherwise difficult to reach, e.g., brain (e.g., to cross blood brain barrier (BBB), e.g., via endogenous receptor-mediated transport processes).

In an embodiment, one or more nucleic acid molecules (e.g., DNA molecules) other than the components of a Cas system, e.g., the Cas9 molecule component and/or the gRNA molecule component described herein, are delivered. In an embodiment, the nucleic acid molecule is delivered at the same time as one or more of the components of the Cas system are delivered. In an embodiment, the nucleic acid molecule is delivered before or after (e.g., less than about 30 minutes, 1 hour, 2 hours, 3 hours, 6 hours, 9 hours, 12 hours, 1 day, 2 days, 3 days, 1 week, 2 weeks, or 4 weeks) one or more of the components of the Cas system are delivered. In an embodiment, the nucleic acid molecule is delivered by a different means than one or more of the components of the Cas system, e.g., the Cas9 molecule component and/or the gRNA molecule component, are delivered. The nucleic acid molecule can be delivered by any of the delivery methods described herein. For example, the nucleic acid molecule can be delivered by a viral vector, e.g., an integration-deficient lentivirus, and the Cas9 molecule component and/or the gRNA molecule component can be delivered by electroporation, e.g., such that the toxicity caused by nucleic acids (e.g., DNAs) can be reduced. In an embodiment, the nucleic acid molecule encodes a therapeutic protein, e.g., a protein described herein. In an embodiment, the nucleic acid molecule encodes an RNA molecule, e.g., an RNA molecule described herein.

Delivery of RNA Encoding a Cas9 Molecule

RNA encoding Cas9 molecules (e.g., eaCas9 molecules, eiCas9 molecules or eiCas9 fusion proteins) and/or gRNA molecules, can be delivered into cells, e.g., target cells described herein, by art-known methods or as described herein. For example, Cas9-encoding and/or gRNA-encoding RNA can be delivered, e.g., by microinjection, electroporation, lipid-mediated transfection, peptide-mediated delivery, or a combination thereof.

Delivery Cas9 Molecule Protein

Cas9 molecules (e.g., eaCas9 molecules, eiCas9 molecules or eiCas9 fusion proteins) can be delivered into cells by art-known methods or as described herein. For example, Cas9 protein molecules can be delivered, e.g., by microinjection, electroporation, lipid-mediated transfection, peptide-mediated delivery, or a combination thereof. Delivery can be accompanied by DNA encoding a gRNA or by a gRNA.

Route of Administration

Systemic modes of administration include oral and parenteral routes. Parenteral routes include, by way of example, intravenous, intrarterial, intraosseous, intramuscular, intradermal, subcutaneous, intranasal and intraperitoneal routes. Components administered systemically may be modified or formulated to target the components to a specific organ or cell type.

Local modes of administration include, by way of example, intrathecal, intracerebroventricular, intraparenchymal (e.g., localized intraparenchymal delivery to the striatum (e.g., into the caudate or into the putamen)), cerebral cortex, precentral gyrus, hippocampus (e.g., into the dentate gyrus or CA3 region), temporal cortex, amygdala, frontal cortex, thalamus, cerebellum, medulla, hypothalamus, tectum, tegmentum or substantia nigra intraocular, intraorbital, subconjuctival, intravitreal, subretinal or transscleral routes. In an embodiment, significantly smaller amounts of the components (compared with systemic approaches) may exert an effect when administered locally (for example, intraparenchymal or intravitreal) compared to when administered systemically (for example, intravenously). Local modes of administration can reduce or eliminate the incidence of potentially toxic side effects that may occur when therapeutically effective amounts of a component are administered systemically.

In an embodiment, components described herein are delivered by intraparenchymal injection into discrete regions of the brain, including, e.g., regions comprising medium spiny neurons, or regions comprising cortical neurons. Injections may be made directly into more than one region of the brain.

In an embodiment, components described herein are delivered by subretinally, e.g., by subretinal injection. Subretinal injections may be made directly into the macular, e.g., submacular injection.

In an embodiment, components described herein are delivered by intravitreal injection. Intravitreal injection has a relatively low risk of retinal detachment risk. In an embodiment, a nanoparticle or viral vector, e.g., AAV vector, e.g., an AAV2 vector, e.g., a modified AAV2 vector, is delivered intravitreally.

In an embodiment, a nanoparticle or viral vector, e.g., AAV vector, delivery is via intraparenchymal injection.

Methods for administration of agents to the eye are known in the medical arts and can be used to administer components described herein. Exemplary methods include intraocular injection (e.g., retrobulbar, subretinal, submacular, intravitreal and intrachoridal), iontophoresis, eye drops, and intraocular implantation (e.g., intravitreal, sub-Tenons and sub-conjunctival).

Administration may be provided as a periodic bolus (for example, subretinally, intravenously or intravitreally) or as continuous infusion from an internal reservoir (for example, from an implant disposed at an intra- or extra-ocular location (see, U.S. Pat. Nos. 5,443,505 and 5,766,242)) or from an external reservoir (for example, from an intravenous bag). Components may be administered locally, for example, by continuous release from a sustained release drug delivery device immobilized to an inner wall of the eye or via targeted transscleral controlled release into the choroid (see, for example, PCT/US00/00207, PCT/US02/14279, Ambati et al., (2000) INVEST. OPHTHALMOL. VIS. SCI. 41:1181-1185, and Ambati et al., (2000) INVEST. OPHTHALMOL. VIS. SCI. 41:1186-1191). A variety of devices suitable for administering components locally to the inside of the eye are known in the art. See, for example, U.S. Pat. Nos. 6,251,090, 6,299,895, 6,416,777, 6,413,540, and PCT/US00/28187.

In addition, components may be formulated to permit release over a prolonged period of time. A release system can include a matrix of a biodegradable material or a material which releases the incorporated components by diffusion. The components can be homogeneously or heterogeneously distributed within the release system. A variety of release systems may be useful, however, the choice of the appropriate system will depend upon rate of release required by a particular application. Both non-degradable and degradable release systems can be used. Suitable release systems include polymers and polymeric matrices, non-polymeric matrices, or inorganic and organic excipients and diluents such as, but not limited to, calcium carbonate and sugar (for example, trehalose). Release systems may be natural or synthetic. However, synthetic release systems are preferred because generally they are more reliable, more reproducible and produce more defined release profiles. The release system material can be selected so that components having different molecular weights are released by diffusion through or degradation of the material.

Representative synthetic, biodegradable polymers include, for example: polyamides such as poly(amino acids) and poly(peptides); polyesters such as poly(lactic acid), poly(glycolic acid), poly(lactic-co-glycolic acid), and poly(caprolactone); poly(anhydrides); polyorthoesters; polycarbonates; and chemical derivatives thereof (substitutions, additions of chemical groups, for example, alkyl, alkylene, hydroxylations, oxidations, and other modifications routinely made by those skilled in the art), copolymers and mixtures thereof. Representative synthetic, non-degradable polymers include, for example: polyethers such as poly(ethylene oxide), poly(ethylene glycol), and poly(tetramethylene oxide); vinyl polymers-polyacrylates and polymethacrylates such as methyl, ethyl, other alkyl, hydroxyethyl methacrylate, acrylic and methacrylic acids, and others such as poly(vinyl alcohol), poly(vinyl pyrolidone), and poly(vinyl acetate); poly(urethanes); cellulose and its derivatives such as alkyl, hydroxyalkyl, ethers, esters, nitrocellulose, and various cellulose acetates; polysiloxanes; and any chemical derivatives thereof (substitutions, additions of chemical groups, for example, alkyl, alkylene, hydroxylations, oxidations, and other modifications routinely made by those skilled in the art), copolymers and mixtures thereof.

Poly(lactide-co-glycolide) microsphere can also be used for intraocular injection. Typically the microspheres are composed of a polymer of lactic acid and glycolic acid, which are structured to form hollow spheres. The spheres can be approximately 15-30 microns in diameter and can be loaded with components described herein.

Bi-Modal or Differential Delivery of Components

Separate delivery of the components of a Cas system, e.g., the Cas9 molecule component and the gRNA molecule component, and more particularly, delivery of the components by differing modes, can enhance performance, e.g., by improving tissue specificity and safety.

In an embodiment, the Cas9 molecule and the gRNA molecule are delivered by different modes, or as sometimes referred to herein as differential modes. Different or differential modes, as used herein, refer modes of delivery that confer different pharmacodynamic or pharmacokinetic properties on the subject component molecule, e.g., a Cas9 molecule, gRNA molecule, or template nucleic acid. For example, the modes of delivery can result in different tissue distribution, different half-life, or different temporal distribution, e.g., in a selected compartment, tissue, or organ.

Some modes of delivery, e.g., delivery by a nucleic acid vector that persists in a cell, or in progeny of a cell, e.g., by autonomous replication or insertion into cellular nucleic acid, result in more persistent expression of and presence of a component. Examples include viral, e.g., adeno associated virus or lentivirus, delivery.

By way of example, the components, e.g., a Cas9 molecule and a gRNA molecule, can be delivered by modes that differ in terms of resulting half life or persistent of the delivered component the body, or in a particular compartment, tissue or organ. In an embodiment, a gRNA molecule can be delivered by such modes. The Cas9 molecule component can be delivered by a mode which results in less persistence or less exposure of its to the body or a particular compartment or tissue or organ.

More generally, in an embodiment, a first mode of delivery is used to deliver a first component and a second mode of delivery is used to deliver a second component. The first mode of delivery confers a first pharmacodynamic or pharmacokinetic property. The first pharmacodynamic property can be, e.g., distribution, persistence, or exposure, of the component, or of a nucleic acid that encodes the component, in the body, a compartment, tissue or organ. The second mode of delivery confers a second pharmacodynamic or pharmacokinetic property. The second pharmacodynamic property can be, e.g., distribution, persistence, or exposure, of the component, or of a nucleic acid that encodes the component, in the body, a compartment, tissue or organ.

In an embodiment, the first pharmacodynamic or pharmacokinetic property, e.g., distribution, persistence or exposure, is more limited than the second pharmacodynamic or pharmacokinetic property.

In an embodiment, the first mode of delivery is selected to optimize, e.g., minimize, a pharmacodynamic or pharmacokinetic property, e.g., distribution, persistence or exposure.

In an embodiment, the second mode of delivery is selected to optimize, e.g., maximize, a pharmacodynamic or pharmcokinetic property, e.g., distribution, persistence or exposure.

In an embodiment, the first mode of delivery comprises the use of a relatively persistent element, e.g., a nucleic acid, e.g., a plasmid or viral vector, e.g., an AAV or lentivirus. As such vectors are relatively persistent product transcribed from them would be relatively persistent.

In an embodiment, the second mode of delivery comprises a relatively transient element, e.g., an RNA or protein.

In an embodiment, the first component comprises gRNA, and the delivery mode is relatively persistent, e.g., the gRNA is transcribed from a plasmid or viral vector, e.g., an AAV or lentivirus. Transcription of these genes would be of little physiological consequence because the genes do not encode for a protein product, and the gRNAs are incapable of acting in isolation. The second component, a Cas9 molecule, is delivered in a transient manner, for example as mRNA or as protein, ensuring that the full Cas9 molecule/gRNA molecule complex is only present and active for a short period of time.

Furthermore, the components can be delivered in different molecular form or with different delivery vectors that complement one another to enhance safety and tissue specificity.

Use of differential delivery modes can enhance performance, safety and efficacy. For example, the likelihood of an eventual off-target modification can be reduced. Delivery of immunogenic components, e.g., Cas9 molecules, by less persistent modes can reduce immunogenicity, as peptides from the bacterially-derived Cas enzyme are displayed on the surface of the cell by MHC molecules. A two-part delivery system can alleviate these drawbacks.

Differential delivery modes can be used to deliver components to different, but overlapping target regions. The formation active complex is minimized outside the overlap of the target regions. Thus, in an embodiment, a first component, e.g., a gRNA molecule is delivered by a first delivery mode that results in a first spatial, e.g., tissue, distribution. A second component, e.g., a Cas9 molecule is delivered by a second delivery mode that results in a second spatial, e.g., tissue, distribution. In an embodiment, the first mode comprises a first element selected from a liposome, nanoparticle, e.g., polymeric nanoparticle, and a nucleic acid, e.g., viral vector. The second mode comprises a second element selected from the group. In an embodiment, the first mode of delivery comprises a first targeting element, e.g., a cell specific receptor or an antibody, and the second mode of delivery does not include that element. In an embodiment, the second mode of delivery comprises a second targeting element, e.g., a second cell specific receptor or second antibody.

When the Cas9 molecule is delivered in a virus delivery vector, a liposome, or polymeric nanoparticle, there is the potential for delivery to and therapeutic activity in multiple tissues, when it may be desirable to only target a single tissue. A two-part delivery system can resolve this challenge and enhance tissue specificity. If the gRNA molecule and the Cas9 molecule are packaged in separated delivery vehicles with distinct but overlapping tissue tropism, the fully functional complex is only be formed in the tissue that is targeted by both vectors.

While not wishing to be bound by theory, it is believed that the sequence specificity of the gRNA molecule of an eiCas9 molecule/gRNA molecule complex contributes to a specific interaction with the target sequence, thereby effecting the delivery of a payload associated with, e.g., covalently or noncovalently coupled to, the Cas9 molecule/gRNA molecule complex.

In an embodiment, the payload is covalently or non-covalently coupled to a Cas9, e.g., an eiCas9 molecule. In an embodiment, the payload is covalently or non-covalently coupled to a gRNA molecule. In an embodiment, the payload is linked to a Cas9 molecule, or gRNA molecule, by a linker, e.g., a linker which comprises a bond cleavable under physiological conditions. In an embodiment the bond is not cleavable or is only poorly cleavable, under physiological conditions. In an embodiment, "covalently coupled" means as part of a fusion protein containing a Cas9 molecule.

Delivery of Multiple Payloads

In an embodiment, a first payload molecule is delivered by a first Cas9 molecule and a second payload molecule is delivered by a second Cas9 molecule. In an embodiment, the first and second payloads are the same. In an embodiment, first and second Cas9 molecules are the same, e.g. are from the same species, have the same PAM, and/or have the same sequence. In an embodiment, first and second Cas9 molecules are different, e.g. are from different species, have the different PAMs, and/or have different sequences. Examples of configurations are provided in Table VI-1. Typically the Cas9 molecules of Table VI-1 are eiCas9 molecules. In an embodiment, a Cas9 molecule is selected such that payload delivery and cleavage are both effected. In an embodiment, multiple payloads, e.g., two payloads, is delivered with a single Cas9 molecule.

TABLE VI-1

Configurations for delivery of payloads by more than one Cas9 molecule/gRNA molecule complex

| First Cas9 molecule | Second Cas9 molecule | First Payload | Second Payload | Comments |
|---|---|---|---|---|
| C1 | C1 | P1 | P1 | In this embodiment, both Cas9 molecules are the same, as are both payloads. In an embodiment, the first and second Cas9 molecule are guided by different gRNA molecules. |
| C1 | C1 | P1 | P2 | In this embodiment, both Cas9 molecules are the same but each delivers a different Payloads. In an embodiment, the first and second Cas9 molecule are guided by different gRNA molecules. |
| C1 | C2 | P1 | P1 | In this embodiment, the Cas9 molecules are different but each delivers the same payload. In an embodiment, the first and second Cas9 molecule are guided by different gRNA molecules. |
| C1 | C2 | P1 | P2 | In this embodiment, the Cas9 molecules are different as are the payloads. In an embodiment, the first and second Cas9 molecule are guided by different gRNA molecules. |

VI. Payloads

Cas9 molecules, typically eiCas9 molecules and gRNA molecules, e.g., an eiCas9 molecule/gRNA molecule complex, can be used to deliver a wide variety of payloads. In an embodiment, the payload is delivered to target nucleic acids or to chromatin, or other components, near or associated with a target nucleic acid.

In an embodiment, two different drugs are delivered. In an embodiment, a first payload, e.g., a drug, coupled by a first linker to a first Cas9 molecule and a second payload, e.g., a drug, coupled by a second linker to a second Cas9 molecule are delivered. In an embodiment, the first and second payloads are the same, and, in an embodiment, are coupled to the respective Cas9 molecule by different linkers, e.g., having different release kinetics. In an embodiment, the first and second payloads are different, and, in an embodiment, are coupled to the respective Cas9 molecule by the same linker. In an embodiment, the first and second payload interact. E.g., the first and second payloads form a complex, e.g., a dimeric or multimeric complex, e.g., a dimeric protein. In an embodiment, the first payload can activate the second payload, e.g., the first payload can modify, e.g., cleave or phosphorylate, the second payload. In an embodiment the first payload interacts with the second payload to modify, e.g., increase or decrease, an activity of the second payload.

A payload can be delivered in vitro, ex vivo, or in vivo.

Classes of Payloads

A payload can comprise a large molecule or biologics (e.g., antibody molecules), a fusion protein, an amino acid sequence fused, as a fusion partner, to a Cas9 molecule, e.g., an eiCas9 molecule, an enzyme, a small molecules (e.g., HDAC and other chromatin modifiers/inhibitors, exon skipping molecules, transcription inhibitors), a microsatellite extension inhibitor, a carbohydrate, and DNA degraders (e.g., in an infectious disease or "foreign" DNA setting), a nucleic acid, e.g., a DNA, RNA, mRNA, siRNA, RNAi, or an antisense oligonucleotide.

Table VI-2 provides exemplary classes of payloads.

TABLE VI-2

Exemplary Classes of Payloads

Large Molecules
Small Molecules
Polymers
Biologics
Proteins and polypeptides, e.g., antibodies,
enzymes, structural peptides, ligands, receptors,
fusion proteins, fusion partners (as a fusion protein
with a Cas9, e.g., and eiCas9)
Carbohydrates
HDAC and other chromatin modifiers/inhibitors
Exon skipping molecules,
Transcription inhibitors
Micro satellite extension inhibitors
Entities that degrade DNA Large Molecules In an embodiment a payload comprises a polymer, e.g., a biological polymer, e.g., a protein, nucleic acid, or carbohydrate.

In an embodiment the payload comprises a protein, biologic, or other large molecule (i.e., a molecule having a molecular weight of at least, 3, 5, 10, 20, 30, 40, 50, 60, 70, 80, 90, or 100 kD). In an embodiment a payload comprises a polymer, e.g., a biological polymer, e.g., a protein, nucleic acid, or carbohydrate. The polymer can be a naturally occurring or non-naturally occurring polymer. In an embodiment, the payload is a natural product. For example, the natural product can be a large molecule or a small molecule.

Polypeptides, Proteins

In an embodiment the payload comprises a protein or polypeptide, e.g., a protein or polypeptide covalently or non-covalently coupled to a Cas9 molecule.

In an embodiment, the protein or polypeptide is dimeric or multimeric, and each subunit is delivered by a Cas9 molecule. In an embodiment, a first protein and second protein are delivered by one or more Cas9 molecules, e.g., each by a separate Cas9 molecule or both by the same Cas9 molecule.

In an embodiment, the protein or polypeptide is linked to a Cas9 molecule by a linker, e.g., a linker which comprises a bond cleavable under physiological conditions. In an embodiment, a linker is a linker from Section XI herein. In an embodiment, the bond is not cleavable under physiological conditions.

Specific Binding Ligands, Antibodies

In an embodiment the payload comprises a ligand, e.g., a protein, having specific affinity for a counter ligand. In an embodiment, the ligand can be a receptor (or the ligand for a receptor), or an antibody.

In an embodiment a payload comprises an antibody molecule. Exemplary antibody molecules include, e.g., proteins or polypeptides that include at least one immunoglobulin variable domain. For example, an antibody can include a heavy (H) chain variable region (abbreviated herein as VH), and a light (L) chain variable region (abbreviated herein as VL). In another example, an antibody includes two heavy (H) chain variable regions and two light (L) chain variable regions. The term "antibody" encompasses antigen-binding fragments of antibodies (e.g., single chain antibodies, Fab and sFab fragments, F(ab')2, Fd fragments, Fv fragments, scFv, and domain antibodies (dAb) fragments (de Wildt et al., EUR J IMMUNOL. 1996; 26(3):629-639)). For example, antigen-binding fragments of antibodies can include, e.g., (i) a Fab fragment, a monovalent fragment consisting of the VL, VH, CL and CH1 domains; (ii) a F(ab')2 fragment, a bivalent fragment including two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) NATURE 341:544-546), which consists of a VH domain; and (vi) an isolated complementarity determining region (CDR) that retains functionality. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules known as single chain Fv (scFv). See, e.g., U.S. Pat. Nos. 5,260,203, 4,946,778, and 4,881,175; Bird et al., (1988) SCIENCE 242:423-426; and Huston et al., (1988) PROC. NATL. ACAD. SCI. USA 85:5879-5883. An antibody can have the structural features of IgA, IgG, IgE, IgD, IgM (as well as subtypes thereof). Antibodies may be from any source, but primate (human and non-human primate) and primatized are preferred. In an embodiment, the antibody is a human antibody or humanized antibody.

In an embodiment, the antibody molecule is a single-domain antibody (e.g., an sdAb, e.g., a nanobody), e.g., an antibody fragment consisting of a single monomeric variable antibody domain. In an embodiment, the molecular weight of the single-domain antibody is about 12-15 kDa. For example, the single-domain antibody can be engineered from heavy-chain antibodies found in camelids (e.g., VHH fragments). Cartilaginous fishes also have heavy-chain antibodies (IgNAR, 'immunoglobulin new antigen receptor'), from which single-domain antibodies called VNAR fragments can be obtained. An alternative approach is to split the dimeric variable domains from common immunoglobulin G (IgG), e.g., from humans or mice, into monomers. Single-domain antibodies derived from either heavy or light chain can be obtained to bind specifically to target epitopes. For example, a single-domain antibody can be peptide chain of about 110 amino acids long, comprising one variable domain (VH) of a heavy-chain antibody, or of a common IgG.

Single-domain antibodies can have similar affinity to antigens as whole antibodies. They can also be more heat-resistant and/or stable towards detergents and high concentrations of urea. Those, e.g., derived from camelid and fish antibodies can be less lipophilic and more soluble in water, owing to their complementarity determining region 3 (CDR3), which forms an extended loop covering the lipophilic site that normally binds to a light chain. In an embodiment, the single-domain antibody does not show complement system triggered cytotoxicity, e.g., because they lack an Fc region. Single-domain antibodies, e.g., camelid and fish derived sdAbs, can bind to hidden antigens that may not be accessible to whole antibodies, for example to the active sites of enzymes. This property can result from their extended CDR3 loop, which is able to penetrate such sites.

A single-domain antibody can be obtained by immunization of, e.g., dromedaries, camels, llamas, alpacas or sharks with the desired antigen and subsequent isolation of the mRNA coding for heavy-chain antibodies. By reverse transcription and polymerase chain reaction, a gene library of single-domain antibodies containing several million clones is produced. Screening techniques like phage display and ribosome display help to identify the clones binding the antigen.

A different method uses gene libraries from animals that have not been immunized beforehand. Such naïve libraries usually contain only antibodies with low affinity to the desired antigen, making it necessary to apply affinity maturation by random mutagenesis as an additional step.

When the most potent clones have been identified, their DNA sequence can be optimized, for example to improve their stability towards enzymes. Another goal is humanization to prevent immunological reactions of the human organism against the antibody. The final step is the translation of the optimized single-domain antibody in *E. coli, Saccharomyces cerevisiae* or other suitable organisms.

Alternatively, single-domain antibodies can be made from common murine or human IgG with four chains. The process is similar, comprising gene libraries from immunized or naïve donors and display techniques for identification of the most specific antigens. Monomerization is usually accomplished by replacing lipophilic by hydrophilic amino acids. If affinity can be retained, the single-domain antibodies can likewise be produced in *E. coli, S. cerevisiae* or other organisms.

In an embodiment, a payload comprises a transcription activator protein or domain, e.g., a VP16 protein or domain, or a transcription repressor protein or domain.

Fusion Proteins and Fusion Partners

In an embodiment the payload comprises a fusion protein. Exemplary fusion proteins include a first and second fusion partner, which can possess different functional properties or which can be derived from different proteins. In an embodiment, the fusion protein can comprise a first fusion partner that binds a nucleic acid and a second fusion partner that that comprises an enzymatic activity or that promotes or inhibits gene expression. In an embodiment, the payload itself is a fusion protein. In an embodiment, the payload is fused to a Cas9 molecule.

For example, the fusion protein can contain a segment that adds stability and/or deliverability to the fused protein. In an embodiment, the fusion protein can be a protein described herein (e.g., a receptor) fused to an immunoglobulin fragment (e.g., Fc fragment), transferring, or a plasma protein, e.g., albumin. The fusion protein can also contain a segment that adds toxicity to the fused protein (e.g. conveyed by toxins, enzymes or cytokines). Fusion proteins can also be used to enable delivery and/or targeting routes (e.g., by HIV-1 TAT protein). Other examples include, e.g., fusions that allow for mutivalency, such as streptavidin fusions, or fusions of two active components (e.g., with or without a cleavable linker in between).

In an embodiment, the protein or polypeptide is a fusion partner with a Cas9 molecule, e.g., an eiCas9 molecule.

In an embodiment, a payload comprises fusion partner with a Cas9 molecule comprising a transcription activator protein or domain, e.g., a VP16 protein or domain, or a transcription repressor protein or domain.

Enzymes

In an embodiment a payload comprises an enzyme. Exemplary enzymes include, e.g., oxidoreductases (e.g., catalyze oxidation/reduction reactions), transferases (e.g., transfer a functional group (e.g. a methyl or phosphate group)), hydrolases (e.g., catalyze the hydrolysis of various bonds), lyases (e.g., cleave various bonds by means other than hydrolysis and oxidation), isomerases (catalyze isomerization changes within a single molecule), and ligases (e.g., join two molecules with covalent bonds). In an embodiment an enzymes mediates or is associated with one or more functions in the cell nucleus, e.g., DNA synthesis, transcription, epigenetic modification of DNA and histones, RNA post-transcriptional modification, cell cycle control, DNA damage repair, or genomic instability.

Small Molecules

In an embodiment a payload comprises a small molecule compounds.

In an embodiment a small molecule is a regulator of a biological process. For example, a small molecule can bind to a second molecule, e.g., biopolymer, e.g., a carbohydrate, protein, polypeptide, or a nucleic acid, and in an embodiment, alter one or more of the structure, distribution, activity, or function of the second molecule. In an embodiment, the size of the small molecule is on the order of $10^{-9}$ m. In an embodiment, the molecular weight of the small molecule is, e.g., between 200 amu and 500 amu, between 300 amu and 700 amu, between 500 amu and 700 amu, between 700 amu and 900 amu, or between 500 amu and 900 amu.

Exemplary small molecules include histone deacetylase (HDAC) inhibitors (e.g., suberoylanilide hydroxamic acid (SAHA), or romidepsin), histone methyltransferase inhibitors (DNA methyltransferase inhibitors (e.g., azacitidine (or 5-azacitidine), decitabine (or 5-aza-2'-deoxycytidine), or DNA replication inhibitors. Small molecules can also include, e.g., small nucleic acid molecules (1-4 bases depending upon the base, e.g., that would be under 2 kD) and peptides.

Microsatellite Extension Inhibitors

In an embodiment a payload comprises a microsatellite extension inhibitor. In an embodiment, the microsatellite extension inhibitor is a DNA mismatch repair protein. Exemplary DNA mismatch repair proteins that can be delivered by the molecules and methods described herein include, e.g., MSH2, MSH3, MSH6, MLH1, MLH3, PMS1, PMS2.

Signal Generators, Radionuclides, Reporter Molecules, Diagnostic Probes

In an embodiment a payload comprises a molecule that generates a signal. Such payloads are useful, e.g., in research, therapeutic (e.g., cancer therapy) and diagnostic applications. In an embodiment, the signal comprises: an electromagnetic emission, e.g., in the infrared, visible, or ultraviolet range; a particle, e.g., a product of radioactive decay, e.g., an alpha, beta, or gamma particle; a detectable substrate, e.g., a colored substrate; a reaction product, e.g., the product of an enzymatic reaction; or a ligand detectable by a specific binding agent, e.g., an antibody; or a dye. In an embodiment the signal comprises a fluorescent emission, e.g., by a fluorescent protein. Exemplary fluorescent proteins include, Blue/UV Proteins (e.g., TagBFP, mTagBFP, Azurite, EBFP2, mKalama1, Sirius, Sapphire, T-Sapphire), Cyan Proteins (e.g., ECFP, Cerulean, SCFP3A, mTurquoise, mTurquoise2, monomeric Midoriishi-Cyan, TagCFP, mTFP1), Green Proteins (e.g., EGFP, Emerald, Superfolder GFP, Monomeric Azami Green, TagGFP2, mUKG, mWasabi, Clover, mNeonGreen), Yellow Proteins (e.g., EYFP, Citrine, Venus, SYFP2, TagYFP), Orange Proteins (e.g., Monomeric Kusabira-Orange, mKOK, mKO2, mOrange, mOrange2), Red Proteins (mRaspberry, mCherry, mStrawberry, mTangerine, tdTomato, TagRFP, TagRFP-T, mApple, mRuby, mRuby2), Far-Red Proteins (e.g., mPlum, HcRed-Tandem, mKate2, mNeptune, NirFP, TagRFP657, IFP1.4, iRFP), Long Stokes Shift Proteins (e.g., mKeima Red, LSS-mKate1, LSS-mKate2, mBeRFP), Photoactivatible Proteins (e.g., PA-GFP, PAmCherryl, PATagRFP), Photoconvertible Proteins (e.g., Kaede (green), Kaede (red), KikGR1 (green), KikGR1 (red), PS-CFP2, mEos2 (green), mEos2 (red), mEos3.2 (green), mEos3.2 (red), PSmOrange), Photoswitchable Proteins (e.g., Dronpa).

In an embodiment, a signal producing moiety is provided as the fusion partner of a Cas9 molecule, e.g., an eiCas9 molecule.

Signal generators or reporters, useful, e.g., for labeling polypeptides include, but are not limited to, the following: radioisotopes or radionuclides (e.g., indium ($^{111}$In) iodine ($^{131}$I or $^{125}$I), yttrium ($^{90}$Y), lutetium ($^{177}$Lu), actinium ($^{225}$Ac), bismuth ($^{212}$Bi or $^{213}$Bi), sulfur ($^{35}$S), carbon ($^{14}$C), tritium ($^{3}$H), rhodium ($^{188}$Rh), technetium ($^{99m}$Tc), praseodymium, or phosphorous ($^{32}$P) or a positron-emitting radionuclide, e.g., carbon-11 ($^{11}$C), potassium-40 ($^{40}$K), nitrogen-13 ($^{13}$N), oxygen-15 ($^{15}$O), fluorine-18 ($^{18}$F), and iodine-121 (121rI)), fluorescent labels (e.g., FITC, rhodamine, lanthanide phosphors), enzymatic labels (e.g., horseradish peroxidase, beta-galactosidase, luciferase, alkaline phosphatase), chemiluminescent, biotinyl groups (which can be detected by a marked avidin, e.g., a molecule containing a streptavidin moiety and a fluorescent marker or an enzymatic activity that can be detected by optical or calorimetric methods), and predetermined polypeptide epitopes recognized by a secondary reporter (e.g., leucine zipper pair sequences, binding sites for secondary antibodies, metal binding domains, epitope tags). In an embodiment, labels are attached by spacer arms of various lengths to reduce potential steric hindrance.

In an embodiment, a payload comprises a radionuclide. The radionuclide can be incorporated into the gRNA molecule, the Cas9 molecule, or into a payload molecule.

Exemplary radionuclides include, e.g., beta emitters, alpha emitters or gamma emitters. In an embodiment the radionuclide is iodine, e.g., $^{131}$I or $^{125}$I, yttrium, e.g., $^{90}$Y, lutetium, e.g., $^{177}$Lu, Actinium, e.g., $^{225}$Ac, bismuth, e.g. $^{212}$Bi or $^{213}$Bi), sulfur, e.g., $^{35}$S), carbon, e.g., $^{14}$C, tritium, $^{3}$H), rhodium, e.g., $^{188}$Rh, technetium, e.g., $^{99}$Tc, praseodymium, or phosphorous, e.g., $^{32}$P.

Modulators of DNA and Chromatin Structure

In an embodiment, a payload comprises an endogenous or exogenous modulator of DNA structure. A modulator, as is typical of payloads, can be delivered in vitro, ex vivo, or in vivo.

In an embodiment, the payload comprises a modulator of an epigenetic state or characteristic of DNA. In an embodiment an epigenetic state or characteristic can be altered to treat a disorder, or to influence the developmental or other state of a cell.

In an embodiment, the epigenetic state or characteristic comprises DNA methylation. For example, the payloads described herein can modulate the addition of methyl groups to DNA, e.g., to convert cytosine to 5-methylcytosine, e.g., at CpG sites.

Aberrant DNA methylation patterns (e.g., hypermethylation and hypomethylation compared to normal tissue) are associated with various diseases and conditions, e.g., cancer. The modulators described herein can be used to reactivate transcriptionally silenced genes or to inhibit transcriptionally hyperactive genes, e.g., to treat diseases, e.g., cancer.

DNA methylation can affect gene transcription. Genes with high levels of 5-methylcytosine, e.g., in their promoter region, can be transcriptionally less active or silent. Thus, methods described herein can be used to target and suppress transcriptional activity, e.g., of genes described herein.

In an embodiment, the modulator promotes maintenance of DNA methylation. For example, the modulators can have DNA methyltransferase (DNMT) activity or modulate DNMT activity, e.g., to maintain DNA methylation or reduce passive DNA demethylation, e.g., after DNA replication.

In an embodiment, the modulator promotes de novo DNA methylation. For example, the modulators described herein can have de novo DNA methyltransferase (DNMT) (e.g., DNMT3a, DNMT3b, DNMT3L) activity or modulate de novo DNMT (e.g., DNMT3a, DNMT3b, DNMT3L) activity, e.g., to produce DNA methylation patterns, e.g., early in development.

Epigenetic changes in DNA (e.g., methylation), can be evaluated by art-known methods or as described herein. Exemplary methods for detecting DNA methylation include, e.g., Methylation-Specific PCR (MSP), whole genome bisulfite sequencing (BS-Seq), HELP (Hpall tiny fragment Enrichment by Ligation-mediated PCR) assay, ChIP-on-chip assays, restriction landmark genomic scanning, Methylated DNA immunoprecipitation (MeDIP), pyrosequencing of bisulfite treated DNA, molecular break light assay for DNA adenine methyltransferase activity, methyl sensitive Southern Blotting, separation of native DNA into methylated and unmethylated fractions using MethylCpG Binding Proteins (MBPs) and fusion proteins containing just the Methyl Binding Domain (MBD).

In an embodiment, the modulator cleaves DNA. For example, a modulator can catalyze the hydrolytic cleavage of phosphodiester linkages in the DNA backbone. In an embodiment, the modulator (e.g., DNase I) cleaves DNA preferentially at phosphodiester linkages adjacent to a pyrimidine nucleotide, yielding 5'-phosphate-terminated polynucleotides with a free hydroxyl group on position 3'. In an embodiment, the modulator (e.g., DNase II) hydrolyzes deoxyribonucleotide linkages in DNA, yielding products with 3'-phosphates. In an embodiment, the modulator comprises endodeoxyribonuclease activity. In an embodiment, the modulator comprises exodeoxyribonuclease activity (e.g., having 3' to 5' or 5' to 3' exodeoxyribonuclease activity). In an embodiment, the modulator recognizes a specific DNA sequence (e.g., a restriction enzyme). In an embodiment, the modulator does not cleave DNA in a sequence-specific manner. A modulator can cleave single-stranded DNA (e.g., having nickase activity), double-stranded DNA, or both.

In an embodiment, modulator affects, e.g., alters or preserves, tertiary or quaternary DNA structure. For example, the modulators described herein can modulate tertiary structure, e.g., handedness (right or left), length of the helix turn, number of base pairs per turn, and/or difference in size between the major and minor grooves. In an embodiment, the modulator mediates the formation of B-DNA, A-DNA, and/or Z-DNA. The modulators described herein can also modulate quaternary structure, e.g., the interaction of DNA with other molecules (DNA or non-DNA molecules, e.g., histones), e.g., in the form of chromatin. In an embodiment, the modulator that mediate or modify tertiary or quaternary DNA structure comprises DNA helicases activity or modulates DNA helicase activity.

In an embodiment, the modulator promotes or inhibits DNA damage response and/or repair. For example, a modulator can promote one or more DNA damage response and repair mechanisms, e.g., direct reversal, base excision repair (BER), nucleotide excision repair (NER) (e.g., global genomic repair (GG-NER), transcription-coupled repair (TC-NER)), mismatch repair (MMR), non-homologous end joining (NHEJ), microhomology-mediated end joining (MMEJ), homologous recombination, and/or translesion synthesis (TLS). In an embodiment, a modulator promotes the step of damage recognition. In an embodiment, a modulator promotes the step of DNA repair.

Aberrant DNA damage repair is associated with various diseases and conditions, e.g., aging, hereditary DNA repair disorders, and cancer. For example, DNA repair gene mutations that can increase cancer risk include, e.g., BRCA1 and BRCA2 (e.g., involved in homologous recombination repair (HRR) of double-strand breaks and daughter strand gaps, e.g., in breast and ovarian cancer); ATM (e.g., different mutations reduce HRR, single strand annealing (SSA), NHEJ or homology-directed DSBR (HDR), e.g., in leukemia, lymphoma, and breast cancer), NBS (e.g., involved in NHEJ, e.g., in lymphoid malignancies); MRE11 (e.g., involved in HRR, e.g., in breast cancer); BLM (e.g., involved in HRR, e.g., in leukemia, lymphoma, colon, breast, skin, auditory canal, tongue, esophagus, stomach, tonsil, larynx, lung, and uterus cancer); WRN (e.g., involved in HRR, NHEJ, long-patch BER, e.g., in soft tissue sarcomas, colorectal, skin, thyroid, and pancreatic cancer); RECQ4 (RECQL4) (e.g., involved in HRR, e.g., causing Rothmund-Thomson syndrome (RTS), RAPADILINO syndrome or Baller Gerold syndrome, cutaneous carcinomas, including basal cell carcinoma, squamous cell carcinoma, and Bowen's disease); FANCA, FANCB, FANCC, FANCD1, FANCD2, FANCE, FANCF, FANCG, FANCI, FANCJ, FANCL, FANCM, and FANCN (e.g., involved in HRR and TLS, e.g., in leukemia, liver tumors, solid tumors in many locations), XPC and XPE(DDB2) (e.g., involved in NER(GGR type), e.g., in skin cancer (melanoma and non-melanoma)); XPA, XPB, XPD, XPF, and XPG (e.g., involved in NER (both GGR type and TCR type), e.g., in skin cancer (melanoma and non-melanoma) and central nervous system); XPV(POLH) (e.g., involved in TLS, e.g., in skin cancer (melanoma and non-melanoma)); hMSH2, hMSH6, hMLH1, and hPMS2 (involved in MMR, e.g., in colorectal, endometrial and ovarian cancer); MUTYH (e.g., involved in BER of A mispaired with 8OH-dG, as well as mispairs with G, FapydG and C, e.g., in colon cancer)

Modulators can be used to treat a disease or condition associated with aberrant DNA damage repair, e.g., by modulating one or more DNA damage repair mechanisms described herein.

In an embodiment, the modulator is selected from, or modulates, one or more proteins involved in direct reversal, e.g., methyl guanine methyl transferase (MGMT).

In an embodiment, the modulator is selected from, or modulates, one or more proteins involved in BER, e.g., DNA glycosylase, AP endonuclease, DNA polymerase, DNA ligase.

In an embodiment, the modulator is selected from, or modulates, one or more proteins involved in GG-NER, e.g., XPC, HR23b, CAK, TFIIH, XPA, RPA, XPG, XPF, ERCC1, TFIIH, PCNA, RFC, ADN Pol, and Ligase I.

In an embodiment, the modulator is selected from, or modulates, one or more proteins involved in TC-NER, e.g., CSB, XPA, RPA, XPG, XPF, ERCC1, CSA-CNS, TFIIH, CAK, PCNA, RFC, Ligase I, and RNA Polymerase II.

In an embodiment, the modulator is selected from, or modulates, one or more DNA mismatch repair proteins.

In an embodiment, the modulator is selected from, or modulates, one or more proteins involved in NHEJ, e.g., Ku70/80, DNA-PKcs, DNA Ligase IV, XRCC4, XLF, Artemis, DNA polymerase mu, DNA polymerase lambda, PNKP, Aprataxin, and APLF.

In an embodiment, the modulator is selected from, or modulates, one or more proteins involved in homologous recombination, e.g., as described herein.

In an embodiment, the modulator is selected from, or modulates, one or more proteins involved in TLS, e.g., DNA polymerase eta, iota, kappa, zeta, and PCNA.

In an embodiment, a modulator can modulate global response to DNA damage, e.g., DNA damage checkpoints and/or transcriptional responses to DNA damage. For example, DNA damage checkpoints can occur at the G1/S and G2/M boundaries. An intra-S checkpoint can also exist. Checkpoint activation can be modulated by two master kinases, ATM and ATR. ATM can respond to DNA double-strand breaks and disruptions in chromatin structure and ATR can respond to stalled replication forks. These kinases can phosphorylate downstream targets in a signal transduction cascade, e.g., leading to cell cycle arrest. A class of checkpoint mediator proteins (e.g., BRCA1, MDC1, and 53BP1), which transmit the checkpoint activation signal to downstream proteins, can be modulated. Exemplary downstream proteins that can be modulated include, e.g., p53, p21, and cyclin/cyclin-dependent kinase complexes.

In an embodiment, the modulator modulates nuclear DNA damage response and repair. In an embodiment, the modulator modulates mitochondrial DNA damage response and repair.

In an embodiment, the modulator promotes or inhibits DNA replication. For example, a modulator can promote or inhibit one or more stages of DNA replication, e.g., initiation (e.g., assembly of pre-replicative complex and/or initiation complex), elongation (e.g., formation of replication fork), and termination (e.g., formation of replication fork barrier). In an embodiment, the modulator is selected from, or modulates, one or more proteins involved in initiation, e.g., the origin recognition complex (ORC), CDC6, CDT1, minichromosome maintenance proteins (e.g., MCM2, MCM3, MCM4, MCM5, MCM6, MCM7, and MCM10), CDC45, CDK, DDK, CDC101, CDC102, CDC103, and CDC105. In an embodiment, the modulator is selected from, or modulates, one or more proteins involved in elongation, e.g., DNA helicases, DNA polymerase, PCNA, CDC45-MCM-GINS helicase complex, and Replication Factor C complex.

In an embodiment, the modulator is selected, from or modulates, one or more proteins involved in termination, e.g., type II topoisomerase and telomerase. In an embodiment, the modulator is selected from, or modulates, one or more replication checkpoint proteins, e.g., ATM, ATR, ATRIP, TOPBP1, RAD9, HUS1, Rad1, and CHK1.

In an embodiment, the payload comprises a modulator of nuclear DNA replication. In an embodiment, the modulator promotes or inhibits mitochondrial DNA replication.

Defects in DNA replication can be associated with various diseases and conditions, e.g., cancer and neurological diseases (e.g., Alzheimer's disease). Defects in mitochondrial DNA replication can also be associated with diseases and conditions, e.g., mtDNA depletion syndromes (e.g., Alpers or early infantile hepatocerebral syndromes) and mtDNA deletion disorders (e.g., progressive external ophthalmoplegia (PEO), ataxia-neuropathy, or mitochondrial neurogastrointestinal encephalomyopathy (MNGIE)). A modulator can be used to treat a disease or condition associated with aberrant DNA replication, e.g., by modulating DNA replication as described herein.

Exemplary endogenous or exogenous modulators of DNA structure are described herein, e.g., in Table VI-3.

TABLE VI-3

| | |
|---|---|
| DNA2 | DNA replication helicase/nuclease 2 |
| DNAAF1 | dynein, axonemal, assembly factor 1 |
| DNAAF2 | dynein, axonemal, assembly factor 2 |
| DNAAF3 | dynein, axonemal, assembly factor 3 |
| DNAH1 | dynein, axonemal, heavy chain 1 |
| DNAH2 | dynein, axonemal, heavy chain 2 |
| DNAH3 | dynein, axonemal, heavy chain 3 |
| DNAH5 | dynein, axonemal, heavy chain 5 |
| DNAH6 | dynein, axonemal, heavy chain 6 |
| DNAH7 | dynein, axonemal, heavy chain 7 |
| DNAH8 | dynein, axonemal, heavy chain 8 |
| DNAH9 | dynein, axonemal, heavy chain 9 |
| DNAH10 | dynein, axonemal, heavy chain 10 |
| DNAH10OS | dynein, axonemal, heavy chain 10 opposite strand |
| DNAH11 | dynein, axonemal, heavy chain 11 |
| DNAH12 | dynein, axonemal, heavy chain 12 |
| DNAH14 | dynein, axonemal, heavy chain 14 |
| DNAH17 | dynein, axonemal, heavy chain 17 |
| DNAH17-AS1 | DNAH17 antisense RNA 1 |
| DNAI1 | dynein, axonemal, intermediate chain 1 |
| DNAI2 | dynein, axonemal, intermediate chain 2 |
| DNAJB8-AS1 | DNAJB8 antisense RNA 1 |
| DNAJC3-AS1 | DNAJC3 antisense RNA 1 (head to head) |
| DNAJC9-AS1 | DNAJC9 antisense RNA 1 |
| DNAJC25-GNG10 | DNAJC25-GNG10 readthrough |
| DNAJC27-AS1 | DNAJC27 antisense RNA 1 |
| DNAL1 | dynein, axonemal, light chain 1 |
| DNAL4 | dynein, axonemal, light chain 4 |
| DNALI1 | dynein, axonemal, light intermediate chain 1 |
| DNASE1 | deoxyribonuclease I |
| DNASE1L1 | deoxyribonuclease I-like 1 |
| DNASE1L2 | deoxyribonuclease I-like 2 |
| DNASE1L3 | deoxyribonuclease I-like 3 |
| DNASE2 | deoxyribonuclease II, lysosomal |
| DNASE2B | deoxyribonuclease II beta |
| CD226 | CD226 molecule |
| FAM120A | family with sequence similarity 120A |
| GAK | cyclin G associated kinase |
| GCFC2 | GC-rich sequence DNA-binding factor 2 |
| MCM10 | minichromosome maintenance complex component 10 |
| PRKDC | protein kinase, DNA-activated, catalytic polypeptide |
| SACS | spastic ataxia of Charlevoix-Saguenay (sacsin) |
| SCNN1D | sodium channel, non-voltage-gated 1, delta subunit |
| SPATS2L | spermatogenesis associated, serine-rich 2-like |
| MT7SDNA | mitochondrially encoded 7S DNA |
| DCLRE1A | DNA cross-link repair 1A |
| DCLRE1B | DNA cross-link repair 1B |
| DCLRE1C | DNA cross-link repair 1C |
| DDIT3 | DNA-damage-inducible transcript 3 |
| DDIT4 | DNA-damage-inducible transcript 4 |
| DDIT4L | DNA-damage-inducible transcript 4-like |
| DFFA | DNA fragmentation factor, 45 kDa, alpha polypeptide |
| DFFB | DNA fragmentation factor, 40 kDa, beta polypeptide (caspase-activated DNase) |
| DMAP1 | DNA methyltransferase 1 associated protein 1 |
| DMC1 | DNA meiotic recombinase 1 |
| DNMT1 | DNA (cytosine-5-)-methyltransferase 1 |
| DNMT3A | DNA (cytosine-5-)-methyltransferase 3 alpha |
| DNMT3B | DNA (cytosine-5-)-methyltransferase 3 beta |
| DNMT3L | DNA (cytosine-5-)-methyltransferase 3-like |
| DNTT | DNA nucleotidylexotransferase |
| DRAM1 | DNA-damage regulated autophagy modulator 1 |
| DRAM2 | DNA-damage regulated autophagy modulator 2 |
| DSCC1 | DNA replication and sister chromatid cohesion 1 |
| ZBP1 | Z-DNA binding protein 1 |
| SON | SON DNA binding protein |
| TARDBP | TAR DNA binding protein |
| BMF | Bcl2 modifying factor |

TABLE VI-3-continued

| | |
|---|---|
| CENPBD1 | CENPB DNA-binding domains containing 1 |
| UNG | uracil-DNA glycosylase |
| PDRG1 | p53 and DNA-damage regulated 1 |
| TDG | thymine-DNA glycosylase |
| TDP1 | tyrosyl-DNA phosphodiesterase 1 |
| TDP2 | tyrosyl-DNA phosphodiesterase 2 |
| AHDC1 | AT hook, DNA binding motif, containing 1 |
| GMNN | geminin, DNA replication inhibitor |
| PRIM1 | primase, DNA, polypeptide 1 (49 kDa) |
| PRIM2 | primase, DNA, polypeptide 2 (58 kDa) |
| HELB | helicase (DNA) B |
| LIG1 | ligase I, DNA, ATP-dependent |
| SUMF1 | sulfatase modifying factor 1 |
| SUMF2 | sulfatase modifying factor 2 |
| LIG4 | ligase IV, DNA, ATP-dependent |
| LIG3 | ligase III, DNA, ATP-dependent |
| MDC1 | mediator of DNA-damage checkpoint 1 |
| MMS22L | MMS22-like, DNA repair protein |
| POLA1 | polymerase (DNA directed), alpha 1, catalytic subunit |
| POLA2 | polymerase (DNA directed), alpha 2, accessory subunit |
| POLB | polymerase (DNA directed), beta |
| POLD1 | polymerase (DNA directed), delta 1, catalytic subunit |
| POLD2 | polymerase (DNA directed), delta 2, accessory subunit |
| POLD3 | polymerase (DNA-directed), delta 3, accessory subunit |
| POLD4 | polymerase (DNA directed), delta 4, accessory subunit |
| POLDIP2 | polymerase (DNA-directed), delta interacting protein 2 |
| POLDIP3 | polymerase (DNA-directed), delta interacting protein 3 |
| POLE | polymerase (DNA directed), epsilon, catalytic subunit |
| POLE2 | polymerase (DNA directed), epsilon 2, accessory subunit |
| POLE3 | polymerase (DNA directed), epsilon 3, accessory subunit |
| POLE4 | polymerase (DNA-directed), epsilon 4, accessory subunit |
| POLG | polymerase (DNA directed), gamma |
| POLG2 | polymerase (DNA directed), gamma 2, accessory subunit |
| POLH | polymerase (DNA directed), eta |
| POLI | polymerase (DNA directed) iota |
| POLK | polymerase (DNA directed) kappa |
| POLL | polymerase (DNA directed), lambda |
| POLM | polymerase (DNA directed), mu |
| POLN | polymerase (DNA directed) nu |
| POLQ | polymerase (DNA directed), theta |
| ID1 | inhibitor of DNA binding 1, dominant negative helix-loop-helix protein |
| ID2 | inhibitor of DNA binding 2, dominant negative helix-loop-helix protein |
| ID3 | inhibitor of DNA binding 3, dominant negative helix-loop-helix protein |
| ID4 | inhibitor of DNA binding 4, dominant negative helix-loop-helix protein |
| OGG1 | 8-oxoguanine DNA glycosylase |
| MSANTD1 | Myb/SANT-like DNA-binding domain containing 1 |
| MSANTD2 | Myb/SANT-like DNA-binding domain containing 2 |
| MSANTD3 | Myb/SANT-like DNA-binding domain containing 3 |
| MSANTD4 | Myb/SANT-like DNA-binding domain containing 4 with coiled-coils |
| PIF1 | PIF1 5'-to-3' DNA helicase |
| TONSL | tonsoku-like, DNA repair protein |
| MPG | N-methylpurine-DNA glycosylase |
| TOP1 | topoisomerase (DNA) I |
| TOP1MT | topoisomerase (DNA) I, mitochondrial |
| TOP2A | topoisomerase (DNA) II alpha 170 kDa |
| TOP2B | topoisomerase (DNA) II beta 180 kDa |
| TOP3A | topoisomerase (DNA) III alpha |
| TOP3B | topoisomerase (DNA) III beta |
| TOPBP1 | topoisomerase (DNA) II binding protein 1 |
| DDB1 | damage-specific DNA binding protein 1, 127 kDa |
| DDB2 | damage-specific DNA binding protein 2, 48 kDa |
| SSBP1 | single-stranded DNA binding protein 1, mitochondrial |
| SSBP2 | single-stranded DNA binding protein 2 |
| SSBP3 | single stranded DNA binding protein 3 |
| SSBP4 | single stranded DNA binding protein 4 |
| GADD45A | growth arrest and DNA-damage-inducible, alpha |
| GADD45B | growth arrest and DNA-damage-inducible, beta |
| GADD45G | growth arrest and DNA-damage-inducible, gamma |
| GADD45GIP1 | growth arrest and DNA-damage-inducible, gamma interacting protein 1 |
| MGMT | O-6-methylguanine-DNA methyltransferase |
| REV1 | REV1, polymerase (DNA directed) |
| RECQL | RecQ protein-like (DNA helicase Q1-like) |
| CCDC6 | coiled-coil domain containing 6 |
| KLRK1 | killer cell lectin-like receptor subfamily K, member 1 |
| N6AMT1 | N-6 adenine-specific DNA methyltransferase 1 (putative) |
| N6AMT2 | N-6 adenine-specific DNA methyltransferase 2 (putative) |
| POLR2A | polymerase (RNA) II (DNA directed) polypeptide A, 220 kDa |
| POLR2B | polymerase (RNA) II (DNA directed) polypeptide B, 140 kDa |
| POLR2C | polymerase (RNA) II (DNA directed) polypeptide C, 33 kDa |
| POLR2D | polymerase (RNA) II (DNA directed) polypeptide D |

TABLE VI-3-continued

| | |
|---|---|
| POLR2E | polymerase (RNA) II (DNA directed) polypeptide E, 25 kDa |
| POLR2F | polymerase (RNA) II (DNA directed) polypeptide F |
| POLR2G | polymerase (RNA) II (DNA directed) polypeptide G |
| POLR2H | polymerase (RNA) II (DNA directed) polypeptide H |
| POLR2I | polymerase (RNA) II (DNA directed) polypeptide I, 14.5 kDa |
| POLR2J | polymerase (RNA) II (DNA directed) polypeptide J, 13.3 kDa |
| POLR2J2 | polymerase (RNA) II (DNA directed) polypeptide J2 |
| POLR2J3 | polymerase (RNA) II (DNA directed) polypeptide J3 |
| POLR2K | polymerase (RNA) II (DNA directed) polypeptide K, 7.0 kDa |
| POLR2L | polymerase (RNA) II (DNA directed) polypeptide L, 7.6 kDa |
| POLR2M | polymerase (RNA) II (DNA directed) polypeptide M |
| TRDMT1 | tRNA aspartic acid methyltransferase 1 |
| CHD1 | chromodomain helicase DNA binding protein 1 |
| CHD1L | chromodomain helicase DNA binding protein 1-like |
| CHD2 | chromodomain helicase DNA binding protein 2 |
| CHD3 | chromodomain helicase DNA binding protein 3 |
| CHD4 | chromodomain helicase DNA binding protein 4 |
| CHD5 | chromodomain helicase DNA binding protein 5 |
| CHD6 | chromodomain helicase DNA binding protein 6 |
| CHD7 | chromodomain helicase DNA binding protein 7 |
| CHD8 | chromodomain helicase DNA binding protein 8 |
| CHD9 | chromodomain helicase DNA binding protein 9 |
| KLLN | killin, p53-regulated DNA replication inhibitor |
| POLR3A | polymerase (RNA) III (DNA directed) polypeptide A, 155 kDa |
| POLR3B | polymerase (RNA) III (DNA directed) polypeptide B |
| POLR3C | polymerase (RNA) III (DNA directed) polypeptide C (62 kD) |
| POLR3D | polymerase (RNA) III (DNA directed) polypeptide D, 44 kDa |
| POLR3E | polymerase (RNA) III (DNA directed) polypeptide E (80 kD) |
| POLR3F | polymerase (RNA) III (DNA directed) polypeptide F, 39 kDa |
| POLR3G | polymerase (RNA) III (DNA directed) polypeptide G (32 kD) |
| POLR3GL | polymerase (RNA) III (DNA directed) polypeptide G (32 kD)-like |
| POLR3H | polymerase (RNA) III (DNA directed) polypeptide H (22.9 kD) |
| POLR3K | polymerase (RNA) III (DNA directed) polypeptide K, 12.3 kDa |
| WDHD1 | WD repeat and HMG-box DNA binding protein 1 |
| PGAP1 | post-GPI attachment to proteins 1 |
| PGAP2 | post-GPI attachment to proteins 2 |
| PGAP3 | post-GPI attachment to proteins 3 |
| REV3L | REV3-like, polymerase (DNA directed), zeta, catalytic subunit |
| CDT1 | chromatin licensing and DNA replication factor 1 |
| PANDAR | promoter of CDKN1A antisense DNA damage activated RNA |
| APEX1 | APEX nuclease (multifunctional DNA repair enzyme) 1 |
| CHMP1A | charged multivesicular body protein 1A |
| CHMP1B | charged multivesicular body protein 1B |
| CHMP2A | charged multivesicular body protein 2A |
| CHMP2B | charged multivesicular body protein 2B |
| CHMP4A | charged multivesicular body protein 4A |
| CHMP4B | charged multivesicular body protein 4B |
| CHMP4C | charged multivesicular body protein 4C |
| CHMP5 | charged multivesicular body protein 5 |
| CHMP6 | charged multivesicular body protein 6 |
| POLRMT | polymerase (RNA) mitochondrial (DNA directed) |
| SPIDR | scaffolding protein involved in DNA repair |
| MCIDAS | multiciliate differentiation and DNA synthesis associated cell cycle protein |
| PAPD7 | PAP associated domain containing 7 |
| RFX8 | RFX family member 8, lacking RFX DNA binding domain |
| DEK | DEK oncogene |
| NUB1 | negative regulator of ubiquitin-like proteins 1 |
| PAXBP1 | PAX3 and PAX7 binding protein 1 |
| RAMP1 | receptor (G protein-coupled) activity modifying protein 1 |
| RAMP2 | receptor (G protein-coupled) activity modifying protein 2 |
| RAMP3 | receptor (G protein-coupled) activity modifying protein 3 |
| RC3H2 | ring finger and CCCH-type domains 2 |
| ARHGAP35 | Rho GTPase activating protein 35 |
| SMUG1 | single-strand-selective monofunctional uracil-DNA glycosylase 1 |
| CXXC1 | CXXC finger protein 1 |
| FAM50A | family with sequence similarity 50, member A |
| FANCG | Fanconi anemia, complementation group G |
| GLI3 | GLI family zinc finger 3 |
| GTF2H5 | general transcription factor IIH, polypeptide 5 |
| LAGE3 | L antigen family, member 3 |
| MYCNOS | MYCN opposite strand/antisense RNA |
| NFRKB | nuclear factor related to kappaB binding protein |
| RAD51D | RAD51 paralog D |
| RFX2 | regulatory factor X, 2 (influences HLA class II expression) |
| RFXANK | regulatory factor X-associated ankyrin-containing protein |
| RRP1 | ribosomal RNA processing 1 |
| SPRTN | SprT-like N-terminal domain |
| XRCC4 | X-ray repair complementing defective repair in Chinese hamster cells 4 |
| CDK11A | cyclin-dependent kinase 11A |
| CDK11B | cyclin-dependent kinase 11B |

TABLE VI-3-continued

| | |
|---|---|
| LURAP1L | leucine rich adaptor protein 1-like |
| MAD2L2 | MAD2 mitotic arrest deficient-like 2 (yeast) |
| PRDM2 | PR domain containing 2, with ZNF domain |
| NABP2 | nucleic acid binding protein 2 |
| NABP1 | nucleic acid binding protein 1 |
| PPP1R15A | protein phosphatase 1, regulatory subunit 15A |
| TATDN1 | TatD DNase domain containing 1 |
| TATDN2 | TatD DNase domain containing 2 |
| TATDN3 | TatD DNase domain containing 3 |
| CEBPB | CCAAT/enhancer binding protein (C/EBP), beta |
| INIP | INTS3 and NABP interacting protein |
| INTS3 | integrator complex subunit 3 |
| SDIM1 | stress responsive DNAJB4 interacting membrane protein 1 |
| DHX9 | DEAH (Asp-Glu-Ala-His) (SEQ ID NO: 39) box helicase 9 |
| SATB1 | SATB homeobox 1 |
| FEN1 | flap structure-specific endonuclease 1 |
| HCST | hematopoietic cell signal transducer |
| TYROBP | TYRO protein tyrosine kinase binding protein |
| AFA | ankyloblepharon filiforme adnatum |
| C9orf169 | chromosome 9 open reading frame 169 |
| TSPO2 | translocator protein 2 |
| TCIRG1 | T-cell, immune regulator 1, ATPase, H+ transporting, lysosomal V0 subunit A3 |
| C1orf61 | chromosome 1 open reading frame 61 |
| HLA-DOA | major histocompatibility complex, class II, DO alpha |
| SPINK13 | serine peptidase inhibitor, Kazal type 13 (putative) |

In an embodiment, the payload comprises a modulator of an epigenetic state or characteristic of a component of chromatin, e.g., a chromatin associated protein, e.g., a histone. For example, the epigenetic state or characteristic can comprise histone acetylation, deacetylation, methylation (e.g., mono, di, or tri-methylation), demethylation, phosphorylation, dephosphorylation, ubiquitination (e.g., mono or polyubiquitination), deubiquitination, sumoylation, ADP-ribosylation, deimination, or a combination thereof.

In an embodiment, the modulator is selected from, or modulates, one or more histone modifying enzymes. In an embodiment, the histone modifying enzyme is a histone methyltransferase (HMT). In an embodiment, the histone modifying enzyme is a histone demethyltransferase (HDMT). In an embodiment, the histone modification enzyme is a histone acetyltransferase (HAT). In an embodiment, the histone modifying enzyme is a histone deacetylase (HDAC). In an embodiment, the histone modification enzyme is a kinase. In an embodiment, the histone modifying enzyme is a phosphatase. In an embodiment, the histone modifying enzyme is ubiquitin-activating enzymes (E1s), ubiquitin-conjugating enzymes (E2s), or ubiquitin ligases (E3s). In an embodiment, the histone modifying enzyme is a deubiquitinating (DUB) enzyme.

In an embodiment, histone modifications involved in regulation of gene transcription are modulated. For example, mono-methylation of H3K4, H3K9, H3K27, H3K79, H4K20, H2BK5, di-methylation of H3K79, tri-methylation of H3K4, H3K79, H3K36, and acetylation of H3K9, H3K14, H3K27, can be associated with transcription activation. As another example, di-methylation of H3K9, H3K27, and tri-methylation of H3K9, H3K27, H3K79, H2BK5 can be associated with transcription repression. In an embodiment, the modulator modulates trimethylation of H3 lysine 4 (H3K4Me3) and/or trimethylation of H3 lysine 36 (H3K36Me3), e.g., in active genes. In an embodiment, the modulator modulates trimethylation of H3 lysine 27 (H3K27Me3), di- and tri-methylation of H3 lysine 9 (H3K9Me2/3), and/or trimethylation of H4 lysine 20 (H4K20Me3), e.g., in repressed genes. In an embodiment, the modulator modulates both activating (e.g., H3K4Me3) and repressing (e.g., H3K27Me3) marks, e.g., in stem cells.

In an embodiment, histone modifications involved in DNA damage response and repair are modulated. For example, the modulators described herein can modulate phosphorylation of H2AX at Serine 139 and/or acetylation of H3 lysine 56 (H3K56Ac).

Aberrant histone modifications are associated with various diseases and conditions, e.g., cancer, cardiovascular disease, and neurodegenerative disorder. The modulators described herein can be used to treat a disease or condition described herein, e.g., by modulating one or more histone modifications, as described herein.

Epigenetic changes in histones can be evaluated by art-known methods or as described herein. Exemplary methods for detecting histone modifications include, e.g., chromatin immunoprecipitation (ChIP) using antibodies against modified histones, e.g., followed by quantitative PCR.

Exemplary endogenous or exogenous modulators of chromatin structure are described herein, e.g., in Table VI-4.

TABLE VI-4

| Approved Symbol | Approved Name | Synonyms | Ref Seq IDs |
|---|---|---|---|
| SUV39H1 | suppressor of variegation 3-9 homolog 1 (*Drosophila*) | KMT1A | NM_003173 |
| SUV39H2 | suppressor of variegation 3-9 homolog 2 (*Drosophila*) | FLJ23414, KMT1B | NM_024670 |
| EHMT2 | euchromatic histone-lysine N-methyltransferase 2 | G9A, Em: AF134726.3, NG36/G9a, KMT1C | NM_006709 |
| EHMT1 | euchromatic histone-lysine N-methyltransferase 1 | Eu-HMTase1, FLJ12879, KIAA1876, | NM_024757 |

TABLE VI-4-continued

| Approved Symbol | Approved Name | Synonyms | Ref Seq IDs |
|---|---|---|---|
| SETDB1 | SET domain, bifurcated 1 | bA188C12.1, KMT1D KG1T, KIAA0067, ESET, KMT1E, TDRD21 | |
| SETDB2 | SET domain, bifurcated 2 | CLLD8, CLLL8, KMT1F | NM_031915 |
| KMT2A | lysine (K)-specific methyltransferase 2A | TRX1, HRX, ALL-1, HTRX1, CXXC7, MLL1A | NM_005933 |
| KMT2B | lysine (K)-specific methyltransferase 2B | KIAA0304, MLL2, TRX2, HRX2, WBP7, MLL1B, MLL4 | NM_014727 |
| KMT2C | lysine (K)-specific methyltransferase 2C | KIAA1506, HALR | |
| KMT2D | lysine (K)-specific methyltransferase 2D | ALR, MLL4, CAGL114 | |
| KMT2E | lysine (K)-specific methyltransferase 2E | HDCMC04P | |
| SETD1A | SET domain containing 1A | KIAA0339, Set1, KMT2F | NM_014712 |
| SETD1B | SET domain containing 1B | KIAA1076, Set1B, KMT2G | XM_037523 |
| ASH1L | ash1 (absent, small, or homeotic)-like (*Drosophila*) | huASH1, ASH1, ASH1L1, KMT2H | NM_018489 |
| SETD2 | SET domain containing 2 | HYPB, HIF-1, KIAA1732, FLJ23184, KMT3A | NM_014159 |
| NSD1 | nuclear receptor binding SET domain protein 1 | ARA267, FLJ22263, KMT3B | NM_172349 |
| SMYD2 | SET and MYND domain containing 2 | HSKM-B, ZMYND14, KMT3C | NM_020197 |
| SMYD1 | SET and MYND domain containing 1 | BOP, ZMYND22, KMT3D | XM_097915 |
| SMYD3 | SET and MYND domain containing 3 | KMT3E | NM_022743 |
| DOT1L | DOT1-like histone H3K79 methyltransferase | KIAA1814, DOT1, KMT4 | NM_032482 |
| SETD8 | SET domain containing (lysine methyltransferase) 8 | SET8, SET07, PR-Set7, KMT5A | NM_020382 |
| SUV420H1 | suppressor of variegation 4-20 homolog 1 (*Drosophila*) | CGI-85, KMT5B | NM_017635 |
| SUV420H2 | suppressor of variegation 4-20 homolog 2 (*Drosophila*) | MGC2705, KMT5C | NM_032701 |
| EZH2 | enhancer of zeste homolog 2 (*Drosophila*) | EZH1, ENX-1, KMT6, KMT6A | |
| EZH1 | enhancer of zeste homolog 1 (*Drosophila*) | KIAA0388, KMT6B | NM_001991 |
| SETD7 | SET domain containing (lysine methyltransferase) 7 | KIAA1717, SET7, SET7/9, Set9, KMT7 | NM_030648 |
| PRDM2 | PR domain containing 2, with ZNF domain | RIZ, RIZ1, RIZ2, KMT8, MTB-ZF, HUMHOXY1 | NM_012231 |
| HAT1 | histone acetyltransferase 1 | KAT1 | NM_003642 |
| KAT2A | K(lysine) acetyltransferase 2A | GCN5, PCAF-b | NM_021078 |
| KAT2B | K(lysine) acetyltransferase 2B | P/CAF, GCN5, GCN5L | NM_003884 |
| CREBBP | CREB binding protein | RTS, CBP, KAT3A | NM_004380 |
| EP300 | E1A binding protein p300 | p300, KAT3B | NM_001429 |
| TAF1 | TAF1 RNA polymerase II, TATA box binding protein (TBP)-associated factor, 250 kDa | NSCL2, TAFII250, KAT4, DYT3/TAF1 | NM_004606 |
| KAT5 | K(lysine) acetyltransferase 5 | TIP60, PLIP, cPLA2, HTATIP1, ESA1, ZC2HC5 | NM_006388 |
| KAT6A | K(lysine) acetyltransferase 6A | MOZ, ZC2HC6A | NM_006766 |
| KAT6B | K(lysine) acetyltransferase 6B | querkopf, qkf, Morf, MOZ2, ZC2HC6B | NM_012330 |
| KAT7 | K(lysine) acetyltransferase 7 | HBOA, HBO1, ZC2HC7 | NM_007067 |
| KAT8 | K(lysine) acetyltransferase 8 | MOF, FLJ14040, hMOF, ZC2HC8 | NM_032188 |
| ELP3 | elongator acetyltransferase complex subunit 3 | FLJ10422, KAT9 | NM_018091 |
| GTF3C4 | general transcription factor IIIC, polypeptide 4, 90 kDa | TFIIIC90, KAT12 | |
| NCOA1 | nuclear receptor coactivator 1 | SRC1, F-SRC-1, NCoA-1, KAT13A, RIP160, bHLHe74 | NM_147223 |
| NCOA3 | nuclear receptor coactivator 3 | RAC3, AIB1, ACTR, p/CIP, TRAM-1, CAGH16, TNRC16, KAT13B, bHLHe42, SRC-3, SRC3 | NM_006534 |
| NCOA2 | nuclear receptor coactivator 2 | TIF2, GRIP1, NCoA-2, KAT13C, bHLHe75 | |
| CLOCK | clock circadian regulator | KIAA0334, KAT13D, bHLHe8 | NM_004898 |
| KDM1A | lysine (K)-specific demethylase 1A | KIAA0601, BHC110, LSD1 | NM_015013 |
| KDM1B | lysine (K)-specific demethylase 1B | FLJ34109, FLJ33898, dJ298J15.2, bA204B7.3, FLJ43328, LSD2 | NM_153042 |
| KDM2A | lysine (K)-specific demethylase 2A | KIAA1004, FBL11, LILINA, DKFZP434M1735, FBL7, FLJ00115, CXXC8, JHDM1A | NM_012308 |
| KDM2B | lysine (K)-specific demethylase 2B | PCCX2, CXXC2, Fbl10, | NM_032590 |

TABLE VI-4-continued

| Approved Symbol | Approved Name | Synonyms | Ref Seq IDs |
|---|---|---|---|
| | | JHDM1B | |
| KDM3A | lysine (K)-specific demethylase 3A | TSGA, KIAA0742, JHMD2A | NM_018433 |
| KDM3B | lysine (K)-specific demethylase 3B | KIAA1082, NET22 | NM_016604 |
| KDM4A | lysine (K)-specific demethylase 4A | KIAA0677, JHDM3A, TDRD14A | NM_014663 |
| KDM4B | lysine (K)-specific demethylase 4B | KIAA0876, TDRD14B | NM_015015 |
| KDM4C | lysine (K)-specific demethylase 4C | GASC1, KIAA0780, TDRD14C | NM_015061 |
| KDM4D | lysine (K)-specific demethylase 4D | FLJ10251 | NM_018039 |
| KDM4E | lysine (K)-specific demethylase 4E | JMJD2E | NM_001161630 |
| KDM5A | lysine (K)-specific demethylase 5A | | NM_005056 |
| KDM5B | lysine (K)-specific demethylase 5B | RBBP2H1A, PLU-1, CT31 | NM_006618 |
| KDM5C | lysine (K)-specific demethylase 5C | DXS1272E, XE169 | NM_004187 |
| KDM5D | lysine (K)-specific demethylase 5D | KIAA0234 | NM_004653 |
| KDM6A | lysine (K)-specific demethylase 6A | | NM_021140 |
| KDM6B | lysine (K)-specific demethylase 6B | KIAA0346 | XM_043272 |
| JHDM1D | jumonji C domain containing histone demethylase 1 homolog D (S. cerevisiae) | KIAA1718 | NM_030647 |
| PHF8 | PHD finger protein 8 | ZNF422, KIAA1111, JHDM1F | NM_015107 |
| PHF2 | PHD finger protein 2 | KIAA0662, JHDM1E, CENP-35 | NM_005392 |
| KDM8 | lysine (K)-specific demethylase 8 | FLJ13798 | NM_024773 |

Modulators of Gene Expression

In an embodiment a payload comprises a modulator of gene expression. A modulator of gene expression can be delivered in vitro, ex vivo, or in vivo.

In an embodiment, the payload comprises a transcription factor. Transcription factors can bind to specific DNA sequences (e.g., an enhancer or promoter region) adjacent to the genes that they regulate. For example, transcription factors can stabilize or inhibit the binding of RNA polymerase to DNA, catalyze the acetylation or deacetylation of histone proteins (e.g., directly or by recruiting other proteins with such catalytic activity), or recruit coactivator or corepressor proteins to the transcription factor/DNA complex. Modulators of gene expression also include, e.g., any proteins that interact with transcription factors directly or indirectly.

In an embodiment, the transcription factor is a general transcription factor, e.g., is ubiquitous and interacts with the core promoter region surrounding the transcription start site(s) of many, most or all class II genes. Exemplary general transcription factors include, e.g., TFIIA, TFIIB, TFIID, TFIIE, TFIIF, and TFIIH. In an embodiment, the transcription factor is an upstream transcription factor, e.g., binds upstream of the initiation site to stimulate or repress transcription. In an embodiment, the transcription factor is a specific transcription factor, e.g., a transcription factor dependent on a recognition sequence present in the proximity of the gene. Exemplary specific transcription factors include, e.g., SP1, AP-1, C/EBP, heat shock factor, ATF/CREB, -Myc, OCT-1, and NF-1.

In an embodiment, the transcription factor is constitutively active, e.g., a general transcription factor, SP1, NF-1, or CCAAT. In an embodiment, the transcription factor is conditionally active, e.g. it requires activation, e.g., developmental (e.g., GATA, HNF, PIT-1, MyoD, Myf5, Hox, Winged Helix), signal-dependent (e.g., extracellular ligand (endocrine or paracrine)-dependent, intracellular ligand (autocrine)-dependent (e.g., SREBP, p53, orphan nuclear receptors), cell membrane receptor-dependent (e.g., resident nuclear factors (e.g., CREB, AP-1, Mef2) or latent cytoplasmic factors (e.g., STAT, R-SMAD, NF-κB, Notch, TUBBY, NFAT).

Other exemplary transcription factors are described herein, e.g., in Table VI-5.

TABLE VI-5

Selected Transcription Factors with Anotations

| Transcription factor family (# genes/family) | Comments |
|---|---|
| AF-4(4) | Exemplary diseases include acute lymphoblastic leukemia (AF4 and AFF3) and mental retardation (FMR2). |
| CBF(1) | Exemplary functions include regulator of hematopoiesis. For example, CBF is also involved in the chondrocyte differentiation and ossification. |
| CSL(2) | Exemplary functions include universal transcriptional effector of Notch signaling. For example, Notch signaling is dysregulated in many cancers and faulty notch signaling is implicated in many diseases. Exemplary disease include T-ALL (T-cell acute lymphoblastic leukemia), CADASIL (Cerebral Autosomal-Dominant Arteriopathy with Sub-cortical Infarcts and Leukoencephalopathy), MS (Multiple Sclerosis), Tetralogy of Fallot, Alagille syndrome. |
| ETS(29) | Exemplary functions include regulation of cellular differentiation, cell cycle control, cell migration, cell proliferation, apoptosis (programmed cell death) and angiogenesis. Exemplary diseases include dieases associated with cancer, such as through gene fusion, e.g., prostate cancer. |
| HMGI/HMGY(2) | Overexpression in certain cancers |

TABLE VI-5-continued

Selected Transcription Factors with Anotations

| Transcription factor family (# genes/family) | Comments |
|---|---|
| MH1(8) | Exemplary diseases include cancer, fibrosis and autoimmune diseases. |
| Nuclear orphan receptor(3) | Exemplary functions include superfamily of transcription regulators that are involved in widely diverse physiological functions, including control of embryonic development, cell differentiation and homeostasis. Exemplary diseases include inflammation, cancer, and metabolic disorders. |
| PC4(1) | Exemplary functions include replication, DNA repair and transcription. |
| RFX(8) | Exemplary functions include regulation of development and function of cilia. Exemplary diseases include Bardet-Biedl syndrome. |
| STAT(7) | Exemplary functions include regulation of many aspects of growth, survival and differentiation in cells. Exemplary diseases include angiogenesis, enhanced survival of tumors and immunosuppression. |
| Thyroid hormone receptor(25) | Involved in widely diverse physiological functions, including control of embryonic development, cell differentiation and homeostasis |
| zf-C2HC(6) | Highly transcribed in the developing nervous system. Exemplary diseases include Duane Radial Ray Syndrome. |
| Androgen receptor(1) | Exemplary functions include diverse physiological functions, including control of embryonic development, cell differentiation and homeostasis. Exemplary diseases include X-linked spinal, bulbar muscular atrophy and prostate cancer. |
| CG-1(2) | Exemplary functions include calcium signaling by direct binding of calmodulin. |
| CTF/NFI(4) | Exemplary functions include both viral DNA replication and regulation of gene expression. Exemplary diseases include leukemia, juvenile myelomonocytic. |
| Fork head(49) | Involvement in early developmental decisions of cell fates during embryogenesis. Exemplary diseases include lymphedema-distichiasis, developmental verbal dyspraxia, autoimmune diseases. |
| Homeobox(205) | Exemplary functions include involvement in a wide range of critical activities during development. Exemplary diseases include limb malformations, eye disorders, and abnormal head, face, and tooth development. Additionally, increased or decreased activity of certain homeobox genes has been associated with several forms of cancer. |
| MYB(25) | Exemplary functions include regulator of proliferation, differentiation and cell fate. Exemplary diseases include cancer (e.g., oncogenic disease). |
| Oestrogen receptor(1) | Control of embryonic development, cell differentiation and homeostasis. Exemplary diseases include estrogen resistance, familial breast cancer, migrane, myocardial infaction. |
| POU(21) | Wide variety of functions, related to the function of the neuroendocrine system and the development of an organism. Exemplary diseases include non-syndromic deafness. |
| RHD(10) | Exemplary diseases include autoimmune arthritis, asthma, septic shock, lung fibrosis, glomerulonephritis, atherosclerosis, and AIDS. |

T-box(17)
TSC22(4)
zf-GATA(14)
AP-2(5)
COE(4)
CUT(7)
GCM(2)
HSF(8)
NDT80/PhoG(1)
Other nuclear receptor(2)
PPAR receptor(3)
ROR receptor(4)
TEA(4)
Tub(5)
zf-LITAF-like(2)
ARID(15)
COUP(3)
DM(7)
GCR(1)
HTH(2)
NF-YA(1)
Others(3)
Progesterone receptor(1)
Runt(3)
TF_bZIP(46)

TABLE VI-5-continued

Selected Transcription Factors with Anotations

| Transcription factor family (# genes/family) | Comments |
|---|---|
| ZBTB(48) | |
| zf-MIZ(7) | |
| bHLH(106) | |
| CP2(7) | |
| E2F(11) | |
| GTF2I(5) | |
| IRF(9) | |
| NF-YB/C(2) | |
| P53(3) | |
| Prox1(2) | |
| SAND(8) | |
| TF_Otx(3) | |
| zf-BED(5) | |
| zf-NF-X1(2) | |
| C/EBP(10) | |
| CSD(8) | |
| Ecdystd receptor(2) | |
| HMG(50) | |
| MBD(9) | |
| Nrf1(1) | |
| PAX(9) | |
| Retinoic acid receptor(7) | |
| SRF(6) | |
| THAP(12) | |
| zf-C2H2(634) | |
| CRX | Exemplary diseases include dominant cone-rod dystrophy. Repair mutation. |
| FOCX2 | Exemplary diseases include lymphedema-distichiasis. Repair mutation. |
| FOXP2 | Exemplary diseases include developmental verbal dyspraxia. Repair mutation. |
| FOXP3 | Exemplary diseases include autoimmune diseases. Repair mutation. |
| GAT4 | Exemplary diseases include congenital heart defects. Repair mutation. |
| HNF1 through HNF6 | Exemplary diseases include mature onset diabetes of the young (MODY), hepatic adenomas and renal cysts. Repair mutation. |
| LHX3 | Exemplary diseases include Pituitary disease. Repair mutation. |
| MECP2 | Exemplary diseases include Rett syndrome. Repair mutation. |
| MEF2A | Exemplary diseases include Coronary artery disease. Repair mutation. |
| NARA2 | Exemplary diseases include Parkinson disease. Repair mutation. |
| NF-κB Activation | Exemplary diseases include autoimmune arthritis, asthma, septic shock, lung fibrosis, glomerulonephritis, atherosclerosis, and AIDS. Repair mutation. |
| NF-κB Inhibition | Exemplary diseases include apoptosis, inappropriate immune cell development, and delayed cell growth. Repair mutation. |
| NIKX2-5 | Exemplary diseases include cardiac malformations and atrioventricular conduction abnormalities. |
| NOTCH1 | Exemplary diseases include aortic valve abnormalities. |

Modulators of Alternative Splicing

In an embodiment, the modulator of gene expression modulates splicing. For example, a modulator can modulate exon skipping or cassette exon, mutually exclusive exons, alternative donor site, alternative acceptor site, intron retention, or a combination thereof. In an embodiment, the modulator is selected from or modulates one or more general or alternative splicing factors, e.g., ASF1. In an embodiment, the modulator modulates alternative splicing (e.g., influences splice site selection) in a concentration-dependent manner.

Modulators of Post-Transcriptional Modification

In an embodiment, the modulator of gene expression modulates post-transcriptional modification. For example, the modulators described herein can promote or inhibit 5' capping, 3' polyadenylation, and RNA splicing. In an embodiment, the modulator is selected from, or modulates, one or more factors involved in 5' capping, e.g., phosphatase and guanosyl transferase. In an embodiment, the modulator is selected from, or modulates, one or more factors involved in 3' polyadenylation, e.g., polyadenylate polymerase, cleavage and polyadenylation specificity factor (CPSF), and poly(A) binding proteins. In an embodiment, the modulator is selected from, or modulates, one or more factors involved in RNA splicing, e.g., general or alternative splicing factors.

Exemplary endogenous or exogenous modulators of post-transcriptional modification are described herein, e.g., in Table VI-6.

TABLE VI-6

POST-TRANSCRIPTIONAL CONTROL MODULATORS mRNA processing
    Polyadenylation
        PARN: polyadenylation specific ribonuclease

TABLE VI-6-continued

POST-TRANSCRIPTIONAL CONTROL MODULATORS

PAN: PolyA nuclease
CPSF: cleavage/polyadenylation specificity factor
CstF: cleavage stimulation factor
PAP: polyadenylate polymerase
PABP: polyadenylate binding protein
PAB2: polyadenylate binding protein 2
CFI: cleavage factor I
CFII: cleavage factor II
Capping/Methylation of 5'end
    RNA triposphatase
    RNA gluanyltransferase
    RNA mehyltransferase
    SAM synthase
    ubiquitin-conjugating enzyme E2R1
Splicing
    SR proteins SFRS1 - SFR11 which, when bound to exons, tend to promote
    hnRNP proteins: coded by the following genes: HNRNPA0, HNRNPA1, HNRNPA1L1, HNRNPA1L2, HNRNPA3, HNRNPA2B1, HNRNPAB, HNRNPB1, HNRNPC, HNRNPCL1, HNRNPD, HNRPDL, HNRNPF, HNRNPH1, HNRNPH2, HNRNPH3, HNRNPK, HNRNPL, HNRPLL, HNRNPM, HNRNPR, HNRNPU, HNRNPUL1, HNRNPUL2, HNRNPUL3
Editing protein
    ADAR
Nuclear export proteins
    Mex67
    Mtr2
    Nab2
    DEAD-box helicase ("DEAD" disclosed as SEQ ID NO: 40)
TRANSLATION
  Initiation
    eIF4A, eIF4B, eIF4E, and eIF4G: Eukaryotic initiation factors
    GEF: Guanine exchange factor
    GCN2, PKR, HRI and PERK: Kinases involved in phosphorylating some of the initiation factors
  Elongation
    eEF1 and eEF2: elongation factors
    GCN: kinase
  Termination
    eRF3: translation termination factor
POST-TRANSLATIONAL CONTROL
  mRNA Degradation
    ARE-specific binding proteins
    EXRN1: exonuclease
    DCP1, DCP2: Decapping enzymes
    RCK/p54, CPEB, eIF4E: Translation repression
    microRNAs and siRNAs: Probably regulate 30% of all genes
    DICER
    Ago proteins
    Nonsense-mediated mRNA decay proteins
      UPF3A
      UPF3B
      eIF4A3
      MLN51
      Y14/MAGOH
      MG-1
      SMG-5
      SMG-6
      SMG-7
  mRNA Modification
    Enzymes carry the following functions
      Phosphorylation
      N-linked glycosylation
      Acetylation
      Amidation
      Hydroxylation
      Methylation
      O-linked glycosylation
      Ubiquitylation Inhibitors In an embodiment a payload comprises an inhibitor of a payload described above, e.g., an inhibitor of an enzyme transcription factor. In an embodiment a payload comprises an inhibitor of any of the aforementioned payload molecules, processes, activities or mechanisms. In an embodiment, the inhibitor is an antibody molecule (e.g., a full antibody or antigen binding fragment thereof) specific for one of the payload molecules described herein. In an embodiment the inhibitor is a small molecule compound. In an embodiment, the inhibitor is a nucleic acid (e.g., siRNA, shRNA, ribozyme, antisense-oligonucleotide, and aptamer). For example, the payload is an inhibitor of a target, e.g., a transcription factor, a post-translational modification enzyme, a post-transcriptional modification enzyme, etc., or a nucleic acid sequence encoding any of the foregoing.

Orthologs

If a non-human gene or protein is recited herein it is understood that the invention also comprises the human counterpart or ortholog and uses thereof.

VIIA. Targets: Cells

Cas9 molecules and gRNA molecules, e.g., a Cas9 molecule/gRNA molecule complex, can be used to manipulate a cell (e.g., an animal cell or a plant cell), e.g., to deliver a payload, or edit a target nucleic acid, in a wide variety of cells. Typically an eiCas9 molecule/gRNA molecule complex is used to deliver a payload and an eaCas9 molecule/gRNA complex is used to edit or alter the structure of a target nucleic acid. Delivery or editing can be performed in vitro, ex vivo, or in vivo.

In an embodiment, a cell is manipulated by editing (e.g., introducing a mutation or correcting) one or more target genes, e.g., as described herein. In an embodiment, a cell is manipulated by delivering a payload comprising one or more modulators (e.g., as described herein) to the cell, e.g., to a target sequence in the genome of the cell. In an embodiment, the expression of one or more target genes (e.g., one or more target genes described herein) is modulated, e.g., in vivo. In an embodiment, the expression of one or more target genes (e.g., one or more target genes described herein) is modulated, e.g., ex vivo.

In an embodiment, the cells are manipulated (e.g., converted or differentiated) from one cell type to another. In an embodiment, a pancreatic cell is manipulated into a beta islet cell. In an embodiment, a fibroblast is manipulated into an iPS cell. In an embodiment, a preadipocyte is manipulated into a brown fat cell. Other exemplary cells include, e.g., muscle cells, neural cells, leukocytes, and lymphocytes.

In an embodiment, the cell is a diseased or mutant-bearing cell. Such cells can be manipulated to treat the disease, e.g., to correct a mutation, or to alter the phenotype of the cell, e.g., to inhibit the growth of a cancer cell. For examples, a cell is associated with one or more diseases or conditions describe herein. In an embodiment, the cell is a cancer stem cell. For example, cancer stem cells can be manipulated by modulating the expression of one or more genes selected from: TWIST (TF), HIF-1α, HER2/neu, Snail (TF), or Wnt.

In an embodiment, the manipulated cell is a normal cell.

In an embodiment, the manipulated cell is a stem cell or progenitor cell (e.g., iPS, embryonic, hematopoietic, adipose, germline, lung, or neural stem or progenitor cells).

In an embodiment, the manipulated cells are suitable for producing a recombinant biological product. For example, the cells can be CHO cells or fibroblasts. In an embodiment, a manipulated cell is a cell that has been engineered to express a protein.

In an embodiment, the cell being manipulated is selected from fibroblasts, monocytic precursors, B cells, exocrine cells, pancreatic progenitors, endocrine progenitors, hepatoblasts, myoblasts, or preadipocytes. In an embodiment, the cell is manipulated (e.g., converted or differentiated) into muscle cells, erythroid-megakaryocytic cells, eosinophils, iPS cells, macrophages, T cells, islet beta-cells, neurons, cardiomyocytes, blood cells, endocrine progenitors, exocrine progenitors, ductal cells, acinar cells, alpha cells, beta cells, delta cells, PP cells, hepatocytes, cholangiocytes, or brown adipocytes.

In an embodiment, the cell is a muscle cell, erythroid-megakaryocytic cell, eosinophil, iPS cell, macrophage, T cell, islet beta-cell, neuron, cardiomyocyte, blood cell, endocrine progenitor, exocrine progenitor, ductal cell, acinar cell, alpha cell, beta cell, delta cell, PP cell, hepatocyte, cholangiocyte, or white or brown adipocyte.

The Cas9 and gRNA molecules described herein can be delivered to a target cell. In an embodiment, the target cell is a normal cell.

In an embodiment, the target cell is a stem cell or progenitor cell (e.g., iPS, embryonic, hematopoietic, adipose, germline, lung, or neural stem or progenitor cells).

In an embodiment, the target cell is a CHO cell.

In an embodiment, the target cell is a fibroblast, monocytic precursor, B cells exocrine cell, pancreatic progenitor, endocrine progenitor, hepatoblast, myoblast, or preadipocyte.

In an embodiment, the target cell is a muscle cell, erythroid-megakaryocytic cell, eosinophil, iPS cell, macrophage, T cell, islet beta-cell, neurons (e.g., a neuron in the brain, e.g., a neuron in the striatum (e.g., a medium spiny neuron), cerebral cortex, precentral gyms, hippocampus (e.g., a neuron in the dentate gyrus or the CA3 region of the hippocampus), temporal cortex, amygdala, frontal cortex, thalamus, cerebellum, medulla, putamen, hypothalamus, tectum, tegmentum or substantia nigra), cardiomyocyte, blood cell, endocrine progenitor, exocrine progenitor, ductal cell, acinar cell, alpha cell, beta cell, delta cell, PP cell, hepatocyte, cholangiocyte, or brown adipocyte.

In an embodiment, the target cell is manipulated ex vivo by editing (e.g., introducing a mutation or correcting) one or more target genes and/or modulating the expression of one or more target genes, and administered to the subject.

Exemplary cells that can be manipulated and exemplary genes that can be modulated are described in Table VII-8.

TABLE VII-8

| Cell starting point | Differentiated state | Exemplary payload manipulation | Exemplary gene(s) to modify expression of |
|---|---|---|---|
| fibroblasts | Muscle cells | Deliver Cas9-activators to target activation of transcription factors required for differentiation in vivo. | MyoD |
| Monocytic precursors | Erythroid-megakaryocytic cells, eosinophils | Deliver Cas9-activators to target activation of transcription factors required for differentiation in vivo. | GATA1 |
| fibroblasts | iPS cells | Deliver Cas9-activators to target activation of transcription factors required for differentiation in vivo. Multiplex. | Oct4 Sox2 Klf4 Myc |
| B cells | Macrophages | Deliver Cas9-activators to target activation of transcription factors required for differentiation in vivo. | C/EBPα |
| B cells | T cells, macrophages | Delivery Cas9-repressors OR deliver Cas9 endonuclease to ablate Pax5 | Pax5 |
| Exocrine cells | Islet β-cells | Deliver Cas9-activators to target activation of transcription factors required for differentiation in vivo. Multiplex. | Pdx1 Ngn3 MafA |
| Fibroblasts | Neurons | Deliver Cas9-activators to target activation of transcription factors required for differentiation in vivo. Multiplex. | Ascl1 Brn2 Myt1l |
| fibroblasts | cardiomyocytes | Deliver Cas9-activators to target activation of transcription factors required for differentiation in vivo. Multiplex. | Gata4 Mef2c Tbx5 |
| Fibroblasts | Blood cells | Deliver Cas9-activators to target activation of transcription factors required for differentiation in vivo. | Oct4 |
| Fibroblasts | cardiomyocytes | Deliver Cas9-activators to target activation of transcription factors required for differentiation in vivo. Multiplex. | Oct4 Sox2 Klf4 |
| Pancreatic progenitor | Endocrine progenitor | Deliver Cas9-activators to target activation of transcription factors | Ngn3 |

TABLE VII-8-continued

| Cell starting point | Differentiated state | Exemplary payload manipulation | Exemplary gene(s) to modify expression of |
|---|---|---|---|
| Pancreatic progenitor | Exocrine progenitor | Deliver Cas9-activators to target activation of transcription factors required for differentiation in vivo. | P48 |
| Pancreatic progenitor | Duct | Deliver Cas9-activators to target activation of transcription factors required for differentiation in vivo. | Hnf6/OC-1 |
| Pancreatic progenitor | acinar | Deliver Cas9-activators to target activation of transcription factors required for differentiation in vivo. Multiplex. | Ptf1a Rpbjl |
| Endocrine progenitor (to make glucagon) | α cell | Deliver Cas9-activators to target activation of transcription factors required for differentiation in vivo. Multiplex. | Foxa2 Nkx2.2 Pax6 Arx |
| Endocrine progenitor (to make insulin) | β cell | Deliver Cas9-activators to target activation of transcription factors required for differentiation in vivo. Multiplex. | Mafa Pdx1 Hlxb9 Pax4 Pax6 Isl1 Nkx2.2 Nkx6.1 |
| Endocrine progenitor (to make somatostatin) | δ cell | Deliver Cas9-activators to target activation of transcription factors required for differentiation in vivo. Multiplex. | Pax4 Pax6 |
| Endocrine progenitor (to make pancreatic polypeptide) | PP cell | Deliver Cas9-activators to target activation of transcription factors required for differentiation in vivo. | Nkx2.2 |
| Hepatoblast | hepatocyte | Deliver Cas9-activators to target activation of transcription factors required for differentiation in vivo. | Hnf4 |
| Hepatoblast | Cholangiocyte | Deliver Cas9-activators to target activation of transcription factors required for differentiation in vivo. | Hnf6/OC-1 |
| Myoblasts | Brown adipocyte | Deliver Cas9-activators to target activation of transcription factors required for differentiation in vivo. Multiplex. | PRDM16 C/EBP PGC1α PPARγ |
| preadipocytes | Brown adipocyte | Deliver Cas9-activators to target activation of transcription factors required for differentiation in vivo. Multiplex. | PRDM16 C/EBP |

TABLE VII-9

Exemplary cells for manipulation

Pancreatic cells, e.g., beta cells
Muscle cells
Adipocytes
Pre-adipocytes
Neural cells
Blood cells
Leukocytes
Lymphocyes
B cells
T cells

TABLE VII-10

Exemplary stem cells for manipulation embryonic stem cells
non-embryonic stem cells
hematopoietic stem cells
adipose stem cells
germline stem cells
lung stem cells
neural stem cells

TABLE VII-11

Exemplary cancer cells for manipulation lung cancer cells
breast cancer cells
skin cancer cells
brain cancer cells,
pancreatic cancer cells
hematopoietic cancer cells
liver cancer cells
kidney cancer cells
ovarian cancer cells

TABLE VII-12

Exemplary non-human cells for manipulation

Plant cells, e.g., crop cells, e.g., corn, wheat, soybean, citrus or vegetable cells
Animal cells, e.g., a cow, pig, horse, goat, dog or cat cell Exemplary endogenous or exogenous modulators of cancer stem cells (CSCs) are described herein, e.g., in Table VII-13.

TABLE VII-13

TWIST 1 (TF)
HIF-1α (TF)
HER2/neu
Snail (TF)
Wnt
TGFβ
FGF
EGF
HGF
STAT3 (TF)
Notch
P63 (TF)
PI3K)/AKT
Hedgehog
NF-κB (TF)
ATF2 (TF)
miR-200 and miR-34
P53 (TF)
E-cadherin
Transcription factors that inhibit E-cadherin directly
ZEB1
ZEB2
E47
KLF8
Transcription factors that inhibit E-cadherin directly
TCF4
SIX1
FOXC2
G-CSF and CD34 in AML
PML and FOXO in CML
CD133 in glioblastoma multiforme, osteosarcoma, Ewing's sarcoma, endometrial, hepatocellular, colon and lung carcinomas and ovarian and pancreatic adenocarcinoma
CD44 in head and neck cancer, prostate, gastric and colorectal carcinoma stem cells
CD34 in leukemia
CD38 in leukemia
IL3Rα in leukemia
EpCAM in colon carcinoma and pancreatic adenocarcinoma stem cells
ALDH in melanoma, colorectal, breast, prostate and squamous cell carcinomas, pancreatic adenocarcinoma, and osteosarcoma
MAP2 in melanoma
α6-integrin in glioblastoma
SSEA-1 in gliobalstoma
CD24 in breast cancer and other tumors Cas9 molecules and gRNA molecules, e.g., a Cas9 molecule/gRNA molecule complex, can be used to manipulate a cell (e.g., a cell described herein), e.g., to deliver a payload, or edit a target nucleic acid, e.g., to increase cell engraftment, e.g., to achieve stable engraftment of cells into a native microenvironment. The engrafting cells, the cells in the native microenvironment, or both, can be manipulated. Typically an eiCas9 molecule/gRNA molecule complex is used to deliver a payload and an eaCas9 molecule/gRNA complex is used to edit or alter the structure of a target nucleic acid.

For example, increased efficiency of engraftment of cells can be achieved by: increasing the expression of one or more of the genes described herein, e.g., homing genes, adhesion genes, survival genes, proliferative genes, immune evasion genes, and/or cell protection genes, and/or decreasing the expression of one or more of the genes described herein, e.g., quiescence genes, death/apoptosis genes, and/or immune recognition genes.

In an embodiment, the gene encodes a homing receptor or an adhesion molecule, e.g., that is involved in directing cell migration towards a tissue in association with a tissue-expressed ligand or region rich in soluble cytokine. In an embodiment, the homing receptor or adhesion molecule is expressed on leukocytes, e.g., lymphocytes or hematopoietic stem cells. In an embodiment, the tissue is bone marrow, e.g., extracellular matrix or stromal cells. In an embodiment, the homing receptor or adhesion molecule is C-X-C chemokine receptor type 4 (CXCR4, also known as fusin or CD184). For example, the expression of CXCR4 on hematopoietic stem cells is upregulated. In an embodiment, the ligand is stromal-derived-factor-1 (SDF-1, also known as CXCL12). In an embodiment, the homing receptor or adhesion molecule is CD34. In an embodiment, the ligand is addressin (also known as mucosal vascular addressin cell adhesion molecule 1 (MAdCAM-1)).

In an embodiment, the gene encodes a receptor, e.g., expressed on a stem cell or progenitor cell, that binds to a ligand, e.g., a chemokine or cytokine. For example, the receptor can be associated with stemness of the cell and/or attracting the cell to a desired microenvironment. In an embodiment, the receptor is expressed on a hematopoietic stem cell. In an embodiment, the receptor is expressed on a neural stem cell. In an embodiment, the receptor is mast/stem cell growth factor receptor (SCFR, also known as proto-oncogene c-Kit or tyrosine-protein kinase Kit or CD117). In an embodiment, the ligand is stem cell factor (SCF, also known as steel factor or c-kit ligand). In an embodiment, the receptor is myeloproliferative leukemia virus oncogene (MPL, also known as CD110). In an embodiment, the ligand is thrombopoietin (TPO).

In an embodiment, the gene encodes a marker, e.g., that promotes survival or proliferation of the cells expressing that marker, or allows the cells expressing that marker to evade an immune response or to be protected from an adverse environment, e.g., that leads to cell death. For example, cells expressing CD47 (also known as integrin associated protein (IAP)) can avoid phagocytosis, e.g., during cell migration. As another example, cells that express BCL2 can be protected from apoptosis. In an embodiment, the cell is a blood cell, e.g., an erythrocyte or leukocyte. In an embodiment, the cell is a hematopoietic stem cell or progenitor cell.

In an embodiment, the expression of one or more of CXCR4, SDF1, CD117, MPL, CD47, or BCL2, in a stem cell or progenitor cell, e.g., a hematopoietic stem cell or progenitor cell, is upregulated.

Cas9 molecules and gRNA molecules, e.g., a Cas9 molecule/gRNA molecule complex, can be used to manipulate a cell (e.g., a cell described herein), e.g., to deliver a payload, or edit a target nucleic acid, e.g., to manipulate (e.g., dictate) the fate of a targeted cell, e.g., to better target specific cell type of interest and/or as a suicide mechanism. Typically an eiCas9 molecule/gRNA molecule complex is used to deliver a payload and/or an eaCas9 molecule/gRNA complex is used to edit or alter the structure of a target nucleic acid. Exemplary genes that can be modulated include, e.g., one or more of chemotherapy resistance genes, chemotherapy sensitivity genes, antibiotic resistance genes, antibiotic sensitivity genes, and cell surface receptor genes, e.g., as described herein.

In an embodiment, a chemotherapy resistance gene, a chemotherapy sensitivity gene, an antibiotic resistance gene, and/or an antibiotic sensitivity gene is modulated, e.g., such that modified or undesirable cells (e.g., modified or undesirable hematopoietic stem cells (HSCs), e.g., in bone marrow) can be reduced or removed, e.g., by chemotherapeutic or antibiotic treatment.

For example, genes or gene products that modulate (e.g., increase) chemotherapy resistance or antibiotic resistance can be delivered into the cells. Cells modified by the chemotherapy or antibiotic resistance gene or gene product can have a higher (e.g., at least about 2, 3, 4, 5, 6, 7, 8, 9, 10, 25, 50, 75, or 100 fold higher) survival rate than cells without such modification after chemotherapeutic or antibiotic treatment. In an embodiment, the chemotherapeutic or antibiotic treatment is performed in vivo. In an embodiment, the chemotherapeutic or antibiotic treatment is performed in vitro or ex vivo. In an embodiment, the chemotherapy resistance gene is a gene encoding $O^6$-alkylguanine DNA alkyltransferase (MGMT). In an embodiment, the chemotherapy comprises temozolomide.

As another example, genes or gene products that modulate (e.g., increase) chemotherapy sensitivity or antibiotic sensitivity can be delivered into the cells. The genes or gene products that confer chemotherapy sensitivity or antibiotic sensitivity can be used as suicide signals, e.g., causing apoptosis of the cells. Cells modified by the chemotherapy or antibiotic sensitivity gene or gene product can have a lower (e.g., at least about 2, 3, 4, 5, 6, 7, 8, 9, 10, 25, 50, 75, or 100 fold lower) survival rate than cells without such modification after chemotherapeutic or antibiotic treatment. In an embodiment, the chemotherapeutic or antibiotic treatment is performed in vivo. In an embodiment, the chemotherapeutic or antibiotic treatment is performed in vitro or ex vivo.

The method described herein can be used to select or enrich cells that have a modified or desired phenotype, e.g., chemotherapy resistance and/or antibiotic resistance. The method described herein can also be used to remove or reduce the number of cells that have a modified or undesired phenotype, e.g., chemotherapy sensitivity and/or antibiotic sensitivity. For example, cells that exhibit an undesired effect, e.g., an off-target effect or a cancer phenotype, e.g., caused by editing of a nucleic acid in an undesired genomic location or cell type, can be removed.

In an embodiment, a cell surface receptor gene is modulated (e.g., the expression of the cell surface receptor is increased or decreased), such that a therapeutic agent (e.g., a therapeutic antibody) can be used to target a cell (e.g., to kill the cell) that has increased or decreased expression of the cell surface receptor. In an embodiment, the cell surface receptor is CD20. In an embodiment, the therapeutic antibody is Rituximab.

In an embodiment, the cell surface receptor is selected from, e.g., CD52, VEGFR, CD30, EGFR, CD33, or ErbB2. In an embodiment, the therapeutic antibody is selected from, e.g., Alemtuzumab, Rituximab, Cetuximab, Panitumumab, Gentuzaumab, and Trastuzumab. In an embodiment, the cell surface receptor is CD52 and the therapeutic antibody is Alemtuzumab. In an embodiment, the gene encodes VEGF and the therapeutic antibody is Rituximab. In an embodiment, the cell surface receptor is EGFR and the therapeutic antibody is Cetuximab or Panitumumab. In an embodiment, the cell surface receptor is CD33 and the therapeutic antibody is Gentuzaumab. In an embodiment, the cell surface receptor is ErbB2 and the therapeutic antibody is Trastuzumab.

In an embodiment, the expression or activity of the Cas9 molecule and/or the gRNA molecule is induced or repressed, e.g., when the cell is treated with a drug, e.g., an antibiotic, e.g., in vivo. For example, the induction or repression of the expression or activity of the Cas9 molecule and/or the gRNA molecule can be used to reduce toxicity and/or off-target effects, e.g., in certain tissues. In an embodiment, the expression of the Cas9 molecule, the gRNA molecule, or both, is driven by an inducible promoter. In an embodiment, binding of a drug (e.g., an antibiotic) to the Cas9 molecule and/or the gRNA molecule activates or inhibits the activity of the Cas9 molecule and/or the gRNA molecule. In an embodiment, the drug (e.g., antibiotic) is administered locally. In an embodiment, the cell treated with the drug (e.g., antibiotic) is located in the eye, ear, nose, mouth, or skin.

Cas9 molecules and gRNA molecules, e.g., a Cas9 molecule/gRNA molecule complex, can be used to manipulate a cell (e.g., a cell described herein), e.g., to deliver a payload, or edit a target nucleic acid, e.g., in directed enzyme prodrug therapy (DEPT). Typically an eiCas9 molecule/gRNA molecule complex is used to deliver a payload and an eaCas9 molecule/gRNA complex is used to edit or alter the structure of a target nucleic acid.

Directed enzyme prodrug therapy (DEPT) uses enzymes artificially introduced into the body to convert prodrugs, which have no or poor biological activity, to the active form in the desired location within the body. For example, directed enzyme prodrug therapy can be used to reduce the systemic toxicity of a drug, by achieving high levels of the active drug only at the desired site.

In an embodiment, an enzyme required for prodrug conversion or a gene encoding such an enzyme is delivered to a target cell, e.g., a cancer cell. For example, the enzymes or genes can be delivered by a method described herein. In an embodiment, the gene encoding the enzyme required for prodrug conversion is delivered by a viral vector.

Cas9 molecules and gRNA molecules, e.g., a Cas9 molecule/gRNA molecule complex, can be used to manipulate a cell (e.g., a cell described herein), e.g., to deliver a payload, or edit a target nucleic acid, e.g., to improve immunotherapy, e.g. cancer immunotherapy. Typically an eiCas9 molecule/gRNA molecule complex is used to deliver a payload and an eaCas9 molecule/gRNA complex is used to edit or alter the structure of a target nucleic acid. Exemplary genes that can be modulated include, e.g., one or more genes described herein, e.g., PD-L1 and/or PD-L2 genes.

VIIB. Targets: Pathways and Genes

Cas9 molecules and gRNA molecules, e.g., a Cas9 molecule/gRNA molecule complex, can be used to manipulate one, two, three or more, elements or a pathway, e.g., by targeting sequences that encode an RNA or protein of a pathway, or sequences that control the expression of an RNA or protein of a pathway. In an embodiment, an element of a first pathway and an element of a second pathway are manipulated. In an embodiment, manipulation comprises delivery of a payload to, or editing, a target nucleic acid. Typically an eiCas9 molecule/gRNA molecule complex is used to deliver a payload and an eaCas9 molecule/gRNA complex is used to edit or alter the structure of a target nucleic acid. Delivery or editing can be performed in vitro, ex vivo, or in vivo.

An element of a pathway can be up or down regulated, e.g., the expression of a gene encoding a protein of a pathway can be increased or decreased. The increase or decrease can be effected by delivery of a payload (e.g., a transcription factor or inhibitor of a transcription factor) or by editing a target nucleic acid (e.g., the use of a template nucleic acid to alter a sequence, e.g., correct or introduce a mutation, in e.g., a control or coding region).

Exemplary pathways comprise pathways associated with: cell proliferation; cell cycle; carbon metabolism; energy metabolism; glycolysis, anerobic respiration, anerobic respiration; transmembrane signal transduction, angiogenesis, DNA replication or repair, or pain.

Exemplary pathways and genes are discussed herein. It will be understood that a pathway or gene can be associated with one or more aspect of cell or organismal function, e.g., a pathway or gene can be involved in both cancer and energy metabolism. Manipulation of a pathway or gene is not limited to the exemplary cell or organismal function listed below. In an embodiment a pathway is associated with one or more diseases or conditions.

In an embodiment, the pathway is associated with cancer, e.g., associated with proliferation (e.g., RAF pathway), evading growth repressors, resisting cell death, enabling replicative immortality/aging, inducing angiogenesis, activating invasion and metastasis, energy metabolism and evading, cancer stem cells, cytokine-receptor interactions, or tumor suppressors. In an embodiment, the pathway is associated with cell cycle control. In an embodiment, the pathway is associated with angiogenesis.

Pathways and genes associated with cancer are described herein, e.g., include the following:

TABLE VII-14

Target Genes from Selected Pathways

| Protein/Gene | Pathway | Disease | CRISPR Regulation |
|---|---|---|---|
| Cancer | | | |
| PI3K | Proliferation | | Down |
| B-Raf | Proliferation | 66% of all melanoma cancers have a single substitution in codon 599 | Down |
| AKT | Proliferation | | Down |
| PTEN | Proliferation | Germline mutations leading to a predisposition to breast and thyroid cancer Mutations found in sporadic brain, breast and prostate | Down |
| mTOR | Proliferation | | Down |
| JUN | Proliferation | | Down |
| FOS | Proliferation | | Down |
| ERK | Proliferation | | Down |
| MEK | Proliferation | | Down |
| TGF-b | Proliferation | | Down |
| Myc | Proliferation | | Down |
| K-Ras | Proliferation | Mutated in lung cancer (10% of all Asians and 30% of all Caucasians) | Down |
| Src | Proliferation | | Down |
| PYK2 | Proliferation | | Down |
| PAK | Proliferation | | Down |
| FAK | Proliferation | | Down |
| PKA | Proliferation | | Down |
| RAC | Proliferation | | Down |
| ALK | Proliferation | Mutated in a subset (2-7%) of lung cancers | |
| Rb | Evading growth suppressors/pro-apoptotic | | Up |
| P53 | Evading growth suppressors/pro-apoptotic | Mutation in colon, lung, esophagus, breast, liver, brain reticuloendothelial tissues, and hemopoietic tissues | Up |
| APC | Evading growth suppressors/pro-apoptotic | Mutations found in colon and intestine | |
| CDK4/6 | Evading growth suppressors/pro-apoptotic | | Up |
| INK4B | Evading growth suppressors/pro-apoptotic | | Up |
| CDK2 | Evading growth suppressors/pro-apoptotic | | Up |
| WNT | Evading growth suppressors/pro-apoptotic | | Up |
| WAF1 | Evading growth suppressors/pro-apoptotic | | Up |
| Frizzled | Evading growth suppressors/pro-apoptotic | | Up |

TABLE VII-14-continued

Target Genes from Selected Pathways

| Protein/Gene | Pathway | Disease | CRISPR Regulation |
|---|---|---|---|
| VHL | Evading growth suppressors/pro-apoptotic | Mutated in all clear cell renal carcinomas | Up |
| Fas ligand | Resisting cell death/anti-apoptotic | | Down |
| Fas receptor | Resisting cell death/anti-apoptotic | | Down |
| Caspase 8 | Resisting cell death/anti-apoptotic | | Down |
| Caspase 9 | Resisting cell death/anti-apoptotic | | Down |
| Bcl-2 | Resisting cell death/anti-apoptotic | Correct mutation large deletion in follicular lymphoma, breast prostate CLL, melanoma | Down |
| Bcl-xL | Resisting cell death/anti-apoptotic | | Down |
| Bcl-w | Resisting cell death/anti-apoptotic | | Down |
| Mcl-1 | Resisting cell death/anti-apoptotic | | Down |
| Bax | Resisting cell death/anti-apoptotic | | Down |
| Bak | Resisting cell death/anti-apoptotic | | Down |
| IGF-1 | Resisting cell death/anti-apoptotic | | Down |
| Puma | Resisting cell death/anti-apoptotic | | Down |
| Bim | Resisting cell death/anti-apoptotic | | Down |
| Beclin-1 | Resisting cell death/anti-apoptotic | | Down |
| TGF-b | Enabling replicative immortality/aging | | |
| Telomerase/TERT | Enabling replicative immortality/aging | | Down |
| ATAD2 | Enabling replicative immortality/aging | | |
| DAF-2 | Enabling replicative immortality/aging | | |
| SRT | Enabling replicative immortality/aging | | |
| Eph-A/B | Inducing angiogenesis | | Down |
| Robo | Inducing angiogenesis | | Down |
| Neuropilin | Inducing angiogenesis | | Down |
| Notch | Inducing angiogenesis | | Down |
| Endostatin | Inducing angiogenesis | | Down |
| Angiostatin | Inducing angiogenesis | | Down |
| FGF family | Inducing angiogenesis | | Down |
| Extracellular matrix-degrading proteases (e.g., MMP-2 &MMP-9) | Inducing angiogenesis | | Down |
| VEGF-A | Inducing angiogenesis | | Down |
| TSP-1 | Inducing angiogenesis | | Down |
| VEGFR-1 | Inducing angiogenesis | | Down |
| VEGFR-2 | Inducing angiogenesis | | Down |
| VEGFR-3 | Inducing angiogenesis | | Down |
| NF2 | Activating invasion and metastasis | | Down |
| LKB1 | Activating invasion and metastasis | Up- regulated in multiple cancer, including intestine | Down |
| Snail | Activating invasion and metastasis | | Down |
| Slug | Activating invasion and metastasis | | Down |
| Twist | Activating invasion and metastasis | | Down |
| Zeb1/2 | Activating invasion and metastasis | | Down |
| CCLR5 | Activating invasion and metastasis | | Down |
| cysteine cathepsin protease family | Activating invasion and metastasis | | Down |

TABLE VII-14-continued

Target Genes from Selected Pathways

| Protein/Gene | Pathway | Disease | CRISPR Regulation |
|---|---|---|---|
| Extracellular matrix-degrading proteases (e.g., MMP-2 &MMP-9) | Activating invasion and metastasis | | Down |
| EGF | Activating invasion and metastasis | | Down |
| CSF-1 | Activating invasion and metastasis | | |
| PP2 | Energy metabolism | | Down |
| eIF4E | Energy metabolism | | Down |
| RSK | Energy metabolism | | Down |
| PIK3CA | Energy metabolism | Mutated in many breast, bladder cancers and hepatocellular carcinoma | Down |
| BAP1 | Energy metabolism | Mutated in renal cell carcinoma | Down |
| TWIST (TF) | Cancer Stem Cells | | Down |
| HIF-1α | Cancer Stem Cells | Over expressed in renal cell carcinoma | Down |
| HER2/neu | Cancer Stem Cells | | Down |
| Snail (TF) | Cancer Stem Cells | | Down |
| Wnt | Cancer Stem Cells | | Down |
| EPCAM | Cancer Stem Cells | Overexpressed in breast, colon, uterus and other cancers | Down |
| EGF | Cytokine-receptor interactions | | Down |
| TGFa | Cytokine-receptor interactions | | Down |
| PDGF | Cytokine-receptor interactions | | Down |
| IGF-1 | | | |
| KILTLG | | | |
| FLT3LG | Cytokine-receptor interactions | | Down |
| HGF | Cytokine-receptor interactions | | Down |
| FGF | Cytokine-receptor interactions | | Down |
| EGFR | Cytokine-receptor interactions | Mutated in lung cancer (40% of all Asians and 10-15% of all Caucasians) | Down |
| ERBB2 | Cytokine-receptor interactions | | Down |
| PDGFR | Cytokine-receptor interactions | | Down |
| IGFR | Cytokine-receptor interactions | | Down |
| c-KIT | Cytokine-receptor interactions | | Down |
| FLT3 | Cytokine-receptor interactions | | Down |
| MET | Cytokine-receptor interactions | | Down |
| FGFR | Cytokine-receptor interactions | Mutations in bladder cancer | Down |
| DNA damage and genomic instability | | | |
| DNMT1 | Methyl transferases | | |
| DNMT2 | Methyl transferases | | |
| DNMT3a | Methyl transferases | | |
| DNMT3b | Methyl transferases | | |
| H3K9Me3 | Histone methylation | | |
| H3K27Me | Histone methylation | | |
| Lsh | Helicase activity | | |
| BLM | Helicase activity | Bloom's syndrome > Cancer | Correct |
| WRN | Helicase activity | Werner's syndrome > Cancer | Correct |
| RTS | Helicase activity | Rothmund-Thompson > Cancer | Correct |
| XPA through XPG | Nucleotide excision repair | Xeroderma pigmentosa | |
| XPB | Nucleotide excision repair | Cockayne's syndrome | |
| XAB2 | Nucleotide excision repair | | |
| XPD | Nucleotide excision repair | Cockayne's syndrome | |
| TFIIH | Nucleotide excision repair | | |
| RFC | Nucleotide excision repair | | |

TABLE VII-14-continued

Target Genes from Selected Pathways

| Protein/Gene | Pathway | Disease | CRISPR Regulation |
|---|---|---|---|
| PCNA | Nucleotide excision repair | | |
| LIG 1 | Nucleotide excision repair | | |
| Flap endonueclease 1 | Nucleotide excision repair | | |
| MNAT | Nucleotide excision repair | | |
| MMS19 | Nucleotide excision repair | | |
| RAD23A | Nucleotide excision repair | | |
| RAD23B | Nucleotide excision repair | | |
| RPA1 | Nucleotide excision repair | | |
| RPA2 | Nucleotide excision repair | | |
| CCNH | Nucleotide excision repair | | |
| CDK7 | Nucleotide excision repair | | |
| CETN2 | Nucleotide excision repair | | |
| DDB1 | Nucleotide excision repair | | |
| DDB2 | Nucleotide excision repair | | |
| ERCC1 | Nucleotide excision repair | | |
| ATM | Recombinational repair | | |
| NBN | Recombinational repair | | |
| BRCA1 | Recombinational repair | Breast, ovarian and pancreatic cancer susceptibility | Correct or Up |
| BRCA2 | Recombinational repair | Breast cancer and ovarian susceptibility | Correct or UP |
| RAD51 | Recombinational repair | | |
| RAD52 | Recombinational repair | | |
| WRN | Recombinational repair | | |
| BLM | Recombinational repair | | |
| FANCB | Recombinational repair | | |
| MLH1 | Mismatch repair | Multiple (including colon and uterus) | |
| MLH2 | Mismatch repair | Multiple (including colon and uterus) | |
| MSH2 | Mismatch repair | | |
| MSH3 | Mismatch repair | | |
| MSH4 | Mismatch repair | | |
| MSH5 | Mismatch repair | | |
| MSH6 | Mismatch repair | Multiple (including colon and uterus) | |
| PMS1 | Mismatch repair | | |
| PMS2 | Mismatch repair | Multiple (including colon and uterus) | |
| PMS2L3 | Mismatch repair | | |

Aging

DAF-2
IGF-1
SRT1

TABLE VII-15

Genes Mutated in Common Cancers

| | |
|---|---|
| Bladder | FGFR3, RB1, HRAS, KRAS, TP53, TSC1, FGFR3 |
| Breast and Ovarian | BRCA, BRCA 2, BARD1, BRIP1, CHEK2, MRE11A, NBN, PALB2, PTEN, RAD50, RAD50, RAD51C, RAD51D, PPMID, TP53, BRIP1, RAD54L, SLC22A1L, PIK3CA, RB1CC1, |
| Cervical | FGFR3 |
| Colon and Rectal | PT53, STK11, PTEN, BMPR1A, SMAD, MLH1, MSH2, MSH6, PMS, EPCAM, AKT1, APC, MYH, PTPRJ, AXIN2 |
| Endometrial/Uterine | MLH1, MSH2, MSH6, PMS, EPCAM |
| Esophageal | DLEC1, TGFBR2, RNF6, LZT1S1, WWOX |
| Hepatocellular carcinoma | PDGFRL, CTNNB1, TP53, MET, CASP8, PIK3CA |
| Renal | VHL, PBRMQ, BAP1, SETD2, HIF1-α |

TABLE VII-15-continued

| Genes Mutated in Common Cancers | |
|---|---|
| Lung | KRAS, EGFR, ALK, BRAF, ERBB2, FLCN, DIRC2, RNF139, OGG1, PRCC, TFE, MET, PPP2R1B, RASSF1, SLC22A1L |
| Melanoma | BRAF, CDKA, CDKN2A, CDKN2B, CDKND, MC1R, TERT, ATF1, CREB1, EWSR1 |
| Non-Hodgkin Lymphoma | CASP10, EGFR, IRF1, PIK3CA |
| Osteosarcoma | CKEK2, LOJ18CR1, RB1 |
| Ovarian | PRKN, AKT1 |
| Pancreatic | KRAS, BRCA2, CDKN2A, MANF, PALB2, SMAD4, TP53, IPF1 |
| Prostate | MLH1, MSH2, MSH6, and PMS2, BRCA 1, HOXB13, CHEK2, ELAC2, EPHB2, SDR5A2, PRKAR1A, PMC1 |
| Papillary and Follicular Thyroid | BRAF, NARAS, ERC1, FOXE1, GOLGA5, NCOA4, NKX2-1, PMC1, RET, TFG, TPR, TRIM24, TRIM27, TRIM33 |
| Erwing Sarcoma | ERG, ETV1, ETV4, EWSR1, FLI1 |
| Leukemia | BRC, AMCR2, GMPS, JAK2, AF10, ARFGEF12, CEBPA, FLT3, KIT, LPP, MLF1, NPM1, NSD1, NUP214, PICALM, RUNX1, SH3GL1, WHSC1L1, ETV6, RARA, BCR, ARHGAP26, NF1, PTPN11, GATA1 |

Any of the following cancer associated genes provided in Table VII-16 can be targeted.

TABLE VII-16

Exemplary Target Genes Associated With Cancer

ABL1, ABL2, ACSL3, AF15Q14, AF1Q, AF3p21, AF5q31, AKAP9, AKT1, AKT2, ALDH2, ALK, ALO17, APC, ARHGEF12, ARHH, ARID1A, ARID2, ARNT, ASPSCR1, ASXL1, ATF1, ATIC, ATM, ATRX, AXIN1, BAP1, BCL10, BCL11A, BCL11B, BCL2, BCL3, BCL5, BCL6, BCL7A, BCL9, BCOR, BCR, BHD, BIRC3, BLM, BMPR1A, BRAF, BRCA1, BRCA2, BRD3, BRD4, BRIP1, BTG1, BUB1B, C12orf9, C15orf21, C15orf55, C16orf75, C2orf44, CAMTA1, CANT1, CARD11, CARS, CBFA2T1, CBFA2T3, CBFB, CBL, CBLB, CBLC, CCDC6, CCNB1IP1, CCND1, CCND2, CCND3, CCNE1, CD273, CD274, CD74, CD79A, CD79B, CDH1, CDH11, CDK12, CDK4, CDK6, CDKN2A, CDKN2a(p14), CDKN2C, CDX2, CEBPA, CEP1, CHCHD7, CHEK2, CHIC2, CHN1, CIC, CIITA, CLTC, CLTCL1, CMKOR1, CNOT3, COL1A1, COPEB, COX6C, CREB1, CREB3L1, CREB3L2, CREBBP, CRLF2, CRTC3, CTNNB1, CYLD, D10S170, DAXX, DDB2, DDIT3, DDX10, DDX5, DDX6, DEK, DICER1, DNM2, DNMT3A, DUX4, EBF1, ECT2L, EGFR, EIF4A2, ELF4, ELK4, ELKS, ELL, ELN, EML4, EP300, EPS15, ERBB2, ERCC2, ERCC3, ERCC4, ERCC5, ERG, ETV1, ETV4, ETV5, ETV6, EVI1, EWSR1, EXT1, EXT2, EZH2, EZR, FACL6, FAM22A, FAM22B, FAM46C, FANCA, FANCC, FANCD2, FANCE, FANCF, FANCG, FBXO11, FBXW7, FCGR2B, FEV, FGFR1, FGFR1OP, FGFR2, FGFR3, FH, FHIT, FIP1L1, FLI1, FLJ27352, FLT3, FNBP1, FOXL2, FOXO1A, FOXO3A, FOXP1, FSTL3, FUBP1, FUS, FVT1, GAS7, GATA1, GATA2, GATA3, GMPS, GNA11, GNAQ, GNAS, GOLGA5, GOPC, GPC3, GPHN, GRAF, H3F3A, HCMOGT-1, HEAB, HERPUD1, HEY1, HIP1, HIST1H3B, HIST1H4I, HLF, HLXB9, HMGA1, HMGA2, HNRNPA2B1, HOOK3, HOXA11, HOXA13, HOXA9, HOXC11, HOXC13, HOXD11, HOXD13, HRAS, HRPT2, HSPCA, HSPCB, IDH1, IDH2, IGH@, IGK@, IGL@, IKZF1, IL2, IL21R, IL6ST, IL7R, IRF4, IRTA1, ITK, JAK1, JAK2, JAK3, JAZF1, JUN, KCNJ5, KDM5A, KDM5C, KDM6A, KDR, KIAA1549, KIF5B, KIT, KLF4, KLK2, KRAS, KTN1, LAF4, LASP1, LCK, LCP1, LCX, LHFP, LIFR, LMO1, LMO2, LPP, LRIG3, LYL1, MADH4, MAF, MAFB, MALT1, MAML2, MAP2K1, MAP2K2, MAP2K4, MAX, MDM2, MDM4, MDS1, MDS2, MECT1, MED12, MEN1, MET, MITF, MKL1, MLF1, MLH1, MLL, MLL2, MLL3, MLLT1, MLLT10, MLLT2, MLLT3, MLLT4, MLLT6, MLLT7, MN1, MPL, MSF, MSH2, MSH6, MSI2, MSN, MTCP1, MUC1, MUTYH, MYB, MYC, MYCL1, MYCN, MYD88, MYH11, MYH9, MYST4, NACA, NBS1, NCOA1, NCOA2, NCOA4, NDRG1, NF1, NF2, NFE2L2, NFIB, NFKB2, NIN, NKX2-1, NONO, NOTCH1, NOTCH2, NPM1, NR4A3, NRAS, NSD1, NT5C2, NTRK1, NTRK3, NUMA1, NUP214, NUP98, OLIG2, OMD, P2RY8, PAFAH1B2, PALB2, PAX3, PAX5, PAX7, PAX8, PBRM1, PBX1, PCM1, PCSK7, PDE4DIP, PDGFB, PDGFRA, PDGFRB, PER1, PHF6, PHOX2B, PICALM, PIK3CA, PIK3R1, PIM1, PLAG1, PML, PMS1, PMS2, PMX1, PNUTL1, POT1, POU2AF1, POU5F1, PPARG, PPP2R1A, PRCC, PRDM1, PRDM16, PRF1, PRKAR1A, PRO1073, PSIP2, PTCH, PTEN, PTPN11, RAB5EP, RAC1, RAD51L1, RAF1, RALGDS, RANBP17, RAP1GDS1, RARA, RB1, RBM15, RECQL4, REL, RET, RNF43, ROS1, RPL10, RPL22, RPL5, RPN1, RUNDC2A, RUNX1, RUNXBP2, SBDS, SDC4, SDH5, SDHB, SDHC, SDHD, SEPT6, SET, SETBP1, SETD2, SF3B1, SFPQ, SFRS3, SH2B3, SH3GL1, SIL, SLC34A2, SLC45A3, SMARCA4, SMARCB1, SMARCE1, SMO, SOCS1, SOX2, SRGAP3, SRSF2, SS18, SS18L1, SSH3BP1, SSX1, SSX2, SSX4, STAT3, STK11, STL, SUFU, SUZ12, SYK, TAF15, TAL1, TAL2, TCEA1, TCF1, TCF12, TCF3, TCF7L2, TCL1A, TCL6, TERT, TET2, TFE3, TFEB, TFG, TFPT, TFRC, THRAP3, TIF1, TLX1, TLX3, TMPRSS2, TNFAIP3, TNFRSF14, TNFRSF17, TNFRSF6, TOP1, TP53, TPM3, TPM4, TPR, TRA@, TRAF7, TRB@, TRD@, TRIM27, TRIM33, TRIP11, TSC1, TSC2, TSHR, TTL, U2AF1, USP6, VHL, VTI1A, WAS, WHSC1, WHSC1L1, WIF1, WRN, WT1, WTX, WWTR1, XPA, XPC, XPO1, YWHAE, ZNF145, ZNF198, ZNF278, ZNF331, ZNF384, ZNF521, ZNF9, or ZRSR2

Exemplary pathways and genes associated with energy metabolism are provided in Table VII-17. Exemplary metabolic targets disclosed herein may be modulated using CRISPR/Cas9 as described herein. Modulation may be used to knockdown a gene of interest, correct a defect or mutation in the gene, or to activate a gene of interest.

TABLE VII-17

Exemplary Metabolic Target List

| Target | How to Modulate |
| --- | --- |
| ACAT, acyl-CoA:cholesterol acyltransferase | Knock down |
| AGPAT2, 1-acyl-glcero-3-phosphate acyltransferase 2 | Knock down |
| DGAT, diacylglycerol acyltransferase | Knock down |
| GL, gastric lipase | Knock down |
| PL, pancreatic lipase | Knock down |
| sPLA2, secretory phospholipase A2 | Knock down |
| ACC, acetyl-CoA carboxylase | Knock down |
| CPT, carnitine palmitoyl transferase | Knock down |
| FAS, fatty-acid synthase | Knock down |
| MTP, microsomal triglyceride-transfer protein | Knock down |
| Insulin receptor | Correct defects or activate |
| SU receptor/K+ ATP channel | Activate with mutation |
| a-glucosidase | Knock down |
| PPARy | Activate with mutation |
| Glycogen phosphorylase | Knock down |
| Fructose-1,6-bisphosphatase | Knock down |
| glucose-6-phosphatase | Knock down |
| PTP-1B | Knock down |
| SHIP-2 | Knock down |
| GSK-3 | Knock down |
| lkB kinase | Knock down |
| PKCq | Knock down |
| GLP1R | Correct mutation |
| GIPR | Correct mutation |
| GPR40 | Correct mutation |
| GPR119 | Correct mutation |
| GPR41 | Correct mutation |
| GPR43 | Correct mutation |
| GPR120 | Correct mutation |
| GCGR | Correct mutation |
| PAC1 | Correct mutation |
| VPAC2 | Correct mutation |
| Y1 | Knock down |
| GHSR | Knock down |
| CCKAR | Correct mutation |
| b2 | Correct mutation |
| a2 | Knock down |
| MT1 | Knock down |
| M3 | Correct mutation |
| CB1 | Knock down |
| P2Y | Correct mutation |
| H3 | Inhibit |
| MCH-R1 | Correct mutation |
| MCH-R2 | Correct mutation |
| Ghrelin R | Inhibit |
| FASN | Inhibit |
| Bombesin-R3 | Inhibit |
| CCK-A Receptor | Correct mutation |
| Seratonin System | Correct mutation |
| CBI Cannabinoid Receptors | Inhibit |
| Dopaminergic System | Correct mutation |
| Entero statin | Mutate to super agonist |
| CNTF | Mutate to super agonist |
| CNTF-R | Correct mutation |
| SOCS-3 | Knock down |
| 46a | Knock down |
| PrPP Receptors | Correct mutation |
| Amylin | Mutate to super agonist |
| CRH System | Mutate to super agonist |
| Galanin Receptors | Knock down |
| Orexin Receptors | Knock down |
| Noradrenalin System | Mutate to super agonist |
| CART | Mutate to super agonist |
| FATP4 | Knock down |
| Pancreatic Lipase | Knock down |
| ACRP30 | Super agonist mutations |
| Thyroid Hormone | Correct mutation |
| B-3 Adrenergic Receptor | Correct mutation |
| UCPs | Upregulate |
| PTP-1B | Knock down |

TABLE VII-17-continued

Exemplary Metabolic Target List

| Target | How to Modulate |
|---|---|
| MC3 | Correct mutation |
| ACC2 | Knock down |
| Perilipin | Knock down |
| HMGIC | Knock down |
| 11BHSD-1 | Knock down |
| Glucagon R | Knock down |
| Glucocoricoid R | Knock down |
| 11beta-HSD I | Knock down |
| PGC-1 | Correct mutation |
| DPPP-IV | Knock down |
| GLP | Mutate to super agonist |
| GIP | Mutate to super agonist |
| GLP-IR | Correct mutation |
| AMP Kinase | Correct mutation |
| IKK-b | Knock down |
| PPARa/g | Knock down |
| INS-R | Knock down |
| SGLT | Knock down |
| a-glucosidase | Knock down |
| HMGCR | Knock down |
| PCSK9 | Knock down |
| ApoB-100 | Knock down |
| Leptin | Mutate to super agonist |
| Leptin Receptor | Mutate to constitutively active receptor |
| MC4R | Mutate to constitutively active receptor |
| VOMC | Mutate MSH region to super agonist |
| AGRP | Knock down |
| IVPY Receptors | Introduce constitutively active mutations |
| 5HT2C | Introduce constitutively active mutations |
| GLP-1 | Mutate to super agonist |
| GLP-1 Receptor | Mutate to constitutively active receptor |

In an embodiment, the pathways and genes described herein, e.g., in Table VII-17, are also associated with diabetes, obesity, and/or cholesterol and lipids.

Exemplary pathways and genes associated with the cell cycle are provided in Table VII-18.

TABLE VII-18

CELL CYCLE PATHWAYS and REPRESENTATIVE GENES

| DNA Damage | Mismatch repair | Apoptosis |
|---|---|---|
| ATM | PMS2 | Fas-L |
| MRE11 | MLH1 | FasR |
| NBS1 | MSH6 | Trail-L |
| RAD50 | MSH2 | Trail-R |
| 53BP1 | RFC | TNF-α |
| P53 | PCNA | TNF-R1 |
| CHKE | MSH3 | FADD |
| E2F1 | MutS homolog | TRADD |
| PML | MutL homolog | RIPI |
| FANCD2 | Exonuclease | MyD88 |
| SMC1 | DNA Polymerase delta | IRAK |
| BLM1 | (POLD1, POLD2, POLD3, | NIL |
| BRCA1 | and POLD4 -genes | IKK |
| H2AX | encoding subunits) | NF-Kβ |
| ATR | Topoisomerase 1 | IκBα |
| RPA | Topoisomerase 2 | IAP |
| ATRIP | RNAseH1 | Caspase 3 |
| RAD9 | Ligase 1 | Caspase 6 |
| RAD1 | DNA polymerase 1 | Caspase 7 |
| HUS | DNA polymerase 3 | Caspase 8 |
| RAD17 | Primase | Caspase 10 |
| RFC | Helicase | HDAC1 |
| CHK1 | Single-strand binding | HDAC2 |

TABLE VII-18-continued

CELL CYCLE PATHWAYS and REPRESENTATIVE GENES

| | | |
|---|---|---|
| TLK1 | proteins | Cytochrome C |
| CDC25 | | Bxl-xL |
| | | STAT3 |
| | | STAT5 |
| | | DFF45 |
| | | Vcl-2 |
| | | ENDO-G |
| | | PI3K |
| | | Akt |
| | | Calpain |
| | | Bad |
| | | Bax |

| Ubiquitin-mediated proteolysis | | | Hypoxia | Cell Proliferation |
|---|---|---|---|---|
| | | | HIF-1α | MAPK |
| E1 | HERC1 | TRAF6 | HIF-1β | MAPKK |
| E2 | UBE2Q | MEKK1 | Refl | MAPKKK |
| E3 | UBE2R | COP1 | HSP90 | c-Met |
| UBLE1A | UBE2S | PIFH2 | VEGF | HGF |
| UBLE1B | UBE2U | cIAP | PAS | ERKS1/2 |
| UBLE1C | UBE2W | PIAS | ARNT | ATK |
| UBE2A | UBE2Z | SYVN | VHL | PKCs |
| UBE2B | AFCLLCN | NHLRC1 | HLF | Paxilin |
| UBE2C | UBE1 | AIRE | EPF | FAK |
| UBE2A | E6AP | MGRN1 | VDU2 | Adducin |
| UBE2E | UBE3B | BRCA1 | SUMORESUME | PYK1 |
| UBE2F | Smurf | FANCL | SENP1 | RB |
| UBE2G1 | Itch | MID1 | Calcineurin A | RB1 |
| UBE2G2 | HERC2 | Cdc20 | RACK1 | Raf-1 |
| UBE2I | HERC3 | Cdh1 | PTB | A-Raf |
| UBE2J1 | HERC4 | Apc1 | Hur | B-raf |
| UBE2J2 | UBE4A | Apc2 | PHD2 | MEK1/2 |
| UBE2L3 | UBE4B | Apc3 | SSAT2 | ERK1/2 |
| UBE2L6 | CHIP | Apc4 | SSAT1 | Ets |
| UBE2M | CYC4 | Apc5 | GSK3β | Elk1 |
| UBE2N | PPR19 | Apc6 | CBP | SAP1 |
| UBE2O | UIP5 | Apc7 | FOXO4 | cPLA2 |
| WWPI | Mdm2 | Apc8 | FIH-1 | |
| WWP2 | Parkin | Apc9 | | |
| TRIP12 | Trim32 | Apc10 | | |
| NEED4 | Trim37 | Apc11 | | |
| ARF-BP1 | SIAH-1 | Apc12 | | |
| EDD1 | PML | | | |

| Cell survival | Cell cycle arrest |
|---|---|
| SMAD1 | P21 |
| SMAD5 | BAX |
| SAMD8 | MDR |
| LEF1 | DRAIL IGFBP3 |
| TCF3 | GADD45 |
| TCF4 | |
| P300 | |
| HAT1 | |
| PI3K | |
| Akt | |
| GF1 | |

Exemplary cell cycle genes characterized by their function are provided in Table VII-19.

TABLE VII-19

CELL CYCLE GENES

| Translation initiation factors | Cyclins | Cyclin-dependent Kinases |
|---|---|---|
| E2F1 | CCNA1, CCNA2, CCNB1, | (DKs) |
| E2F2 | CCNB2, CCNB3, CCNC, | CDK1, CDK2, CDK3, CDK5, |
| E2F3 | CCND1, CCND2, CCND3, | CDK6, CDK7, CDK8, CDK9, |
| E2F4 | CCNE1, CCNE2, CCNF, | CDK11, |
| E2F5 | CCNG1, CCNG2, CCNH, | |
| E2F6 | CCNI, CCNI2,, CCNO, | |

TABLE VII-19-continued

| CELL CYCLE GENES | | |
|---|---|---|
| E2F8 | CCNT1, CCNT2, CCNY, CCNYL1, CCNYL2, CCNYL3 | |
| Cyclin regulators | CDK inhibitory proteins | CDK regulators (both |
| c-Jun | (CDKIs) | positive and negative) |
| c-Fos | INK4 family | RINGO/Speedy family |
| | P15 | P53 |
| | P16 | MDM2 |
| | P18 | RB |
| | P19 | CHK1 |
| | CIP/KIP family | CHk2 |
| | P21 | ATM |
| | P27 | ATR |
| | P57 | CDC2 |
| | | HDAC1 |
| | | HDAC2 |

Exemplary pathways and genes associated with the angiogenesis are described provided in Table VII-20.

TABLE VII-20

| ANGIOGENESIS PATHWAY GENES | | | |
|---|---|---|---|
| Extracellular ligands | Cell surface receptors | Signal transduction | Transcription factors |
| PLGF | VEGFR1 | PLCγ | c-FOS |
| VEGF | VEGFR2 | SHC | E2F7 |
| VEGFB | VEGFR3 | PI3K | |
| VEGFC | Nrp1 | PIP3 | |
| VEGFD | | IP3 | |
| | | DAG | |
| | | GRB2 | |
| | | SOS | |
| | | Akt | |
| | | PKB | |
| | | PKC | |
| | | Ras | |
| | | RAF1 | |
| | | DAG | |
| | | eNOS | |
| | | NO | |
| | | ERK1 | |
| | | ERK2 | |
| | | cPLA2 | |
| | | MEK1 | |
| | | MEK2 | |

Exemplary pathways and genes associated with the mitochondrial function are provided in Table VII-24.

TABLE VII-24

| Pathways and genes associated with mitochondrial function | | | |
|---|---|---|---|
| B-oxidation | TCA Cycle | Mitochondrial apoptosis | Valine oxidation pathway |
| acyl CoA dehydrogenase | Citrate synthase | | Transaminase |
| enoyl CoA hydratase | Aconitase | | BCKADH complex |
| 3-hydroxyacyl-CoA dehydrogenase | Isocitrate dehydrogenase | | ACAD-8 |
| β-ketothiolase | Alpha-ketoglutarate dehydrogenase | | Crotonoase |
| | Succinyl-CoA synthetase | | HIBCH |
| | Succinate dehydrogenase | | HIBADH |
| | Fumarase | | MMSDH |
| | Malate dehydrogenase | | Aminotransferase |
| | | | Hydratase |
| | | | Deacylase |
| | | | Dehydrogenase |
| | | | Carboxylase |
| | | | Mutase |
| Fatty add oxidation disorders (enzyme deficiencies) | | Leucine Oxidation Pathway | Isoleucine oxidation pathway |
| OCTN2 | | Aminotransferase | Aminotransferase |
| FATP1-6 | | Branched chain aminotransferase 2, mitochondrial | Branched chain aminotransferase 2, mitochondrial |
| CPT-1 | | | |
| CACT | | Isobutytyl-CoA dehydrogenase | 2-methylbutytyl-CoA Dehydrogenase |
| CPT-II | | | |
| SCAD | | (Branched Chain Keto Acid Dehydrogase Complex) | (Branched Chain Keto Acid Dehydrogenase Complex) |
| MCAD | | | |
| VLCAD | | | |
| ETF-DH | | | |
| Alpha-ETF | | Hydratase | Hydratase |
| Beta-ETF | | HMG-CoA lyase | 2-methyl-3-OH-butyryl-CoA dehydrogenase |
| SCHAD | | | |
| LCHAD | | | |

TABLE VII-24-continued

| | | | |
|---|---|---|---|
| MTP | | | 3-Oxothiolase |
| LKAT | | | |
| DECR1 | | | |
| HMGCS2 | | | |
| HMGCL | | | |

Additional mitochondrial genes and related diseases caused by mutations

| | |
|---|---|
| Mt-ND1 | Leber's hereditary optic neuropathy |
| Mt-ND4 | Leber's hereditary optic neuropathy |
| Mt-ND6 | Leber's hereditary optic neuropathy |
| OPA1 | Autosomal dominant optic atrophy |
| CMT2A | Charcot-Marie-Toothhereditary neuropathy type 2A |
| mt-TK | Myoclonic epilepsy with ragged red fibres |

| Mitochondrial Respiratory chain genes | Related diseases |
|---|---|
| NADH CoQ Reductase | Alpers, Alzheimer's, Parkinsonism, Cardiomyopathy, Deficiency (Barth and/or Lethal Infantile), Encephalopathy, Infantile CNS, Leber's, Leigh, Longevity, MELAS, MERRF, Myopathy ± CNS, PEO, Spinal cord disorders |
| Succinate-CoQ Reductase | Kearns-Sayre, Leigh's, Myopathy (e.g., Infantile ± CNS), Paraganglioma, Pheochromocytoma |
| CoQ-Cytochrome C Reductase | Cardiomyopathy, Fatal infantile, GRACILE, Leber's, Myopathy (e.g., ± CNS, PEO) |
| Cytochrome C Oxidase | Alper's, Ataxia, Deafness, Leber's, Leigh's, Myopathy (e.g., Infantile (e.g., Fatal, Benign), Adult), Rhabdomyolysis, PEO, KSS, MNGIE, MERRF, MELAS |
| ATP Synthase | Cardiomyopathy, Encephalopathy, Leber's, Leigh, Multisystem, NARP |

Complex I (NADH-Ubiquinone Oxidoreductase)

| Nuclear encoded proteins | Mitochondral DNA encoded proteins | Supernumerary subunits | Subunits involved in regulation of |
|---|---|---|---|
| NDUFS1: Childhood encephalopathy; Most common Complex I mutations (3%) | ND1 | NDUFAB1 (SDAP): Carrier of fatty acid chain | Complext I activity NDUFS4 (AQDQ) Functions: |
| | ND2 | | |
| | ND3 | | |
| NDUFS2: Cardiomyopathy + Encephalomyopathy | ND4 | NDUFA1 (MWFE) Primarily expressed in heart & skeletal muscle | Increased Complex I activity with phosphorylation |
| | ND4L | | |
| | ND5 | | Disorders: |
| NDUFS3: Leigh | ND6 | Disorders: | Multisystem childhood encephalopathy with Complex I deficiency; Leigh syndrome |
| NDUFS7: Leigh | | Encephalopathies | |
| NDUFS8: Leigh | | NDUFA2: | |
| NDUFV1: Childhood encephalopathy | | Encephalopathy & Cardiomyopathy | |
| NDUFV2: Encephalopathy + Cardiomyopathy | | NDUFA9: Leigh syndrome | |
| ELAC2: Cardiomyopathy, Hypertrophic | | NDUFA10: Leigh syndrome | |
| | | NDUFA11 Disorder: Encephalopathy & Cardiomyopathy | |
| | | NDUFA12: Leigh syndrome | |
| | | NDUFB9: Hypotonia | |
| | | NDUFS6: Lethal Infantile Mitochondrial Disease | |
| Proteins involved in Complex I assembly | Other | | |
| NDUFAF1: Cardiomyopathy + Encephalomyopathy | NDUFA13: Thyroid carcinoma (Hurthle cell) | | |
| NDUFAF2 (NDUFA12L): Childhood encephalopathy; Usually null mutations | NDUFB3: Severe lethal mitochondrial complex I deficiency | | |
| | MTHFR deficiency | | |
| | MGME1: PEO + Myopathy | | |
| NDUFAF3: Lethal neonatal encephalopathy | | | |
| NDUFAF4: Encephalopathy | | | |

TABLE VII-24-continued

C6ORF66: Encephalopathy
C8orf38: Leigh syndrome
C20orf7: Lethal neonatal
NUBPL: Encephalomyopathy
ACAD9: Fatigue & Exercise intolerance; Most missense mutations
FOXRED1: Leigh syndrome
Ecsit
AIF(AIFM1; PDCD8)
Ind1

Complex I (NADH-Ubiquinone Oxidoreductase)

| | |
|---|---|
| Flavoprotein: FAD (SDHA; Fp) | Mutations cause Leigh syndrome with Complex II deficiency Late onset neurodegenerative disorder) |
| Iron-Sulfur protein: SDHB (Ip) | Mutations cause Reduced tumor suppression Neoplasms: Pheochromocytoma & Paraganglioma |
| SDHC; SDHD (cytochrome C subunits) | mutations lead to paraganglioma |

Complex III (Cytochrome reductase)

| | |
|---|---|
| Cytochrome c1 (CYC1) | |
| Rieske FeS protein (UQCRFS1) | |
| Ubiquinol-cytochrome c reductase core protein I (UQCRC1; QCR; Subunit 1) | May mediate formation of complex between cytochromes c and c1 |
| Ubiquinol-cytochrome c reductase core protein II (UQCRC2; QCR2; Subunit 2) | Required for assembly of complex III |
| UQCRH (Subunit 6) | May mediate formation of complex between cytochromes c and c1 |
| Ubiquinone-binding protein (UQBC; UQPC; UQCRB; UQBP; Subunit 7) | Redox-linked proton pumping |
| UQCRO (Subunit 8) | Binds to ubiquinone |
| Ubiquinol-cytochrome C reductase complex, 7.2-KD Subunit (UCRC; UQCR10; Subunit 9) | Interacts with cytochrome c1 |
| UQCR (UQCR11; Subunit 10) | function as iron-sulfur protein binding factor |
| Cleavage product of UQCRFS1 (Cytochrome b-c1 complex subunit 11) | |

Inner membrane proteins and related disorders

ABCB7: Ataxia + Anemia
ACADVL: Myopathy
ADCK3: SACR9
AGK: Sengers
ATP5A1: Encephalopathy, neonatal
ATP5E: Retardation + Neuropathy
BRP44L: Encephalopathy
c12orf62: Encephalocardiomyopathy
Cardiolipin: Barth
COX4I2: Pancreas + Anemia
COX6B1: Encephalomyopathy
CPT2: Myopathy
CRAT: Encephalomyopathy
CYC1: Hyperglycemia & Encephalopathy
CYCS
CYP11A1
CYP11B1
CYP11B2
CYP24A1
CYP27A1: Cerebrotendinous Xanthomatosis
CYP27B1
DHODH
DNAJC19: Cardiac + Ataxia
FASTKD2: Encephalomyopathy
GPD2
HADHA: Multisystem; Myopathy
HADHB: Encephalomyopathy
HCCS: MIDAS
L2HGDH: Encephalopathy TABLE VII-24-continued MMAA
MPV17: Hepatocerebral
NDUFA1: Encephalopathy
NDUFA2: Leigh + Cardiac
NDUFA4: Leigh
NDUFA9: Leigh
NDUFA10: Leigh
NDUFA11: Encephalocardiomyopathy
NDUFA12: Leigh
NDUFA13
NDUFB3: Lethal infantile
NDUFB9: Encephalopathy
NDUFV1: Encephalopathy
NDUFV2: Encephalopathy + Cardiac
NDUFS1: Leukodystrophy
NDUFS2: Encephalopathy + Cardiac
NDUFS3: Dystonia
NDUFS4: Encephalopathy
NDUFS6: Lethal infantile
NDUFS7: Encephalopathy
NDUFS8: CNS + Cardiac
OPA1: Optic atrophy
OPA3: Optic atrophy
PDSS1: Coenzyme Q10 deficiency
SDHA: Leigh; Cardiac; Paraganglioma
SDHB: Paraganglioma
SDHC: Paraganglioma
SDHD: Paraganglioma
SLC25A carriers
SLC25A1: Epileptic encephalopathy
SLC25A3: Cardiac; Exercise intolerance
SLC25A4: PEOA2
SLC25A12: Hypomyelination
SLC25A13: Citrullinemia
SLC25A15: HHH
SLC25A19: Microcephaly
SLC25A20: Encephalocardiomyopathy
SLC25A22: Myoclonic epilepsy
SLC25A38: Anemia
Paraplegin: SPG7
TIMM8A: Deaf-Dystonia-Dementia
UCP1
UCP2
UCP3
UQCRB: Hypoglycemia, Hepatic
UQCRC2: Episodic metabolic encephalopathy
UQCRQ: Encephalopathy Pathways and genes associated with DNA damage and genomic instability include the following methyl transferases, histone methylation, helicase activity, nucleotide excision repair, recombinational repair, or mismatch repair provided in Table VII-21. See also Table VI-22.

TABLE VII-21

PATHWAYS and GENES ASSOCIATED with DNA DAMAGE and GENOMIC INSTABILITY

| Double-stranded Breaks | Replication Stress | DNA Methylation | Non-Homologous |
|---|---|---|---|
| ATM | ATR | DNMT1 | End-Joining |
| RAD50 | RAD17 | DNMT2 | Ku70 |
| MRE119 | ATRIP | DNMT3A | Ku80 |
| NBS1 | RAD9 | DNMT3B | DNA |
| CRCA1 | RPA | DNMT3L | PKc |
| H2AX | CHK1 | MeCP2 | XRCC4 |
| 53BP1 | BLM | MBD2 | DNA ligase 4 |
| MDC1 | H2AX | | XLF |
| SMC1 | 53BP1 | | Rad50 |
| P53 | P53 | | Artemis |
| | | | Rad27 |
| | | | TdT |
| Base-Excision repair | Nucleotide-Excision | Homologous | Mismatch repair |
| APE1 | Repair | Recombination | PMS2 |
| APE2 | UvrA | RecA | MLH1 |
| NEIL1 | UvrB | SSB | MSH6 |
| NEIL2 | UvrC | Mre11 | MSH2 |

TABLE VII-21-continued

PATHWAYS and GENES ASSOCIATED with DNA DAMAGE and GENOMIC INSTABILITY

| | | | |
|---|---|---|---|
| NEIL3 | XPC | Rad50 | RFC |
| XRCC1 | Rad23B | Nbs1 | PCNA |
| PNKP | CEN2 | CtIP | MSH3 |
| Tdp1 | DDB1 | RPA | MutS |
| APTX | XPE | Rad51 | MutL |
| DNA polymerase β | CSA, | Rad52 | Exonuclease |
| DNA polymerase δ | CSB | Rad54 | Topoisomerase 1 |
| DNA polymerase ε | TFIIH | BRCA1 | Topoisomerase 2 |
| PCNA | XPB | BRCA2 | RNAseH1 |
| FEN1 | XPD | Exo1 | Ligase 1 |
| RFC | XPA | BLM | DNA polymerase 1 |
| PARP1 | RPA | TopIIIα | DNA polymerase 3 |
| Lig1 | XPG | GEN1 | Primase |
| Lig3 | ERCC1 | Yen1 | Helicase |
| UNG | XPF | Slx1 | SSBs |
| MUTY | DNA polymerase δ | Slx4 | |
| SMUG | DNA polymerase ε | Mus8 | |
| MBD4 | | Eme1 | |
| | | Dss1 | |
| Histone Methylation | | | |
| ASH1L | SETD4 | | |
| DOT1L | SETD5 | | |
| EHMT1 | SETD6 | | |
| EHMT2 | SETD7 | | |
| EZH1 | SETD8 | | |
| EZH2 | SETD9 | | |
| MLL | SETDB1 | | |
| MLL2 | SETDB2 | | |
| MLL3 | SETMAR | | |
| MLL4 | SMYD1 | | |
| MLL5 | SMYD2 | | |
| NSD1 | SMYD3 | | |
| PRDM2 | SMYD4 | | |
| SET | SMYD5 | | |
| SETBP1 | SUV39H1 | | |
| SETD1A | SUV39H2 | | |
| SETD1B | SUV420H1 | | |
| SETD2 | SUV420H2 | | |
| SETD3 | | | |

TABLE VII-22

Selected Transcription FactorsTranscription factors

| | |
|---|---|
| NIKX2-5 | Cardiac malformations and atrioventricular conduction abnormalities |
| MECP2 | Rett syndrome |
| HNF1 through HNF6 | Mature onset diabetes of the young (MODY), hepatic adenomas and renal cysts |
| FOXP2 | Developmental verbal dyspraxia |
| FOXP3 | Autoimmune diseases |
| NOTCH1 | Aortic valve abnormalities |
| MEF2A | Coronary artery disease |
| CRX | Dominant cone-rod dystrophy |
| FOCX2 | Lymphedema-distichiasis |
| NF-κB Activation | Autoimmune arthritis, asthma, septic shock, lung fibrosis, glomerulonephritis, atherosclerosis, and AIDS |
| NF-κB Inhibition | Apoptosis, inappropriate immune cell development, and delayed cell growth |
| NARA2 | Parkinson disease |
| LHX3 | Pituitary disease |
| GAT4 | Congenital heart defects |
| P53, APC | Cancer |
| CTCF | Epigenetics and cell growth regulation |
| EGR2 | Congenital hypomyelinating neuropathy (CHN) and Charcot-Marie-Tooth type 1 (CMT1) |
| STAT family | Cancer and immunosuppression |
| NF-AT family | Cancer and inflammation |
| AP-1 family | Cancer and inflammation |

A gene including receptors and ionophores relevant to pain in this table can be targeted, by editing or payload delivery. Pathways and genes associated with pain are described herein, e.g., include the following those in Table VII-23.

TABLE VII-23

| Type of pain | Part of nervous system | Target | Area | How to affect |
|---|---|---|---|---|
| nociceptive | central | 5-HT | central inhibition | |
| nociceptive | central | 5HT1A | central inhibition | agonists (activation) serve as analgesic, |

TABLE VII-23-continued

| Type of pain | Part of nervous system | Target | Area | How to affect |
|---|---|---|---|---|
| | | | | antidepressants, anxiolytics, psychosis |
| nociceptive | central | 5HT1A | central inhibition | antagonists can work as antidepressants, nootropics |
| nociceptive | central | 5HT1B | central inhibition | migraines |
| nociceptive | central | 5HT1D | central inhibition | migraines |
| nociceptive | central | 5HT1E | central inhibition | |
| nociceptive | central | 5HT1F | central inhibition | agonists - psychedelics |
| nociceptive | central | 5HT1F | central inhibition | antagonists - atypical antipsychotics, NaSSAsm treatig sertonin syndrome, sleeping aid |
| nociceptive | central | 5HT2A | central inhibition | agonists - psychadelics |
| nociceptive | central | 5HT2A | central inhibition | antagonists - atypical antipsychotics, NaSSAs, treating seratonin syndrome, sleeping aid |
| nociceptive | central | 5HT2B | central inhibition | migraines |
| nociceptive | central | 5HT2C | central inhibition | antidepressant, orexigenic, anorectic, antipsychotic |
| nociceptive | central | 5HT3 | central inhibition | antiemetic |
| nociceptive | central | 5HT4 | central inhibition | gastroproknetics |
| nociceptive | central | 5HT5A | central inhibition | |
| nociceptive | central | 5HT5B | central inhibition | |
| nociceptive | central | 5HT6 | central inhibition | antidepressant (antagonists and agonists), anxiolytic (antagonists and agonists), nootropic (antagonists), anorectic (antagonists) |
| nociceptive | central | 5HT7 | central inhibition | antidepressant (antagonists), anxiolytics (antagonists), nootropic (antagonists) |
| nociceptive | central | CB1 | central inhibition | |
| nociceptive | central | GABA | central inhibition | |
| nociceptive | central | GABAA-$ | central inhibition | |
| nociceptive | central | GABAB-R | central inhibition | |
| nociceptive | central | Glucine-R | central inhibition | |
| nociceptive | central | NE | central inhibition | |
| nociceptive | central | Opiod receptors | central inhibition | |
| nociceptive | central | c-fos | gene expression | |
| nociceptive | central | c-jun | gene expression | |
| nociceptive | central | CREB | gene expression | |
| nociceptive | central | DREAM | gene expression | |
| nociceptive | peripheral | K+ channel | membrane excitability of primary afferents | |
| nociceptive | peripheral | Nav1.8 | membrane excitability of primary afferents | |
| nociceptive | peripheral | Nav1.9 | membrane excitability of primary afferents | |
| nociceptive | peripheral | CaMKIV | peripheral sensitization | |
| nociceptive | peripheral | COX2 | peripheral sensitization | |
| nociceptive | peripheral | cPLA2 | peripheral sensitization | |
| nociceptive | peripheral | EP1 | peripheral sensitization | |
| nociceptive | peripheral | EP3 | peripheral sensitization | |
| nociceptive | peripheral | EP4 | peripheral sensitization | |
| nociceptive | peripheral | ERK1/2 | peripheral sensitization | |
| nociceptive | peripheral | IL-1 beta | peripheral sensitization | |
| nociceptive | peripheral | JNK | peripheral sensitization | |
| nociceptive | peripheral | Nav1.8 | peripheral sensitization | |
| nociceptive | peripheral | NGF | peripheral sensitization | |

TABLE VII-23-continued

| Type of pain | Part of nervous system | Target | Area | How to affect |
|---|---|---|---|---|
| nociceptive | peripheral | p38 | peripheral sensitization | |
| nociceptive | peripheral | PKA | peripheral sensitization | |
| nociceptive | peripheral | PKC isoforms | peripheral sensitization | |
| nociceptive | peripheral | TNFalpha | peripheral sensitization | |
| nociceptive | peripheral | TrkA | peripheral sensitization | |
| nociceptive | peripheral | TRPV1 | peripheral sensitization | |
| nociceptive | central | AMPA/kainate-R | postsynaptic transmission | |
| nociceptive | central | K+ channels | postsynaptic transmission | |
| nociceptive | central | mGlu-$ | postsynaptic transmission | |
| nociceptive | central | Nav1.3 | postsynaptic transmission | |
| nociceptive | central | NK1 | postsynaptic transmission | |
| nociceptive | central | NMDA-R | postsynaptic transmission | |
| nociceptive | peripheral | Adenosine-R | presynaptic transmission | |
| nociceptive | peripheral | mGluR | presynaptic transmission | |
| nociceptive | peripheral | VGCC | presynaptic transmission | |
| nociceptive | central | ERK | signal transduction | |
| nociceptive | central | JNK | signal transduction | |
| nociceptive | central | p38 | signal transduction | |
| nociceptive | central | PKA | signal transduction | |
| nociceptive | central | PKC isoforms | signal transduction | |
| nociceptive | peripheral | ASIC | transduction | |
| nociceptive | peripheral | BK1 | transduction | |
| nociceptive | peripheral | BK2 | transduction | |
| nociceptive | peripheral | DRASIC | transduction | |
| nociceptive | peripheral | MDEG | transduction | |
| nociceptive | peripheral | P2X3 | transduction | |
| nociceptive | peripheral | TREK-1 | transduction | |
| nociceptive | peripheral | TRPM8 | transduction | |
| nociceptive | peripheral | TRPV1 | transduction | |
| nociceptive | peripheral | TRPV2 | transduction | |
| nociceptive | peripheral | TRPV3 | transduction | |
| neuropathic pain | | | | |
| Inflammatory pain | | histamine | | |
| Inflammatory pain | | ATP | | |
| Inflammatory pain | | bradykinin | | |
| Inflammatory pain | | CB2 | | |
| Inflammatory pain | | Endothelins | | |
| Inflammatory pain | | H+ | | |
| Inflammatory pain | | Interleukins | | |
| Inflammatory pain | | NGF | | |
| Inflammatory pain | | prostaglandins | | |
| Inflammatory pain | | serotonin | | |
| Inflammatory pain | | TNFalpha | | |

VIII. Targets: Disorders Associated with Disease Causing Organisms

Cas9 molecules, typically eiCas9 molecules or eaCas9 molecules, and gRNA molecules, e.g., an eiCas9 molecule/gRNA molecule complex, e.g., an eaCas9 molecule/gRNA molecule complex, can be used to treat or control diseases associated with disease causing organisms, e.g., to treat infectious diseases. In an embodiment, the infectious disease is treated by editing (e.g., correcting) one or more target genes, e.g., of the organism or of the subject. In an embodiment, the infectious disease is treated by delivering one or more payloads (e.g., as described herein) to the cell of a disease causing organism or to an infected cell of the subject, e.g., to a target gene. In an embodiment, the target gene is in the infectious pathogen. Exemplary infectious pathogens include, e.g., viruses, bacteria, fungi, protozoa, or mutlicellular parasites.

In an embodiment, the target gene is in the host cell. For example, modulation of a target gene in the host cell can result in resistance to the infectious pathogen. Host genes involved in any stage of the life cycle of the infectious pathogen (e.g., entry, replication, latency) can be modulated. In an embodiment, the target gene encodes a cellular receptor or co-receptor for the infectious pathogen. In an embodiment, the infectious pathogen is a virus, e.g., a virus described herein, e.g., HIV. In an embodiment, the target gene encodes a co-receptor for HIV, e.g., CCR5 or CXCR4.

Exemplary infectious diseases that can be treated by the molecules and methods described herein, include, e.g., AIDS, Hepatitis A, Hepatitis B, Hepatitis C, Herpes simplex, HPV infection, or Influenza.

Exemplary targets are provided in Table VIII-1. The disease and causative organism are provided.

TABLE VIII-1

| DISEASE | SOURCE OF DISEASE |
|---|---|
| *Acinetobacter* infections | *Acinetobacter baumannii* |
| Actinomycosis | *Actinomyces israelii, Actinomyces gerencseriae* and *Propionibacterium propionicus* |
| African sleeping sickness (African trypanosomiasis) | *Trypanosoma brucei* |
| AIDS (Acquired immunodeficiency syndrome) | HIV (Human immunodeficiency virus) |
| Amebiasis | *Entamoeba histolytica* |
| Anaplasmosis | *Anaplasma* genus |
| Anthrax | *Bacillus anthracis* |
| *Arcanobacterium haemolyticum* infection | *Arcanobacterium haemolyticum* |
| Argentine hemorrhagic fever | Junin virus |
| Ascariasis | *Ascaris lumbricoides* |
| Aspergillosis | *Aspergillus* genus |
| Astrovirus infection | Astroviridae family |
| Babesiosis | *Babesia* genus |
| *Bacillus cereus* infection | *Bacillus cereus* |
| Bacterial pneumonia | multiple bacteria |
| Bacterial vaginosis (BV) | multiple bacteria |
| *Bacteroides* infection | *Bacteroides* genus |
| Balantidiasis | *Balantidium coli* |
| *Baylisascaris* infection | *Baylisascaris* genus |
| BK virus infection | BK virus |
| Black piedra | *Piedraia hortae* |
| *Blastocystis hominis* infection | *Blastocystis hominis* |
| Blastomycosis | *Blastomyces dermatitidis* |
| Bolivian hemorrhagic fever | Machupo virus |
| *Borrelia* infection | *Borrelia* genus |
| Botulism (and Infant botulism) | *Clostridium botulinum*; Note: Botulism is not an infection by *Clostridium botulinum* but caused by the intake of *botulinum* toxin. |
| Brazilian hemorrhagic fever | Sabia |
| Brucellosis | *Brucella* genus |
| Bubonic plague | the bacterial family Enterobacteriaceae |
| *Burkholderia* infection | usually *Burkholderia cepacia* and other *Burkholderia* species |
| Buruli ulcer | *Mycobacterium ulcerans* |
| Calicivirus infection (Norovirus and Sapovirus) | Caliciviridae family |
| Campylobacteriosis | *Campylobacter* genus |
| Candidiasis (Moniliasis; Thrush) | usually *Candida albicans* and other *Candida* species |
| Cat-scratch disease | *Bartonella henselae* |
| Cellulitis | usually Group A *Streptococcus* and *Staphylococcus* |
| Chagas Disease (American trypanosomiasis) | *Trypanosoma cruzi* |
| Chancroid | *Haemophilus ducreyi* |
| Chickenpox | Varicella zoster virus (VZV) |
| *Chlamydia* | *Chlamydia trachomatis* |
| *Chlamydophila pneumoniae* infection (Taiwan acute respiratory agent or TWAR) | *Chlamydophila pneumoniae* |
| Cholera | *Vibrio cholerae* |

TABLE VIII-1-continued

| DISEASE | SOURCE OF DISEASE |
| --- | --- |
| Chromoblastomycosis | usually *Fonsecaea pedrosoi* |
| Clonorchiasis | *Clonorchis sinensis* |
| *Clostridium difficile* infection | *Clostridium difficile* |
| Coccidioidomycosis | *Coccidioides immitis* and *Coccidioides posadasii* |
| Colorado tick fever (CTF) | Colorado tick fever virus (CTFV) |
| Common cold (Acute viral rhinopharyngitis; Acute coryza) | usually rhinoviruses and coronaviruses. |
| Creutzfeldt-Jakob disease (CJD) | PRNP |
| Crimean-Congo hemorrhagic fever (CCHF) | Crimean-Congo hemorrhagic fever virus |
| Cryptococcosis | *Cryptococcus neoformans* |
| Cryptosporidiosis | *Cryptosporidium* genus |
| Cutaneous larva migrans (CLM) | usually *Ancylostoma braziliense*; multiple other parasites |
| Cyclosporiasis | *Cyclospora cayetanensis* |
| Cysticercosis | *Taenia solium* |
| Cytomegalovirus infection | Cytomegalovirus |
| Dengue fever | Dengue viruses (DEN-1, DEN-2, DEN-3 and DEN-4) - Flaviviruses |
| Dientamoebiasis | *Dientamoeba fragilis* |
| Diphtheria | *Corynebacterium diphtheriae* |
| Diphyllobothriasis | *Diphyllobothrium* |
| Dracunculiasis | *Dracunculus medinensis* |
| Ebola hemorrhagic fever | Ebolavirus (EBOV) |
| Echinococcosis | *Echinococcus* genus |
| Ehrlichiosis | *Ehrlichia* genus |
| Enterobiasis (Pinworm infection) | *Enterobius vermicularis* |
| Enterococcus infection | *Enterococcus* genus |
| Enterovirus infection | Enterovirus genus |
| Epidemic typhus | *Rickettsia prowazekii* |
| Erythema infectiosum (Fifth disease) | Parvovirus B19 |
| Exanthem subitum (Sixth disease) | Human herpesvirus 6 (HHV-6) and Human herpesvirus 7 (HHV-7) |
| Fasciolopsiasis | *Fasciolopsis buski* |
| Fasciolosis | *Fasciola hepatica* and *Fasciola gigantica* |
| Fatal familial insomnia (FFI) | PRNP |
| Filariasis | Filarioidea superfamily |
| Food poisoning by *Clostridium perfringens* | *Clostridium perfringens* |
| Free-living amebic infection | multiple |
| *Fusobacterium* infection | *Fusobacterium* genus |
| Gas gangrene (Clostridial myonecrosis) | usually *Clostridium perfringens*; other *Clostridium* species |
| Geotrichosis | *Geotrichum candidum* |
| Gerstmann-Sträussler-Scheinker syndrome (GSS) | PRNP |
| Giardiasis | *Giardia intestinalis* |
| Glanders | *Burkholderia mallei* |
| Gnathostomiasis | *Gnathostoma spinigerum* and *Gnathostoma hispidum* |
| Gonorrhea | *Neisseria gonorrhoeae* |
| Granuloma inguinale (Donovanosis) | *Klebsiella granulomatis* |
| Group A streptococcal infection | *Streptococcus pyogenes* |
| Group B streptococcal infection | *Streptococcus agalactiae* |
| *Haemophilus influenzae* infection | *Haemophilus influenzae* |
| Hand, foot and mouth disease (HFMD) | Enteroviruses, mainly Coxsackie A virus and Enterovirus 71 (EV71) |
| Hantavirus Pulmonary Syndrome (HPS) | Sin Nombre virus |
| *Helicobacter pylori* infection | *Helicobacter pylori* |
| Hemolytic-uremic syndrome (HUS) | *Escherichia coli* O157:H7, O111 and O104:H4 |
| Hemorrhagic fever with renal syndrome (HFRS) | Bunyaviridae family |
| Hepatitis A | Hepatitis A Virus |
| Hepatitis B | Hepatitis B Virus |
| Hepatitis C | Hepatitis C Virus |
| Hepatitis D | Hepatitis D Virus |
| Hepatitis E | Hepatitis E Virus |
| Herpes simplex | Herpes simplex virus 1 and 2 (HSV-1 and HSV-2) |
| Histoplasmosis | *Histoplasma capsulatum* |
| Hookworm infection | *Ancylostoma duodenale* and *Necator americanus* |

TABLE VIII-1-continued

| DISEASE | SOURCE OF DISEASE |
| --- | --- |
| Human bocavirus infection | Human bocavirus (HBoV) |
| Human *ewingii* ehrlichiosis | *Ehrlichia ewingii* |
| Human granulocytic anaplasmosis (HGA) | *Anaplasma phagocytophilum* |
| Human metapneumovirus infection | Human metapneumovirus (hMPV) |
| Human monocytic ehrlichiosis | *Ehrlichia chaffeensis* |
| Human papillomavirus (HPV) infection | Human papillomavirus (HPV) |
| Human parainfluenza virus infection | Human parainfluenza viruses (HPIV) |
| Hymenolepiasis | *Hymenolepis nana* and *Hymenolepis diminuta* |
| Epstein-Barr Virus Infectious Mononucleosis (Mono) | Epstein-Barr Virus (EBV) |
| Influenza (flu) | Orthomyxoviridae family |
| Isosporiasis | *Isospora belli* |
| Kawasaki disease | unknown; evidence supports that it is infectious |
| Keratitis | multiple |
| *Kingella kingae* infection | *Kingella kingae* |
| Kuru | PRNP |
| Lassa fever | Lassa virus |
| Legionellosis (Legionnaires' disease) | *Legionella pneumophila* |
| Legionellosis (Pontiac fever) | *Legionella pneumophila* |
| Leishmaniasis | *Leishmania* genus |
| Leprosy | *Mycobacterium leprae* and *Mycobacterium lepromatosis* |
| Leptospirosis | *Leptospira* genus |
| Listeriosis | *Listeria monocytogenes* |
| Lyme disease (Lyme borreliosis) | usually *Borrelia burgdorferi* and other *Borrelia* species |
| Lymphatic filariasis (Elephantiasis) | *Wuchereria bancrofti* and *Brugia malayi* |
| Lymphocytic choriomeningitis | Lymphocytic choriomeningitis virus (LCMV) |
| Malaria | *Plasmodium* genus |
| Marburg hemorrhagic fever (MHF) | Marburg virus |
| Measles | Measles virus |
| Melioidosis (Whitmore's disease) | *Burkholderia pseudomallei* |
| Meningitis | multiple |
| Meningococcal disease | *Neisseria meningitidis* |
| Metagonimiasis | usually *Metagonimus yokagawai* |
| Microsporidiosis | *Microsporidia* phylum |
| Molluscum contagiosum (MC) | Molluscum contagiosum virus (MCV) |
| Monkeypox | Monkeypox virus |
| Mumps | Mumps virus |
| Murine typhus (Endemic typhus) | *Rickettsia typhi* |
| *Mycoplasma pneumonia* | *Mycoplasma pneumoniae* |
| Mycetoma | numerous species of bacteria (Actinomycetoma) and fungi (Eumycetoma) |
| Myiasis | parasitic dipterous fly larvae |
| Neonatal conjunctivitis (Ophthalmia neonatorum) | most commonly *Chlamydia trachomatis* and *Neisseria gonorrhoeae* |
| (New) Variant Creutzfeldt-Jakob disease (vCJD, nvCJD) | PRNP |
| Nocardiosis | usually *Nocardia asteroides* and other *Nocardia* species |
| Onchocerciasis (River blindness) | *Onchocerca volvulus* |
| Paracoccidioidomycosis (South American blastomycosis) | *Paracoccidioides brasiliensis* |
| Paragonimiasis | usually *Paragonimus westermani* and other *Paragonimus* species |
| Pasteurellosis | *Pasteurella* genus |
| Pediculosis capitis (Head lice) | *Pediculus humanus capitis* |
| Pediculosis corporis (Body lice) | *Pediculus humanus corporis* |
| Pediculosis pubis (Pubic lice, Crab lice) | *Phthirus pubis* |
| Pelvic inflammatory disease (PID) | multiple |
| Pertussis (Whooping cough) | *Bordetella pertussis* |
| Plague | *Yersinia pestis* |
| Pneumococcal infection | *Streptococcus pneumoniae* |
| Pneumocystis pneumonia (PCP) | *Pneumocystis jirovecii* |
| Pneumonia | multiple |
| Poliomyelitis | Poliovirus |

TABLE VIII-1-continued

| DISEASE | SOURCE OF DISEASE |
|---|---|
| *Prevotellae* infection | *Prevotellae* genus |
| Primary amoebic meningoencephalitis (PAM) | usually *Naegleria fowleri* |
| Progressive multifocal leukoencephalopathy | JC virus |
| Psittacosis | *Chlamydophila psittaci* |
| Q fever | *Coxiella burnetii* |
| Rabies | Rabies virus |
| Rat-bite fever | *Streptobacillus moniliformis* and *Spirillum minus* |
| Respiratory syncytial virus infection | Respiratory syncytial virus (RSV) |
| Rhinosporidiosis | *Rhinosporidium seeberi* |
| Rhinovirus infection | Rhino virus |
| Rickettsial infection | *Rickettsia* genus |
| Rickettsialpox | *Rickettsia akari* |
| Rift Valley fever (RVF) | Rift Valley fever virus |
| Rocky Mountain spotted fever (RMSF) | *Rickettsia rickettsii* |
| Rotavirus infection | Rotavirus |
| Rubella | Rubella virus |
| Salmonellosis | *Salmonella* genus |
| SARS (Severe Acute Respiratory Syndrome) | SARS coronavirus |
| Scabies | *Sarcoptes scabiei* |
| Schistosomiasis | *Schistosoma* genus |
| Sepsis | multiple |
| Shigellosis (Bacillary dysentery) | *Shigella* genus |
| Shingles (Herpes zoster) | Varicella zoster virus (VZV) |
| Smallpox (Variola) | Variola major or Variola minor |
| Sporotrichosis | *Sporothrix schenckii* |
| Staphylococcal food poisoning | *Staphylococcus* genus |
| Staphylococcal infection | *Staphylococcus* genus |
| Strongyloidiasis | *Strongyloides stercoralis* |
| Subacute sclerosing panencephalitis | Measles virus |
| Syphilis | *Treponema pallidum* |
| Taeniasis | *Taenia* genus |
| Tetanus (Lockjaw) | *Clostridium tetani* |
| Tinea barbae (Barber's itch) | usually *Trichophyton* genus |
| Tinea capitis (Ringworm of the Scalp) | usually *Trichophyton tonsurans* |
| Tinea corporis (Ringworm of the Body) | usually *Trichophyton* genus |
| Tinea cruris (Jock itch) | usually *Epidermophyton floccosum*, *Trichophyton rubrum*, and *Trichophyton mentagrophytes* |
| Tinea manuum (Ringworm of the Hand) | Trichophyton rubrum |
| Tinea nigra | usually *Hortaea werneckii* |
| Tinea pedis (Athlete's foot) | usually *Trichophyton* genus |
| Tinea unguium (Onychomycosis) | usually *Trichophyton* genus |
| Tinea versicolor (Pityriasis versicolor) | *Malassezia* genus |
| Toxocariasis (Ocular Larva Migrans (OLM)) | *Toxocara canis* or *Toxocara cati* |
| Toxocariasis (Visceral Larva Migrans (VLM)) | *Toxocara canis* or *Toxocara cati* |
| Toxoplasmosis | *Toxoplasma gondii* |
| Trichinellosis | *Trichinella spiralis* |
| Trichomoniasis | *Trichomonas vaginalis* |
| Trichuriasis (Whipworm infection) | *Trichuris trichiura* |
| Tuberculosis | usually *Mycobacterium tuberculosis* |
| Tularemia | *Francisella tularensis* |
| *Ureaplasma urealyticum* infection | *Ureaplasma urealyticum* |
| Valley fever | *Coccidioides immitis* or *Coccidioides posadasii.* |
| Venezuelan equine encephalitis | Venezuelan equine encephalitis virus |
| Venezuelan hemorrhagic fever | Guanarito virus |
| Viral pneumonia | multiple viruses |
| West Nile Fever | West Nile virus |
| White piedra (Tinea blanca) | *Trichosporon beigelii* |
| *Yersinia pseudotuberculosis* infection | *Yersinia pseudotuberculosis* |
| Yersiniosis | *Yersinia enterocolitica* |
| Yellow fever | Yellow fever virus |

TABLE VIII-1-continued

| DISEASE | SOURCE OF DISEASE |
|---|---|
| Zygomycosis | Mucorales order (Mucormycosis) and Entomophthorales order (Entomophthoramycosis) |

AIDS/HIV

HIV Genomic Structural Elements

Long terminal repeat (LTR) refers to the DNA sequence flanking the genome of integrated proviruses. It contains important regulatory regions, especially those for transcription initiation and polyadenylation.

Target sequence (TAR) for viral transactivation, the binding site for Tat protein and for cellular proteins; consists of approximately the first 45 nucleotides of the viral mRNAs in HIV-1 (or the first 100 nucleotides in HIV-2 and SIV.) TAR RNA forms a hairpin stem-loop structure with a side bulge; the bulge is necessary for Tat binding and function.

Rev responsive element (RPE) refers to an RNA element encoded within the env region of HIV-1. It consists of approximately 200 nucleotides (positions 7327 to 7530 from the start of transcription in HIV-1, spanning the border of gp120 and gp41). The RRE is necessary for Rev function; it contains a high affinity site for Rev; in all, approximately seven binding sites for Rev exist within the RRE RNA. Other lentiviruses (HIV-2, SIV, visna, CAEV) have similar RRE elements in similar locations within env, while HTLVs have an analogous RNA element (RXRE) serving the same purpose within their LTR; RRE is the binding site for Rev protein, while RXRE is the binding site for Rex protein. RRE (and RXRE) form complex secondary structures, necessary for specific protein binding.

Psi elements (PE) are a set of 4 stem-loop structures preceding and overlapping the Gag start codon which are the sites recognized by the cysteine histidine box, a conserved motif with the canonical sequence CysX2CysX4HisX4Cys (SEQ ID NO: 41), present in the Gag p7 MC protein. The Psi Elements are present in unspliced genomic transcripts but absent from spliced viral mRNAs.

SLIP, an TTTTTT slippery site, followed by a stem-loop structure, is responsible for regulating the −1 ribosomal frameshift out of the Gag reading frame into the Pol reading frame.

Cis-acting repressive sequences (CRS) are postulated to inhibit structural protein expression in the absence of Rev. One such site was mapped within the pol region of HIV-1. The exact function has not been defined; splice sites have been postulated to act as CRS sequences.

Inhibitory/Instability RNA sequences (INS) are found within the structural genes of HIV-1 and of other complex retroviruses. Multiple INS elements exist within the genome and can act independently; one of the best characterized elements spans nucleotides 414 to 631 in the gag region of HIV-1. The INS elements have been defined by functional assays as elements that inhibit expression posttranscriptionally. Mutation of the RNA elements was shown to lead to INS inactivation and up regulation of gene expression.

Genes and Gene Products

Essential for Replication

The genomic region (GAG) encoding the capsid proteins (group specific antigens). The precursor is the p55 myristylated protein, which is processed to p17 (MAtrix), p24 (CApsid), p7 (NucleoCapsid), and p6 proteins, by the viral protease. Gag associates with the plasma membrane where the virus assembly takes place. The 55 kDa Gag precursor is called assembling to indicate its role in viral assembly.

The genomic region, POL, encoding the viral enzymes protease, reverse transcriptase, RNAse, and integrase. These enzymes are produced as a Gag-Pol precursor polyprotein, which is processed by the viral protease; the Gag-Pol precursor is produced by ribosome frameshifting near the end of gag.

Viral glycoproteins (e.g., ENV) produced as a precursor (gp160) which is processed to give a noncovalent complex of the external glycoprotein gp120 and the transmembrane glycoprotein gp41. The mature gp120-gp41 proteins are bound by non-covalent interactions and are associated as a trimer on the cell surface. A substantial amount of gp120 can be found released in the medium. gp120 contains the binding site for the CD4 receptor, and the seven transmembrane do-main chemokine receptors that serve as co-receptors for HIV-1.

The transactivator (TAT) of HIV gene expression is one of two essential viral regulatory factors (Tat and Rev) for HIV gene expression. Two forms are known, Tat-1 exon (minor form) of 72 amino acids and Tat-2 exon (major form) of 86 amino acids. Low levels of both proteins are found in persistently infected cells. Tat has been localized primarily in the nucleolus/nucleus by immunofluorescence. It acts by binding to the TAR RNA element and activating transcription initiation and elongation from the LTR promoter, preventing the LTR AATAAA polyadenylation signal from causing premature termination of transcription and polyadenylation. It is the first eukaryotic transcription factor known to interact with RNA rather than DNA and may have similarities with prokaryotic anti-termination factors. Extracellular Tat can be found and can be taken up by cells in culture.

The second necessary regulatory factor for HIV expression is REV. A 19 kDa phosphoprotein, localized primarily in the nucleolus/nucleus, Rev acts by binding to RRE and promoting the nuclear export, stabilization and utilization of the un-spliced viral mRNAs containing RRE. Rev is considered the most functionally conserved regulatory protein of lentiviruses. Rev cycles rapidly between the nucleus and the cytoplasm.

Others

Viral infectivity factor (VIF) is a basic protein of typically 23 kDa. Promotes the infectivity but not the production of viral particles. In the absence of Vif the produced viral particles are defective, while the cell-to-cell transmission of virus is not affected significantly. Found in almost all lentiviruses, Vif is a cytoplasmic protein, existing in both a soluble cytosolic form and a membrane-associated form. The latter form of Vif is a peripheral membrane protein that is tightly associated with the cytoplasmic side of cellular membranes. In 2003, it was discovered that Vif prevents the action of the cellular APOBEC-3G protein which deaminates DNA:RNA heteroduplexes in the cytoplasm.

Viral Protein R (VPR) is a 96-amino acid (14 kDa) protein, which is incorporated into the virion. It interacts with the p6 Gag part of the Pr55 Gag precursor. Vpr detected in the cell is localized to the nucleus. Proposed functions for Vpr include the targeting the nuclear import of preintegration complexes, cell growth arrest, transactivation of cellular genes, and induction of cellular differentiation. In HIV-2, SIV-SMM, SIV-RCM, SIV-MND-2 and SIV-DRL the Vpx gene is apparently the result of a Vpr gene duplication event, possibly by recombination.

Viral Protein U (VPU)) is unique to HIV-1, SIVcpz (the closest SIV relative of HIV-1), SIV-GSN, SIV-MUS, SIV-MON and SIV-DEN. There is no similar gene in HIV-2, SIV-SMM or other SIVs. Vpu is a 16 kDa (81-amino acid) type I integral membrane protein with at least two different biological functions: (a) degradation of CD4 in the endoplasmic reticulum, and (b) enhancement of virion release from the plasma membrane of HIV-1-infected cells. Env and Vpu are expressed from a bicistronic mRNA. Vpu probably possesses an N-terminal hydrophobic membrane anchor and a hydrophilic moiety. It is phosphorylated by casein kinase II at positions Ser52 and Ser56. Vpu is involved in Env maturation and is not found in the virion. Vpu has been found to increase susceptibility of HIV-1 infected cells to Fas killing.

NEF is amultifunctional 27-kDa myristylated protein produced by an ORF located at the 3 0 end of the primate lentiviruses. Other forms of Nef are known, including non-myristylated variants. Nef is predominantly cytoplasmic and associated with the plasma membrane via the myristyl residue linked to the conserved second amino acid (Gly). Nef has also been identified in the nucleus and found associated with the cytoskeleton in some experiments. One of the first HIV proteins to be produced in infected cells, it is the most immunogenic of the accessory proteins. The nef genes of HIV and SIV are dispensable in vitro, but are essential for efficient viral spread and disease progression in vivo. Nef is necessary for the maintenance of high virus loads and for the development of AIDS in macaques, and viruses with defective Nef have been detected in some HIV-1 infected long term survivors. Nef downregulates CD4, the primary viral receptor, and MHC class I molecules, and these functions map to different parts of the protein. Nef interacts with components of host cell signal transduction and clathrin-dependent protein sorting pathways. It increases viral infectivity. Nef contains PxxP motifs that bind to SH3 domains of a subset of Src kinases and are required for the enhanced growth of HIV but not for the downregulation of CD4.

VPX is a virion protein of 12 kDa found in HIV-2, SIV-SMM, SIV-RCM, SIV-MND-2 and SIV-DRL and not in HIV-1 or other SIVs. This accessory gene is a homolog of HIV-1 vpr, and viruses with Vpx carry both vpr and vpx. Vpx function in relation to Vpr is not fully elucidated; both are incorporated into virions at levels comparable to Gag proteins through interactions with Gag p6. Vpx is necessary for efficient replication of SIV-SMM in PBMCs. Progression to AIDS and death in SIV-infected animals can occur in the absence of Vpr or Vpx. Double mutant virus lacking both vpr and vpx was attenuated, whereas the single mutants were not, suggesting a redundancy in the function of Vpr and Vpx related to virus pathogenicity.

Hepatitis A Viral Target Sequences

5' untranslated region contains IRES-internal ribosome entry site

P1 Region of Genome-Capsid Proteins
VP1
VP2
VP3
VP4

P2 Region of Genome
2A
2B
2C
P3 Region of Genome
3A
3B
3C—viral protease
3D—RNA polymerase Hepatitis B Viral Target Sequences Precursor Polypeptide encoding all HCV protein is produced and then spliced into functional proteins. The following are the proteins (coding regions) encoded:
   C—core protein—coding region consists of a Pre-C and Core coding region
   X—function unclear but suspected to play a role in activation of viral transcription process
   P—RNA polymerase
   S—surface antigen—coding region consists of a Pre-S1, Pre-S2 and Surface antigen coding regions Hepatitis C Viral Target Sequences Precursor Polypeptide encoding all HCV protein is produced and then spliced into functional proteins. The following are the proteins (coding regions) encoded:
   RES—non-coding internal ribosome entry site (5' to polyprotein encoding sequence)
   3' non-coding sequences—
   C region—encodes p22 a nucleocapsid protein
   E1 region—encodes gp35 envelope glycoprotein—important in cell entry
   E2 region—encodes gp70 envelope glycoprotein—important in cell entry
   NS1—encodes p7—not necessary for replication but critical in viral morphogenesis
   NS2—encodes p23 a transmembrane protein with protease activity
   NS3—encodes p70 having both serine protease and RNA helicase activities
   NS4A—encodes p8 co-factor
   NS4B—encodes p27 cofactor—important in recruitment of other viral proteins
   NS5A—encodes p56/58 an interferon resistance protein—important in viral replication
   NS5B—encodes RNA polymerase Herpes Simplex Virus Target Sequence

| Gene | Protein | Function/description |
| --- | --- | --- |
| UL1 | Glycoprotein L | Surface and membrane |
| UL2 | UL2 | Uracil-DNA glycosylase |
| UL3 | UL3 | unknown |
| UL4 | UL4 | unknown |
| UL5 | UL5 | DNA replication |
| UL6 | Portal protein UL-6 | Twelve of these proteins constitute the capsid portal ring through which DNA enters and exits the capsid. |
| UL7 | UL7 | Virion maturation |
| UL8 | UL8 | DNA helicase/primase complex-associated protein |
| UL9 | UL9 | Replication origin-binding protein |
| UL10 | Glycoprotein M | Surface and membrane |
| UL11 | UL11 | virion exit and secondary envelopment |

-continued

| Gene | Protein | Function/description |
|---|---|---|
| UL12 | UL12 | Alkaline exonuclease |
| UL13 | UL13 | Serine-threonine protein kinase |
| UL14 | UL14 | Tegument protein |
| UL15 | Terminase | Processing and packaging of DNA |
| UL16 | UL16 | Tegument protein |
| UL17 | UL17 | Processing and packaging DNA |
| UL18 | VP23 | Capsid protein |
| UL19 | VP5 | Major capsid protein |
| UL20 | UL20 | Membrane protein |
| UL21 | UL21 | Tegument protein |
| UL22 | Glycoprotein H | Surface and membrane |
| UL23 | Thymidine kinase | Peripheral to DNA replication |
| UL24 | UL24 | unknown |
| UL25 | UL25 | Processing and packaging DNA |
| UL26 | P40; VP24; VP22A | Capsid protein |
| UL27 | Glycoprotein B | Surface and membrane |
| UL28 | ICP18.5 | Processing and packaging DNA |
| UL29 | UL29; ICP8 | Major DNA-binding protein |
| UL30 | DNA polymerase | DNA replication |
| UL31 | UL31 | Nuclear matrix protein |
| UL32 | UL32 | Envelope glycoprotein |
| UL33 | UL33 | Processing and packaging DNA |
| UL34 | UL34 | Inner nuclear membrane protein |
| UL35 | VP26 | Capsid protein |
| UL36 | UL36 | Large tegument protein |
| UL37 | UL37 | Capsid assembly |
| UL38 | UL38; VP19C | Capsid assembly and DNA maturation |
| UL39 | UL39 | Ribonucleotide reductase (Large subunit) |
| UL40 | UL40 | Ribonucleotide reductase (Small subunit) |
| UL41 | UL41; VHS | Tegument protein; Virion host shutoff |
| UL42 | UL42 | DNA polymerase processivity factor |
| UL43 | UL43 | Membrane protein |
| UL44 | Glycoprotein C | Surface and membrane |
| UL45 | UL45 | Membrane protein; C-type lectin[26] |
| UL46 | VP11/12 | Tegument proteins |
| UL47 | UL47; VP13/14 | Tegument protein |
| UL48 | VP16 (Alpha-TIF) | Virion maturation; activate IE genes by interacting with the cellular transcription factors Oct-1 and HCF. Binds to the sequence 5'TAATGARAT³'. |
| UL49 | UL49A | Envelope protein |
| UL50 | UL50 | dUTP diphosphatase |
| UL51 | UL51 | Tegument protein |
| UL52 | UL52 | DNA helicase/primase complex protein |
| UL53 | Glycoprotein K | Surface and membrane |
| UL54 | IE63; ICP27 | Transcriptional regulation |
| UL55 | UL55 | Unknown |
| UL56 | UL56 | Unknown |
| US1 | ICP22; IE68 | Viral replication |
| US2 | US2 | Unknown |
| US3 | US3 | Serine/threonine-protein kinase |
| US4 | Glycoprotein G | Surface and membrane |
| US5 | Glycoprotein J | Surface and membrane |
| US6 | Glycoprotein D | Surface and membrane |
| US7 | Glycoprotein I | Surface and membrane |
| US8 | Glycoprotein E | Surface and membrane |
| US9 | US9 | Tegument protein |
| US10 | US10 | Capsid/Tegument protein |
| US11 | US11; Vmw21 | Binds DNA and RNA |
| US12 | ICP47; IE12 | Inhibits MHC class I pathway by preventing binding of antigen to TAP |
| RS1 | ICP4; IE175 | Major transcriptional activator. Essential for progression beyond the immediate-early phase of infection. IEG transcription repressor. |
| ICP0 | ICP0; IE110; α0 | E3 ubiquitin ligase that activates viral gene transcription by opposing chromatinization of the viral genome and counteracts intrinsic- and interferon-based antiviral responses.[28] |
| LRP1 | LRP1 | Latency-related protein |
| LRP2 | LRP2 | Latency-related protein |
| RL1 | RL1; ICP34.5 | Neurovirulence factor. Antagonizes PKR by de-phosphorylating eIF4a. Binds to BECN1 and inactivates autophagy. |
| LAT | none | Latency-associated transcript |

HPV Target Sequences

| | |
|---|---|
| E1 | Genome replication: ATP-dependent DNA helicase |
| E2 | Genome replication, transcription, segregation, encapsidation. Regulation of cellular gene expression; cell cycle and apoptosis regulation. Several isoforms of the virus replication/transcription factor E2 have also been noted for a number of HPVs. E2 has an N-terminal domain that mediates protein-protein interactions, a flexible hinge region and a C-terminal DNA binding domain. Truncated E2 proteins may be translated from alternatively spliced E2 RNAs to generate E1^E2 and E8^E2 protein isoforms present in HPV16 and 31-infected cells. These E2 isoforms may act in a dominant-negative manner to modulate the function of full length E2. For example, a full length E2/E8^E2 dimer may bind DNA but fail to recruit E1 to initiate virus replication. Similarly, such a dimer may be unable to interact with cellular transcription factors to alter virus genome transcription. |
| E4 | Remodels cytokeratin network; cell cycle arrest; virion assembly |
| E5 | Control of cell growth and differentiation; immune modulation |
| E6 | Inhibits apoptosis and differentiation; regulates cell shape, polarity, mobility and signaling. Four mRNA isoforms (FLE6, E6*I, E6*II, E6*X) have been observed in HPV16 infected cervical epithelial cells and two in HPV18 infection. A role for the E6*I isoform in antagonizing FLE6 function has been suggested, as has opposing roles for FLE6 and E6*I in |

-continued

| | regulation of procaspase 8 in the extrinsic apoptotic pathway. More recently, a stand-alone function of the E6*I isoform has been determined in cellular protein degradation. |
|---|---|
| E7 | Cell cycle control; controls centrosome duplication |
| L1 | Major capsid protein |
| L2 | Minor capsid protein; recruits L1; virus assembly |
| LCR | Viral long control region (location of early promoters) |
| Keratinocyte/ auxiliary enhancer | |
| $P_{97}$ Promoter | Early (E) gene promoter for subtype HPV16 |
| $P_{105}$ Promoter | Early (E) gene promoter for subtype HPV18 |
| $P_{670}$ Promoter | Late (L) gene promoter for HPV16 |
| $P_{742}$ Promoter | Late (L) gene promoter for HPV31 |

Influenza A Target Sequences

Influenza A is the most common flu virus that infects humans. The influenza A virion is made up of 8 different single stranded RNA segments which encodes 11-14 proteins. These segments can vary in sequence, with most variation occurring in the hemagglutinin (H or HA) surface protein and neuraminidase (NA or N). The eight RNA segments (and the proteins they encode) are:

HA—encodes hemagglutinin (about 500 molecules of hemagglutinin are needed to make one virion).

NA—encodes neuraminidase (about 100 molecules of neuraminidase are needed to make one virion).

NP encodes nucleoprotein.

M encodes two matrix proteins (the M1 and the M2) by using different reading frames from the same RNA segment (about 3000 matrix protein molecules are needed to make one virion). M42 is produced by alternative splicing, and can partially replace an M2.

NS encodes two distinct non-structural proteins (NS1 and NEP) by using different reading frames from the same RNA segment.

PA encodes an RNA polymerase; an alternate form is sometimes made through a ribosomal skip, with +1 frameshift, reading through to the next stop codon.

PB1 encodes an RNA polymerase, plus two other transcripts read from alternate start sites, named PB1-N40 and PB1-F2 protein (induces apoptosis) by using different reading frames from the same RNA segment.

PB2 encodes an RNA polymerase.

M. tuberculosis Target Sequences

The methods and composition described herein can be used to target M. tuberculosis and treat a subject suffering from an infection with M. tuberculosis.

Other

In an embodiment, the target gene is associated with multiple drug resistance (MDR), e.g., in bacterial infection. Infectious pathogens can use a number of mechanisms in attaining multi-drug resistance, e.g., no longer relying on a glycoprotein cell wall, enzymatic deactivation of antibiotics, decreased cell wall permeability to antibiotics, altered target sites of antibiotic, efflux pumps to remove antibiotics, increased mutation rate as a stress response, or a combination thereof.

IX. Targets: Gene Editing/Correction

Candidate Cas9 molecules, candidate gRNA molecules, and/or candidate Cas9 molecule/gRNA molecule complexes, can be used to modulate genes (e.g., mutated genes) responsible for diseases. In an embodiment, the gene is modulated by editing or correcting a target gene, e.g., as described herein. In an embodiment, the human gene is modulated by delivery of one or more regulators/effectors (e.g., as described herein) inside cells to the target gene. For example, the genes described herein can be modulated, in vitro, ex vivo, or in vivo.

TABLE IX-1

Selected Diseases in which a gene can be therapeutically targeted.

Kinases (cancer)
Energy metabolism (cancer)
CFTR (cystic fibrosis)
Color blindness
Hemochromatosis
Hemophilia
Phenylketonuria
Polycystic kidney disease
Sickle-cell disease
Tay-Sachs disease
Siderius X-linked mental retardation syndrome
Lysosomal storage disorders, e.g., Alpha-galactosidase A deficiency
Anderson-Fabry disease
Angiokeratoma Corporis Diffusum
CADASIL syndrome
Carboxylase Deficiency, Multiple, Late-Onset
Cerebelloretinal Angiomatosis, familial
Cerebral arteriopathy with subcortical infarcts and leukoencephalopathy
Cerebral autosomal dominant arteriopathy with subcortical infarcts and leukoencephalopathy
Cerebroside Lipidosis syndrome
Choreoathetosis self-mutilation hyperuricemia syndrome
Classic Galactosemia
Crohn's disease, fibrostenosing
Phenylalanine Hydroxylase Deficiency disease,
Fabry disease
Hereditary coproporphyria
Incontinentia pigmenti
Microcephaly
Polycystic kidney disease
Rett's
Alpha-1 antitrypsin deficiency
Wilson's Disease
Tyrosinemia
Frameshift related diseases
Cystic fibrosis
Triplet repeat diseases (also referred herein as trinucleotide repeat diseases)

Trinucleotide repeat diseases (also known as triplet repeat disease, trinucleotide repeat expansion disorders, triplet repeat expansion disorders, or codon reiteration disorders) are a set of genetic disorders caused by trinucleotide repeat expansion, e.g., a type of mutation where trinucleotide repeats in certain genes exceed the normal and/or stable threshold. The mutation can be a subset of unstable microsatellite repeats that occur in multiple or all genomic sequences. The mutation can increase the repeat count (e.g., result in extra or expanded repeats) and result in a defective gene, e.g., producing an abnormal protein. Trinucleotide repeats can be classified as insertion mutations or as a separate class of mutations. Candidate Cas9 molecules, candidate gRNA molecules, and/or candidate Cas9 molecule/gRNA molecule complexes, can be used to modulate one or more genes (e.g., mutated genes) associated with a trinucleotide repeat disease, e.g., by reducing the number of (e.g., removing) the extra or expanded repeats, such that the normal or wild-type gene product (e.g., protein) can be produced.

Exemplary trinucleotide repeat diseases and target genes involved in trinucleotide repeat diseases are shown in Table IX-1A.

TABLE IX-1A

Exemplary trinucleotide repeat diseases and target genes involved in trinucleotide repeat diseases

| Trinucleotide Repeat Diseases | Gene |
| --- | --- |
| DRPLA (Dentatorubropallidoluysian atrophy) | ATN1 or DRPLA |
| HD (Huntington's disease) | HTT (Huntingtin) |
| SBMA (Spinobulbar muscular atrophy or Kennedy disease) | Androgen receptor on the X chromosome. |
| SCA1 (Spinocerebellar ataxia Type 1) | ATXN1 |
| SCA2 (Spinocerebellar ataxia Type 2) | ATXN2 |
| SCA3 (Spinocerebellar ataxia Type 3 or Machado-Joseph disease) | ATXN3 |
| SCA6 (Spinocerebellar ataxia Type 6) | CACNA1A |
| SCA7 (Spinocerebellar ataxia Type 7) | ATXN7 |
| SCA17 (Spinocerebellar ataxia Type 17) | TBP |
| FRAXA (Fragile X syndrome) | FMR1, on the X-chromosome |
| FXTAS (Fragile X-associated tremor/ataxia syndrome) | FMR1, on the X-chromosome |
| FRAXE (Fragile XE mental retardation) | AFF2 or FMR2, on the X-chromosome |
| FRDA (Friedreich's ataxia) | FXN or X25, (frataxin-reduced expression) |
| DM (Myotonic dystrophy) | DMPK |
| SCA8 (Spinocerebellar ataxia Type 8) | OSCA or SCA8 |
| SCA12 (Spinocerebellar ataxia Type 12) | PPP2R2B or SCA12 |

Exemplary target genes include those genes involved in various diseases or conditions, e.g., cancer (e.g., kinases), energy metabolism, cystic fibrosis (e.g., CFTR), color blindness, hemochromatosis, hemophilia, phenylketonuria, polycystic kidney disease, Sickle-cell disease, Tay-Sachs disease, Siderius X-linked mental retardation syndrome, Lysosomal storage disorders (e.g., Alpha-galactosidase A deficiency), Anderson-Fabry disease, Angiokeratoma Corporis Diffusum, CADASIL syndrome, Carboxylase Deficiency, Multiple, Late-Onset, Cerebelloretinal Angiomatosis, familial, Cerebral arteriopathy with subcortical infarcts and leukoencephalopathy, Cerebral autosomal dominant arteriopathy with subcortical infarcts and leukoencephalopathy, Cerebroside Lipidosis syndrome, Choreoathetosis self-mutilation hyperuricemia syndrome, Classic Galactosemia, Crohn's disease, fibrostenosing, Phenylalanine Hydroxylase Deficiency disease, Fabry disease, Hereditary coproporphyria, Incontinentia pigmenti, Microcephaly, Polycystic kidney disease, Rett's, Alpha-1 antitrypsin deficiency, Wilson's Disease, Tyrosinemia, Frameshift related diseases, and Triplet repeat diseases.

Additional exemplary target genes include genes associated with diseases including, e.g., Crigler-Najjer syndrome, Glycogen storage disease type IV (GSD type IV), Familial hemophagocytic lymphohistiocytosis (FHL-Perforin deficiency), Ornithine transcarbamylase deficiency (OTC deficiency) or other Urea Cycle Disorders, Primary Hyperoxaluria, Leber congenital amaurosis (LCA), Batten disease, Chronic Granulomatous Disease, Wiskott-Aldrich syndrome, Usher Syndrome, and hemoglobinoapthies.

Crigler-Najjer Syndrome.

Crigler-Najjer syndrome is a severe condition characterized by high levels of bilirubin in the blood (hyperbilirubinemia). Bilirubin is produced when red blood cells are broken down. This substance is removed from the body only after it undergoes a chemical reaction in the liver, which converts the toxic form of bilirubin (unconjugated bilirubin) to a nontoxic form (conjugated bilirubin). People with Crigler-Najjer syndrome have a buildup of unconjugated bilirubin in their blood (unconjugated hyperbilirubinemia). Crigler-Najjar syndrome is divided into two types. Type 1 (CN1) is very severe and Type 2 (CN2) is less severe.

Mutations in the UGT1A1 gene can cause Crigler-Najjar syndrome. This gene provides instructions for making the bilirubin uridine diphosphate glucuronosyl transferase (bilirubin-UGT) enzyme, which is found primarily in liver cells and is necessary for the removal of bilirubin from the body. The bilirubin-UGT enzyme is involved in glucuronidation, in which the enzyme transfers glucuronic acid to unconjugated bilirubin, converting it to conjugated bilirubin. Glucuronidation makes bilirubin dissolvable in water so that it can be removed from the body.

Mutations in the UGT1A1 gene that cause Crigler-Najjar syndrome result in reduced or absent function of the bilirubin-UGT enzyme. People with CN1 have no enzyme function, while people with CN2 can have less than 20 percent of normal function. The loss of bilirubin-UGT function decreases glucuronidation of unconjugated bilirubin. This toxic substance then builds up in the body, causing unconjugated hyperbilirubinemia and jaundice.

Glycogen Storage Disease Type IV.

Glycogen storage disease type IV (also known as GSD type IV, Glycogenosis type IV, Glycogen Branching Enzyme Deficiency (GBED), polyglucosan body disease, or Amylopectinosis) is an inherited disorder caused by the buildup of a complex sugar called glycogen in the body's cells. The accumulated glycogen is structurally abnormal and impairs the function of certain organs and tissues, especially the liver and muscles.

Mutations in the GBE1 gene cause GSD IV. The GBE1 gene provides instructions for making the glycogen branching enzyme. This enzyme is involved in the production of glycogen, which is a major source of stored energy in the body. GBE1 gene mutations that cause GSD IV lead to a shortage (deficiency) of the glycogen branching enzyme. As a result, glycogen is not formed properly. Abnormal glycogen molecules called polyglucosan bodies accumulate in cells, leading to damage and cell death. Polyglucosan bodies accumulate in cells throughout the body, but liver cells and muscle cells are most severely affected in GSD IV. Glycogen accumulation in the liver leads to hepatomegaly and interferes with liver functioning. The inability of muscle cells to break down glycogen for energy leads to muscle weakness and wasting.

Generally, the severity of the disorder is linked to the amount of functional glycogen branching enzyme that is produced. Individuals with the fatal perinatal neuromuscular type tend to produce less than 5 percent of usable enzyme, while those with the childhood neuromuscular type may have around 20 percent of enzyme function. The other types of GSD IV are usually associated with between 5 and 20 percent of working enzyme. These estimates, however, vary among the different types.

Familial Hemophagocytic Lymphohistiocytosis.

Familial hemophagocytic lymphohistiocytosis (FHL) is a disorder in which the immune system produces too many activated immune cells (lymphocytes), e.g., T cells, natural killer cells, B cells, and macrophages (histiocytes). Excessive amounts of cytokines are also produced. This overactivation of the immune system causes fever and damages the liver and spleen, resulting in enlargement of these organs.

Familial hemophagocytic lymphohistiocytosis also destroys blood-producing cells in the bone marrow, a process called hemophagocytosis. The brain may also be affected in familial hemophagocytic lymphohistiocytosis. In addition to neurological problems, familial hemophagocytic lymphohistiocytosis can cause abnormalities of the heart, kidneys, and other organs and tissues. Affected individuals also have an increased risk of developing cancers of blood-forming cells (leukemia and lymphoma).

Familial hemophagocytic lymphohistiocytosis may be caused by mutations in any of several genes. These genes provide instructions for making proteins that help destroy or deactivate lymphocytes that are no longer needed. By controlling the number of activated lymphocytes, these genes help regulate immune system function.

Approximately 40 to 60 percent of cases of familial hemophagocytic lymphohistiocytosis are caused by mutations in the PRF1 or UNC13D genes. Smaller numbers of cases are caused by mutations in other known genes such as STX11 or STXBP2. The gene mutations that cause familial hemophagocytic lymphohistiocytosis can impair the body's ability to regulate the immune system. These changes result in the exaggerated immune response characteristic of this condition.

Ornithine Transcarbamylase Deficiency.

Ornithine transcarbamylase deficiency (OTC) is an inherited disorder that causes ammonia to accumulate in the blood.

Mutations in the OTC gene cause ornithine transcarbamylase deficiency.

Ornithine transcarbamylase deficiency belongs to a class of genetic diseases called urea cycle disorders. The urea cycle is a sequence of reactions that occurs in liver cells. It processes excess nitrogen, generated when protein is used by the body, to make a compound called urea that is excreted by the kidneys.

In ornithine transcarbamylase deficiency, the enzyme that starts a specific reaction within the urea cycle is damaged or missing. The urea cycle cannot proceed normally, and nitrogen accumulates in the bloodstream in the form of ammonia. Ammonia is especially damaging to the nervous system, so ornithine transcarbamylase deficiency causes neurological problems as well as eventual damage to the liver.

Other urea cycle disorders and associate genes include, e.g., N-Acetylglutamate synthase deficiency (NAGS), Carbamoyl phosphate synthetase I deficiency (CPS1), "AS deficiency" or citrullinemia (ASS), "AL deficiency" or argininosuccinic aciduria (ASL), and "Arginase deficiency" or argininemia (ARG).

Primary Hyperoxaluria.

Primary hyperoxaluria, e.g., primary hyperoxaluria type 1 (PH1), is a rare, autosomal recessive inherited genetic condition in which an error in the glyoxylate metabolism pathway in the liver leads to an overproduction of oxalate, which crystalizes in soft tissues including the kidney, bone marrow, and eyes. The disease manifests as progressive deterioration of the kidneys, and treatment is a complicated double transplant of kidney (the damaged organ) and liver (the diseased organ).

Primary hyperoxaluria is caused by the deficiency of an enzyme that normally prevents the buildup of oxalate. There are two types of primary hyperoxaluria, distinguished by the enzyme that is deficient. People with type 1 primary hyperoxaluria have a shortage of a liver enzyme called alanine-glyoxylate aminotransferase (AGXT). Type 2 primary hyperoxaluria is characterized by a shortage of an enzyme called glyoxylate reductase/hydroxypyruvate reductase (GRHPR).

Mutations in the AGXT and GRHPR genes cause primary hyperoxaluria. The breakdown and processing of certain sugars and amino acids produces a glyoxylate. Normally, glyoxylate is converted to the amino acid glycine or to glycolate through the action of two enzymes, alanine-glyoxylate aminotransferase and glyoxylate reductase/hydroxypyruvate reductase, respectively. Mutations in the AGXT or GRHPR gene cause a shortage of these enzymes, which prevents the conversion of glyoxylate to glycine or glycolate. As levels of glyoxylate build up, it is converted to oxalate. Oxalate combines with calcium to form calcium oxalate deposits, which can damage the kidneys and other organs.

In an embodiment, the genetic defect in AGXT is corrected, e.g., by homologous recombination, using the Cas9 molecule and gRNA molecule described herein. For example, the functional enzyme encoded by the corrected AGXT gene can be redirected to its proper subcellular organelle. Though >50 mutations have been identified in the gene, the most common (40% in Caucasians) is a missense G17OR mutation. This mutation causes the AGT enzyme to be localized to the mitochondria rather than to the peroxisome, where it must reside to perform its function. Other common mutations include, e.g., I244T (Canary Islands), F152I, G41R, G630A (Italy), and G588A (Italy).

In an embodiment, one or more genes encoding enzymes upstream in the glyoxylate metabolism pathway are targeted, using the Cas9 molecule and gRNA molecule described herein. Exemplary targets include, e.g., glycolate oxidase (gene HAO1, OMIM ID 605023). Glycolate oxidase converts glycolate into glyoxylate, the substrate for AGT. Glycolate oxidase is only expressed in the liver and, because of its peroxisomal localization, makes it a suitable target in this metabolic pathway. In an embodiment, a double-strand break in the HAO1 gene is introduced and upon repair by NHEJ a frame-shift results in a truncated protein. In an embodiment, a transcriptional repressor (e.g., a transcriptional repressor described herein) is delivered as a payload to the HAO1 gene to reduce the expression of HAO1.

Leber Congenital Amaurosis.

Leber congenital amaurosis (LCA) is an eye disorder that primarily affects the retina. People with this disorder typically have severe visual impairment beginning in infancy. The visual impairment tends to be stable, although it may worsen very slowly over time. At least 13 types of Leber congenital amaurosis have been described. The types are distinguished by their genetic cause, patterns of vision loss, and related eye abnormalities.

Leber congenital amaurosis can result from mutations in at least 14 genes, all of which are necessary for normal vision. These genes play a variety of roles in the development and function of the retina. For example, some of the genes associated with this disorder are necessary for the normal development of photoreceptors. Other genes are involved in phototransduction. Still other genes play a role in the function of cilia, which are necessary for the perception of several types of sensory input, including vision.

Mutations in any of the genes associated with Leber congenital amaurosis (e.g., AIPL1, CEP290, CRB1, CRX, GUCY2D, IMPDH1, LCA5, LRAT, RD3, RDH12, RPE65, RPGRIP1, SPATA7, TULP1) can disrupt the development and function of the retina, resulting in early vision loss. Mutations in the CEP290, CRB1, GUCY2D, and RPE65 genes are the most common causes of the disorder, while mutations in the other genes generally account for a smaller percentage of cases.

Batten Disease.

Batten disease or juvenile Batten disease is an inherited disorder that primarily affects the nervous system. After a few years of normal development, children with this condition develop progressive vision loss, intellectual and motor disability, and seizures.

Juvenile Batten disease is one of a group of disorders known as neuronal ceroid lipofuscinoses (NCLs). These disorders all affect the nervous system and typically cause progressive problems with vision, movement, and thinking ability. Some people refer to the entire group of NCLs as Batten disease, while others limit that designation to the juvenile form of the disorder. The different types of NCLs are distinguished by the age at which signs and symptoms first appear.

Most cases of juvenile Batten disease are caused by mutations in the CLN3 gene. These mutations can disrupt the function of cellular structures called lysosomes. Lysosome malfunction leads to a buildup of lipopigments within these cell structures. These accumulations occur in cells throughout the body, but neurons in the brain seem to be particularly vulnerable to the damage caused by lipopigments. The progressive death of cells, especially in the brain, leads to vision loss, seizures, and intellectual decline in people with juvenile Batten disease.

A small percentage of cases of juvenile Batten disease are caused by mutations in other genes (e.g., ATP13A2, CLNS, PPT1, TPP1). Many of these genes are involved in lysosomal function, and when mutated, can cause this or other forms of NCL.

Chronic Granulomatous Disease.

Chronic granulomatous disease is a disorder that causes the immune system to malfunction, resulting in a form of immunodeficiency. Individuals with chronic granulomatous disease have recurrent bacterial and fungal infections. People with this condition often have areas of inflammation (granulomas) in various tissues that can be damaging to those tissues. The features of chronic granulomatous disease usually first appear in childhood, although some individuals do not show symptoms until later in life.

Mutations in the CYBA, CYBB, NCF1, NCF2, or NCF4 gene can cause chronic granulomatous disease. There are five types of this condition that are distinguished by the gene that is involved. The proteins produced from the affected genes are subunits of NADPH oxidase, which plays an important role in the immune system. Specifically, NADPH oxidase is primarily active in phagocytes. Within phagocytes, NADPH oxidase is involved in the production of superoxide, which plays a role in killing foreign invaders and preventing them from reproducing in the body and causing illness. NADPH oxidase also regulates the activity of neutrophils, which play a role in adjusting the inflammatory response to optimize healing and reduce injury to the body.

Mutations in the CYBA, CYBB, NCF1, NCF2, and NCF4 genes result in the production of proteins with little or no function or the production of no protein at all. Without any one of its subunit proteins, NADPH oxidase cannot assemble or function properly. As a result, phagocytes are unable to kill foreign invaders and neutrophil activity is not regulated. A lack of NADPH oxidase leaves affected individuals vulnerable to many types of infection and excessive inflammation.

Wiskott-Aldrich syndrome. Wiskott-Aldrich syndrome is characterized by abnormal immune system function (immune deficiency) and a reduced ability to form blood clots. This condition primarily affects males. Individuals with Wiskott-Aldrich syndrome have microthrombocytopenia, which is a decrease in the number and size of blood cells involved in clotting (platelets), which can lead to easy bruising or episodes of prolonged bleeding following minor trauma. Wiskott-Aldrich syndrome causes many types of white blood cells to be abnormal or nonfunctional, leading to an increased risk of several immune and inflammatory disorders. Many people with this condition develop eczema, an inflammatory skin disorder characterized by abnormal patches of red, irritated skin. Affected individuals also have an increased susceptibility to infection. People with Wiskott-Aldrich syndrome are at greater risk of developing autoimmune disorders. The chance of developing some types of cancer, such as cancer of the immune system cells (lymphoma), is also greater in people with Wiskott-Aldrich syndrome.

Mutations in the WAS gene cause Wiskott-Aldrich syndrome. The WAS gene provides instructions for making WASP protein, which is found in all blood cells. WASP is involved in relaying signals from the surface of blood cells to the actin cytoskeleton. WASP signaling activates the cell when it is needed and triggers its movement and attachment to other cells and tissues (adhesion). In white blood cells, this signaling allows the actin cytoskeleton to establish the interaction between cells and the foreign invaders that they target (immune synapse).

WAS gene mutations that cause Wiskott-Aldrich syndrome lead to a lack of any functional WASP. Loss of WASP signaling disrupts the function of the actin cytoskeleton in developing blood cells. White blood cells that lack WASP have a decreased ability to respond to their environment and form immune synapses. As a result, white blood cells are less able to respond to foreign invaders, causing many of the immune problems related to Wiskott-Aldrich syndrome. Similarly, a lack of functional WASP in platelets impairs their development, leading to reduced size and early cell death.

Usher Syndrome.

Usher syndrome is a condition characterized by hearing loss or deafness and progressive vision loss. The loss of vision is caused by retinitis pigmentosa (RP), which affects the layer of light-sensitive tissue at the back of the eye (the retina). Vision loss occurs as the light-sensing cells of the retina gradually deteriorate.

Three major types of Usher syndrome, designated as types I (subtypes IA through IG), II (subtypes IIA, IIB, and IIC), and III, have been identified. These types are distinguished by their severity and the age when signs and symptoms appear.

Mutations in the CDH23, CLRN1, GPR98, MYO7A, PCDH15, USH1C, USH1G, and USH2A genes can cause Usher syndrome. The genes related to Usher syndrome provide instructions for making proteins that play important roles in normal hearing, balance, and vision. They function in the development and maintenance of hair cells, which are sensory cells in the inner ear that help transmit sound and motion signals to the brain. In the retina, these genes are also involved in determining the structure and function of light-sensing cells called rods and cones. In some cases, the exact role of these genes in hearing and vision is unknown. Most of the mutations responsible for Usher syndrome lead to a loss of hair cells in the inner ear and a gradual loss of rods and cones in the retina. Degeneration of these sensory cells causes hearing loss, balance problems, and vision loss characteristic of this condition.

Usher syndrome type I can result from mutations in the CDH23, MYO7A, PCDH15, USH1C, or USH1G gene. Usher syndrome type II can be caused by mutations in, e.g., USH2A or GPR98 (also called VLGR1) gene. Usher syndrome type III can be caused by mutations in e.g., CLRN1.

Hemoglobinopathies.

Hemoglobinopathies are a group of genetic defects that result in abnormal structure of one of the globin chains of the hemoglobin molecule. Exemplary hemoglobinopathies include, e.g., sickle cell disease, alpha thalassemia, and beta thalassemia.

In an embodiment, a genetic defect in alpha globulin or beta globulin is corrected, e.g., by homologous recombination, using the Cas9 molecule and gRNA molecule described herein.

In an embodiment, a hemoglobinopathies-associated gene is targeted, using the Cas9 molecule and gRNA molecule described herein. Exemplary targets include, e.g., genes associated with control of the gamma-globin genes. In an embodiment, the target is BCL11A.

Fetal hemoglobin (also hemoglobin F or HbF or $\alpha 2\gamma 2$) is a tetramer of two adult alpha-globin polypeptides and two fetal beta-like gamma-globin polypeptides. HbF is the main oxygen transport protein in the human fetus during the last seven months of development in the uterus and in the newborn until roughly 6 months old. Functionally, fetal hemoglobin differs most from adult hemoglobin in that it is able to bind oxygen with greater affinity than the adult form, giving the developing fetus better access to oxygen from the mother's bloodstream.

In newborns, fetal hemoglobin is nearly completely replaced by adult hemoglobin by approximately 6 months postnatally. In adults, fetal hemoglobin production can be reactivated pharmacologically, which is useful in the treatment of diseases such as hemoglobinopathies. For example, in certain patients with hemoglobinopathies, higher levels of gamma-globin expression can partially compensate for defective or impaired beta-globin gene production, which can ameliorate the clinical severity in these diseases. Increased HbF levels or F-cell (HbF containing erythrocyte) numbers can ameliorate the disease severity of hemoglobinopathies, e.g., beta-thalassemia major and sickle cell anemia.

Increased HbF levels or F-cell can be associated reduced BCL11A expression in cells. The BCL11A gene encodes a multi-zinc finger transcription factor. In an embodiment, the expression of BCL11A is modulated, e.g., down-regulated. In an embodiment, the BCL11A gene is edited. In an embodiment, the cell is a hemopoietic stem cell or progenitor cell.

Sickle Cell Diseases

Sickle cell disease is a group of disorders that affects hemoglobin. People with this disorder have atypical hemoglobin molecules (hemoglobin S), which can distort red blood cells into a sickle, or crescent, shape. Characteristic features of this disorder include a low number of red blood cells (anemia), repeated infections, and periodic episodes of pain.

Mutations in the HBB gene cause sickle cell disease. The HBB gene provides instructions for making beta-globin. Various versions of beta-globin result from different mutations in the HBB gene. One particular HBB gene mutation produces an abnormal version of beta-globin known as hemoglobin S (HbS). Other mutations in the HBB gene lead to additional abnormal versions of beta-globin such as hemoglobin C (HbC) and hemoglobin E (HbE). HBB gene mutations can also result in an unusually low level of beta-globin, i.e., beta thalassemia.

In people with sickle cell disease, at least one of the beta-globin subunits in hemoglobin is replaced with hemoglobin S. In sickle cell anemia, which is a common form of sickle cell disease, hemoglobin S replaces both beta-globin subunits in hemoglobin. In other types of sickle cell disease, just one beta-globin subunit in hemoglobin is replaced with hemoglobin S. The other beta-globin subunit is replaced with a different abnormal variant, such as hemoglobin C. For example, people with sickle-hemoglobin C (HbSC) disease have hemoglobin molecules with hemoglobin S and hemoglobin C instead of beta-globin. If mutations that produce hemoglobin S and beta thalassemia occur together, individuals have hemoglobin S-beta thalassemia (HbSBetaThal) disease.

Alpha Thalassemia

Alpha thalassemia is a blood disorder that reduces the production of hemoglobin. In people with the characteristic features of alpha thalassemia, a reduction in the amount of hemoglobin prevents enough oxygen from reaching the body's tissues. Affected individuals also have a shortage of red blood cells (anemia), which can cause pale skin, weakness, fatigue, and more serious complications.

Two types of alpha thalassemia can cause health problems. The more severe type is hemoglobin Bart hydrops fetalis syndrome or Hb Bart syndrome. The milder form is HbH disease. Hb Bart syndrome is characterized, e.g., by hydrops fetalis, a condition in which excess fluid builds up in the body before birth. HbH disease can cause, e.g., mild to moderate anemia, hepatosplenomegaly, and yellowing of the eyes and skin (jaundice).

Alpha thalassemia typically results from deletions involving the HBA1 and HBA2 genes. Both of these genes provide instructions for making alpha-globin, which is a subunit of hemoglobin. The different types of alpha thalassemia result from the loss of some or all of these alleles.

Hb Bart syndrome can result from the loss of all four alpha-globin alleles. HbH disease can be caused by a loss of three of the four alpha-globin alleles. In these two conditions, a shortage of alpha-globin prevents cells from making normal hemoglobin. Instead, cells produce abnormal forms of hemoglobin, i.e., hemoglobin Bart (Hb Bart) or hemoglobin H (HbH), which cannot effectively carry oxygen to the body's tissues. The substitution of Hb Bart or HbH for normal hemoglobin can cause anemia and the other serious health problems associated with alpha thalassemia.

Two additional variants of alpha thalassemia are related to a reduced amount of alpha-globin. A loss of two of the four alpha-globin alleles can result in alpha thalassemia trait. People with alpha thalassemia trait may have unusually small, pale red blood cells and mild anemia. A loss of one alpha-globin allele can be found in alpha thalassemia silent carriers.

Beta Thalassemia

Beta thalassemia is a blood disorder that reduces the production of hemoglobin. In people with beta thalassemia, low levels of hemoglobin lead to a lack of oxygen in many parts of the body. Affected individuals also have a shortage of red blood cells (anemia), which can cause pale skin, weakness, fatigue, and more serious complications. People with beta thalassemia are at an increased risk of developing abnormal blood clots.

Beta thalassemia is classified into two types depending on the severity of symptoms: thalassemia major (also known as Cooley's anemia) and thalassemia intermedia. Of the two types, thalassemia major is more severe.

Mutations in the HBB gene cause beta thalassemia. The HBB gene provides instructions for making beta-globin. Some mutations in the HBB gene prevent the production of any beta-globin. The absence of beta-globin is referred to as beta-zero)(B° thalassemia. Other HBB gene mutations allow some beta-globin to be produced but in reduced amounts, i.e., beta-plus (B⁺) thalassemia. People with both types have been diagnosed with thalassemia major and thalassemia intermedia.

In an embodiment, a Cas9 molecule/gRNA molecule complex targeting a first gene is used to treat a disorder characterized by second gene, e.g., a mutation in a second gene. By way of example, targeting of the first gene, e.g., by editing or payload delivery, can compensate for, or inhibit further damage from, the affect of a second gene, e.g., a mutant second gene. In an embodiment the allele(s) of the first gene carried by the subject is not causative of the disorder.

TABLE IX-3

Selected Disorders and Targets for Compensatory Targeting

| | Indication | | | | | | |
|---|---|---|---|---|---|---|---|
| | Age-Related Macular Degeneration | | Atypical Hemolytic Uremic Syndrome | | Non-Hodgkin's lymphoma, Chronic lymphocytic leukemia | Rheumatoid Arthritis | Prevention of organ transplant rejection, renal cell carcinoma |
| | Target | | | | | | |
| | Factor H | C5 | Factor H | C5 | CD20 | CD21 | mTORC1 |
| Up-regulate/Down-regulate | up-regulate | down-regulate | up-regulate | down-regulate | down-regulate | down-regulate | down-regulate |
| Level of evidence: Market proxy or animal model | animal models | | Factor H concentrate | Eculizumab/Soliris c5Ab (Alexion) successful in decreasing mortality | Rituxan (Genentech) CD20 antibody | Rituxan (Genentech) CD20 antibody | everolimus |
| Comment | Muti-genetic origin. Factor H deficiency is a risk factor. Controlling the complement cascade, through fH upregulation or C5 downregulation, may have a beneficial effect. | | aHUS due to fH deficiency. C5 antibody has been shown to vastly improve prognosis. Can approach disease directly through increasing fH levels or controlling complement through C5 downregulation. | | | | |

| | Indication | | | | | | |
|---|---|---|---|---|---|---|---|
| | Devices: stent, pacemaker, hernia mesh-local delivery to prevent restenosis/fibrosis | Graft healing/wound healing/prevention of fibrosis | orthopedics-articular cartilage repair, arthritis | Parkinson's Disease | Allergic rhinitis | Epilepsy | Barrett's esophagus, Stomach ulcer, gastritis |
| | Target | | | | | | |
| | mTORC2, others | VEGF | IL-11 | SNCA, LRRK2, EIF4GI | H1 Receptors nasal mucosa | H1 receptors CNS | H2 receptor pylorus, esophagus |
| Up-regulate/Down-regulate | down-regulate | up-regulate | up-regulate | up-regulate or fix mutations | down-regulate | up-regulate | down-regulate |
| Level of evidence: Market proxy or animal model | everolimus | VEGF local administration aids in tracheal transplant animal models | animal model of cartilage repair | | Hi-anti-histamines, e.g. Zyrtec | animal models | H2-specific antihistamines, e.g. omeprazole, etc. |
| Comment | Embodiments include, e.g., local delivery to tissue via device or injection to prevent fibrosis, restenosis | Useful, e.g., in the promoting wound healing (burns, etc); Embodiments include, e.g., local delivery of growth factors | In an embodiment, the subject sufferes from arthritis or is in need of healing after injury. In embodiments, chondrocytes are targeted post-injury to | | | | In an embodiment, the subject is treated for late-stage barrett's. |

TABLE IX-3-continued

Selected Disorders and Targets for Compensatory Targeting promote
healing.

In an embodiment, Cas9 molecules, gRNA molecules, and/or Cas9 molecule/gRNA molecule complexes can be used to activate genes that regulate growth factors, such as up regulation of Epo to drive RBC production.

In an embodiment, Cas9 molecules, gRNA molecules, and/or Cas9 molecule/gRNA molecule complexes can be used to target, e.g., result in repression of, knockout of, or alteration of promoter for key transcription factors, such as BCL11A and KLF1 for up-regulating of fetal hemoglobin, e.g., for cure for sickle cell anemia and thalassemia.

Candidate Cas9 molecules, candidate gRNA molecules, and/or candidate Cas9 molecule/gRNA molecule complexes, as described herein, can be used to edit/correct a target gene or to deliver a regulator/effector inside cells, e.g., as described herein, at various subcellular locations. In an embodiment, the location is in the nucleus. In an embodiment, the location is in a sub-nuclear domain, e.g., the chromosome territories, nucleolus, nuclear speckles, Cajal bodies, Gems (gemini of Cajal bodies), or promyelocytic leukemia (PML) nuclear bodies. In an embodiment, the location is in the mitochondrion.

Candidate Cas9 molecules, candidate gRNA molecules, and/or candidate Cas9 molecule/gRNA molecule complexes, as described herein, can be used to edit/correct a target gene or to deliver a regulator/effector inside cells, as described herein, at various time points For example, the editing/correction or delivery can occur at different phases of cell cycle, e.g., G0 phase, Interphase (e.g., G1 phase, S phase, G2 phase), or M phase. As another example, the editing/correction or delivery can occur at different stages of disease progression, e.g., at latent stage or active stage of a disorder (e.g., viral infection), or at any stage or subclassification of a disorder (e.g., cancer).

Methods of the invention allow for the treatment of a disorder characterized by unwanted cell proliferation, e.g., cancer. In an embodiment, cancer cells are manipulated to make them more susceptible to treatment or to endogenous immune surveillance. In an embodiment a cancer cell is modulated to make it more susceptible to a therapeutic. In an embodiment, a cancer cell is manipulated so as to increase the expression of a gene that increases the ability of the immune system to recognize or kill the cancer cell. E.g., a Cas9 molecule/gRNA molecule complex can be used to deliver a payload, or edit a target nucleic acid so as to increase the expression of an antigen, e.g., in the case where the cancer cell has downregulated expression of the antigen. In an embodiment, a payload, e.g., a payload comprising a transcription factor or other activator of expression is delivered to the cancer cell. In an embodiment, an increase in expression is effected by cleavage of the target nucleic acid, e.g., cleavage and correction or alteration of the target nucleic acid by a template nucleic acid. In an embodiment, a payload that overrides epigenetic silencing, e.g., a modulator of methylation, is delivered.

In an embodiment, the treatment further comprises administering a second anti-cancer therapy, e.g., immunotherapy, e.g., an antibody that binds the upregulated antigen.

In an embodiment, methods described herein, e.g., targeting of a genomic signature, e.g., a somatic translocation, can be used to target the Cas9 molecule/gRNA molecule to a cancer cell.

In another aspect, the invention features a method of immunizing a subject against an antigen. The method comprises using a method described herein to promote the expression of the antigen from a cell, e.g., a blood cell, such that the antigen promotes an immune response. In an embodiment, the cell is manipulated ex vivo and then returned or introduced into the subject.

X. Modified Nucleosides, Nucleotides, and Nucleic Acids

Modified nucleosides and modified nucleotides can be present in nucleic acids, e.g., particularly gRNA, but also other forms of RNA, e.g., mRNA, RNAi, or siRNA. As described herein "nucleoside" is defined as a compound containing a five-carbon sugar molecule (a pentose or ribose) or derivative thereof, and an organic base, purine or pyrimidine, or a derivative thereof. As described herein, "nucleotide" is defined as a nucleoside further comprising a phosphate group.

Modified nucleosides and nucleotides can include one or more of:

(i) alteration, e.g., replacement, of one or both of the non-linking phosphate oxygens and/or of one or more of the linking phosphate oxygens in the phosphodiester backbone linkage;

(ii) alteration, e.g., replacement, of a constituent of the ribose sugar, e.g., of the 2' hydroxyl on the ribose sugar;

(iii) wholesale replacement of the phosphate moiety with "dephospho" linkers;

(iv) modification or replacement of a naturally occurring nucleobase;

(v) replacement or modification of the ribose-phosphate backbone;

(vi) modification of the 3' end or 5' end of the oligonucleotide, e.g., removal, modification or replacement of a terminal phosphate group or conjugation of a moiety; and (vii) modification of the sugar.

The modifications listed above can be combined to provide modified nucleosides and nucleotides that can have two, three, four, or more modifications. For example, a modified nucleoside or nucleotide can have a modified sugar and a modified nucleobase. In an embodiment, every nucleotide of a gRNA or template nucleic acid is modified, e.g., all nucleotides have a modified phosphate group, e.g., all are phosphorothioate groups. In an embodiment, all, or substantially all, of the phosphate groups of a unimolecular or modular gRNA molecule or template nucleic acid are replaced with phosphorothioate groups.

In an embodiment, modified nucleotides, e.g., nucleotides having modifications as described herein, can be incorporated into a nucleic acid, e.g., a "modified nucleic acid." In an embodiment, the modified nucleic acids comprise one, two, three or more modified nucleotides. In an embodiment, at least 5% (e.g., at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100%) of the positions in a modified nucleic acid are a modified nucleotides.

Unmodified nucleic acids can be prone to degradation by, e.g., cellular nucleases. For example, nucleases can hydrolyze nucleic acid phosphodiester bonds. Accordingly, in one aspect the modified nucleic acids described herein can contain one or more modified nucleosides or nucleotides, e.g., to introduce stability toward nucleases.

In an embodiment, the modified nucleosides, modified nucleotides, and modified nucleic acids described herein can exhibit a reduced innate immune response when introduced into a population of cells, both in vivo and ex vivo. The term "innate immune response" includes a cellular response to exogenous nucleic acids, including single stranded nucleic acids, generally of viral or bacterial origin, which involves the induction of cytokine expression and release, particularly the interferons, and cell death. In an embodiment, the modified nucleosides, modified nucleotides, and modified nucleic acids described herein can disrupt binding of a major groove interacting partner with the nucleic acid. In an embodiment, the modified nucleosides, modified nucleotides, and modified nucleic acids described herein can exhibit a reduced innate immune response when introduced into a population of cells, both in vivo and ex vivo, and also disrupt binding of a major groove interacting partner with the nucleic acid.

In an embodiment, a governing gRNA comprises modifications, e.g., modified nucleotides, modifications to the backbone, and other modifications described herein.

In an embodiment, a template nucleic acid comprises modifications, e.g., modified nucleotides, modifications to the backbone, and other modifications described herein. In an embodiment, the modification improves the stability of the template nucleic acid, e.g., by increasing its resistance to endonucleases and/or exonucleases.

In an embodiment, a template nucleic acid that comprises modifications is double stranded, e.g., is double stranded DNA. In such embodiment, all the modifications are confined to one strand. In an embodiment, modifications are present on both strands. Modifications may be present in the 5' homology arm, the 3' homology arm, or the replacement sequence, or any combination thereof. In an embodiment, modifications are present in one or both homology arms but not the replacement sequence.

In an embodiment, a template nucleic acid that comprises modifications is single stranded, e.g., is single stranded DNA.

Definitions of Chemical Groups

As used herein, "alkyl" is meant to refer to a saturated hydrocarbon group which is straight-chained or branched. Example alkyl groups include methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like. An alkyl group can contain from 1 to about 20, from 2 to about 20, from 1 to about 12, from 1 to about 8, from 1 to about 6, from 1 to about 4, or from 1 to about 3 carbon atoms.

As used herein, "aryl" refers to monocyclic or polycyclic (e.g., having 2, 3 or 4 fused rings) aromatic hydrocarbons such as, for example, phenyl, naphthyl, anthracenyl, phenanthrenyl, indanyl, indenyl, and the like. In an embodiment, aryl groups have from 6 to about 20 carbon atoms.

As used herein, "alkenyl" refers to an aliphatic group containing at least one double bond.

As used herein, "alkynyl" refers to a straight or branched hydrocarbon chain containing 2-12 carbon atoms and characterized in having one or more triple bonds. Examples of alkynyl groups include, but are not limited to, ethynyl, propargyl, and 3-hexynyl.

As used herein, "arylalkyl" or "aralkyl" refers to an alkyl moiety in which an alkyl hydrogen atom is replaced by an aryl group. Aralkyl includes groups in which more than one hydrogen atom has been replaced by an aryl group. Examples of "arylalkyl" or "aralkyl" include benzyl, 2-phenylethyl, 3-phenylpropyl, 9-fluorenyl, benzhydryl, and trityl groups. As used herein, "cycloalkyl" refers to a cyclic, bicyclic, tricyclic, or polycyclic non-aromatic hydrocarbon groups having 3 to 12 carbons. Examples of cycloalkyl moieties include, but are not limited to, cyclopropyl, cyclopentyl, and cyclohexyl.

As used herein, "heterocyclyl" refers to a monovalent radical of a heterocyclic ring system. Representative heterocyclyls include, without limitation, tetrahydrofuranyl, tetrahydrothienyl, pyrrolidinyl, pyrrolidonyl, piperidinyl, pyrrolinyl, piperazinyl, dioxanyl, dioxolanyl, diazepinyl, oxazepinyl, thiazepinyl, and morpholinyl.

As used herein, "heteroaryl" refers to a monovalent radical of a heteroaromatic ring system. Examples of heteroaryl moieties include, but are not limited to, imidazolyl, oxazolyl, thiazolyl, triazolyl, pyrrolyl, furanyl, indolyl, thiophenyl pyrazolyl, pyridinyl, pyrazinyl, pyridazinyl, pyrimidinyl, indolizinyl, purinyl, naphthyridinyl, quinolyl, and pteridinyl.

Phosphate Backbone Modifications

The Phosphate Group

In an embodiment, the phosphate group of a modified nucleotide can be modified by replacing one or more of the oxygens with a different substituent. Further, the modified nucleotide, e.g., modified nucleotide present in a modified nucleic acid, can include the wholesale replacement of an unmodified phosphate moiety with a modified phosphate as described herein. In an embodiment, the modification of the phosphate backbone can include alterations that result in either an uncharged linker or a charged linker with unsymmetrical charge distribution.

Examples of modified phosphate groups include, phosphorothioate, phosphoroselenates, borano phosphates, borano phosphate esters, hydrogen phosphonates, phosphoroamidates, alkyl or aryl phosphonates and phosphotriesters. In an embodiment, one of the non-bridging phosphate oxygen atoms in the phosphate backbone moiety can be replaced by any of the following groups: sulfur (S), selenium (Se), $BR_3$ (wherein R can be, e.g., hydrogen, alkyl, or aryl), C (e.g., an alkyl group, an aryl group, and the like), H, $NR_2$ (wherein R can be, e.g., hydrogen, alkyl, or aryl), or OR (wherein R can be, e.g., alkyl or aryl). The phosphorous atom in an unmodified phosphate group is achiral. However, replacement of one of the non-bridging oxygens with one of the above atoms or groups of atoms can render the phosphorous atom chiral; that is to say that a phosphorous atom in a phosphate group modified in this way is a stereogenic center. The stereogenic phosphorous atom can possess either the "R" configuration (herein Rp) or the "S" configuration (herein Sp).

Phosphorodithioates have both non-bridging oxygens replaced by sulfur. The phosphorus center in the phosphorodithioates is achiral which precludes the formation of oligoribonucleotide diastereomers. In an embodiment, modifications to one or both non-bridging oxygens can also include the replacement of the non-bridging oxygens with a group independently selected from S, Se, B, C, H, N, and OR (R can be, e.g., alkyl or aryl).

The phosphate linker can also be modified by replacement of a bridging oxygen, (i.e., the oxygen that links the phosphate to the nucleoside), with nitrogen (bridged phosphoroamidates), sulfur (bridged phosphorothioates) and carbon (bridged methylenephosphonates). The replacement can occur at either linking oxygen or at both of the linking oxygens.

Replacement of the Phosphate Group

The phosphate group can be replaced by non-phosphorus containing connectors. In an embodiment, the charge phosphate group can be replaced by a neutral moiety.

Examples of moieties which can replace the phosphate group can include, without limitation, e.g., methyl phosphonate, hydroxylamino, siloxane, carbonate, carboxymethyl, carbamate, amide, thioether, ethylene oxide linker, sulfonate, sulfonamide, thioformacetal, formacetal, oxime, methyleneimino, methylenemethylimino, methylenehydrazo, methylenedimethylhydrazo and methyleneoxymethylimino.

Replacement of the Ribophosphate Backbone

Scaffolds that can mimic nucleic acids can also be constructed wherein the phosphate linker and ribose sugar are replaced by nuclease resistant nucleoside or nucleotide surrogates. In an embodiment, the nucleobases can be tethered by a surrogate backbone. Examples can include, without limitation, the morpholino, cyclobutyl, pyrrolidine and peptide nucleic acid (PNA) nucleoside surrogates.

Sugar Modifications

The modified nucleosides and modified nucleotides can include one or more modifications to the sugar group. For example, the 2' hydroxyl group (OH) can be modified or replaced with a number of different "oxy" or "deoxy" substituents. In an embodiment, modifications to the 2' hydroxyl group can enhance the stability of the nucleic acid since the hydroxyl can no longer be deprotonated to form a 2'-alkoxide ion. The 2'-alkoxide can catalyze degradation by intramolecular nucleophilic attack on the linker phosphorus atom.

Examples of "oxy"-2' hydroxyl group modifications can include alkoxy or aryloxy (OR, wherein "R" can be, e.g., alkyl, cycloalkyl, aryl, aralkyl, heteroaryl or a sugar); polyethyleneglycols (PEG), $O(CH_2CH_2O)_nCH_2CH_2OR$ wherein R can be, e.g., H or optionally substituted alkyl, and n can be an integer from 0 to 20 (e.g., from 0 to 4, from 0 to 8, from 0 to 10, from 0 to 16, from 1 to 4, from 1 to 8, from 1 to 10, from 1 to 16, from 1 to 20, from 2 to 4, from 2 to 8, from 2 to 10, from 2 to 16, from 2 to 20, from 4 to 8, from 4 to 10, from 4 to 16, and from 4 to 20). In an embodiment, the "oxy"-2' hydroxyl group modification can include "locked" nucleic acids (LNA) in which the 2' hydroxyl can be connected, e.g., by a $C_{1-6}$ alkylene or $C_{1-6}$ heteroalkylene bridge, to the 4' carbon of the same ribose sugar, where exemplary bridges can include methylene, propylene, ether, or amino bridges; O-amino (wherein amino can be, e.g., $NH_2$; alkylamino, dialkylamino, heterocyclyl, arylamino, diarylamino, heteroarylamino, or diheteroarylamino, ethylenediamine, or polyamino) and aminoalkoxy, $O(CH_2)_n$-amino, (wherein amino can be, e.g., $NH_2$; alkylamino, dialkylamino, heterocyclyl, arylamino, diarylamino, heteroarylamino, or diheteroarylamino, ethylenediamine, or polyamino). In an embodiment, the "oxy"-2' hydroxyl group modification can include the methoxyethyl group (MOE), ($OCH_2CH_2OCH_3$, e.g., a PEG derivative).

"Deoxy" modifications can include hydrogen (i.e. deoxyribose sugars, e.g., at the overhang portions of partially ds RNA); halo (e.g., bromo, chloro, fluoro, or iodo); amino (wherein amino can be, e.g., $NH_2$; alkylamino, dialkylamino, heterocyclyl, arylamino, diarylamino, heteroarylamino, diheteroarylamino, or amino acid); $NH(CH_2CH_2NH)_nCH_2CH_2$-amino (wherein amino can be, e.g., as described herein), —NHC(O)R (wherein R can be, e.g., alkyl, cycloalkyl, aryl, aralkyl, heteroaryl or sugar), cyano; mercapto; alkyl-thio-alkyl; thioalkoxy; and alkyl, cycloalkyl, aryl, alkenyl and alkynyl, which may be optionally substituted with e.g., an amino as described herein.

The sugar group can also contain one or more carbons that possess the opposite stereochemical configuration than that of the corresponding carbon in ribose. Thus, a modified nucleic acid can include nucleotides containing e.g., arabinose, as the sugar. The nucleotide "monomer" can have an alpha linkage at the 1' position on the sugar, e.g., alpha-nucleosides. The modified nucleic acids can also include "abasic" sugars, which lack a nucleobase at C-1'. These abasic sugars can also be further modified at one or more of the constituent sugar atoms. The modified nucleic acids can also include one or more sugars that are in the L form, e.g. L-nucleosides.

Generally, RNA includes the sugar group ribose, which is a 5-membered ring having an oxygen. Exemplary modified nucleosides and modified nucleotides can include, without limitation, replacement of the oxygen in ribose (e.g., with sulfur (S), selenium (Se), or alkylene, such as, e.g., methylene or ethylene); addition of a double bond (e.g., to replace ribose with cyclopentenyl or cyclohexenyl); ring contraction of ribose (e.g., to form a 4-membered ring of cyclobutane or oxetane); ring expansion of ribose (e.g., to form a 6- or 7-membered ring having an additional carbon or heteroatom, such as for example, anhydrohexitol, altritol, mannitol, cyclohexanyl, cyclohexenyl, and morpholino that also has a phosphoramidate backbone). In an embodiment, the modified nucleotides can include multicyclic forms (e.g., tricyclo; and "unlocked" forms, such as glycol nucleic acid (GNA) (e.g., R-GNA or S-GNA, where ribose is replaced by glycol units attached to phosphodiester bonds), threose nucleic acid (TNA, where ribose is replaced with α-L-threofuranosyl-(3'→2')).

Modifications on the Nucleobase

The modified nucleosides and modified nucleotides described herein, which can be incorporated into a modified nucleic acid, can include a modified nucleobase. Examples of nucleobases include, but are not limited to, adenine (A), guanine (G), cytosine (C), and uracil (U). These nucleobases can be modified or wholly replaced to provide modified nucleosides and modified nucleotides that can be incorporated into modified nucleic acids. The nucleobase of the nucleotide can be independently selected from a purine, a pyrimidine, a purine or pyrimidine analog. In an embodiment, the nucleobase can include, for example, naturally-occurring and synthetic derivatives of a base.

Uracil

In an embodiment, the modified nucleobase is a modified uracil. Exemplary nucleobases and nucleosides having a modified uracil include without limitation pseudouridine (ψ), pyridin-4-one ribonucleoside, 5-aza-uridine, 6-aza-uridine, 2-thio-5-aza-uridine, 2-thio-uridine (s2U), 4-thio-uridine (s4U), 4-thio-pseudouridine, 2-thio-pseudouridine, 5-hydroxy-uridine (ho⁵U), 5-aminoallyl-uridine, 5-halo-uridine (e.g., 5-iodo-uridine or 5-bromo-uridine), 3-methyl-uridine (m³U), 5-methoxy-uridine (mo⁵U), uridine 5-oxyacetic acid (cmo⁵U), uridine 5-oxyacetic acid methyl ester (mcmo$^5$U), 5-carboxymethyl-uridine (cm$^5$U), 1-carboxymethyl-pseudouridine, 5-carboxyhydroxymethyl-uridine (chm$^5$U), 5-carboxyhydroxymethyl-uridine methyl ester (mchm$^5$U), 5-methoxycarbonylmethyl-uridine (mcm$^5$U), 5-methoxycarbonylmethyl-2-thio-uridine (mcm$^5$s2U), 5-aminomethyl-2-thio-uridine (nm$^5$s2U), 5-methylaminomethyl-uridine (mnm$^5$U), 5-methylaminomethyl-2-thio-uridine (mnm$^5$s2U), 5-methylaminomethyl-2-seleno-uridine (mnm$^5$se$^2$U), 5-carbamoylmethyl-uridine (ncm$^5$U), 5-carboxymethylaminomethyl-uridine (cmnm$^5$U), 5-carboxymethylaminomethyl-2-thio-uridine (cmnm$^5$s2U), 5-propynyl-uridine, 1-propynyl-pseudouridine, 5-taurinomethyl-uridine (τcm$^5$U), 1-taurinomethyl-pseudouridine, 5-taurinomethyl-2-thio-uridine(τm$^5$s2U), 1-taurinomethyl-4-thio-pseudouridine, 5-methyl-uridine (m$^5$U, i.e., having the nucleobase deoxythymine), 1-methyl-pseudouridine (m$^1$ψ), 5-methyl-2-thio-uridine (m$^5$s2U), 1-methyl-4-thio-pseudouridine (m$^1$s$^4$ψ), 4-thio-1-methyl-pseudouridine, 3-methyl-pseudouridine (m$^3$ψ), 2-thio-1-methyl-pseudouridine, 1-methyl-1-deaza-pseudouridine, 2-thio-1-methyl-1-deaza-pseudouridine, dihydrouridine (D), dihydropseudouridine, 5,6-dihydrouridine, 5-methyl-dihydrouridine (m$^5$D), 2-thio-dihydrouridine, 2-thio-dihydropseudouridine, 2-methoxy-uridine, 2-methoxy-4-thio-uridine, 4-methoxy-pseudouridine, 4-methoxy-2-thio-pseudouridine, N1-methyl-pseudouridine, 3-(3-amino-3-carboxypropyl)uridine (acp$^3$U), 1-methyl-3-(3-amino-3-carboxypropyl)pseudouridine (acp$^3$ψ), 5-(isopentenylaminomethyl)uridine (inm$^5$U), 5-(isopentenylaminomethyl)-2-thio-uridine (inm$^5$s2U), α-thio-uridine, 2'-O-methyl-uridine (Um), 5,2'-O-dimethyl-uridine (m$^5$Um), 2'-O-methyl-pseudouridine (ψm), 2-thio-2'-O-methyl-uridine (s2Um), 5-methoxycarbonylmethyl-2'-O-methyl-uridine (mcm$^5$Um), 5-carbamoylmethyl-2'-O-methyl-uridine (ncm$^5$Um), 5-carboxymethylaminomethyl-2'-O-methyl-uridine (cmnm $^5$Um), 3,2'-O-dimethyl-uridine (m$^3$Um), 5-(isopentenylaminomethyl)-2'-O-methyl-uridine (inm $^5$Um), 1-thio-uridine, deoxythymidine, 2'-F-ara-uridine, 2'-F-uridine, 2'-OH-ara-uridine, 5-(2-carbomethoxyvinyl) uridine, 5-[3-(1-E-propenylamino)uridine, pyrazolo[3,4-d]pyrimidines, xanthine, and hypoxanthine.

Cytosine

In an embodiment, the modified nucleobase is a modified cytosine. Exemplary nucleobases and nucleosides having a modified cytosine include without limitation 5-aza-cytidine, 6-aza-cytidine, pseudoisocytidine, 3-methyl-cytidine (m$^3$C), N4-acetyl-cytidine (act), 5-formyl-cytidine (f$^5$C), N4-methyl-cytidine (m$^4$C), 5-methyl-cytidine (m$^5$C), 5-halo-cytidine (e.g., 5-iodo-cytidine), 5-hydroxymethyl-cytidine (hm$^5$C), 1-methyl-pseudoisocytidine, pyrrolo-cytidine, pyrrolo-pseudoisocytidine, 2-thio-cytidine (s2C), 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, 4-methoxy-1-methyl-pseudoisocytidine, lysidine (k$^2$C), α-thio-cytidine, 2'-O-methyl-cytidine (Cm), 5,2'-O-dimethyl-cytidine (m$^5$Cm), N4-acetyl-2'-O-methyl-cytidine (ac$^4$Cm), N4,2'-O-dimethyl-cytidine (m$^4$Cm), 5-formyl-2'-O-methyl-cytidine (f $^5$Cm), N4,N4,2'-O-trimethyl-cytidine (m$^4{}_2$ Cm), 1-thio-cytidine, 2'-F-ara-cytidine, 2'-F-cytidine, and 2'-OH-ara-cytidine.

Adenine

In an embodiment, the modified nucleobase is a modified adenine. Exemplary nucleobases and nucleosides having a modified adenine include without limitation 2-amino-purine, 2,6-diaminopurine, 2-amino-6-halo-purine (e.g., 2-amino-6-chloro-purine), 6-halo-purine (e.g., 6-chloro-purine), 2-amino-6-methyl-purine, 8-azido-adenosine, 7-deaza-adenine, 7-deaza-8-aza-adenine, 7-deaza-2-amino-purine, 7-deaza-8-aza-2-amino-purine, 7-deaza-2,6-diaminopurine, 7-deaza-8-aza-2,6-diaminopurine, 1-methyl-adenosine (m$^1$A), 2-methyl-adenine (m$^2$A), N6-methyl-adenosine (m$^6$A), 2-methylthio-N6-methyl-adenosine (ms2m$^6$A), N6-isopentenyl-adenosine (i$^6$A), 2-methylthio-N6-isopentenyl-adenosine (ms$^2$i$^6$A), N6-(cis-hydroxyisopentenyl)adenosine (io$^6$A), 2-methylthio-N6-(cis-hydroxyisopentenyl)adenosine (ms2io$^6$A), N6-glycinylcarbamoyl-adenosine (g$^6$A), N6-threonylcarbamoyl-adenosine (t$^6$A), N6-methyl-N6-threonylcarbamoyl-adenosine (m$^6$t$^6$A), 2-methylthio-N6-threonylcarbamoyl-adenosine (ms$^2$g$^6$A), N6,N6-dimethyl-adenosine (m$^6{}_2$A), N6-hydroxynorvalylcarbamoyl-adenosine (hn$^6$A), 2-methylthio-N6-hydroxynorvalylcarbamoyl-adenosine (ms2hn$^6$A), N6-acetyl-adenosine (ac$^6$A), 7-methyl-adenine, 2-methylthio-adenine, 2-methoxy-adenine, α-thio-adenosine, 2'-O-methyl-adenosine (Am), N$^6$,2'-O-dimethyl-adenosine (m$^6$Am), N$^6$-Methyl-2'-deoxyadenosine, N6,N6,2'-O-trimethyl-adenosine (m$^6$2 Am), 1,2'-O-dimethyl-adenosine (m$^1$Am), 2'-O-ribosyladenosine (phosphate) (Ar(p)), 2-amino-N6-methyl-purine, 1-thio-adenosine, 8-azido-adenosine, 2'-F-ara-adenosine, 2'-F-adenosine, 2'-OH-ara-adenosine, and N6-(19-aminopentaoxanonadecyl)-adenosine.

Guanine

In an embodiment, the modified nucleobase is a modified guanine. Exemplary nucleobases and nucleosides having a modified guanine include without limitation inosine (I), 1-methyl-inosine (m$^1$I), wyosine (imG), methylwyosine (mimG), 4-demethyl-wyosine (imG-14), isowyosine (imG2), wybutosine (yW), peroxywybutosine (o2yW), hydroxywybutosine (OHyW), undermodified hydroxywybutosine (OHyW*), 7-deaza-guanosine, queuosine (Q), epoxyqueuosine (oQ), galactosyl-queuosine (galQ), mannosyl-queuosine (manQ), 7-cyano-7-deaza-guanosine (preQ$_0$), 7-aminomethyl-7-deaza-guanosine (preQ$_1$), archaeosine (G$^+$), 7-deaza-8-aza-guanosine, 6-thio-guanosine, 6-thio-7-deaza-guanosine, 6-thio-7-deaza-8-aza-guanosine, 7-methyl-guanosine (m$^7$G), 6-thio-7-methyl-guanosine, 7-methyl-inosine, 6-methoxy-guanosine, 1-methyl-guanosine (m'G), N2-methyl-guanosine (m$^2$G), N2,N2-dimethyl-guanosine (m$^2$ 2 G), N2,7-dimethyl-guanosine (m$^2$,7G), N2,N2,7-dimethyl-guanosine (m$^2$,2,7G), 8-oxo-guanosine, 7-methyl-8-oxo-guanosine, 1-meth thio-guanosine, N2-methyl-6-thio-guanosine, N2,N2-dimethyl-6-thio-guanosine, α-thio-guanosine, 2'-O-methyl-guanosine (Gm), N2-methyl-2'-O-methyl-guanosine (m$^2$Gm), N2,N2-dimethyl-2'-O-methyl-guanosine (m$^2$ 2 Gm), 1-methyl-2'-O-methyl-guanosine (m'Gm), N2,7-dimethyl-2'-O-methyl-guanosine (m$^2$,7Gm), 2'-O-methyl-inosine (Im), 1,2'-O-dimethyl-inosine (m'Im), O$^6$-phenyl-2'-deoxyinosine, 2'-O-ribosylguanosine (phosphate) (Gr(p)), 1-thio-guanosine, O$^6$-methyl-guanosine, O$^6$-Methyl-2'-deoxyguanosine, 2'-F-ara-guanosine, and 2'-F-guanosine.

Modified gRNAs

In an embodiment, the modified nucleic acids can be modified gRNAs. In an embodiment, gRNAs can be modified at the 3' end. In this embodiment, the gRNAs can be modified at the 3' terminal U ribose. For example, the two terminal hydroxyl groups of the U ribose can be oxidized to aldehyde groups and a concomitant opening of the ribose ring to afford a modified nucleoside as shown below:

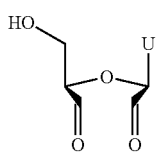

wherein "U" can be an unmodified or modified uridine.

In another embodiment, the 3' terminal U can be modified with a 2'3' cyclic phosphate as shown below:

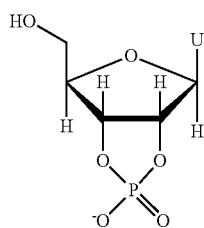

wherein "U" can be an unmodified or modified uridine.

In an embodiment, the gRNA molecules may contain 3' nucleotides which can be stabilized against degradation, e.g., by incorporating one or more of the modified nucleotides described herein. In this embodiment, e.g., uridines can be replaced with modified uridines, e.g., 5-(2-amino)propyl uridine, and 5-bromo uridine, or with any of the modified uridines described herein; adenosines and guanosines can be replaced with modified adenosines and guanosines, e.g., with modifications at the 8-position, e.g., 8-bromo guanosine, or with any of the modified adenosines or guanosines described herein. In an embodiment, deaza nucleotides, e.g., 7-deaza-adenosine, can be incorporated into the gRNA. In an embodiment, 0- and N-alkylated nucleotides, e.g., N6-methyl andenosine, can be incorporated into the gRNA. In an embodiment, sugar-modified ribonucleotides can be incorporated, e.g., wherein the 2' OH-group is replaced by a group selected from H, —OR, —R (wherein R can be, e.g., alkyl, cycloalkyl, aryl, aralkyl, heteroaryl or sugar), halo, —SH, —SR (wherein R can be, e.g., alkyl, cycloalkyl, aryl, aralkyl, heteroaryl or sugar), amino (wherein amino can be, e.g., $NH_2$; alkylamino, dialkylamino, heterocyclyl, arylamino, diarylamino, heteroarylamino, diheteroarylamino, or amino acid); or cyano (—CN). In an embodiment, the phosphate backbone can be modified as described herein, e.g., with a phosphothioate group. In an embodiment, the nucleotides in the overhang region of the gRNA can each independently be a modified or unmodified nucleotide including, but not limited to 2'-sugar modified, such as, 2-F 2'-O-methyl, thymidine (T), 2'-O-methoxyethyl-5-methyluridine (Teo), 2'-O-methoxyethyladenosine (Aeo), 2'-O-methoxyethyl-5-methylcytidine (m5Ceo), and any combinations thereof.

In an embodiment, a one or more or all of the nucleotides in single stranded overhang of an RNA molecule, e.g., a gRNA molecule, are deoxynucleotides.

XI. Linkers

In an embodiment, the payload can be linked to the Cas9 molecules or the gRNA, e.g., by a covalent linker. This linker may be cleavable or non-cleavable. In an embodiment, a cleavable linker may be used to release the payload after transport to the desired target.

Linkers can comprise a direct bond or an atom such as, e.g., an oxygen (O) or sulfur (S), a unit such as —NR— wherein R is hydrogen or alkyl, —C(O)—, —C(O)O—, —C(O)NH—, SO, $SO_2$, —$SO_2$NH— or a chain of atoms, such as substituted or unsubstituted alkyl, substituted or unsubstituted alkenyl, substituted or unsubstituted alkynyl, arylalkyl, heteroarylalkyl. In an embodiment, one or more methylenes in the chain of atoms can be replaced with one or more of O, S, S(O), $SO_2$, —$SO_2$NH—, —NR—, —C(O)—, —C(O)O—, —C(O)NH—, a cleavable linking group, substituted or unsubstituted aryl, substituted or unsubstituted heteroaryl, and substituted or unsubstituted heterocyclic.

Non-Cleavable Linkages

In an embodiment, the payload is attached to the Cas9 molecule or gRNA through a linker that is itself is stable under physiological conditions, such as an alkylene chain, and does not result in release of the payload from the Cas9 molecule and/or gRNA for at least 2, 3, 4, 5, 10, 15, 24 or 48 hours or for at least 1, 2, 3, 4, 5, or 10 days when administered to a subject. In an embodiment, the payload and the Cas9 molecule and/or gRNA comprise residues of a functional groups through which reaction and linkage of the payload to the Cas9 molecule or gRNA was achieved. In an embodiment, the functional groups, which may be the same or different, terminal or internal, of the payload or Cas9molecule and/or gRNA comprise an amino, acid, imidazole, hydroxyl, thio, acyl halide, —HC=CH—, —C≡C— group, or derivative thereof. In an embodiment, the linker comprises a hydrocarbylene group wherein one or more methylene groups is optionally replaced by a group Y (provided that none of the Y groups are adjacent to each other), wherein each Y, independently for each occurrence, is selected from, substituted or unsubstituted aryl, heteroaryl, cycloalkyl, heterocycloalkyl, or —O—, —C(=X)— (wherein X is $NR_1$, O or S), —$NR_1$—, —$NR_1$C(O)—, —C(O)$NR_1$—, —S(O)$_n$—, —$NR_1$S(O)$_n$—, —S(O)$_n$$NR_1$—, —$NR_1$C(O)—$NR_1$—; and $R_1$, independently for each occurrence, represents H or a lower alkyl and wherein n is 0, 1, or 2.

In an embodiment, the linker comprises an alkylene moiety or a heteroalkylene moiety (e.g., an alkylene glycol moiety such as ethylene glycol). In an embodiment, a linker comprises a poly-L-glutamic acid, polylactic acid, poly (ethyleneimine), an oligosaccharide, an amino acid (e.g., glycine), an amino acid chain, or any other suitable linkage. The linker groups can be biologically inactive, such as a PEG, polyglycolic acid, or polylactic acid chain. In an embodiment, the linker group represents a derivatized or non-derivatized amino acid (e.g., glycine).

Cleavable Linkages

A cleavable linking group is one which is sufficiently stable outside the cell, but which upon entry into a target cell is cleaved to release the two parts the linker is holding together. In one embodiment, the cleavable linking group is cleaved at least 10 times or more, or at least 100 times faster in the target cell or under a first reference condition (which can, e.g., be selected to mimic or represent intracellular conditions) than in the blood of a subject, or under a second reference condition (which can, e.g., be selected to mimic or represent conditions found in the blood or serum).

Cleavable linking groups are susceptible to cleavage agents, e.g., pH, redox potential or the presence of degradative molecules. Examples of such degradative agents include: redox agents which are selected for particular substrates or which have no substrate specificity, including, e.g., oxidative or reductive enzymes or reductive agents such as mercaptans, present in cells, that can degrade a redox cleavable linking group by reduction; esterases; endosomes or agents that can create an acidic environment, e.g., those that result in a pH of five or lower; enzymes that can hydrolyze or degrade an acid cleavable linking group by acting as a general acid, peptidases (which can be substrate specific), and phosphatases.

A cleavable linkage group, such as a disulfide bond (—S—S—) can be susceptible to pH. The pH of human serum is 7.4, while the average intracellular pH is slightly lower, ranging from about 7.1-7.3. Endosomes have a more acidic pH, in the range of 5.5-6.0, and lysosomes have an even more acidic pH at around 5.0. Some linkers will have a cleavable linking group that is cleaved at a preferred pH. A linker can include a cleavable linking group that is cleavable by a particular enzyme.

In general, the suitability of a candidate cleavable linking group can be evaluated by testing the ability of a degradative agent (or condition) to cleave the candidate linking group. The candidate cleavable linking group can also be tested for the ability to resist cleavage in the blood or when in contact with other non-target tissue. Thus one can determine the relative susceptibility to cleavage between a first and a second condition, where the first is selected to be indicative of cleavage in a target cell and the second is selected to be indicative of cleavage in other tissues or biological fluids, e.g., blood or serum. The evaluations can be carried out in cell free systems, in cells, in cell culture, in organ or tissue culture, or in whole animals. It may be useful to make initial evaluations in cell-free or culture conditions and to confirm by further evaluations in whole animals.

In an embodiment, the cleavable linkers include redox cleavable linkers, such as a disulfide group (—S—S—) and phosphate cleavable linkers, such as, e.g., —O—P(O)(OR)—O—, —O—P(S)(OR)—O—, —O—P(S)(SR)—O—, —S—P(O)(OR)—O—, —O—P(O)(OR)—S—, —S—P(O)(OR)—S—, —O—P(S)(OR)—S—, —S—P(S)(OR)—O—, —O—P(O)(R)—O—, —O—P(S)(R)—O—, —S—P(O)(R)—O—, —S—P(S)(R)—O—, —S—P(O)(R)—S—, —OP(S)(R)—S—, wherein R is hydrogen or alkyl.

Acid Cleavable Linking Groups

Acid cleavable linking groups are linking groups that are cleaved under acidic conditions. In an embodiment, acid cleavable linking groups are cleaved in an acidic environment with a pH of about 6.5 or lower (e.g., about 6.0, 5.5, 5.0, or lower), or by agents such as enzymes that can act as a general acid. Examples of acid cleavable linking groups include but are not limited to hydrazones, esters, and esters of amino acids. Acid cleavable groups can have the general formula —C(=N—)N—, —C(O)O—, or —OC(O)—.

Ester-Based Linking Groups

Ester-based cleavable linking groups are cleaved by enzymes such as esterases and amidases in cells. Examples of ester-based cleavable linking groups include but are not limited to esters of alkylene, alkenylene and alkynylene groups. Ester cleavable linking groups have the general formula —C(O)O—, or —OC(O)—.

XII. Targeting of Genomic Signatures

Cas9 molecules, gRNA molecules, and in particular, Cas9 molecule/gRNA molecule complexes, can be used to target a cell by virtue of sequence specific interaction with a target nucleic acid comprising a selected genomic signature. This provides for targeted destruction of cells having a selected genomic signature. Method and compositions disclosed herein can be used to treat disorders characterized by a selected genomic signature, e.g., a genomic signature present in the germline or a genomic signature that arise as a result of a sporadic or somatic change in the genome, e.g., a germline or acquired mutation in a cancer cell, a viral infection, or other germline or acquired changes to the genome.

While not wishing to be bound by theory, it is believed that complementarity between the targeting domain of a gRNA molecule and the target sequence of a target nucleic acid mediates target sequence-specific interaction of the Cas9 molecule/gRNA molecule complex with the target sequence. This allows targeting of specific sequences or genomic signatures, e.g., rearrangements, e.g., translocations, insertions, deletions, and inversions, and other mutations. A Cas9 molecule/gRNA molecule complex can be used to target specific sequence, e.g., mutations, that are germline, mitochondrial, or somatic. Depending on the Cas9 molecule/gRNA molecule complex used, specific editing, the delivery of a payload, or both, can be effected. In an embodiment, both cleavage and delivery of a payload is effected.

In an embodiment, the Cas9 molecule/gRNA molecule complex that promotes cell death upon recognition of its target genomic sequence. In an embodiment, an eaCas9 molecule/gRNA molecule complex cleaves the target nucleic acid. In an embodiment, it does not deliver a payload. While not wishing to be bound by theory is it believed that endogenous cellular elements, e.g., elements of the DNA damage apoptosis signaling cascade promote apoptosis in these embodiments.

In an embodiment, an eaCas9 molecule/gRNA molecule complex cleaves the target nucleic acid and delivers a payload. The payload can comprises a compound that inhibits growth or cell division, or promotes apoptosis, e.g., an element of the DNA damage apoptosis signaling cascade. In an embodiment, a second Cas9 molecule/gRNA molecule complex is used to deliver a payload comprising a second compound that inhibits growth or cell division, or promotes apoptosis, e.g., an element of the DNA damage apoptosis signaling cascade. The Cas9 molecule/gRNA molecule complex that delivers the second payload can comprise an eiCas9 molecule or an eaCas9 molecule. An additional, e.g., third or fourth, Cas9 molecule/gRNA molecule complex, can be used to deliver additional payload, e.g., an additional compound that inhibits growth or cell division, or promotes apoptosis, e.g., an additional element of the DNA damage apoptosis signaling cascade promote.

In an embodiment, the Cas9 molecule/gRNA molecule complex delivers a payload comprising a compound that inhibits growth or cell division, or promotes apoptosis, e.g., an element of the DNA damage apoptosis signaling cascade, but does not cleave the target nucleic acid. While not wishing to be bound by theory is it believed that endogenous cellular elements, e.g., elements of the DNA damage apoptosis signaling cascade promote apoptosis in these embodiments.

Exemplary compounds that inhibit growth or cell division, or promote apoptosis, e.g., an element of the DNA damage apoptosis signaling cascade, are described herein, e.g., in Table XII-1.

TABLE XII-1

ATM kinases (double-strand breaks)
ATR kinases (single-strand breaks)
RF-C related protein (RAD17)
The 9-1-1 Complex: RAD1, RAD9, and HUS1
Checkpoint proteins CHK1, CHK2
P53
ZIP Kinase (ZIPK)

TABLE XII-1-continued

Fast Death-Domain Associated Protein XX (DAXX)
Promyelocytic leukemia protein (PML)
Apoptosis-inducing factor (AIF)
Caspase-activated DNAse (CAD) (in the absence of its inhibitor ICAD)

In an embodiment, a Cas9 molecule/gRNA molecule complex targets a sequence that includes or is near the breakpoint of a rearrangement, e.g., a translocation, inversion, insertion, or deletion. In an embodiment, the rearrangement confers unwanted properties, e.g., unwanted proliferation, on the cell. In an embodiment, the cell harboring the rearrangement is a cancer cell. In an embodiment, the rearrangement comprises a kinase gene and results in unwanted, increased, or constitutive expression of the kinase activity. In an embodiment, the rearrangement disrupts the expression of a tumor suppressor.

In an embodiment, the Cas9 molecule/gRNA molecule complex:

specifically targets, and e.g., cleaves, the genome of a cell comprising a rearrangement, e.g., by targeting a mutation, e.g., a breakpoint or junction of a rearrangement; or targets, e.g., for cleavage or payload delivery, a nucleotide sequence within 200, 100, 150, 100, 50, 25, 10, or 5 nucleotides of a mutation, e.g., a rearrangement breakpoint.

The invention includes a method of manipulating a cell comprising a genomic signature, comprising:

administering a Cas9 molecule/gRNA molecule complex that targets said genomic signature, thereby manipulating said cell.

In an embodiment, manipulating comprises inhibiting the growth or division of, or killing, said cell.

In an embodiment, said cell is a cancer cell or cell having a viral infection.

In an embodiment, the method comprises treating a subject, e.g., a human subject, for a disorder characterized by a cell having said genomic signature, e.g., a cancer or a viral infection.

In an embodiment, a Cas9 molecule/gRNA molecule complex disrupts a rearrangement, e.g., by introduction of a stop codon from a template nucleic acid, e.g., a stop codon is inserted into a fusion protein, e.g., a fusion protein comprising kinase activity.

The invention includes a method of treating a cancer having a translocation of a kinase gene to a non-kinase gene, which places the kinase domain under the control of the non-kinase gene control region comprising:

administering a Cas9 molecule/gRNA molecule complex that targets the translocation. In an embodiment, the control region, e.g., the promoter, or the coding sequence, of the kinase translocation, is edited to reduce expression.

XIII. Combination Therapy

The Cas9 molecules, gRNA molecules, and in particular, Cas9 molecule/gRNA molecule complexes, can be used in combination with a second therapeutic agent, e.g., a cancer drug. In an embodiment, the second therapeutic agent (e.g., a cancer drug) and the Cas9 molecule, gRNA molecule, and in particular, Cas9 molecule/gRNA molecule complex target different (e.g., non-overlapping) pathways. In an embodiment, the second therapeutic agent (e.g., a cancer drug) and the Cas9 molecule, gRNA molecule, and in particular, Cas9 molecule/gRNA molecule complex target a same or overlapping pathway.

Exemplary combination therapies include, e.g.:

mTOR inhibitors (e.g., Temsirolimus (Torisel®) or Everolimus (Afinitor®)) together with a AKT-specific Cas9/gRNA molecule;

Tyrosine kinase inhibitors such as Imatinib mesylate (Gleevec®); Dasatinib (Sprycel®); Bosutinib (Bosulif®); Trastuzumab (Herceptin®); Pertuzumab (Perjeta™); Lapatinib (Tykerb®); Gefitinib (Iressa®); Erlotinib (Tarceva®) together with a HDAC-specific Cas9/gRNA molecule; and Any chemotherapeutic agent together with one or more Cas9/gRNAs against multidrug resistance genes such as MDR1 gene.

XIV. Treatment of Genetic Disorder, e.g., Duchenne Muscular Dystrophy (DMD)

In another aspect, the invention features, a method of altering a cell, e.g., reducing or abolishing the effect of a genetic signature, e.g., a stop codon, e.g., a premature stop codon. The method comprises contacting said cell with:

a Cas9 molecule/gRNA molecule complex that cleaves at or upstream from the genetic signature, e.g., a premature stop codon, thereby altering the cell.

While not wishing to be bound by theory it is believed that, in an embodiment, cleavage and subsequent exonuclease activity, and non-homologous end joining results in an altered sequence in which the genetic signature, e.g., a premature stop codon is eliminated, e.g., by being placed in a different frame. In an embodiment, the same series of events restores the proper reading frame to the sequence that follows the signature, e.g., premature stop codon.

When the method is carried out to correct a frameshift mutation in order to remove a premature stop codon, repair can be carried out at various sites in the DNA. One may direct cleavage at the mutation, thereby correcting the frameshift entirely and returning the protein to its wild-type (or nearly wild-type) sequence. One may also direct cleavage at or near the premature stop codon, so that all (or nearly all) amino acids of the protein C-terminal of the codon where repair was effected are wild-type. In the latter case, the resulting protein may have one or more frameshifted amino acids between the mutation and the repair site; however the protein may still be functional because it is full-length and has wild-type sequence across most of its length.

A genetic signature is a particular DNA sequence at a particular portion of the genome, that causes a phenotype (such as a genetic disease or a symptom thereof). For instance, the genetic signature may be a premature stop codon that prevents expression of a protein. In this scenario, the premature stop codon can arise from a mutation that directly creates a stop codon, or from a mutation that causes a frameshift leading to a premature stop codon being formed downstream. A genetic signature may also be a point mutation that alters the identity of an important amino acid in a protein, disrupting the protein's function.

In an embodiment, the Cas9 molecule/gRNA molecule complex mediates a double stranded break in said target nucleic acid.

In an embodiment, the genetic signature, e.g., a premature stop codon, results from a point mutation, an insertion, a deletion, or a rearrangement. In an embodiment, a mutation causes a frameshift, resulting in a genetic signature, e.g., a premature stop codon downstream of the mutation.

In an embodiment, the premature stop codon is within the target nucleic acid. In an embodiment, the target nucleic acid is upstream of the premature stop codon. The mutation may be upstream of the target nucleic acid, within the target nucleic acid, or downstream of the target nucleic acid.

In an embodiment the double stranded break is within 500, 200, 100, 50, 30, 20, 10, 5, or 2 nucleotides of the mutation. In an embodiment, the double stranded break is within 500, 200, 100, 50, 30, 20, 10, 5, or 2 nucleotides of the genetic signature, e.g., a premature stop codon.

In an embodiment, the Cas9 molecule/gRNA molecule complex mediates exonuclease digestion of the target nucleic acid. In an embodiment, the Cas9 molecule/gRNA molecule complex removes 1, 2, 3, 4, or 5 nucleotides at the double stranded break.

In an embodiment, the double stranded break is resolved by non-homologous end joining.

In an embodiment the mutation and/or genetic signature, e.g., premature stop codon is in the dystrophin gene, e.g., in exon 51, or in the intron preceding or following exon 51. The premature stop codon may also be caused by a mutation in the dystrophin gene at one or more of codons 54, 645, 773, 3335, and 3340. In an embodiment, the premature stop codon in the dystrophin gene results from a deletion of codons 2305 through 2366.

In an embodiment, contacting the cell with a Cas9 molecule/gRNA molecule complex comprises contacting the cell with a nucleic acid encoding a Cas9 molecule. In an embodiment, contacting the cell with a Cas9 molecule/gRNA molecule complex comprises transfecting the cell with a nucleic acid, e.g., a plasmid, or using a viral vector such as adeno-associated virus (AAV).

In an embodiment, the method results in increased levels of the protein in which the genetic signature, e.g., a premature stop codon, was previously located. For instance, protein levels (e.g., dystrophin levels) may be increased by at least 3%, 4%, 5%, 10%, 15%, 20%, 25%, or 30% in a cell or in a tissue. In an embodiment, the method results in increased levels of the mRNA in which the premature stop codon was previously located, for instance by preventing the mRNA from undergoing nonsense-mediated mRNA decay.

In an embodiment, one or more of the target nucleic acid, the genetic signature, e.g., premature stop codon, and the mutation are located in the dystrophin gene (which is mutated in DMD). One or more of the target nucleic acid, the genetic signature, e.g., premature stop codon, and the mutation may also be located in the COL7A1 gene (mutated in type VII-associated dystrophic epidermolysis bullosa), the FKTN gene (mutated in Fukuyama congenital muscular dystrophy), the dysferlin gene (mutated in limb-girdle muscular dystrophy type 2B), the CFTR gene (mutated in cystic fibrosis), HEXA (mutated in Tay-Sachs disease), the IDS gene (mutated in Hunter syndrome), the FVIII gene (mutated in hemophilia), the IDUA gene (mutated in Hurler syndrome), the PPT1 gene (mutated in infantile neuronal ceroid lipofuscinosis), a tumor suppressor such as the ATM gene (mutated in cancers like gliomas and B-Cell Chronic Lymphocytic Leukemia), RP2 (mutated in X-linked retinitis pigmentosa), the CTNS gene (mutated in nephropathic cystinosis), and the AVPR2 gene (mutated in Congenital nephrogenic diabetes insipidus).

In an embodiment, the method is performed in cultured cells. In an embodiment, the method further comprises administering the cell to a patient. The cell may be, for example, an induced pluripotent stem cell, a bone marrow derived progenitor, a skeletal muscle progenitor, a CD133+ cell, a mesoangioblast, or a MyoD-transduced dermal fibroblast.

In an embodiment, the method comprises contacting the cell with a template nucleic acid under conditions that allow for homology-directed repair between the target nucleic acid and the template nucleic acid to correct the mutation or the premature stop codon.

In another aspect, the invention features a method of treating a human subject having a disorder associated with a genetic signature, e.g., premature stop codon, e.g., DMD, comprising providing to the human subject:

1) a Cas9 molecule/gRNA molecule complex that cleaves at or upstream from the premature stop codon or 2) a cell that has been contacted with such complex,
thereby treating the subject.

In an embodiment, the Cas9 molecule/gRNA molecule complex mediates a double stranded break in said target nucleic acid.

In an embodiment, genetic signature, e.g., premature stop codon results from a point mutation, an insertion, a deletion, or a rearrangement. In an embodiment, a mutation causes a frameshift, resulting in a premature stop codon downstream of the mutation.

In an embodiment the double stranded break is within 500, 200, 100, 50, 30, 20, 10, 5, or 2 nucleotides of the mutation. In an embodiment the double stranded break is within 500, 200, 100, 50, 30, 20, 10, 5, or 2 nucleotides of the premature stop codon.

In an embodiment, the genetic signature, e.g., premature stop codon is within the target nucleic acid of the Cas9 molecule/gRNA molecule complex. In an embodiment, the target nucleic acid is upstream of the genetic signature, e.g., premature stop codon. The mutation may be upstream of the target nucleic acid, within the target nucleic acid, or downstream of the target nucleic acid.

In an embodiment, the Cas9 molecule/gRNA molecule complex mediates exonuclease digestion of the target nucleic acid. In an embodiment, the Cas9 molecule/gRNA molecule complex removes 1, 2, 3, 4, or 5 nucleotides at the double stranded break.

In an embodiment, the double stranded break is resolved by non-homologous end joining.

In an embodiment, the mutation and/or genetic signature, e.g., premature stop codon is in the dystrophin gene, e.g., in exon 51, or in the intron preceding or following exon 51. The premature stop codon may also be caused by a mutation in the dystrophin gene at one or more of codons 54, 645, 773, 3335, and 3340. In an embodiment, the premature stop codon in the dystrophin gene results from a deletion of codons 2305 through 2366.

In an embodiment, contacting the cell with a Cas9 molecule/gRNA molecule complex comprises contacting the cell with a nucleic acid encoding a Cas9 molecule. In an embodiment, contacting the cell with a Cas9 molecule/gRNA molecule complex comprises transfecting the cell with a nucleic acid, e.g., a plasmid, or using a viral vector such as adeno-associated virus (AAV).

In an embodiment, the method results in increased levels of the protein in which the genetic signature, e.g., premature stop codon was previously located. For instance, protein levels (e.g., dystrophin levels) may be increased by at least 3%, 4%, 5%, 10%, 15%, 20%, 25%, or 30% in a cell or in a tissue. In an embodiment, the method results in increased levels of the mRNA in which the premature stop codon was previously located, for instance by preventing the mRNA from undergoing nonsense-mediated mRNA decay.

In an embodiment, one or more of the target nucleic acid, the genetic signature, e.g., premature stop codon, and the mutation are located in the dystrophin gene (which is mutated in DMD). One or more of the target nucleic acid, the genetic signature, e.g., premature stop codon, and the mutation may also be located in the COL7A1 gene (mutated in type VII-associated dystrophic epidermolysis bullosa), the FKTN gene (mutated in Fukuyama congenital muscular dystrophy), the dysferlin gene (mutated in limb-girdle muscular dystrophy type 2B), the CFTR gene (mutated in cystic fibrosis), HEXA (mutated in Tay-Sachs disease), the IDS gene (mutated in Hunter syndrome), the FVIII gene (mutated in hemophilia), the IDUA gene (mutated in Hurler syndrome), the PPT1 gene (mutated in infantile neuronal ceroid lipofuscinosis), a tumor suppressor such as the ATM gene (mutated in cancers like gliomas and B-Cell Chronic Lymphocytic Leukemia), RP2 (mutated in X-linked retinitis pigmentosa), the CTNS gene (mutated in nephropathic cystinosis), and the AVPR2 gene (mutated in Congenital nephrogenic diabetes insipidus).

In an embodiment, the method is performed in cultured cells. In an embodiment, the method further comprises administering the cell to a patient. The cell may be, for example, an induced pluripotent stem cell, a bone marrow derived progenitor, a skeletal muscle progenitor, a CD133+ cell, a mesoangioblast, or a MyoD-transduced dermal fibroblast.

In an embodiment, the method comprises contacting the cell with a template nucleic acid under conditions that allow for homology-directed repair between the target nucleic acid and the template nucleic acid to correct the mutation or the premature stop codon.

In an embodiment, the subject has a disorder selected from Duchenne Muscular Dystrophy (DMD), collagen type VII-associated dystrophic epidermolysis bullosa, Fukuyama congenital muscular dystrophy, and limb-girdle muscular dystrophy type 2B, cystic fibrosis, lysosomal storage disorders (such as Tay-Sachs disease, Hunter syndrome, and nephropathic cystinosis), hemophilia, Hurler syndrome, infantile neuronal ceroid lipofuscinosis, X-linked retinitis pigmentosa (RP2), cancers (such as gliomas and B-Cell Chronic Lymphocytic Leukemia), and Congenital nephrogenic diabetes insipidus.

XV. Treatment of Disorders Characterized by Lack of Mature Specialized Cells, e.g., Impaired Hearing, with Loss of Hair Cells, Supporting Cells, or Spiral Ganglion Neurons; or for Diabetes, with Loss of Beta Islet Cells In another aspect, the invention features, a method of altering a cell, e.g., to promote the development of other mature specialized cells, e.g, in regeneration therapy. For example, proliferation genes can be upregulated and/or checkpoint inhibitors can be inhibited, e.g., to drive down one or more differenation pathways.

In an embodiment, the method includes induction of proliferation and specified lineage maturation.

In an embodiment, the method comprises, e.g., for restoration or improvement of hearing, contacting said cell with:

a Cas9 molecule/gRNA molecule complex that up-regulates a gene that promotes the development of hair cells, or down-regulates a gene that inhibits the development of hair cells thereby altering the cell.

In an embodiment, the Cas9 molecule/gRNA molecule delivers a payload that up-regulates a gene that promotes hair cell development.

In an embodiment, the Cas9 molecule/gRNA molecule delivers a payload that down-regulates a gene that inhibits hair growth.

In an embodiment, the Cas9 molecule/gRNA molecule complex edits the genome of a cell to up-regulate a gene that promotes hair growth. In an embodiment, a template nucleic acid is used to effect a Cas9 molecule/gRNA molecule complex alteration to the genome that up-regulates a gene that promotes hair growth.

In an embodiment, the Cas9 molecule/gRNA molecule complex edits the genome of a cell to down-regulate a gene that inhibits hair growth. In an embodiment, a template nucleic acid is used to effect a Cas9 molecule/gRNA molecule complex alteration to the genome that down-regulates a gene that promotes hair growth.

In an embodiment, said cell is an iPS cell, a native hair cell progenitor, or a mature hair cell.

In an embodiment, the Cas9 molecule/gRNA molecule and modifies expression of a gene, e.g., by modifying the structure of the gene (e.g., by editing the genome) or by delivery of a payload that modulates a gene. In an embodiment, the gene is a transcription factor or other regulatory gene.

In an embodiment, for hair cell or other mature cell regeneration, the method includes one or more or all of the following:

contacting the cell with a Cas9 molecule/gRNA molecule complex that results in up-regulation one or more of the following for cell proliferation: c-Myc, GATA3, Oct4, Sox2, Wnt, TCF3;

contacting the cell with a Cas9 molecule/gRNA molecule complex that results in down-regulation one or more of the following for check point: BCL2, BMP, Hes1, Hes5, Notch, p27. Prox1, TGFβ; and contacting the cell with a Cas9 molecule/gRNA molecule complex that results in turning on a maturation pathway. For hair cells this would include one or more of the following: Atoh1 (Math1), Barhl1, Gfi1, Myo7a, p63, PAX2, PAX8, Pou4f3 and for neurons would include one or more of the following: NEFH, Neurod1, Neurog1, POU4F1, In an embodiment, the method comprises generation of inner ear hair cells, outer ear hair cells, spiral ganglion neurons, and ear supporting cells.

In an embodiment, one or more growth factors can be modulated, e.g., upregulated, e.g., TPO can be upregulated for production of platelets and GCSF can be upregulated for production of neutrophils.

In another aspect, the invention provides altered cell described herein, e.g., in this Section XV.

In another aspect, the invention features a method of treating impaired hearing. The method comprises administering to said subject, an altered cell described herein, e.g., in this section XV. In an embodiment, the cell is autologous. In an embodiment, the cell is allogeneic. In an embodiment, the cell is xenogeneic.

In another aspect, the invention features a method of treating subject, e.g., for impaired hearing. The method comprises administering to said subject:

a Cas9 molecule/gRNA molecule complex that up-regulates a gene that promotes the growth of hair, or down-regulates a gene that inhibits the growth of hair thereby altering the cell.

In an embodiment, the Cas9 molecule/gRNA molecule delivers a payload that up-regulates a gene that promotes hair growth.

In an embodiment, the Cas9 molecule/gRNA molecule delivers a payload that down-regulates a gene that inhibits hair growth.

In an embodiment, the Cas9 molecule/gRNA molecule complex edits the genome of a cell to up-regulate a gene that promotes hair growth. In an embodiment, a template nucleic acid is used to effect a Cas9 molecule/gRNA molecule complex alteration to the genome that up-regulates a gene that promotes hair growth.

In an embodiment, the Cas9 molecule/gRNA molecule complex edits the genome of a cell to down-regulate a gene that inhibits hair growth. In an embodiment, a template nucleic acid is used to effect a Cas9 molecule/gRNA molecule complex alteration to the genome that down-regulates a gene that promotes hair growth.

In an embodiment, the Cas9 molecule/gRNA molecule and modifies expression of a gene, e.g., by modifying the structure of the gene (e.g., by editing the genome) or by delivery of a payload that modulates a gene. In an embodiment, the gene is a transcription factor or other regulatory gene.

In an embodiment, the method includes one or more or all of the following:

administering a Cas9 molecule/gRNA molecule complex that results in up-regulation one or more of the following: c-Myc, GATA3, Oct4, Sox2, Wnt, or TCF3;

administering a Cas9 molecule/gRNA molecule complex that results in turning on a maturation pathway. For hair cells this would include one or more of the following: Atoh1 (Math1). Barhl1, Gfi1, Myo7a, p63, PAX2, PAX8, or Pou4f3 and for neurons would include one or more of the following: NEFH, Neurod1, Neurog1, or POU4F1.

XVI. Governing gRNA Molecules and Their Use to Limit the Activity of a Cas9 System As discussed herein, methods and compositions that use, or include, a nucleic acid, e.g., DNA, that encodes a Cas9 molecule or a gRNA molecule, can, in addition, use or include a governing gRNA molecule. The governing gRNA molecule can complex with the Cas9 molecule to inactivate or silence a component of the system, e.g., the nucleic acid that encodes the Cas9 molecule or the nucleic acid that encodes the gRNA molecule. In either case, the governing gRNA, e.g., a Cas9-targeting gRNA molecule, or a gRNA targeting gRNA molecule, limits the effect of the Cas9/gRNA complex mediated gene targeting, and can place temporal limits on activity or reduce off-target activity. Governing gRNA molecules can act as to inhibit, e.g., entirely or substantially inhibit, the production of a component of the Cas9 system and thereby limit, or govern, its activity.

Typically a nucleic acid sequence encoding a governing gRNA molecule, e.g., a Cas9-targeting gRNA molecule, is under the control of a different control region, e.g., promoter, than is the component it negatively modulates, e.g., a nucleic acid encoding the Cas9 molecule. In an embodiment, different refers to simply not being under the control of one control region, e.g., promoter, that is functionally coupled to both controlled sequences. In an embodiment, different refers to different in kind or type. For example, the sequence encoding a governing gRNA molecule, e.g., a Cas9-targeting gRNA molecule, is under the control of a control region, e.g., a promoter, that has a lower level of expression, or is expressed later than the sequence which encodes the component it negatively modulates, e.g., a nucleic acid encoding the Cas9 molecule.

By way of example a sequence that encodes a governing gRNA molecule, e.g., a Cas9-targeting gRNA molecule, can be under the control of a control region (e.g., a promoter) described herein, e.g., humanU6 small nuclear promoter, or human H1 promoter. In an embodiment, a sequence that encodes the component it negatively regulates, e.g. a nucleic acid encoding the Cas9 molecule, can be under the control of a control region (e.g., a promoter) described herein, e.g., human U6 small nuclear promoter, human H1 promoter, or a PolII promoter, e.g., a CMV promoter, a CAGGS promoter, or a CB promoter.

EXAMPLES

The following Examples are merely illustrative and are not intended to limit the scope or content of the invention in any way.

Example 1: In Silico Design of Governing gRNA Sequences Targeting S. pyogenes and S. aureus Cas9

Governing guide RNAs (gRNAs) targeting S. pyogenes and S. aureus Cas9s were identified using a DNA sequence searching algorithm. In addition to identifying potential gRNA sites adjacent to PAM sequences, the software also identifies all PAM adjacent sequences that differ by 1, 2, 3 or more nucleotides from the selected gRNA sites in the human genome. Genomic DNA sequence for each Cas9 gene was obtained from the UCSC Genome browser and sequences were screened for repeat elements using the publically available RepeatMasker program. RepeatMasker searches input DNA sequences for repeated elements and regions of low complexity. The output is a detailed annotation of the repeats present in a given query sequence.

Following identification, governing gRNAs were ranked into tiers based on their cleavage position within the Cas9 coding sequence, their orthogonality and presence of a 5' G (based on identification of close matches in the human genome containing a PAM). Orthogonality refers to the number of sequences in the human genome that contain a minimum number of mismatches to the target sequence. A "high level of orthogonality" or "good orthogonality" may, for example, refer to 20-mer gRNAs that have no identical sequences in the human genome besides the intended target, nor any sequences that contain one or two mismatches in the target sequence. Targeting domains with good orthogonality are selected to minimize off-target DNA cleavage.

Tier 1 includes all gRNAs that target the first 500 nucleotides of coding sequence of Cas9, have good orthogonality, and begin with a 5' G. Tier 2 includes all gRNAs that target the first 500 nucleotides of coding sequence of Cas9, have good orthogonality, but don't begin with a 5' G. Tier 3 includes all gRNAs that target the first 500 nucleotides of coding sequence of Cas9, have poor orthogonality, and begin with a 5' G. Tier 4 includes all gRNAs that target the first 500 nucleotides of coding sequence of Cas9, have poor orthogonality, but don't begin with a 5' G. Tier 5 includes all gRNAs that target the remaining coding sequence. In the case of S. aureus, there is a $6^{th}$ tier that includes all gRNAs whose targets have a non-optimal PAM of NNGRRV.

For all S. pyogenes targets, 17-mer, or 20-mer gRNAs were designed. For all S. aureus targets, 20-mer gRNAs were designed. gRNAs were identified for both single-gRNA nuclease cleavage and for a dual-gRNA paired "nickase" strategy. The designed governing gRNAs are listed in Tables E-1 to E-12.

TABLE E-1

| Exemplary guide RNA pairs for S. pyogenes (SP) nickase | Group A | Group B | Group A guides can be paired with any from Group B. |

TABLE E-1-continued

| antiSPCas9-2, antiSPCas9-18 Group C | antiSPCas9-3, antiSPCas9-24 Group D | Group C guides can be paired | 5 |
|---|---|---|---|

| | | | | with any from Group D. |
|---|---|---|---|---|
| | antiSPCas9-7, antiSPCas9-70 | antiSPCas9-30, antiSPCas9-72 | | |

TABLE E-2

First 500 bp of coding sequence downstream of start codon, good orthogonality, starts with G

| S. pyogenes 1st Tier gRNA Name | DNA Strand | Targeting Domain | Target Site Length | SEQ ID NO |
|---|---|---|---|---|
| antiSPCas9-1 | − | GCCCUCCUAUUCGAUAG | 17 | 304 |
| antiSPCas9-2 | − | GCCUGAAACGAACCGCU | 17 | 305 |
| antiSPCas9-3 | + | GCCACUAUCGAAUAGGA | 17 | 306 |
| antiSPCas9-4 | − | GCACUAAUUCCGUUGGA | 17 | 307 |
| antiSPCas9-5 | − | GAACGGCACCCCAUCUU | 17 | 308 |
| antiSPCas9-6 | − | GGUGCCCUCCUAUUCGAUAG | 20 | 309 |
| antiSPCas9-7 | − | GCCCAUAUGAUAAAGUUCCG | 20 | 310 |
| antiSPCas9-8 | + | GCCCACGGAACUUUAUCAUA | 20 | 311 |

TABLE E-3

First 500 bp of coding sequence downstream of start codon, good orthogonality, does not start with G

| S. pyogenes 2nd Tier gRNA Name | DNA Strand | Targeting Domain | Target Site Length | SEQ ID NO |
|---|---|---|---|---|
| antiSPCas9-9 | + | UCCGAGCGGUUCGUUUC | 17 | 312 |
| antiSPCas9-10 | − | AACGAACCGCUCGGAGA | 17 | 313 |
| antiSPCas9-11 | + | CGCCACUAUCGAAUAGG | 17 | 314 |
| antiSPCas9-12 | − | AUCGGCACUAAUUCCGU | 17 | 315 |
| antiSPCas9-13 | + | UUUCGCCACUAUCGAAU | 17 | 316 |
| antiSPCas9-14 | − | AUUCGAUAGUGGCGAAA | 17 | 317 |
| antiSPCas9-15 | − | UAGUGGCGAAACGGCAG | 17 | 318 |
| antiSPCas9-16 | + | CCGUUUCGCCACUAUCGAAU | 20 | 319 |
| antiSPCas9-17 | − | GACAUCGGCACUAAUUCCGU | 20 | 320 |
| antiSPCas9-18 | − | CUCGCCUGAAACGAACCGCU | 20 | 321 |
| antiSPCas9-19 | + | UUCUCCGAGCGGUUCGUUUC | 20 | 322 |
| antiSPCas9-20 | − | UGAAACGAACCGCUCGGAGA | 20 | 323 |
| antiSPCas9-21 | + | UUUCGCCACUAUCGAAUAGG | 20 | 324 |
| antiSPCas9-22 | − | UCGGCACUAAUUCCGUUGGA | 20 | 325 |
| antiSPCas9-23 | − | CGAUAGUGGCGAAACGGCAG | 20 | 326 |
| antiSPCas9-24 | + | UUCGCCACUAUCGAAUAGGA | 20 | 327 |
| antiSPCas9-25 | + | ACGUGUAUACCUUCUCCGAG | 20 | 328 |
| antiSPCas9-26 | − | CGGCACUAAUUCCGUUGGAU | 20 | 329 |

TABLE E-3-continued

| S. pyogenes | First 500 bp of coding sequence downstream of start codon, good orthogonality, does not start with G | | | |
|---|---|---|---|---|
| 2nd Tier gRNA Name | DNA Strand | Targeting Domain | Target Site Length | SEQ ID NO |
| antiSPCas9-27 | − | CCUAUUCGAUAGUGGCGAAA | 20 | 330 |
| antiSPCas9-28 | − | CCCAUAUGAUAAAGUUCCGU | 20 | 331 |

TABLE E-4

| S. pyogenes | First 500 bp of coding sequence downstream of start codon, poor orthogonality, starts with G | | | |
|---|---|---|---|---|
| 3rd Tier gRNA Name | DNA Strand | Targeting Domain | Target Site Length | SEQ ID NO |
| antiSPCas9-29 | + | GAAAGAAUCGUCAACUU | 17 | 332 |
| antiSPCas9-30 | + | GAGCCAAGUAGAUUAACCUC | 20 | 333 |
| antiSPCas9-31 | − | GAUAAAAGUAUUCUAU | 17 | 334 |
| antiSPCas9-32 | + | GAUUCUUUUUAAUCGAAUGA | 20 | 335 |
| antiSPCas9-33 | + | GGAAGGACUCUUCCAAA | 17 | 336 |
| antiSPCas9-34 | − | GGACCUGAGGUUAAUCUACU | 20 | 337 |
| antiSPCas9-35 | − | GGGCACUUUCUCAUUGA | 17 | 338 |
| antiSPCas9-36 | + | GGUUAUGACAGCCCAUCCAA | 20 | 339 |
| antiSPCas9-37 | + | GUCCUCUUCGACAAGGA | 17 | 340 |
| antiSPCas9-38 | − | GUCCUUCCUUGUCGAAG | 17 | 341 |
| antiSPCas9-39 | + | GUUUCUUGUCCUCUUCGACA | 20 | 342 |

TABLE E-5

| S. pyogenes | First 500 bp of coding sequence downstream of start codon, poor orthogonality, does not start with G | | | |
|---|---|---|---|---|
| 4th Tier gRNA Name | DNA Strand | Targeting Domain | Target Site Length | SEQ ID NO |
| antiSPCas9-40 | − | AAACAUAGUAGAUGAGG | 17 | 343 |
| antiSPCas9-41 | + | AAAGAAAGAAUCGUCAACUU | 20 | 344 |
| antiSPCas9-42 | − | AAAGAAAUUUAAGGUGU | 17 | 345 |
| antiSPCas9-43 | + | AACACCUUAAAUUUCUUUGA | 20 | 346 |
| antiSPCas9-44 | − | AAGAAAUUUAAGGUGUU | 17 | 347 |
| antiSPCas9-45 | − | AAGAGGACAAGAAACAUGAA | 20 | 348 |
| antiSPCas9-46 | − | AAUUUUUAGCAAUGAGA | 17 | 349 |
| antiSPCas9-47 | + | ACCUUAAAUUUCUUUGA | 17 | 350 |
| antiSPCas9-48 | − | ACCUUCAAAGAAAUUUA | 17 | 351 |
| antiSPCas9-49 | + | ACGGAACUUUAUCAUAU | 17 | 352 |
| antiSPCas9-50 | + | ACUAUGUUUCCAAAGAU | 17 | 353 |
| antiSPCas9-51 | − | AGAAAUUUAAGGUGUUG | 17 | 354 |

TABLE E-5-continued

| S. pyogenes | First 500 bp of coding sequence downstream of start codon, poor orthogonality, does not start with G | | | |
|---|---|---|---|---|
| 4th Tier gRNA Name | DNA Strand | Targeting Domain | Target Site Length | SEQ ID NO |
| antiSPCas9-52 | − | AGAAAUUUUUAGCAAUGAGA | 20 | 355 |
| antiSPCas9-53 | − | AGAGUCCUUCCUUGUCGAAG | 20 | 356 |
| antiSPCas9-54 | − | AGGACAAGAAACAUGAA | 17 | 357 |
| antiSPCas9-55 | + | AGGUACUUUGUAUUCAU | 17 | 358 |
| antiSPCas9-56 | − | AGUACCUUCAAAGAAAUUUA | 20 | 359 |
| antiSPCas9-57 | + | AGUCAACUAGCUUUUUUCUG | 20 | 360 |
| antiSPCas9-58 | − | AGUUGACUCAACUGAUAAAG | 20 | 361 |
| antiSPCas9-59 | − | AUAUGAUAAAGUUCCGU | 17 | 362 |
| antiSPCas9-60 | + | AUCUACUAUGUUUCCAAAGA | 20 | 363 |
| antiSPCas9-61 | − | AUGGAUAAAAGUAUUCUAU | 20 | 364 |
| antiSPCas9-62 | − | AUUAAAAAGAAUCUUAU | 17 | 365 |
| antiSPCas9-63 | − | CAAAGAAAUUUAAGGUGUUG | 20 | 366 |
| antiSPCas9-64 | + | CAACUAGCUUUUUUCUG | 17 | 367 |
| antiSPCas9-65 | − | CAACUGAUAAAGCGGACCUG | 20 | 368 |
| antiSPCas9-66 | + | CAAGGAAGGACUCUUCCAAA | 20 | 369 |
| antiSPCas9-67 | + | CAAUGAGAAAGUGCCCA | 17 | 370 |
| antiSPCas9-68 | + | CACGGAACUUUAUCAUA | 17 | 371 |
| antiSPCas9-69 | − | CACUAAUUCCGUUGGAU | 17 | 372 |
| antiSPCas9-70 | − | CAUAUGAUAAAGUUCCG | 17 | 373 |
| antiSPCas9-71 | − | CAUGAACGGCACCCCAUCUU | 20 | 374 |
| antiSPCas9-72 | + | CCAAGUAGAUUAACCUC | 17 | 375 |
| antiSPCas9-73 | + | CCCACGGAACUUUAUCAUAU | 20 | 376 |
| antiSPCas9-74 | − | CCGUGGGCACUUUCUCAUUG | 20 | 377 |
| antiSPCas9-75 | + | CCUCAAUGAGAAAGUGCCCA | 20 | 378 |
| antiSPCas9-76 | − | CCUGAGGUUAAUCUACU | 17 | 379 |
| antiSPCas9-77 | − | CGAUUCUUUCUUUCACCGUU | 20 | 380 |
| antiSPCas9-78 | − | CGUGGGCACUUUCUCAUUGA | 20 | 381 |
| antiSPCas9-79 | + | CUACUAUGUUUCCAAAGAUG | 20 | 382 |
| antiSPCas9-80 | + | CUAUGUUUCCAAAGAUG | 17 | 383 |
| antiSPCas9-81 | + | CUGAGGUGAUAAAUCGU | 17 | 384 |
| antiSPCas9-82 | − | CUGAUAAAGCGGACCUG | 17 | 385 |
| antiSPCas9-83 | + | CUUGUAAGUAACAUAUU | 17 | 386 |
| antiSPCas9-84 | + | CUUGUCCUCUUCGACAAGGA | 20 | 387 |
| antiSPCas9-85 | − | CUUUGGAAACAUAGUAGAUG | 20 | 388 |
| antiSPCas9-86 | + | UACUAUGUUUCCAAAGA | 17 | 389 |
| antiSPCas9-87 | + | UAUGACAGCCCAUCCAA | 17 | 390 |
| antiSPCas9-88 | − | UAUUCUAUUGGUUUAGACAU | 20 | 391 |

TABLE E-5-continued

First 500 bp of coding sequence downstream of start codon, poor orthogonality, does not start with G

| S. pyogenes 4th Tier gRNA Name | DNA Strand | Targeting Domain | Target Site Length | SEQ ID NO |
|---|---|---|---|---|
| antiSPCas9-89 | − | UCAAAGAAAUUUAAGGUGUUU | 20 | 392 |
| antiSPCas9-90 | − | UCGAUUAAAAAGAAUCUUAU | 20 | 393 |
| antiSPCas9-91 | + | UCUACUAUGUUUCCAAAGAU | 20 | 394 |
| antiSPCas9-92 | − | UCUAUUGGUUUAGACAU | 17 | 395 |
| antiSPCas9-93 | + | UCUUGUCCUCUUCGACA | 17 | 396 |
| antiSPCas9-94 | + | UCUUUUUAAUCGAAUGA | 17 | 397 |
| antiSPCas9-95 | + | UGAAGGUACUUUGUAUUCAU | 20 | 398 |
| antiSPCas9-96 | − | UGACUCAACUGAUAAAG | 17 | 399 |
| antiSPCas9-97 | + | UGAGGUGAUAAAUCGUU | 17 | 400 |
| antiSPCas9-98 | − | UGGAAACAUAGUAGAUG | 17 | 401 |
| antiSPCas9-99 | − | UGGAAACAUAGUAGAUGAGG | 20 | 402 |
| antiSPCas9-100 | − | UGGGCACUUUCUCAUUG | 17 | 403 |
| antiSPCas9-101 | + | UGUAUACCUUCUCCGAG | 17 | 404 |
| antiSPCas9-102 | − | UUCAAAGAAAUUUAAGGUGU | 20 | 405 |
| antiSPCas9-103 | + | UUCUGAGGUGAUAAAUCGUU | 20 | 406 |
| antiSPCas9-104 | − | UUCUUUCUUUCACCGUU | 17 | 407 |
| antiSPCas9-105 | + | UUUCUGAGGUGAUAAAUCGU | 20 | 408 |
| antiSPCas9-106 | + | UUUCUUGUAAGUAACAUAUU | 20 | 409 |

TABLE E-6

Rest of gene

| 5th Tier gRNA Name | DNA Strand | Targeting Domain | Target Site Length | SEQ ID NO |
|---|---|---|---|---|
| antiSPCas9-107 | − | GCGUCGCUAUACGGGCU | 17 | 410 |
| antiSPCas9-108 | − | GGCGUCGCUAUACGGGC | 17 | 411 |
| antiSPCas9-109 | − | UCGAAAAACGGGUACGC | 17 | 412 |
| antiSPCas9-110 | − | CGCUCGGAUAAGAACCG | 17 | 413 |
| antiSPCas9-111 | − | CGUCGCUAUACGGGCUG | 17 | 414 |
| antiSPCas9-112 | + | GAUAAGCGUCGUGCGCA | 17 | 415 |
| antiSPCas9-113 | + | CGGGUAAUUGUGCGAUC | 17 | 416 |
| antiSPCas9-114 | − | GAUCGCGAAAAGCGAAC | 17 | 417 |
| antiSPCas9-115 | − | GCGACGGCUUCGCCAAU | 17 | 418 |
| antiSPCas9-116 | + | UAACCUUAUCGUCGAAC | 17 | 419 |
| antiSPCas9-117 | + | AGCGGAUAACGGCGCCU | 17 | 420 |
| antiSPCas9-118 | − | AAGAGGCGUCGCUAUAC | 17 | 421 |
| antiSPCas9-119 | + | AAGCGUCGUGCGCAUGG | 17 | 422 |

TABLE E-6-continued

| 5th Tier gRNA Name | DNA Strand | Targeting Domain | Target Site Length | SEQ ID NO |
|---|---|---|---|---|
| antiSPCas9-120 | - | CGGAUGUUGGCUAGCGC | 17 | 423 |
| antiSPCas9-121 | - | CGAUCUCGACAAUCUAC | 17 | 424 |
| antiSPCas9-122 | + | UCGACAUCCGAGUUGUC | 17 | 425 |
| antiSPCas9-123 | + | GAGUGCGGUCCCUACGA | 17 | 426 |
| antiSPCas9-124 | - | CGCGGAAACUUAUCAAC | 17 | 427 |
| antiSPCas9-125 | - | AUCUUAAUGCCGUCGUA | 17 | 428 |
| antiSPCas9-126 | - | CUCAAUCGUUCAUCGAG | 17 | 429 |
| antiSPCas9-127 | + | UCCGCCUGCUCACGUAU | 17 | 430 |
| antiSPCas9-128 | - | UCACCUGUUCGACGAUA | 17 | 431 |
| antiSPCas9-129 | - | GCUCAUCGCUCGUAAAA | 17 | 432 |
| antiSPCas9-130 | - | GCUCGGAUAAGAACCGA | 17 | 433 |
| antiSPCas9-131 | - | UAUCUUAAUGCCGUCGU | 17 | 434 |
| antiSPCas9-132 | - | CGGCGGAGCGAGUCAAG | 17 | 435 |
| antiSPCas9-133 | - | UCGCGGAAACUUAUCAA | 17 | 436 |
| antiSPCas9-134 | - | CGAUUUAAUGCGUCACU | 17 | 437 |
| antiSPCas9-135 | - | UCGCUCGUAAAAGGAC | 17 | 438 |
| antiSPCas9-136 | - | GACCCGAAAAGUACGG | 17 | 439 |
| antiSPCas9-137 | + | GCCGUCGGGAUUUAGAG | 17 | 440 |
| antiSPCas9-138 | - | AAAGAGGCGUCGCUAUA | 17 | 441 |
| antiSPCas9-139 | - | CGCAUACCUUACUAUGU | 17 | 442 |
| antiSPCas9-140 | + | CGAACCGAGAGUUCCCU | 17 | 443 |
| antiSPCas9-141 | - | GGAACUCUCGGUUCGCA | 17 | 444 |
| antiSPCas9-142 | - | UGGCCGAAAACGGAUGU | 17 | 445 |
| antiSPCas9-143 | + | CGCGUCUAGCACCUCCU | 17 | 446 |
| antiSPCas9-144 | + | UCACCGUCGCGAAGUCC | 17 | 447 |
| antiSPCas9-145 | - | UAUUAAACGUCAGCUCG | 17 | 448 |
| antiSPCas9-146 | - | CGCUCGUAAAAGGACU | 17 | 449 |
| antiSPCas9-147 | + | UUCCGCCUGCUCACGUA | 17 | 450 |
| antiSPCas9-148 | + | CUAGUGAGAGCGCUAUA | 17 | 451 |
| antiSPCas9-149 | + | CGUCGUAAUCAGAUAAA | 17 | 452 |
| antiSPCas9-150 | - | CUGAUCGCACAAUUACC | 17 | 453 |
| antiSPCas9-151 | - | UCGCAUACCUUACUAUG | 17 | 454 |
| antiSPCas9-152 | - | CGCCGGAGAGCUUCAAA | 17 | 455 |
| antiSPCas9-153 | - | GCUGGGGACGAUUGUCG | 17 | 456 |
| antiSPCas9-154 | + | CGCCUCAAGGAAGUCGA | 17 | 457 |
| antiSPCas9-155 | - | CUUAUAGCGCUCUCACU | 17 | 458 |
| antiSPCas9-156 | - | UUCUGUCGAGAUCUCCG | 17 | 459 |
| antiSPCas9-157 | - | CAUAUUGCGAAUCUUGC | 17 | 460 |

TABLE E-6-continued

Rest of gene

| 5th Tier gRNA Name | DNA Strand | Targeting Domain | Target Site Length | SEQ ID NO |
|---|---|---|---|---|
| antiSPCas9-158 | − | GGGCCGGGACUUCGCGA | 17 | 461 |
| antiSPCas9-159 | − | UAAACCCAUACGUGAGC | 17 | 462 |
| antiSPCas9-160 | + | UUUACGACUUCCUCGCU | 17 | 463 |
| antiSPCas9-161 | − | GCGCAUACAACAAGCAC | 17 | 464 |
| antiSPCas9-162 | − | GCAGGUUAUAUUGACGG | 17 | 465 |
| antiSPCas9-163 | + | UUUUCGCGAUCAUCUUA | 17 | 466 |
| antiSPCas9-164 | − | UCGUAUGGGAUAAGGGC | 17 | 467 |
| antiSPCas9-165 | + | AUAAUCCCGUGAUGGAU | 17 | 468 |
| antiSPCas9-166 | − | ACGAUACACUUCUACCA | 17 | 469 |
| antiSPCas9-167 | + | CAGUUGCUGACGGACUA | 17 | 470 |
| antiSPCas9-168 | − | GAACGAUAAGCUGAUUC | 17 | 471 |
| antiSPCas9-169 | − | UCUAAAUCCGGACAACU | 17 | 472 |
| antiSPCas9-170 | − | CAGCGGACUUUCGACAA | 17 | 473 |
| antiSPCas9-171 | − | CAUGGGACGUCACAAAC | 17 | 474 |
| antiSPCas9-172 | + | CAGGUUUUCUAGCCGUC | 17 | 475 |
| antiSPCas9-173 | − | CCGCUUCAAUGAUCAAA | 17 | 476 |
| antiSPCas9-174 | + | UAGCCAACAUCCGUUUU | 17 | 477 |
| antiSPCas9-175 | + | GGAGGAUUGCAUCGCUA | 17 | 478 |
| antiSPCas9-176 | + | CAUGCAAUUCGCCUAAG | 17 | 479 |
| antiSPCas9-177 | − | AAGUGGCGUGGAUGCGA | 17 | 480 |
| antiSPCas9-178 | − | CGUAUGGGAUAAGGGCC | 17 | 481 |
| antiSPCas9-179 | − | GACAGGUGAAAUCGUAU | 17 | 482 |
| antiSPCas9-180 | + | GAACCGAGAGUUCCCUC | 17 | 483 |
| antiSPCas9-181 | + | AAAUCGAUCUUCUACCC | 17 | 484 |
| antiSPCas9-182 | + | AAUGGGACGCUAAAUAC | 17 | 485 |
| antiSPCas9-183 | − | UAAAGUGCUUACACGCU | 17 | 486 |
| antiSPCas9-184 | − | UACGCAGGUUAUAUUGA | 17 | 487 |
| antiSPCas9-185 | − | AUUCUGUCGAGAUCUCC | 17 | 488 |
| antiSPCas9-186 | − | GAUUCUGUCGAGAUCUC | 17 | 489 |
| antiSPCas9-187 | − | GCCUCUCUAAAUCCCGA | 17 | 490 |
| antiSPCas9-188 | + | UGCAUCGCUAAGGUUUU | 17 | 491 |
| antiSPCas9-189 | + | GCAGUUGCUGACGGACU | 17 | 492 |
| antiSPCas9-190 | − | CGGGAUUAUAUGAAACU | 17 | 493 |
| antiSPCas9-191 | − | ACCCAUACGUGAGCAGG | 17 | 494 |
| antiSPCas9-192 | + | AGGGGUCCCACAUAGUA | 17 | 495 |
| antiSPCas9-193 | + | AGCCACCGUACUUUUUC | 17 | 496 |
| antiSPCas9-194 | − | AUUGGGGAUAACGAUUA | 17 | 497 |

TABLE E-6-continued

Rest of gene

| 5th Tier gRNA Name | DNA Strand | Targeting Domain | Target Site Length | SEQ ID NO |
|---|---|---|---|---|
| antiSPCas9-195 | - | UGACAAUGUUCCAAGCG | 17 | 498 |
| antiSPCas9-196 | - | GGUGUCGGACUUCAGAA | 17 | 499 |
| antiSPCas9-197 | + | UCUCCGCUUAGAAAGGC | 17 | 500 |
| antiSPCas9-198 | + | UGUAACCUUUCGCCUCA | 17 | 501 |
| antiSPCas9-199 | - | ACAGGUUUCCGGACAAG | 17 | 502 |
| antiSPCas9-200 | - | UGGGACCCGAAAAAGUA | 17 | 503 |
| antiSPCas9-201 | + | UUCAUAUAAUCCCGUGA | 17 | 504 |
| antiSPCas9-202 | - | CACAGGUUUCCGGACAA | 17 | 505 |
| antiSPCas9-203 | + | AUAGUAAGGUAUGCGAA | 17 | 506 |
| antiSPCas9-204 | + | AACUGUCACUUUGCGGU | 17 | 507 |
| antiSPCas9-205 | - | UUACUAUGUGGGACCCC | 17 | 508 |
| antiSPCas9-206 | + | AUGCGGCUGGAGCGCCG | 17 | 509 |
| antiSPCas9-207 | - | UAAGACGGAAAUCACUC | 17 | 510 |
| antiSPCas9-208 | + | CGCCACUUGCAUUUAUA | 17 | 511 |
| antiSPCas9-209 | - | CCCCAUCGACUUCCUUG | 17 | 512 |
| antiSPCas9-210 | + | GCCUCAAGGAAGUCGAU | 17 | 513 |
| antiSPCas9-211 | - | UUGAUCAGUCGAAAAAC | 17 | 514 |
| antiSPCas9-212 | + | UCGGGAUUUAGAGAGGC | 17 | 515 |
| antiSPCas9-213 | + | CAAUGAGUCCCCUUGUC | 17 | 516 |
| antiSPCas9-214 | + | UCAGGUUUUCUAGCCGU | 17 | 517 |
| antiSPCas9-215 | - | GACCGGAGGGUUUUCAA | 17 | 518 |
| antiSPCas9-216 | + | AAGCCACCGUACUUUUU | 17 | 519 |
| antiSPCas9-217 | + | CUGUUCUCCGCUUAGAA | 17 | 520 |
| antiSPCas9-218 | + | AUCAUUGAAGCGGAUAA | 17 | 521 |
| antiSPCas9-219 | - | UUCGCCAGCCAUCAAAA | 17 | 522 |
| antiSPCas9-220 | - | GCCGGAGAGCUUCAAAA | 17 | 523 |
| antiSPCas9-221 | - | AGAACGAUAAGCUGAUU | 17 | 524 |
| antiSPCas9-222 | - | GCACAGGUUUCCGGACA | 17 | 525 |
| antiSPCas9-223 | - | UCGCCAGCCAUCAAAAA | 17 | 526 |
| antiSPCas9-224 | + | AAGGUAUGCGAAAGGUU | 17 | 527 |
| antiSPCas9-225 | + | GGCAAUACUUUUUCGUU | 17 | 528 |
| antiSPCas9-226 | - | GAGGAAGUUGUCGAUAA | 17 | 529 |
| antiSPCas9-227 | + | CUGACGUUUAAUAAAUC | 17 | 530 |
| antiSPCas9-228 | - | AAACCCGCCUUUCUAAG | 17 | 531 |
| antiSPCas9-229 | - | UAUAAAUGCAAGUGGCG | 17 | 532 |
| antiSPCas9-230 | + | CCACUACUUUGACUGUC | 17 | 533 |
| antiSPCas9-231 | + | GAGAGUUCCCUCGGGCC | 17 | 534 |
| antiSPCas9-232 | + | UAUAGGUUUGUACUAAC | 17 | 535 |

TABLE E-6-continued

| 5th Tier gRNA Name | DNA Strand | Targeting Domain | Target Site Length | SEQ ID NO |
|---|---|---|---|---|
| antiSPCas9-233 | − | CAUUACGAGAAGUUGAA | 17 | 536 |
| antiSPCas9-234 | − | GUAUGUUGAUCAGGAAC | 17 | 537 |
| antiSPCas9-235 | + | CGUAUUUCGUAUUCAUU | 17 | 538 |
| antiSPCas9-236 | − | UGAGGGUGAUCUAAAUC | 17 | 539 |
| antiSPCas9-237 | + | CCUCAAGGAAGUCGAUG | 17 | 540 |
| antiSPCas9-238 | − | GAAAUCGUAUGGGAUAA | 17 | 541 |
| antiSPCas9-239 | + | UGGAGUAAUCGUUUCUU | 17 | 542 |
| antiSPCas9-240 | − | UGCUAUACUUAGAAGGC | 17 | 543 |
| antiSPCas9-241 | − | CCGGAGAGCUUCAAAAG | 17 | 544 |
| antiSPCas9-242 | − | AGACAGGUGAAAUCGUA | 17 | 545 |
| antiSPCas9-243 | − | GAGCUAGUUAAGGUCAU | 17 | 546 |
| antiSPCas9-244 | + | GAGUUCCCUCGGGCCAG | 17 | 547 |
| antiSPCas9-245 | + | CUUUCAACUUCUCGUAA | 17 | 548 |
| antiSPCas9-246 | + | AGAGUUCCCUCGGGCCA | 17 | 549 |
| antiSPCas9-247 | − | AGAUCGGGAAAUGAUUG | 17 | 550 |
| antiSPCas9-248 | − | UGAGGCGAAAGGUUACA | 17 | 551 |
| antiSPCas9-249 | − | UGGCCCGAGGGAACUCU | 17 | 552 |
| antiSPCas9-250 | + | GUUUCUCGUUCUGCAAU | 17 | 553 |
| antiSPCas9-251 | + | ACGCCACUUGCAUUUAU | 17 | 554 |
| antiSPCas9-252 | + | CACUACUAGGACAGAAU | 17 | 555 |
| antiSPCas9-253 | − | AUCUACUGCGAAAGCAG | 17 | 556 |
| antiSPCas9-254 | + | GUCGGGAUUUAGAGAGG | 17 | 557 |
| antiSPCas9-255 | − | CCUAGCUGAUGCCAAUC | 17 | 558 |
| antiSPCas9-256 | + | UUCUCCGCUUAGAAAGG | 17 | 559 |
| antiSPCas9-257 | − | ACUGAGGUGCAGACCGG | 17 | 560 |
| antiSPCas9-258 | − | UGCAUGCUAUACUUAGA | 17 | 561 |
| antiSPCas9-259 | − | CUGAGGUGCAGACCGGA | 17 | 562 |
| antiSPCas9-260 | + | AUGCCCUUUUGAUGGC | 17 | 563 |
| antiSPCas9-261 | − | AUUCACCAAUCCAUCAC | 17 | 564 |
| antiSPCas9-262 | − | UGGGACCCCUGGCCCGA | 17 | 565 |
| antiSPCas9-263 | + | UUUCAACUUCUCGUAAU | 17 | 566 |
| antiSPCas9-264 | + | GUAUUUCGUAUUCAUUC | 17 | 567 |
| antiSPCas9-265 | − | AGUGGAUGAGCUAGUUA | 17 | 568 |
| antiSPCas9-266 | + | GAGUAUGCCCUUUUUGA | 17 | 569 |
| antiSPCas9-267 | − | AUCAAACGACUCAGAAG | 17 | 570 |
| antiSPCas9-268 | + | CAUUCUCUUCGUUAUCC | 17 | 571 |
| antiSPCas9-269 | − | AUACACUUCUACCAAGG | 17 | 572 |

TABLE E-6-continued

Rest of gene

| 5th Tier gRNA Name | DNA Strand | Targeting Domain | Target Site Length | SEQ ID NO |
|---|---|---|---|---|
| antiSPCas9-270 | − | GACUUCCUUGAGGCGAA | 17 | 573 |
| antiSPCas9-271 | − | ACCCCAAUCCUUUUUGA | 17 | 574 |
| antiSPCas9-272 | + | UGAAUCGUCCUUCAAAA | 17 | 575 |
| antiSPCas9-273 | − | UACCCUCUUUGAAGAUC | 17 | 576 |
| antiSPCas9-274 | − | UCUGAACUUGACAAGGC | 17 | 577 |
| antiSPCas9-275 | + | CGAUUGUCUUUGAGGAA | 17 | 578 |
| antiSPCas9-276 | − | GGACAUGUAUGUUGAUC | 17 | 579 |
| antiSPCas9-277 | − | CGCAUACAACAAGCACA | 17 | 580 |
| antiSPCas9-278 | + | UCGAUUACAAUGUUUUC | 17 | 581 |
| antiSPCas9-279 | + | CGUCCUUCAAAAAGGAU | 17 | 582 |
| antiSPCas9-280 | + | CUUACUAAGCUGCAAUU | 17 | 583 |
| antiSPCas9-281 | − | AAGAAACGAUUACUCCA | 17 | 584 |
| antiSPCas9-282 | + | CAACUUUUGCCACUACU | 17 | 585 |
| antiSPCas9-283 | − | CUAUUCUGUCCUAGUAG | 17 | 586 |
| antiSPCas9-284 | + | CUGCAUAAAGUUCCUAU | 17 | 587 |
| antiSPCas9-285 | − | GUGGGACCCCUGGCCCG | 17 | 588 |
| antiSPCas9-286 | − | GUAUGCGGACUUAUUUU | 17 | 589 |
| antiSPCas9-287 | + | CCUAAGUGGAUUUGAUG | 17 | 590 |
| antiSPCas9-288 | − | GAUUUCUAAAGAGCGA | 17 | 591 |
| antiSPCas9-289 | − | GGGCAGCCAGAUCUUAA | 17 | 592 |
| antiSPCas9-290 | − | CAAAUUGCAGCUUAGUA | 17 | 593 |
| antiSPCas9-291 | − | UGAAAUCGUAUGGGAUA | 17 | 594 |
| antiSPCas9-292 | − | UUUACUCUUACCAACCU | 17 | 595 |
| antiSPCas9-293 | + | GAUGCUCCUUUAAGAUC | 17 | 596 |
| antiSPCas9-294 | + | CUCUCAGUAUGUCAGAU | 17 | 597 |
| antiSPCas9-295 | + | AAAUACUUGAAUGCGGC | 17 | 598 |
| antiSPCas9-296 | − | ACUUAACUAAAGCUGAG | 17 | 599 |
| antiSPCas9-297 | − | CGAACAGGAGAUAGGCA | 17 | 600 |
| antiSPCas9-298 | − | GAUUCACCAAUCCAUCA | 17 | 601 |
| antiSPCas9-299 | − | UUUGAUCAGUCGAAAAA | 17 | 602 |
| antiSPCas9-300 | − | CUUAAAGGAGCAUCCUG | 17 | 603 |
| antiSPCas9-301 | + | CCUUUUGAUCAUUGAAG | 17 | 604 |
| antiSPCas9-302 | − | UGAGCUAGUUAAGGUCA | 17 | 605 |
| antiSPCas9-303 | − | AAACAUUGUAAUCGAGA | 17 | 606 |
| antiSPCas9-304 | + | CCAGAUUGGCAUCAGCU | 17 | 607 |
| antiSPCas9-305 | + | AAUUGGGUAUUUUCCAC | 17 | 608 |
| antiSPCas9-306 | + | UCAAACAGACUAUACUU | 17 | 609 |
| antiSPCas9-307 | − | CCACAUCAAAUCCACUU | 17 | 610 |

TABLE E-6-continued

| 5th Tier gRNA Name | DNA Strand | Targeting Domain | Target Site Length | SEQ ID NO |
|---|---|---|---|---|
| antiSPCas9-308 | − | GGAUAUACAAAAGGCAC | 17 | 611 |
| antiSPCas9-309 | − | AAUCUACUGGCACAAAU | 17 | 612 |
| antiSPCas9-310 | + | UCAGUAUGUCAGAUAGG | 17 | 613 |
| antiSPCas9-311 | − | AGUUAAGUAUGUCACUG | 17 | 614 |
| antiSPCas9-312 | + | AAGUUCGACUUAAAAUU | 17 | 615 |
| antiSPCas9-313 | + | UUCUGUUCGUUAUCUUC | 17 | 616 |
| antiSPCas9-314 | − | GAGGGUAUUAAAGAACU | 17 | 617 |
| antiSPCas9-315 | − | GUUAAGUAUGUCACUGA | 17 | 618 |
| antiSPCas9-316 | + | GCUUAACUGUCACUUUG | 17 | 619 |
| antiSPCas9-317 | − | AGAUUUGUCACAGCUUG | 17 | 620 |
| antiSPCas9-318 | − | AGACUUGACACUUCUCA | 17 | 621 |
| antiSPCas9-319 | − | CCAGACAGUCAAAGUAG | 17 | 622 |
| antiSPCas9-320 | + | CCCCUUUUGAAGCUCUC | 17 | 623 |
| antiSPCas9-321 | + | UUAUCAGUUUCGCAUUU | 17 | 624 |
| antiSPCas9-322 | − | AAAUCAAACGACUCAGA | 17 | 625 |
| antiSPCas9-323 | − | AAUCGAUUCUUCCAAAA | 17 | 626 |
| antiSPCas9-324 | + | UUCCCGAUCUUCAAAGA | 17 | 627 |
| antiSPCas9-325 | − | GUCAGUCAAAGAAUUAU | 17 | 628 |
| antiSPCas9-326 | − | GAUUUGUCACAGCUUGG | 17 | 629 |
| antiSPCas9-327 | − | GAAACCAAUGGGGAGAC | 17 | 630 |
| antiSPCas9-328 | + | AGGUUAAAGAGUCAUCA | 17 | 631 |
| antiSPCas9-329 | − | AGAGGGUAUUAAAGAAC | 17 | 632 |
| antiSPCas9-330 | + | ACAGAAUAGGCAACUGU | 17 | 633 |
| antiSPCas9-331 | + | UUUCACGAUUGUCUUUG | 17 | 634 |
| antiSPCas9-332 | + | GUCCUUCAAAAAGGAUU | 17 | 635 |
| antiSPCas9-333 | + | AUGCUUUGUGAUUUGGC | 17 | 636 |
| antiSPCas9-334 | + | UGAGAAGUGUCAAGUCU | 17 | 637 |
| antiSPCas9-335 | − | UAAAGAUAAGGACUUCC | 17 | 638 |
| antiSPCas9-336 | + | UUUCUCGUUCUGCAAUU | 17 | 639 |
| antiSPCas9-337 | + | CCAUUGGUUUCAAUUAA | 17 | 640 |
| antiSPCas9-338 | + | AUCCAUCUUCUCUAAUA | 17 | 641 |
| antiSPCas9-339 | − | UAAUACUGAGAUUACCA | 17 | 642 |
| antiSPCas9-340 | + | UUCACCUGUCUCCCCAU | 17 | 643 |
| antiSPCas9-341 | − | AUAGAUUUGUCACAGCU | 17 | 644 |
| antiSPCas9-342 | − | CUUGUCUGAACUUGACA | 17 | 645 |
| antiSPCas9-343 | − | CUUAACUAAAGCUGAGA | 17 | 646 |
| antiSPCas9-344 | − | CAGUCAAAGAAUUAUUG | 17 | 647 |

TABLE E-6-continued

| 5th Tier gRNA Name | Rest of gene | | | |
|---|---|---|---|---|
| | DNA Strand | Targeting Domain | Target Site Length | SEQ ID NO |
| antiSPCas9-345 | + | AAAUUCACGUAUUUAGA | 17 | 648 |
| antiSPCas9-346 | - | UAGAUUUGUCACAGCUU | 17 | 649 |
| antiSPCas9-347 | + | UAAUACUUUGUCCAGAU | 17 | 650 |
| antiSPCas9-348 | + | ACUCACUUUCUAGCUUC | 17 | 651 |
| antiSPCas9-349 | - | CCUUUAAUUGAAACCAA | 17 | 652 |
| antiSPCas9-350 | - | UACUCCAUGGAAUUUUG | 17 | 653 |
| antiSPCas9-351 | + | GUCAAAAUACUUGAAUG | 17 | 654 |
| antiSPCas9-352 | + | ACUUAAAAUUUGGUGUC | 17 | 655 |
| antiSPCas9-353 | - | CUCUAUUACCUACAAAA | 17 | 656 |
| antiSPCas9-354 | - | CUCUUUAACCUUCAAAG | 17 | 657 |
| antiSPCas9-355 | + | CUUUACUAUGUUGACUU | 17 | 658 |
| antiSPCas9-356 | + | CAACAUGCUUUGUGAUU | 17 | 659 |
| antiSPCas9-357 | - | AAUUGGAGAUCAGUAUG | 17 | 660 |
| antiSPCas9-358 | + | CAUUUUGUAGGUAAUAG | 17 | 661 |
| antiSPCas9-359 | + | GACUGACUUCAGUUUCU | 17 | 662 |
| antiSPCas9-360 | - | ACUAAAGCUGAGAGGGG | 17 | 663 |
| antiSPCas9-361 | - | AAAAGCGAACAGGAGAU | 17 | 664 |
| antiSPCas9-362 | - | AACCCUAUAAAUGCAAG | 17 | 665 |
| antiSPCas9-363 | - | ACCCAUAUUAGAGAAGA | 17 | 666 |
| antiSPCas9-364 | + | GUAUUUCUUAAUGAGUG | 17 | 667 |
| antiSPCas9-365 | + | UAUGUUGACUUGGGGCA | 17 | 668 |
| antiSPCas9-366 | - | CAAAAGGCACAGGUUUC | 17 | 669 |
| antiSPCas9-367 | + | UUUCCCGAUCUUCAAAG | 17 | 670 |
| antiSPCas9-368 | - | UUACCCUCUUUGAAGAU | 17 | 671 |
| antiSPCas9-369 | - | UAUUAGAGAAGAUGGAU | 17 | 672 |
| antiSPCas9-370 | - | UUAACUAAAGCUGAGAG | 17 | 673 |
| antiSPCas9-371 | - | AGUUAAGCAAUUGAAAG | 17 | 674 |
| antiSPCas9-372 | - | AAAGUCAAAAUUGGUGU | 17 | 675 |
| antiSPCas9-373 | + | UUCAAACAACUGAUUAU | 17 | 676 |
| antiSPCas9-374 | - | GUGGCAAAAGUUGAGAA | 17 | 677 |
| antiSPCas9-375 | + | UAAAGUAAACUGUGCUU | 17 | 678 |
| antiSPCas9-376 | + | CAUUGUCACUUUUCCCU | 17 | 679 |
| antiSPCas9-377 | + | UUCCUUUGAAAACCCUC | 17 | 680 |
| antiSPCas9-378 | + | AACUCACUUUCUAGCUU | 17 | 681 |
| antiSPCas9-379 | - | ACUGCCUGAGAAAUAUA | 17 | 682 |
| antiSPCas9-380 | + | CAUGCUUUGUGAUUUGG | 17 | 683 |
| antiSPCas9-381 | - | AGUGGCAAAAGUUGAGA | 17 | 684 |
| antiSPCas9-382 | - | CUGUUUGAGUUAGAAAA | 17 | 685 |

TABLE E-6-continued

| 5th Tier gRNA Name | DNA Strand | Targeting Domain | Target Site Length | SEQ ID NO |
|---|---|---|---|---|
| antiSPCas9-383 | - | UAGAAAAUGGCCGAAAA | 17 | 686 |
| antiSPCas9-384 | + | UUUACUAUGUUGACUUG | 17 | 687 |
| antiSPCas9-385 | - | AUUACCUACAAAAUGGA | 17 | 688 |
| antiSPCas9-386 | - | GAAAGUGAGUUUGUGUA | 17 | 689 |
| antiSPCas9-387 | + | UCCAUCUUCUCUAAUAU | 17 | 690 |
| antiSPCas9-388 | - | CUUUAAUUGAAACCAAU | 17 | 691 |
| antiSPCas9-389 | - | UCAGUCAAAGAAUUAUU | 17 | 692 |
| antiSPCas9-390 | - | AAUCAAACGACUCAGAA | 17 | 693 |
| antiSPCas9-391 | + | UGUCCCUUCCAUUUUGU | 17 | 694 |
| antiSPCas9-392 | - | UUUAAUUGAAACCAAUG | 17 | 695 |
| antiSPCas9-393 | + | UAAAUUCUUGUCAAAGU | 17 | 696 |
| antiSPCas9-394 | + | UUGUAUAUCCUCUUUGA | 17 | 697 |
| antiSPCas9-395 | + | CUUUAAUUAUCUUUAGG | 17 | 698 |
| antiSPCas9-396 | - | AAAUGAAGAACUAUUGG | 17 | 699 |
| antiSPCas9-397 | + | UCUUUACUAUGUUGACU | 17 | 700 |
| antiSPCas9-398 | - | CCGGAGAGAAGAAAAAU | 17 | 701 |
| antiSPCas9-399 | - | AAUCAUAGAGCAAAUUU | 17 | 702 |
| antiSPCas9-400 | - | CCCGGAGAGAAGAAAAA | 17 | 703 |
| antiSPCas9-401 | - | UUACCUACAAAAUGGAA | 17 | 704 |
| antiSPCas9-402 | + | UCUCAGGCAGUUGCUGA | 17 | 705 |
| antiSPCas9-403 | + | UCCUUCAAAAAGGAUUG | 17 | 706 |
| antiSPCas9-404 | - | UUCAAUUCUAUAAAGUU | 17 | 707 |
| antiSPCas9-405 | + | UGGUAAGAGUAAACAAA | 17 | 708 |
| antiSPCas9-406 | - | UCAAUUCUAUAAAGUUA | 17 | 709 |
| antiSPCas9-407 | - | GAAAUCACUCUGGCAAA | 17 | 710 |
| antiSPCas9-408 | + | ACUUCCUCAAAAUUCCA | 17 | 711 |
| antiSPCas9-409 | + | UUAUCACUAUUCCUUUU | 17 | 712 |
| antiSPCas9-410 | - | CACUUUAAAGUCAAAAU | 17 | 713 |
| antiSPCas9-411 | - | AUAUUAGAGAAGAUGGA | 17 | 714 |
| antiSPCas9-412 | + | CCCAUUUUUCUUCUCUC | 17 | 715 |
| antiSPCas9-413 | - | AAAAAAACAGUCGAGAG | 17 | 716 |
| antiSPCas9-414 | - | UUAUGAAACAGUUAAAG | 17 | 717 |
| antiSPCas9-415 | - | AAGAAAAUGGGUUGUU | 17 | 718 |
| antiSPCas9-416 | + | CCAUUUUUCUUCUCUCC | 17 | 719 |
| antiSPCas9-417 | - | CAUAGUAAAGAAAACUG | 17 | 720 |
| antiSPCas9-418 | - | AUAAGAGACAAGCAAAG | 17 | 721 |
| antiSPCas9-419 | - | GAUGAAGAGAAUAGAAG | 17 | 722 |

TABLE E-6-continued

| | Rest of gene | | | |
|---|---|---|---|---|
| 5th Tier gRNA Name | DNA Strand | Targeting Domain | Target Site Length | SEQ ID NO |
| antiSPCas9-420 | + | GGCUGGAGCGCCGAGGU | 17 | 723 |
| antiSPCas9-421 | + | AUUUCCUUAUAUUUCUC | 17 | 724 |
| antiSPCas9-422 | + | CAGAAUAGGCAACUGUA | 17 | 725 |
| antiSPCas9-423 | − | UAUGAAUUUCUUUAAGA | 17 | 726 |
| antiSPCas9-424 | − | AGAAAAUGAAGAACUAU | 17 | 727 |
| antiSPCas9-425 | − | UUACAAGGAAGUAAAAA | 17 | 728 |
| antiSPCas9-426 | − | AGAGAAGAUGGAUGGGA | 17 | 729 |
| antiSPCas9-427 | − | AAAACUGAGGUGCAGAC | 17 | 730 |
| antiSPCas9-428 | + | UAUCUUUAAUUAUCUUU | 17 | 731 |
| antiSPCas9-429 | + | AGAAUAAAGAAGUAUU | 17 | 732 |
| antiSPCas9-430 | − | AUGAAGAAUAGAAGA | 17 | 733 |
| antiSPCas9-431 | − | AAAGAUAAUUAAAGAUA | 17 | 734 |
| antiSPCas9-432 | − | UAUACUUAGAAGGCAGG | 17 | 735 |
| antiSPCas9-433 | − | CAAAGAGGAUAUACAAA | 17 | 736 |
| antiSPCas9-434 | − | CAGUCGAAAACGGGUACGC | 20 | 737 |
| antiSPCas9-435 | − | CACGCUCGGAUAAGAACCGA | 20 | 738 |
| antiSPCas9-436 | + | UAAGAUAAGCGUCGUGCGCA | 20 | 739 |
| antiSPCas9-437 | − | CGCUCACCUGUUCGACGAUA | 20 | 740 |
| antiSPCas9-438 | + | GAUAAGCGUCGUGCGCAUGG | 20 | 741 |
| antiSPCas9-439 | − | CGAUUCUGUCGAGAUCUCCG | 20 | 742 |
| antiSPCas9-440 | − | AGAGGCGUCGCUAUACGGGC | 20 | 743 |
| antiSPCas9-441 | − | UUAAAGAGGCGUCGCUAUAC | 20 | 744 |
| antiSPCas9-442 | − | AGGCGUCGCUAUACGGGCUG | 20 | 745 |
| antiSPCas9-443 | + | CGCUUUUCGCGAUCAUCUUA | 20 | 746 |
| antiSPCas9-444 | − | AGAGCGACGGCUUCGCCAAU | 20 | 747 |
| antiSPCas9-445 | + | UGAAGCGGAUAACGGCGCCU | 20 | 748 |
| antiSPCas9-446 | − | ACACGCUCGGAUAAGAACCG | 20 | 749 |
| antiSPCas9-447 | − | GAGGCGUCGCUAUACGGGCU | 20 | 750 |
| antiSPCas9-448 | − | GAUGAUCGCGAAAAGCGAAC | 20 | 751 |
| antiSPCas9-449 | − | UAAGGGCCGGGACUUCGCGA | 20 | 752 |
| antiSPCas9-450 | + | CGUAAUGGGACGCUAAAUAC | 20 | 753 |
| antiSPCas9-451 | + | CUCCGGGUAAUUGUGCGAUC | 20 | 754 |
| antiSPCas9-452 | − | UGUCGCGGAAACUUAUCAAC | 20 | 755 |
| antiSPCas9-453 | + | CGCUAGCCAACAUCCGUUUU | 20 | 756 |
| antiSPCas9-454 | + | AAUGAGUGCGGUCCCUACGA | 20 | 757 |
| antiSPCas9-455 | − | UACGCAGGUUAUAUUGACGG | 20 | 758 |
| antiSPCas9-456 | − | UGACGAUCUCGACAAUCUAC | 20 | 759 |
| antiSPCas9-457 | − | GUUAAAGAGGCGUCGCUAUA | 20 | 760 |

TABLE E-6-continued

Rest of gene

| 5th Tier gRNA Name | DNA Strand | Targeting Domain | Target Site Length | SEQ ID NO |
|---|---|---|---|---|
| antiSPCas9-458 | + | CGACGUCGUAAUCAGAUAAA | 20 | 761 |
| antiSPCas9-459 | + | UCAUAACCUUAUCGUCGAAC | 20 | 762 |
| antiSPCas9-460 | − | GCUUAUCUUAAUGCCGUCGU | 20 | 763 |
| antiSPCas9-461 | − | AAACGGAUGUUGGCUAGCGC | 20 | 764 |
| antiSPCas9-462 | + | UUGUCGACAUCCGAGUUGUC | 20 | 765 |
| antiSPCas9-463 | − | CAGCUCAAUCGUUCAUCGAG | 20 | 766 |
| antiSPCas9-464 | − | GAUCGAUUUAAUGCGUCACU | 20 | 767 |
| antiSPCas9-465 | − | CUUAUCUUAAUGCCGUCGUA | 20 | 768 |
| antiSPCas9-466 | − | UGACGGCGGAGCGAGUCAAG | 20 | 769 |
| antiSPCas9-467 | + | CUAGCCGUCGGGAUUUAGAG | 20 | 770 |
| antiSPCas9-468 | − | UCAUCGCUCGUAAAAGGAC | 20 | 771 |
| antiSPCas9-469 | − | CGAGAACGAUAAGCUGAUUC | 20 | 772 |
| antiSPCas9-470 | + | AUGCGAACCGAGAGUUCCCU | 20 | 773 |
| antiSPCas9-471 | − | UAAGCUCAUCGCUCGUAAAA | 20 | 774 |
| antiSPCas9-472 | − | UUGUCGCGGAAACUUAUCAA | 20 | 775 |
| antiSPCas9-473 | − | UCGAUUCUGUCGAGAUCUCC | 20 | 776 |
| antiSPCas9-474 | + | UGUCGCGUCUAGCACCUCCU | 20 | 777 |
| antiSPCas9-475 | − | UGGGACCCGAAAAAGUACGG | 20 | 778 |
| antiSPCas9-476 | + | GGCCUAGUGAGAGCGCUAUA | 20 | 779 |
| antiSPCas9-477 | − | GGAUAAACCCAUACGUGAGC | 20 | 780 |
| antiSPCas9-478 | + | CCGUCGGGAUUUAGAGAGGC | 20 | 781 |
| antiSPCas9-479 | + | UUUUCCGCCUGCUCACGUAU | 20 | 782 |
| antiSPCas9-480 | − | CAUCGCUCGUAAAAGGACU | 20 | 783 |
| antiSPCas9-481 | − | AACCUUAUAGCGCUCUCACU | 20 | 784 |
| antiSPCas9-482 | − | AUCGACUUCCUUGAGGCGAA | 20 | 785 |
| antiSPCas9-483 | + | CGAUCAGGUUUUCUAGCCGU | 20 | 786 |
| antiSPCas9-484 | + | CGUCGUAUUUCGUAUUCAUU | 20 | 787 |
| antiSPCas9-485 | + | UCGAAGCCACCGUACUUUUU | 20 | 788 |
| antiSPCas9-486 | + | UGCGAACCGAGAGUUCCCUC | 20 | 789 |
| antiSPCas9-487 | − | UAGCGCCGGAGAGCUUCAAA | 20 | 790 |
| antiSPCas9-488 | − | AACCUGAUCGCACAAUUACC | 20 | 791 |
| antiSPCas9-489 | − | GGGUACGCAGGUUAUAUUGA | 20 | 792 |
| antiSPCas9-490 | − | GAGGGAACUCUCGGUUCGCA | 20 | 793 |
| antiSPCas9-491 | − | ACGAGAACGAUAAGCUGAUU | 20 | 794 |
| antiSPCas9-492 | − | CCCGCCUCUCUAAAUCCCGA | 20 | 795 |
| antiSPCas9-493 | − | CGGGCUGGGGACGAUUGUCG | 20 | 796 |
| antiSPCas9-494 | − | CGUAAACCCGCCUUUCUAAG | 20 | 797 |

TABLE E-6-continued

Rest of gene

| 5th Tier gRNA Name | DNA Strand | Targeting Domain | Target Site Length | SEQ ID NO |
|---|---|---|---|---|
| antiSPCas9-495 | + | CAUAUAAUCCCGUGAUGGAU | 20 | 798 |
| antiSPCas9-496 | - | UUCGAUUCUGUCGAGAUCUC | 20 | 799 |
| antiSPCas9-497 | + | CGAAGCCACCGUACUUUUUC | 20 | 800 |
| antiSPCas9-498 | - | CCGAAGAAACGAUUACUCCA | 20 | 801 |
| antiSPCas9-499 | + | GUCGUAUUUCGUAUUCAUUC | 20 | 802 |
| antiSPCas9-500 | - | AGCGCCGGAGAGCUUCAAAA | 20 | 803 |
| antiSPCas9-501 | + | UUCUCACCGUCGCGAAGUCC | 20 | 804 |
| antiSPCas9-502 | - | UGAUCUAAAUCCGGACAACU | 20 | 805 |
| antiSPCas9-503 | + | GAUCAGGUUUUCUAGCCGUC | 20 | 806 |
| antiSPCas9-504 | - | GGUUCGCCAGCCAUCAAAAA | 20 | 807 |
| antiSPCas9-505 | + | UUCGCCUCAAGGAAGUCGAU | 20 | 808 |
| antiSPCas9-506 | + | UCGCCUAAGUGGAUUUGAUG | 20 | 809 |
| antiSPCas9-507 | - | UGGUUCGCCAGCCAUCAAAA | 20 | 810 |
| antiSPCas9-508 | + | UCGCCUCAAGGAAGUCGAUG | 20 | 811 |
| antiSPCas9-509 | + | ACCGAGAGUUCCCUCGGGCC | 20 | 812 |
| antiSPCas9-510 | + | AUAGGAGGAUUGCAUCGCUA | 20 | 813 |
| antiSPCas9-511 | + | GCCGUCGGGAUUUAGAGAGG | 20 | 814 |
| antiSPCas9-512 | - | CAAUAAAGUGCUUACACGCU | 20 | 815 |
| antiSPCas9-513 | + | AUUUUCCGCCUGCUCACGUA | 20 | 816 |
| antiSPCas9-514 | - | GAACCCCAUCGACUUCCUUG | 20 | 817 |
| antiSPCas9-515 | - | GCGCCGGAGAGCUUCAAAAG | 20 | 818 |
| antiSPCas9-516 | - | ACGAUACACUUCUACCAAGG | 20 | 819 |
| antiSPCas9-517 | - | AAAUGGCCGAAAACGGAUGU | 20 | 820 |
| antiSPCas9-518 | + | UAGCAUGCAAUUCGCCUAAG | 20 | 821 |
| antiSPCas9-519 | - | UAAGCGCAUACAACAAGCAC | 20 | 822 |
| antiSPCas9-520 | + | UUUCGCCUCAAGGAAGUCGA | 20 | 823 |
| antiSPCas9-521 | + | UGAAUGCGGCUGGAGCGCCG | 20 | 824 |
| antiSPCas9-522 | + | GUGCAAUGAGUCCCCUUGUC | 20 | 825 |
| antiSPCas9-523 | - | UGCAAGUGGCGUGGAUGCGA | 20 | 826 |
| antiSPCas9-524 | - | AAGCAGCGGACUUUCGACAA | 20 | 827 |
| antiSPCas9-525 | - | UAAACCCAUACGUGAGCAGG | 20 | 828 |
| antiSPCas9-526 | - | CCCUAUAAAUGCAAGUGGCG | 20 | 829 |
| antiSPCas9-527 | - | UUUCGCAUACCUUACUAUGU | 20 | 830 |
| antiSPCas9-528 | + | GCGUUAUCAGUUUCGCAUUU | 20 | 831 |
| antiSPCas9-529 | - | GGUCAUGGGACGUCACAAAC | 20 | 832 |
| antiSPCas9-530 | + | CGAGAGUUCCCUCGGGCCAG | 20 | 833 |
| antiSPCas9-531 | + | UUCUUUACGACUUCCUCGCU | 20 | 834 |
| antiSPCas9-532 | - | CAAACGAUACACUUCUACCA | 20 | 835 |

TABLE E-6-continued

| 5th Tier gRNA Name | DNA Strand | Targeting Domain | Target Site Length | SEQ ID NO |
|---|---|---|---|---|
| antiSPCas9-533 | - | ACCUUACUAUGUGGGACCCC | 20 | 836 |
| antiSPCas9-534 | + | GAUUGCAUCGCUAAGGUUUU | 20 | 837 |
| antiSPCas9-535 | - | CUUUCGCAUACCUUACUAUG | 20 | 838 |
| antiSPCas9-536 | + | UUGAUCAUUGAAGCGGAUAA | 20 | 839 |
| antiSPCas9-537 | - | CUCGAUUUUCUAAAGAGCGA | 20 | 840 |
| antiSPCas9-538 | + | UCGAAGUUCGACUUAAAAUU | 20 | 841 |
| antiSPCas9-539 | + | AGGCAGUUGCUGACGGACUA | 20 | 842 |
| antiSPCas9-540 | - | UAUCCGCUUCAAUGAUCAAA | 20 | 843 |
| antiSPCas9-541 | - | GACUGGGACCCGAAAAAGUA | 20 | 844 |
| antiSPCas9-542 | + | CCGAGAGUUCCCUCGGGCCA | 20 | 845 |
| antiSPCas9-543 | - | GCAUGCUAUACUUAGAAGGC | 20 | 846 |
| antiSPCas9-544 | - | AAUCGUAUGGGAUAAGGGCC | 20 | 847 |
| antiSPCas9-545 | + | GUCCUUACUAAGCUGCAAUU | 20 | 848 |
| antiSPCas9-546 | + | UGUUCUCCGCUUAGAAAGGC | 20 | 849 |
| antiSPCas9-547 | - | CGACCUUUAAUUGAAACCAA | 20 | 850 |
| antiSPCas9-548 | - | AAAUCGUAUGGGAUAAGGGC | 20 | 851 |
| antiSPCas9-549 | - | GAACAUAUUGCGAAUCUUGC | 20 | 852 |
| antiSPCas9-550 | + | GAGCUGACGUUUAAUAAAUC | 20 | 853 |
| antiSPCas9-551 | + | CUUAACUGUCACUUUGCGGU | 20 | 854 |
| antiSPCas9-552 | + | AUUAAAUCGAUCUUCUACCC | 20 | 855 |
| antiSPCas9-553 | - | GGCACAGGUUUCCGGACAAG | 20 | 856 |
| antiSPCas9-554 | + | CACAUAGUAAGGUAUGCGAA | 20 | 857 |
| antiSPCas9-555 | + | AGUAAGGUAUGCGAAAGGUU | 20 | 858 |
| antiSPCas9-556 | + | CCAUGGAGUAAUCGUUUCUU | 20 | 859 |
| antiSPCas9-557 | + | CGGGUAUUUCUUAAUGAGUG | 20 | 860 |
| antiSPCas9-558 | - | UAUGUGGGACCCCUGGCCCG | 20 | 861 |
| antiSPCas9-559 | + | CCUUGUAACCUUUCGCCUCA | 20 | 862 |
| antiSPCas9-560 | + | UCCACGCCACUUGCAUUUAU | 20 | 863 |
| antiSPCas9-561 | - | UCCCAUUACGAGAAGUUGAA | 20 | 864 |
| antiSPCas9-562 | - | AUGGUGUCGGACUUCAGAA | 20 | 865 |
| antiSPCas9-563 | + | AGUUUCAUAUAAUCCCGUGA | 20 | 866 |
| antiSPCas9-564 | - | GGUGAAAUCGUAUGGGAUAA | 20 | 867 |
| antiSPCas9-565 | - | AUUAUUGGGGAUAACGAUUA | 20 | 868 |
| antiSPCas9-566 | - | UCACGGGAUUAUAUGAAACU | 20 | 869 |
| antiSPCas9-567 | - | AAGUGACAAUGUUCCAAGCG | 20 | 870 |
| antiSPCas9-568 | - | GCGAAAAGCGAACAGGAGAU | 20 | 871 |
| antiSPCas9-569 | - | GGAGACAGGUGAAAUCGUAU | 20 | 872 |

TABLE E-6-continued

Rest of gene

| 5th Tier gRNA Name | DNA Strand | Targeting Domain | Target Site Length | SEQ ID NO |
|---|---|---|---|---|
| antiSPCas9-570 | + | ACCUUUCAACUUCUCGUAAU | 20 | 873 |
| antiSPCas9-571 | - | GCAGACCGGAGGGUUUUCAA | 20 | 874 |
| antiSPCas9-572 | + | UGCCACUACUAGGACAGAAU | 20 | 875 |
| antiSPCas9-573 | + | CCACGCCACUUGCAUUUAUA | 20 | 876 |
| antiSPCas9-574 | - | AUUUAUUAAACGUCAGCUCG | 20 | 877 |
| antiSPCas9-575 | + | AACCUUUCAACUUCUCGUAA | 20 | 878 |
| antiSPCas9-576 | - | CGAAAAUCAAACGACUCAGA | 20 | 879 |
| antiSPCas9-577 | - | UCUUUGAUCAGUCGAAAAAC | 20 | 880 |
| antiSPCas9-578 | + | CGGUAAAUUCUUGUCAAAGU | 20 | 881 |
| antiSPCas9-579 | - | AUGUGGGACCCCUGGCCCGA | 20 | 882 |
| antiSPCas9-580 | - | CGGAUAGAUUUGUCACAGCU | 20 | 883 |
| antiSPCas9-581 | + | UCGACUUAAAAUUUGGUGUC | 20 | 884 |
| antiSPCas9-582 | - | CAUCCUAGCUGAUGCCAAUC | 20 | 885 |
| antiSPCas9-583 | + | CAUCCACUACUUUGACUGUC | 20 | 886 |
| antiSPCas9-584 | - | AGGCACAGGUUUCCGGACAA | 20 | 887 |
| antiSPCas9-585 | + | GCCAGGGGUCCCACAUAGUA | 20 | 888 |
| antiSPCas9-586 | + | UCGUAAAGUAAACUGUGCUU | 20 | 889 |
| antiSPCas9-587 | + | CAGGCAGUUGCUGACGGACU | 20 | 890 |
| antiSPCas9-588 | - | CUGAUUCACCAAUCCAUCAC | 20 | 891 |
| antiSPCas9-589 | - | UGCCUAUUCUGUCCUAGUAG | 20 | 892 |
| antiSPCas9-590 | - | GAUGAGCUAGUUAAGGUCAU | 20 | 893 |
| antiSPCas9-591 | + | AGUAUGCCCUUUUUGAUGGC | 20 | 894 |
| antiSPCas9-592 | - | GGGAGACAGGUGAAAUCGUA | 20 | 895 |
| antiSPCas9-593 | + | GAUUGAAUCGUCCUUCAAAA | 20 | 896 |
| antiSPCas9-594 | + | CUGUUCUCCGCUUAGAAAGG | 20 | 897 |
| antiSPCas9-595 | - | AAGAUCUACUGCGAAAGCAG | 20 | 898 |
| antiSPCas9-596 | - | UUGUCUGAACUUGACAAGGC | 20 | 899 |
| antiSPCas9-597 | + | UGCGGCUGGAGCGCCGAGGU | 20 | 900 |
| antiSPCas9-598 | - | CAUGUAUGUUGAUCAGGAAC | 20 | 901 |
| antiSPCas9-599 | - | GACAAUCUACUGGCACAAAU | 20 | 902 |
| antiSPCas9-600 | - | CCUUGAGGCGAAAGGUUACA | 20 | 903 |
| antiSPCas9-601 | + | GCUUAAUACUUUGUCCAGAU | 20 | 904 |
| antiSPCas9-602 | - | AGGUGAAAUCGUAUGGGAUA | 20 | 905 |
| antiSPCas9-603 | - | AAGGCACAGGUUUCCGGACA | 20 | 906 |
| antiSPCas9-604 | + | AUCGUCCUUCAAAAGGAUU | 20 | 907 |
| antiSPCas9-605 | + | CAGCUGCAUAAAGUUCCUAU | 20 | 908 |
| antiSPCas9-606 | - | GAUCUUAAAGGAGCAUCCUG | 20 | 909 |
| antiSPCas9-607 | + | GUACCUUUUGAUCAUUGAAG | 20 | 910 |

TABLE E-6-continued

Rest of gene

| 5th Tier gRNA Name | DNA Strand | Targeting Domain | Target Site Length | SEQ ID NO |
|---|---|---|---|---|
| antiSPCas9-608 | - | UGAAGAUCGGGAAAUGAUUG | 20 | 911 |
| antiSPCas9-609 | - | UGCCAAAUUGCAGCUUAGUA | 20 | 912 |
| antiSPCas9-610 | - | GGAUGAGCUAGUUAAGGUCA | 20 | 913 |
| antiSPCas9-611 | + | CGAUUCCUUUGAAAACCCUC | 20 | 914 |
| antiSPCas9-612 | + | CUUCUGUUCUCCGCUUAGAA | 20 | 915 |
| antiSPCas9-613 | - | UUUGAGGAAGUUGUCGAUAA | 20 | 916 |
| antiSPCas9-614 | + | UCAAAAUACUUGAAUGCGGC | 20 | 917 |
| antiSPCas9-615 | - | ACUGGGCAGCCAGAUCUUAA | 20 | 918 |
| antiSPCas9-616 | - | GAUAGAUUUGUCACAGCUUG | 20 | 919 |
| antiSPCas9-617 | + | CCUUGAGAAGUGUCAAGUCU | 20 | 920 |
| antiSPCas9-618 | + | AUCUCGAUUACAAUGUUUUC | 20 | 921 |
| antiSPCas9-619 | + | UCACGAUUGUCUUUGAGGAA | 20 | 922 |
| antiSPCas9-620 | + | CUGGAGUAUGCCCUUUUUGA | 20 | 923 |
| antiSPCas9-621 | + | AAAGUUUCUCGUUCUGCAAU | 20 | 924 |
| antiSPCas9-622 | - | UUGUUUACUCUUACCAACCU | 20 | 925 |
| antiSPCas9-623 | - | AAGCGCAUACAACAAGCACA | 20 | 926 |
| antiSPCas9-624 | + | AAUCGUCCUUCAAAAAGGAU | 20 | 927 |
| antiSPCas9-625 | + | UGCAAUUGGGUAUUUUCCAC | 20 | 928 |
| antiSPCas9-626 | + | CUCUCAGUAUGUCAGAUAGG | 20 | 929 |
| antiSPCas9-627 | + | UGCUUCUGUUCGUUAUCUUC | 20 | 930 |
| antiSPCas9-628 | - | GGAUAGAUUUGUCACAGCUU | 20 | 931 |
| antiSPCas9-629 | - | UGUACCCCAAUCCUUUUUGA | 20 | 932 |
| antiSPCas9-630 | - | UGGCUUGUCUGAACUUGACA | 20 | 933 |
| antiSPCas9-631 | - | AAGGGACAUGUAUGUUGAUC | 20 | 934 |
| antiSPCas9-632 | + | GAUUUCACCUGUCUCCCCAU | 20 | 935 |
| antiSPCas9-633 | + | UUAGGCAAUACUUUUUCGUU | 20 | 936 |
| antiSPCas9-634 | + | UAACUCUCAGUAUGUCAGAU | 20 | 937 |
| antiSPCas9-635 | + | GUUCCCCUUUUGAAGCUCUC | 20 | 938 |
| antiSPCas9-636 | - | UCAGUAUGCGGACUUAUUUU | 20 | 939 |
| antiSPCas9-637 | + | UCUCAACUUUUGCCACUACU | 20 | 940 |
| antiSPCas9-638 | + | GAUUAUAGGUUUGUACUAAC | 20 | 941 |
| antiSPCas9-639 | - | GACCUUUAAUUGAAACCAAU | 20 | 942 |
| antiSPCas9-640 | - | AGGAAUCGAUUCUUCCAAAA | 20 | 943 |
| antiSPCas9-641 | - | CUUUAAGACGGAAAUCACUC | 20 | 944 |
| antiSPCas9-642 | + | AAGUUUCUCGUUCUGCAAUU | 20 | 945 |
| antiSPCas9-643 | + | GUGCAACAUGCUUUGUGAUU | 20 | 946 |
| antiSPCas9-644 | - | AUUGAAACCAAUGGGGAGAC | 20 | 947 |

TABLE E-6-continued

Rest of gene

| 5th Tier gRNA Name | DNA Strand | Targeting Domain | Target Site Length | SEQ ID NO |
|---|---|---|---|---|
| antiSPCas9-645 | - | ACUCCAGACAGUCAAAGUAG | 20 | 948 |
| antiSPCas9-646 | - | AAUUGCAUGCUAUACUUAGA | 20 | 949 |
| antiSPCas9-647 | + | AACUCAAACAGACUAUACUU | 20 | 950 |
| antiSPCas9-648 | - | GAUUACUCCAUGGAAUUUUG | 20 | 951 |
| antiSPCas9-649 | - | GGAAAACAUUGUAAUCGAGA | 20 | 952 |
| antiSPCas9-650 | - | AGUAGUGGAUGAGCUAGUUA | 20 | 953 |
| antiSPCas9-651 | + | CAGGAUGCUCCUUUAAGAUC | 20 | 954 |
| antiSPCas9-652 | - | CAUUGAGGGUGAUCUAAAUC | 20 | 955 |
| antiSPCas9-653 | - | CCAAGACUUGACACUUCUCA | 20 | 956 |
| antiSPCas9-654 | + | UCCCCAUUGGUUUCAAUUAA | 20 | 957 |
| antiSPCas9-655 | - | AUAACUUAACUAAAGCUGAG | 20 | 958 |
| antiSPCas9-656 | + | CCCAUCCAUCUUCUCUAAUA | 20 | 959 |
| antiSPCas9-657 | - | GAGAACCCUAUAAAUGCAAG | 20 | 960 |
| antiSPCas9-658 | - | AAAACUGAGGUGCAGACCGG | 20 | 961 |
| antiSPCas9-659 | - | GGCAAAAAAACAGUCGAGAG | 20 | 962 |
| antiSPCas9-660 | + | AGGAAAUUCACGUAUUUAGA | 20 | 963 |
| antiSPCas9-661 | - | AAGCGAACAGGAGAUAGGCA | 20 | 964 |
| antiSPCas9-662 | - | UCUUACCCUCUUUGAAGAUC | 20 | 965 |
| antiSPCas9-663 | - | CCCUGGCCCGAGGGAACUCU | 20 | 966 |
| antiSPCas9-664 | - | CGAAAUCAUAGAGCAAAUUU | 20 | 967 |
| antiSPCas9-665 | - | UUCUUUGAUCAGUCGAAAAA | 20 | 968 |
| antiSPCas9-666 | - | UGACUCUUUAACCUUCAAAG | 20 | 969 |
| antiSPCas9-667 | + | AGGACAGAAUAGGCAACUGU | 20 | 970 |
| antiSPCas9-668 | - | AGUUAAUACUGAGAUUACCA | 20 | 971 |
| antiSPCas9-669 | - | ACCUUUAAUUGAAACCAAUG | 20 | 972 |
| antiSPCas9-670 | - | AUUCCACAUCAAAUCCACUU | 20 | 973 |
| antiSPCas9-671 | + | AGCUUAUCACUAUUCCUUUU | 20 | 974 |
| antiSPCas9-672 | + | UGUCCAGAUUGGCAUCAGCU | 20 | 975 |
| antiSPCas9-673 | - | GAAAGUUAAGUAUGUCACUG | 20 | 976 |
| antiSPCas9-674 | + | AACAUGCUUUGUGAUUUGGC | 20 | 977 |
| antiSPCas9-675 | + | CAUUUCCCGAUCUUCAAAGA | 20 | 978 |
| antiSPCas9-676 | - | CCAUAUUAGAGAAGAUGGAU | 20 | 979 |
| antiSPCas9-677 | - | UACCUCUAUUACCUACAAAA | 20 | 980 |
| antiSPCas9-678 | - | AUAGAUUUGUCACAGCUUGG | 20 | 981 |
| antiSPCas9-679 | + | GGUUGGUAAGAGUAAACAAA | 20 | 982 |
| antiSPCas9-680 | + | UCAUUUCCCGAUCUUCAAAG | 20 | 983 |
| antiSPCas9-681 | - | ACGGAAAUCACUCUGGCAAA | 20 | 984 |
| antiSPCas9-682 | + | UGAAGGUUAAAGAGUCAUCA | 20 | 985 |

TABLE E-6-continued

Rest of gene

| 5th Tier gRNA Name | DNA Strand | Targeting Domain | Target Site Length | SEQ ID NO |
|---|---|---|---|---|
| antiSPCas9-683 | + | CUCUUCAAACAACUGAUUAU | 20 | 986 |
| antiSPCas9-684 | + | CUUCAUUCUCUUCGUUAUCC | 20 | 987 |
| antiSPCas9-685 | − | AUACAAAAGGCACAGGUUUC | 20 | 988 |
| antiSPCas9-686 | − | GUAGUGGCAAAAGUUGAGAA | 20 | 989 |
| antiSPCas9-687 | − | AGUCAGUCAAAGAAUUAUUG | 20 | 990 |
| antiSPCas9-688 | − | GCAACUGCCUGAGAAAUAUA | 20 | 991 |
| antiSPCas9-689 | − | CUAGAAAGUGAGUUUGUGUA | 20 | 992 |
| antiSPCas9-690 | + | GAACAUUGUCACUUUUCCCU | 20 | 993 |
| antiSPCas9-691 | − | CCCAUAUUAGAGAAGAUGGA | 20 | 994 |
| antiSPCas9-692 | + | CAACAUGCUUUGUGAUUUGG | 20 | 995 |
| antiSPCas9-693 | + | ACAUGUCCCUUCCAUUUUGU | 20 | 996 |
| antiSPCas9-694 | − | CUCUUACCCUCUUUGAAGAU | 20 | 997 |
| antiSPCas9-695 | − | ACAAAUUGGAGAUCAGUAUG | 20 | 998 |
| antiSPCas9-696 | − | AAACUGAGGUGCAGACCGGA | 20 | 999 |
| antiSPCas9-697 | − | UACCCGGAGAGAAGAAAAAU | 20 | 1000 |
| antiSPCas9-698 | − | UUAACUAAAGCUGAGAGGGG | 20 | 1001 |
| antiSPCas9-699 | − | GAAGUCAGUCAAAGAAUUAU | 20 | 1002 |
| antiSPCas9-700 | − | AAAGUUAAGUAUGUCACUGA | 20 | 1003 |
| antiSPCas9-701 | − | UCUAUUACCUACAAAAUGGA | 20 | 1004 |
| antiSPCas9-702 | − | AACUUAACUAAAGCUGAGAG | 20 | 1005 |
| antiSPCas9-703 | − | AAUUAAAGAUAAGGACUUCC | 20 | 1006 |
| antiSPCas9-704 | − | AGUAGUGGCAAAAGUUGAGA | 20 | 1007 |
| antiSPCas9-705 | − | AGAGGAUAUACAAAAGGCAC | 20 | 1008 |
| antiSPCas9-706 | + | UCUUUUCACGAUUGUCUUUG | 20 | 1009 |
| antiSPCas9-707 | − | CAAACCCAUAUUAGAGAAGA | 20 | 1010 |
| antiSPCas9-708 | + | UGUGUCAAAAUACUUGAAUG | 20 | 1011 |
| antiSPCas9-709 | − | GACAGUUAAGCAAUUGAAAG | 20 | 1012 |
| antiSPCas9-710 | − | GAAGAGGGUAUUAAAGAACU | 20 | 1013 |
| antiSPCas9-711 | + | UUCCAUUUUGUAGGUAAUAG | 20 | 1014 |
| antiSPCas9-712 | − | GCGGAUGAAGAGAAUAGAAG | 20 | 1015 |
| antiSPCas9-713 | − | CUAUUACCUACAAAAUGGAA | 20 | 1016 |
| antiSPCas9-714 | + | AUUGCUUAACUGUCACUUUG | 20 | 1017 |
| antiSPCas9-715 | − | AGUCUGUUUGAGUUAGAAAA | 20 | 1018 |
| antiSPCas9-716 | + | ACAAACUCACUUUCUAGCUU | 20 | 1019 |
| antiSPCas9-717 | − | AAAAUCAAACGACUCAGAAG | 20 | 1020 |
| antiSPCas9-718 | − | AGAAGAGGGUAUUAAAGAAC | 20 | 1021 |
| antiSPCas9-719 | + | CAAACUCACUUUCUAGCUUC | 20 | 1022 |

TABLE E-6-continued

Rest of gene

| 5th Tier gRNA Name | DNA Strand | Targeting Domain | Target Site Length | SEQ ID NO |
|---|---|---|---|---|
| antiSPCas9-720 | − | UUACCCGGAGAGAAGAAAAA | 20 | 1023 |
| antiSPCas9-721 | + | AUUUCUCAGGCAGUUGCUGA | 20 | 1024 |
| antiSPCas9-722 | − | AGUUAGAAAAUGGCCGAAAA | 20 | 1025 |
| antiSPCas9-723 | − | UAACUUAACUAAAGCUGAGA | 20 | 1026 |
| antiSPCas9-724 | + | GGACAGAAUAGGCAACUGUA | 20 | 1027 |
| antiSPCas9-725 | − | AAGUCAGUCAAAGAAUUAUU | 20 | 1028 |
| antiSPCas9-726 | − | AGGUUAUGAAACAGUUAAAG | 20 | 1029 |
| antiSPCas9-727 | + | UUUGACUGACUUCAGUUUCU | 20 | 1030 |
| antiSPCas9-728 | + | CAACCCAUUUUUCUUCUCUC | 20 | 1031 |
| antiSPCas9-729 | + | UCGUCCUUCAAAAAGGAUUG | 20 | 1032 |
| antiSPCas9-730 | + | UACUAUGUUGACUUGGGGCA | 20 | 1033 |
| antiSPCas9-731 | − | UGCUAUACUUAGAAGGCAGG | 20 | 1034 |
| antiSPCas9-732 | + | ACAACUUCCUCAAAAUUCCA | 20 | 1035 |
| antiSPCas9-733 | − | UUUAAAGUCAAAAUUGGUGU | 20 | 1036 |
| antiSPCas9-734 | − | CGGAUGAAGAGAAUAGAAGA | 20 | 1037 |
| antiSPCas9-735 | + | CUUUUGUAUAUCCUCUUUGA | 20 | 1038 |
| antiSPCas9-736 | + | AACCCAUUUUUCUUCUCUCC | 20 | 1039 |
| antiSPCas9-737 | + | CCAUCCAUCUUCUCUAAUAU | 20 | 1040 |
| antiSPCas9-738 | − | AUUAGAGAAGAUGGAUGGGA | 20 | 1041 |
| antiSPCas9-739 | − | ACUGAUUCACCAAUCCAUCA | 20 | 1042 |
| antiSPCas9-740 | − | CCUAAAGAUAAUUAAAGAUA | 20 | 1043 |
| antiSPCas9-741 | − | GGGAUAAGAGACAAGCAAAG | 20 | 1044 |
| antiSPCas9-742 | + | UUCUUUACUAUGUUGACUUG | 20 | 1045 |
| antiSPCas9-743 | − | GAAAAUCAAACGACUCAGAA | 20 | 1046 |
| antiSPCas9-744 | + | UUUCUUUACUAUGUUGACUU | 20 | 1047 |
| antiSPCas9-745 | + | CCUUAUCUUUAAUUAUCUUU | 20 | 1048 |
| antiSPCas9-746 | − | AAUCACUUUAAAGUCAAAAU | 20 | 1049 |
| antiSPCas9-747 | − | AGAAAAUGAAGAACUAUUGG | 20 | 1050 |
| antiSPCas9-748 | + | GUUAGAAUAAAGAAGUAUU | 20 | 1051 |
| antiSPCas9-749 | − | CAACAUAGUAAAGAAAACUG | 20 | 1052 |
| antiSPCas9-750 | − | AGGUUACAAGGAAGUAAAAA | 20 | 1053 |
| antiSPCas9-751 | + | UAUCUUUAAUUAUCUUUAGG | 20 | 1054 |
| antiSPCas9-752 | − | GAGAAGAAAAAUGGGUUGUU | 20 | 1055 |
| antiSPCas9-753 | − | CAUUAUGAAUUUCUUUAAGA | 20 | 1056 |
| antiSPCas9-754 | + | UUUUCUUUACUAUGUUGACU | 20 | 1057 |
| antiSPCas9-755 | − | AUUUUCAAUUCUAUAAAGUU | 20 | 1058 |
| antiSPCas9-756 | + | AAUAUUUCCUUAUAUUUCUC | 20 | 1059 |
| antiSPCas9-757 | − | UUUUCAAUUCUAUAAAGUUA | 20 | 1060 |

TABLE E-6-continued

Rest of gene

| 5th Tier gRNA Name | DNA Strand | Targeting Domain | Target Site Length | SEQ ID NO |
|---|---|---|---|---|
| antiSPCas9-758 | − | UAAAGAAAAUGAAGAACUAU | 20 | 1061 |
| antiSPCas9-759 | − | AAGAAAACUGAGGUGCAGAC | 20 | 1062 |
| antiSPCas9-760 | − | CUUCAAAGAGGAUAUACAAA | 20 | 1063 |

TABLE E-7

| Exemplary guide RNA pairs for S. aureus (SA) nickase | Group A | Group B | Group A guides can be paired with any from Group B. | Group C | Group D | Group C guides can be paired with any from Group D. |
|---|---|---|---|---|---|---|
| | antiSACas9-8, antiSACas9-9 | antiSACas9-5 antiSACas9-2 | | antiSACas9-7 | antiSACas9-11 | |

TABLE E-8

| S. aureus | First 500 bp of coding sequence downstream of start codon, good orthogonality, starts with G | | | |
|---|---|---|---|---|
| 1st Tier gRNA Name | DNA Strand | Targeting Domain | Target Site Length | SEQ ID NO |
| antiSACas9-1 | − | GGACAUCGGGAUUACAAGCG | 20 | 1064 |
| antiSACas9-2 | + | GUAAUCCCGAUGUCCAGCCC | 20 | 1065 |
| antiSACas9-5 | − | GGAAUUAAUCCUUAUGAAGC | 20 | 1068 |
| antiSACas9-6 | + | GCCUUUCACCCUGGCUUCAU | 20 | 1069 |

TABLE E-9

| S. aureus | First 500 bp of coding sequence downstream of start codon, good orthogonaility, does not start with G | | | |
|---|---|---|---|---|
| 2nd Tier gRNA Name | DNA Strand | Targeting Domain | Target Site Length | SEQ ID NO |
| antiSACas9-7 | − | CUGCACCUGGCUAAGCGCCG | 20 | 1070 |
| antiSACas9-8 | − | ACCGACCAUUCUGAGCUGAG | 20 | 1071 |
| antiSACas9-9 | − | UGCUGACCGACCAUUCUGAG | 20 | 1072 |
| antiSACas9-10 | + | AACAGCAGUUUCUUCACCCU | 20 | 1073 |
| antiSACas9-11 | + | AGGAUUAAUUCCACUCAGCU | 20 | 1074 |
| antiSACas9-12 | − | UACAUUCUGGGGCUGGACAU | 20 | 1075 |
| antiSACas9-13 | − | AUGAAGCCAGGGUGAAAGGC | 20 | 1076 |
| antiSACas9-14 | − | CUGAAACGACGGAGAAGGCA | 20 | 1079 |
| antiSACas9-15 | − | CGGAGAAGGCACAGAAUCCA | 20 | 1080 |

TABLE E-10

S. aureus: First 500 bp of coding sequence downstream of start codon, poor orthogonality, starts with G

| 3rd Tier gRNA Name | DNA Strand | Targeting Domain | Target Site Length | SEQ ID NO |
|---|---|---|---|---|
| antiSACas9-16 | − | GAGUCAGAAGCUGUCAGAGG | 20 | 1081 |
| antiSACas9-17 | − | GAAGAAAGAUGGCGAGGUGA | 20 | 1082 |
| antiSACas9-18 | − | GGGAUUACAAGCGUGGGGUA | 20 | 1083 |

TABLE E-11

S. aureus: Rest of gene

| 5th Tier gRNA Name | DNA Strand | Targeting Domain | Target Site Length | SEQ ID NO |
|---|---|---|---|---|
| antiSACas9-19 | − | GAUACGCUACUCGCGGCCUG | 20 | 1084 |
| antiSACas9-20 | + | AUGAUCGACCUCGUAGUUGA | 20 | 1085 |
| antiSACas9-21 | − | AUGAAUGAUAAGCGCCCCCC | 20 | 1086 |
| antiSACas9-22 | − | ACGCAGAUCUGUACAACGCC | 20 | 1087 |
| antiSACas9-23 | − | ACUACAAGUACUCUCACCGG | 20 | 1088 |
| antiSACas9-24 | + | CGCCGUUGUCCAGAUAGACA | 20 | 1089 |
| antiSACas9-25 | − | UCAUUGAGAACGCCGAACUG | 20 | 1090 |
| antiSACas9-26 | + | UAAUAUGAUCGACCUCGUAG | 20 | 1091 |
| antiSACas9-27 | + | GCGUUCUCUUUCCCGGUAGU | 20 | 1092 |
| antiSACas9-28 | − | GGCGAACUGUAUAGGGUCAU | 20 | 1093 |
| antiSACas9-29 | − | GCCCGAAAUCGAGACAGAAC | 20 | 1094 |
| antiSACas9-30 | − | AUCUGCUGAACCGCAUUGAA | 20 | 1095 |
| antiSACas9-31 | + | CCGUUCAGAUUGUUCACAAU | 20 | 1096 |
| antiSACas9-32 | + | UCGGAGCUCUGGUAGAUAGU | 20 | 1097 |
| antiSACas9-33 | + | GACCACCUUGUUGCGACUGU | 20 | 1098 |
| antiSACas9-34 | + | UUUGUAUGCCACAGCUCAUC | 20 | 1099 |
| antiSACas9-35 | + | GGGCUUUUUAUCCACCCGGU | 20 | 1100 |
| antiSACas9-36 | + | GUUGAGUACUUUUUGAUACU | 20 | 1101 |
| antiSACas9-37 | − | AAGAUCAAUGGCGAACUGUA | 20 | 1102 |
| antiSACas9-38 | − | GAAAGUCAAGUCCAUCAACG | 20 | 1103 |
| antiSACas9-39 | + | GGUCCCUCAUAGUAGGUUCU | 20 | 1104 |
| antiSACas9-40 | − | CCUAUUUCCGGGUGAACAAU | 20 | 1105 |
| antiSACas9-41 | + | CGCAGCAGAUUCAUCAGGCC | 20 | 1106 |
| antiSACas9-42 | + | CAGGUUUCCCAGAAUGUCGG | 20 | 1107 |
| antiSACas9-43 | − | CGAACAGAUUAGUAAUCUGA | 20 | 1108 |
| antiSACas9-44 | + | CCAGAUUGUUCACCCGGAAA | 20 | 1109 |
| antiSACas9-45 | + | AAAUCGUCCACCAGUGUGGU | 20 | 1110 |
| antiSACas9-46 | − | CUUCGGAUGGAAAGACAUCA | 20 | 1111 |
| antiSACas9-47 | − | AAAUGCCGACUUCAUCUUUA | 20 | 1112 |

TABLE E-11-continued

| S. aureus 5th Tier gRNA Name | DNA Strand | Rest of gene Targeting Domain | Target Site Length | SEQ ID NO |
|---|---|---|---|---|
| antiSACas9-48 | − | UCAACAGAUUCUCCGUCCAG | 20 | 1113 |
| antiSACas9-49 | + | GCGUUGAUCACUUUGAUGCU | 20 | 1114 |
| antiSACas9-50 | − | AAGGACUACAAGUACUCUCA | 20 | 1115 |
| antiSACas9-51 | + | CUCCGCUUGACCACGGGUGA | 20 | 1116 |
| antiSACas9-52 | − | GGUGACAAGCACUGGAAAAC | 20 | 1117 |
| antiSACas9-53 | − | ACCUGACCAAGUAUAGCAAA | 20 | 1118 |
| antiSACas9-54 | + | GGAUGAAGCUCCGCUUGACC | 20 | 1119 |
| antiSACas9-55 | − | CCGCAUCAGCAAGACCAAAA | 20 | 1120 |
| antiSACas9-56 | − | UCCAGAAGGAUUUUAUUAAC | 20 | 1121 |
| antiSACas9-57 | + | UUGAUAUGCUUGAUCUGGUG | 20 | 1122 |
| antiSACas9-58 | − | UGUAUAAAUUUGUGACUGUC | 20 | 1123 |
| antiSACas9-59 | − | CUCACCAGAUCAAGCAUAUC | 20 | 1124 |
| antiSACas9-60 | − | UGCAGAAGGCUUACCACCAG | 20 | 1125 |
| antiSACas9-61 | + | UUGAUGUCCUCUUCGUUGAC | 20 | 1126 |
| antiSACas9-62 | + | CUAAUCUGUUCGAUCUCUUC | 20 | 1127 |
| antiSACas9-63 | + | GACCAGCACCUUGUUGUUAA | 20 | 1128 |
| antiSACas9-64 | − | GAAGAGGACAUCAAGGGCUA | 20 | 1129 |
| antiSACas9-65 | + | UAAUAAAAUCCUUCUGGACG | 20 | 1130 |
| antiSACas9-66 | − | UGGUCCCAAAAAAGGUGGAC | 20 | 1131 |
| antiSACas9-67 | + | CUCUUCAUAGUACUUAUACA | 20 | 1132 |
| antiSACas9-68 | − | AAUCUGCUGCGAUCCUAUUU | 20 | 1133 |
| antiSACas9-69 | + | GAACUAGACAGGUACUGGAA | 20 | 1134 |
| antiSACas9-70 | + | AAAGGUUUCGUAAGAGAUCU | 20 | 1135 |
| antiSACas9-71 | + | CCCUUUCCUUUGGCCAGAUU | 20 | 1136 |
| antiSACas9-72 | + | UCGUCUUUUCUUGUACUAUA | 20 | 1137 |
| antiSACas9-73 | + | AGGAGUCCUAUUGCCCUUUU | 20 | 1138 |
| antiSACas9-74 | − | UAUGAUUGACAUCACUUACC | 20 | 1139 |
| antiSACas9-75 | + | UUCACCUCAUACAGGUUUCC | 20 | 1140 |
| antiSACas9-76 | + | CUCCAGGGGAUGGCCUCCA | 20 | 1141 |
| antiSACas9-77 | − | UGAAAGCUAUCAAUCUGAUU | 20 | 1142 |
| antiSACas9-78 | − | UCAAGUACUAUGGGAACAAG | 20 | 1143 |
| antiSACas9-79 | − | UGAACAACCUGGUCAUCACC | 20 | 1144 |
| antiSACas9-80 | + | UUGUUCAGCAGGUCCUCCAG | 20 | 1145 |
| antiSACas9-81 | − | ACCGAGAGUAUCUGGAAAAC | 20 | 1146 |
| antiSACas9-82 | − | GUUUAAAAAGGAGCGCAACA | 20 | 1147 |
| antiSACas9-83 | + | CUUCAGUUUCUGAUAUGUCU | 20 | 1148 |
| antiSACas9-84 | − | AAACAAUUGCCUCUAAGACU | 20 | 1149 |

TABLE E-11-continued

| S. aureus | | Rest of gene | | |
|---|---|---|---|---|
| 5th Tier gRNA Name | DNA Strand | Targeting Domain | Target Site Length | SEQ ID NO |
| antiSACas9-85 | − | GAAAAAGAUUAGCAACCAGG | 20 | 1150 |
| antiSACas9-86 | − | CAGGGAUGAAAACGAGAAAC | 20 | 1151 |
| antiSACas9-87 | + | UUCAGGUUAGUCAGCUCUUC | 20 | 1152 |
| antiSACas9-88 | + | UUGUCGAAGGACACGCUUCU | 20 | 1153 |
| antiSACas9-89 | − | AAACCUUUAAAAAGCACAUU | 20 | 1154 |
| antiSACas9-90 | − | ACCAGGAGAAGGGAGCCCCU | 20 | 1155 |
| antiSACas9-91 | − | GUACAAGAAAAGACGAUAAG | 20 | 1156 |
| antiSACas9-92 | − | GAUGUUCGAAGAGAAGCAGG | 20 | 1157 |
| antiSACas9-93 | − | AAAAGGAGAACUACUAUGAA | 20 | 1158 |
| antiSACas9-94 | − | AAUUUGUGACUGUCAAGAAU | 20 | 1159 |

TABLE E-12

| S. aureus | | Suboptimal PAM-NNGRRV | | |
|---|---|---|---|---|
| 6th Tier gRNA Name | DNA Strand | Targeting Domain | Target Site Length | SEQ ID NO |
| antiSACas9-95 | + | GAAGCAGGCCGAAUCUAUGC | 20 | 1160 |
| antiSACas9-96 | + | AGGAAUGGUACGAGAUGCUG | 20 | 1161 |
| antiSACas9-97 | + | UCCGGGUGAACAAUCUGGAU | 20 | 1162 |
| antiSACas9-98 | + | AGACUCGGAGAACCUACUAU | 20 | 1163 |
| antiSACas9-99 | + | GGACGCACAGAAGAUGAUCA | 20 | 1164 |
| antiSACas9-100 | − | UCACAUCCAGAUUGUUCACC | 20 | 1165 |
| antiSACas9-101 | + | GGAGAAGGGAGCCCCUUCGG | 20 | 1166 |
| antiSACas9-102 | + | CCGGCAACGAGCUGUCUACA | 20 | 1167 |
| antiSACas9-103 | + | AAGUACUCAACCGACAUUCU | 20 | 1168 |
| antiSACas9-104 | + | AAUGACACCCUGUAUAGUAC | 20 | 1169 |
| antiSACas9-105 | + | ACUGUUCAAGGAGGCCAACG | 20 | 1170 |
| antiSACas9-106 | + | CCGACUUCAUCUUUAAGGAG | 20 | 1171 |
| antiSACas9-107 | − | GAAUCUGAACUAGACAGGUA | 20 | 1172 |
| antiSACas9-108 | + | CGGGUGGAUAAAAAGCCCAA | 20 | 1173 |
| antiSACas9-109 | + | ACCAGAGCUCCGAGGACAUC | 20 | 1174 |
| antiSACas9-110 | − | GGUGGUACAUCAGCAGCUUC | 20 | 1175 |
| antiSACas9-111 | + | CCGGAACACACAACCUGUCC | 20 | 1176 |
| antiSACas9-112 | − | GUGCUUUUUAAAGGUUUCGU | 20 | 1177 |
| antiSACas9-113 | − | UUCACAUCCAGAUUGUUCAC | 20 | 1178 |
| antiSACas9-114 | − | UUCCAGAGCUUUGCUAUUGC | 20 | 1179 |
| antiSACas9-115 | + | ACAUCUUUUCUGAGGCGCAA | 20 | 1180 |
| antiSACas9-116 | + | AAAGCUGAUCAACAAAAGUC | 20 | 1181 |
| antiSACas9-117 | + | GAAUCUGGAUGUCAUCAAAA | 20 | 1182 |

TABLE E-12-continued

| S. aureus | Suboptimal PAM-NNGRRV | | | |
|---|---|---|---|---|
| 6th Tier gRNA Name | DNA Strand | Targeting Domain | Target Site Length | SEQ ID NO |
| antiSACas9-118 | + | UAUAAGUACUAUGAAGAGAC | 20 | 1183 |
| antiSACas9-119 | + | CAUCACUUACCGAGAGUAUC | 20 | 1184 |
| antiSACas9-120 | + | UAUCAUUAUCGAGCUGGCUA | 20 | 1185 |
| antiSACas9-121 | + | CAAGGUGCUGGUCAAGCAGG | 20 | 1186 |
| antiSACas9-122 | + | AAAGUACUCAACCGACAUUC | 20 | 1187 |
| antiSACas9-123 | − | AUUGUCGAAGGACACGCUUC | 20 | 1188 |
| antiSACas9-124 | + | GAGUGCAUAACGUCAAUGAG | 20 | 1189 |
| antiSACas9-125 | + | AGUAUGUCGCAGAGCUGCAG | 20 | 1190 |
| antiSACas9-126 | − | GAAAUCGUCCACCAGUGUGG | 20 | 1191 |
| antiSACas9-127 | + | ACCAUGAUCCUCAGACAUAU | 20 | 1192 |
| antiSACas9-128 | − | CUUGACGCUUCUCAGCUCUU | 20 | 1193 |
| antiSACas9-129 | + | GUAUAAGUACUAUGAAGAGA | 20 | 1194 |
| antiSACas9-130 | + | GGGGUAUGGGAUUAUUGACU | 20 | 1195 |
| antiSACas9-131 | + | CCCACUGUAUAAGUACUAUG | 20 | 1196 |
| antiSACas9-132 | + | UCGAAAACGUGUUUAAGCAG | 20 | 1197 |
| antiSACas9-133 | + | AGACCAAAAAGGAGUACCUG | 20 | 1198 |
| antiSACas9-134 | − | UUAAACACGUUUUCGAUGAU | 20 | 1199 |
| antiSACas9-135 | − | GCUUGACCACGGGUGACAGA | 20 | 1200 |
| antiSACas9-136 | − | UUAAACUUCCAUUUGCGCCU | 20 | 1201 |
| antiSACas9-137 | + | AUGAGGGACGGAGAAGCAAG | 20 | 1202 |
| antiSACas9-138 | − | CUGACUCAGGUCCACCUUUU | 20 | 1203 |
| antiSACas9-139 | + | GAAAGACAUCAAGGAAUGGU | 20 | 1204 |
| antiSACas9-140 | + | UAAGGACAUCACAGCACGGA | 20 | 1205 |
| antiSACas9-141 | + | AAAAGGUGGACCUGAGUCAG | 20 | 1206 |
| antiSACas9-142 | + | AAUAUGAUUGACAUCACUUA | 20 | 1207 |
| antiSACas9-143 | + | GAGAAGGGAGCCCCUUCGGA | 20 | 1208 |
| antiSACas9-144 | + | GAUUAUCCGAACUACCGGGA | 20 | 1209 |
| antiSACas9-145 | + | UCAAAGAAGCCAAGCAGCUG | 20 | 1210 |
| antiSACas9-146 | − | GGUGAGAGUACUUGUAGUCC | 20 | 1211 |
| antiSACas9-147 | + | ACCUGAACAGCGAGCUGACC | 20 | 1212 |
| antiSACas9-148 | + | GACCGACCAUUCUGAGCUGA | 20 | 1213 |
| antiSACas9-149 | − | GCUUGAUCUGGUGAGGAGUG | 20 | 1214 |
| antiSACas9-150 | − | UGACCAGCACCUUGUUGUUA | 20 | 1215 |
| antiSACas9-151 | + | CAAGCUGCACGAUAUGCAGG | 20 | 1216 |
| antiSACas9-152 | − | UAAAGGUUUCGUAAGAGAUC | 20 | 1217 |
| antiSACas9-153 | + | GCACCUAUUUUCCAGAAGAG | 20 | 1218 |
| antiSACas9-154 | + | AAACGAGAAACUGGAAUACU | 20 | 1219 |

TABLE E-12-continued

| S. aureus | Suboptimal PAM-NNGRRV | | | |
|---|---|---|---|---|
| 6th Tier gRNA Name | DNA Strand | Targeting Domain | Target Site Length | SEQ ID NO |
| antiSACas9-155 | + | UGAAGAGAUUAUCCGAACUA | 20 | 1220 |
| antiSACas9-156 | + | GGCUGAAGAAAGAUGGCGAG | 20 | 1221 |
| antiSACas9-157 | + | GUCCAGAAGGAUUUUAUUAA | 20 | 1222 |
| antiSACas9-158 | + | GAACAGCGAGCUGACCCAGG | 20 | 1223 |
| antiSACas9-159 | + | AGAACCUACUAUGAGGGACC | 20 | 1224 |
| antiSACas9-160 | − | AGCCAGGUGCAGCAGAGCUG | 20 | 1225 |
| antiSACas9-161 | + | CUACUAUGAGGGACCAGGAG | 20 | 1226 |
| antiSACas9-162 | + | GAAAACCAGAGUUCACCAAU | 20 | 1227 |
| antiSACas9-163 | + | ACAACAAGGUGCUGGUCAAG | 20 | 1228 |
| antiSACas9-164 | + | GCAGACCAAUGAACGCAUUG | 20 | 1229 |
| antiSACas9-165 | + | GGAAAAGCUGGACAAAGCC | 20 | 1230 |
| antiSACas9-166 | + | UUCAGAUUCCAAGAUCUCUU | 20 | 1231 |
| antiSACas9-167 | + | AGCUGCAGCUGGAACGGCUG | 20 | 1232 |
| antiSACas9-168 | + | GAUUAUGGAGCAGUACGGCG | 20 | 1233 |
| antiSACas9-169 | − | AGAAUCAGAUUGAUAGCUUU | 20 | 1234 |
| antiSACas9-170 | − | UCCUCCAGGGGAUGGCCUC | 20 | 1235 |
| antiSACas9-171 | + | GGGAUUAUUGACUAUGAAAC | 20 | 1236 |
| antiSACas9-172 | + | UCUCACGCAAUAGCAAAGCU | 20 | 1237 |
| antiSACas9-173 | + | ACGUGGAAAACAAUGAGGGA | 20 | 1238 |
| antiSACas9-174 | − | UUGACGCUUCUCAGCUCUUC | 20 | 1239 |
| antiSACas9-175 | + | GAUAUCAUUAUCGAGCUGGC | 20 | 1240 |
| antiSACas9-176 | − | GUUAAUAAAAUCCUUCUGGA | 20 | 1241 |
| antiSACas9-177 | + | CAACCUGGUCAUCACCAGGG | 20 | 1242 |
| antiSACas9-178 | + | GCACAUUCUGAAUCUGGCCA | 20 | 1243 |
| antiSACas9-179 | + | GGUGGACCUGAGUCAGCAGA | 20 | 1244 |
| antiSACas9-180 | + | AUAUUAAGGACAUCACAGCA | 20 | 1245 |
| antiSACas9-181 | + | CUACAUUCUGGGGCUGGACA | 20 | 1246 |
| antiSACas9-182 | + | GCAAGAGGGGAGCCAGGCGC | 20 | 1247 |
| antiSACas9-183 | + | CCAGGGAUGAAAACGAGAAA | 20 | 1248 |
| antiSACas9-184 | − | UAGCCAGGUGCAGCAGAGCU | 20 | 1249 |
| antiSACas9-185 | + | GGGCUACCGGGUGACAAGCA | 20 | 1250 |
| antiSACas9-186 | + | GGUCAUCACCAGGGAUGAAA | 20 | 1251 |
| antiSACas9-187 | + | GAGCCAGGCGCCUGAAACGA | 20 | 1252 |
| antiSACas9-188 | + | GCUACGAAGAGGCUAAAAAG | 20 | 1253 |
| antiSACas9-189 | + | GGACAAAGCCAAGAAAGUGA | 20 | 1254 |
| antiSACas9-190 | − | UUGGGCUUUUAUCCACCCG | 20 | 1255 |
| antiSACas9-191 | + | GACUGUUCAAGGAGGCCAAC | 20 | 1256 |
| antiSACas9-192 | + | AAAAGUACUCAACCGACAUU | 20 | 1257 |

TABLE E-12-continued

| S. aureus | | Suboptimal PAM-NNGRRV | | |
|---|---|---|---|---|
| 6th Tier gRNA Name | DNA Strand | Targeting Domain | Target Site Length | SEQ ID NO |
| antiSACas9-193 | + | UAGUAAUCUGAAGGGGUACA | 20 | 1258 |
| antiSACas9-194 | + | GGCCGAAUCUAUGCCCGAAA | 20 | 1259 |
| antiSACas9-195 | + | UCAAGCUGCACGAUAUGCAG | 20 | 1260 |
| antiSACas9-196 | + | CUGAACAACCUGGUCAUCAC | 20 | 1261 |
| antiSACas9-197 | + | GGCACAGAAUCCAGAGGGUG | 20 | 1262 |
| antiSACas9-198 | + | ACGCAAUAGCAAAGCUCUGG | 20 | 1263 |
| antiSACas9-199 | + | AGAGAACGCAAAGUACCUGA | 20 | 1264 |
| antiSACas9-200 | + | UCAUCACCAGGGAUGAAAAC | 20 | 1265 |
| antiSACas9-201 | + | AAGGAGUACCUGCUGGAAGA | 20 | 1266 |
| antiSACas9-202 | + | AGCAGAAGAAAAGCCUACA | 20 | 1267 |
| antiSACas9-203 | + | ACAUCACUUACCGAGAGUAU | 20 | 1268 |
| antiSACas9-204 | + | CACAGCACGGAAAGAAAUCA | 20 | 1269 |
| antiSACas9-205 | + | AGAAGAUGAUCAAUGAGAUG | 20 | 1270 |
| antiSACas9-206 | + | AAGCUGCACGAUAUGCAGGA | 20 | 1271 |
| antiSACas9-207 | − | AUUGUUCAGCAGGUCCUCCA | 20 | 1272 |
| antiSACas9-208 | + | GAUAUUAAGGACAUCACAGC | 20 | 1273 |
| antiSACas9-209 | + | CUAUGAGAAGUUCCAGAUCA | 20 | 1274 |
| antiSACas9-210 | + | GAAGAGAUUAUCCGAACUAC | 20 | 1275 |
| antiSACas9-211 | + | UACACUGAAACAGAUUGCUA | 20 | 1276 |
| antiSACas9-212 | + | AGUACAAGAAAAGACGAUAA | 20 | 1277 |
| antiSACas9-213 | + | CGGGAUUACAAGCGUGGGGU | 20 | 1278 |
| antiSACas9-214 | + | GGCUACCGGUGACAAGCAC | 20 | 1279 |
| antiSACas9-215 | + | AUAUCGACCUGCUGGAGACU | 20 | 1280 |
| antiSACas9-216 | + | UUAAUCCUUAUGAAGCCAGG | 20 | 1281 |
| antiSACas9-217 | + | CGAGACAGAACAGGAGUACA | 20 | 1282 |
| antiSACas9-218 | + | GAUCAAGAAGAUCAAGUACU | 20 | 1283 |
| antiSACas9-219 | + | GCCGACUUCAUCUUUAAGGA | 20 | 1284 |
| antiSACas9-220 | + | AAGAGAUUAUCCGAACUACC | 20 | 1285 |
| antiSACas9-221 | + | AUGAUCAAUGAGAUGCAGAA | 20 | 1286 |
| antiSACas9-222 | + | AGGCCAACGUGGAAAACAAU | 20 | 1287 |
| antiSACas9-223 | + | AUCAAGAAGAUCAAGUACUA | 20 | 1288 |
| antiSACas9-224 | + | CACAUUCUGAAUCUGGCCAA | 20 | 1289 |
| antiSACas9-225 | + | ACGACAAAGAUAAUGACAAG | 20 | 1290 |
| antiSACas9-226 | − | AAUCUGAACUAGACAGGUAC | 20 | 1291 |
| antiSACas9-227 | + | GCCUGAGUCAGAAGCUGUCA | 20 | 1292 |
| antiSACas9-228 | + | CGAUACUUAUAUCGACCUGC | 20 | 1293 |
| antiSACas9-229 | + | UAGUACAAGAAAAGACGAUA | 20 | 1294 |

TABLE E-12-continued

| S. aureus | Suboptimal PAM-NNGRRV | | | |
|---|---|---|---|---|
| 6th Tier gRNA Name | DNA Strand | Targeting Domain | Target Site Length | SEQ ID NO |
| antiSACas9-230 | + | CCUUCGGAUGGAAAGACAUC | 20 | 1295 |
| antiSACas9-231 | + | GAUGGAGAACCAGAUGUUCG | 20 | 1296 |
| antiSACas9-232 | - | CGGCGCUUAGCCAGGUGCAG | 20 | 1297 |
| antiSACas9-233 | + | AGUAAUCUGAAGGGGUACAC | 20 | 1298 |
| antiSACas9-234 | + | CGACCUGAUUAAGAUCAAUG | 20 | 1299 |
| antiSACas9-235 | + | AGCUAUCAAUCUGAUUCUGG | 20 | 1300 |
| antiSACas9-236 | + | AAAGGAACUACAUUCUGGGG | 20 | 1301 |
| antiSACas9-237 | + | GGCCAACGUGGAAAACAAUG | 20 | 1302 |
| antiSACas9-238 | + | UCUUUAAGGAGUGGAAAAAG | 20 | 1303 |
| antiSACas9-239 | + | AGGAGUACCUGCUGGAAGAG | 20 | 1304 |
| antiSACas9-240 | + | UGACUAUCUACCAGAGCUCC | 20 | 1305 |
| antiSACas9-241 | - | GUGGUACAUCAGCAGCUUCU | 20 | 1306 |
| antiSACas9-242 | + | AGGAGAUCCUGGUCAACGAA | 20 | 1307 |
| antiSACas9-243 | - | UGUUGUUAAAGGAAUUGUCG | 20 | 1308 |
| antiSACas9-244 | + | ACAUUGCACCUAUUUUCCAG | 20 | 1309 |
| antiSACas9-245 | + | GAGAACUCUAAAAAGGGCAA | 20 | 1310 |
| antiSACas9-246 | + | AGAGCUGACUAACCUGAACA | 20 | 1311 |
| antiSACas9-247 | + | CAUACAGAUUCGAUGUCUAU | 20 | 1312 |
| antiSACas9-248 | + | UUCUGAAUCUGGCCAAAGGA | 20 | 1313 |
| antiSACas9-249 | - | UGACUCAGGUCCACCUUUUU | 20 | 1314 |
| antiSACas9-250 | + | AACUGUAUAGGGUCAUCGGG | 20 | 1315 |
| antiSACas9-251 | - | GAAUCAGAUUGAUAGCUUUC | 20 | 1316 |
| antiSACas9-252 | + | UGGCUAGGGAGAAGAACAGC | 20 | 1317 |
| antiSACas9-253 | + | UCCAGGAAGAGCUGACUAAC | 20 | 1318 |
| antiSACas9-254 | - | CUUUGACGUAGUCGCUUGUC | 20 | 1319 |
| antiSACas9-255 | + | AUAAGUACUAUGAAGAGACU | 20 | 1320 |
| antiSACas9-256 | - | UUCCGGUUAAUAAAAUCCUU | 20 | 1321 |
| antiSACas9-257 | + | UGAAGCUGGUCCCAAAAAAG | 20 | 1322 |
| antiSACas9-258 | - | UAGAUUCGGCCUGCUUCUCU | 20 | 1323 |
| antiSACas9-259 | + | UCAAGAAGAUCAAGUACUAU | 20 | 1324 |
| antiSACas9-260 | + | AUUUUAUUAACCGGAAUCUG | 20 | 1325 |
| antiSACas9-261 | + | UGGGAAACCUGUAUGAGGUG | 20 | 1326 |
| antiSACas9-262 | + | UCAGAAACUGAAGCUGAUUA | 20 | 1327 |
| antiSACas9-263 | + | AGGCUUACCACCAGCUGGAU | 20 | 1328 |
| antiSACas9-264 | + | UGCUGCGAUCCUAUUUCCGG | 20 | 1329 |
| antiSACas9-265 | + | AUAACGUCAAUGAGGUGGAA | 20 | 1330 |
| antiSACas9-266 | + | GAACGCAUUGAAGAGAUUAU | 20 | 1331 |
| antiSACas9-267 | + | UUCUGUCACCCGUGGUCAAG | 20 | 1332 |

TABLE E-12-continued

| S. aureus | Suboptimal PAM-NNGRRV | | | |
|---|---|---|---|---|
| 6th Tier gRNA Name | DNA Strand | Targeting Domain | Target Site Length | SEQ ID NO |
| antiSACas9-268 | + | GCGCAAAUGGAAGUUUAAAA | 20 | 1333 |
| antiSACas9-269 | − | UAAACACGUUUUCGAUGAUC | 20 | 1334 |
| antiSACas9-270 | − | GUACUUGAUCUUCUUGAUCA | 20 | 1335 |
| antiSACas9-271 | − | AAGUCGGCAUUUGCGAUAAU | 20 | 1336 |
| antiSACas9-272 | + | CGAGCUGACCCAGGAAGAGA | 20 | 1337 |
| antiSACas9-273 | + | UCAAGCAUAUCAAGGAUUUC | 20 | 1338 |
| antiSACas9-274 | + | AGGUGCUGGUCAAGCAGGAA | 20 | 1339 |
| antiSACas9-275 | + | CUCUGGAGGCCAUCCCCCUG | 20 | 1340 |
| antiSACas9-276 | + | ACUAUGAGGGACCAGGAGAA | 20 | 1341 |
| antiSACas9-277 | + | GAGCUCCGAGGACAUCCAGG | 20 | 1342 |
| antiSACas9-278 | + | CAAAAAGGAGUACCUGCUGG | 20 | 1343 |
| antiSACas9-279 | + | AUACCCUGAUUGUGAACAAU | 20 | 1344 |
| antiSACas9-280 | + | UCUGGAAGAGAAGUAUGUCG | 20 | 1345 |
| antiSACas9-281 | + | AUAAGGGGAAUACCCUGAUU | 20 | 1346 |
| antiSACas9-282 | − | CCAGCUCGAUAAUGAUAUCA | 20 | 1347 |
| antiSACas9-283 | + | GGAUUAUUGACUAUGAAACA | 20 | 1348 |
| antiSACas9-284 | + | GAGGGACGGAGAAGCAAGAG | 20 | 1349 |
| antiSACas9-285 | − | CAGCUCUUCCUGGAUGUCCU | 20 | 1350 |
| antiSACas9-286 | + | GAAAGAAAUCAUUGAGAACG | 20 | 1351 |
| antiSACas9-287 | + | CAGCACGGAAAGAAAUCAUU | 20 | 1352 |
| antiSACas9-288 | + | GACUCGGAGAACCUACUAUG | 20 | 1353 |
| antiSACas9-289 | − | AAGAUGUGAACCCGCCGUUG | 20 | 1354 |
| antiSACas9-290 | + | GGUGGAUAAAAAGCCCAACA | 20 | 1355 |
| antiSACas9-291 | + | UCGGGGUGAACAAUGAUCUG | 20 | 1356 |
| antiSACas9-292 | + | UGUACAACGCCCUGAAUGAC | 20 | 1357 |
| antiSACas9-293 | − | ACUCCUGUUCUGUCUCGAUU | 20 | 1358 |
| antiSACas9-294 | + | AUCUAUGCCCGAAAUCGAGA | 20 | 1359 |
| antiSACas9-295 | + | GGAACAAGCUGAAUGCCCAU | 20 | 1360 |
| antiSACas9-296 | − | ACCAGGUUGUUCAGGUCAUU | 20 | 1361 |
| antiSACas9-297 | + | ACAAAGCCAAGAAAGUGAUG | 20 | 1362 |
| antiSACas9-298 | + | CAACCUGCUGACCGACCAUU | 20 | 1363 |
| antiSACas9-299 | + | AUCUGGAUGUCAUCAAAAAG | 20 | 1364 |
| antiSACas9-300 | + | CCAUCCCCUGGAGGACCUG | 20 | 1365 |
| antiSACas9-301 | − | GGUCGGUCAGCAGGUUGUAA | 20 | 1366 |
| antiSACas9-302 | + | UGAAAGUGUAUCACGAUAUU | 20 | 1367 |
| antiSACas9-303 | + | CUAAGAUCCUGACUAUCUAC | 20 | 1368 |
| antiSACas9-304 | + | UGGUCAAGCGGAGCUUCAUC | 20 | 1369 |

TABLE E-12-continued

| S. aureus | Suboptimal PAM-NNGRRV | | | |
|---|---|---|---|---|
| 6th Tier gRNA Name | DNA Strand | Targeting Domain | Target Site Length | SEQ ID NO |
| antiSACas9-305 | + | CGGCAACGAGCUGUCUACAA | 20 | 1370 |
| antiSACas9-306 | + | AGCAGGAAGAGAACUCUAAA | 20 | 1371 |
| antiSACas9-307 | + | GAAACGAAACCGGCAGACCA | 20 | 1372 |
| antiSACas9-308 | − | CUUGAUGUCUUUCCAUCCGA | 20 | 1373 |
| antiSACas9-309 | + | CCUGAUUGUGAACAAUCUGA | 20 | 1374 |
| antiSACas9-310 | + | UUAUCGAGCUGGCUAGGGAG | 20 | 1375 |
| antiSACas9-311 | − | CGUGAUACACUUUCAGAUUG | 20 | 1376 |
| antiSACas9-312 | + | AAGAGAUCCCAACCACACUG | 20 | 1377 |
| antiSACas9-313 | − | UUCGUAAGAGAUCUUGGAAU | 20 | 1378 |
| antiSACas9-314 | + | CCUGCCCAAUGAUAUCAUUA | 20 | 1379 |
| antiSACas9-315 | + | AUCGACCUGCUGGAGACUCG | 20 | 1380 |
| antiSACas9-316 | − | UGUCAUUGAUCAGCUCUCUG | 20 | 1381 |
| antiSACas9-317 | + | UGGAGCAGUACGGCGACGAG | 20 | 1382 |
| antiSACas9-318 | − | AUUUGCGCCUCAGAAAAGAU | 20 | 1383 |
| antiSACas9-319 | − | UGUUUUCCACGUUGGCCUCC | 20 | 1384 |
| antiSACas9-320 | − | CGUUGUUGUAAAAGGAGGCG | 20 | 1385 |
| antiSACas9-321 | + | AGCACCCUCAGAUUAUCAAA | 20 | 1386 |
| antiSACas9-322 | − | UCUGCGACAUACUUCUCUUC | 20 | 1387 |
| antiSACas9-323 | + | GGAAUGGUACGAGAUGCUGA | 20 | 1388 |
| antiSACas9-324 | + | GUAUGUCGCAGAGCUGCAGC | 20 | 1389 |
| antiSACas9-325 | + | UGGUCAACGAAGAGGACAUC | 20 | 1390 |
| antiSACas9-326 | + | GGUGGAAGAGGACACCGGCA | 20 | 1391 |
| antiSACas9-327 | − | UAAUCGUCUGUGAUGUCCAG | 20 | 1392 |
| antiSACas9-328 | + | UUAUCCGAACUACCGGGAAA | 20 | 1393 |
| antiSACas9-329 | − | AAUUGUUUGAUAAUUCGAG | 20 | 1394 |
| antiSACas9-330 | + | GACCAAAAGGAGUACCUGC | 20 | 1395 |
| antiSACas9-331 | + | CAUCAAAAGGAGAACUACU | 20 | 1396 |
| antiSACas9-332 | + | AGUGAAUAGCAAGUGCUACG | 20 | 1397 |
| antiSACas9-333 | + | CGACAUUCUGGGAAACCUGU | 20 | 1398 |
| antiSACas9-334 | + | CCGAGGAGUGCAUAACGUCA | 20 | 1399 |
| antiSACas9-335 | + | AGGCCUGAGUCAGAAGCUGU | 20 | 1400 |
| antiSACas9-336 | + | GCAAUAGCAAAGCUCUGGAA | 20 | 1401 |
| antiSACas9-337 | + | ACCUAUUUUCCAGAAGAGCU | 20 | 1402 |
| antiSACas9-338 | − | UCAGCUCUUCCUGGAUGUCC | 20 | 1403 |
| antiSACas9-339 | − | GCAGGUCGAUAUAAGUAUCG | 20 | 1404 |
| antiSACas9-340 | − | CUUGAUAUGCUUGAUCUGGU | 20 | 1405 |
| antiSACas9-341 | + | AGUGCAUAACGUCAAUGAGG | 20 | 1406 |
| antiSACas9-342 | − | AGCUUCAGUUUCUGAUAUGU | 20 | 1407 |

TABLE E-12-continued

| S. aureus | | Suboptimal PAM-NNGRRV | | |
|---|---|---|---|---|
| 6th Tier gRNA Name | DNA Strand | Targeting Domain | Target Site Length | SEQ ID NO |
| antiSACas9-343 | − | GGCAAUUGUUUUGAUAAUUC | 20 | 1408 |
| antiSACas9-344 | + | CAACAAGGUGCUGGUCAAGC | 20 | 1409 |
| antiSACas9-345 | + | AGUGAUGGAGAACCAGAUGU | 20 | 1410 |
| antiSACas9-346 | + | GGGAAAGUGUCUGUAUUCUC | 20 | 1411 |
| antiSACas9-347 | + | AGGGAAAGUGUCUGUAUUCU | 20 | 1412 |
| antiSACas9-348 | + | AGAUCGAACAGAUUAGUAAU | 20 | 1413 |
| antiSACas9-349 | − | GAUUGUUCAGCAGGUCCUCC | 20 | 1414 |
| antiSACas9-350 | + | AAUCAAGCUGCACGAUAUGC | 20 | 1415 |
| antiSACas9-351 | + | GUGGAAAACAAUGAGGGACG | 20 | 1416 |
| antiSACas9-352 | + | GCCAGGCGCCUGAAACGACG | 20 | 1417 |
| antiSACas9-353 | + | UCGAUACUUAUAUCGACCUG | 20 | 1418 |
| antiSACas9-354 | + | AGGAUAAUGGCCCCGUGAUC | 20 | 1419 |
| antiSACas9-355 | + | UCAUUAUCGAGCUGGCUAGG | 20 | 1420 |
| antiSACas9-356 | + | AACCUACUAUGAGGGACCAG | 20 | 1421 |
| antiSACas9-357 | + | ACAAUGAGGGACGGAGAAGC | 20 | 1422 |
| antiSACas9-358 | + | UGAAGUGAAUAGCAAGUGCU | 20 | 1423 |
| antiSACas9-359 | + | AUUCUCUGGAGGCCAUCCCC | 20 | 1424 |
| antiSACas9-360 | + | CUGAAGAAAGAUGGCGAGGU | 20 | 1425 |
| antiSACas9-361 | + | UGGCGAACUGUAUAGGGUCA | 20 | 1426 |
| antiSACas9-362 | + | UACUAUGAGGGACCAGGAGA | 20 | 1427 |
| antiSACas9-363 | − | CAAUUGUUUUGAUAAUUCGA | 20 | 1428 |
| antiSACas9-364 | + | GCUGAGUGGAAUUAAUCCUU | 20 | 1429 |
| antiSACas9-365 | + | CUGCUGCACCUGGCUAAGCG | 20 | 1430 |
| antiSACas9-366 | + | CCAGAGCUCCGAGGACAUCC | 20 | 1431 |
| antiSACas9-367 | − | AAUUGUCGAAGGACACGCUU | 20 | 1432 |
| antiSACas9-368 | + | UAUAUCGACCUGCUGGAGAC | 20 | 1433 |
| antiSACas9-369 | + | AGCUGAUCAACAAAAGUCCC | 20 | 1434 |
| antiSACas9-370 | + | AGAAGAACAGCAAGGACGCA | 20 | 1435 |
| antiSACas9-371 | + | UGGAGAACCAGAUGUUCGAA | 20 | 1436 |
| antiSACas9-372 | + | AGAUUGCAAUCUUUAACCGG | 20 | 1437 |
| antiSACas9-373 | + | UUCUCUGGAGGCCAUCCCCC | 20 | 1438 |
| antiSACas9-374 | + | AAUGAGGGACGGAGAAGCAA | 20 | 1439 |
| antiSACas9-375 | − | UCCUUGAUAUGCUUGAUCUG | 20 | 1440 |
| antiSACas9-376 | + | GGGACAUUGCACCUAUUUUC | 20 | 1441 |
| antiSACas9-377 | + | AAGUGAUCAACGCCAUCAUC | 20 | 1442 |
| antiSACas9-378 | + | GCUGCACCUGGCUAAGCGCC | 20 | 1443 |
| antiSACas9-379 | + | GGAACGGCUGAAGAAAGAUG | 20 | 1444 |

TABLE E-12-continued

| S. aureus | Suboptimal PAM-NNGRRV | | | |
|---|---|---|---|---|
| 6th Tier gRNA Name | DNA Strand | Targeting Domain | Target Site Length | SEQ ID NO |
| antiSACas9-380 | - | CCUUGAUGUCUUUCCAUCCG | 20 | 1445 |
| antiSACas9-381 | + | GGAGGCCAACGUGGAAAACA | 20 | 1446 |
| antiSACas9-382 | + | ACGGCGGGUUCACAUCUUUU | 20 | 1447 |
| antiSACas9-383 | + | GAGGUCGAUCAUAUUAUCCC | 20 | 1448 |
| antiSACas9-384 | + | UCGAACAGAUUAGUAAUCUG | 20 | 1449 |
| antiSACas9-385 | + | CAAUGAUCUGCUGAACCGCA | 20 | 1450 |
| antiSACas9-386 | + | CCUGACUAUCUACCAGAGCU | 20 | 1451 |
| antiSACas9-387 | + | ACGAGAAACUGGAAUACUAU | 20 | 1452 |
| antiSACas9-388 | + | CGCAGGCGUCAGACUGUUCA | 20 | 1453 |
| antiSACas9-389 | - | AUUCCUUGAUGUCUUUCCAU | 20 | 1454 |
| antiSACas9-390 | + | CCGGCAGACCAAUGAACGCA | 20 | 1455 |
| antiSACas9-391 | + | AGAAUCUGGAUGUCAUCAAA | 20 | 1456 |
| antiSACas9-392 | + | UGCUAAGGAGAUCCUGGUCA | 20 | 1457 |
| antiSACas9-393 | - | AGUACUUGAUCUUCUUGAUC | 20 | 1458 |
| antiSACas9-394 | + | AUAUCAUUAUCGAGCUGGCU | 20 | 1459 |
| antiSACas9-395 | + | AAAUCAAGCUGCACGAUAUG | 20 | 1460 |
| antiSACas9-396 | + | CAGAGCUGCAGCUGGAACGG | 20 | 1461 |
| antiSACas9-397 | + | GAACCCACUGUAUAAGUACU | 20 | 1462 |
| antiSACas9-398 | - | UGAUCACUUUGAUGCUCUGG | 20 | 1463 |
| antiSACas9-399 | + | GCUGAACAAUCCAUUCAACU | 20 | 1464 |
| antiSACas9-400 | + | CAUCUUUUCUGAGGCGCAAA | 20 | 1465 |
| antiSACas9-401 | + | GCCGCAUCAGCAAGACCAAA | 20 | 1466 |
| antiSACas9-402 | + | AUCAGAAACUGAAGCUGAUU | 20 | 1467 |
| antiSACas9-403 | + | AUCCUCAGACAUAUCAGAAA | 20 | 1468 |
| antiSACas9-404 | + | ACGCAGGCGUCAGACUGUUC | 20 | 1469 |
| antiSACas9-405 | - | CCUUGUUGUUAAAGGAAUUG | 20 | 1470 |
| antiSACas9-406 | + | CUCACGCAAUAGCAAAGCUC | 20 | 1471 |
| antiSACas9-407 | + | CAAAUGCCGACUUCAUCUUU | 20 | 1472 |
| antiSACas9-408 | + | UUAUGGAGCAGUACGGCGAC | 20 | 1473 |
| antiSACas9-409 | - | GCUUUUCCACUCCUUAAAG | 20 | 1474 |
| antiSACas9-410 | + | UCAUCGAAAACGUGUUUAAG | 20 | 1475 |
| antiSACas9-411 | + | CCAGGGUGAAAGGCCUGAGU | 20 | 1476 |
| antiSACas9-412 | - | GGUUAAUAAAAUCCUUCUGG | 20 | 1477 |
| antiSACas9-413 | + | ACAAGGUGGUCAAGCUGUCA | 20 | 1478 |
| antiSACas9-414 | + | GAGAACCUACUAUGAGGGAC | 20 | 1479 |
| antiSACas9-415 | + | CAAAGGGUACAAGCACCAUG | 20 | 1480 |
| antiSACas9-416 | + | AACGUGGAAAACAAUGAGGG | 20 | 1481 |
| antiSACas9-417 | + | UUCUGGGAAACCUGUAUGAG | 20 | 1482 |

TABLE E-12-continued

S. aureus — Suboptimal PAM-NNGRRV

| 6th Tier gRNA Name | DNA Strand | Targeting Domain | Target Site Length | SEQ ID NO |
|---|---|---|---|---|
| antiSACas9-418 | + | UGAGGGACGGAGAAGCAAGA | 20 | 1483 |
| antiSACas9-419 | + | CAAGACAAGCGACUACGUCA | 20 | 1484 |
| antiSACas9-420 | + | GGAGCCAGGCGCCUGAAACG | 20 | 1485 |
| antiSACas9-421 | + | ACAUCAACAGAUUCUCCGUC | 20 | 1486 |
| antiSACas9-422 | − | UGAACUAGACAGGUACUGGA | 20 | 1487 |
| antiSACas9-423 | + | CUACACUGAAACAGAUUGCU | 20 | 1488 |
| antiSACas9-424 | + | GACGGAGAAGGCACAGAAUC | 20 | 1489 |
| antiSACas9-425 | − | CUUUUUGAUACUCUGAGUCU | 20 | 1490 |
| antiSACas9-426 | + | UGGACAAAGCCAAGAAAGUG | 20 | 1491 |
| antiSACas9-427 | + | AUUCUGUCACCCGUGGUCAA | 20 | 1492 |
| antiSACas9-428 | + | AUAGUACAAGAAAAGACGAU | 20 | 1493 |
| antiSACas9-429 | + | CCUGAACAGCGAGCUGACCC | 20 | 1494 |
| antiSACas9-430 | − | GAGGCAAUUGUUUUGAUAAU | 20 | 1495 |
| antiSACas9-431 | − | AAUCAGGUCGUUGUUGUAAA | 20 | 1496 |
| antiSACas9-432 | − | GCAAUUGUUUUGAUAAUUCG | 20 | 1497 |
| antiSACas9-433 | + | GGCGCAAAUGGAAGUUUAAA | 20 | 1498 |
| antiSACas9-434 | + | UCGAGACAGAACAGGAGUAC | 20 | 1499 |
| antiSACas9-435 | + | CCAAGCAGCUGCUGAAAGUG | 20 | 1500 |
| antiSACas9-436 | + | UGGACAUCGGGAUUACAAGC | 20 | 1501 |
| antiSACas9-437 | + | GAAGGCACAGAAUCCAGAGG | 20 | 1502 |
| antiSACas9-438 | + | UAAGGAGAUCCUGGUCAACG | 20 | 1503 |
| antiSACas9-439 | − | UAAUCAGGUCGUUGUUGUAA | 20 | 1504 |
| antiSACas9-440 | − | GGAUUGUUCAGCAGGUCCUC | 20 | 1505 |
| antiSACas9-441 | + | GCAUAACGUCAAUGAGGUGG | 20 | 1506 |
| antiSACas9-442 | + | GGAGACUCGGAGAACCUACU | 20 | 1507 |
| antiSACas9-443 | + | CCUGAGUCAGAAGCUGUCAG | 20 | 1508 |
| antiSACas9-444 | + | UGCCCGAAAUCGAGACAGAA | 20 | 1509 |

Example 2: Efficacy of Governing gRNAs Targeting Cas9 Co-Transfected with a gRNA Targeting VEGF in 293T Cells In this study, 293T cells (120,000 cells per well in a 24 well plate) were transfected with 750 ng of a plasmid expressing epitope-tagged (3× Flag-tagged) S. pyogenes Cas9 together with 125 ng of a construct expressing a gRNA targeting the VEGF gene (gRNA sequence GGT-GAGUGAGUGUGUGCGUG (SEQ ID NO: 1510), see the 20mer of VEGFA Site 3 (Target Site 3) from FIG. 1d of Fu et al, Improving CIRSPR-Cas nuclease specificity using truncated guide RNAs. Nat Biotechnol 32, 279-284 (2014)). Simultaneously, the cells were transfected with 125 ng of one of three gRNA expression constructs: a construct expressing a gRNA targeting the CCR5 gene (serving as a control), a construct expressing governing gRNA anti-SP-Cas9-175 (see Example 1) targeting S. pyogenes Cas9, or a construct expressing governing gRNA anti-SPCas9-1 (see Example 1) targeting S. pyogenes Cas9. Cells were harvested for analysis one day, two days, three days, six days and nine days after transfection.

To quantify mutation rates of the endogenous VEGF and plasmid-borne Cas9 genes, total genomic DNA was isolated at each time point, and regions encompassing the VEGF gRNA and Cas9 governing gRNA targeting sequences were amplified by PCR. Amplified PCR products were denatured and re-annealed, followed by treatment with T7E1 nuclease. Mutation rates (indel frequency) were measured using a capillary electrophoresis instrument as described in Reyon, D. et al, FLASH assembly of TALENs for high-throughput genome editing. Nat Biotechnol 30, 460-465 (2012). Mutation frequencies (% indels±standard deviation) of VEGF and Cas9 for the three treatment groups are shown in Table E-13. These results confirm that both Cas9-targeted governing gRNAs induce mutations in the Cas9 gene, and that the endogenous VEGF locus is mutated to a similar extent in the presence or absence of a co-transfected Cas9-targeted governing gRNA.

Figure 7:
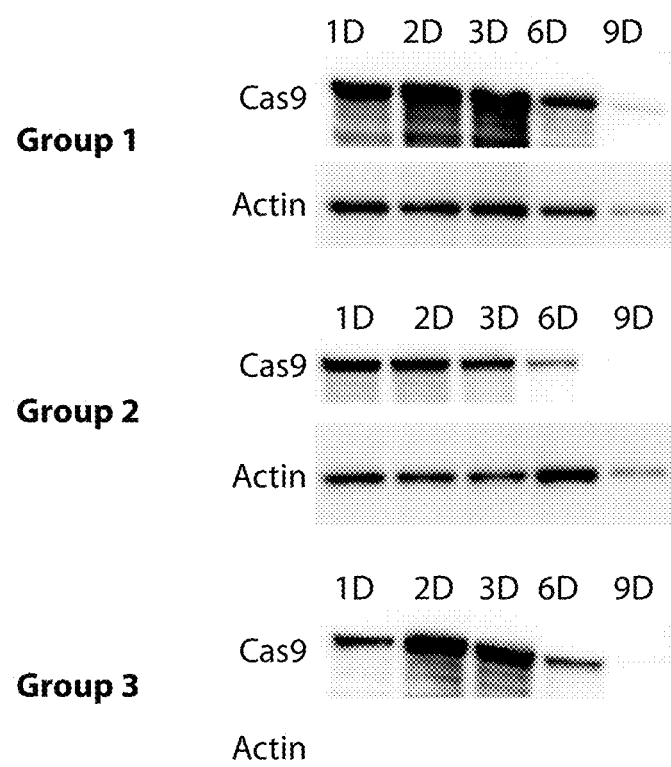
FIG. 7 depicts the levels of Cas9 protein expression in cells transfected with each of the Cas9-targeted governing gRNAs at 1, 2, 3, 6 and 9 days following transfection.

To assess levels of Cas9 protein during the time course of the experiment, total protein lysates were prepared from each treatment group at each time point. Protein samples (15 ug) were separated by SDS-PAGE, blotted to PVDF membrane, and probed with an antibody specific for the 3λFlag epitope tag. An antibody specific for cytoskeletal actin was used as a loading control. As shown in FIG. 7, co-transfection with each of the Cas9-targeted governing gRNAs leads to reduced levels of Cas9 protein, especially at six and nine days following transfection.

TABLE E-13

VEGF and Cas9 mutation rates

| Group | Co-transfected gRNA | target locus | time point | % indel | std. dev. |
|---|---|---|---|---|---|
| 1 | CCR5 (control) | VEGF | day 1 | 14.6 | 0.39 |
|   |   |   | day 2 | 30.6 | 5.16 |
|   |   |   | day 3 | 23.4 | 1.38 |
|   |   |   | day 6 | 25.7 | n.d. |
|   |   |   | day 9 | 15.9 | 1.37 |
|   |   | Cas9 | day 1 | n.a. | n.a. |
|   |   |   | day 2 | n.a. | n.a. |
|   |   |   | day 3 | n.a. | n.a. |
|   |   |   | day 6 | n.a. | n.a. |
|   |   |   | day 9 | n.a. | n.a. |
| 2 | Cas9 governing gRNA (anti-SPCas9-175) | VEGF | day 1 | 9.7 | 1.33 |
|   |   |   | day 2 | 21.6 | 9.76 |
|   |   |   | day 3 | 23.5 | 0.77 |
|   |   |   | day 6 | 25.5 | 2.37 |
|   |   |   | day 9 | 15.6 | n.d. |
|   |   | Cas9 | day 1 | 6.6 | 0.83 |
|   |   |   | day 2 | 7.4 | n.d. |
|   |   |   | day 3 | 11.7 | 1.19 |
|   |   |   | day 6 | 29.1 | 4.19 |
|   |   |   | day 9 | 24.0 |   |
| 3 | Cas9 governing gRNA (anti-SPCas9-1) | VEGF | day 1 | 13.2 | 2.84 |
|   |   |   | day 2 | 18.2 | 3.35 |
|   |   |   | day 3 | 26.9 | 2.13 |
|   |   |   | day 6 | 16.8 | 0.49 |
|   |   |   | day 9 | 22.4 | 0.48 |
|   |   | Cas9 | day 1 | 0 | 0 |
|   |   |   | day 2 | 10.1 | 1.15 |
|   |   |   | day 3 | 11.7 | n.d. |
|   |   |   | day 6 | 16.5 | 0.99 |
|   |   |   | day 9 | 21.4 | 1.44 |

Example 3: Activity Comparison of *S. aureus* gRNAs of Various Lengths

In this study, HEK-293T cells stably expressing GFP were co-transfected with constructs expressing gRNAs with targeting domains of various lengths (from 15-20 nucleotides) together with a construct expressing *S. aureus* Cas9. The gRNAs targeted several different genes: VEGF (total of 22 gRNAs), CCR5 (total of 15 gRNAs) and GFP (total of 10 gRNAs). The targeting domains of all the tested gRNAs initiated with a G nucleotide, and all of the gRNA target sites were associated with NNGRRT PAM sequences.

To quantify activity of the VEGF and CCR5 targeting gRNAs, total genomic DNA was isolated from cells two days following transfection and regions encompassing the VEGF and CCR5 gRNA target sites were amplified by PCR. Amplified PCR products were denatured and re-annealed, followed by treatment with T7E1 nuclease. Mutation rates (indel frequency) were measured using a capillary electrophoresis instrument as described in Reyon, D. et al., FLASH assembly of TALENs for high-throughput genome editing. *Nat Biotechnol* 30, 460-465 (2012). To quantify activity of the GFP targeting gRNAs, cells were harvested three days following transfection and the percentage of GFP-negative cells (indicating mutation of the GFP gene) were measured by flow cytometry. The mean activity of all gRNAs of each targeting domain length was calculated and compared to the mean activity of the gRNAs with 20 nucleotide targeting domains. As shown in Table E-14, gRNAs with shorter targeting domains have lower average activity than those with 20 nucleotide targeting domains.

TABLE E-14

Mean activity of *S. aureus* gRNAs with various length targeting domains compared to gRNAs with 20 nucleotide targeting domains.

| Targeting Domain Length | Mean Activity Compared to 20 nt Targeting Domain | st. dev. |
|---|---|---|
| 20 | 1 | 0.179 |
| 19 | 0.395 | 0.126 |
| 18 | 0.244 | 0.087 |
| 17 | 0.028 | 0.014 |
| 16 | 0.012 | 0.005 |
| 15 | 0.005 | 0.004 |

INCORPORATION BY REFERENCE

All publications, patents, and patent applications mentioned herein are hereby incorporated by reference in their entirety as if each individual publication, patent or patent application was specifically and individually indicated to be incorporated by reference. In case of conflict, the present application, including any definitions herein, will control.

EQUIVALENTS

Those skilled in the art will recognize, or be able to ascertain using no more than routine experimentation, many equivalents to the specific embodiments of the invention described herein. While this invention has been disclosed with reference to specific aspects, it is apparent that other aspects and variations of this invention may be devised by others skilled in the art without departing from the true spirit and scope of the invention. The appended claims are intended to be construed to include all such aspects and equivalent variations.

Other embodiments are within the following claims.

The invention claimed is:

1. A composition comprising:
a nucleic acid encoding a first guide RNA (gRNA) molecule;
a Cas9 molecule, or a nucleic acid encoding a Cas9 molecule, wherein the Cas9 molecule is an *S. aureus* or *S. pyogenes* Cas9 molecule, and a payload comprising an inhibitor of a transcription factor, a post-translational modification enzyme, or a post-transcriptional modification enzyme.

2. The composition of claim 1, wherein the inhibitor is a siRNA, a shRNA, a ribozyme, an antisense-oligonucleotide, an antibody, or an aptamer.

3. The composition of claim 1, wherein the inhibitor is a siRNA.

4. The composition of claim 1, wherein the inhibitor is a shRNA.

5. The composition of claim 1, wherein the inhibitor is a ribozyme.

6. The composition of claim 1, wherein the inhibitor is an antisense-oligonucleotide.

7. The composition of claim 1, wherein the inhibitor is an antibody.

8. The composition of claim 1, wherein the inhibitor is an aptamer.

* * * * *